US006929911B2

(12) United States Patent
Oefner et al.

(10) Patent No.: US 6,929,911 B2
(45) Date of Patent: Aug. 16, 2005

(54) METHOD FOR DETERMINING GENETIC AFFILIATION, SUBSTRUCTURE AND GENE FLOW WITHIN HUMAN POPULATIONS

(75) Inventors: Peter J. Oefner, Redwood City, CA (US); Peter A. Underhill, Palo Alto, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 117 days.

(21) Appl. No.: 10/002,623

(22) Filed: Nov. 1, 2001

(65) Prior Publication Data

US 2003/0134285 A1 Jul. 17, 2003

Related U.S. Application Data

(60) Provisional application No. 60/245,355, filed on Nov. 1, 2000.

(51) Int. Cl.[7] .......................... C12Q 1/68; C12P 19/34; C07H 21/02; C07H 21/04
(52) U.S. Cl. ........................ 435/6; 435/91.2; 536/23.5; 536/24.31; 536/24.33
(58) Field of Search ........................ 435/6, 91.1, 91.2; 536/23.1, 24.3, 24.33

(56) References Cited

U.S. PATENT DOCUMENTS

| 4,683,194 A | 7/1987 | Saiki et al. |
| 5,364,759 A | 11/1994 | Caskey et al. |

OTHER PUBLICATIONS

Shen et al.(PNAS Jun. 20, 2000) vol. 97 No. 13 pp. 7354–7359.*
Bosch et al. (2001) *Am. J. Hum. Genet.* 68:1019–1029.
Botstein et al. (1980) *Am. J. Hum.Genet.* 32:314–331.
Engelke et al. (1988) *Proc. Natl. Acad. Sci.* U.S.A. 85:544–548.
Jin et al. (1999) *Proc. Natl. Acad. Sci.* USA, vol. 96 pp. 3796–3800.
Ke et al. (2001) *Science*, 292:1152–1153.
Litt & Luty (1989) *Am Hum Genet*, 44:397–401.
Oefner & Underhill (1998) *Current Protocols in Human Genetics*, Supplement No. 19, 7.10.1–7.10.12.
Renfrew et al. (2000) *Nat. Genet.* Vol 26, pp. 253–254.
Shen et al. *PNAS* (2000), 97(13): 7354–7359.
Tautz D. (1989) Hyper variability of Simple Sequences as a General Source for Polymorphic DNA Markers, *Nuc. Acids Res.*, 17(16) 6463–70.
Thomson et al. (2000) *PNAS*, 97(13): 7360–7365.
Underhill et al. (2001) *Ann. Hum. Genet*, 65:43–62. Jan.
Underhill et al. (1997) Genome Research, 7:996–1005.
Underhill et al. (2000) *Nat. Genet.* vol. 26, pp. 358–361, Nov. 1.
Wallace et al. (1981) *Nucl. Acids Res.* 9(4), 879–894.
Weber & May, (1989) *Am Hum Genet* 44:388.
Wells et al. (2001) *PNAS*, 98(18): 10244–10249.
White & Lalouel, (1988) *Sci. Am.* 258, 40–48.
Wong et al. (1987) *Nature* 330, 384–386.

* cited by examiner

Primary Examiner—Jeffrey Fredman
Assistant Examiner—Sally A. Sakelaris
(74) Attorney, Agent, or Firm—Carol L. Francis; Edward J. Baba; Bozicevi, Field & Francis LLP

(57) ABSTRACT

The present invention provides novel polymorphisms on the Y chromosome and methods of using these polymorphisms as well as known polymorphisms on the Y chromosome as indicators of evolutionary heritage. The polymorphisms of the present invention clustered to specific regions of the Y chromosome, and polymorphisms of particular use to the present methods are found in the non-recombining region of the human Y chromosome (NRY). These polymorphisms, including SNPs, insertions, and deletions, may be useful for numerous applications, including forensics, paternity testing, diagnosis and the like.

40 Claims, 4 Drawing Sheets

SEQUENCE LISTING

<160> NUMBER OF SEQ ID NOS: 952

<210> SEQ ID NO 1
<211> LENGTH: 209
<212> TYPE: DNA
<213> ORGANISM: Homo Sapiens

<400> SEQUENCE: 1
aggcactggt cagaatgaag tgaatggcac acaggacaag tccagaccca ggaaggtcca    60

```
gtaacatggg agaagaacgg aaggagttct aaaattcagg gctcccttgg gctccctgt      120 ttaaaaatgt aggttttatt attatatttc attgttaaca aaagtccrtg agatctgtgg     180
aggataaagg gggagctgta ttttccatt                                       209
```

```
<210> SEQ ID NO 2
<211> LENGTH: 20
<212> TYPE: DNA
<213> ORGANISM: Artificial Sequence
<220> FEATURE:
<223> OTHER INFORMATION: synthetic oligo

<400> SEQUENCE: 2
aggcactggt cagaatgaag                                                  20
```

```
<210> SEQ ID NO 3
<211> LENGTH: 20
<212> TYPE: DNA
<213> ORGANISM: Artificial Sequence
<220> FEATURE:
<223> OTHER INFORMATION: synthetic oligo

<400> SEQUENCE: 3
aatggaaaat acagctcccc                                                  20
```

```
<210> SEQ ID NO 4
<211> LENGTH: 241
<212> TYPE: DNA
<213> ORGANISM: Homo Sapiens

<400> SEQUENCE: 4
taatcagtct cctcccagca agtgatatgc aactgagatt ccttatgaca catctgaaca      60
ctagtggatt tgctttgtag taggaacaag gtacattcgc gggataaatg tggccaagtt     120
ttatctgctg ccagggcttt caaataggtt gacctgacaa tgggtcacct ctgggactga     180
yaattaggaa gagctggtac ctaaaatgaa agatgccctt aaatttcaga ttcacaattt     240
t                                                                     241
```

```
<210> SEQ ID NO 5
<211> LENGTH: 20
<212> TYPE: DNA
<213> ORGANISM: Artificial Sequence
<220> FEATURE:
<223> OTHER INFORMATION: synthetic oligo

<400> SEQUENCE: 5
taatcagtct cctcccagca                                                  20
```

```
<210> SEQ ID NO 6
<211> LENGTH: 25
<212> TYPE: DNA
<213> ORGANISM: Artificial Sequence
<220> FEATURE:
<223> OTHER INFORMATION: synthetic oligo

<400> SEQUENCE: 6
aaaattgtga atctgaaatt taagg                                            25
```

```
<210> SEQ ID NO 7
<211> LENGTH: 273
<212> TYPE: DNA
<213> ORGANISM: Homo Sapiens
```

<400> SEQUENCE: 7

```
tcctaggtta tgattacaga gcgaggatta ttataatatt ggaataaaga ataattgcta      60
caaactaatg attaatgata ttcatatrta atcatatcta agatctatat ctagtataac     120
tattcttatt ttatatattt tattgtactg aacagcttg tgcccttggt ctcttgcctc      180
ggcacctggg tggcttgcca tccacagaag tgttttaaca gcaaaaatta ctgtgaattt    240
tctgcccaaa accttgtcat gtttacaaga cgt                                  273
```

<210> SEQ ID NO 8
<211> LENGTH: 23
<212> TYPE: DNA
<213> ORGANISM: Artificial Sequence
<220> FEATURE:
<223> OTHER INFORMATION: synthetic oligo

<400> SEQUENCE: 8

```
tcctaggtta tgattacaga gcg                                              23
```

<210> SEQ ID NO 9
<211> LENGTH: 22
<212> TYPE: DNA
<213> ORGANISM: Artificial Sequence
<220> FEATURE:
<223> OTHER INFORMATION: synthetic oligo

<400> SEQUENCE: 9

```
acgtcttgta aacatgacaa gg                                               22
```

<210> SEQ ID NO 10
<211> LENGTH: 322
<212> TYPE: DNA
<213> ORGANISM: Homo Sapiens

<400> SEQUENCE: 10

```
gggtttatac tgacctgcca atgttaaaag ggacctaaat tcactttggg gaagtggcca      60
gaaaggaaga agyagaagga gaagagtgca agaaacctcc agttgtgggg gttgagcctc     120
caggataaga aagaaagaaa tctccagtag gggggattga gcctaacaca aacctttggt    180
aatagacaag gcaagacatt tccaataggg gagattgagt gtcacctcaa aactattaag   240
atgggaaata ccccaggtaa gatagagggt aaaaaaggat aaagctagca gcaataacat   300
tcccctgaa agttcccaat aa                                               322
```

<210> SEQ ID NO 11
<211> LENGTH: 25
<212> TYPE: DNA
<213> ORGANISM: Artificial Sequence
<220> FEATURE:
<223> OTHER INFORMATION: synthetic oligo

<400> SEQUENCE: 11

```
gggtttatac tgacctgcca atgtt                                            25
```

<210> SEQ ID NO 12
<211> LENGTH: 20
<212> TYPE: DNA
<213> ORGANISM: Artificial Sequence
<220> FEATURE:
<223> OTHER INFORMATION: synthetic oligo

<400> SEQUENCE: 12

```
ttattgggaa ctttcagggg                                                  20
```

<210> SEQ ID NO 13
<211> LENGTH: 656
<212> TYPE: DNA
<213> ORGANISM: Homo Sapiens

<400> SEQUENCE: 13
gggtttatac tgacctgcca atgttaaaag ggacctaaat tcactttggg gaagtggcca      60
gaaaggaaga agcagaagga gaagagtgca agaaacctcc agttgtgggg gttgagcctc     120
caggataaga aagaaagaaa tctccagtag gggggattga gcctaacaca aacctttggt     180
aatagacaag gcaagacatt tccaataggg gagattgagt gtcacctcaa aactattaag     240
atgggaaata ccccaggtaa gatagagggt aaaaaaggat aaagctagca gcaataacat     300 tcccctgaa agttcccaat aatttatgct aaaatattgg aaagacaacg aaaggactaa      360
gcacaagaga aagcaacaga tgataaatat tgttatgtca tttgaaccca ggaaccaatc     420
ttcgaaccct cagttttctg gccaaagttg gagtcaaatg aggattggat ttgtcagctt     480
ttaatagaac atatgatgac aaaaccttca tctcccagga ggagataaat tatgccctat     540
gttggtggca aggacctgtc ctcctttacc ctctaaaaac tggagggaga aagtcaaaga     600
ctaactcctc tgaaaaagat aaagtcccta ttcctagaca gcccagcaac acacgg        656

<210> SEQ ID NO 14
<211> LENGTH: 25
<212> TYPE: DNA
<213> ORGANISM: Artificial Sequence
<220> FEATURE:
<223> OTHER INFORMATION: synthetic oligo

<400> SEQUENCE: 14
gggtttatac tgacctgcca atgtt                                            25

<210> SEQ ID NO 15
<211> LENGTH: 20
<212> TYPE: DNA
<213> ORGANISM: Artificial Sequence
<220> FEATURE:
<223> OTHER INFORMATION: synthetic oligo

<400> SEQUENCE: 15
ccgtgtgttg ctgggctgtc                                                  20

<210> SEQ ID NO 16
<211> LENGTH: 218
<212> TYPE: DNA
<213> ORGANISM: Homo Sapiens

<400> SEQUENCE: 16
cactaccaca tttctggttg gcttgtagtt ctttctygga aaaatattat tctaatttcc      60
ttatagtatt agccatcaaa gtaggggaag cagatcaaat ctaccataag accaagtcat     120
aggaagaaga tcaaattaag atgctaggca aaagtctcag cacatatgga ttatgagaag     180
cacattcaca catccaaact caaagaatgg actcagcg                             218

<210> SEQ ID NO 17
<211> LENGTH: 21
<212> TYPE: DNA
<213> ORGANISM: Artificial Sequence
<220> FEATURE:
<223> OTHER INFORMATION: synthetic oligo

```
<400> SEQUENCE: 17
cactaccaca tttctggttg g                                              21

<210> SEQ ID NO 18
<211> LENGTH: 20
<212> TYPE: DNA
<213> ORGANISM: Artificial Sequence
<220> FEATURE:
<223> OTHER INFORMATION: synthetic oligo

<400> SEQUENCE: 18
cgctgagtcc attctttgag                                                20

<210> SEQ ID NO 19
<211> LENGTH: 300
<212> TYPE: DNA
<213> ORGANISM: Homo Sapiens

<400> SEQUENCE: 19
actgtgagcg agctgaaaat gcctgatttt ctcccttggt ttaatgtaaa ggaagggatc    60
caaaggctta gggagattgg gatggtggat tagtcacttt agacctactc attccaatag   120
ggagggtcca gaagatgtac ccttgaccaa tgccttgcaa aatagattcg tgagggcagc   180
acctgcatca ccaaagggca tgtaatcatt cctctctgta tgtcagatct aacaasaaga   240
agaacagtaa ctcaactaca aaatttaaac acaatggaaa taattggttc acaaggctgc   300

<210> SEQ ID NO 20
<211> LENGTH: 20
<212> TYPE: DNA
<213> ORGANISM: Artificial Sequence
<220> FEATURE:
<223> OTHER INFORMATION: synthetic oligo

<400> SEQUENCE: 20
actgtgagcg agctgaaaat                                                20

<210> SEQ ID NO 21
<211> LENGTH: 20
<212> TYPE: DNA
<213> ORGANISM: Artificial Sequence
<220> FEATURE:
<223> OTHER INFORMATION: synthetic oligo

<400> SEQUENCE: 21
gcagccttgt gaaccaatta                                                20

<210> SEQ ID NO 22
<211> LENGTH: 267
<212> TYPE: DNA
<213> ORGANISM: Homo Sapiens

<400> SEQUENCE: 22
cccacccact tcagtatgaa ttttgggatc tgttacctat tttttgatat aaaatcaact    60
gcaagtttag tgcctcagta tcacaaacac tgtatttgct catatgtctg tgaatcaata   120
acttggactg ggttcakttg ggcagttctt ctattggtct tgcctggggt ctttaatgca   180
gcttccattt tctggcagct tgatgagact ggatggtcta aggtacattc atgaacacat   240
ctgtttggtg gacttgtctg tcagcct                                       267
```

```
<210> SEQ ID NO 23
<211> LENGTH: 20
<212> TYPE: DNA
<213> ORGANISM: Artificial Sequence
<220> FEATURE:
<223> OTHER INFORMATION: synthetic oligo

<400> SEQUENCE: 23
cccacccact tcagtatgaa                                                   20

<210> SEQ ID NO 24
<211> LENGTH: 20
<212> TYPE: DNA
<213> ORGANISM: Artificial Sequence
<220> FEATURE:
<223> OTHER INFORMATION: synthetic oligo

<400> SEQUENCE: 24
aggctgacag acaagtccac                                                   20

<210> SEQ ID NO 25
<211> LENGTH: 340
<212> TYPE: DNA
<213> ORGANISM: Homo Sapiens

<400> SEQUENCE: 25
gcagcatata aaactttcag gaccctgaaa tacagaactg caaagaaacg gcctaagatg        60
gttgaatsct ctttatttt ctttaattta gacatgttca aacgttcaat gtcttacata       120
cttagttatg taagtaaggt agcgcttact tcattatgca tttcaatact caaaaaaaat      180
tcctttgtga aatgttgaaa tatttttcta atctgtttca cgagcttcaa aaatgaggaa      240
aaaagattca gtttacattt cagcaaaatg cctctttta atcggattta tgtttactta      300
acatttacag tacatttacg cttgagcaaa gttaggtttt                            340

<210> SEQ ID NO 26
<211> LENGTH: 21
<212> TYPE: DNA
<213> ORGANISM: Artificial Sequence
<220> FEATURE:
<223> OTHER INFORMATION: synthetic oligo

<400> SEQUENCE: 26
gcagcatata aaactttcag g                                                 21

<210> SEQ ID NO 27
<211> LENGTH: 21
<212> TYPE: DNA
<213> ORGANISM: Artificial Sequence
<220> FEATURE:
<223> OTHER INFORMATION: synthetic oligo

<400> SEQUENCE: 27
aaaacctaac tttgctcaag c                                                 21

<210> SEQ ID NO 28
<211> LENGTH: 343
<212> TYPE: DNA
<213> ORGANISM: Homo Sapiens

<400> SEQUENCE: 28
gcattgctat aagttacctg caatttataa agttgtgaaa tagttcaaga caatgaaggg        60
agagactctc tggtaactac agagtatgag ctcatcattg cttagtttcc acaagaggta      120
```

```
tctctgaatt tttttgttta ttcccaatga tcttayagca cttgtaaagt ttttacatta     180
gttacaaaat gcaatttgaa gtgaaagaaa cagaaataca aaatattagt ttctcttttt     240
ctcctacatt cctacatgga tttgtagaag agctgacctt tacttataaa ataaatcagc     300
aaatgagtgt cttttctaga atgggtgac ccaattttta tta                       343
```

<210> SEQ ID NO 29
<211> LENGTH: 21
<212> TYPE: DNA
<213> ORGANISM: Artificial Sequence
<220> FEATURE:
<223> OTHER INFORMATION: synthetic oligo

<400> SEQUENCE: 29

```
gcattgctat aagttacctg c                                               21
```

<210> SEQ ID NO 30
<211> LENGTH: 20
<212> TYPE: DNA
<213> ORGANISM: Artificial Sequence
<220> FEATURE:
<223> OTHER INFORMATION: synthetic oligo

<400> SEQUENCE: 30

```
taataaaaat tgggtcaccc                                                 20
```

<210> SEQ ID NO 31
<211> LENGTH: 222
<212> TYPE: DNA
<213> ORGANISM: Homo Sapiens

<400> SEQUENCE: 31

```
tctctctgtc tgtctctccc tccctctctc cttgtattct aacrgaaagg tttagaactt     60
gcataattgg gaaagaagct gttgcctgaa cttactgggg gattcagcat tgtcattttg     120
gacatgtcac ttatcctcag tatttgcttc ccccaggaga gagctgtaat aaaaaagcat     180
tgcaatttaa tacataagct cagtaagttc ttgtttatgc tc                        222
```

<210> SEQ ID NO 32
<211> LENGTH: 23
<212> TYPE: DNA
<213> ORGANISM: Artificial Sequence
<220> FEATURE:
<223> OTHER INFORMATION: synthetic oligo

<400> SEQUENCE: 32

```
tctctctgtc tgtctctccc tcc                                             23
```

<210> SEQ ID NO 33
<211> LENGTH: 25
<212> TYPE: DNA
<213> ORGANISM: Artificial Sequence
<220> FEATURE:
<223> OTHER INFORMATION: synthetic oligo

<400> SEQUENCE: 33

```
gagcataaac aagaacttac tgagc                                           25
```

<210> SEQ ID NO 34
<211> LENGTH: 309
<212> TYPE: DNA
<213> ORGANISM: Homo Sapiens

```
<400> SEQUENCE: 34
actaaaacac cattagaaac aaaggactta aactaggaat taattatttc tctttctctt    60
tccatggcca acaaacattg aaaaaaaatt gccatctttt tttttatttg tttgttagag   120
atggggatct cactctgttt cttagattgt agtgccatgg cacaataatg gctcactgca   180
gcctcaaact cctgggctca agtgatcacc cccatacaga ctcccgagta gctgggaaca   240
caggcacatg ccaccacccc tagctaattt tttattattt gtagakatgg gggtcactat   300
gttgctcag                                                          309

<210> SEQ ID NO 35
<211> LENGTH: 25
<212> TYPE: DNA
<213> ORGANISM: Artificial Sequence
<220> FEATURE:
<223> OTHER INFORMATION: synthetic oligo

<400> SEQUENCE: 35
actaaaacac cattagaaac aaagg                                         25

<210> SEQ ID NO 36
<211> LENGTH: 20
<212> TYPE: DNA
<213> ORGANISM: Artificial Sequence
<220> FEATURE:
<223> OTHER INFORMATION: synthetic oligo

<400> SEQUENCE: 36
ctgagcaaca tagtgacccc                                               20

<210> SEQ ID NO 37
<211> LENGTH: 233
<212> TYPE: DNA
<213> ORGANISM: Homo Sapiens

<400> SEQUENCE: 37
tcctaacctg gtggtctttc attgttttac aaaggtgatt tagttttggg aaggactatt    60
ctcctttaaa ctatagacta aattttttctc aaagttaggt tagtttatgc ccaggaatga  120
acaagggcag taggtaggtt aagggcaaga cggttasatc agttctctgt tactgttata   180
attttctcat tgttatattt tttgcaaatg tggttggata aaatcatggc tca          233

<210> SEQ ID NO 38
<211> LENGTH: 20
<212> TYPE: DNA
<213> ORGANISM: Artificial Sequence
<220> FEATURE:
<223> OTHER INFORMATION: synthetic oligo

<400> SEQUENCE: 38
tcctaacctg gtggtctttc                                               20

<210> SEQ ID NO 39
<211> LENGTH: 21
<212> TYPE: DNA
<213> ORGANISM: Artificial Sequence
<220> FEATURE:
<223> OTHER INFORMATION: synthetic oligo

<400> SEQUENCE: 39
tgagccatga ttttatccaa c                                             21
```

<210> SEQ ID NO 40
<211> LENGTH: 287
<212> TYPE: DNA
<213> ORGANISM: Homo Sapiens

<400> SEQUENCE: 40
agacggttag atcagttctc tgttactgtt ataattttct cattgttata ttttttgcaa    60
atgtggttgg ataaaatcat ggctcataca aatatacaaa aaatacatat taaaatttta    120
tttaacataa aacattaaaa tttatttaat aaattataaa tgaaaaaatc agtaacatgy    180
tataagcagt ttaaaaaagt taatgaagct cagtttttaac atgaagtata ggaatggtga    240
aattatataa atgaaatttg taaatggtgt caatgtgctt ttatcta                  287

<210> SEQ ID NO 41
<211> LENGTH: 22
<212> TYPE: DNA
<213> ORGANISM: Artificial Sequence
<220> FEATURE:
<223> OTHER INFORMATION: synthetic oligo

<400> SEQUENCE: 41
agacggttag atcagttctc tg                                              22

<210> SEQ ID NO 42
<211> LENGTH: 22
<212> TYPE: DNA
<213> ORGANISM: Artificial Sequence
<220> FEATURE:
<223> OTHER INFORMATION: synthetic oligo

<400> SEQUENCE: 42
tagataaaag cacattgaca cc                                              22

<210> SEQ ID NO 43
<211> LENGTH: 304
<212> TYPE: DNA
<213> ORGANISM: Homo Sapiens

<400> SEQUENCE: 43
acaaatcctg aacaatcgcc atcacctatt tggtggacgc ataggcctgg tctctgatct    60
ggtcgcatgt ccagagggtc tgctaaccca ctgcacctag ggagacattg tacagagaca    120
ttgtaccacc ttttctctac tcttcccaga ctcaacacat ttgattgtat atgcgcatga    180
ggtagaaata taagatgaag cagggacaga gtcaacaagc cagaactaga tgcttctacc    240
tggacagaag acctagaatt ctttttttgga tcctaaattc accaggaaat tttaaccaca    300
tgca                                                                  304

<210> SEQ ID NO 44
<211> LENGTH: 19
<212> TYPE: DNA
<213> ORGANISM: Artificial Sequence
<220> FEATURE:
<223> OTHER INFORMATION: synthetic oligo

<400> SEQUENCE: 44
acaaatcctg aacaatcgc                                                  19

<210> SEQ ID NO 45
<211> LENGTH: 20
<212> TYPE: DNA
<213> ORGANISM: Artificial Sequence

```
<220> FEATURE:
<223> OTHER INFORMATION: synthetic oligo

<400> SEQUENCE: 45
tgcatgtggt taaaatttcc                                               20

<210> SEQ ID NO 46
<211> LENGTH: 17
<212> TYPE: DNA
<213> ORGANISM: Artificial Sequence
<220> FEATURE:
<223> OTHER INFORMATION: synthetic oligo

<400> SEQUENCE: 46
gacattgtac agagaca                                                  17

<210> SEQ ID NO 47
<211> LENGTH: 8
<212> TYPE: DNA
<213> ORGANISM: Artificial Sequence
<220> FEATURE:
<223> OTHER INFORMATION: synthetic oligo

<400> SEQUENCE: 47 gacaggca                                                             8

<210> SEQ ID NO 48
<211> LENGTH: 266
<212> TYPE: DNA
<213> ORGANISM: Homo Sapiens

<400> SEQUENCE: 48
tgttatgtca tttgaaccca ggaaccaatc ttcgaacmct cagttttctg gccaaagttg    60
gagtcaaatg aggattggat ttgtcagctt taatagaac atatgatgac aaaaccttca    120
tctcccagga ggagataaat tatgccctat gttggtggca aggacctgtc ctcctttacc   180
ctctaaaaac tggagggaga aagtcaaaga ctaactcctc tgaaaaagat aaagtcccta   240
ttcctagaca gcccagcaac acacgg                                        266

<210> SEQ ID NO 49
<211> LENGTH: 21
<212> TYPE: DNA
<213> ORGANISM: Artificial Sequence
<220> FEATURE:
<223> OTHER INFORMATION: synthetic oligo

<400> SEQUENCE: 49
tgttatgtca tttgaaccca g                                             21

<210> SEQ ID NO 50
<211> LENGTH: 19
<212> TYPE: DNA
<213> ORGANISM: Artificial Sequence
<220> FEATURE:
<223> OTHER INFORMATION: synthetic oligo

<400> SEQUENCE: 50
ccgtgtgttg ctgggctgt                                                19

<210> SEQ ID NO 51
<211> LENGTH: 333
<212> TYPE: DNA
<213> ORGANISM: Homo Sapiens
```

-continued

<400> SEQUENCE: 51

```
ctggtcataa cactggaaat cagattctgt ctactcacca gagtttgtgg ttgctggttg     60
ttacggggtt tttttaagtg aattttgggg tttgttaagt ggccaaacta ttttgtgaa     120
gactgttgta tgtgggtttc agatgtctct acatcagttt gtggtcagct agtgagttaa   180
attttatgaa aagcctggag aaacaagaat agcagtaaaa acttccagtc tttgtagatt   240
gggtgtcttc agtgcttagc tgggcaattt aaaacttacc ttaagtagta cagttggccc   300
tttgtgtctg tgagtttcac atttgtaggt tca                                 333
```

<210> SEQ ID NO 52
<211> LENGTH: 21
<212> TYPE: DNA
<213> ORGANISM: Artificial Sequence
<220> FEATURE:
<223> OTHER INFORMATION: synthetic oligo

<400> SEQUENCE: 52

```
ctggtcataa cactggaaat c                                              21
```

<210> SEQ ID NO 53
<211> LENGTH: 21
<212> TYPE: DNA
<213> ORGANISM: Artificial Sequence
<220> FEATURE:
<223> OTHER INFORMATION: synthetic oligo

<400> SEQUENCE: 53

```
tgaacctaca aatgtgaaac t                                              21
```

<210> SEQ ID NO 54
<211> LENGTH: 335
<212> TYPE: DNA
<213> ORGANISM: Homo Sapiens

<400> SEQUENCE: 54

```
ctggtcataa cactggaaat cagattctgt ctactcacca gagtttgtgg ttgctggttg     60
ttaaacgggg ttttttttaag tgaattttgg ggtttgttaa gtggccaaac tattttttgtg   120
aagactgttg tatgtgggtt tcagatgtct ctacatcagt ttgtggtcag ctagtgagtt   180
aaattttatg aaaagcctgg agaaacaaga atagcagtaa aaacttccag tctttgtaga   240
ttgggtgtct tcagtgctta gctgggcaat ttaaaactta ccttaagtag tacagttggc   300
cctttgtgtc tgtgagtttc acatttgtag gttca                               335
```

<210> SEQ ID NO 55
<211> LENGTH: 21
<212> TYPE: DNA
<213> ORGANISM: Artificial Sequence
<220> FEATURE:
<223> OTHER INFORMATION: synthetic oligo

<400> SEQUENCE: 55

```
ctggtcataa cactggaaat c                                              21
```

<210> SEQ ID NO 56
<211> LENGTH: 22
<212> TYPE: DNA
<213> ORGANISM: Artificial Sequence
<220> FEATURE:
<223> OTHER INFORMATION: synthetic oligo

<400> SEQUENCE: 56
tgaacctaca aatgtgaaac tc                                                22

<210> SEQ ID NO 57
<211> LENGTH: 333
<212> TYPE: DNA
<213> ORGANISM: Homo Sapiens

<400> SEQUENCE: 57
ctggtcataa cactggaaat cagattctgt ctactcacca gagtttgtgg ttgctggttg        60
ttacggggtt tttttaagtg aattttgggg tttgttaagt ggccaaacta tttttgtgaa       120
gactgttgta wgtgggtttc agatgtctct acatcagttt gtggtcagct agtgagttaa      180
attttatgaa aagcctggag aaacaagaat agcagtaaaa acttccagtc tttgtagatt      240
gggtgtcttc agtgcttagc tgggcaattt aaaacttacc ttaagtagta cagttggccc      300
tttgtgtctg tgagtttcac atttgtaggt tca                                   333

<210> SEQ ID NO 58
<211> LENGTH: 21
<212> TYPE: DNA
<213> ORGANISM: Artificial Sequence
<220> FEATURE:
<223> OTHER INFORMATION: synthetic oligo

<400> SEQUENCE: 58
ctggtcataa cactggaaat c                                                21

<210> SEQ ID NO 59
<211> LENGTH: 22
<212> TYPE: DNA
<213> ORGANISM: Artificial Sequence
<220> FEATURE:
<223> OTHER INFORMATION: synthetic oligo

<400> SEQUENCE: 59
tgaacctaca aatgtgaaac tc                                                22

<210> SEQ ID NO 60
<211> LENGTH: 413
<212> TYPE: DNA
<213> ORGANISM: Homo Sapiens

<400> SEQUENCE: 60
gattgggtgt cttcagtgct tagctgggca atttaaaact taccttaagt agtacagttg        60 gcccttttgtg tctgtgagtt tcacatttgt aggttcaacc aactgtggat tgaaaatrtt      120
tgaaaaatta aaaatagatg gttgcatttg cactgaacat gtagactttt ttttcttgta      180
atttctctta aaccatacag cataacaact ctttacatag catgtacatt gtattaggta      240
ttctgagtac tctaaagtat acgggaggat gtgtgtaggt tatgtgcaaa tactataaca      300
ttatatgtaa gggatttgaa aattctggga ttttggtatt tgcaggtggt gtgggatggg      360
ggtctgcctg gaaccaagga atgccccaaa ggaggatggt gccttgttgt gtg             413

<210> SEQ ID NO 61
<211> LENGTH: 20
<212> TYPE: DNA
<213> ORGANISM: Artificial Sequence
<220> FEATURE:
<223> OTHER INFORMATION: synthetic oligo

<400> SEQUENCE: 61
gattgggtgt cttcagtgct                                                    20

<210> SEQ ID NO 62
<211> LENGTH: 18
<212> TYPE: DNA
<213> ORGANISM: Artificial Sequence
<220> FEATURE:
<223> OTHER INFORMATION: synthetic oligo

<400> SEQUENCE: 62
cacacaacaa ggcaccat                                                      18

<210> SEQ ID NO 63
<211> LENGTH: 415
<212> TYPE: DNA
<213> ORGANISM: Homo Sapiens

<400> SEQUENCE: 63
cttttatttc tgactacagg gccctctttt gcattgtttt tgtaggtcag atttattagt         60
agtatgttct ttcagctttt gtgtatctgg gaatatttca gtttctcctt tattttgaag       120
gatagtcttt gagttttttcc tacttaacag atcctggagc ttcttggatg tgtaaattaa      180 tgatttttcat caaatgtgaa gttgttttcg gctattctgc agatatcctt taccacccct      240
ttgctgcctc ttcctattgt gggtaatagg catgtctctg tatgttggag agaatcaaag       300
gtcttttaag cccttgattt ttatttatct tttgttttt gttcctcaga ctgtatwgtt        360
tcagttgact tagcttccag tttgttgatt cttctgcctg ctcaaatctg ctgtt            415

<210> SEQ ID NO 64
<211> LENGTH: 21
<212> TYPE: DNA
<213> ORGANISM: Artificial Sequence
<220> FEATURE:
<223> OTHER INFORMATION: synthetic oligo

<400> SEQUENCE: 64
cttttatttc tgactacagg g                                                  21

<210> SEQ ID NO 65
<211> LENGTH: 19
<212> TYPE: DNA
<213> ORGANISM: Artificial Sequence
<220> FEATURE:
<223> OTHER INFORMATION: synthetic oligo

<400> SEQUENCE: 65
aacagcagat ttgagcagg                                                     19

<210> SEQ ID NO 66
<211> LENGTH: 327
<212> TYPE: DNA
<213> ORGANISM: Homo Sapiens

<400> SEQUENCE: 66
agaagggtct gaaagcaggt tcgtgatttc acccttttaca gtttaataca agggatttta       60
catacagaca tataagctga tagtcctggt ttccctattt gttttaaggt gccattcctg       120
gtggctctrc ctccttcccc cagtgcccat atgggcccctt agtctgctgt aggcatgctc      180
aggcaagccc ttgagcaaat tcccttaatc tgcacgaaac atgggctgga gattcagtgg      240

```
gacccttct    ttagtgtctg    cctaatgcaa    gctggctaac    tcctttcaaa    agttttgtct       300
tgctgatgaa    gcctccaggt    agtaggc                                                   327
```

<210> SEQ ID NO 67
<211> LENGTH: 20
<212> TYPE: DNA
<213> ORGANISM: Artificial Sequence
<220> FEATURE:
<223> OTHER INFORMATION: synthetic oligo

<400> SEQUENCE: 67

```
agaagggtct gaaagcaggt                                                                  20
```

<210> SEQ ID NO 68
<211> LENGTH: 19
<212> TYPE: DNA
<213> ORGANISM: Artificial Sequence
<220> FEATURE:
<223> OTHER INFORMATION: synthetic oligo

<400> SEQUENCE: 68

```
gcctactacc tggaggctt                                                                   19
```

<210> SEQ ID NO 69
<211> LENGTH: 327
<212> TYPE: DNA
<213> ORGANISM: Homo Sapiens

<400> SEQUENCE: 69

```
tctctaactt    ctgtgagcca    ctctagcaaa    ttaattgaac    caaaggagga    ggttaaggac       60
agcatagttt    acaaaatgag    ccctgtttct    gacatctgaa    gtgggggcag    tctagtgggc      120
ctgacctctt    aacttgtaga    acattctttt    ctttctagrt    gactagtgac    cagaattaaa      180
ttgaatccta    ggccacccat    ttattgtctt    ctgcagaatt    ggcgagaatg    gagaggaatc      240
ctcacctatc    ggtgaccaga    gatgaaatat    tctgaattga    gagtttaaaa    gagcacactt      300
agaagagatt    tagagtttag    tttttcc                                                   327
```

<210> SEQ ID NO 70
<211> LENGTH: 21
<212> TYPE: DNA
<213> ORGANISM: Artificial Sequence
<220> FEATURE:
<223> OTHER INFORMATION: synthetic oligo

<400> SEQUENCE: 70

```
tctctaactt ctgtgagcca c                                                                21
```

<210> SEQ ID NO 71
<211> LENGTH: 24
<212> TYPE: DNA
<213> ORGANISM: Artificial Sequence
<220> FEATURE:
<223> OTHER INFORMATION: synthetic oligo

<400> SEQUENCE: 71

```
ggaaaaacta aactctaaat ctct                                                             24
```

<210> SEQ ID NO 72
<211> LENGTH: 509
<212> TYPE: DNA
<213> ORGANISM: Homo Sapiens

<400> SEQUENCE: 72

```
acagcacatt agctggtatg acagggagga tgtgattaat tgacctactg ataagactca    60
tttcagtaaa tgccacacaa gaatgtataa taggctgggt gctgtgggtc acacctgtaa   120
tcccagccct tcgagaggtc aaggcgagcg gatcacaggg tggaagagat tgagaccatc   180
ctggccaaca tggtgaaact gggtctctac taaaaataca aaaaattagc tgggcgtggt   240
gacatgtgcc tgtaatccca gttactcggg aggctgaggc agaagaatca tttgaactca   300
tgaggcagag gttgcagtaa gctgagattg cgccgctgca ccccagcctg gcaacagagc   360
gagactttgt ctcaaaaaaa awaaataaat aaataaataa ataaacaata ataaaaaaag   420
cgtaatagct agcctatcct accctatatt ctaaaattca aaagtaatgg tttttgttat   480
gaaatctcgt aagtcttgcc ataaagaga                                     509
```

<210> SEQ ID NO 73
<211> LENGTH: 22
<212> TYPE: DNA
<213> ORGANISM: Artificial Sequence
<220> FEATURE:
<223> OTHER INFORMATION: synthetic oligo

<400> SEQUENCE: 73

```
acagcacatt agctggtatg ac                                             22
```

<210> SEQ ID NO 74
<211> LENGTH: 22
<212> TYPE: DNA
<213> ORGANISM: Artificial Sequence
<220> FEATURE:
<223> OTHER INFORMATION: synthetic oligo

<400> SEQUENCE: 74

```
tctctttatg gcaagactta cg                                             22
```

<210> SEQ ID NO 75
<211> LENGTH: 340
<212> TYPE: DNA
<213> ORGANISM: Homo Sapiens

<400> SEQUENCE: 75

```
aaagcgagag attcaatcca ggatgacaga atgcgttcac ctttaaaggg attaaaagaa    60
gtataataca gtctgtatta ttagatcacc cagagacaca caaaacaaga accgtgaatt   120
saattagtgg tatactaata gagtggtttt acctgaaata tttacacatc aatcctactg   180
aattcttaca acaaatgatt tagattagct attgtattca ccagttgaaa gaacagaaaa   240
tattgaggga gataacttgt gtcagtgcaa cttaatcaga tttaggacac aaaagcaact   300
acataatgaa aaagagagct ggtgacttaa cttgctaaaa                         340
```

<210> SEQ ID NO 76
<211> LENGTH: 21
<212> TYPE: DNA
<213> ORGANISM: Artificial Sequence
<220> FEATURE:
<223> OTHER INFORMATION: synthetic oligo

<400> SEQUENCE: 76

```
aaagcgagag attcaatcca g                                              21
```

```
<210> SEQ ID NO 77
<211> LENGTH: 23
<212> TYPE: DNA
<213> ORGANISM: Artificial Sequence
<220> FEATURE:
<223> OTHER INFORMATION: synthetic oligo

<400> SEQUENCE: 77
ttttagcaag ttaagtcacc agc                                              23

<210> SEQ ID NO 78
<211> LENGTH: 321
<212> TYPE: DNA
<213> ORGANISM: Homo Sapiens

<400> SEQUENCE: 78
ccagtggtaa agttttatta caatttttt aaaccaagat tcaatttttt tctgaattag        60
aattatcrca gagaacactg aatggcctat gaaattcaat ttttgctgca gatttcgtca      120
tgtttcttaa tgaacatata actaacttct aatcacaaga taaattcttg cctatgtgca      180
aaaacttagt gctgcatcct tgtgtatggt tttaaaaagt gtcaaaactg gcccctcatg      240
tcaaatacag ccccaattag gggaggcaac ctaagaaagg tgtacaactg tcctgacatt      300
ggattgcctg cttactgtga a                                               321

<210> SEQ ID NO 79
<211> LENGTH: 26
<212> TYPE: DNA
<213> ORGANISM: Artificial Sequence
<220> FEATURE:
<223> OTHER INFORMATION: synthetic oligo

<400> SEQUENCE: 79
ccagtggtaa agttttatta caattt                                           26

<210> SEQ ID NO 80
<211> LENGTH: 21
<212> TYPE: DNA
<213> ORGANISM: Artificial Sequence
<220> FEATURE:
<223> OTHER INFORMATION: synthetic oligo

<400> SEQUENCE: 80
ttcacagtaa gcaggcaatc c                                                21

<210> SEQ ID NO 81
<211> LENGTH: 526
<212> TYPE: DNA
<213> ORGANISM: Homo Sapiens

<400> SEQUENCE: 81
cggaagtcaa agttatagtt actggaaata caaactgtgg cagtagaaaa ccctaggcac       60
aagggaagta aaatattaac cactccaggc tggagtgcag tggcgcaatc tgggctcaca      120
gcaagctctg cctcctgggt tcacaccatt ctcctgcctc aggctcccga gtagcaggga      180
gtacaggcac ccgccaccag gcctggctag tttttttgt attttttagt agagatgggg      240
ttttactgtg ttagccagta tggcctcgat ttcctgacct cgtgatccgc ccacgtcagc      300
ctcctaaagt gtgggatta caggagtgag ccaccatgcc cagctgaaac aatagttctt      360
cacaatggca tctaccacta tgtccacatt tgcacctstg tcctgaacct cgattcctat      420
```

```
aggttgatgt gttgagaacc agacaatacg aaatagaaga caaatcatga gcttacagaa    480
cctgaaactt tttacactgg gcagtgtggt agacagaaca gcagtg                    526

<210> SEQ ID NO 82
<211> LENGTH: 25
<212> TYPE: DNA
<213> ORGANISM: Artificial Sequence
<220> FEATURE:
<223> OTHER INFORMATION: synthetic oligo

<400> SEQUENCE: 82
cggaagtcaa agttatagtt actgg                                           25

<210> SEQ ID NO 83
<211> LENGTH: 22
<212> TYPE: DNA
<213> ORGANISM: Artificial Sequence
<220> FEATURE:
<223> OTHER INFORMATION: synthetic oligo

<400> SEQUENCE: 83
cactgctgtt ctgtctacca ca                                              22

<210> SEQ ID NO 84
<211> LENGTH: 332
<212> TYPE: DNA
<213> ORGANISM: Homo Sapiens

<400> SEQUENCE: 84
gcttacttgg gacacaggct agttctctcc tgaagctatt gagcagtatg tgttgaggtg    60
cgctacgcca gttgaggtga agctgttaca cagtatgaaa gccgggcttt gtagctgcag   120
ctgcgcattg cacccccagc tacgcagtct cctttccttc tcagtcacag gaccggatgg   180
caagtggccg cagccagtcg gtgagaccga ctgagctctg ggcttcagt tcttgacgct    240 acctacatgg ctacatctcc agccaaggat gagaggkgat gccagaggac ctcgatctaa   300
attgggcacc attatcgtat gacaacttct ct                                  332

<210> SEQ ID NO 85
<211> LENGTH: 20
<212> TYPE: DNA
<213> ORGANISM: Artificial Sequence
<220> FEATURE:
<223> OTHER INFORMATION: synthetic oligo

<400> SEQUENCE: 85
gcttacttgg gacacaggct                                                 20

<210> SEQ ID NO 86
<211> LENGTH: 24
<212> TYPE: DNA
<213> ORGANISM: Artificial Sequence
<220> FEATURE:
<223> OTHER INFORMATION: synthetic oligo

<400> SEQUENCE: 86
agagaagttg tcatacgata atgg                                            24

<210> SEQ ID NO 87
<211> LENGTH: 486
<212> TYPE: DNA
<213> ORGANISM: Homo Sapiens
```

<400> SEQUENCE: 87

```
gaaccagaca atacgaaata gaagacaaat catgagctta cagaacctga aactttttac      60
actgggcagt gtggtagaca gaacagcagt ggctgcccaa agatgatcat gttttaagtc     120
ctgacatctg traattatca tattgggaaa aggtgttatt gtagatgttg tttaaagtta     180
ggattttgag agaggaaaat tatgtagggt tatctggctg tgcccagtga atcacaaga     240
atctttataa atgaaaaaag aaagcagaag aatcagaacc agagacacgg cattatgcat     300
aggactggac ttgtcattac tagttttaaa ggtagaggaa gcagagatct aagaaatgca     360
ggcagcctct aactaatgtt aacaaatctc attttctaat attgtaagcc tgtggaagag     420
gctagggcac agatgctccc atagagtctc cagaaggaac ctaaggtaat gagataagcc     480
gctaaa                                                                486
```

<210> SEQ ID NO 88
<211> LENGTH: 24
<212> TYPE: DNA
<213> ORGANISM: Artificial Sequence
<220> FEATURE:
<223> OTHER INFORMATION: synthetic oligo

<400> SEQUENCE: 88

```
gaaccagaca atacgaaata gaag                                             24
```

<210> SEQ ID NO 89
<211> LENGTH: 22
<212> TYPE: DNA
<213> ORGANISM: Artificial Sequence
<220> FEATURE:
<223> OTHER INFORMATION: synthetic oligo

<400> SEQUENCE: 89

```
tttagcggct tatctcatta cc                                               22
```

<210> SEQ ID NO 90
<211> LENGTH: 486
<212> TYPE: DNA
<213> ORGANISM: Homo Sapiens

<400> SEQUENCE: 90

```
gaaccagaca atacgaaata gaagacaaat catgagctta cagaacctga aactttttac      60
actgggcagt stggtagaca gaacagcagt ggctgcccaa agatgatcat gttttaagtc     120
ctgacatctg tgaattatca tattgggaaa aggtgttatt gtagatgttg tttaaagtta     180
ggattttgag agaggaaaat tatgtagggt tatctggctg tgcccagtga atcacaaga     240
atctttataa atgaaaaaag aaagcagaag aatcagaacc agagacacgg cattatgcat     300
aggactggac ttgtcattac tagttttaaa ggtagaggaa gcagagatct aagaaatgca     360
ggcagcctct aactaatgtt aacaaatctc attttctaat attgtaagcc tgtggaagag     420
gctagggcac agatgctccc atagagtctc cagaaggaac ctaaggtaat gagataagcc     480
gctaaa                                                                486
```

<210> SEQ ID NO 91
<211> LENGTH: 24
<212> TYPE: DNA
<213> ORGANISM: Artificial Sequence
<220> FEATURE:
<223> OTHER INFORMATION: synthetic oligo

```
<400> SEQUENCE: 91
gaaccagaca atacgaaata gaag                                              24

<210> SEQ ID NO 92
<211> LENGTH: 22
<212> TYPE: DNA
<213> ORGANISM: Artificial Sequence
<220> FEATURE:
<223> OTHER INFORMATION: synthetic oligo

<400> SEQUENCE: 92
tttagcggct tatctcatta cc                                                22

<210> SEQ ID NO 93
<211> LENGTH: 370
<212> TYPE: DNA
<213> ORGANISM: Homo Sapiens

<400> SEQUENCE: 93
ttgaaaaaat acagtggaac aaagatcctc tgtatctctg ctcctaagat agcagagaca        60
gcatactggc ttctgttcaa ttttcctttg attacacaac ttcattggct acggtgttta      120
atatgaccgt cataggctga gacaagatct gttcagttta tctcayaagt tactagttaa      180
atctcagaca tattatactt ttgtaactga gtgactccca ttgtaaggat aactacttca      240
atgtgcgtat aaatgagtca gttgtctctc tgggggctt caacaaataa gcaaagataa       300
cctcattgtg gagagcactt cacatttgtt tttagggtta catagtctac tctgtatcct      360
taaacacttg                                                             370

<210> SEQ ID NO 94
<211> LENGTH: 20
<212> TYPE: DNA
<213> ORGANISM: Artificial Sequence
<220> FEATURE:
<223> OTHER INFORMATION: synthetic oligo

<400> SEQUENCE: 94
ttgaaaaaat acagtggaac                                                   20

<210> SEQ ID NO 95
<211> LENGTH: 23
<212> TYPE: DNA
<213> ORGANISM: Artificial Sequence
<220> FEATURE:
<223> OTHER INFORMATION: synthetic oligo

<400> SEQUENCE: 95
atactggctt ctgttcaatt ttc                                               23

<210> SEQ ID NO 96
<211> LENGTH: 20
<212> TYPE: DNA
<213> ORGANISM: Artificial Sequence
<220> FEATURE:
<223> OTHER INFORMATION: synthetic oligo

<400> SEQUENCE: 96
caagtgttta aggatacaga                                                   20

<210> SEQ ID NO 97
<211> LENGTH: 370
<212> TYPE: DNA
<213> ORGANISM: Homo Sapiens
```

```
<400> SEQUENCE: 97
ttgaaaaaat acagtggaac aaagatcctc tgtatctctg ctcctaagat agcagagaca      60
gcatactggc ttctgttcaa ttttcctttg attacacaac ttcattggct acggtgttta     120
atatgaccgt cataggctga gacaagatct gttcagttta tctcataagt tactagttam    180
atctcagaca tattatactt ttgtaactga gtgactccca ttgtaaggat aactacttca    240
atgtgcgtat aaatgagtca gttgtctctc ttgggggctt caacaaataa gcaaagataa    300
cctcattgtg gagagcactt cacatttgtt tttagggtta catagtctac tctgtatcct    360
taaacacttg                                                            370

<210> SEQ ID NO 98
<211> LENGTH: 20
<212> TYPE: DNA
<213> ORGANISM: Artificial Sequence
<220> FEATURE:
<223> OTHER INFORMATION: synthetic oligo

<400> SEQUENCE: 98
ttgaaaaaat acagtggaac                                                  20

<210> SEQ ID NO 99
<211> LENGTH: 23
<212> TYPE: DNA
<213> ORGANISM: Artificial Sequence
<220> FEATURE:
<223> OTHER INFORMATION: synthetic oligo

<400> SEQUENCE: 99
atactggctt ctgttcaatt ttc                                              23

<210> SEQ ID NO 100
<211> LENGTH: 20
<212> TYPE: DNA
<213> ORGANISM: Artificial Sequence
<220> FEATURE:
<223> OTHER INFORMATION: synthetic oligo

<400> SEQUENCE: 100
caagtgttta aggatacaga                                                  20

<210> SEQ ID NO 101
<211> LENGTH: 372
<212> TYPE: DNA
<213> ORGANISM: Homo Sapiens

<400> SEQUENCE: 101
cacttcacat ttgtttttag ggttacatag tctactctgt atccttaaac acttgaagat      60
ctgttataac tacatctgag atagtagtca cagtgttttc tcatgttaat gcctggcttc    120
cacccaggag kcacatgtgg tgtgtctgca aataaagtgt ttatgattat tggggtcccc    180
caagctggac ctgtatccat gttcaagtgg ccacagggtt acttgcttta gcatggctcc    240
ttggctggct gttaagtgaa taattaaact gagtcttttt tgcaggagct aactgagacc    300
aatcaatcag tcaattttcc ctttctgtgt gtaacacaag ctggatgtcc ctggaatgac    360
taaataatga ct                                                         372

<210> SEQ ID NO 102
<211> LENGTH: 21
<212> TYPE: DNA
<213> ORGANISM: Artificial Sequence
```

-continued

```
<220> FEATURE:
<223> OTHER INFORMATION: synthetic oligo

<400> SEQUENCE: 102
cacttcacat tgtttttag g                                                    21

<210> SEQ ID NO 103
<211> LENGTH: 22
<212> TYPE: DNA
<213> ORGANISM: Artificial Sequence
<220> FEATURE:
<223> OTHER INFORMATION: synthetic oligo

<400> SEQUENCE: 103
agtcattatt tagtcattcc ag                                                  22

<210> SEQ ID NO 104
<211> LENGTH: 514
<212> TYPE: DNA
<213> ORGANISM: Homo Sapiens

<400> SEQUENCE: 104
taagcctaaa gagcagtcag agtagaatgc tgaattttca gaagttttat attaacataa          60
tcattcatct tttttgtcct gataattact caggaggaaa ctgagagggc atggtccctt         120
tctatggata gcaatactca gtgtcccaat tttcctttgg gacactgsga cacaggcaga         180
gactccgaaa gtctgcatgg attagttgtt cattcaccac agctccttag tgtgccagga         240
gaactatata tggcctttgg tttcattcag ggacagggaa acttgaaccc atgcctattc         300
attctcatta aagtagcaga agtcatgtta gagacagtat tgctgcattc agtactcctg         360
cctttaacgc ttctgacgct tcctgaaagc agccccagct ctccatatgg caaaacaaag         420
gcaaccttat gcaaagcctt ctcagggaac cctcagaaag gtttaaactt aggttcacag         480
tttttagaga ataatgtcct cattgctccc tctg                                     514

<210> SEQ ID NO 105
<211> LENGTH: 22
<212> TYPE: DNA
<213> ORGANISM: Artificial Sequence
<220> FEATURE:
<223> OTHER INFORMATION: synthetic oligo

<400> SEQUENCE: 105
taagcctaaa gagcagtcag ag                                                  22

<210> SEQ ID NO 106
<211> LENGTH: 20
<212> TYPE: DNA
<213> ORGANISM: Artificial Sequence
<220> FEATURE:
<223> OTHER INFORMATION: synthetic oligo

<400> SEQUENCE: 106
cagagggagc aatgaggaca                                                     20

<210> SEQ ID NO 107
<211> LENGTH: 436
<212> TYPE: DNA
<213> ORGANISM: Homo Sapiens

<400> SEQUENCE: 107
agatcatccc aaaacaatca taacttgttt aaattgttca tagcaaaagt tacatattat          60
aaagagttat gagkgtctta ggcagtgaat agtaactgaa tatcctttta tagttgtcct         120
```

```
tcactagcag gaagccttat tccctgccct tttacatatc ttaacttaga atgttactgt        180
ctaaatagtg gttaggcaag agtagttctt aaacgtgcag taattatctt gcactacatt        240
taagggctaa atagctagta gtggtgcttg ataattgaag aaatttgtac agctggagga        300
agtacctgct aaattttcaa aagttacctg aatttaatag gtaaatctgt ttttaattag        360
agctatatca ttttactctg aatgtcttaa catagaagtt tacataaaat ttacagattg        420
gattgatttc agcctt                                                        436

<210> SEQ ID NO 108
<211> LENGTH: 23
<212> TYPE: DNA
<213> ORGANISM: Artificial Sequence
<220> FEATURE:
<223> OTHER INFORMATION: synthetic oligo

<400> SEQUENCE: 108
agatcatccc aaaacaatca taa                                                 23

<210> SEQ ID NO 109
<211> LENGTH: 23
<212> TYPE: DNA
<213> ORGANISM: Artificial Sequence
<220> FEATURE:
<223> OTHER INFORMATION: synthetic oligo

<400> SEQUENCE: 109
aaggctgaaa tcaatccaat ctg                                                 23

<210> SEQ ID NO 110
<211> LENGTH: 422
<212> TYPE: DNA
<213> ORGANISM: Homo Sapiens

<400> SEQUENCE: 110
cagattggat tgatttcagc cttcttctgg tactttttaa aatcttatta atcattagga         60
aaagaagttt tattattgat gcaagcccta acactctttt cgactccaga ggagaagctg        120
gcagctctct gtaagaaata tgctgatctt gtgagtattt atttaatgga gcaaggaaca        180
cagaaaataa aatctatgtg tgyttgataa gattttttaaa tattattttg atgtaacttt       240
aaatgtaaaa tgatatttta tctcaaaatt gaaaacaatc tcctttcttt agtacttatg        300
attggtgtgt gtgacttcat cttatgaaat gatgtataga acataataat acttttttaa        360
atgtgaaata aatttcctaa aacttaatat gctagatcag cagtttttttt ttttttgtatg      420 ct                                                                       422

<210> SEQ ID NO 111
<211> LENGTH: 23
<212> TYPE: DNA
<213> ORGANISM: Artificial Sequence
<220> FEATURE:
<223> OTHER INFORMATION: synthetic oligo

<400> SEQUENCE: 111
cagattggat tgatttcagc ctt                                                 23

<210> SEQ ID NO 112
<211> LENGTH: 23
<212> TYPE: DNA
<213> ORGANISM: Artificial Sequence
<220> FEATURE:
<223> OTHER INFORMATION: synthetic oligo
```

-continued

```
<400> SEQUENCE: 112
agcatacaaa aaaaaaaaac tgc                                             23

<210> SEQ ID NO 113
<211> LENGTH: 337
<212> TYPE: DNA
<213> ORGANISM: Homo Sapiens

<400> SEQUENCE: 113 cagttttttag agaataatgt cctcattgct ccctctggca ctagcagttt gtaccaggag    60
atctgttggc tactgttacc ctagggtatg gcaatggtat gtaggcaatg aaaaatctta   120
cagtacttat tatggaaaac caactktttt attcagtaag cattcccctg tgttgtaagg   180
tttttaaaag attgtggaag tatgaaaaag tttattatga cagatgtgcc agctccagct   240
gttttgtgga gagtgaccct tggattttcg tatgccccca ttatatgatg ataccttgta   300
atgatttaat tttagcatct gcttttcttt tctttaa                            337

<210> SEQ ID NO 114
<211> LENGTH: 23
<212> TYPE: DNA
<213> ORGANISM: Artificial Sequence
<220> FEATURE:
<223> OTHER INFORMATION: synthetic oligo

<400> SEQUENCE: 114 cagttttttag agaataatgt cct                                           23

<210> SEQ ID NO 115
<211> LENGTH: 22
<212> TYPE: DNA
<213> ORGANISM: Artificial Sequence
<220> FEATURE:
<223> OTHER INFORMATION: synthetic oligo

<400> SEQUENCE: 115
ttaaagaaaa gaaaagcaga tg                                             22

<210> SEQ ID NO 116
<211> LENGTH: 337
<212> TYPE: DNA
<213> ORGANISM: Homo Sapiens

<400> SEQUENCE: 116 cagttttttag agaataatgt cctcattgct ccctctggca ctagcagttt gtaccaggag    60
atctgttggc tactgttacc ctagggtatg gcaatggtat gtaggcaatg aaaaatctta   120
cagtacttat tatggaaaac caactttttt attcagtaag cattcccctg tgttgtaagg   180
tttttaaaag attgtggaag tatgaaaaag tttattatga cagatgtgcc agctccagct   240
gttttgtgga gagtgaccct tggattttcg tatgccccca ttatatgatg ataccttgta   300
atgatttaat tttagcatct gcttttcttt tctttaa                            337

<210> SEQ ID NO 117
<211> LENGTH: 23
<212> TYPE: DNA
<213> ORGANISM: Artificial Sequence
<220> FEATURE:
<223> OTHER INFORMATION: synthetic oligo

<400> SEQUENCE: 117 cagttttttag agaataatgt cct                                           23
```

```
<210> SEQ ID NO 118
<211> LENGTH: 22
<212> TYPE: DNA
<213> ORGANISM: Artificial Sequence
<220> FEATURE:
<223> OTHER INFORMATION: synthetic oligo

<400> SEQUENCE: 118
ttaaagaaaa gaaaagcaga tg                                              22

<210> SEQ ID NO 119
<211> LENGTH: 218
<212> TYPE: DNA
<213> ORGANISM: Homo Sapiens

<400> SEQUENCE: 119
gtataatagg ctgggtgctg tgggtcacac ctgtaatccc agcccttcga gaggtcaagg      60
caagcggatc acaggtggag agagattgag accatcctgg ccaacatggt gaaactkggt     120
ctctactaaa aatacaaaaa attagctggg cgtggtgaca tgtgcctgta atcccagtta    180
ctcgggaggc tgaggcagaa gaatcatttg aactcatg                            218

<210> SEQ ID NO 120
<211> LENGTH: 20
<212> TYPE: DNA
<213> ORGANISM: Artificial Sequence
<220> FEATURE:
<223> OTHER INFORMATION: synthetic oligo

<400> SEQUENCE: 120
gtataatagg ctgggtgctg                                                 20

<210> SEQ ID NO 121
<211> LENGTH: 20
<212> TYPE: DNA
<213> ORGANISM: Artificial Sequence
<220> FEATURE:
<223> OTHER INFORMATION: synthetic oligo

<400> SEQUENCE: 121
catgagttca aatgattctt                                                 20

<210> SEQ ID NO 122
<211> LENGTH: 340
<212> TYPE: DNA
<213> ORGANISM: Homo Sapiens

<400> SEQUENCE: 122
aaagcgagag attcaatcca ggatgacaga atgcgttcac ctttaagggg attaaaagaa      60
gtataataca gtctgtatta ttagatcacc cagagacaca caaaacaaga accgtgaatt    120
gaattagtgg tatactaata gagtggtttt acctgaaata tttacacatc aatcctactg    180
aattcttaca acaaatgatt tagattagct attgtattca ccagttgaaa gaacagaaaa    240
tattgaggga gataacttgt gtcagtgcaa cttaatcaga tttaggacac aaaagcwact    300
acataatgaa aaagagagct ggtgacttaa cttgctaaaa                          340

<210> SEQ ID NO 123
<211> LENGTH: 21
<212> TYPE: DNA
<213> ORGANISM: Artificial Sequence
<220> FEATURE:
<223> OTHER INFORMATION: synthetic oligo
```

-continued

```
<400> SEQUENCE: 123
aaagcgagag attcaatcca g                                              21

<210> SEQ ID NO 124
<211> LENGTH: 23
<212> TYPE: DNA
<213> ORGANISM: Artificial Sequence
<220> FEATURE:
<223> OTHER INFORMATION: synthetic oligo

<400> SEQUENCE: 124
ttttagcaag ttaagtcacc agc                                            23

<210> SEQ ID NO 125
<211> LENGTH: 309
<212> TYPE: DNA
<213> ORGANISM: Homo Sapiens

<400> SEQUENCE: 125
actaaaacac cattagaaac aaaggactta aactaggaat taattatttc tctttctctt    60
tccatggcca acaaacrttg aaaaaaaatt gccatctttt tttttatttg tttgttagag   120
atggggatct cactctgttt cttagattgt agtgccatgg cacaataatg gctcactgca   180
gcctcaaact cctgggctca agtgatcacc cccatacaga ctcccgagta gctgggaaca   240
caggcacatg ccaccacccc tagctaattt tttattattt gtagagatgg gggtcactat   300
gttgctcag                                                           309

<210> SEQ ID NO 126
<211> LENGTH: 25
<212> TYPE: DNA
<213> ORGANISM: Artificial Sequence
<220> FEATURE:
<223> OTHER INFORMATION: synthetic oligo

<400> SEQUENCE: 126
actaaaacac cattagaaac aaagg                                          25

<210> SEQ ID NO 127
<211> LENGTH: 20
<212> TYPE: DNA
<213> ORGANISM: Artificial Sequence
<220> FEATURE:
<223> OTHER INFORMATION: synthetic oligo

<400> SEQUENCE: 127
ctgagcaaca tagtgacccc                                                20

<210> SEQ ID NO 128
<211> LENGTH: 389
<212> TYPE: DNA
<213> ORGANISM: Homo Sapiens

<400> SEQUENCE: 128
ctggcacctt ctgatatttt gagaagcagg aatccctgag cataaatgta aatagcttag    60
aactgtccaa aagcaaagac agcagaaaat aaaattgttg cttgctatgt tcaggaaagg   120
aatgcttcca ttggatatgg aagccagtct caattgttac atcagcctga ggaaactcat   180
gcgagaaatg ccagaaaaag aagacagcaa caaagaagat aaaagaagaa ctgacaaaag   240
cattgaattt ctggtagaaa aascagtgta ctagaaggtt aggagatttc ctagctgtca   300
```

```
gccatgaaag ggttggggaa gaaagagcaa tttggttgca tactgtagca tggtcatcta      360
gggtggtcct caaacacata gaaatcaca                                        389
```

<210> SEQ ID NO 129
<211> LENGTH: 23
<212> TYPE: DNA
<213> ORGANISM: Artificial Sequence
<220> FEATURE:
<223> OTHER INFORMATION: synthetic oligo

<400> SEQUENCE: 129

```
ctggcacctt ctgatatttt gag                                             23
```

<210> SEQ ID NO 130
<211> LENGTH: 24
<212> TYPE: DNA
<213> ORGANISM: Artificial Sequence
<220> FEATURE:
<223> OTHER INFORMATION: synthetic oligo

<400> SEQUENCE: 130

```
tgtgatttct atgtgtttga ggac                                            24
```

<210> SEQ ID NO 131
<211> LENGTH: 352
<212> TYPE: DNA
<213> ORGANISM: Homo Sapiens

<400> SEQUENCE: 131

```
gctggcaaga cacttctgag catcggggtg tggactttac gaaccaacct tttaacagta      60
actctaggag agaggatatc aaaaattggc agtgaaaaat tatagatarg caaaaagctc     120
cttctgaggt ccaggccagg agatagtagg atttaagaaa caaacaaaca aaaacaacca    180
caaatgacct ttggtgccac tgtcacaact gttgctcatc agagtaggag agttgtagca    240
aaggcattaa agaaggacaa gcagctgaag agcctgaatc cttgtgttgt aagctatttt    300
ggtttccttt caagaaaggg ctgtggtctg tggaaggtgt caggaacata tt            352
```

<210> SEQ ID NO 132
<211> LENGTH: 20
<212> TYPE: DNA
<213> ORGANISM: Homo Sapiens

<400> SEQUENCE: 132

```
gctggcaaga cacttctgag                                                 20
```

<210> SEQ ID NO 133
<211> LENGTH: 21
<212> TYPE: DNA
<213> ORGANISM: Homo Sapiens

<400> SEQUENCE: 133

```
aatatgttcc tgacaccttc c                                               21
```

<210> SEQ ID NO 134
<211> LENGTH: 436
<212> TYPE: DNA
<213> ORGANISM: Homo Sapiens

<400> SEQUENCE: 134

```
agatcatccc aaaacaatca taacttgttt aaattgttca tagcaaaagt tacatattat      60
aaagagttat gagtgtctta ggcagtgaat agtaactgaa tatcctttta tagttgtcct    120
```

| | | |
|---|---|---|
| tcactagcag gaagccttat tccctgccct tttacatatc ttaacttaga atgttactgt | 180 |
| ctaaatagtg gttaggcaag agtagttctt aaacgtgcag taattatctt gcactacatt | 240 |
| taagggctaa atagctagta gtggtgcttg ataattgaag aaatttgtac agctggagga | 300 |
| agtacctgct aaattttcaa aagttacctg aatttaatag gtaaatctgt ttttaattag | 360 |
| agctatatca ttttactctg aatgtcttaa cataraagtt tacataaaat ttacagattg | 420 |
| gattgatttc agcctt | 436 |

<210> SEQ ID NO 135
<211> LENGTH: 23
<212> TYPE: DNA
<213> ORGANISM: Homo Sapiens

<400> SEQUENCE: 135
agatcatccc aaaacaatca taa    23

<210> SEQ ID NO 136
<211> LENGTH: 23
<212> TYPE: DNA
<213> ORGANISM: Homo Sapiens

<400> SEQUENCE: 136
aaggctgaaa tcaatccaat ctg    23

<210> SEQ ID NO 137
<211> LENGTH: 240
<212> TYPE: DNA
<213> ORGANISM: Homo Sapiens

<400> SEQUENCE: 137

| | |
|---|---|
| aaacaatatg tatgctaatt ttgcttaaaa gattatacac tgaaatttag agaggatata | 60 |
| atgttatctg tagtgtagaa agagtttaaat aagactgatt tttagaattt gttttatccc | 120 |
| ttccactctt agcttgacaa ttaggattaa gaatatgatr tgtcaaattt catgactgaa | 180 |
| atctgaaatg ccttaatagt tgccctcagt gtttcatcct tatactaaca tttacattga | 240 |

<210> SEQ ID NO 138
<211> LENGTH: 25
<212> TYPE: DNA
<213> ORGANISM: Homo Sapiens

<400> SEQUENCE: 138
aaacaatatg tatgctaatt ttgct    25

<210> SEQ ID NO 139
<211> LENGTH: 26
<212> TYPE: DNA
<213> ORGANISM: Homo Sapiens

<400> SEQUENCE: 139
tcaatgtaaa tgttagtata aggatg    26

<210> SEQ ID NO 140
<211> LENGTH: 354
<212> TYPE: DNA
<213> ORGANISM: Homo Sapiens

<400> SEQUENCE: 140

| | |
|---|---|
| cggcaacagt gaggacagta gctccaggtc tgggcggaag gtggtgcggt gaaaggtgca | 60 |
| gggacagact gggttagagg ccactcttgg tcttatcctc catggccaca acagaggtga | 120 |

| | |
|---|---|
| caaatacatg ggtcactcag ttatgtttag ccaacagcct acccaaacca cacctgtctt | 180 |
| accagagccc tttcctggag ccatgttctc aggactggtc acactgtcyc cattctccag | 240 |
| cagcccttgg acctatcgga aaaaaagaat gggtaacaat aattgagctg atgaaccagg | 300 |
| tcctatcttt cctcccacaa ctccaaaact tgggagcctc tatctcctga agca | 354 |

<210> SEQ ID NO 141
<211> LENGTH: 19
<212> TYPE: DNA
<213> ORGANISM: Homo Sapiens

<400> SEQUENCE: 141

| | |
|---|---|
| cggcaacagt gaggacagt | 19 |

<210> SEQ ID NO 142
<211> LENGTH: 21
<212> TYPE: DNA
<213> ORGANISM: Homo Sapiens

<400> SEQUENCE: 142

| | |
|---|---|
| tgcttcagga gatagaggct c | 21 |

<210> SEQ ID NO 143
<211> LENGTH: 354
<212> TYPE: DNA
<213> ORGANISM: Homo Sapiens

<400> SEQUENCE: 143

| | |
|---|---|
| cggcaacagt gaggacagta gctccaggtc tgggcggaag gtggtgcggt gaaaggtgca | 60 |
| gggacagact gggttagagg ccactcttgg tcttatcctc catggccaca acagaggtga | 120 |
| caaatacatg ggtcactcag ttatgtttag ccaacagcct acccaaacca caccygtctt | 180 |
| accagagccc tttcctggag ccatgttctc aggactggtc acactgtctc cattctccag | 240 |
| cagcccttgg acctatcgga aaaaaagaat gggtaacaat aattgagctg atgaaccagg | 300 |
| tcctatcttt cctcccacaa ctccaaaact tgggagcctc tatctcctga agca | 354 |

<210> SEQ ID NO 144
<211> LENGTH: 19
<212> TYPE: DNA
<213> ORGANISM: Homo Sapiens

<400> SEQUENCE: 144

| | |
|---|---|
| cggcaacagt gaggacagt | 19 |

<210> SEQ ID NO 145
<211> LENGTH: 21
<212> TYPE: DNA
<213> ORGANISM: Homo Sapiens

<400> SEQUENCE: 145

| | |
|---|---|
| tgcttcagga gatagaggct c | 21 |

<210> SEQ ID NO 146
<211> LENGTH: 339
<212> TYPE: DNA
<213> ORGANISM: Homo Sapiens

<400> SEQUENCE: 146

| | |
|---|---|
| gagcctctat ctcctgaagc agagtagaca cargcttcca acagggatca gagtttaggg | 60 |
| atctggatag gtatagaatg gagcaaaggg actaggccaa aggagattga aaactgggga | 120 |

```
acagggacaa gactggagct acaagaagga caggggctag aagacagaaa tatgaggaca    180
atggctggcc tggaaagctc accttagaaa tattgttgcc actgccttct ctgatagggt    240
cacaggcagt ggctgaagtg tagactgagg cctcctctgg tctgggtttg gcctgtagct    300
gttggcgaag ctcagccagc tgtcgcaaca gagcagtca                           339

<210> SEQ ID NO 147
<211> LENGTH: 20
<212> TYPE: DNA
<213> ORGANISM: Homo Sapiens

<400> SEQUENCE: 147
gagcctctat ctcctgaagc                                                 20

<210> SEQ ID NO 148
<211> LENGTH: 19
<212> TYPE: DNA
<213> ORGANISM: Homo Sapiens

<400> SEQUENCE: 148
tgactgctct gttgcgaca                                                  19

<210> SEQ ID NO 149
<211> LENGTH: 534
<212> TYPE: DNA
<213> ORGANISM: Homo Sapiens

<400> SEQUENCE: 149
actgtagcat ggtcatctag ggtggtcctc aaacacatag aaatcacaca agaattgtca     60
aattgaagat ttggatttag tagatctgaa aacgcacttt gtaaaattgg ccacagtaga    120
ggtggaagtg actgaaatac tgcattattt atttatttaa ttaatttatt ttagtcagag    180
tcttgcactg tcgctaaggc tggtatacca tggttcagtc acagttcact acagtcttga    240
actcctaggc tcaaacaatt ctcctgtatc ggcctcctga gtacctggca ctacagacat    300
gcacaagcat gcatggctaa ttttaaaaaa atttttgtag aaatggagtc atgaactcct    360
gggctcaagt gatcctccca cctcaacttc ccagagtgtt gagtgagatt acagttatga    420
gccaccatcc ctggccaata aaggtgtttt taatacctat aagaatattg cctgcamgga    480
tgtttgatag gtttcttgat atttcattct ctctcttgaa atgtttgctt cgtc          534

<210> SEQ ID NO 150
<211> LENGTH: 24
<212> TYPE: DNA
<213> ORGANISM: Homo Sapiens

<400> SEQUENCE: 150
actgtagcat ggtcatctag ggtg                                            24

<210> SEQ ID NO 151
<211> LENGTH: 24
<212> TYPE: DNA
<213> ORGANISM: Homo Sapiens

<400> SEQUENCE: 151
gacgaagcaa acatttcaag agag                                            24

<210> SEQ ID NO 152
<211> LENGTH: 509
<212> TYPE: DNA
<213> ORGANISM: Homo Sapiens
```

```
<400> SEQUENCE: 152
acagcacatt agctggtatg acaggggaga tgtgattaat tgacctactg ataagactca        60
tttcagtaaa tgccacacaa gaatgtataa taggctgggt gctgtgggtc acacctgtaa       120
tcccagccct tcgagaggtc aaggcgagcg gatcacaggg tggaagagat tgagaccatc       180
ctggccaaca tggtgaaact gggtctctac taaaaataca aaaaattagc tgggcgtggt       240
gacatgtgcc tgtaatccca gttactcggg aggctgaggc agaagaatca tttgaactca       300
tgaggcagag gttgcagtaa gctgagattg cgccgctgca ccccagcctg gcaacagagc       360
gagactttgt ctcaaaaaaa ataaawaaat aaataaataa ataaacaata ataaaaaaag       420
cgtaatagct agcctatcct accctatatt ctaaaattca aaagtaatgg ttttttgttat      480 gaaatctcgt aagtcttgcc ataaagaga                                        509

<210> SEQ ID NO 153
<211> LENGTH: 22
<212> TYPE: DNA
<213> ORGANISM: Homo Sapiens

<400> SEQUENCE: 153
acagcacatt agctggtatg ac                                                22

<210> SEQ ID NO 154
<211> LENGTH: 22
<212> TYPE: DNA
<213> ORGANISM: Homo Sapiens

<400> SEQUENCE: 154
tctctttatg gcaagactta cg                                                22

<210> SEQ ID NO 155
<211> LENGTH: 360
<212> TYPE: DNA
<213> ORGANISM: Homo Sapiens

<400> SEQUENCE: 155
cctcctctgg tctgggtttg gcctgtagct gttggcgaag ctcagccagc tgtcgcaaca        60
gagcagtcac atcttcagag gccagagcct ttctggcacg gtcttgccag ccaatggccc       120
tctctgtgag acactgaagg gcctcaccct caggcagccg cacrggcagc ctctgcaggg       180
caaccagcaa ggctaggatt gtctctaggc gtggccgtcg tgagcgcata cacagtggac       240
acaggaattt tgtgtcccat tcccaccagg ctagcagtgg agatgaagtg agactgggct       300
ttggagaggt gaggagatgg ggcactgaca cacactgccc atggaaccag tcctgacaca       360

<210> SEQ ID NO 156
<211> LENGTH: 19
<212> TYPE: DNA
<213> ORGANISM: Homo Sapiens

<400> SEQUENCE: 156
cctcctctgg tctgggttt                                                    19

<210> SEQ ID NO 157
<211> LENGTH: 20
<212> TYPE: DNA
<213> ORGANISM: Homo Sapiens
```

```
<400> SEQUENCE: 157
tgtgtcagga ctggttccat                                                    20

<210> SEQ ID NO 158
<211> LENGTH: 382
<212> TYPE: DNA
<213> ORGANISM: Homo Sapiens

<400> SEQUENCE: 158
cgtaggcgtt tgacagcagt taatagagac tacagatatc aaagtcagag agtccagctt        60
cctgagaaaa cgttaacagt attaatctgc taccactatg gctactaata ccatgccacc       120
acggtactac ctggctagta ccattccaca gaagaacaga aataaataca aataggtggg       180
gcaagagaaa agaaacatgt gaaaaggccc ctggatggtt taagttayat tttcatcagt       240
catccagtta agagttaaag aatgaggaag agatgtaaaa acagccatta ggattcagaa       300
gtagtagctt tcacagtgag acaaaacatc tattaagcca gaaactgaag tacaaatgca       360
atgggaggat tacgaagaaa gg                                                382

<210> SEQ ID NO 159
<211> LENGTH: 19
<212> TYPE: DNA
<213> ORGANISM: Homo Sapiens

<400> SEQUENCE: 159
cgtaggcgtt tgacagcag                                                     19

<210> SEQ ID NO 160
<211> LENGTH: 20
<212> TYPE: DNA
<213> ORGANISM: Homo Sapiens

<400> SEQUENCE: 160
cctttcttcg taatcctccc                                                    20

<210> SEQ ID NO 161
<211> LENGTH: 399
<212> TYPE: DNA
<213> ORGANISM: Homo Sapiens

<400> SEQUENCE: 161
ccagaaactg aagtacaaat gcaatgggag gattacgawg aaaggagggc taagtgatga        60
taagtatggt cagaataata aatttattct agacaagaaa tgagagttca ttatgtcaga       120
agcaaaatag tactacagga tgacaacttc tgagatttac tctttggttc caactgccta       180
caagacaaag aaaactgaag aggccaggaa gttaaatgca tgaggaaaac ttgaggcaga       240
ttaaaatgga aatgcagggc atgttatttg ggtatcatgg gttcaatctg gaaaagcctt       300
atttctcctg aaccacagta gggaaaggag ttatccagaa aagtgaaatt tattctaaaa       360
ttttaagttt ccatgtttta aagagaggca gcaatgaga                              399

<210> SEQ ID NO 162
<211> LENGTH: 22
<212> TYPE: DNA
<213> ORGANISM: Homo Sapiens

<400> SEQUENCE: 162
ccagaaactg aagtacaaat gc                                                 22
```

<210> SEQ ID NO 163
<211> LENGTH: 20
<212> TYPE: DNA
<213> ORGANISM: Homo Sapiens

<400> SEQUENCE: 163
tctcattgct gcctctcttt                                                  20

<210> SEQ ID NO 164
<211> LENGTH: 327
<212> TYPE: DNA
<213> ORGANISM: Homo Sapiens

<400> SEQUENCE: 164
attgggagga agtggtttct gtatttaaaa ttttccgaag gaattctgca gattcaagct      60
ctaaccattc ttgattaaaa ttgtgagtta gataagattg tttagtaaaa ttgtactatg     120
gctcaggaaa taattatttt aatatctact gtatgccaag cattgttctt ttttccatct    180
tccagggaaa ttcacctctt ctatagaaga gtttgttttg aactatacga tttgaaacaa    240
aattcttttt ttggagacta tggaaacatt ctcaacaggg aaaccctact agactttgta    300
aagcaaataa tggaaaagat acagaac                                        327

<210> SEQ ID NO 165
<211> LENGTH: 21
<212> TYPE: DNA
<213> ORGANISM: Homo Sapiens

<400> SEQUENCE: 165
attgggagga agtggtttct g                                               21

<210> SEQ ID NO 166
<211> LENGTH: 25
<212> TYPE: DNA
<213> ORGANISM: Homo Sapiens

<400> SEQUENCE: 166
gttctgtatc ttttccatta tttgc                                           25

<210> SEQ ID NO 167
<211> LENGTH: 327
<212> TYPE: DNA
<213> ORGANISM: Homo Sapiens

<400> SEQUENCE: 167
tctctaactt ctgtgagcca ctctagcaaa ttaattgaac caaaggagga ggttaaggac      60
agcatagttt acaaaatgag ccctgttttct gacatctgaa gtgggggcag tctagtgggc    120
ctgacctctt aacttgtaga aacattcttt cttctagat gactagtgac cagaattaaa     180
ttgaatccta ggccacccat ttattgtctt ctgcagaatt ggcragaatg gagaggaatc    240
ctcacctatc ggtgaccaga gatgaaatat tctgaattga gagtttaaaa gagcacactt   300
agaagagatt tagagtttag tttttcc                                        327

<210> SEQ ID NO 168
<211> LENGTH: 21
<212> TYPE: DNA
<213> ORGANISM: Homo Sapiens

<400> SEQUENCE: 168
tctctaactt ctgtgagcca c                                               21

<210> SEQ ID NO 169
<211> LENGTH: 24
<212> TYPE: DNA
<213> ORGANISM: Homo Sapiens

<400> SEQUENCE: 169
ggaaaaacta aactctaaat ctct                                           24

<210> SEQ ID NO 170
<211> LENGTH: 354
<212> TYPE: DNA
<213> ORGANISM: Homo Sapiens

<400> SEQUENCE: 170
cggcaacagt gaggacagta gctccaggtc tgggcggaag gtggtgcggt gaaaggtgca    60
gggacagact gggttagagg ccactcttgg tcttatcctc catggccaca acagaggtga   120
caaatacatg ggtcactcag ttatgtttag ccaacagcct acccaaacca cacctgtctt   180
accagagccc tttcctggag ccatgttctc aggactggtc acactgtctc cattctccag   240
cagcccttgg acctatcgga aaaaagaat gggtaacamt aattgagctg atgaaccagg    300
tcctatcttt cctcccacaa ctccaaaact tgggagcctc tatctcctga agca         354

<210> SEQ ID NO 171
<211> LENGTH: 19
<212> TYPE: DNA
<213> ORGANISM: Homo Sapiens

<400> SEQUENCE: 171
cggcaacagt gaggacagt                                                 19

<210> SEQ ID NO 172
<211> LENGTH: 21
<212> TYPE: DNA
<213> ORGANISM: Homo Sapiens

<400> SEQUENCE: 172
tgcttcagga gatagaggct c                                              21

<210> SEQ ID NO 173
<211> LENGTH: 389
<212> TYPE: DNA
<213> ORGANISM: Homo Sapiens

<400> SEQUENCE: 173
gcactggcgt tcatcatctg ggagcagctc aaaagcctct cgctcagcct ccgtgacgcc    60
ctgggggtgt tcaacccaca tatactgtaa agactaggag tagggttgtg gacacccac    120 ctcagccaac actgagccct gatgtggact caaccttgta aggaaagctg tagagaaatt   180
ggaagaaaaa atataaacac atacagactc tgtctttaca tttcaaaatg catgacttaa   240
agtatcaggc acacagtggt tactcaatgt tggtctgtgt ctctgtaacg taatatatgt   300
gactaaatcc ctaagctctg ctcttgacca cccaccttct ccaaaagggc ctttcgtaga   360
cgtcgctcct cctgaaccat aatgaacat                                      389

<210> SEQ ID NO 174
<211> LENGTH: 19
<212> TYPE: DNA
<213> ORGANISM: Homo Sapiens

```
<400> SEQUENCE: 174
gcactggcgt tcatcatct                                                   19

<210> SEQ ID NO 175
<211> LENGTH: 22
<212> TYPE: DNA
<213> ORGANISM: Homo Sapiens

<400> SEQUENCE: 175
atgttcatta tggttcagga gg                                               22

<210> SEQ ID NO 176
<211> LENGTH: 190
<212> TYPE: DNA
<213> ORGANISM: Homo Sapiens

<400> SEQUENCE: 176
attggattga tttcagcctt cttctggtac tttttaaaat cttattaatc attaggaaaa      60
gaagttttat tattgatgca agccctaaac actctttyga ctccagagga gaagctggca    120
gctctctgta agaaatatgc tgatcttgtg agtatttatt taatggagca aggaacacag    180
aaaataaaat                                                           190

<210> SEQ ID NO 177
<211> LENGTH: 21
<212> TYPE: DNA
<213> ORGANISM: Homo Sapiens

<400> SEQUENCE: 177
attggattga tttcagcctt c                                                21

<210> SEQ ID NO 178
<211> LENGTH: 23
<212> TYPE: DNA
<213> ORGANISM: Homo Sapiens

<400> SEQUENCE: 178
attttatttt ctgtgttcct tgc                                              23

<210> SEQ ID NO 179
<211> LENGTH: 309
<212> TYPE: DNA
<213> ORGANISM: Homo Sapiens

<400> SEQUENCE: 179
actaaaacac cattagaaac aaaggactta aactaggaat taattatttc tctttctcty      60
tccatggcca acaaacattg aaaaaaaatt gccatctttt tttttatttg tttgttagag    120
atggggatct cactctgttt cttagattgt agtgccatgg cacaataatg gctcactgca    180
gcctcaaact cctgggctca agtgatcacc cccatacaga ctcccgagta gctgggaaca    240
caggcacatg ccaccacccc tagctaattt tttattattt gtagagatgg gggtcactat    300
gttgctcag                                                            309

<210> SEQ ID NO 180
<211> LENGTH: 25
<212> TYPE: DNA
<213> ORGANISM: Homo Sapiens

<400> SEQUENCE: 180
actaaaacac cattagaaac aaagg                                            25
```

```
<210> SEQ ID NO 181
<211> LENGTH: 20
<212> TYPE: DNA
<213> ORGANISM: Homo Sapiens

<400> SEQUENCE: 181
ctgagcaaca tagtgacccc                                                    20

<210> SEQ ID NO 182
<211> LENGTH: 308
<212> TYPE: DNA
<213> ORGANISM: Homo Sapiens

<400> SEQUENCE: 182
ctcttccctt ggttcctatt ctgacacgct caggtacctc aargaatcct ccaacttccc        60
accttcactt tctagcacaa cccaaccgag taaaaactat aaagtatatc tatctctctt       120
ctaactgctg gcctgacgca gtaaagcaga aatactgatc ctcacttgga tctcatccac       180
atcagcaatc caagcttgtg ccttagtcag agcttctttg agagcctgga tgttaggcag       240
gtgaacaggg atgttttctg tctcacgaat tatggcttcc aatgtggctg gtggatgctt       300
ctgcctaa                                                                308

<210> SEQ ID NO 183
<211> LENGTH: 21
<212> TYPE: DNA
<213> ORGANISM: Homo Sapiens

<400> SEQUENCE: 183
ctcttccctt ggttcctatt c                                                  21

<210> SEQ ID NO 184
<211> LENGTH: 19
<212> TYPE: DNA
<213> ORGANISM: Homo Sapiens

<400> SEQUENCE: 184
ttaggcagaa gcatccacc                                                     19

<210> SEQ ID NO 185
<211> LENGTH: 325
<212> TYPE: DNA
<213> ORGANISM: Homo Sapiens

<400> SEQUENCE: 185
tatagaccct gactactcaa gagaaaagtc caatccaaag aaaaaataca aagaaaaca         60 aaatcacatc aggccacaaa ccagtttaag ggccctcacc acatggttgg ctccagactg       120
aaacatttca tagggtaaa taatgcgttc gtaatgtgat cgtagcaggg agccaatgtt       180
tttgcctggt gggtagtgga gacgctgggc aactcgagcc caccgacgat ccttgcagat       240
ggcttcatag ccaccttcct caatcacaat ctgaaagtrt aagaaacaat atggatgaac       300
tgtgaacaga ctggaaaggg ctacc                                              325

<210> SEQ ID NO 186
<211> LENGTH: 25
<212> TYPE: DNA
<213> ORGANISM: Homo Sapiens

<400> SEQUENCE: 186
tatagaccct gactactcaa gagaa                                              25
```

```
<210> SEQ ID NO 187
<211> LENGTH: 20
<212> TYPE: DNA
<213> ORGANISM: Homo Sapiens

<400> SEQUENCE: 187
ggtagccctt tccagtctgt                                                 20

<210> SEQ ID NO 188
<211> LENGTH: 436
<212> TYPE: DNA
<213> ORGANISM: Homo Sapiens

<400> SEQUENCE: 188
ttctgatgcc agcttgttcg ggtcagaaaa gttaaatgag aaatttggtg ctaagggttt     60
ctggtcatga gtgtaaataa cgcctcgcca agtggtaaac tgccccaacg ttcaaaccaa    120
aggctaccca ttcccaaatt ttgtttcaaa gwcttaccgc gggtgggcgg attttgcaga    180
tgccagactt ctctgctatg ggccttattt tcgcaatgta gccaagcggg tcttggaatt    240
cagcccagct aggctcaaaa accgggcact ccggtggcgg caggaactcg tcacaccccg    300
gttccatgtc gggccttaat gctaagctgt aaaataagaa tcacattgtc tttaatgacg    360
cgctggttcc tcctactaaa aggcctatga aaatttcatt ttcttgagaa tttcaaggtt    420
actttaatcc cgtagc                                                    436

<210> SEQ ID NO 189
<211> LENGTH: 20
<212> TYPE: DNA
<213> ORGANISM: Homo Sapiens

<400> SEQUENCE: 189
ttctgatgcc agcttgttcg                                                 20

<210> SEQ ID NO 190
<211> LENGTH: 23
<212> TYPE: DNA
<213> ORGANISM: Homo Sapiens

<400> SEQUENCE: 190
gctacgggat taaagtaacc ttg                                             23

<210> SEQ ID NO 191
<211> LENGTH: 415
<212> TYPE: DNA
<213> ORGANISM: Homo Sapiens

<400> SEQUENCE: 191
ctgtgtaaca ccatcaagtg cacccatata tgcagaatgg gaatttcgta agaaaagaga     60
aggaaaaagg cagaacagtt gaagcaaaaa tggttaaaca atttccaaat ttgtggaaag    120
ccctgaaagt ctacmaccaa gaagctcagt gcactccaac tagataaact ccaggagaca    180
caacatagtc gaaccaacaa aaggtaagac accaagatgg agtttgaaag cagtatgaca    240
gacatgattc ttcgcatata atggatgctt aatagaatta tcaatagatt tctcattaga    300
aataacggag gccagaagcc agttggatga cacgttaaaa gtcatgcaat gggaaaaaaa    360
attaaataaa ttgacagaga attaaaaatt gtggaagtat gtctccagaa gatgt         415
```

<210> SEQ ID NO 192
<211> LENGTH: 21
<212> TYPE: DNA
<213> ORGANISM: Homo Sapiens

<400> SEQUENCE: 192
ctgtgtaaca ccatcaagtg c                                       21

<210> SEQ ID NO 193
<211> LENGTH: 23
<212> TYPE: DNA
<213> ORGANISM: Homo Sapiens

<400> SEQUENCE: 193
acatcttctg gagacatact tcc                                     23

<210> SEQ ID NO 194
<211> LENGTH: 409
<212> TYPE: DNA
<213> ORGANISM: Homo Sapiens

<400> SEQUENCE: 194
ccatattctt tatactttct acctgcaggc ccactgcatg ctcactcacc cagtcagcag    60
tacaaaagtt gacagcttca gcaaaattgt agccttggtt aaaaccactg tggtaagcac   120
gaggaaaagt gatgacaaac tcccctgcac actggtttgt gcggacaacc taaaaaggag   180
aaaaaagcag aaagaggtgt gggtcagaac taatgggcca gatgtgaact caaagatgtc   240
tctagatgct gtaacagatg taggaagagt ggaaaggctc tatcttcaag tacgtgtcct   300
aaaagaaaaa tgagattgtg aatttaaaag tggtattcat agaaaagtac tcaaaatatg   360
tgtaattcaa aaacawata tagaggggtc cacgaacaag tgaaaagac              409

<210> SEQ ID NO 195
<211> LENGTH: 26
<212> TYPE: DNA
<213> ORGANISM: Homo Sapiens

<400> SEQUENCE: 195
ccatattctt tatactttct acctgc                                  26

<210> SEQ ID NO 196
<211> LENGTH: 22
<212> TYPE: DNA
<213> ORGANISM: Homo Sapiens

<400> SEQUENCE: 196
gtcttttcac ttgttcgtgg ac                                      22

<210> SEQ ID NO 197
<211> LENGTH: 386
<212> TYPE: DNA
<213> ORGANISM: Homo Sapiens

<400> SEQUENCE: 197
ccagtcagca gtacaaaagt tgacagcttc agcaaaattg tagccttggt taaaaccact    60
gtggtaagca cgaggaaaag tgatgacaaa ctcccctgca cactggtttg tgcggacaac   120
ctaaaaagga gaaaaaagca gaaagaggtg tgggtcagaa ctaatgggcc agatgtgaac   180
tcaaagatgt ctctagatgc tgtaacagat gtaggaagag tggaaaggct ctatcttcaa   240
gtacgtgtcc taaaagaaaa tgagattgtg aatttaaaag tggtattcat agaaaagtac   300

```
tcaaaatatg tgtaattcaa aaaacawata tagagggtc cacgaacaag tgaaaagact    360
ctttgcttct ataatcaaag aaatgc                                        386

<210> SEQ ID NO 198
<211> LENGTH: 22
<212> TYPE: DNA
<213> ORGANISM: Homo Sapiens

<400> SEQUENCE: 198
ccagtcagca gtacaaaagt tg                                            22

<210> SEQ ID NO 199
<211> LENGTH: 24
<212> TYPE: DNA
<213> ORGANISM: Homo Sapiens

<400> SEQUENCE: 199
gcatttcttt gattatagaa gcaa                                          24

<210> SEQ ID NO 200
<211> LENGTH: 409
<212> TYPE: DNA
<213> ORGANISM: Homo Sapiens

<400> SEQUENCE: 200
ccatattctt tatactttct acctgcaggc ccactgcatg ctcactcacc cagtcagcag    60
tacaaaagtt gacagcttca gcaaaattgt agccttggtt aaaaccactg tggtaagcac   120
gaggaaaagt gatgacaaac tcccctgcac actggtttgt gcggacaacc taaaaaggag   180
aaaaaagcag aaagaggtgt gggtcagaac taatgggcca gatgtgaact caaagatgtc   240
tctagatgct gtaacagatg taggaagrgt ggaaaggctc tatcttcaag tacgtgtcct   300
aaaagaaaaa tgagattgtg aatttaaaag tggtattcat agaaaagtac tcaaaatatg   360
tgtaattcaa aaaacaaata tagagggtc cacgaacaag tgaaaagac                409

<210> SEQ ID NO 201
<211> LENGTH: 26
<212> TYPE: DNA
<213> ORGANISM: Homo Sapiens

<400> SEQUENCE: 201
ccatattctt tatactttct acctgc                                        26

<210> SEQ ID NO 202
<211> LENGTH: 22
<212> TYPE: DNA
<213> ORGANISM: Homo Sapiens

<400> SEQUENCE: 202
gtcttttcac ttgttcgtgg ac                                            22

<210> SEQ ID NO 203
<211> LENGTH: 386
<212> TYPE: DNA
<213> ORGANISM: Homo Sapiens

<400> SEQUENCE: 203
ccagtcagca gtacaaaagt tgacagcttc agcaaaattg tagccttggt taaaaccact    60
gtggtaagca cgaggaaaag tgatgacaaa ctcccctgca cactggtttg tgcggacaac   120
ctaaaaagga gaaaaaagca gaaagaggtg tgggtcagaa ctaatgggcc agatgtgaac   180
```

```
tcaaagatgt ctctagatgc tgtaacagat gtaggaagrg tggaaaggct ctatcttcaa    240
gtacgtgtcc taaaagaaaa tgagattgtg aatttaaaag tggtattcat agaaaagtac    300 tcaaatatg tgtaattcaa aaacaaata tagaggggtc cacgaacaag tgaaaagact     360
ctttgcttct ataatcaaag aaatgc                                          386

<210> SEQ ID NO 204
<211> LENGTH: 22
<212> TYPE: DNA
<213> ORGANISM: Homo Sapiens

<400> SEQUENCE: 204
ccagtcagca gtacaaaagt tg                                              22

<210> SEQ ID NO 205
<211> LENGTH: 24
<212> TYPE: DNA
<213> ORGANISM: Homo Sapiens

<400> SEQUENCE: 205
gcatttcttt gattatagaa gcaa                                            24

<210> SEQ ID NO 206
<211> LENGTH: 257
<212> TYPE: DNA
<213> ORGANISM: Homo Sapiens

<400> SEQUENCE: 206
ggttatcata gcccactata ctttggactc atgtctccat gagaactaag actaccacaa    60
cagaatccct atagtccagc cctcagatca catacatgta caggcatgtt gaagtagtcg   120
gacttgaagg aatcagccat ttcaccaaaa ctctgcaaac tgtactcctg ggtagcctgt   180
tcaaatccaa aagcttcagg aggctgttta cactcctgaa ayaaaatata tttcagcaag   240
acaaagggaa taaagat                                                   257

<210> SEQ ID NO 207
<211> LENGTH: 25
<212> TYPE: DNA
<213> ORGANISM: Homo Sapiens

<400> SEQUENCE: 207
ggttatcata gcccactata ctttg                                           25

<210> SEQ ID NO 208
<211> LENGTH: 23
<212> TYPE: DNA
<213> ORGANISM: Homo Sapiens

<400> SEQUENCE: 208
atctttattc cctttgtctt gct                                             23

<210> SEQ ID NO 209
<211> LENGTH: 257
<212> TYPE: DNA
<213> ORGANISM: Homo Sapiens

<400> SEQUENCE: 209
ggttatcata gcccactata ctttggactc atgtctccat gagamctaag actaccacaa    60
cagaatccct atagtccagc cctcagatca catacatgta caggcatgtt gaagtagtcg   120
gacttgaagg aatcagccat ttcaccaaaa ctctgcaaac tgtactcctg ggtagcctgt   180
```

```
tcaaatccaa aagcttcagg aggctgttta cactcctgaa ataaaatata tttcagcaag    240
acaaagggaa taaagat                                                   257

<210> SEQ ID NO 210
<211> LENGTH: 25
<212> TYPE: DNA
<213> ORGANISM: Homo Sapiens

<400> SEQUENCE: 210
ggttatcata gcccactata ctttg                                          25

<210> SEQ ID NO 211
<211> LENGTH: 23
<212> TYPE: DNA
<213> ORGANISM: Homo Sapiens

<400> SEQUENCE: 211
atctttattc cctttgtctt gct                                            23

<210> SEQ ID NO 212
<211> LENGTH: 328
<212> TYPE: DNA
<213> ORGANISM: Homo Sapiens

<400> SEQUENCE: 212
ttgaattata gtcccttgcc tctggttcag tcaagtctct atcattctag agttagtgtg    60
ttcaatcgtt cttgtatagt agctcactga tagcttaatc aaaacctaac acaaatatta   120
acttataaaa gggcagaaac taccttccca aaacccagaa ggggagatta cagaaaatca   180
ccaaccaaaa ataaagyatc tgtgacagac agatcttacc gccaagatac attttgggca   240
cctccagatg cctctgggga tttcaggaag gggtggtaac aagcagaaga tgtggtaatt   300
gtcatcacag ccatcacaga aaagaagc                                      328

<210> SEQ ID NO 213
<211> LENGTH: 22
<212> TYPE: DNA
<213> ORGANISM: Homo Sapiens

<400> SEQUENCE: 213
ttgaattata gtcccttgcc tc                                             22

<210> SEQ ID NO 214
<211> LENGTH: 21
<212> TYPE: DNA
<213> ORGANISM: Homo Sapiens

<400> SEQUENCE: 214
gcttcttttc tgtgatggct g                                              21

<210> SEQ ID NO 215
<211> LENGTH: 328
<212> TYPE: DNA
<213> ORGANISM: Homo Sapiens

<400> SEQUENCE: 215
ttgaattata gtcccttgcc tctggttcag tcaagtctct atcattctag agttagtgtg    60
ttcaatcgtt cttgtatagt agctcactga tagcttaatc aaaacctaac acaaatatta   120
acttataaaa gggcagaaac taccttccca aaacccrgaa ggggagatta cagaaaatca   180
ccaaccaaaa ataaagcatc tgtgacagac agatcttacc gccaagatac attttgggca   240
```

```
cctccagatg cctctgggga tttcaggaag gggtggtaac aagcagaaga tgtggtaatt    300
gtcatcacag ccatcacaga aaagaagc                                       328

<210> SEQ ID NO 216
<211> LENGTH: 22
<212> TYPE: DNA
<213> ORGANISM: Homo Sapiens

<400> SEQUENCE: 216
ttgaattata gtcccttgcc tc                                              22

<210> SEQ ID NO 217
<211> LENGTH: 21
<212> TYPE: DNA
<213> ORGANISM: Homo Sapiens

<400> SEQUENCE: 217
gcttcttttc tgtgatggct g                                               21

<210> SEQ ID NO 218
<211> LENGTH: 361
<212> TYPE: DNA
<213> ORGANISM: Homo Sapiens

<400> SEQUENCE: 218
cagaataata ggagaatttt tggtcaaata aaggccata ttatatttct tttgataaaa      60
gtatcatgtg ttcagtatgt tttattattt gaaataatta acatgacagg aatatatttg    120
aaaaaaattc caaaaaagc taaatataca aactaagaaa attatatgat tatacttatc     180
tgcagtattg taaacaata gttccaaaaa cttctgaatt acaagtttaa tacatacaac     240
ttcaattttc aactacattg tggttagacg ttcagaggaa tcacaaagga cctcaacatg    300
ctagataaga aaatgtattt tttaaatgtt ttggctcagc tgcttagaaa ataaggaaaa    360
t                                                                    361

<210> SEQ ID NO 219
<211> LENGTH: 24
<212> TYPE: DNA
<213> ORGANISM: Homo Sapiens

<400> SEQUENCE: 219
cagaataata ggagaatttt tggt                                            24

<210> SEQ ID NO 220
<211> LENGTH: 23
<212> TYPE: DNA
<213> ORGANISM: Homo Sapiens

<400> SEQUENCE: 220
attttcctta ttttctaagc agc                                             23

<210> SEQ ID NO 221
<211> LENGTH: 385
<212> TYPE: DNA
<213> ORGANISM: Homo Sapiens

<400> SEQUENCE: 221
atgctataat aactaggtgt tgaagataaa atcagtttaa tttaaataag aggataaaag     60
aagtatgagc agaaaaggt tttcaatatt aactaggaaa gtctgaaaaa taatcagaaa    120
ttctaaagat aaaaacataa cattaaaaat tataaactaa gttgtttaat agattaggta    180
```

```
tttaaaaac tggtrcattt ttaagttgct ttaagtaagt tacttaaaag acaacagcag    240
caaaagaatt aaaaaaaat gaaaggtgaa gaaacacata caagagaacc ttagaacagt    300
aaggttctag ctaacaggag aaataaatta cagactgtaa aagttgatga ccaagaattt   360
tttcagaagt ggtaaaagct gaatt                                        385
```

<210> SEQ ID NO 222
<211> LENGTH: 25
<212> TYPE: DNA
<213> ORGANISM: Homo Sapiens

<400> SEQUENCE: 222

```
atgctataat aactaggtgt tgaag                                         25
```

<210> SEQ ID NO 223
<211> LENGTH: 24
<212> TYPE: DNA
<213> ORGANISM: Homo Sapiens

<400> SEQUENCE: 223

```
aattcagctt ttaccacttc tgaa                                          24
```

<210> SEQ ID NO 224
<211> LENGTH: 355
<212> TYPE: DNA
<213> ORGANISM: Homo Sapiens

<400> SEQUENCE: 224

```
gctaacagga gaaataaatt acagactgta aaagttgatg accaagaatt tttcagaagt    60
ggtaaaagct gaattctcaa gtttgagaat tcctatctat tcccagaaat attaagtaaa   120
aagtcacatt ccacacatca agaaaacttg caagacacta aaagagatat tatagcagtc   180
aaatagaaaa agcaaaatag actactacaa attaatgtaa gattcagaat tgacttgtca   240
aaagccaaaa cagatttcta atgtactgtg aaaagacaat tatcaaacca catccrtata   300
tatacagaga ataccttta taagaataaa aattcacaaa tgcctctgtt caata         355
```

<210> SEQ ID NO 225
<211> LENGTH: 26
<212> TYPE: DNA
<213> ORGANISM: Homo Sapiens

<400> SEQUENCE: 225

```
gctaacagga gaaataaatt acagac                                        26
```

<210> SEQ ID NO 226
<211> LENGTH: 22
<212> TYPE: DNA
<213> ORGANISM: Homo Sapiens

<400> SEQUENCE: 226

```
tattgaacag aggcatttgt ga                                            22
```

<210> SEQ ID NO 227
<211> LENGTH: 493
<212> TYPE: DNA
<213> ORGANISM: Homo Sapiens

<400> SEQUENCE: 227

```
tagaagtagc agattgggag aggacatgtg ttcaagttgt actacttgta tgtcttgttt    60
agatattaca gtcttttct tttatcagaa aataattgaa taatgataaa atcagttgca    120
```

```
gattaagaca gattatctgt tgcagtcttc tcaaaactta atttaagtac attattttca      180
gctagcattt cttccttcac atagaacctc catgtgtgga gggatttcct aatgagtcta      240
ttgtatgtac aatagcactt aatgacatag cttttaaata ataacaggat tttaccaaat      300
gtttaatatg tgccaggcat caagcacctt acacagttka attattgcat agatttggac      360
agcaactctg caagttaggt atggtcatga acctttgcag ataaggaaac tgtgtttcac      420
aaggagaaga aattgtcctg gatcatacaa taagctagga tttgctccag accatttttt      480
tcattttatc agg                                                         493

<210> SEQ ID NO 228
<211> LENGTH: 23
<212> TYPE: DNA
<213> ORGANISM: Homo Sapiens

<400> SEQUENCE: 228
tagaagtagc agattgggag agg                                              23

<210> SEQ ID NO 229
<211> LENGTH: 24
<212> TYPE: DNA
<213> ORGANISM: Homo Sapiens

<400> SEQUENCE: 229
cctgataaaa tgaaaaaaat ggtc                                             24

<210> SEQ ID NO 230
<211> LENGTH: 371
<212> TYPE: DNA
<213> ORGANISM: Homo Sapiens

<400> SEQUENCE: 230
cttttcttcc cttagctgtt cctttcctgt ggttttaaaa aagtgaccag aaactaggtc       60
tctattttca ttgctttgct gcatattctt ttaacctgct tttatctttt acagagttga      120
ggggctttyt aaataaccta gacaatgtca agattcttag ctgcgttttc tgtctaaaag      180
tgtagatgtc tagttattcc tcatgtaaaa cacaacattt caaccctgag tactataaac      240
tttattatgc ttctaggtta cttttttctct ttaagcaatt attcctacat tcctaagtgt      300
tcaccagtgg aacagataag agatagaagt agttagaaat tgagataatt gggttgacct      360
gtcattgttg c                                                           371

<210> SEQ ID NO 231
<211> LENGTH: 22
<212> TYPE: DNA
<213> ORGANISM: Homo Sapiens

<400> SEQUENCE: 231
cttttcttcc cttagctgtt cc                                               22

<210> SEQ ID NO 232
<211> LENGTH: 20
<212> TYPE: DNA
<213> ORGANISM: Homo Sapiens

<400> SEQUENCE: 232
gcaacaatga caggtcaacc                                                  20
```

<210> SEQ ID NO 233
<211> LENGTH: 301
<212> TYPE: DNA
<213> ORGANISM: Homo Sapiens

<400> SEQUENCE: 233
cttcaggcat tattttttt ggttctccac tacaggagaa atgtaaatgt gatgagtcag    60
aatttaggat ggctgtatgg gtttctttga ctaatacaag aaatcacttt gtaatgaatg   120
aaatcagtgg tttctgcatt actccgtatg ttcgacatga acacaaattg atacacttaa   180
caaagatact tctttcygcc cttccaaata tttcaaaata agctggtcat agtacttgct   240
tttcataaaa agatggtaag cttccaatat ttagatttaa ggaaaggtga aggaacacta   300
t                                                                  301

<210> SEQ ID NO 234
<211> LENGTH: 23
<212> TYPE: DNA
<213> ORGANISM: Homo Sapiens

<400> SEQUENCE: 234
cttcaggcat tattttttt ggt                                            23

<210> SEQ ID NO 235
<211> LENGTH: 23
<212> TYPE: DNA
<213> ORGANISM: Homo Sapiens

<400> SEQUENCE: 235
atagtgttcc ttcacctttc ctt                                           23

<210> SEQ ID NO 236
<211> LENGTH: 425
<212> TYPE: DNA
<213> ORGANISM: Homo Sapiens

<400> SEQUENCE: 236
agccagttgg atgacacgtt aaaagtcatg caatgggaaa aaaaattaaa taaattgaca    60
gagaattaaa aattgtggaa gtatgtctcc agaagatgtg cctacaggga aaacagaagg   120
actccttcag gctgacatga aaggatatta ctgagtagtt cagagctaca taagaaagt    180 aatacccctg agaaaggcaa ctataaaaaa aatataaaag ttagtattac atatacagca   240
cgagagacaa aaaaaatata gttagttcag aactagaatc agaaagcaag acaaatggtg   300
ttaattagat tgcttgatga gctcattatc atcaatatat ttttcttgtg agacgaggaa   360
tactaggaaa aaaaaggtac aagttagaat tcataaaatg tataaaatgt caggaaacga   420
agagg                                                              425

<210> SEQ ID NO 237
<211> LENGTH: 20
<212> TYPE: DNA
<213> ORGANISM: Homo Sapiens

<400> SEQUENCE: 237
agccagttgg atgacacgtt                                               20

<210> SEQ ID NO 238
<211> LENGTH: 21
<212> TYPE: DNA
<213> ORGANISM: Homo Sapiens

```
<400> SEQUENCE: 238
cctcttcgtt tcctgacatt t                                           21

<210> SEQ ID NO 239
<211> LENGTH: 290
<212> TYPE: DNA
<213> ORGANISM: Homo Sapiens

<400> SEQUENCE: 239
actttctctt cttttagggt gaccaattaa ttctgatttg ccttgatttt tttttggcat    60
ttttatggca ccataaaaac cataaatgat ttgtattcat tttggcaacc ctagttccag   120
gttgattgtg atggctggtt gtgatggcta ttttgaaagt tggctttcct ctgtcccaga   180
tattttctct aaaaccttta taattttgtc ttatggctag ctacatagaa ttttaaaata   240
ttacaaatgg ccagacagtc ctacttcacc ataagatttt gtgtgtgtgt             290

<210> SEQ ID NO 240
<211> LENGTH: 24
<212> TYPE: DNA
<213> ORGANISM: Homo Sapiens

<400> SEQUENCE: 240
actttctctt cttttagggt gacc                                         24

<210> SEQ ID NO 241
<211> LENGTH: 22
<212> TYPE: DNA
<213> ORGANISM: Homo Sapiens

<400> SEQUENCE: 241
acacacacac aaaatcttat gg                                           22

<210> SEQ ID NO 242
<211> LENGTH: 422
<212> TYPE: DNA
<213> ORGANISM: Homo Sapiens

<400> SEQUENCE: 242
acttaattta tagtttcaat ccctcagtaa ttttaactta cttctatttt aagaactata    60
accaaactat ctgtaagact tttaagcact atcatactca gctacacatc tcttaacaaa   120
agaggtaaat tttgtccttt tttgaaygtc atagagtata ctcacacaaa ccaagaagaa   180
acaatctact acatacctac gctatatggt ataatactat tgctcctagg ctacaaatta   240
gtgcgacact attgtactga atattatagg ccatgtaaca caatggttta agtatctgtg   300
cctctaaaca cagaaaagat atagtgaaag tacagtattg ctcctttatt aaactcaaaa   360
tgttatgcag catatgaccg actataaaat agcgcttatc cagatacaga catctccatg   420
aa                                                                  422

<210> SEQ ID NO 243
<211> LENGTH: 26
<212> TYPE: DNA
<213> ORGANISM: Homo Sapiens

<400> SEQUENCE: 243
acttaattta tagtttcaat ccctca                                       26
```

```
<210> SEQ ID NO 244
<211> LENGTH: 23
<212> TYPE: DNA
<213> ORGANISM: Homo Sapiens

<400> SEQUENCE: 244
ttcatggaga tgtctgtatc tgg                                              23

<210> SEQ ID NO 245
<211> LENGTH: 328
<212> TYPE: DNA
<213> ORGANISM: Homo Sapiens

<400> SEQUENCE: 245
ctgtactcct gggtagcctg ttcaaatcca aaagcttcag gaggctgttt acactcctga      60 aataaatat atttcagcaa gacaaaggga ataaagatcc aaaaaaacag gagagctaag      120
gggagataaa ttttcatgt tacattcaat atctcatgca ataattctgc attttcatat      180
gtttccaggt aggtttgttt cttcagtagg tattaaacat tattttataa tctttcctta    240
catgcttcat gccatttgaa ttatagtccc ttgcctctgg ttcagtcaag tctctatcat    300
tctagagtta gtgtgttcaa tcgttctt                                       328

<210> SEQ ID NO 246
<211> LENGTH: 21
<212> TYPE: DNA
<213> ORGANISM: Homo Sapiens

<400> SEQUENCE: 246
ctgtactcct gggtagcctg t                                               21

<210> SEQ ID NO 247
<211> LENGTH: 24
<212> TYPE: DNA
<213> ORGANISM: Homo Sapiens

<400> SEQUENCE: 247
aagaacgatt gaacacacta actc                                            24

<210> SEQ ID NO 248
<211> LENGTH: 503
<212> TYPE: DNA
<213> ORGANISM: Homo Sapiens

<400> SEQUENCE: 248
gggaaaggag ttatccagaa aagtgaaatt tattctaaaa ttttaagttt ccatgtttta      60 agagaggca gcaatgagaa aaaaggttaa gaacaagtag gaaatactga ataatgggy      120 caggcacggt ggctcatgct tgtaatccca gcactttggg aggccaaggc aggcagatca    180
caaggtgagg agattgaaac catcctggct aacatggtga accccatct ctactaaaaa     240 tacaaaaaaa ttagccaggt gtggtggcac acacctgtag acccagctac ttgggaggct    300
gaggcaggat aatggcctga acccgggagg tggagcttgc aatgagctga gatcgtgcca    360
ctgcactcca gccagggtga cagagtgaga ccccgtctca aaaaaaaaaa aaagaatatt    420
tgaaataatg tgtctctaaa atatgacaga catgagaatg aagacaaaac ataagaaact    480
aagctaagta agcatgggtc att                                            503
```

<210> SEQ ID NO 249
<211> LENGTH: 21
<212> TYPE: DNA
<213> ORGANISM: Homo Sapiens

<400> SEQUENCE: 249
gggaaaggag ttatccagaa a                                              21

<210> SEQ ID NO 250
<211> LENGTH: 21
<212> TYPE: DNA
<213> ORGANISM: Homo Sapiens

<400> SEQUENCE: 250
aatgacccat gcttacttag c                                              21

<210> SEQ ID NO 251
<211> LENGTH: 439
<212> TYPE: DNA
<213> ORGANISM: Homo Sapiens

<400> SEQUENCE: 251
ccctctccaa ctgagttcaa gatggaaaca gttaagacag gaaaaattct attccattta     60
aactcatatc attagaatca taactgcttt cagaccacaa tataatcaca aacctgggaa    120
aatggaaact cattaagtat caaaatacaa atcatatgcc acatatatta tataccattt    180
tcagcacttg tctcttctta gaggacactg taaaatatat tttatcattg tttaaaataa    240
tttgttatat tttgaaatta agctctatta cattttccgt ttattttaaa gctttattct    300
tacaaatttt ctatacagag gtaagttttc ttctatttac atatataaac atacatgtat    360
acacagagag acacagtaac atattttatg cttttttttt attcccacgg caatttctgg    420
aagcagaaac gtatattgc                                                 439

<210> SEQ ID NO 252
<211> LENGTH: 21
<212> TYPE: DNA
<213> ORGANISM: Homo Sapiens

<400> SEQUENCE: 252
ccctctccaa ctgagttcaa g                                              21

<210> SEQ ID NO 253
<211> LENGTH: 22
<212> TYPE: DNA
<213> ORGANISM: Homo Sapiens

<400> SEQUENCE: 253
gcaatatacg tttctgcttc ca                                             22

<210> SEQ ID NO 254
<211> LENGTH: 568
<212> TYPE: DNA
<213> ORGANISM: Homo Sapiens

<400> SEQUENCE: 254
aacagaatta tcaggaaaag gtttcataaa ataaaaatct tttaaactta tgaaagatgc     60
tcaatataaa aaactgtaaa ccagggaaat gcaaataaaa attacaatga aatactacac    120
acctcccaga atggctaaaa tgaaaacaaa actgtcaatt ctaagtgtta gtgaggacat    180
gtggtaacca gaactggcat ccaatactag ctgataaact cgtcaatcat ttgtaaaaac    240

```
agtctgacaa taatccacta gtgaaaatat acatagtctc agtcacagca attctatcct    300
gtctatctag gtaacagaaa tgtctacata cgttacctag aaacatatac tttaatatcc    360
acagaattac ttgaaatagc caaaaattgg taactaccaa aagttgaatg gtaaaacaga    420
tagaaaaaaa gctatgmcta acaaaactac acttaataga acacaagcgt gagcattaat    480
agaaccatat aaatgcattt tttgaaccac taaaagaaga agccaataca aaagaggtga    540
ttaattgaaa gtacacgaac aagtaaaa                                       568

<210> SEQ ID NO 255
<211> LENGTH: 24
<212> TYPE: DNA
<213> ORGANISM: Homo Sapiens

<400> SEQUENCE: 255
aacagaatta tcaggaaaag gttt                                           24

<210> SEQ ID NO 256
<211> LENGTH: 22
<212> TYPE: DNA
<213> ORGANISM: Homo Sapiens

<400> SEQUENCE: 256
gcaatatacg tttctgcttc ca                                             22

<210> SEQ ID NO 257
<211> LENGTH: 324
<212> TYPE: DNA
<213> ORGANISM: Homo Sapiens

<400> SEQUENCE: 257
tcccattatt tgctatattt gctacataca tctaaggtca tatcaaagaa agaaaacacc    60
agtccaagtg gttaacacac aagcktatat aacttgcttc tgtcatagat caagtacttc    120
tgagtaagct attttttttgc ggttaaatgt aataaaagct tgtgtatgcc taaactatat   180
ttaataacag cagaacgtag aaatatttga atcttatatt tttgtcccta cagcagtcag    240
atgtttagaa ccccgtggaa tgtggcgatc tgatactaat attctgatgc cagcttgttc    300
gggtcagaaa agttaaatga gaaa                                           324

<210> SEQ ID NO 258
<211> LENGTH: 23
<212> TYPE: DNA
<213> ORGANISM: Homo Sapiens

<400> SEQUENCE: 258
tcccattatt tgctatattt gct                                            23

<210> SEQ ID NO 259
<211> LENGTH: 24
<212> TYPE: DNA
<213> ORGANISM: Homo Sapiens

<400> SEQUENCE: 259
tttctcattt aacttttctg accc                                           24

<210> SEQ ID NO 260
<211> LENGTH: 324
<212> TYPE: DNA
<213> ORGANISM: Homo Sapiens
```

```
<400> SEQUENCE: 260
tcccattatt tgctatattt gctacataca tctaaggtca tatcaaagaa agaaaacacc      60
agtccaagtg gttaacacac aagcttatat aacttgcttc tgtcatagat caagtacttc     120
tgagtaagct attttttgc ggttaaatgt aataaaagct tgtgtatgcc taaactatat     180
ttaataacag cagaacgtag aaatatttga atcttatatt tttgtcccta cagcagtcag     240
atgtttagaa ccccgtggaa tgtggcgatc tgatacyaat attctgatgc cagcttgttc     300
gggtcagaaa agttaaatga gaaa                                            324

<210> SEQ ID NO 261
<211> LENGTH: 23
<212> TYPE: DNA
<213> ORGANISM: Homo Sapiens

<400> SEQUENCE: 261
tcccattatt tgctatattt gct                                              23

<210> SEQ ID NO 262
<211> LENGTH: 24
<212> TYPE: DNA
<213> ORGANISM: Homo Sapiens

<400> SEQUENCE: 262
tttctcattt aacttttctg accc                                             24

<210> SEQ ID NO 263
<211> LENGTH: 314
<212> TYPE: DNA
<213> ORGANISM: Homo Sapiens

<400> SEQUENCE: 263
attctagggt caggcaacta gggaatactg ctgtagccta gagcctgcca aaattattca      60
aactagccaa tcccatactt cttatcctgc tctgtcttgc ctttcccttg gtaaacccaa     120
tataggctat ggcctaggtg cttttcttat tcctgcttct ctgcrtatc caagataggt      180 tttcctctct agcactgtgt agcatatagt gactacctct ctaaggcctg tgataataat     240
aaactttgct ttcctgagtc tctgtggtca cacctactga ccatcacatg gaagaccata    300
gaatagaaca aaca                                                       314

<210> SEQ ID NO 264
<211> LENGTH: 22
<212> TYPE: DNA
<213> ORGANISM: Homo Sapiens

<400> SEQUENCE: 264
attctagggt caggcaacta gg                                               22

<210> SEQ ID NO 265
<211> LENGTH: 25
<212> TYPE: DNA
<213> ORGANISM: Homo Sapiens

<400> SEQUENCE: 265
tgtttgttct attctatggt cttcc                                            25

<210> SEQ ID NO 266
<211> LENGTH: 527
<212> TYPE: DNA
<213> ORGANISM: Homo Sapiens
```

```
<400> SEQUENCE: 266
agaagcagat tgatgtccca cttaaagaag cagtctagcc acattttggt agagcagctg      60
tggtgtgcca gggagtccct ttcatcccct ggtcagtttt gtttgcgctc tcctaaacct     120
gcaggctgga acagctgagc catccaaaca gcaaggatga caaccttccc tttctcctaa     180
gaactctgcc ccattcaagc ttggcccaac actgttgcca ggggctggct ggaattccaa     240
gctggtgagt cttatcctat gaggtgccat gaaagtgggg cccacagaag gatgctgctc     300
agcttcctgg attcagctct cttcctaagg ttatgtacaa aaatctyatc tctcactttg     360
cctgagttgc agctaccttt gctggtgatc ctggacccaa agtgtgccag cctctcctga     420
tactctgtgt gtacctgagc agctattctg ccaagacttc acacagctct gtgcatgaaa     480
cccaaggcct tagtgaagtg ggatcatgag gggatctcct aactgga                   527

<210> SEQ ID NO 267
<211> LENGTH: 22
<212> TYPE: DNA
<213> ORGANISM: Homo Sapiens

<400> SEQUENCE: 267
agaagcagat tgatgtccca ct                                               22

<210> SEQ ID NO 268
<211> LENGTH: 21
<212> TYPE: DNA
<213> ORGANISM: Homo Sapiens

<400> SEQUENCE: 268
tccagttagg agatcccctc a                                                21

<210> SEQ ID NO 269
<211> LENGTH: 331
<212> TYPE: DNA
<213> ORGANISM: Homo Sapiens

<400> SEQUENCE: 269
tgatgtttct tcagtctttg aggttgctgt cttttggatt tttgaaaaaa tcctatttaa      60
taacttagtg ggttggtttg tagcaacagt gaattcaatc aactggcttt atttctagaa     120
tattttaaag atattttatc tcaggatttc tggatggtgt tctgtaacts tagggactgg     180
gaatgagctt tggctttgtt cctttacacc ctgaggttag aaatctgctg cactggaggg     240
accaagatgc tctcagagaa atggtcacaa cactctaatg attggtagta gccaatgtgc     300
ttcatatgcg ggtggtagca ggattcatct t                                    331

<210> SEQ ID NO 270
<211> LENGTH: 23
<212> TYPE: DNA
<213> ORGANISM: Homo Sapiens

<400> SEQUENCE: 270
tgatgtttct tcagtctttg agg                                              23

<210> SEQ ID NO 271
<211> LENGTH: 21
<212> TYPE: DNA
<213> ORGANISM: Homo Sapiens

<400> SEQUENCE: 271
aagatgaatc ctgctaccac c                                                21
```

<210> SEQ ID NO 272
<211> LENGTH: 495
<212> TYPE: DNA
<213> ORGANISM: Homo Sapiens

<400> SEQUENCE: 272

```
gagcttggac tttaggacgg ggaaaagaag tgctaaatgt ttttgaataa aacctttact      60
gcacatgata aacatccctt aaaaattacc taggagcacc ctaaatttta aaatgatcac     120
aaagacctgg acagattaca gtaaaccttc aacatcgcta aacacacgta ccataaatca     180
aaagaaacac actgctaatg atccgttttt tgatgtggaa atatcatgct gttttttaagg    240
gaaattatac tttattgcga tgttttattt caaaacaaga tgttacactt tatttcctat     300
aatttattt acaatatttt acacccgtta agcaaaaatc cccctacatt gctattctgt      360
ttttttttaa tcagttcact actgtagtat cttttttgttc tccatatatt tttgaaaaat    420
acgcaaaagg taagttttaa aaatcaaatg gtagatttta tttggaaggg cactgccaga    480
agtgccttaa agttt                                                     495
```

<210> SEQ ID NO 273
<211> LENGTH: 20
<212> TYPE: DNA
<213> ORGANISM: Homo Sapiens

<400> SEQUENCE: 273

```
gagcttggac tttaggacgg                                                 20
```

<210> SEQ ID NO 274
<211> LENGTH: 21
<212> TYPE: DNA
<213> ORGANISM: Homo Sapiens

<400> SEQUENCE: 274

```
aaactttaag gcacttctgg c                                               21
```

<210> SEQ ID NO 275
<211> LENGTH: 470
<212> TYPE: DNA
<213> ORGANISM: Homo Sapiens

<400> SEQUENCE: 275

```
ttgaatttcc cagaattttg caatctgatc caaatagttc aatttcactc tagtttgggc      60
ctgggaaaga gagggcctta taagattggc atactcctta acctgacttc atcgagtatg    120
cagtaaatga acaagtatta ttctatgcta tctacacttc tccaccaacg tgccggagcc    180
ccagcttcac tgtcttatct caccagcggg gtccacaaaa agctcaaata agctgagtct    240
taatctata aagagctaag aatgtgccgt cttaggatca acatcatgtc taaatttaag    300
gaattattct tggacttaaa ggtggcttga ccaaaaatay gtaggctcca acagtattta    360
gactcaatat catcaagaca ctcatttaga atgtactgat atataattca aagaattaaa    420
atatttttct agttcatgta aaagagctgg acacaaaacc agtttctgaa                470
```

<210> SEQ ID NO 276
<211> LENGTH: 21
<212> TYPE: DNA
<213> ORGANISM: Homo Sapiens

```
<400> SEQUENCE: 276
ttgaatttcc cagaattttg c                                              21

<210> SEQ ID NO 277
<211> LENGTH: 22
<212> TYPE: DNA
<213> ORGANISM: Homo Sapiens

<400> SEQUENCE: 277
ttcagaaact ggttttgtgt cc                                             22

<210> SEQ ID NO 278
<211> LENGTH: 504
<212> TYPE: DNA
<213> ORGANISM: Homo Sapiens

<400> SEQUENCE: 278
aacaaaacaa aacaaaaata ctgaatcttt agaattatgt acgctaagtg aaacatgttt    60
ataaacataa atacacagtt tttataaaat attttaaagt tttacggata ataaaaccta   120
aaaactggcc agtcgtggtg gctcatgcct gtaatcccaa cactttggaa ggctgagtca   180
ggtagatcac gaggtcaaag gatcgagact atcctggcca acatggtgaa accccatctc   240
tacgaaaaat acaaaaatga gtgggcatag tcacgcgcct gtagcccag ctactcagga    300 ggctgaggca ggagaatcac ttcaatccag gaggtggagg ccgcctggcc agagtgataa   360
gctgcctcaa aaacaaaaca aacaaacaaa caaacaaaaa caattaactt attatgtaaa   420
attaccctgc taaatcagtt tccacaccct gagttaaayc caagtcacac caagctttta   480
acctaaacta tcttcaagtg aacc                                          504

<210> SEQ ID NO 279
<211> LENGTH: 25
<212> TYPE: DNA
<213> ORGANISM: Homo Sapiens

<400> SEQUENCE: 279
aacaaaacaa aacaaaaata ctgaa                                          25

<210> SEQ ID NO 280
<211> LENGTH: 26
<212> TYPE: DNA
<213> ORGANISM: Homo Sapiens

<400> SEQUENCE: 280
ggttcacttg aagatagttt aggtta                                         26

<210> SEQ ID NO 281
<211> LENGTH: 405
<212> TYPE: DNA
<213> ORGANISM: Homo Sapiens

<400> SEQUENCE: 281
cacatggaga acagagaaat gcagtgcagg gcaagggccc acccagaagc aacacagtca    60
atggagcctc cttcacccag gaaactgcaa actgaatgca tgatcctagg atcctctccc   120
atggatcttt gcaactttca ggtcaggaga tccagtcagg gacccattcc actagggcct   180
tcagttagaa acacagagct catggagtct tatcagagta gctgttmagg catgcatagg   240
gacccaggag cttttataca ccctgaccgta aagtccccag caaatatgac tgaaattcaa   300
```

```
gcaaggtgga acactaacct ttgcacatac acttgggaag ggagtggaaa tcaagatgcc      360
aagcagcatt ggtctgtgaa ccccactttc acaacatttc acaag                      405
```

<210> SEQ ID NO 282
<211> LENGTH: 22
<212> TYPE: DNA
<213> ORGANISM: Homo Sapiens

<400> SEQUENCE: 282

```
cacatggaga acagagaaat gc                                                22
```

<210> SEQ ID NO 283
<211> LENGTH: 23
<212> TYPE: DNA
<213> ORGANISM: Homo Sapiens

<400> SEQUENCE: 283

```
cttgtgaaat gttgtgaaag tgg                                               23
```

<210> SEQ ID NO 284
<211> LENGTH: 480
<212> TYPE: DNA
<213> ORGANISM: Homo Sapiens

<400> SEQUENCE: 284

```
gagtggaaat caagatgcca agcagcattg gtctgtgaac cccactttca acatttca         60 caagctaaaa gcccactggc ttggatttcc agtcagctgc cagcaatagt gttgcacctt      120
cttgggatca aatggagttc ctgaggataa ggaaagacta ccatattagt gytggatggc     180
ttagcctttc aacctgtag gcttaggaga gtccagactt actagggatg taagggatcc      240
tcttacacaa aacaggtgca ctaccaaaat gtggccagag tgctttaaac aggaccttga     300
cccatttctc atctctggga aggacctcac aactggggcc ttcaaacaca cccaccctca     360
ttgtctggct gacaaagttt ttacttattg ctgaaaaata gtgccctgag ggaaaggcag     420
gctcccatca ctgatgcttt aatgactcat ctgttctagt ctccaggtta cagaaagccc     480
```

<210> SEQ ID NO 285
<211> LENGTH: 22
<212> TYPE: DNA
<213> ORGANISM: Homo Sapiens

<400> SEQUENCE: 285

```
gagtggaaat caagatgcca ag                                                22
```

<210> SEQ ID NO 286
<211> LENGTH: 21
<212> TYPE: DNA
<213> ORGANISM: Homo Sapiens

<400> SEQUENCE: 286

```
gggctttctg taacctggag a                                                 21
```

<210> SEQ ID NO 287
<211> LENGTH: 440
<212> TYPE: DNA
<213> ORGANISM: Homo Sapiens

<400> SEQUENCE: 287

```
gttgccctct cacagagcac tttaaagtga gctgtgatgt gtaacttgga aaacaggtct       60
ctcataatas gataaaacac tcaggtataa tattaaaaac ctatggcaaa atatatggtc      120
```

```
ctttacaaag caacaaagtg ggtgggtgaa tctcttcatt cttggctggc catcagttcc    180
tgttactgta caggagtggg aaaacagtag ccctgggaaa tgggttaaaa ctgagtaggc    240
atctcctgtg tccaataaga actcaatatt tttgtctgct atatcaaggg ttacttgagg    300
ctcctctgtg gagatggtaa gttgtccagt gggagatata gagaatgtta ggccttatag    360
gttctctact tttttggcca ttatgagtct gaatgtctca aactccctt ttatcctggt    420 gcaatccttc cagtgacctt                                                440

<210> SEQ ID NO 288
<211> LENGTH: 20
<212> TYPE: DNA
<213> ORGANISM: Homo Sapiens

<400> SEQUENCE: 288
gttgccctct cacagagcac                                                 20

<210> SEQ ID NO 289
<211> LENGTH: 20
<212> TYPE: DNA
<213> ORGANISM: Homo Sapiens

<400> SEQUENCE: 289
aaggtcactg gaaggattgc                                                 20

<210> SEQ ID NO 290
<211> LENGTH: 440
<212> TYPE: DNA
<213> ORGANISM: Homo Sapiens

<400> SEQUENCE: 290
gttgccctct cacagagcac tttaaagtga gctgtgatgt gtaacttgga aaacaggtct     60
ctcataatag gataaaacac tcaggtataa tattaaaaac ctatggcaaa atatatggtc    120
ctttacaaag caacaaagtg ggtgggtgaa tctcttcatt cttggctggc catcagttcc    180
tgttactgta caggagtggg aaaacagtag ccctgggaaa tgggttaaaa ctgagtaggc    240
atctcctgtg tccaataaga actcaatatt tttgtctgct atatcaaggg ttacttgagg    300
ctcctctgtg gagatggtaa gttgtccagt gggagatata gagaatgtta ggccktatag    360
gttctctact tttttggcca ttatgagtct gaatgtctca aactccctt ttatcctggt    420 gcaatccttc cagtgacctt                                                440

<210> SEQ ID NO 291
<211> LENGTH: 20
<212> TYPE: DNA
<213> ORGANISM: Homo Sapiens

<400> SEQUENCE: 291
gttgccctct cacagagcac                                                 20

<210> SEQ ID NO 292
<211> LENGTH: 20
<212> TYPE: DNA
<213> ORGANISM: Homo Sapiens

<400> SEQUENCE: 292
aaggtcactg gaaggattgc                                                 20
```

<210> SEQ ID NO 293
<211> LENGTH: 395
<212> TYPE: DNA
<213> ORGANISM: Homo Sapiens

<400> SEQUENCE: 293

| gaatgggtg ttacatggag actacagggc tgttatattc ataactttag gctatcatta | 60 |
| ttgagggctg gatgtccctc tgagcctcag gattcaaagg atactgtttt gttttgtttt | 120 |
| gttttgtttt gttttttccc acgggtaatt aacactgsgt tttaggacag tctggactgg | 180 |
| gggtacatta acagttgtac tagaaacttc catgtctcaa acagagggt ctactagaga | 240 |
| agcaatatgt catggaaggc agttcttctc catatctgtg taaaggcaag tatttgaagc | 300 |
| taggagaact gttccttctg gcctgttgcc ctctcacaga gcactttaaa gtgagctgtg | 360 |
| atgtgtaact tggaaaacag gtctctcata atagg | 395 |

<210> SEQ ID NO 294
<211> LENGTH: 21
<212> TYPE: DNA
<213> ORGANISM: Homo Sapiens

<400> SEQUENCE: 294

| gaatgggtg ttacatggag a | 21 |

<210> SEQ ID NO 295
<211> LENGTH: 24
<212> TYPE: DNA
<213> ORGANISM: Homo Sapiens

<400> SEQUENCE: 295

| cctattatga gagacctgtt ttcc | 24 |

<210> SEQ ID NO 296
<211> LENGTH: 395
<212> TYPE: DNA
<213> ORGANISM: Homo Sapiens

<400> SEQUENCE: 296

| gaatgggtg ttacatggag actacagggc tgttatattc ataactttag gctatcatta | 60 |
| ttgagggctg gatgtccctc tgagcctcag gattcaaagg atactgtttt gttttgtttt | 120 |
| gttttgtttt gttttttccc acgggtaatt aacactgggt tttaggacag tctggactgg | 180 |
| gggtacatta acagttgtac tagaaacttc catgtctcaa acagagggt ctactagaga | 240 |
| agcaatatgt catggaaggc agttcttctc catatctgtg taaaggcaag tatttgaagc | 300 |
| taggagaact gttccttctg gcctgttgcc ctctcacaga gcactttaaa gtgagctgtg | 360 |
| atgtgtaact tggaaaacag gtctctcata atagg | 395 |

<210> SEQ ID NO 297
<211> LENGTH: 21
<212> TYPE: DNA
<213> ORGANISM: Homo Sapiens

<400> SEQUENCE: 297

| gaatgggtg ttacatggag a | 21 |

<210> SEQ ID NO 298
<211> LENGTH: 24
<212> TYPE: DNA
<213> ORGANISM: Homo Sapiens

<400> SEQUENCE: 298
cctattatga gagacctgtt ttcc    24

<210> SEQ ID NO 299
<211> LENGTH: 395
<212> TYPE: DNA
<213> ORGANISM: Homo Sapiens

<400> SEQUENCE: 299
gaatggggtg ttacatggag actacagggc tgttatattc ataactttag gctatcatta    60
ttgagggctg gatgtccctc tgagcctcag gattcaaagg atactgtttt gttttgtttt   120
gttttgtttt gttttttccc acgggtaatt aacactgggt tttaggacag tctggactgg   180
gggtacatta acagttgtac tagaaacttc catgtctcaa acagagggt ctactagaga    240
agcaatatgt catggaaggc agttcttctc catatctgtg taaaggcaag tatttgaagc   300
taggagaact gttccttctg gcctgttgcc ctctcacaga gcactttaaa gtgagctgtg   360
atgtgtaact tggaaaacag gtctctcata atagg                              395

<210> SEQ ID NO 300
<211> LENGTH: 21
<212> TYPE: DNA
<213> ORGANISM: Homo Sapiens

<400> SEQUENCE: 300
gaatggggtg ttacatggag a    21

<210> SEQ ID NO 301
<211> LENGTH: 24
<212> TYPE: DNA
<213> ORGANISM: Homo Sapiens

<400> SEQUENCE: 301
cctattatga gagacctgtt ttcc    24

<210> SEQ ID NO 302
<211> LENGTH: 460
<212> TYPE: DNA
<213> ORGANISM: Homo Sapiens

<400> SEQUENCE: 302
tcacagcagc ttcagcaaac acagatttct ggtgttggag gacagattta actacagaaa    60
attctgttgg gcaatcggaa gcctcaatct atacagactt ttaggaggag cctgcctgtt   120
tggttcaaat ttagccaaaa tattttttt ttaycactga ttcagtaaat ctcctaactt    180
tgcaggaact gggatcctaa aaattatgga acgaattgta gaaactcaag caactttctc   240
caaagcctag ggttcagcaa gagtaagcaa gaggcactga gccgctggag tctgcacatt   300
gataaattta cttacagtcg taaataaatt gcatcatctt cagctagtaa cacagagtct   360
aattttttata gcggcatact tgcctccacg actttcctag acaccagaaa gaaaggcgag   420
agccagcctt agcctaatca agaaccatga tccaaaaagg                         460

<210> SEQ ID NO 303
<211> LENGTH: 19
<212> TYPE: DNA
<213> ORGANISM: Homo Sapiens

<400> SEQUENCE: 303
tcacagcagc ttcagcaaa    19

```
<210> SEQ ID NO 304
<211> LENGTH: 27
<212> TYPE: DNA
<213> ORGANISM: Homo Sapiens

<400> SEQUENCE: 304
ataaaaatta gactctgtgt tactagc                                 27

<210> SEQ ID NO 305
<211> LENGTH: 21
<212> TYPE: DNA
<213> ORGANISM: Homo Sapiens

<400> SEQUENCE: 305 ccttttttgga tcatggttct t                                      21

<210> SEQ ID NO 306
<211> LENGTH: 479
<212> TYPE: DNA
<213> ORGANISM: Homo Sapiens

<400> SEQUENCE: 306
aaactgggac acttgtaatg aataattact ttgtttgtaa atcacaatag agattctcca    60
tatcaaagct gtgaactgta ttctatagta tttaggcaaa taagatagct acaaatttaa   120
gtactgtaat aatagatgcc tgacaatatg tgctataggt aaatctttga aatttattaa   180
atgaagtata gattgaatac aagtaatatg taataataca ttataattta ataacattta   240
gaataattac attttataca aaataaaat taagataaaa ttcacatagt gcaatggtga    300
staagatgtg aaaagacaat aagaataaac agcattaaaa ttattgatag agtttgtaaa   360 accccctagag attaaggaaa acaaacatag gaataaatta gaaaactaga gacaataata   420
atttctgtaa attataggct accaaaacca gaataagaat aaacaaggac tcaaaaaac    479

<210> SEQ ID NO 307
<211> LENGTH: 23
<212> TYPE: DNA
<213> ORGANISM: Homo Sapiens

<400> SEQUENCE: 307
aaactgggac acttgtaatg aat                                     23

<210> SEQ ID NO 308
<211> LENGTH: 24
<212> TYPE: DNA
<213> ORGANISM: Homo Sapiens

<400> SEQUENCE: 308
taaaattcac atagtgcaat ggtg                                    24

<210> SEQ ID NO 309
<211> LENGTH: 25
<212> TYPE: DNA
<213> ORGANISM: Homo Sapiens

<400> SEQUENCE: 309 gtttttttgag tccttgttta ttctt                                  25

<210> SEQ ID NO 310
<211> LENGTH: 463
<212> TYPE: DNA
<213> ORGANISM: Homo Sapiens
```

<400> SEQUENCE: 310

```
cagtaagtga actcacacat aattccacag gcatctgagc ccgtagcagc ctcagctgcc      60
attttgatgg caacctagat actggggttc tacagacaca actgcagcca ctgtactgct     120
ccaaggacac agaacaggta tacacacaca cccatggagg ggtatttgcc acattgctat     180
gagctgctgt tgagactgag aattggccag accatgctct tcacagcttc ttgctcctgc     240
tccttgccta ggttctccyc caccttctct ggtcttgaac ccaatatgcc attttagaga     300
gtttgatgtt ggatagtacc ccaccottgg cctgagttca ggttgatgca gttgcagtcg     360
ctgcccatcc aagaagagac aaaaacacta ggctatcctc ttcatactta gaataatatc     420
cactgctctg caacaagacg ctgtgaaact gaaataaaac tgg                       463
```

<210> SEQ ID NO 311
<211> LENGTH: 26
<212> TYPE: DNA
<213> ORGANISM: Homo Sapiens

<400> SEQUENCE: 311

```
cagtaagtga actcacacat aattcc                                           26
```

<210> SEQ ID NO 312
<211> LENGTH: 24
<212> TYPE: DNA
<213> ORGANISM: Homo Sapiens

<400> SEQUENCE: 312

```
ccagttttat ttcagtttca cagc                                             24
```

<210> SEQ ID NO 313
<211> LENGTH: 288
<212> TYPE: DNA
<213> ORGANISM: Homo Sapiens

<400> SEQUENCE: 313

```
gaacttgtcg ggaggcaatg gtgacattca ttgtgacctt agccagagct cacaatcaac      60
catggtgcac tgagactagc tcatgcacat tcatcaggca gattcaggca cctggctgtc     120
agagctgtca gccttcctca gtagaggaaa atgctacagt crgcactggc ctggtatcag     180
gaaaatagat gcctgcaaaa ayccactgtg ggaccctaaa agtcttgacc tcaggtcccc     240
tttgtgctgt ctctgttgtc aggatccact aaaggaggaa gtgtatca                  288
```

<210> SEQ ID NO 314
<211> LENGTH: 19
<212> TYPE: DNA
<213> ORGANISM: Homo Sapiens

<400> SEQUENCE: 314

```
gaacttgtcg ggaggcaat                                                   19
```

<210> SEQ ID NO 315
<211> LENGTH: 23
<212> TYPE: DNA
<213> ORGANISM: Homo Sapiens

<400> SEQUENCE: 315

```
tgatacactt cctcctttag tgg                                              23
```

<210> SEQ ID NO 316
<211> LENGTH: 572
<212> TYPE: DNA
<213> ORGANISM: Homo Sapiens

<400> SEQUENCE: 316

| | | | | | |
|---|---|---|---|---|---|
| gggaggcaac | ctaagaaagg | tgtacaactg | tcctgacatt | ggattgcctg | cttactgtga | 60 |
| agtatgtgaa | caatttgtga | ctcagaactt | tagtgagatt | tttataggca | gaagttctca | 120 |
| tcatgcctca | tcagaatttt | ccgttaacaa | gtgtcagaga | atctgtaatg | gcttgagaat | 180 |
| catgactttc | ctcctatttta | tggaagagga | gaaaaaagaa | atttcgaaga | caattctcag | 240 |
| atttagataa | attatctcag | gatttttctat | atatttttacc | tggtccctat | ggtgtggtaa | 300 |
| ggtaaagtac | actgtacttg | gacaggtgaa | gcaatttcta | ctctactagg | tcatcaccaa | 360 |
| gcatagcttt | gttactggga | aagctaatta | tagttcccta | tgacagtatc | aaagaaagaa | 420 |
| agaggtgaaa | agagtagaca | ataaggaagg | taggtatgat | tataggcatg | agaaatgyta | 480 |
| tgggtaataa | cgtgttctac | actgactcaa | gtcagcaagg | agtaggtgga | aaagcgagag | 540 |
| attcaatcca | ggatgacaga | atgcgttcac | ct | | | 572 |

<210> SEQ ID NO 317
<211> LENGTH: 19
<212> TYPE: DNA
<213> ORGANISM: Homo Sapiens

<400> SEQUENCE: 317
gggaggcaac ctaagaaag          19

<210> SEQ ID NO 318
<211> LENGTH: 20
<212> TYPE: DNA
<213> ORGANISM: Homo Sapiens

<400> SEQUENCE: 318
aggtgaacgc attctgtcat          20

<210> SEQ ID NO 319
<211> LENGTH: 572
<212> TYPE: DNA
<213> ORGANISM: Homo Sapiens

<400> SEQUENCE: 319

| | | | | | |
|---|---|---|---|---|---|
| gggaggcaac | ctaagaaagg | tgtacaactg | tcctgacatt | ggattgcctg | cttactgtga | 60 |
| agtatgtgaa | caatttgtga | ctcagaactt | tagtgagatt | tttataggca | gaagttctca | 120 |
| tcatgcctca | tcagaatttt | ccgttaacaa | gtgtcagaga | atctgtaatg | gcttgagaat | 180 |
| catgactttc | ctcctatttta | tggaagagga | gaaaaaagaa | atttcgaaga | caattctcag | 240 |
| atttagataa | attatctcag | gatttttctat | atatttttacc | tggtccctat | ggtgtggtaa | 300 |
| ggtaaagtac | actgtacttg | gacaggtgaa | gcaatttcta | ctctactagg | tcatcaccaa | 360 |
| gcatagcttt | gttactggga | aagctaatta | tagttcccta | tgacagtatc | raagaaagaa | 420 |
| agaggtgaaa | agagtagaca | ataaggaagg | taggtatgat | tataggcatg | agaaatgcta | 480 |
| tgggtaataa | cgtgttctac | actgactcaa | gtcagcaagg | agtaggtgga | aaagcgagag | 540 |
| attcaatcca | ggatgacaga | atgcgttcac | ct | | | 572 |

-continued

<210> SEQ ID NO 320
<211> LENGTH: 19
<212> TYPE: DNA
<213> ORGANISM: Homo Sapiens

<400> SEQUENCE: 320
gggaggcaac ctaagaaag                                                      19

<210> SEQ ID NO 321
<211> LENGTH: 20
<212> TYPE: DNA
<213> ORGANISM: Homo Sapiens

<400> SEQUENCE: 321
aggtgaacgc attctgtcat                                                     20

<210> SEQ ID NO 322
<211> LENGTH: 376
<212> TYPE: DNA
<213> ORGANISM: Homo Sapiens

<400> SEQUENCE: 322
caaaagcact cgggttcctt gtttcaatcc cacctcacat acacataagc atcattaaca         60
gtacagcgtg gggctcttta tcccatcttg tgcaccgctt gcctgagaga atttgctact        120
ggtcctgggg agccctgtca tattcccttta gcaggcctgc aaagatctgt gtccatttct       180
tttccaaaaa gtcattttttc tctcaacatc ccaatctcat ttccaaaact gtcaataaat       240
atcaagtttc ttagatttta ctcatttctt aagccaacgt attaaccttc taatttcrtg        300
aatgctaata gaaagcatga gacacctatg catcatataa aagtgttttt tattcgttgc        360
ataagtggga gtaaag                                                        376

<210> SEQ ID NO 323
<211> LENGTH: 19
<212> TYPE: DNA
<213> ORGANISM: Homo Sapiens

<400> SEQUENCE: 323
caaaagcact cgggttcct                                                      19

<210> SEQ ID NO 324
<211> LENGTH: 22
<212> TYPE: DNA
<213> ORGANISM: Homo Sapiens

<400> SEQUENCE: 324
ctttactccc acttatgcaa cg                                                  22

<210> SEQ ID NO 325
<211> LENGTH: 321
<212> TYPE: DNA
<213> ORGANISM: Homo Sapiens

<400> SEQUENCE: 325
agatggagcc agcagaaagg agagaagtag atgaacatcy gaaactatac ctgaatgtca         60
gagaaaagtg gattgacttc agaggaacag cttgatggtg taactttgga gaagaatccg        120
gctggagact ttagtgatct gggtagaaga taaaatcatc cacaatattt actgggttt        180 ttttttgcatt tcctgaattt gaatcttggc cagagtaaag ggaaatattc atccctcctc      240

```
cttttttagca cccattccca cttaaagcca cctctatcac ataaaatcct ccacatttac     300
catcattcaa ttcatctgtg t                                                321
```

<210> SEQ ID NO 326
<211> LENGTH: 19
<212> TYPE: DNA
<213> ORGANISM: Homo Sapiens

<400> SEQUENCE: 326

```
agatggagcc agcagaaag                                                    19
```

<210> SEQ ID NO 327
<211> LENGTH: 23
<212> TYPE: DNA
<213> ORGANISM: Homo Sapiens

<400> SEQUENCE: 327

```
acacagatga attgaatgat ggt                                               23
```

<210> SEQ ID NO 328
<211> LENGTH: 312
<212> TYPE: DNA
<213> ORGANISM: Homo Sapiens

<400> SEQUENCE: 328

```
gggtatcaaa tgtcttcaac ctaaagtaca aggaattatt tctcagtgtt tggaatgact      60
tgacttcctt gaaatatttg ttgcagagtt ggggactact tttaaaatat cctccattga     120
atgtaattct acatgaaagc ttgattttc aagtgcaaaa tgcaagtgag aaataaggca      180
tatcattcat taacccctaa ttccagcact tttaaatgag ctactttctt gtataatatt    240
ttagctatta aggaacaaat tgtygcttaa gaaatgtatc tatcttaaaa atgcaagtag    300
caggaaattc cc                                                         312
```

<210> SEQ ID NO 329
<211> LENGTH: 22
<212> TYPE: DNA
<213> ORGANISM: Homo Sapiens

<400> SEQUENCE: 329

```
gggtatcaaa tgtcttcaac ct                                               22
```

<210> SEQ ID NO 330
<211> LENGTH: 20
<212> TYPE: DNA
<213> ORGANISM: Homo Sapiens

<400> SEQUENCE: 330

```
gggaatttcc tgctacttgc                                                  20
```

<210> SEQ ID NO 331
<211> LENGTH: 389
<212> TYPE: DNA
<213> ORGANISM: Homo Sapiens

<400> SEQUENCE: 331

```
cagggaagga ccgtaaaagg ctgtggtgct gatcaacgaa ggatttctcg gagaaaattc      60
ctcctttgcg gaaatgtccg tagaaacgca cctttttttt ttcctgccag gacaaaccgc     120
cggcgatatc cgttcatgtg aaagtgttta ctaacattct ctgaagactc actgggttct    180
cagctcgaga acgttcctgt cacaagacgt ttaggaggca ggatgccggt acaatgtatt    240
```

| | |
|---|---|
| yatgttcttg taaactgttg cattaacagt gcacttcaag tgggcacatt tgtcgttgga | 300 |
| tttttttacca actcgagctt ggactttagg acggggaaaa gaagtgctaa atgtttttga | 360 |
| ataaaaccctt tactgcacat gataaacat | 389 |

<210> SEQ ID NO 332
<211> LENGTH: 20
<212> TYPE: DNA
<213> ORGANISM: Homo Sapiens

<400> SEQUENCE: 332

| | |
|---|---|
| cagggaagga ccgtaaaagg | 20 |

<210> SEQ ID NO 333
<211> LENGTH: 25
<212> TYPE: DNA
<213> ORGANISM: Homo Sapiens

<400> SEQUENCE: 333

| | |
|---|---|
| atgtttatca tgtgcagtaa aggtt | 25 |

<210> SEQ ID NO 334
<211> LENGTH: 393
<212> TYPE: DNA
<213> ORGANISM: Homo Sapiens

<400> SEQUENCE: 334

| | |
|---|---|
| aatcttctgc aaagggttcc tttgggtttt gttgttgttg ttgtttccaa tgctagccag | 60 |
| agcaataatt ctgaaaggaa accaaattcc aaaatacaat gcagatcttc gtaatattgt | 120 |
| attgtaacac agtgtatcta acataaacag tatgccaaaa acaacagaac aagttctgtt | 180 |
| tttcacattg ttttctcccc aaaatttacc tttcacacaa aacaagtacc acaaagaagt | 240 |
| gtcacagcct aagaaactgc cttagtataa cattaagagc ttacatccag atttacatct | 300 |
| gataaaatat gactgctggt attaacttta gggcatataa ggtatcttca tctcttctga | 360 |
| aagaagtggg tccagtattt tgttttgtag ctg | 393 |

<210> SEQ ID NO 335
<211> LENGTH: 20
<212> TYPE: DNA
<213> ORGANISM: Homo Sapiens

<400> SEQUENCE: 335

| | |
|---|---|
| aatcttctgc aaagggttcc | 20 |

<210> SEQ ID NO 336
<211> LENGTH: 24
<212> TYPE: DNA
<213> ORGANISM: Homo Sapiens

<400> SEQUENCE: 336

| | |
|---|---|
| cagctacaaa acaaaatact ggac | 24 |

<210> SEQ ID NO 337
<211> LENGTH: 445
<212> TYPE: DNA
<213> ORGANISM: Homo Sapiens

<400> SEQUENCE: 337

| | |
|---|---|
| acttttttcca acagttattt ttgaacttca ctgttacaca gttgaggtga cattcattat | 60 |
| aaagaataca cagaggctac tatattaacc attatatcta tatctttagt taacctgaac | 120 |

```
gaagttgagt agataaaata agattcacat taggtaaaaa aacaaaaaca aaaacaaaaa      180
caaaaacaaa aaacacaaac tctacagaag tcttgaaaag caaagagaaa ctgcctctta      240
taaaatcata tccttaaaaa agaggtgaga taaaaacaaa gcagtrtttt tatcagtact      300
gcatcctttt tttcacagtt attttcattt acagtttgaa agaggtagat aattctgcaa      360
cagacaagaa ttgaactgtg attatcaggt gtaataaaat agttccatta acttagaaat      420
attggtctca tcatcaagaa atata                                            445
```

<210> SEQ ID NO 338
<211> LENGTH: 24
<212> TYPE: DNA
<213> ORGANISM: Homo Sapiens

<400> SEQUENCE: 338

```
acttttccca acagttattt ttga                                              24
```

<210> SEQ ID NO 339
<211> LENGTH: 25
<212> TYPE: DNA
<213> ORGANISM: Homo Sapiens

<400> SEQUENCE: 339

```
tatatttctt gatgatgaga ccaat                                             25
```

<210> SEQ ID NO 340
<211> LENGTH: 445
<212> TYPE: DNA
<213> ORGANISM: Homo Sapiens

<400> SEQUENCE: 340

```
acttttccca acagttattt ttgaacttca ctgttacaca gttgaggtga cattcattat       60
aaagaataca cagaggctac tatattaacc attatatcta tatctttagt traccctgaac     120 gaagttgagt agataaaata agattcacat taggtaaaaa aacaaaaaca aaaacaaaaa      180
caaaaacaaa aaacacaaac tctacagaag tcttgaaaag caaagagaaa ctgcctctta      240
taaaatcata tccttaaaaa agaggtgaga taaaaacaaa gcagtgtttt tatcagtact      300
gcatcctttt tttcacagtt attttcattt acagtttgaa agaggtagat aattctgcaa      360
cagacaagaa ttgaactgtg attatcaggt gtaataaaat agttccatta acttagaaat      420
attggtctca tcatcaagaa atata                                            445
```

<210> SEQ ID NO 341
<211> LENGTH: 24
<212> TYPE: DNA
<213> ORGANISM: Homo Sapiens

<400> SEQUENCE: 341

```
acttttccca acagttattt ttga                                              24
```

<210> SEQ ID NO 342
<211> LENGTH: 25
<212> TYPE: DNA
<213> ORGANISM: Homo Sapiens

<400> SEQUENCE: 342

```
tatatttctt gatgatgaga ccaat                                             25
```

<210> SEQ ID NO 343
<211> LENGTH: 434
<212> TYPE: DNA
<213> ORGANISM: Homo Sapiens

<400> SEQUENCE: 343

| | | |
|---|---|---|
| ttaccacaca gttgagtagt tctaaaaaaa cagagatatg gtagaaaaag gagaggaaat | 60 |
| tttcattaca aaatcaatag ttacaactaa aagagaaaca tgtacacaaa atatatccat | 120 |
| cagtacaatg atcacactta atcttaatca atgcctagag gagatcctgt ggagagggct | 180 |
| tttgagtagc attttacttc attcattcct ttggggtcag cctccagatg gactcctggg | 240 |
| gctcttttag aggaagtgtt cagcatattg gaagaatcca ggtcagcaca ggaatgcgtc | 300 |
| acaggcactg ctaaatctac atctgctact ttcacagaga cctgcccttt cagaattccc | 360 |
| agtttctcac tgagttcatt cctttcyatt tgaagagcct tgtacagctt ctctaaccgc | 420 |
| tccaatttta tttg | 434 |

<210> SEQ ID NO 344
<211> LENGTH: 26
<212> TYPE: DNA
<213> ORGANISM: Homo Sapiens

<400> SEQUENCE: 344
ttaccacaca gttgagtagt tctaaa 26

<210> SEQ ID NO 345
<211> LENGTH: 21
<212> TYPE: DNA
<213> ORGANISM: Homo Sapiens

<400> SEQUENCE: 345
caaataaaat tggagcggtt a 21

<210> SEQ ID NO 346
<211> LENGTH: 413
<212> TYPE: DNA
<213> ORGANISM: Homo Sapiens

<400> SEQUENCE: 346

| | | |
|---|---|---|
| agtttacagt cacatcaatt tggaaagtca tacaaatatt gtcaaaaaac tgatctgaat | 60 |
| caaatatgcc atgcttgttt cttaatccat tgaagtttta cttatcattt aaatgacttg | 120 |
| acaatattag tcagtttata ttttctttta tgtagatatt atgggctcca gagtttaaat | 180 |
| tagtatttga tttcacatta ygaaaccatt ataaaaagt ctcaaattaa gataatttaa | 240 |
| ggtgatgaac acacaaacgt acactttgaa aggagaaggc aatgaaaaca tgcattccaa | 300 |
| taaaggggga aaatgaggct gatgtgcaac atagttgggg aaattggtaa gaagctttct | 360 |
| gttaccacac agttgagtag ttctaaaaaa acagagatat ggtagaaaaa gga | 413 |

<210> SEQ ID NO 347
<211> LENGTH: 24
<212> TYPE: DNA
<213> ORGANISM: Homo Sapiens

<400> SEQUENCE: 347
agtttacagt cacatcaatt tgga 24

<210> SEQ ID NO 348
<211> LENGTH: 25
<212> TYPE: DNA
<213> ORGANISM: Homo Sapiens

<400> SEQUENCE: 348
tcctttttct accatatctc tgttt                                   25

<210> SEQ ID NO 349
<211> LENGTH: 429
<212> TYPE: DNA
<213> ORGANISM: Homo Sapiens

<400> SEQUENCE: 349
aagtatgact tatgaagtac gaagaaaatc aaggctatta atcaaaaata ccagcaaaac    60
ttttcctata gaagcaaaga taatgttata attgttaatt tcttttttat ataaaataac   120
tcaccaaagg aatgcacatc tatctgcttt ctgaaaaaat aatttcaaac tgatahctgt   180
caattttaat tatcttaatt aaaataagcc atattatgtt tttctatcat ctaataagct   240
ctttagtgaa gagctaaaaa tatatataaa gaacataaaa tcatatccaa ctattaaggg   300
aagatgctat tttcatctac ttgcagtttt tctacccaaa tataaataat ttgttttagc   360
catattatct cattactgaa gtatcatagg atgactgagt agactgctca ttgtaaaatc   420
taactgaat                                                          429

<210> SEQ ID NO 350
<211> LENGTH: 27
<212> TYPE: DNA
<213> ORGANISM: Homo Sapiens

<400> SEQUENCE: 350
aagtatgact tatgaagtac gaagaaa                                 27

<210> SEQ ID NO 351
<211> LENGTH: 25
<212> TYPE: DNA
<213> ORGANISM: Homo Sapiens

<400> SEQUENCE: 351
attcagttag attttacaat gagca                                   25

<210> SEQ ID NO 352
<211> LENGTH: 429
<212> TYPE: DNA
<213> ORGANISM: Homo Sapiens

<400> SEQUENCE: 352
aagtatgact tatgaagtac gaagaaaatc aaggctatta atcaaaaata ccagcaaaac    60
ttttcctata gaagcaaaga taatgttata attgttaatt tcttttttat ataaaataac   120
tcaccaaagg aatgcacatc tatctgcttt ctgaaaaaat aatttcaaac tgataactgt   180
caattttaat tatcttaatt aaaataagcc atattatgtt tttctatcat ctaataagct   240
ctttagtgaa gagctaaaaa tatatataaa gaacataaaa tcatatccaa ctattaaggg   300
aagatgctat tttcatctac ttgcagtttt tctacccaaa tataaataat ttgttttagc   360
catattatct cattactgaa gtatcatagg atgactgagt agactgctca ttgtaaaatc   420
taactgaat                                                          429

```
<210> SEQ ID NO 353
<211> LENGTH: 26
<212> TYPE: DNA
<213> ORGANISM: Homo Sapiens

<400> SEQUENCE: 353
aagtatgact tatgaagtac gaagaa                                          26

<210> SEQ ID NO 354
<211> LENGTH: 25
<212> TYPE: DNA
<213> ORGANISM: Homo Sapiens

<400> SEQUENCE: 354
attcagttag attttacaat gagca                                           25

<210> SEQ ID NO 355
<211> LENGTH: 478
<212> TYPE: DNA
<213> ORGANISM: Homo Sapiens

<400> SEQUENCE: 355
attctaagtt tcacttcctg atccaccaca gaaatcactt tacaatgttc ttcccttcct     60
ccatcactgc attcttctca accagctgac acttgtgttt tctttatawg agtaagtggt    120
atctttcttt tgttagtaaa gtttatctca gaagctccta tggtaaaagc agcagtaacc    180
aaagcagaag tttcacatta aaagaaaaca aagttgttgt ccttaatttc aagggaatca    240
gcacatggta gctgaattct ctcaattaag actgatgtgt agctcagctc aggtgtggac    300
agtagagctg agacctcctg ctcctgaagt atatgaaaaa atgtccccga gttttctgga    360
gaaatgataa attacactaa tccatcagat tattttatat actgtcagtc ccaaagtagc    420
tcaagaatct gaaaggaaat cagtgtaaga gctagaggta gcgtaattta gggaacta     478

<210> SEQ ID NO 356
<211> LENGTH: 24
<212> TYPE: DNA
<213> ORGANISM: Homo Sapiens

<400> SEQUENCE: 356
attctaagtt tcacttcctg atcc                                            24

<210> SEQ ID NO 357
<211> LENGTH: 24
<212> TYPE: DNA
<213> ORGANISM: Homo Sapiens

<400> SEQUENCE: 357
tagttcccta aattacgcta cctc                                            24

<210> SEQ ID NO 358
<211> LENGTH: 330
<212> TYPE: DNA
<213> ORGANISM: Homo Sapiens

<400> SEQUENCE: 358
gaatgcttat gaatttccca gacacagcta ctgtactatc tccaatcagc acatttaaa     60 gaaatcttaa cttaaatagg gaaatgccaa ggtaaatgac tcaccctaag gaagtcacga    120
agtgcaagtt agagatctca gtttcagagt ttatgctcca aaccgcagtg ctatgtgttt    180
atttggggag acagataatt ctgctcttta aaattgctat tttmgcctgt atgctgaatt    240
```

| | |
|---|---|
| ggaataaccc ataacatttt tctacatcta attttaaaaa acggtttaaa ttttgtatta | 300 |
| attaagaata catcttgtat attgtgtgaa | 330 |

<210> SEQ ID NO 359
<211> LENGTH: 22
<212> TYPE: DNA
<213> ORGANISM: Homo Sapiens

<400> SEQUENCE: 359

| | |
|---|---|
| gaatgcttat gaatttccca ga | 22 |

<210> SEQ ID NO 360
<211> LENGTH: 27
<212> TYPE: DNA
<213> ORGANISM: Homo Sapiens

<400> SEQUENCE: 360

| | |
|---|---|
| ttcacacaat atacaagatg tattctt | 27 |

<210> SEQ ID NO 361
<211> LENGTH: 495
<212> TYPE: DNA
<213> ORGANISM: Homo Sapiens

<400> SEQUENCE: 361

| | |
|---|---|
| gagcttggac tttaggacgg ggaaaagaag tgctaaatgt ttttgaataa aacctttact | 60 |
| gcacatgata aacatccctt aaaaattacc taggagcacc ctaaatttta aaatgatcac | 120 |
| aaagacctgg acagattaca gtaaaccttc aacatcgcta aacacacgta ccataaatca | 180 |
| aaagaaacac actgctaatg atccgttttt tgatgtggaa ataycatgct gttttttaagg | 240 |
| gaaattatac tttattgcga tgttttattt caaaacaaga tgttacactt tatttcctat | 300 |
| aattttattt acaatatttt acacccgtta agcaaaaatc cccctacatt gctattctgt | 360 |
| tttttttttaa tcagttcact actgtagtat cttttttgttc tccatatatt tttgaaaaat | 420 |
| acgcaaaagg taagttttaa aaatcaaatg gtagattta tttggaaggg cactgccaga | 480 |
| agtgccttaa agttt | 495 |

<210> SEQ ID NO 362
<211> LENGTH: 20
<212> TYPE: DNA
<213> ORGANISM: Homo Sapiens

<400> SEQUENCE: 362

| | |
|---|---|
| gagcttggac tttaggacgg | 20 |

<210> SEQ ID NO 363
<211> LENGTH: 21
<212> TYPE: DNA
<213> ORGANISM: Homo Sapiens

<400> SEQUENCE: 363

| | |
|---|---|
| aaactttaag gcacttctgg c | 21 |

<210> SEQ ID NO 364
<211> LENGTH: 495
<212> TYPE: DNA
<213> ORGANISM: Homo Sapiens

<400> SEQUENCE: 364

```
gagcttggac tttaggacgg ggaaaagaag tgctaaatgt ttttgaataa aaccttact      60
gcacatgata acatcccctt aaaaattacc taggagcacc ctaaatttta aaatgatcac    120
aaagacctgg acagattaca gtaaaccttc aacatcgcta acacacgta ccataaatca    180
aaagaaacac actgctaatg atccgttttt tgatgtggaa atatcatgct gttttttaagg   240
gaaattatac tttattgcga tgttttattt caaaacaaga tgttacactt tatttcctat    300
aattttattt acaatatttt acacccgtta agcaaaaatc cccctacatt gctattctgt    360
ttttttttaa tcagttcact actgtagtat cttttttgttc tccatatatt tttgaaaaat   420
acgcaaaagg taagttttaa aaatcaaatg gtagatttta tttggaaggg cactgccaga    480
agtgccttaa agttt                                                      495
```

<210> SEQ ID NO 365
<211> LENGTH: 20
<212> TYPE: DNA
<213> ORGANISM: Homo Sapiens

<400> SEQUENCE: 365

```
gagcttggac tttaggacgg                                                  20
```

<210> SEQ ID NO 366
<211> LENGTH: 21
<212> TYPE: DNA
<213> ORGANISM: Homo Sapiens

<400> SEQUENCE: 366

```
aaactttaag gcacttctgg c                                                21
```

<210> SEQ ID NO 367
<211> LENGTH: 393
<212> TYPE: DNA
<213> ORGANISM: Homo Sapiens

<400> SEQUENCE: 367

```
tggtaaactc tacttagttg ccttttggaa atgaataaat caaggtagaa aagcaattga     60
gatactaatt caygctctca ggggaaaatc tgaataaagc tatcttttct aacacagagc    120
aagtgactct caaagtcaca gtatctgaac tagcatatca gcatcgcctg aatacctaga    180
aatgcaaatt cctgggcaac accagaatct aacaaagcaa aaaactatgg ggggaacagg    240
gaagtcggtt taataatact gagtttgtgc aacctcaact ttgctttata ggaaagcaaa    300
atctcaatat gataaagttt tcttcaacaa aactctgaga taactatgtt gagggaaaga    360
agttgatcac atgcaagaaa atctaattcg ctg                                 393
```

<210> SEQ ID NO 368
<211> LENGTH: 25
<212> TYPE: DNA
<213> ORGANISM: Homo Sapiens

<400> SEQUENCE: 368

```
tggtaaactc tacttagttg ccttt                                           25
```

<210> SEQ ID NO 369
<211> LENGTH: 21
<212> TYPE: DNA
<213> ORGANISM: Homo Sapiens

```
<400> SEQUENCE: 369
cagcgaatta gattttcttg c                                              21

<210> SEQ ID NO 370
<211> LENGTH: 393
<212> TYPE: DNA
<213> ORGANISM: Homo Sapiens

<400> SEQUENCE: 370
tggtaaactc tacttagttg cctttggaa atgaataaat caaggtagaa aagcaattga      60
gatactaatt catgctctca ggggaaaatc tgaataaagc tatcttttct aacacagagc    120
aagtgactct caaagtcaca gtatctgaac tagcatatca rcatcgcctg aatacctaga    180
aatgcaaatt cctgggcaac accagaatct aacaaagcaa aaaactatgg ggggaacagg    240
gaagtcggtt taataatact gagtttgtgc aacctcaact ttgctttata ggaaagcaaa    300
atctcaatat gataaagttt tcttcaacaa aactctgaga taactatgtt gagggaaaga    360
agttgatcac atgcaagaaa atctaattcg ctg                                  393

<210> SEQ ID NO 371
<211> LENGTH: 25
<212> TYPE: DNA
<213> ORGANISM: Homo Sapiens

<400> SEQUENCE: 371
tggtaaactc tacttagttg ccttt                                           25

<210> SEQ ID NO 372
<211> LENGTH: 21
<212> TYPE: DNA
<213> ORGANISM: Homo Sapiens

<400> SEQUENCE: 372
cagcgaatta gattttcttg c                                               21

<210> SEQ ID NO 373
<211> LENGTH: 393
<212> TYPE: DNA
<213> ORGANISM: Homo Sapiens

<400> SEQUENCE: 373
tggtaaactc tacttagttg cctttggaa atgaataaat caaggtagaa aagcaattga      60
gatactaatt catgctctca ggggaaaatc tgaataaagc tatcttttct aacacagagc    120
aagtgactct caaagtcaca gtatctgaac tagcatatca gcatcgcctg aatacctaga    180
aatgcaaatt cctgggcaac accagaatct aacaaagcaa aaaactatgg ggggaacagg    240
gaagtyggtt taataatact gagtttgtgc aacctcaact ttgctttata ggaaagcaaa    300
atctcaatat gataaagttt tcttcaacaa aactctgaga taactatgtt gagggaaaga    360
agttgatcac atgcaagaaa atctaattcg ctg                                  393

<210> SEQ ID NO 374
<211> LENGTH: 25
<212> TYPE: DNA
<213> ORGANISM: Homo Sapiens

<400> SEQUENCE: 374
tggtaaactc tacttagttg ccttt                                           25
```

<210> SEQ ID NO 375
<211> LENGTH: 21
<212> TYPE: DNA
<213> ORGANISM: Homo Sapiens

<400> SEQUENCE: 375
cagcgaatta gattttcttg c                                       21

<210> SEQ ID NO 376
<211> LENGTH: 367
<212> TYPE: DNA
<213> ORGANISM: Homo Sapiens

<400> SEQUENCE: 376
gccaccctct tatgcctctg gcctttacaa agacagctgg taagaggctg cccagctcat    60
ctgaagtaca ggataagatt gtctgacttg gagataccat tttccactta gcagccatgt   120
aatctttcat attcattttt tctaagtggc acttttctca gatgtaaaat ggggataatg   180
agtttattca tctttgagtt gctcccaagc agaagtcaac ttgagactat aaacttgtgc   240
tcactgcagt gcttgaaacc gagtttgtac ttaataaata gctgcataca tcttttctcta   300 yacatgtcag atgcttaatt gtgtttcccg aagatgttgc caagccgggt cctcacataa   360
ctcctga                                                             367

<210> SEQ ID NO 377
<211> LENGTH: 19
<212> TYPE: DNA
<213> ORGANISM: Homo Sapiens

<400> SEQUENCE: 377
gccaccctct tatgcctct                                         19

<210> SEQ ID NO 378
<211> LENGTH: 21
<212> TYPE: DNA
<213> ORGANISM: Homo Sapiens

<400> SEQUENCE: 378
tcaggagtta tgtgaggacc c                                       21

<210> SEQ ID NO 379
<211> LENGTH: 367
<212> TYPE: DNA
<213> ORGANISM: Homo Sapiens

<400> SEQUENCE: 379
gccaccctct tatgcctctg gcctttacaa agacagctgg taagaggctg cccagctcat    60
ctgaagtaca ggataagatt gtctgacttg gagataccat tttccactta gcagccatgt   120
aatctttcat attcattttt tctaagtggc acttttctca gatgtaaaat ggggataatg   180
agtttattca tctttgagtt gctcccaagc agaagtcaac ttgagactat aaacttgtgc   240
tcactgcagt gcttgaaacc gagtttgtac ttaataaata gctgcataca tcttttctcta   300 tacatgtcag atgcttaatt gtgtttcccg aagatgttgc caagccgggt cctcacataa   360
ctcctga                                                             367

<210> SEQ ID NO 380
<211> LENGTH: 19
<212> TYPE: DNA
<213> ORGANISM: Homo Sapiens -continued

<400> SEQUENCE: 380
gccaccctct tatgcctct                                                    19

<210> SEQ ID NO 381
<211> LENGTH: 21
<212> TYPE: DNA
<213> ORGANISM: Homo Sapiens

<400> SEQUENCE: 381
tcaggagtta tgtgaggacc c                                                 21

<210> SEQ ID NO 382
<211> LENGTH: 412
<212> TYPE: DNA
<213> ORGANISM: Homo Sapiens

<400> SEQUENCE: 382
tgaaaggaaa tcagtgtaag agctagaggt agcgtaattt agggaactaa tcaggaaaga       60
ggtattaaca tttctgaatc cttagtttca cttatccttt caattcacaa gattgcttta      120
tttcacattt tgataaagac caaaatggtc caaaataag gggaggaaga acctatacta       180
caagaaccga attcccagac actcaggata aactttaggt atatccttca atcagctttg      240
ttccaaatac aggtaacgag ccaggcaatg ttacggaaaa taagggtaag ataaagcaaa      300
tatcctgtgc tttggttaac aaacaaaact gtatcacaag tcaaactcgt acaaaaggca      360
ggagaagagg tmtggaagat ctgttaggtg ctgaactaca gtcacccttta ca             412

<210> SEQ ID NO 383
<211> LENGTH: 23
<212> TYPE: DNA
<213> ORGANISM: Homo Sapiens

<400> SEQUENCE: 383
tgaaaggaaa tcagtgtaag agc                                               23

<210> SEQ ID NO 384
<211> LENGTH: 24
<212> TYPE: DNA
<213> ORGANISM: Homo Sapiens

<400> SEQUENCE: 384
tgtaaaggtg actgtagttc agca                                              24

<210> SEQ ID NO 385
<211> LENGTH: 445
<212> TYPE: DNA
<213> ORGANISM: Homo Sapiens

<400> SEQUENCE: 385 acttttttcca acagttattt ttgaacttca ctgttacaca gttgaggtga cattcattat     60
aaagaataca cagaggctac tatattaacc attatatcta tatctttagt taacctgaac     120
gaagttgagt agataaaata agattcacat taggtaaaaa aacaaaaaca aaacaaaaa       180 caaaacaaa aaacacaaac tctacagaag tcttgaaaag caaagagaa ctgcctctta        240 taaaatcata tccttaaaaa agaggtgaga taaaaacaaa gcagtgtttt tatcagtact     300
gcatcctttt tttcacagtt attttcattt acagtttgaa agaggtagat aattctgcaa     360
cagacaagaa ttgaactgtg attatcaggt gtaataaaat agttccatta acttagaaat     420
attggtctca tcatcaagaa atata                                            445

```
<210> SEQ ID NO 386
<211> LENGTH: 24
<212> TYPE: DNA
<213> ORGANISM: Homo Sapiens

<400> SEQUENCE: 386
acttttccca acagttattt ttga                                              24

<210> SEQ ID NO 387
<211> LENGTH: 25
<212> TYPE: DNA
<213> ORGANISM: Homo Sapiens

<400> SEQUENCE: 387
tatatttctt gatgatgaga ccaat                                             25

<210> SEQ ID NO 388
<211> LENGTH: 255
<212> TYPE: DNA
<213> ORGANISM: Homo Sapiens

<400> SEQUENCE: 388
aatggcttac tacaaagaac atttctgtag tatattttta tgtatgtatg tattatgtat       60
ttatttattt atttatttttt gagacagagt cacaatgctg cccaggccct agtgcagtgg     120
tgtgatctta gcttactgca acatctgctt ctgtgttcaa gagattctcc tgccttagcc     180
tgtggagtag ctggaattac aggtgcacac caccaagccc rgctaatttt tatcttcttt     240
ggtagagacc gtgta                                                      255

<210> SEQ ID NO 389
<211> LENGTH: 25
<212> TYPE: DNA
<213> ORGANISM: Homo Sapiens

<400> SEQUENCE: 389
aatggcttac tacaaagaac atttc                                             25

<210> SEQ ID NO 390
<211> LENGTH: 23
<212> TYPE: DNA
<213> ORGANISM: Homo Sapiens

<400> SEQUENCE: 390
tacacggtct ctaccaaaga aga                                               23

<210> SEQ ID NO 391
<211> LENGTH: 306
<212> TYPE: DNA
<213> ORGANISM: Homo Sapiens

<400> SEQUENCE: 391
cacacccaga atacaataat tttaaaaaca taataaaggt caatttagag cagagaaatt       60
attcttttaa attacaaatg tttgctgttc aggcaaatta cacagaaagt taagaataac     120
cctttaaatg ataggaaaag gcattagtaa gataaaatgt gattactatt gagataaata     180
tttgctataa aaataattca atttggttaa acacaaattg acttcttaaa taatcttaaa     240
cattaagtag aagtaatttt agcttatcag taaatttgag aaaatgtaca cttgtagaat     300
aaaaag                                                                306
```

```
<210> SEQ ID NO 392
<211> LENGTH: 23
<212> TYPE: DNA
<213> ORGANISM: Homo Sapiens

<400> SEQUENCE: 392
cacacccaga atacaataat ttt                                              23

<210> SEQ ID NO 393
<211> LENGTH: 27
<212> TYPE: DNA
<213> ORGANISM: Homo Sapiens

<400> SEQUENCE: 393 cttttttattc tacaagtgta cattttc                                         27

<210> SEQ ID NO 394
<211> LENGTH: 568
<212> TYPE: DNA
<213> ORGANISM: Homo Sapiens

<400> SEQUENCE: 394
aacagaatta tcaggaaaag gtttcataaa ataaaaatct tttaaactta tgaaagatgc      60
tcaatataaa aaactgtaaa ccagggaaat gcaaataaaa attacaatga aatactacac     120
acctcccaga atggctaaaa tgaaaacaaa actgtcaatt ctaagtgtta gtgaggacat     180
gtggtaacca gaactggcat ccaatactag ctgataaact cgtcaatcat ttgtaaaaac     240
agtctgacaa taatccacta gtgaaaatat acatagtctc agtcacagca attctatcct     300
gtctatctag gtaacagaaa tgtctacata cgttacctag aaacatatac tttaatatcc     360
acagaattac ttgaaatagc caaaaattgg taactaccaa aagttgaatg gtaaaacaga     420
tagaaaaaaa gctatgccta acaaaactac acttaataga acacaagcgt gagcattaat     480
akaaccatat aaatgcattt tttgaaccac taaaagaaga agccaataca aaagaggtga     540
ttaattgaaa gtacacgaac aagtaaaa                                        568

<210> SEQ ID NO 395
<211> LENGTH: 24
<212> TYPE: DNA
<213> ORGANISM: Homo Sapiens

<400> SEQUENCE: 395
aacagaatta tcaggaaaag gttt                                             24

<210> SEQ ID NO 396
<211> LENGTH: 24
<212> TYPE: DNA
<213> ORGANISM: Homo Sapiens

<400> SEQUENCE: 396
ttttacttgt tcgtgtactt tcaa                                             24

<210> SEQ ID NO 397
<211> LENGTH: 211
<212> TYPE: DNA
<213> ORGANISM: Homo Sapiens

<400> SEQUENCE: 397
tgaaatggaa atcaataaac tcagtttcct caaagttcaa atacatgag actgcctacc       60 ctccttggaa ggcaaggtgg ggctttctga agcaaatacc agctttaaaa aaaaatgtat     120
```

```
atatatatga agatatatac aaaaaaaaaa tttccccaca accagacaat cagaatcatc      180
aaacccagaa gggttaaaga aaagaaaag g                                     211

<210> SEQ ID NO 398
<211> LENGTH: 25
<212> TYPE: DNA
<213> ORGANISM: Homo Sapiens

<400> SEQUENCE: 398
tgaaatggaa atcaataaac tcagt                                            25

<210> SEQ ID NO 399
<211> LENGTH: 24
<212> TYPE: DNA
<213> ORGANISM: Homo Sapiens

<400> SEQUENCE: 399
cctttctttt ttctttaacc cttc                                             24

<210> SEQ ID NO 400
<211> LENGTH: 232
<212> TYPE: DNA
<213> ORGANISM: Homo Sapiens

<400> SEQUENCE: 400
agaatcatca aacccagaag ggttaaagaa aagaaaagg cccaggaaag tatgattggt       60
ggggatcaaa agtatctctc cacagtggta aatgagaatt ctcaaaaaga gtaaaattat    120
aattctcatg cacatataaa ataaatatgt attacagatt ttacttaaac catatagctc    180
aaaattagct aacaaggaag acattataac ctgttcaaag agaagccaaa ga            232

<210> SEQ ID NO 401
<211> LENGTH: 21
<212> TYPE: DNA
<213> ORGANISM: Homo Sapiens

<400> SEQUENCE: 401
agaatcatca aacccagaag g                                                21

<210> SEQ ID NO 402
<211> LENGTH: 22
<212> TYPE: DNA
<213> ORGANISM: Homo Sapiens

<400> SEQUENCE: 402
tctttggctt ctctttgaac ag                                               22

<210> SEQ ID NO 403
<211> LENGTH: 212
<212> TYPE: DNA
<213> ORGANISM: Homo Sapiens

<400> SEQUENCE: 403
tgaaatggaa atcaataaac tcagtttcct caaagttcaa atacatgag actgcctacc       60 ctccttggaa ggcaaggtgg ggctttctga agcaaatacc agctttaaaa aaaaatgtat    120 atatatga agatatatac aaaaaaaaac atttccccac aaccagacaa tcagaatcat     180
caaacccaga agggttaaag aaaagaaaa gg                                   212
```

```
<210> SEQ ID NO 404
<211> LENGTH: 25
<212> TYPE: DNA
<213> ORGANISM: Homo Sapiens

<400> SEQUENCE: 404
tgaaatggaa atcaataaac tcagt                                            25

<210> SEQ ID NO 405
<211> LENGTH: 24
<212> TYPE: DNA
<213> ORGANISM: Homo Sapiens

<400> SEQUENCE: 405
cctttctttt ttctttaacc cttc                                             24

<210> SEQ ID NO 406
<211> LENGTH: 339
<212> TYPE: DNA
<213> ORGANISM: Homo Sapiens

<400> SEQUENCE: 406
atgtgaagac aacactgtgt gggagaacct aggaaagtaa ttttacatgc taaaatgagt      60
ttccctagtt aatgttaaca tgaactacca accgtattac cttctcctca ggagataagt     120
tttgtttgct attgctgaca ggaaagccac tgccaaattc tttggaatga atatcagctc     180
catattcaac tgtcaygtct tcctcaatgc tgctcaccag cctccagaat tccttctcta     240
caagttctgt aggcaccatc tgtgaaaaca catgtaaaag gttatcatag cccactatac     300
tttggactca tgtctccatg agaactaaga ctaccacaa                            339

<210> SEQ ID NO 407
<211> LENGTH: 22
<212> TYPE: DNA
<213> ORGANISM: Homo Sapiens

<400> SEQUENCE: 407
atgtgaagac aacactgtgt gg                                               22

<210> SEQ ID NO 408
<211> LENGTH: 24
<212> TYPE: DNA
<213> ORGANISM: Homo Sapiens

<400> SEQUENCE: 408
ttgtggtagt cttagttctc atgg                                             24

<210> SEQ ID NO 409
<211> LENGTH: 393
<212> TYPE: DNA
<213> ORGANISM: Homo Sapiens

<400> SEQUENCE: 409
tggtaaactc tacttagttg cctttggaa atgaataaat caaggtagaa aagcaattga       60
gatactaatt catgctctca ggggaaaatc tgaataaagc tatcttttct aacacagagc     120
aagtgactct caaagtcaca gtatctgaac tagcatatca gcatcgcctg aatacctaga     180
aatgcaaatt cctgggcaac accagaatct aacaaagcaa aaaactatgg ggggaacagg     240
gaagtcggtt taataatact gagtttgtgc aacctcaact ttgctttaya ggaaagcaaa     300
```

```
atctcaatat gataaagttt tcttcaacaa aactctgaga taactatgtt gagggaaaga        360
agttgatcac atgcaagaaa atctaattcg ctg                                    393
```

<210> SEQ ID NO 410
<211> LENGTH: 25
<212> TYPE: DNA
<213> ORGANISM: Homo Sapiens

<400> SEQUENCE: 410

```
tggtaaactc tacttagttg cctttt                                             25
```

<210> SEQ ID NO 411
<211> LENGTH: 21
<212> TYPE: DNA
<213> ORGANISM: Homo Sapiens

<400> SEQUENCE: 411

```
cagcgaatta gattttcttg c                                                  21
```

<210> SEQ ID NO 412
<211> LENGTH: 442
<212> TYPE: DNA
<213> ORGANISM: Homo Sapiens

<400> SEQUENCE: 412

```
aacttccaaa actgtgaaaa gattgttttt aaaaggctat aacagtgact ttcaggtgaa         60
gacttggaca aatagataat ttctgtaccc attaaaatca ggggctgtta ctatgtttga        120
agacattgtc gccacagctt gaagtctgta aggaaaacct gtaaaattag tgggtgccca        180
ctctagtttt aatcatttga gtttccactc ctcattgtgg ttgaactatt ttataactct        240
gcaaaatcta gaaagttgaa aagaaaccaa agatactttc ccttttcttc ycacttctcc        300 taccccttggc ccacctcctt ctccacctac tactccacat ggaacctgga gatttgagtc       360
ggggagtgat gtaatacctg cggcgcgttg gcccctttaca cacctgtcag ccatttcaag       420
gcctgaaggg gctgctttaa tc                                                442
```

<210> SEQ ID NO 413
<211> LENGTH: 24
<212> TYPE: DNA
<213> ORGANISM: Homo Sapiens

<400> SEQUENCE: 413

```
aacttccaaa actgtgaaaa gatt                                               24
```

<210> SEQ ID NO 414
<211> LENGTH: 20
<212> TYPE: DNA
<213> ORGANISM: Homo Sapiens

<400> SEQUENCE: 414

```
gattaaagca gccccttcag                                                    20
```

<210> SEQ ID NO 415
<211> LENGTH: 460
<212> TYPE: DNA
<213> ORGANISM: Homo Sapiens

<400> SEQUENCE: 415

```
ttactgataa tgccatattg ttttggctta atatcaggct aagtaaccac agtattctga         60
tttaaaaaaa aacatactag agagcaagtt tattgacaaa tctttaggaa cttcaggtac        120
```

```
agcatatgat tctgaacta tgtgtgtaaa taaggttttg tttattcaaa tttaacacag    180
ggtagtctgt gtatgccttc cgatttgata gctctaataa aacactttaa tagtaccata    240
tcaaataaat tttatcatca tcgattttct tcttaatatg aaataacaca tatttgtgat    300
ttttctaaga gtcaaaatct caaaaatcat tttaggtata aaatatatccc cgaaagtttt    360 attttattcc attttataat taatctgact tggaaagggg gaaaaaagct caaagggtat    420
gtgaacattt cattaagata ggaccattgg tgtctgagaa                          460

<210> SEQ ID NO 416
<211> LENGTH: 25
<212> TYPE: DNA
<213> ORGANISM: Homo Sapiens

<400> SEQUENCE: 416
ttactgataa tgccatattg ttttg                                           25

<210> SEQ ID NO 417
<211> LENGTH: 21
<212> TYPE: DNA
<213> ORGANISM: Homo Sapiens

<400> SEQUENCE: 417
ttctcagaca ccaatggtcc t                                               21

<210> SEQ ID NO 418
<211> LENGTH: 460
<212> TYPE: DNA
<213> ORGANISM: Homo Sapiens

<400> SEQUENCE: 418
ttactgataa tgccatattg ttttggctta atatcaggct aagtaaccac agtattctga    60
tttaaaaaaa aaacatacta gagagcaagt ttattgacaa atctttagga acttcaggta    120
cagcatatga tttctgaact atgtgtgtaa ataaggtttt gtttattcaa atttaacaca    180
gggtagtctg tgtatgcctt ccgatttgat agctctaata aaacacttta atagtaccat    240
atcaaataaa tttatcatc atcgattttc tcttaatat gaaataacac atatttgtga    300
tttttctaag agtcaaaatc tcaaaaatca tttaggtat aaaatatacc cgaaagttt    360 tattttattc cattttataa ttaatctgac ttggaaaggg gaaaaaagct caaagggtat    420
gtgaacattt cattaagata ggaccattgg tgtctgagaa                          460

<210> SEQ ID NO 419
<211> LENGTH: 25
<212> TYPE: DNA
<213> ORGANISM: Homo Sapiens

<400> SEQUENCE: 419
ttactgataa tgccatattg ttttg                                           25

<210> SEQ ID NO 420
<211> LENGTH: 21
<212> TYPE: DNA
<213> ORGANISM: Homo Sapiens

<400> SEQUENCE: 420
ttctcagaca ccaatggtcc t                                               21
```

<210> SEQ ID NO 421
<211> LENGTH: 424
<212> TYPE: DNA
<213> ORGANISM: Homo Sapiens

<400> SEQUENCE: 421

```
catcttaaaa tacatttcat agcttttcaa actcaaatat gaaaacaatt wgttttttag      60
attttttttt tcttttact tcaagttctt tatattctag actaacactt tagggcagat     120
attggagggt gtgtctctct tggtgcaact attgcctttg cttcaaatgg tggcatatgg    180
aggaggacac aacctgtagg aagtgttcaa ggagtctggt agtgacacct gctcaatatt    240
gctagtgata aaactgtagc cactgtatag caatatctgc ctgtagaatg tcatttcctt    300
tgagggtac attttttta gagtttccta taacctctag agctgaactt cataaaaata     360
ggtaaaggtt ggccttaaaa agcctacatt acacactttc aggatgctag acctaatagt    420
aagc                                                                 424
```

<210> SEQ ID NO 422
<211> LENGTH: 26
<212> TYPE: DNA
<213> ORGANISM: Homo Sapiens

<400> SEQUENCE: 422

```
catcttaaaa tacatttcat agcttt                                          26
```

<210> SEQ ID NO 423
<211> LENGTH: 24
<212> TYPE: DNA
<213> ORGANISM: Homo Sapiens

<400> SEQUENCE: 423

```
gcttactatt aggtctagca tcct                                            24
```

<210> SEQ ID NO 424
<211> LENGTH: 424
<212> TYPE: DNA
<213> ORGANISM: Homo Sapiens

<400> SEQUENCE: 424

```
catcttaaaa tacatttcat agcttttcaa actcaaatat gaaaacaatt tgttttttag     60
attttttttt tcttttact tcaagttctt tatattctag actaacactt tagggcagat     120
attggagggt gtgtctctct tggtgcaact attgcctttg cttcaaatgg tggcatatgg    180
aggaggacac aacctgtagg aagtgttcaa ggagtctggt agtgacacct gctcaatatt    240
gctagtgata aaactgtagc cactgtatag caatatctgc ctgtagaatg tcatttcctt    300
tgagggtac attttttta gagtttccta taacctctag agctgaactt cataaaaata     360
ggtaaaggtt ggccttaaaa agcctacatt acacactttc aggatgctag acctaatagt    420
aagc                                                                 424
```

<210> SEQ ID NO 425
<211> LENGTH: 26
<212> TYPE: DNA
<213> ORGANISM: Homo Sapiens

<400> SEQUENCE: 425

```
catcttaaaa tacatttcat agcttt                                          26
```

```
<210> SEQ ID NO 426
<211> LENGTH: 24
<212> TYPE: DNA
<213> ORGANISM: Homo Sapiens

<400> SEQUENCE: 426
gcttactatt aggtctagca tcct                                           24

<210> SEQ ID NO 427
<211> LENGTH: 385
<212> TYPE: DNA
<213> ORGANISM: Homo Sapiens

<400> SEQUENCE: 427
atgctataat aactaggtgt tgaagataaa atcagtttaa tttaaataag aggataaaag    60
aagtatgagc agaaaaaggt tttcaatatt aactaggaaa gtctgaaaaa taatcagaaa   120
ttctaaagat aaaaacataa cattaaaaat tataaactaa gttgtttaat agattaggta   180
ttttaaaaac tggtgcattt ttaagttgct ttaagtaagt tacttaaaag acaacagcag   240
caaaakaatt aaaaaaaaat gaaaggtgaa gaaacacata caagagaacc ttagaacagt   300
aaggttctag ctaacaggag aaataaatta cagactgtaa aagttgatga ccaagaattt   360
tttcagaagt ggtaaaagct gaatt                                        385

<210> SEQ ID NO 428
<211> LENGTH: 25
<212> TYPE: DNA
<213> ORGANISM: Homo Sapiens

<400> SEQUENCE: 428
atgctataat aactaggtgt tgaag                                         25

<210> SEQ ID NO 429
<211> LENGTH: 24
<212> TYPE: DNA
<213> ORGANISM: Homo Sapiens

<400> SEQUENCE: 429
aattcagctt ttaccacttc tgaa                                          24

<210> SEQ ID NO 430
<211> LENGTH: 452
<212> TYPE: DNA
<213> ORGANISM: Homo Sapiens

<400> SEQUENCE: 430
agcacaaggg tcacattgag aggttttaac tataattaaa ttttcatcta ataaatatga    60
taattataaa gaaaaccagc tggttttttgg aagacatcaa agtgttctgt atcaagcaat   120
aatctccatt aacctattct gaatggcagg agcagtatgg actgcatatt ctgaactttg   180
ggaggtaaat ctgtgttgga gctgctcact gtccatggag gagtggagca caaagtatct   240
gggggtgaag gtcatggcac catttttcag caggggggagg ataattttt ggtttgaaat   300 attcaaaaaa aaatttgaaa aaattaaact gggtatgtgt gyatttgacc atagtaaaaa   360
aattttaaca gacctttttt tgattatcat tacataaatac aaataaaatt tactgataat   420
tcaaaaattt gaacaacaaa aagccttgtc ct                                452
```

```
<210> SEQ ID NO 431
<211> LENGTH: 20
<212> TYPE: DNA
<213> ORGANISM: Homo Sapiens

<400> SEQUENCE: 431
agcacaaggg tcacattgag                                                    20

<210> SEQ ID NO 432
<211> LENGTH: 21
<212> TYPE: DNA
<213> ORGANISM: Homo Sapiens

<400> SEQUENCE: 432
aggacaaggc tttttgttgt t                                                  21

<210> SEQ ID NO 433
<211> LENGTH: 208
<212> TYPE: DNA
<213> ORGANISM: Homo Sapiens

<400> SEQUENCE: 433
ttcagcaaga gtaagcaaga ggcactgagc cgctggagtc tgcacattga taaatttact        60
tacagtcgta aataaattgc atcatcttca gctagtaaca cagagtctaa tttttatagc       120
ggcatacttg cctccacgac tttcctagac accagaaaga aaggcragag ccagccttag       180
cctaatcaag aaccatgatc caaaaagg                                          208

<210> SEQ ID NO 434
<211> LENGTH: 22
<212> TYPE: DNA
<213> ORGANISM: Homo Sapiens

<400> SEQUENCE: 434
ttcagcaaga gtaagcaaga gg                                                 22

<210> SEQ ID NO 435
<211> LENGTH: 21
<212> TYPE: DNA
<213> ORGANISM: Homo Sapiens

<400> SEQUENCE: 435
cctttttgga tcatggttct t                                                  21

<210> SEQ ID NO 436
<211> LENGTH: 395
<212> TYPE: DNA
<213> ORGANISM: Homo Sapiens

<400> SEQUENCE: 436
gaatggggtg ttacatggag actacagggc tgttatattc ataactttag gctatcatta        60
ttgagggctg gatgtccctc tgagcctcag gattcaaagg atactgtttt gttttgtttt       120
gttttgtttt gttttttccc mcgggtaatt aacactgggt tttaggacag tctggactgg       180
gggtacatta acagttgtac tagaaacttc catgtctcaa acagagggt ctactagaga        240 agcaatatgt catggaaggc agttcttctc catatctgtg taaaggcaag tatttgaagc       300
taggagaact gttccttctg gcctgttgcc ctctcacaga gcactttaaa gtgagctgtg       360
atgtgtaact tggaaaacag gtctctcata atagg                                  395
```

<210> SEQ ID NO 437
<211> LENGTH: 21
<212> TYPE: DNA
<213> ORGANISM: Homo Sapiens

<400> SEQUENCE: 437 gaatgggtg ttacatggag a                                        21

<210> SEQ ID NO 438
<211> LENGTH: 24
<212> TYPE: DNA
<213> ORGANISM: Homo Sapiens

<400> SEQUENCE: 438
cctattatga gagacctgtt ttcc                                    24

<210> SEQ ID NO 439
<211> LENGTH: 440
<212> TYPE: DNA
<213> ORGANISM: Homo Sapiens

<400> SEQUENCE: 439
gtattctggg gcaattttag ggcaaaatac ctgaataagc tggtgaaaga aaaaaaaga    60 tactatcaga ttaatataaa ctcatataag tgcaattatg ttttttttgtt tgttttgttt  120 ttttctttca gagacagggt ctccctctgt caccttggct gaagtacagt gacatgatca  180
tggatcactg tagcctcgac ctcctggcct taaacaatcc ttctaccttg gcctccagag  240
tggctggaac tacaactgca caccaccccg tatggccact ttttttttttt tcccactttt  300 gtagcaatat ggtacccagg ctggtcttga actcctcttg tcaagcaatc ttcctatctt  360
ggcctcccaa aatgcttgga ttacaggtgt gagccaccac gcctggccac agttatgctt  420
aaaataacct cttgtatcaa                                             440

<210> SEQ ID NO 440
<211> LENGTH: 21
<212> TYPE: DNA
<213> ORGANISM: Homo Sapiens

<400> SEQUENCE: 440
gtattctggg gcaattttag g                                       21

<210> SEQ ID NO 441
<211> LENGTH: 25
<212> TYPE: DNA
<213> ORGANISM: Homo Sapiens

<400> SEQUENCE: 441
ttgatacaag aggttatttt aagca                                   25

<210> SEQ ID NO 442
<211> LENGTH: 276
<212> TYPE: DNA
<213> ORGANISM: Homo Sapiens

<400> SEQUENCE: 442
gggcaaaata cctgaataag ctggtgaaag aaaaaaaaag atactatcag attaatataa   60
actcatataa gtgcaattat gttttttttgt ttgttttgtt ttttctttc agagacaggg  120 tctccctctg tcaccttggc tgaagtacag tgacatgatc atggatcact gtagcctcga  180

```
cctcctggcc ttaaacaatc cttctacctt ggcctccaga gtggctggaa ctacaactgc      240
acaccacccc gtatggccac ttttttttt ttccca                                  276
```

<210> SEQ ID NO 443
<211> LENGTH: 568
<212> TYPE: DNA
<213> ORGANISM: Homo Sapiens

<400> SEQUENCE: 443

```
aacagaatta tcaggaaaag gtttcataaa ataaaaatct tttaaactta tgaaagatgc      60
tcaatataaa aaactgtaaa ccagggaaat gcaaataaaa attacaatga aatactacac     120
acctcccaga atggctaaaa tgaaaacaaa actgtcaatt ctaagtgtta gtgaggacat     180
gtggtaacca gaactggcat ccaatactag ctgataaact cgtcaatcat ttgtaaaaac     240
agtctgacaa taatccacta gtgaaaatat acatagtctc agtcacagca attctatcct     300
gtctatctag gtarcagaaa tgtctacata cgttacctag aaacatatac tttaatatcc     360
acagaattac ttgaaatagc caaaaattgg taactaccaa agttgaatg gtaaaacaga      420 tagaaaaaaa gctatgccta acaaaactac acttaataga acacaagcgt gagcattaat     480
agaaccatat aaatgcattt tttgaaccac taaaagaaga agccaataca aaagaggtga     540
ttaattgaaa gtacacgaac aagtaaaa                                         568
```

<210> SEQ ID NO 444
<211> LENGTH: 24
<212> TYPE: DNA
<213> ORGANISM: Homo Sapiens

<400> SEQUENCE: 444

```
aacagaatta tcaggaaaag gttt                                             24
```

<210> SEQ ID NO 445
<211> LENGTH: 24
<212> TYPE: DNA
<213> ORGANISM: Homo Sapiens

<400> SEQUENCE: 445

```
ttttacttgt tcgtgtactt tcaa                                             24
```

<210> SEQ ID NO 446
<211> LENGTH: 568
<212> TYPE: DNA
<213> ORGANISM: Homo Sapiens

<400> SEQUENCE: 446

```
aacagaatta tcaggaaaag gtttcataaa ataaaaatct tttaaactta tgaaagatgc      60
tcaatataaa aaactgtaaa ccagggaaat gcaaataaaa attacaatga aatactacac     120
acctcccaga atggctaaaa tgaaaacaaa actgtcaatt ctaagtgtta gtgaggacat     180
gtggtaacca gaactggcat ccaatactag ctgataaact cgtcaatcat ttgtaaaaac     240
agtctgacaa taatccacta gtgaaaatat acatagtctc agtcacagca attctatcct     300
gtctatctag gtaacagaaa tgtctacata cgttacctag aaacatatac tttaatatcc     360
acagaattac ttgaaatagc caaaaattgg taactaccaa agttgaatg gtaaaacaga      420 tagaaaaaaa gctatgccta acaaaactac acttaataga acacaagcrt gagcattaat     480
agaaccatat aaatgcattt tttgaaccac taaaagaaga agccaataca aaagaggtga     540
ttaattgaaa gtacacgaac aagtaaaa                                         568
```

<210> SEQ ID NO 447
<211> LENGTH: 24
<212> TYPE: DNA
<213> ORGANISM: Homo Sapiens

<400> SEQUENCE: 447
aacagaatta tcaggaaaag gttt                                              24

<210> SEQ ID NO 448
<211> LENGTH: 24
<212> TYPE: DNA
<213> ORGANISM: Homo Sapiens

<400> SEQUENCE: 448
ttttacttgt tcgtgtactt tcaa                                              24

<210> SEQ ID NO 449
<211> LENGTH: 289
<212> TYPE: DNA
<213> ORGANISM: Homo Sapiens

<400> SEQUENCE: 449
gcagtggaga tgaagtgaga ctgggctttg gagaggtgag gagatggggc actgacacac       60
actgcccatg gaaccagtcc tgacacaggt cacactgcag aactcccacc ccagctggca      120
cctgcccaca cacacagata gaagtyggag aagaggccat gagggatggt gccagtggac      180
tgggcttggc tgagttggtg cgacgcagct gcaggatacc ctccttctcc ttctgttccc      240
cttccttgaa ggccacaatc tgccatatcc agaagagggg gaaagtagg                 289

<210> SEQ ID NO 450
<211> LENGTH: 21
<212> TYPE: DNA
<213> ORGANISM: Homo Sapiens

<400> SEQUENCE: 450
gcagtggaga tgaagtgaga c                                                 21

<210> SEQ ID NO 451
<211> LENGTH: 20
<212> TYPE: DNA
<213> ORGANISM: Homo Sapiens

<400> SEQUENCE: 451
cctactttcc ccctcttctg                                                   20

<210> SEQ ID NO 452
<211> LENGTH: 422
<212> TYPE: DNA
<213> ORGANISM: Homo Sapiens

<400> SEQUENCE: 452
acttaattta tagtttcaat ccctcagtaa ttttaactta cttctatttt aagaactata       60
accaaactat ctgtaagact tttaagcact atcatactca gctacacatc tcttaacaaa      120
agaggtaaat tttgtccttt tttgaacgtc atagagtata ctcacacaaa ccaagaagaa      180
acaatctact acataccttac gctatatgrt atataactat tgctcctagg ctacaaatta    240
gtgcgacact attgtactga atattatagg ccatgtaaca caatggttta agtatctgtg      300
cctctaaaca cagaaaagat atagtgaaag tacagtattg ctccttttatt aaactcaaaa    360

```
tgttatgcag catatgaccg actataaaat agcgcttatc cagatacaga catctccatg    420
aa                                                                   422

<210> SEQ ID NO 453
<211> LENGTH: 26
<212> TYPE: DNA
<213> ORGANISM: Homo Sapiens

<400> SEQUENCE: 453
acttaattta tagtttcaat ccctca                                         26

<210> SEQ ID NO 454
<211> LENGTH: 23
<212> TYPE: DNA
<213> ORGANISM: Homo Sapiens

<400> SEQUENCE: 454
ttcatggaga tgtctgtatc tgg                                            23

<210> SEQ ID NO 455
<211> LENGTH: 287
<212> TYPE: DNA
<213> ORGANISM: Homo Sapiens

<400> SEQUENCE: 455
aagctatttt ggtttccttt caagaaaggg ctgtggtctg tggaaggtgt caggaacata    60
ttttccacgg tctgctttct cctgataatg ttcttcttct yggcccacct gagacataat    120
ccctgagctc cgagcccttt tgactgaagc tcctgttga acaagattct caacgtttct     180
accctgatcc accttctgcc gccgccgtcg cctctccaga gcccggctcc ttgtccgact    240
cccttgatgt tcaaattttt ccagctgcaa tcataccccac acaaggc                 287

<210> SEQ ID NO 456
<211> LENGTH: 22
<212> TYPE: DNA
<213> ORGANISM: Homo Sapiens

<400> SEQUENCE: 456
aagctatttt ggtttccttt ca                                             22

<210> SEQ ID NO 457
<211> LENGTH: 20
<212> TYPE: DNA
<213> ORGANISM: Homo Sapiens

<400> SEQUENCE: 457
gccttgtgtg ggtatgattg                                                20

<210> SEQ ID NO 458
<211> LENGTH: 459
<212> TYPE: DNA
<213> ORGANISM: Homo Sapiens

<400> SEQUENCE: 458
ttactgataa tgccatattg ttttggctta atatcaggct aagtaaccac agtattctga    60
tttaaaaaaa aacatactag agagcaagtt tattgacaaa tctttaggaa cttcaggtac    120
agcatatgat ttctgaacta tgtgtgtaaa taaggttttg tttattcaaa tttaacacag    180
ggtagtctgt gtatgccttc cgatttgata gctctaataa aacactttaa tagtaccata    240
tcaaataaat tttatcatca tcgatttttct tcttaatatg aaataacaca tatttgtgat   300
```

```
tttctaaga gtcaaaatct caaaaatcat tttaggtata aaatataccc cgaaagtttt      360
attttattcc attttataat taatctgact tggaaagggg aaaaaagctc aaagggtatg      420
tgaacawttc attaagatag gaccattggt gtctgagaa                             459
```

<210> SEQ ID NO 459
<211> LENGTH: 25
<212> TYPE: DNA
<213> ORGANISM: Homo Sapiens

<400> SEQUENCE: 459

```
ttactgataa tgccatattg ttttg                                            25
```

<210> SEQ ID NO 460
<211> LENGTH: 21
<212> TYPE: DNA
<213> ORGANISM: Homo Sapiens

<400> SEQUENCE: 460

```
ttctcagaca ccaatggtcc t                                                21
```

<210> SEQ ID NO 461
<211> LENGTH: 422
<212> TYPE: DNA
<213> ORGANISM: Homo Sapiens

<400> SEQUENCE: 461

```
acttaattta tagtttcaat ccctcagtaa ttttaactta cttctatttt aagaactata      60
accaaactat ctgtaagact tttaagcact atcatactca gctacacatc tcttaacaaa      120
agaggtaaat tttgtccttt tttgaacgtc atagagtata ctcacacaaa ccaagaagaa      180
acaatctact acatacctac gctatatggt atataactat tgctcctagg ctacaaatta      240
gtgcgacact aytgtactga atattatagg ccatgtaaca caatggttta agtatctgtg      300
cctctaaaca cagaaaagat atagtgaaag tacagtattg ctcctttatt aaactcaaaa      360
tgttatgcag catatgaccg actataaaat agcgcttatc cagatacaga catctccatg      420
aa                                                                    422
```

<210> SEQ ID NO 462
<211> LENGTH: 26
<212> TYPE: DNA
<213> ORGANISM: Homo Sapiens

<400> SEQUENCE: 462

```
acttaattta tagtttcaat ccctca                                           26
```

<210> SEQ ID NO 463
<211> LENGTH: 23
<212> TYPE: DNA
<213> ORGANISM: Homo Sapiens

<400> SEQUENCE: 463

```
ttcatggaga tgtctgtatc tgg                                              23
```

<210> SEQ ID NO 464
<211> LENGTH: 327
<212> TYPE: DNA
<213> ORGANISM: Homo Sapiens

<400> SEQUENCE: 464

```
tctctaactt ctgtgagcca ctctagcaaa ttaattgaac caaaggagga ggttaaggac      60
agcatagttt acaaaatgag ccctgtttct gacatctgaa gtgggggcag tctagtgggc     120
ctgacctctt aacttgtaga aacattcttt ctttctagat gactagtgac cagaattaaa     180
ttgaatccta ggccacccat ttattgtctt ctgcagaatt ggcgagaatg gagaggaatc     240
ctcacctatc rgtgaccaga gatgaaatat tctgaattga gagtttaaaa gagcacactt     300
agaagagatt tagagtttag tttttcc                                         327
```

<210> SEQ ID NO 465
<211> LENGTH: 21
<212> TYPE: DNA
<213> ORGANISM: Homo Sapiens

<400> SEQUENCE: 465

```
tctctaactt ctgtgagcca c                                                21
```

<210> SEQ ID NO 466
<211> LENGTH: 24
<212> TYPE: DNA
<213> ORGANISM: Homo Sapiens

<400> SEQUENCE: 466

```
ggaaaaacta aactctaaat ctct                                             24
```

<210> SEQ ID NO 467
<211> LENGTH: 208
<212> TYPE: DNA
<213> ORGANISM: Homo Sapiens

<400> SEQUENCE: 467

```
ttcagcaaga gtaagcaaga ggcactgagc cgctggagtc tgcacattga taaatttact      60
tacagtcgta aataaattgc atcatcttca gctagtaaca cagagtctaa tttttatagc     120
ggcatacttg cctccacgac tttcctrgac accagaaaga aaggcgagag ccagccttag     180
cctaatcaag aaccatgatc caaaaagg                                        208
```

<210> SEQ ID NO 468
<211> LENGTH: 22
<212> TYPE: DNA
<213> ORGANISM: Homo Sapiens

<400> SEQUENCE: 468

```
ttcagcaaga gtaagcaaga gg                                               22
```

<210> SEQ ID NO 469
<211> LENGTH: 21
<212> TYPE: DNA
<213> ORGANISM: Homo Sapiens

<400> SEQUENCE: 469

```
ccttttttgga tcatggttct t                                               21
```

<210> SEQ ID NO 470
<211> LENGTH: 352
<212> TYPE: DNA
<213> ORGANISM: Homo Sapiens
```

```
<400> SEQUENCE: 470
gctggcaaga cacttctgag catcggggtg tggactttac gaaccaacct tttaacagta      60
actctaggag agaggatatc aaaaattggc agtgaaaaat tatagatagg caaaaagctc     120
cttctgaggt ccaggccagg agatagtagg atttaagaaa caaacaaaca aaaacmacca     180
caaatgacct ttggtgccac tgtcacaact gttgctcatc agagtaggag agttgtagca     240
aaggcattaa agaaggacaa gcagctgaag agcctgaatc cttgtgttgt aagctatttt     300
ggtttccttt caagaaaggg ctgtggtctg tggaaggtgt caggaacata tt             352

<210> SEQ ID NO 471
<211> LENGTH: 19
<212> TYPE: DNA
<213> ORGANISM: Homo Sapiens

<400> SEQUENCE: 471
gctggcaaga cacttctga                                                   19

<210> SEQ ID NO 472
<211> LENGTH: 21
<212> TYPE: DNA
<213> ORGANISM: Homo Sapiens

<400> SEQUENCE: 472
aatatgttcc tgacaccttc c                                                21

<210> SEQ ID NO 473
<211> LENGTH: 211
<212> TYPE: DNA
<213> ORGANISM: Homo Sapiens

<400> SEQUENCE: 473
tgaaatggaa atcaataaac tcagtttcct caaagttcaa aatacatgag actgcctacc      60
ctccttggaa ggcaagrtgg ggctttctga agcaaatacc agctttaaaa aaaaatgtat     120
atatatatga agatatatac aaaaaaaaaa tttccccaca accagacaat cagaatcatc     180
aaacccagaa gggttaaaga aaagaaaag g                                     211

<210> SEQ ID NO 474
<211> LENGTH: 25
<212> TYPE: DNA
<213> ORGANISM: Homo Sapiens

<400> SEQUENCE: 474
tgaaatggaa atcaataaac tcagt                                            25

<210> SEQ ID NO 475
<211> LENGTH: 24
<212> TYPE: DNA
<213> ORGANISM: Homo Sapiens

<400> SEQUENCE: 475
ccttttcttt ttctttaacc cttc                                             24

<210> SEQ ID NO 476
<211> LENGTH: 190
<212> TYPE: DNA
<213> ORGANISM: Homo Sapiens
```

-continued

```
<400> SEQUENCE: 476
attggattga tttcagcctt cttctggtac ttttttaaaat cttattaatc attaggaaaa     60
gaagttttat tattgatgca agccctaamc actctttcga ctccagagga gaagctggca    120
gctctctgta agaaatatgc tgatcttgtg agtatttatt taatggagca aggaacacag    180
aaaataaaat                                                            190

<210> SEQ ID NO 477
<211> LENGTH: 21
<212> TYPE: DNA
<213> ORGANISM: Homo Sapiens

<400> SEQUENCE: 477
attggattga tttcagcctt c                                                21

<210> SEQ ID NO 478
<211> LENGTH: 23
<212> TYPE: DNA
<213> ORGANISM: Homo Sapiens

<400> SEQUENCE: 478
attttatttt ctgtgttcct tgc                                              23

<210> SEQ ID NO 479
<211> LENGTH: 361
<212> TYPE: DNA
<213> ORGANISM: Homo Sapiens

<400> SEQUENCE: 479
cagaataata ggagaatttt tggtcaaata aaaggccata ttatatttct tttgataaaa     60
gtatcatgtg ttcagtatgt tttattattt gaaataatta acatgacagg aatatatttg    120
aaaaaaattc caaaaaaagc taaatataca aactaagaaa attatatgat tatacttatc    180
tgcagtattg taaaacaata gttccaaaaa cttctgaatt acaagtttaa tacatacaac    240
ttcaattttc mactacattg tggttagacg ttcagaggaa tcacaaagga cctcaacatg    300
ctagataaga aaatgtattt tttaaatgtt ttggctcagc tgcttagaaa ataaggaaaa    360
t                                                                    361

<210> SEQ ID NO 480
<211> LENGTH: 24
<212> TYPE: DNA
<213> ORGANISM: Homo Sapiens

<400> SEQUENCE: 480
cagaataata ggagaatttt tggt                                             24

<210> SEQ ID NO 481
<211> LENGTH: 23
<212> TYPE: DNA
<213> ORGANISM: Homo Sapiens

<400> SEQUENCE: 481
attttcctta ttttctaagc agc                                              23

<210> SEQ ID NO 482
<211> LENGTH: 460
<212> TYPE: DNA
<213> ORGANISM: Homo Sapiens
```

<400> SEQUENCE: 482

```
tcacagcagc ttcagcaaac acagatttct ggtgttggag gacagattta actacagaaa      60
attctgttgg gcaatcggaa gcctcaatct atacagactt ttaggaggag mctgcctgtt     120
tggttcaaat ttagccaaaa tatttttttt ttaccactga ttcagtaaat ctcctaactt     180
tgcaggaact gggatcctaa aaattatgga acgaattgta gaaactcaag caactttctc     240
caaagcctag ggttcagcaa gagtaagcaa gaggcactga gccgctggag tctgcacatt     300
gataaattta cttacagtcg taaataaatt gcatcatctt cagctagtaa cacagagtct     360
aatttttata gcggcatact tgcctccacg actttcctag acaccagaaa gaaaggcgag     420
agccagcctt agcctaatca agaaccatga tccaaaaagg                           460
```

<210> SEQ ID NO 483
<211> LENGTH: 19
<212> TYPE: DNA
<213> ORGANISM: Homo Sapiens

<400> SEQUENCE: 483

```
tcacagcagc ttcagcaaa                                                   19
```

<210> SEQ ID NO 484
<211> LENGTH: 21
<212> TYPE: DNA
<213> ORGANISM: Homo Sapiens

<400> SEQUENCE: 484

```
ccttttttgga tcatggttct t                                               21
```

<210> SEQ ID NO 485
<211> LENGTH: 27
<212> TYPE: DNA
<213> ORGANISM: Homo Sapiens

<400> SEQUENCE: 485

```
ataaaaatta gactctgtgt tactagc                                          27
```

<210> SEQ ID NO 486
<211> LENGTH: 288
<212> TYPE: DNA
<213> ORGANISM: Homo Sapiens

<400> SEQUENCE: 486

```
gaacttgtcg ggaggcaatg gtgacattca ttgtgaccct agccagagct cacaatcaac      60
catggtgcac tgagactagc tcatgcacat tcatcaggca gattcaggca cctggctgtc     120
agagctgtca gccttcctca gtagaggaaa atgctacagt crgcactggc ctggtatcag     180
gaaaatagat gcctgcaaaa ayccactgtg ggacccbaaa agtcttgacc tcaggtcccc     240
tttgtgctgt ctctgttgtc aggatccact aaaggaggaa gtgtatca                  288
```

<210> SEQ ID NO 487
<211> LENGTH: 19
<212> TYPE: DNA
<213> ORGANISM: Homo Sapiens

<400> SEQUENCE: 487

```
gaacttgtcg ggaggcaat                                                   19
```

```
<210> SEQ ID NO 488
<211> LENGTH: 23
<212> TYPE: DNA
<213> ORGANISM: Homo Sapiens

<400> SEQUENCE: 488
tgatacactt cctcctttag tgg                                            23

<210> SEQ ID NO 489
<211> LENGTH: 340
<212> TYPE: DNA
<213> ORGANISM: Homo Sapiens

<400> SEQUENCE: 489
gcagcatata aaactttcag gaccctgaaa tacagaactg caaagaaacg gcctaagatg     60
gttgaatcct ctttatttt ctttaattta gacatgttca aacgttcaat gtcttacata   120
cttagttatg taagtaaggt agcgcttact tcattatgca tttcaatmct caaaaaaaat   180
tcctttgtga aatgttgaaa tatttttcta atctgtttca cgagcttcaa aaatgaggaa   240
aaaagattca gtttacattt cagcaaaatg cctcttttta atcggattta tgtttactta   300
acatttacag tacatttacg cttgagcaaa gttaggtttt                         340

<210> SEQ ID NO 490
<211> LENGTH: 21
<212> TYPE: DNA
<213> ORGANISM: Homo Sapiens

<400> SEQUENCE: 490
gcagcatata aaactttcag g                                              21

<210> SEQ ID NO 491
<211> LENGTH: 21
<212> TYPE: DNA
<213> ORGANISM: Homo Sapiens

<400> SEQUENCE: 491
aaaacctaac tttgctcaag c                                              21

<210> SEQ ID NO 492
<211> LENGTH: 493
<212> TYPE: DNA
<213> ORGANISM: Homo Sapiens

<400> SEQUENCE: 492
tagaagtagc agattgggag aggacatgtg ttcaagttgt actacttgta tgtcttgttt     60
agatattaca gtcttttct tttatcagaa ataattgaa taatgataaa atcagttgca    120
gattaagaca gattatctgt tgcagtcttc tcaaaactta atttaagtac attattttca   180
gctagcattt cttccttcac atagaacctc catgtgtgga gggatttcct aatgagtcta   240
ttgtatgtac aatagcactt aatgacatag cttttaaata ataacaggat tttaccaaat   300
gtttaatatg tgccaggcat caagcaccyt acacagttta attattgcat agatttggac   360
agcaactctg caagttaggt atggtcatga acctttgcag ataaggaaac tgtgtttcac   420
aaggagaaga aattgtcctg gatcatacaa taagctagga tttgctccag accatttttt   480
tcattttatc agg                                                      493
```

```
<210> SEQ ID NO 493
<211> LENGTH: 23
<212> TYPE: DNA
<213> ORGANISM: Homo Sapiens

<400> SEQUENCE: 493
tagaagtagc agattgggag agg                                              23

<210> SEQ ID NO 494
<211> LENGTH: 24
<212> TYPE: DNA
<213> ORGANISM: Homo Sapiens

<400> SEQUENCE: 494
cctgataaaa tgaaaaaaat ggtc                                             24

<210> SEQ ID NO 495
<211> LENGTH: 340
<212> TYPE: DNA
<213> ORGANISM: Homo Sapiens

<400> SEQUENCE: 495
aaagcgagag attcaatcca ggatgacaga atgcgttcac ctttaaaggg attaaaagaa       60
gtataataca gtctgtatta ttagatcacc cagagacaca caaaacaaga accgtsaatt      120
gaattagtgg tatactaata gagtggtttt acctgaaata tttacacatc aatcctactg      180
aattcttaca acaaatgatt tagattagct attgtattca ccagttgaaa gaacagaaaa      240
tattgaggga gataacttgt gtcagtgcaa cttaatcaga tttaggacac aaaagcaact      300
acataatgaa aagagagct ggtgacttaa cttgctaaaa                             340

<210> SEQ ID NO 496
<211> LENGTH: 21
<212> TYPE: DNA
<213> ORGANISM: Homo Sapiens

<400> SEQUENCE: 496
aaagcgagag attcaatcca g                                                21

<210> SEQ ID NO 497
<211> LENGTH: 23
<212> TYPE: DNA
<213> ORGANISM: Homo Sapiens

<400> SEQUENCE: 497
ttttagcaag ttaagtcacc agc                                              23

<210> SEQ ID NO 498
<211> LENGTH: 393
<212> TYPE: DNA
<213> ORGANISM: Homo Sapiens

<400> SEQUENCE: 498
tggtaaactc tacttagttg cctttggaa atgaataaat caaggtagaa aarcaattga        60
gatactaatt catgctctca ggggaaaatc tgaataaagc tatcttttct aacacagagc      120
aagtgactct caaagtcaca gtatctgaac tagcatatca gcatcgcctg aatacctaga      180
aatgcaaatt cctgggcaac accagaatct aacaaagcaa aaaactatgg ggggaacagg      240
gaagtcggtt taataatact gagtttgtgc aacctcaact ttgctttata ggaaagcaaa      300
```

```
atctcaatat gataaagttt tcttcaacaa aactctgaga taactatgtt gagggaaaga      360
agttgatcac atgcaagaaa atctaattcg ctg                                   393
```

<210> SEQ ID NO 499
<211> LENGTH: 25
<212> TYPE: DNA
<213> ORGANISM: Homo Sapiens

<400> SEQUENCE: 499

```
tggtaaactc tacttagttg cctتt                                            25
```

<210> SEQ ID NO 500
<211> LENGTH: 21
<212> TYPE: DNA
<213> ORGANISM: Homo Sapiens

<400> SEQUENCE: 500

```
cagcgaatta gattttcttg c                                                21
```

<210> SEQ ID NO 501
<211> LENGTH: 473
<212> TYPE: DNA
<213> ORGANISM: Homo Sapiens

<400> SEQUENCE: 501

```
agtttgaggt agaatactgt ttgctggtct taaaaactgt ggtatttttgg tgattccata     60 aattaggtca gatacttcca ctggagggaa acagtttaaa ggatatatgt gatactatta     120
atagaatgag gaagacacac cagatatttta ggagggaatt agcgagcttg aaactaagag    180
ctggtttgaa tgagactggg tcataagtga tttcaagtac cagattaagg cactgagatt     240 ttattttttaa gcactgaagt cagattttttt ccttttaaaa gaaaggattc atgatgaaat   300
ctgctttttg ttttgcagag agcttggaga taattctggt ggctgtgtgg agtatgtgtt     360
ggaggtgagt ygctagctga agaattaaaa caatagtttt agcagtttgg gtaagagatg     420
tttacagaaa tgttttgtgg aataaaactg aacagtcaga gacctatgag att            473
```

<210> SEQ ID NO 502
<211> LENGTH: 25
<212> TYPE: DNA
<213> ORGANISM: Homo Sapiens

<400> SEQUENCE: 502

```
agtttgaggt agaatactgt ttgct                                            25
```

<210> SEQ ID NO 503
<211> LENGTH: 24
<212> TYPE: DNA
<213> ORGANISM: Homo Sapiens

<400> SEQUENCE: 503

```
aatctcatag gtctctgact gttc                                             24
```

<210> SEQ ID NO 504
<211> LENGTH: 473
<212> TYPE: DNA
<213> ORGANISM: Homo Sapiens

<400> SEQUENCE: 504

```
agtttgaggt agaatactgt ttgctggtct taaaaactgt ggtatttttgg tgattccata     60 aattaggtca gatacttcca ctggagggaa acagttyaaa ggatatatgt gatactatta     120
```

| | | |
|---|---|---|
| atagaatgag gaagacacac cagatatttta ggagggaatt agcgagcttg aaactaagag | | 180 |
| ctggtttgaa tgagactggg tcataagtga tttcaagtac cagattaagg cactgagatt | | 240 |
| ttatttttaa gcactgaagt cagatttttt ccttttaaaa gaaaggattc atgatgaaat | | 300 |
| ctgcttttg ttttgcagag agcttggaga taattctggt ggctgtgtgg agtatgtgtt | | 360 |
| ggaggtgagt cgctagctga agaattaaaa caatagtttt agcagtttgg gtaagagatg | | 420 |
| tttacagaaa tgttttgtgg aataaaactg aacagtcaga gacctatgag att | | 473 |

<210> SEQ ID NO 505
<211> LENGTH: 25
<212> TYPE: DNA
<213> ORGANISM: Homo Sapiens

<400> SEQUENCE: 505
agtttgaggt agaatactgt ttgct                                         25

<210> SEQ ID NO 506
<211> LENGTH: 21
<212> TYPE: DNA
<213> ORGANISM: Homo Sapiens

<400> SEQUENCE: 506
ccagggcccc gagggactct t                                             21

<210> SEQ ID NO 507
<211> LENGTH: 405
<212> TYPE: DNA
<213> ORGANISM: Homo Sapiens

<400> SEQUENCE: 507

| | | |
|---|---|---|
| tgcttcacac aaatgcgttt caaatagtaa ctttttttct gaaaggggg aattaatttt | | 60 |
| tattattaac tgtattacag ggttggctag tggatctcat caataaattt ggcacattaa | | 120 |
| atgggttcca gattttgcat gatcgttttt ttaatggatc agcattaaat attcaaataa | | 180 |
| ttgcagctct tattaagtaa gttatgtttt catgtttgtt aaataatttc atgtttgttc | | 240 |
| aaataattgc agctcttatt aagttatgtt ttcatattct gtgcattata caaattacta | | 300 |
| ttttatttac ttaaaaatca ttgttcmttt ttttcagtgt gggttgtgtc tcactgtaaa | | 360 |
| atgaggacct gttttttgtgt ggtcttaaat gttgaaagta attgg | | 405 |

<210> SEQ ID NO 508
<211> LENGTH: 20
<212> TYPE: DNA
<213> ORGANISM: Homo Sapiens

<400> SEQUENCE: 508
tgcttcacac aaatgcgttt                                               20

<210> SEQ ID NO 509
<211> LENGTH: 25
<212> TYPE: DNA
<213> ORGANISM: Homo Sapiens

<400> SEQUENCE: 509
ccaattactt tcaacattta agacc                                         25

<210> SEQ ID NO 510
<211> LENGTH: 473
<212> TYPE: DNA
<213> ORGANISM: Homo Sapiens

<400> SEQUENCE: 510

| | | | | | |
|---|---|---|---|---|---|
| agtttgaggt | agaatactgt | ttgctggtct | taaaaactgt | ggtatttggg | tgattccata | 60 |
| aattaggtca | gatacttcca | ctggagggaa | acagttaaa | ggatatatgt | gatactatta | 120 |
| atagaatgag | gaagacacac | cagatatta | ggagggaatt | agcgagcttg | aaactaagag | 180 |
| ctggtttgaa | tgagactggg | tcataagtga | tttcaagtac | cagattaagg | cactgagatt | 240 |
| ttattttaa | gcactgaagt | cagattttt | ccttttaaaa | gaaaggattc | atgatgaaat | 300 |
| ctgcttttg | ttttgcagag | agcttggaga | taattctggt | ggctgtgtgg | agtatgtgtt | 360 |
| ggaggtgagt | cgctagctga | agaattaaaa | caatagtttt | agcagtttgg | gtaagagatg | 420 |
| tttacagaaa | tgttttgtgs | aataaaactg | aacagtcaga | gacctatgag | att | 473 |

<210> SEQ ID NO 511
<211> LENGTH: 25
<212> TYPE: DNA
<213> ORGANISM: Homo Sapiens

<400> SEQUENCE: 511
agtttgaggt agaatactgt ttgct      25

<210> SEQ ID NO 512
<211> LENGTH: 21
<212> TYPE: DNA
<213> ORGANISM: Homo Sapiens

<400> SEQUENCE: 512
ccagggcccc gagggactct t      21

<210> SEQ ID NO 513
<211> LENGTH: 345
<212> TYPE: DNA
<213> ORGANISM: Homo Sapiens

<400> SEQUENCE: 513

| | | | | | |
|---|---|---|---|---|---|
| ttgaagttac | ttttataatc | taatgcttaa | tctctttaaa | tatttaaaat | taggagccag | 60 |
| atgaccagga | tgccccagat | gagcatgagc | cctctccatc | agaagatgcc | ccattatatc | 120 |
| ctcattcacc | tgcctctcag | tatcaacagg | taaaaaggat | ttttcatttt | tatccccaa | 180 |
| acccattttg | atgcttkact | taaaaggtct | tcaattatta | ttttcttaaa | tattttgaaa | 240 |
| gtccaaactt | tctctgtacc | tggctgatat | ttaaaactgg | ataaactgtt | ccaaaccaac | 300 |
| atggagtgaa | gatggatcca | ctgtgactgt | aaagtaataa | attat | | 345 |

<210> SEQ ID NO 514
<211> LENGTH: 28
<212> TYPE: DNA
<213> ORGANISM: Homo Sapiens

<400> SEQUENCE: 514
ttgaagttac ttttataatc taatgctt      28

<210> SEQ ID NO 515
<211> LENGTH: 28
<212> TYPE: DNA
<213> ORGANISM: Homo Sapiens

<400> SEQUENCE: 515
ataatttatt actttacagt cacagtgg      28

<210> SEQ ID NO 516
<211> LENGTH: 417
<212> TYPE: DNA
<213> ORGANISM: Homo Sapiens

<400> SEQUENCE: 516

```
aagaaatgtt gaactgaaag ttgatgccac ttttcagaaa atggttgtg ttttgtacaa      60
attgaaatac attgtttaaa ataaagcac agtactcact ttaggtttgc catataaatt     120
tactgtaact tcctagaaaa ttggaaataa agtaagaaaa attttcttac aattcaaggg    180
catttagaac mctttgtcat ctgttaatat tcagaaatga taagccagtg ttttgttttc    240
aggatctggg aaaactgcag catttctttt acccatactg agtcagatat atacagatgg    300
tccaggagaa gctttgaagg ctgtgaaggt aaaggttttg ttataaaatc agacatttt     360
gttttaaaaa gctttgcaaa gccctgttga cttttctaac ggatgccaga tacacct       417
```

<210> SEQ ID NO 517
<211> LENGTH: 25
<212> TYPE: DNA
<213> ORGANISM: Homo Sapiens

<400> SEQUENCE: 517

```
aagaaatgtt gaactgaaag ttgat                                           25
```

<210> SEQ ID NO 518
<211> LENGTH: 21
<212> TYPE: DNA
<213> ORGANISM: Homo Sapiens

<400> SEQUENCE: 518

```
aggtgtatct ggcatccgtt a                                               21
```

<210> SEQ ID NO 519
<211> LENGTH: 348
<212> TYPE: DNA
<213> ORGANISM: Homo Sapiens

<400> SEQUENCE: 519

```
acatctcaga tcgttgtttg gttcataaaa atctgtttct tccatgtacc aagcaaaata     60
aacacatcac taaaatttga cgttcataga tgtttctgtt ttaggtatga tgcactgtgc    120
gttcttctcc gtcacagcaa aaatgtacgt ttttggttta ctcataatgt ccttttaat    180
gtatcaaatc gcttctctga ataccttctg gagtgcccya gtgcagaagt gagggggtgca   240
tttgcaaaac ttatagtgtt tattgcacac ttttccttgc aagatgggtc ttgtccttct   300
ccttttgcat ctccaggacc ttctagtcag gtaattgcat ggctttttt                348
```

<210> SEQ ID NO 520
<211> LENGTH: 22
<212> TYPE: DNA
<213> ORGANISM: Homo Sapiens

<400> SEQUENCE: 520

```
acatctcaga tcgttgtttg gt                                              22
```

<210> SEQ ID NO 521
<211> LENGTH: 21
<212> TYPE: DNA
<213> ORGANISM: Homo Sapiens -continued

<400> SEQUENCE: 521
aaaaagccat gcaattacct g                                          21

<210> SEQ ID NO 522
<211> LENGTH: 444
<212> TYPE: DNA
<213> ORGANISM: Homo Sapiens

<400> SEQUENCE: 522
ttgagcaaga aaaatagtac ccaaatcaac tcaactccag tgatttaaac tctctgaatc      60
aggcacatgc cttctcactt ctcttctcaa gaatgaacag aaacaaaggt atcagtagaa     120
aaaaaggtat cattaatatt ctttactcaa aagtatttca tttaaaaata cttactttca     180
gcattggaca agtacatgg attacagtca atcaaggcta actgaaaatg ctgcaagaga      240
aaagtaaaaa tattaatgca ctaaattaag agtgcataaa agtacatttt ctattttagc     300 cttttcaatgt ctatcataaa ataacaaagc tatgctatac accaatgcac tacactcgac    360
caaataaaat tactgtaatt ccaaatttat tttgaaaatg taagtgctaa tcaagttatt     420
tccctgagat agttaagaat ggag                                           444

<210> SEQ ID NO 523
<211> LENGTH: 23
<212> TYPE: DNA
<213> ORGANISM: Homo Sapiens

<400> SEQUENCE: 523
ttgagcaaga aaaatagtac cca                                        23

<210> SEQ ID NO 524
<211> LENGTH: 24
<212> TYPE: DNA
<213> ORGANISM: Homo Sapiens

<400> SEQUENCE: 524
ctccattctt aactatctca ggga                                       24

<210> SEQ ID NO 525
<211> LENGTH: 515
<212> TYPE: DNA
<213> ORGANISM: Homo Sapiens

<400> SEQUENCE: 525
taagcctaaa gagcagtcag agtagaatgc tgaattttca gaagtttat attaacataa       60 tcattcatct tttttgtcct gataattact caggaggaaa ctgagagggc atggtccctt     120
tctatggata gcaatactca gtgtcccaat tttcctttgg gacactggga cacaggcaga     180
gactccgaaa gtctgcatgg attagttgtt cattcaccay agctccttag tgtgccagga     240
gaactatata tggccttttgg tttcattcag ggacagggaa acttgaaccc atgcctattc    300
attctcatta aagtagcaga agtcatgtta gagacagtat tgctgcattc agtactcctg     360
cctttaacgc ttctgacgct tcctgaaagc agcccagct ctccatatgg caaaacaaag      420
gcaaccttat gcaaagcctt ctcagggaac cctcagaaag gtttaaactt aggttcacag     480
tttttagaga ataatgtcct cattgctccc tctag                               515

<210> SEQ ID NO 526
<211> LENGTH: 22
<212> TYPE: DNA
<213> ORGANISM: Homo Sapiens

<400> SEQUENCE: 526
taagcctaaa gagcagtcag ag                                                    22

<210> SEQ ID NO 527
<211> LENGTH: 20
<212> TYPE: DNA
<213> ORGANISM: Homo Sapiens

<400> SEQUENCE: 527
cagagggagc aatgaggaca                                                       20

<210> SEQ ID NO 528
<211> LENGTH: 426
<212> TYPE: DNA
<213> ORGANISM: Homo Sapiens

<400> SEQUENCE: 528
attatgcaga attaagatga ccagtgcaga aaaatggaaa gagattatta ataaaaatta           60
aatgtgtttg aaattgcaat gtgttcttat tataaactgt atcatatcct atccatgtaa          120
cagagatgta ttattaacaa tactcatcgc ctagtggagc tttgtgtggc caagttgtcc          180
caagattggt ttccacttct agaacttctc gccatggcct taaatcctca ctgcaagttt          240
catatctaca atggtacacg tccgtgtgaa ttaatttcct caaatgctca gttgcctgaa          300
gatgaattat ttgctygttc ttcagatcct cgatcaccaa aagtgcgttg gtttgttatt          360
ttcaagatta aatattaatt tttttatttg catttgccac agaccattag tgatgtgaac          420
ctgtct                                                                    426

<210> SEQ ID NO 529
<211> LENGTH: 25
<212> TYPE: DNA
<213> ORGANISM: Homo Sapiens

<400> SEQUENCE: 529
acactactgt gctgtaattt gtgaa                                                 25

<210> SEQ ID NO 530
<211> LENGTH: 23
<212> TYPE: DNA
<213> ORGANISM: Homo Sapiens

<400> SEQUENCE: 530
agacaggttc acatcactaa tgg                                                   23

<210> SEQ ID NO 531
<211> LENGTH: 447
<212> TYPE: DNA
<213> ORGANISM: Homo Sapiens

<400> SEQUENCE: 531
acactactgt gctgtaattt gtgaatgtat acataatttg gacttttgaa ttcctactta           60
atattattta gaagttggag acatgttttt atttcgcttt ttaaaaaaat ttcttttag           120 tttcagcatt gaattttttgt attacattta ggaatggata cagcaaaata atatcttatc         180
catagtcttg caagacagtc ttcatcaacc acaatatgta gaaaagctag agaaaattct          240
tcgttttgtg attaaagaaa aggctcttac attacaggac cttgataata tctgggcagc          300
acaggtaaga aagtgagatg atagctattt tctaagaaag ataccaaaaa ggagaaaatt          360

```
tttggtaacc cttatataat ggccagcaat ttagtattgc cygactttta ctaatgcatg    420
tgctgttcat gtagagaaat cttacca                                        447

<210> SEQ ID NO 532
<211> LENGTH: 25
<212> TYPE: DNA
<213> ORGANISM: Homo Sapiens

<400> SEQUENCE: 532
acactactgt gctgtaattt gtgaa                                           25

<210> SEQ ID NO 533
<211> LENGTH: 25
<212> TYPE: DNA
<213> ORGANISM: Homo Sapiens

<400> SEQUENCE: 533
tggtaagatt tctctacatg aacag                                           25

<210> SEQ ID NO 534
<211> LENGTH: 232
<212> TYPE: DNA
<213> ORGANISM: Homo Sapiens

<400> SEQUENCE: 534
caggaccttg ataatatctg ggcagcacag gtaagaaagt gagatgatag ctattttcta    60
agaaagatac caaaaggag aaaattttg gtaaccctta tataatggcc agcaatttag     120
tattgccyga cttttactaa tgcatgtgct gttcatgtag agaaatctta ccaagaattt   180
ttaaacaaaa ataacatttt ttctgtcttt gtatatatat tcatggtagc aa           232

<210> SEQ ID NO 535
<211> LENGTH: 20
<212> TYPE: DNA
<213> ORGANISM: Homo Sapiens

<400> SEQUENCE: 535
caggaccttg ataatatctg                                                20

<210> SEQ ID NO 536
<211> LENGTH: 22
<212> TYPE: DNA
<213> ORGANISM: Homo Sapiens

<400> SEQUENCE: 536
ttgctaccat gaatatatat ac                                             22

<210> SEQ ID NO 537
<211> LENGTH: 294
<212> TYPE: DNA
<213> ORGANISM: Homo Sapiens

<400> SEQUENCE: 537
gcttttattt attctacttt tgttttttca acaggcagga aaacatgaag ccattgtgaa    60
gaatgtacat gatctgctag caaagttggc ttgggatttt tctcctggac aacttgatca   120 tcttttttgay tgctttaagg tagtagcttg aatagtaaag tattgccaaa tagtaaatat   180
tgccagttaa ttctaagtaa agtttaattc gttagatttc ttttgcttat agctagtgtg   240
cttaactaac attttcatgg aagaatctct gatgaaaaag aattggtcat tgtt         294
```

```
<210> SEQ ID NO 538
<211> LENGTH: 27
<212> TYPE: DNA
<213> ORGANISM: Homo Sapiens

<400> SEQUENCE: 538
gcttttattt attctacttt tgtttttt                                            27

<210> SEQ ID NO 539
<211> LENGTH: 23
<212> TYPE: DNA
<213> ORGANISM: Homo Sapiens

<400> SEQUENCE: 539
aacaatgacc aattctttttt cat                                                23

<210> SEQ ID NO 540
<211> LENGTH: 364
<212> TYPE: DNA
<213> ORGANISM: Homo Sapiens

<400> SEQUENCE: 540
tattcaaaga cttaaagcag tggttaatgt aaacaaaygt aataaattat gtggtattta         60
tatcatttaa atactttctt taggcaagtt ggacaaatgc aagtaaaaag caacgtgaaa        120
agctccttga gttgatacgc cgtcttgcag aagatgataa agatggtgtg atggcacaca        180
aagtgttgaa ccttctttgg aacctggctc agagtgatga tgtgcctgta gacatcatgg        240
accttgctct tagtgcccac ataaaaatac tagattatag ttgttcccag gtatgggagt        300
gtttctttgt tcagttttct gactttcctt cacaagtagg ataacttagt tacaagatga        360
ttcc                                                                    364

<210> SEQ ID NO 541
<211> LENGTH: 26
<212> TYPE: DNA
<213> ORGANISM: Homo Sapiens

<400> SEQUENCE: 541
tattcaaaga cttaaagcag tggtta                                              26

<210> SEQ ID NO 542
<211> LENGTH: 27
<212> TYPE: DNA
<213> ORGANISM: Homo Sapiens

<400> SEQUENCE: 542
ggaatcatct tgtaactaag ttatcct                                             27

<210> SEQ ID NO 543
<211> LENGTH: 427
<212> TYPE: DNA
<213> ORGANISM: Homo Sapiens

<400> SEQUENCE: 543
actgggtaaa tatgactatg attgagttac ctttaaattg acattttact gcttttatt          60 agattgatgt cacatttcat ttgtaaacaa cctggattat ctgtatttgt ccattattta        120
taggtggtta tccatgaaga cttcattcag tcttgctttg atcgtttaaa agcatcatat        180
gatacactgt gtgttttga tggtgacaaa acagcatta attgtgcaag acaagaagcc          240
attcgaatgg ttagagtatt aactgttata aaagagtaca ttaatgaatg tgacagtgat        300
```

| | |
|---|---|
| tatcacaagg aaagaatgat tctmcctatg tcgaggtttg tgtgaagttg atctctagtg | 360 |
| ttaatttaca attacttaat attttcttag aaatttactt aggaaagtaa aataggtta | 420 |
| aaaggaa | 427 |

<210> SEQ ID NO 544
<211> LENGTH: 26
<212> TYPE: DNA
<213> ORGANISM: Homo Sapiens

<400> SEQUENCE: 544

| | |
|---|---|
| actgggtaaa tatgactatg attgag | 26 |

<210> SEQ ID NO 545
<211> LENGTH: 26
<212> TYPE: DNA
<213> ORGANISM: Homo Sapiens

<400> SEQUENCE: 545

| | |
|---|---|
| ttccttttaa cctattatta ctttcc | 26 |

<210> SEQ ID NO 546
<211> LENGTH: 305
<212> TYPE: DNA
<213> ORGANISM: Homo Sapiens

<400> SEQUENCE: 546

| | |
|---|---|
| cactttattt tagtctgtgt cttttccctt tgcagataga acagctgtag aaaaattacg | 60 |
| arctgtttgt ttggaccatg caaaacttgg agaaggcaaa cttagtccac cccttgactc | 120 |
| tcttttcttt ggtccttctg cctcccaagt tctataccta acagaggttg gttttttgcct | 180 |
| ttgcaaaaat gtaattttta tattatacgg taatgtgaag aacactgata agactgtaaa | 240 |
| gaaagttttt taaatagtcg aatttcttag caatgatcag aggagaaata gatgttacta | 300 |
| agttt | 305 |

<210> SEQ ID NO 547
<211> LENGTH: 27
<212> TYPE: DNA
<213> ORGANISM: Homo Sapiens

<400> SEQUENCE: 547

| | |
|---|---|
| cactttattt tagtctgtgt ctttttc | 27 |

<210> SEQ ID NO 548
<211> LENGTH: 27
<212> TYPE: DNA
<213> ORGANISM: Homo Sapiens

<400> SEQUENCE: 548

| | |
|---|---|
| aaacttagta acatctattt ctcctct | 27 |

<210> SEQ ID NO 549
<211> LENGTH: 430
<212> TYPE: DNA
<213> ORGANISM: Homo Sapiens

<400> SEQUENCE: 549

| | |
|---|---|
| ggagtaccta tcactgaatg tgcttcttaa atcccccttg gagtatatcc caaagagcct | 60 |
| ctctagccgc aagtgaagag tctgaggcyg catggtcttt accaagtagg caattgtaaa | 120 |
| tgttaaccag agggtttgtg aatttcttct tgaatatgtc tctagtaac ttgctcctga | 180 |

| | |
|---|---|
| ttctaatttt gcagaccacc aatggaagca ataagctgga ggtggaagat gaacaagttt | 240 |
| gctgtgaagc actggaagtg atgaccttat gttttgcttt acttccaaca gcgttggatg | 300 |
| cacttagtaa agaaaaagcc tggcagacct tcatcattga cttattattg cactgtccaa | 360 |
| gcaagtatgt gattttatg tgtaatttga aggaaggctt accttaccgt tccaagcaga | 420 |
| aatgaatgac | 430 |

<210> SEQ ID NO 550
<211> LENGTH: 23
<212> TYPE: DNA
<213> ORGANISM: Homo Sapiens

<400> SEQUENCE: 550

| | |
|---|---|
| ggagtaccta tcactgaatg tgc | 23 |

<210> SEQ ID NO 551
<211> LENGTH: 22
<212> TYPE: DNA
<213> ORGANISM: Homo Sapiens

<400> SEQUENCE: 551

| | |
|---|---|
| gtcattcatt tctgcttgga ac | 22 |

<210> SEQ ID NO 552
<211> LENGTH: 365
<212> TYPE: DNA
<213> ORGANISM: Homo Sapiens

<400> SEQUENCE: 552

| | |
|---|---|
| ttgcatttac tgttctagag agttctcaaa aagaaatagg aaaccacttg aacagtttgg | 60 |
| ggaagttgta tagaagatct catttccttc cagctctctg ttctcctaac tccttgtcct | 120 |
| tttctatctc catgttgtga gttgggccta taatattttt cctttttgcag gataatgtta | 180 |
| aaaacacagg tgaaacaggt gtcgaagagc caatactgga aggccacctt ggggtaacaa | 240 |
| aagagttatt ggccttttcaa acttctgaga aaaagtatca ctttggttgt gaaaaaggag | 300 |
| gtgctaatct cattaaagta agtactttt tttttctttt tttgagatgg agtcttgctc | 360 |
| tgtgg | 365 |

<210> SEQ ID NO 553
<211> LENGTH: 26
<212> TYPE: DNA
<213> ORGANISM: Homo Sapiens

<400> SEQUENCE: 553

| | |
|---|---|
| ttgcatttac tgttctagag agttct | 26 |

<210> SEQ ID NO 554
<211> LENGTH: 20
<212> TYPE: DNA
<213> ORGANISM: Homo Sapiens

<400> SEQUENCE: 554

| | |
|---|---|
| ccacagagca agactccatc | 20 |

<210> SEQ ID NO 555
<211> LENGTH: 25
<212> TYPE: DNA
<213> ORGANISM: Homo Sapiens

```
<400> SEQUENCE: 555
gtacttactt taatgagatt agcac                                           25

<210> SEQ ID NO 556
<211> LENGTH: 366
<212> TYPE: DNA
<213> ORGANISM: Homo Sapiens

<400> SEQUENCE: 556
ttgcatttac tgttctagag agttctcaaa agaaatagg  aaaccacttg aacagtttgg    60
ggaagttgta tagaagatct catttccttc cagctctctg ttctcctaac tccttgtcct   120
tttctatctc catgttgtga gttgggccta taatatttt  ccttttgcag dataatgtta   180
aaaacacagg tgaaacaggt gtcgaagagc caatactgga aggccacctt ggggtaacaa   240
aagagttatt ggcctttcaa acttctgaga aaagtatca ctttggttgt gaaaaggag    300 gtgctaatct cattaaagta agtactttt  tttttctttt ttgagatg  gagtcttgct   360 ctgtgg                                                              366

<210> SEQ ID NO 557
<211> LENGTH: 26
<212> TYPE: DNA
<213> ORGANISM: Homo Sapiens

<400> SEQUENCE: 557
ttgcatttac tgttctagag agttct                                         26

<210> SEQ ID NO 558
<211> LENGTH: 20
<212> TYPE: DNA
<213> ORGANISM: Homo Sapiens

<400> SEQUENCE: 558
ccacagagca agactccatc                                                20

<210> SEQ ID NO 559
<211> LENGTH: 25
<212> TYPE: DNA
<213> ORGANISM: Homo Sapiens

<400> SEQUENCE: 559
gtacttactt taatgagatt agcac                                          25

<210> SEQ ID NO 560
<211> LENGTH: 401
<212> TYPE: DNA
<213> ORGANISM: Homo Sapiens

<400> SEQUENCE: 560
gtattccctt tgaagaaaca tattgttcct aacctatatt ttctactaat aacatgtaat    60 gtcttttct  aacttactag gaattaattg atgatttcat ctttcccgca tccaaagttt   120
acctgcagta tttaagaagt ggagaactac cagctgagca ggctattcca gtctgtagtt   180
caccygttac catcaatgcc ggttttgagc tacttgtagc attagctatt ggctgtgtga   240
ggaatctcaa acagatagta gactgtttga ctgaaatgta ttacatgggc acagcaatta   300
ctagtgagta tttaaaatta taaagctgtt ttgttcatta ataatacttc actgtaaaat   360
tttatttggt gttttagaaa aaattaactt gtgatggact t                       401
```

```
<210> SEQ ID NO 561
<211> LENGTH: 25
<212> TYPE: DNA
<213> ORGANISM: Homo Sapiens

<400> SEQUENCE: 561
gtattccctt tgaagaaaca tattg                                              25

<210> SEQ ID NO 562
<211> LENGTH: 25
<212> TYPE: DNA
<213> ORGANISM: Homo Sapiens

<400> SEQUENCE: 562
aagtccatca caagttaatt ttttc                                              25

<210> SEQ ID NO 563
<211> LENGTH: 378
<212> TYPE: DNA
<213> ORGANISM: Homo Sapiens

<400> SEQUENCE: 563
actctcagct tatgtttgtc attgttattt ttgttgttat aaaatatgga tattctaggc        60
atgtattaca taactcattt tgtttccttt ccttcttagg ctttggggtg aacctgttaa       120
tctccgtgaa caacatgatg ccttagagtt ttttaattct ttggtggata gtttagatga       180
agctttaaaa kctttaggac acccggctat actaagtaaa gtcctaggag ctcctttgc        240 tgatcagaag atctgccaag gctgcccaca taggtaagtg ctaattatgt ttttaatgta       300
tacttcgtgt tgttttttt taataatag tgtaaatctt tcattagtac ttatataaaa        360
gcagagtgta ccaaaagc                                                    378

<210> SEQ ID NO 564
<211> LENGTH: 24
<212> TYPE: DNA
<213> ORGANISM: Homo Sapiens

<400> SEQUENCE: 564
actctcagct tatgtttgtc attg                                               24

<210> SEQ ID NO 565
<211> LENGTH: 22
<212> TYPE: DNA
<213> ORGANISM: Homo Sapiens

<400> SEQUENCE: 565
gcttttggta cactctgctt tt                                                 22

<210> SEQ ID NO 566
<211> LENGTH: 346
<212> TYPE: DNA
<213> ORGANISM: Homo Sapiens

<400> SEQUENCE: 566
ctctgtcaca agtaaggaaa tgatcgtgaa attttttgtat tagcatttta agctgatact       60
gaaaatcatt ctraattcta aatagttta ttttttcta aagggtaacg gagatcttaa        120
aagaaaatgg acctgggcag tggaatggct aggagatgaa cttgaaagaa gaccatatac      180
tggcaatcct cagtatagtt acaacaattg gtctcctcca gtacaaagca atgaaacagc      240
```

```
aaatggttat tcttagaaa gatcacatag tgctaggatg acacttgcaa aagcttgtga      300
actctgtcca gaagaggtaa aaaaaaaaaa ggctaccaat ggacag                    346
```

<210> SEQ ID NO 567
<211> LENGTH: 24
<212> TYPE: DNA
<213> ORGANISM: Homo Sapiens

<400> SEQUENCE: 567

```
ctctgtcaca agtaaggaaa tgat                                            24
```

<210> SEQ ID NO 568
<211> LENGTH: 21
<212> TYPE: DNA
<213> ORGANISM: Homo Sapiens

<400> SEQUENCE: 568

```
ctgtccattg gtagccttt t                                                21
```

<210> SEQ ID NO 569
<211> LENGTH: 429
<212> TYPE: DNA
<213> ORGANISM: Homo Sapiens

<400> SEQUENCE: 569

```
ttgcatttgt catggttggt tgacctggac atctttaaaa tttggcaggt aataccaggc     60
cgacatggca gctaagtttg tggtacagga taagattgga atctaggtct catttgtctt    120
ttgtgatgtt atctgttctt gtgtatcagc atgtgagcta ttgatatctc ttctagcttg    180
ctaatctgga cctgaactct gaaaaacaga gtggaggagc aagtacagcg agcagtaagt    240 aaaactttt ttaaaaatgg agtgtttatc agagcttaat gttaatgtct tactggactt    300 gttaattta aatttacatt ttttctttta caacttgact akatgaaaat atgagatatt    360
ttggtgtgtc tgggtaataa aatacactgt ttacctatgt ctgctgaaaa tacaaaaaat    420
tatcctggc                                                            429
```

<210> SEQ ID NO 570
<211> LENGTH: 20
<212> TYPE: DNA
<213> ORGANISM: Homo Sapiens

<400> SEQUENCE: 570

```
ttgcatttgt catggttggt                                                 20
```

<210> SEQ ID NO 571
<211> LENGTH: 24
<212> TYPE: DNA
<213> ORGANISM: Homo Sapiens

<400> SEQUENCE: 571

```
gccaggataa tttttgtat tttc                                             24
```

<210> SEQ ID NO 572
<211> LENGTH: 457
<212> TYPE: DNA
<213> ORGANISM: Homo Sapiens

<400> SEQUENCE: 572

```
catgggctgc tgacattttg caggcagggc tcagggtgtt agatgtcctg taattcaggg     60
acattcacag tagaaaatac tttggttagg atttaaacct acaaaattgc tttaaacata    120
```

```
aactcaaaag tattcttagg ctggttgcag tggcttgtgt ctgcaatccc agcactttgg      180
gaggccaaag caggcagatc cyttgagctc aggagtttga gcccagcttg ggcaaaatga      240
caaaacccct tctcagttaa aaaaaaaaaa ttagcctggc atggtgggtg gtgtgcaact      300
gcggtcccag ctaccgggag gctaaggtga attacctgaa cctgggaggt ggatgctgca      360
gtgagccaag atcccaccac tgcactccag cctggatgag gaagtgagat cttgtcacaa      420
aaacaaaaac aaacaaacaa acaaaccaaa aggattt                              457
```

<210> SEQ ID NO 573
<211> LENGTH: 19
<212> TYPE: DNA
<213> ORGANISM: Homo Sapiens

<400> SEQUENCE: 573

```
catgggctgc tgacatttt                                                    19
```

<210> SEQ ID NO 574
<211> LENGTH: 23
<212> TYPE: DNA
<213> ORGANISM: Homo Sapiens

<400> SEQUENCE: 574

```
aaatccttt ggtttgtttg ttt                                               23
```

<210> SEQ ID NO 575
<211> LENGTH: 430
<212> TYPE: DNA
<213> ORGANISM: Homo Sapiens

<400> SEQUENCE: 575

```
gcctggatga ggaagtgagt cctgtcacaa aaacaaaaac aaacaaacaa acaaacaaac       60
caaaaggatt tttgaatact ttaaacatac agggagtgtt ttttttcccc ccgagaaggc      120
aacgactgta taaatttata ttgtttttac cattttagaa atactaccgt ttgcaacccct     180 gttcataata cagtgagttg tgaatacatt ctgtttgtat ttgcagctaa attaggcaac      240
cacttgtgta tttgtcagtg tagcagtggc ggtcatttac atgccaaaat acatatttta      300
ttataaatat tcttttaatt atataataat taggtttgtt aggggccaga ggggtgtcat      360
tgtgcatcat ttgagtttat ttctttggga ggcaaagaga gaggaaagga aggtcaaaaa      420
tggagaaggc                                                             430
```

<210> SEQ ID NO 576
<211> LENGTH: 19
<212> TYPE: DNA
<213> ORGANISM: Homo Sapiens

<400> SEQUENCE: 576

```
gcctggatga ggaagtgag                                                    19
```

<210> SEQ ID NO 577
<211> LENGTH: 20
<212> TYPE: DNA
<213> ORGANISM: Homo Sapiens

<400> SEQUENCE: 577

```
gccttctcca tttttgacct                                                   20
```

<210> SEQ ID NO 578
<211> LENGTH: 426
<212> TYPE: DNA
<213> ORGANISM: Homo Sapiens

<400> SEQUENCE: 578

```
gcctggatga ggaagtgagt cctgtcacaa aaacaaaaac aaacaaacaa acaaaccaaa      60
aggattttg aatactttaa acatacaggg agtgttttty ttcccccga gaaggcaacg       120
actgtataaa tttatattgt ttttaccatt ttagaaatac taccgtttgc aaccctgttc     180
ataatacagt gagttgtgaa tacattctgt ttgtatttgc agctaaatta ggcaaccact     240
tgtgtatttg tcagtgtagc agtggcggtc attttacatgc caaaatacat attttattat    300
aaatattctt ttaattatat aataattagg tttgttaggg gccagagggg tgtcattgtg     360
catcatttga gtttatttct tgggaggca aagagagagg aaaggaaggt caaaaatgga      420
gaaggc                                                               426
```

<210> SEQ ID NO 579
<211> LENGTH: 19
<212> TYPE: DNA
<213> ORGANISM: Homo Sapiens

<400> SEQUENCE: 579

```
gcctggatga ggaagtgag                                                  19
```

<210> SEQ ID NO 580
<211> LENGTH: 20
<212> TYPE: DNA
<213> ORGANISM: Homo Sapiens

<400> SEQUENCE: 580

```
gccttctcca ttttttgacct                                                20
```

<210> SEQ ID NO 581
<211> LENGTH: 515
<212> TYPE: DNA
<213> ORGANISM: Homo Sapiens

<400> SEQUENCE: 581

```
ccactcagct ttcctcaggt gcagtcaggt ccatcctgca gagggacctt ctgcggacct      60
gttctttcac ctccctaacc tgaagattgt attcaaacca ccgtggatcg ctcacgtaaa     120
atggtcactg cgcctaacac ctgggatccc gtaacccctta tctatcttgg cttcagagag    180
tttttttgact agttccaact ttgctgaagc ttgtcaaagg taggtgacgg ctagttggaa    240
cggaaaaatt ttacgaaact tcctattctc agaagtaaaa gggaagagag agtgcttaag    300
gaagaaggga agttgagggt gggtaaggag ggagcgggag ttagtggtag attgtcactg    360
tgtttaagat ttccccaagg cgaaaaaggc gaaagatatc ttgctagatc cctagaattc    420
gaaggcattr ggagagggcg gggatagcaa acatcgcgcg aattttgaga ggcgctggga    480
ctacgtaatc ccgcgatctt atgactaaac gaacg                               515
```

<210> SEQ ID NO 582
<211> LENGTH: 20
<212> TYPE: DNA
<213> ORGANISM: Homo Sapiens

<400> SEQUENCE: 582

```
ccactcagct ttcctcaggt                                                 20
```

<210> SEQ ID NO 583
<211> LENGTH: 22
<212> TYPE: DNA
<213> ORGANISM: Homo Sapiens

<400> SEQUENCE: 583
cgttcgttta gtcataagat cg                                              22

<210> SEQ ID NO 584
<211> LENGTH: 445
<212> TYPE: DNA
<213> ORGANISM: Homo Sapiens

<400> SEQUENCE: 584
ttagacaact tactactttg atgtcctgtt ggctcagtaa tgctcacgat accaattgtt     60
ttgacaaaat aaatttacta aacttggcct aaaatcaaac cttggcacag aggtatgata    120
caactttaac aggagtcatc aattcatcca taaatataaa aagggaaaaa aacttaaggc    180
agtagtctgc attaggactg tttgagtttt gcagacttgg ggttgggaga acatcttaaa    240
gcattaaagc atagttttt gtatggccaa ccttactaaa ttaagttctg acttgctcac    300
tctatcctgg ataggcactt gggaacttas actctttaag ccattccagt catgatgagg    360
tggaatgtat cagtatacca attaatattt ttgaaagagc tcttttaggt taatttaagt    420
acagcaattt ctcatgtaat gttta                                         445

<210> SEQ ID NO 585
<211> LENGTH: 27
<212> TYPE: DNA
<213> ORGANISM: Homo Sapiens

<400> SEQUENCE: 585
ttagacaact tactactttg atgtcct                                         27

<210> SEQ ID NO 586
<211> LENGTH: 25
<212> TYPE: DNA
<213> ORGANISM: Homo Sapiens

<400> SEQUENCE: 586
taaacattac atgagaaatt gctgt                                           25

<210> SEQ ID NO 587
<211> LENGTH: 408
<212> TYPE: DNA
<213> ORGANISM: Homo Sapiens

<400> SEQUENCE: 587
tcagacagtt tagttggtta cttccattaa tatgttagta taaaacagaa attgcgacag     60
atacagcatt ttatatctgc tatgtttact tctgtattta cttgyatttg attaacctgg    120
ttaaatttct tggcagttta gcgatattga catgggagaa attatcatgg ggaacattga    180
acttactcgc tatactcgtc ctactccagt gcaaaaacat gccattccta ttattaaggg    240
aaaaagagac ttaatggctt gtgcccaaac aggtaagctt actcaataca agtgaaagt    300 taagaatacc tgatcagact tactttaaaa gtagtatgtt ctgaagggga tgtctgaatc    360
ctgtgtttag catttgaggt aggtaaagat tagctgagga tgtgtctt                408

```
<210> SEQ ID NO 588
<211> LENGTH: 25
<212> TYPE: DNA
<213> ORGANISM: Homo Sapiens

<400> SEQUENCE: 588
tcagacagtt tagttggtta cttcc                                           25

<210> SEQ ID NO 589
<211> LENGTH: 24
<212> TYPE: DNA
<213> ORGANISM: Homo Sapiens

<400> SEQUENCE: 589
aagacacatc ctcagctaat cttt                                            24

<210> SEQ ID NO 590
<211> LENGTH: 444
<212> TYPE: DNA
<213> ORGANISM: Homo Sapiens

<400> SEQUENCE: 590
tgaggtggaa tgtatcagta taccaattaa tattttgaa agagytcttt taggttaatt      60
taagtacagc aatttctcat gtaatgttta gggagtttat tctaacctag gcaaacggca   120
tgctatcaca agaaaggttt aaagctttga taaaatgggg gagatttaat cagttttttt   180
aatgcctgct ataaaaattt gaatattag aatggccgac catggcagtg accaggcctc    240
actacaggcc tggttggatt ctggtcttta atgcatgcta gtgttgatgt ttttggtca    300 agaacggttt aaacaggaag gattgtgcag caggctttaa tttaatgtag attcatactg   360
ctctgttaaa gctgcattga atgttaaaa tggcttacac ttgcagactt tgcaaatctt    420
aagactaaca aatccttgaa atca                                          444

<210> SEQ ID NO 591
<211> LENGTH: 24
<212> TYPE: DNA
<213> ORGANISM: Homo Sapiens

<400> SEQUENCE: 591
tgaggtggaa tgtatcagta tacc                                            24

<210> SEQ ID NO 592
<211> LENGTH: 24
<212> TYPE: DNA
<213> ORGANISM: Homo Sapiens

<400> SEQUENCE: 592
tgatttcaag gatttgttag tctt                                            24

<210> SEQ ID NO 593
<211> LENGTH: 445
<212> TYPE: DNA
<213> ORGANISM: Homo Sapiens

<400> SEQUENCE: 593
tgaggtggaa tgtatcagta taccaattaa tattttgaa agagctcttt taggttaatt      60
taagtacagc aatttctcat gtaatgttta gggagtttat tctaacctag gcaaacggca   120
tgctatcaca agaaaggttt aaagctttga taaaatgggg gagatttaat cagttttttt   180
aatgcctgct ataaaaattt gaatattag aatggccgac catggcagtg accaggcctc    240
```

```
actacaggcc tggttggatt ctggtctttta atgcatgcta gtgttgatgt tttttggtca    300
agaacggttt aaacaggaag gattgtgcag caggctttaa tttaatgtag attcatactg    360
ctctgttaaa gctgcattga aatgttaaaa tggcttacac ttggcagact ttgcaaatct    420
taagactaac aaatccttga aatca                                          445

<210> SEQ ID NO 594
<211> LENGTH: 24
<212> TYPE: DNA
<213> ORGANISM: Homo Sapiens

<400> SEQUENCE: 594
tgaggtggaa tgtatcagta tacc                                           24

<210> SEQ ID NO 595
<211> LENGTH: 24
<212> TYPE: DNA
<213> ORGANISM: Homo Sapiens

<400> SEQUENCE: 595
tgatttcaag gatttgttag tctt                                           24

<210> SEQ ID NO 596
<211> LENGTH: 429
<212> TYPE: DNA
<213> ORGANISM: Homo Sapiens

<400> SEQUENCE: 596
ggcttacact tgcagacttt gcaaatctta agactaacaa atccttgaaa tcacacagct    60
tgcaaatacg tactaaactg cacaaggtgt gtgttctata tgtgcagttt tagcgtatttt   120 tagttgcata ggtttccatg gtatttatag tctcttgtgc taaatttggc caaagatgat    180
tgtccaccac taaaaatgcc tctcccactt ggaattctgt actgattttg tggccagatg    240
caatgatctt taaaaacaaa tcttttcaat ggcataagaa gttgacaaaa atttcttaaa    300
gtgcaataga ttttcaartg tattgtgcct tgttctaaaa cttttaagta ggtgcacttg    360
acagtattga ggtcatttgt taaggtgcta tttcaattag tgtaggttta gactcttgta    420
catttctcc                                                            429

<210> SEQ ID NO 597
<211> LENGTH: 21
<212> TYPE: DNA
<213> ORGANISM: Homo Sapiens

<400> SEQUENCE: 597
ggcttacact tgcagactttt g                                             21

<210> SEQ ID NO 598
<211> LENGTH: 25
<212> TYPE: DNA
<213> ORGANISM: Homo Sapiens

<400> SEQUENCE: 598
ggagaaatgt acaagagtct aaacc                                          25

<210> SEQ ID NO 599
<211> LENGTH: 326
<212> TYPE: DNA
<213> ORGANISM: Homo Sapiens
```

```
<400> SEQUENCE: 599
tatgcatttg ttgagtatat gtcaaattgt gacactgcaa tagttactac ttgagttact        60
atattagtgc aattaattac acaactatat atagtaatta gtttctcaga tctaataatc       120
cagtatcaac tgaggktttt cgtaataggt acttagtgtt ggatgaagct gataggatgc       180
tggatatggg atttgaacct cagatacgtc gtatagttga acaagatact atgccaccaa       240
agggcgttcg tcacaccatg atgtttagtg ctacttttcc taaggaaata caggtactgt       300
ttgacgtttg aactttcatt cagaac                                            326

<210> SEQ ID NO 600
<211> LENGTH: 27
<212> TYPE: DNA
<213> ORGANISM: Homo Sapiens

<400> SEQUENCE: 600
ttagtttctc agatctaata atccagt                                            27

<210> SEQ ID NO 601
<211> LENGTH: 22
<212> TYPE: DNA
<213> ORGANISM: Homo Sapiens

<400> SEQUENCE: 601
gttctgaatg aaagttcaaa cg                                                 22

<210> SEQ ID NO 602
<211> LENGTH: 392
<212> TYPE: DNA
<213> ORGANISM: Homo Sapiens

<400> SEQUENCE: 602
ggaattgcag ggtttaagca gtaattttca gtttaattga actttgtact taacactgcc        60
atgccatatt tttgcttaca gtaatagatt cagtggagga tttggtgcca gagactatcg       120
acaaagtagt ggttccagca gttctggctt tggtgctagt cgcggaagca gcagccgcag       180
tggtggaggt ggttacggca acagcagagg atttggtgga ggtaatgtta attttttcttt      240 taggaagggc ttttttgttkt tctttttttt ttttttttga gatggagtcc cactctgtca      300
ctcaagctgg agtgcagtgg cctgatctcg gctcactgga agtgactctc ctgcctcagc      360
ctcctaagta ggtgggatta caggtgggtg gc                                    392

<210> SEQ ID NO 603
<211> LENGTH: 19
<212> TYPE: DNA
<213> ORGANISM: Homo Sapiens

<400> SEQUENCE: 603
ggaattgcag ggtttaagc                                                    19

<210> SEQ ID NO 604
<211> LENGTH: 18
<212> TYPE: DNA
<213> ORGANISM: Homo Sapiens

<400> SEQUENCE: 604
gccacccacc tgtaatcc                                                     18
```

-continued

```
<210> SEQ ID NO 605
<211> LENGTH: 503
<212> TYPE: DNA
<213> ORGANISM: Homo Sapiens

<400> SEQUENCE: 605
gagtgccaag ctgaggatga ccccgtcatc aacgtgggca agctgcgtcc aggccttccc      60
ggagagtatc gccagccaac caggcgggtg atggaggtgc gtacctgtcc atgccaccaa     120
gcgcctccct ttcctcgact gtcaggctaa cagactcctc ttcactctcg cggctcgctt     180
ttccttccgc cattttcttt gcctcatcac cgaaggcaac agcggcggta gtgagcgaca     240
ctgcgcasga tttcatggaa acaacaaatt tccaagtccc acgacgatac ccaaccttaa     300
tcgagtagtt gaaaagacgc cttcaatcgc tgcttgagac tgtgacgcca attttatcgc     360
ctcctcagcg gctgcaagga aaaagctga ggcaaagact taagctaccg aagcacgggc      420
agcggaactc ggctacctgg atcacatctg ggaaactaca gggaaggcag aagctcgcag     480
tgctggagag cacagcagaa ttt                                             503

<210> SEQ ID NO 606
<211> LENGTH: 20
<212> TYPE: DNA
<213> ORGANISM: Homo Sapiens

<400> SEQUENCE: 606
gagtgccaag ctgaggatga                                                  20

<210> SEQ ID NO 607
<211> LENGTH: 20
<212> TYPE: DNA
<213> ORGANISM: Homo Sapiens

<400> SEQUENCE: 607
aaattctgct gtgctctcca                                                  20

<210> SEQ ID NO 608
<211> LENGTH: 21
<212> TYPE: DNA
<213> ORGANISM: Homo Sapiens

<400> SEQUENCE: 608
tccttggcag ccgctgagga g                                                21

<210> SEQ ID NO 609
<211> LENGTH: 486
<212> TYPE: DNA
<213> ORGANISM: Homo Sapiens

<400> SEQUENCE: 609
aaggggcgaa gtattccaga gtacggggac agcaaaggca agaaacactt ttccgacccc      60
ttggccatgg agcagagcca aaataaatac tggctgggcg gtaaggaacg cggggccttg     120
gtagagcaaa gtgcggacca agactttgc gtctggttgc ttttaccttg cctagtaggg      180
tcttcgttct ggcgccatct tcatgaagcc tcacgaaccc gaagagacgg ctgkagagag     240
agagacacag agcttgttaa tggtctgaga aagccagtga cttgctcctt cccgagtcca     300
agagcgcacg cgacagattg gtgagtgcca agctgaggat gaccccgtca tcaacgtggg     360
caagctgcgt ccaggccttc ccggagagta tcgccagcca accaggcggg tgatggaggt     420
```

```
gcgtacctgt ccatgccacc aagcgcctcc ctttcctcga ctgtcaggct aacagactcc    480
tcttca                                                               486
```

<210> SEQ ID NO 610
<211> LENGTH: 19
<212> TYPE: DNA
<213> ORGANISM: Homo Sapiens

<400> SEQUENCE: 610

```
aagggggcgaa gtattccag                                                19
```

<210> SEQ ID NO 611
<211> LENGTH: 22
<212> TYPE: DNA
<213> ORGANISM: Homo Sapiens

<400> SEQUENCE: 611

```
tgaagaggag tctgttagcc tg                                             22
```

<210> SEQ ID NO 612
<211> LENGTH: 541
<212> TYPE: DNA
<213> ORGANISM: Homo Sapiens

<400> SEQUENCE: 612

```
gtataatact gtggttggaa agcactaaaa tttaattttg gcttacagca ttatgcctat    60
aaataaattt tgccaccwga gtcacagaca aaacaggcaa aacaatctta tttggcaatt    120
taaataatat caaatgttcc ctagttattt caatttgact cttttaaaag ctagctagtt    180
agtaataaaa gtaggctgga tgcagtggct cactcctgta atcccagcac tttgggaggc    240
tgaggagagc agatcacctg aggtcaggag ttccagacca gcctggccaa catgatgaaa    300
ccctgtctct actacaaata caaaaaatta gccaagcatg gtggtggata cctgtaatcc    360
cagctacttg ggaggctgag gcaggagaat cacttgaacc cagaacacag aggttgcagt    420
gaggtgagac cgcactattc cactccagcc agggcaacaa gagtgaaaact ccatctcggg    480
ggaaaaaaaa gtaaagtaaa ccaataccag aaaagtgccc atttattatc acatagtttg    540
g                                                                    541
```

<210> SEQ ID NO 613
<211> LENGTH: 24
<212> TYPE: DNA
<213> ORGANISM: Homo Sapiens

<400> SEQUENCE: 613

```
gtataatact gtggttggaa agca                                           24
```

<210> SEQ ID NO 614
<211> LENGTH: 24
<212> TYPE: DNA
<213> ORGANISM: Homo Sapiens

<400> SEQUENCE: 614

```
ccaaactatg tgataataaa tggg                                           24
```

<210> SEQ ID NO 615
<211> LENGTH: 423
<212> TYPE: DNA
<213> ORGANISM: Homo Sapiens

```
<400> SEQUENCE: 615
aggaaaaatc agaagtatcc ctgaagaagg aaaaaacgtt acaactatgg ggcaaatgta      60
agtcaagcaa gaaatttara aagagaataa caatacctt tgaataatct tccaacaaga     120
ggttgaagtg acctaattgg caaaagaagt cagactccac ttttccttca gcttttaaga    180
ttaaagattc gtagcagcga acagcctaga aataaaaatt ataaacatta agaaaaaggc    240
atgtccttcc tggaagaata catacatctg cacgagattc ttaaagaaat caaagcaacc    300
ataaatgtat gtcatttctt ccataggcat aggattaaat tcggcatttc agagaggaaa    360
taacttctct ttaagaattt actaatgaag aaattagatc ccaaggattc ttggtgaatt    420
ttg                                                                  423

<210> SEQ ID NO 616
<211> LENGTH: 23
<212> TYPE: DNA
<213> ORGANISM: Homo Sapiens

<400> SEQUENCE: 616
aggaaaaatc agaagtatcc ctg                                             23

<210> SEQ ID NO 617
<211> LENGTH: 22
<212> TYPE: DNA
<213> ORGANISM: Homo Sapiens

<400> SEQUENCE: 617
caaaattcac caagaatcct tg                                              22

<210> SEQ ID NO 618
<211> LENGTH: 507
<212> TYPE: DNA
<213> ORGANISM: Homo Sapiens

<400> SEQUENCE: 618
ataaatacaa aatccacctga tggatatgca aaaatttatc agctttacaa agacatataa     60
taccattcta tgagcacaag tttattgcaa tattttgtcc tttactgtca acaaaagaac    120
acagccacat gatataggaa aaatctatat tctttacaaa ttttccatga atctctagct    180
aaaagatcat atgacatata tgcaacgatt tatcagcttt cagagcttta attgatattc    240
attacttgtg ggttctgtta tttgactcac gaaaatttat atatacacaa atcaatact    300 taatgatggt ttcaaagata ttcacagacc tgctcagggc agcaataaat tygacccact    360
ggatacacac tcccagctaa tgttagaagc ggtgggcctt tctctgactt catgtgtcaa    420
gtattctaaa caaacaggct tttcctgctg tatgcagtgt cacattttc tgattttgc    480 tcttttgtta gtaatttcgc tgttaa                                         507

<210> SEQ ID NO 619
<211> LENGTH: 25
<212> TYPE: DNA
<213> ORGANISM: Homo Sapiens

<400> SEQUENCE: 619
ataaatacaa aatcacctga tggat                                           25

<210> SEQ ID NO 620
<211> LENGTH: 25
<212> TYPE: DNA
<213> ORGANISM: Homo Sapiens
```

```
<400> SEQUENCE: 620
ttaaacagcg aaattactaa caaaa                                           25

<210> SEQ ID NO 621
<211> LENGTH: 550
<212> TYPE: DNA
<213> ORGANISM: Homo Sapiens

<400> SEQUENCE: 621
cactgtcttc cacaatggtt gaactagttt acagttccac caacagtgta taagttttcc     60
tatttctcca tatcctctcc agcacctgtt gacattacta aataacatt  ctcatcaagg    120 tcatcagggt ctcagaactg gctacataca acctccaaga agtttcgtt  ctttctgttt    180 ttgcaatgtg ttctgccaca aattcatcag ttctcaaagc taacagaact tttactagtt    240
gcccaatgca tcaattccat agttctgaga gcatgggcat gaatgtctga aaacctgagg    300
tatgatcact aatatgctat tctctgaact tctcaattgc attttcctcc ttgaataaat    360
cagactaaat tagtgacacc acaaattgtg atcattgaga aatctctaaa ggttttttcag   420 aagccgagta ggaagctatc tatgactttt taaaactctg actgaattct raatatattt    480
aattggacat tacatgaaga cgttgtgtat ttaacttctg aatgcaggga agataaatac    540
aaaatcacct                                                          550

<210> SEQ ID NO 622
<211> LENGTH: 21
<212> TYPE: DNA
<213> ORGANISM: Homo Sapiens

<400> SEQUENCE: 622
cactgtcttc cacaatggtt g                                              21

<210> SEQ ID NO 623
<211> LENGTH: 24
<212> TYPE: DNA
<213> ORGANISM: Homo Sapiens

<400> SEQUENCE: 623
aggtgatttt gtatttatct tccc                                           24

<210> SEQ ID NO 624
<211> LENGTH: 550
<212> TYPE: DNA
<213> ORGANISM: Homo Sapiens

<400> SEQUENCE: 624
cactgtcttc cacaatggtt gaactagttt acagttccac caacagtgta taagttttcc     60
tatttctcca tatcctctcc agcacctgtt gacattacta aataacatt  ctcatcaagg    120 tcatcagggt ctcagaactg gctacataca acctccaaga agtttcgtt  ctttctgttt    180 ttgcaatgtg ttctgccaca aattcatcag ttctcaaagc taacagaact tttactagtt    240
gcccaatgca tcaattccat agttctgaga gcatgggcat gaatgtctga aaacctgagg    300
tatgatcact aatatgctat tctctgaact tctcaattgc attttcctcc ttgaataaat    360
cagactaaat tagtgacacc acaaattgtg atcattgaga aatctctaaa ggttttttcag   420 aagccgagta ggaagctatc tatgactttt taaaactctg wctgaattct aaatatattt    480
aattggacat tacatgaaga cgttgtgtat ttaacttctg aatgcaggga agataaatac    540
aaaatcacct                                                          550
```

<210> SEQ ID NO 625
<211> LENGTH: 21
<212> TYPE: DNA
<213> ORGANISM: Homo Sapiens

<400> SEQUENCE: 625
cactgtcttc cacaatggtt g                                              21

<210> SEQ ID NO 626
<211> LENGTH: 24
<212> TYPE: DNA
<213> ORGANISM: Homo Sapiens

<400> SEQUENCE: 626
aggtgatttt gtatttatct tccc                                           24

<210> SEQ ID NO 627
<211> LENGTH: 538
<212> TYPE: DNA
<213> ORGANISM: Homo Sapiens

<400> SEQUENCE: 627
caattcacta tttgaggaat ccaagtattc ccctggggc acagtttagg tataaacaca      60
cttccactac taactatctc cagcagttgc ctacctataa gctccaccta caggcctgaa    120
gtccaggtca cacagccagc tgcaatcact gacaacacaa gtgcacaaac acaggaagca    180
gaacatacta ccgatgctag tatcactgca cacactacac tgaccaccta ggggctcaga    240
aactcattta cccacccaat ccactgctac cacactggca tctaagaagt ccacccagag    300
gcccaccacg tggtccacct ggaattgcca atacagatgc tggcaaacaa tgtcgtaggc    360
aaaaggatgt taacaacaag yacaccactg agaccagtga acctgactca caggcctaac    420
tggcactgca gtttccagca aatttctcca cagcctccat tagtaaccac atcctagtat    480
accaaggaaa ccacaggtac cattaagggt atatactgcc aaataaatca gagacttc     538

<210> SEQ ID NO 628
<211> LENGTH: 23
<212> TYPE: DNA
<213> ORGANISM: Homo Sapiens

<400> SEQUENCE: 628
caattcacta tttgaggaat cca                                            23

<210> SEQ ID NO 629
<211> LENGTH: 23
<212> TYPE: DNA
<213> ORGANISM: Homo Sapiens

<400> SEQUENCE: 629
gaagtctctg atttatttgg cag                                            23

<210> SEQ ID NO 630
<211> LENGTH: 409
<212> TYPE: DNA
<213> ORGANISM: Homo Sapiens

<400> SEQUENCE: 630
tataatcaag ttaccaatta ctggccaaga tgaaagaatg atgggctgaa cttgattaga     60
aactgcagta aaataagtga tactactgga aatgtatggt tacagacatt aaaatcacca   120
tttactggaa acaaatggta taagtcaact taccaatgaa atgcattgta gtagaagtag   180

```
accaaaccaa ggccatataa aaacgcagca ttctgttaat ataaaacaca aaamaacctt    240
tataacagat tttatatcta ttactattac atatattaat aagaagtcat gtaacgagat    300
gttttaagtt ctgaatattt taccatatat tacaatattc ttctctactt tttctcaagt    360
tctctccatt ttgaaaattg gaatcaattt gccattcaat gttacaaaa                409
```

<210> SEQ ID NO 631
<211> LENGTH: 25
<212> TYPE: DNA
<213> ORGANISM: Homo Sapiens

<400> SEQUENCE: 631

```
tataatcaag ttaccaatta ctggc                                          25
```

<210> SEQ ID NO 632
<211> LENGTH: 22
<212> TYPE: DNA
<213> ORGANISM: Homo Sapiens

<400> SEQUENCE: 632

```
ttttgtaaca ttgaatggca aa                                             22
```

<210> SEQ ID NO 633
<211> LENGTH: 409
<212> TYPE: DNA
<213> ORGANISM: Homo Sapiens

<400> SEQUENCE: 633

```
tataatcaag ttaccaatta ctggccaaga tgaaagaatg atgggctgaa cttgattaga    60
aactgcagta aataagtga tactactgga aatgtatggt tacagacatt aaaatcacca    120
tttactggaa acaaatggta taagtcaact taccaatgaa atgcattgta gtagaagtag    180
accaaaccaa ggccatataa aaacgcagca ttctgttaat ataaaacaca aaacaacctt    240
tataacagat tttatatcta ttactattac atatattaat aagaagtcay gtaacgagat    300
gttttaagtt ctgaatattt taccatatat tacaatattc ttctctactt tttctcaagt    360
tctctccatt ttgaaaattg gaatcaattt gccattcaat gttacaaaa                409
```

<210> SEQ ID NO 634
<211> LENGTH: 25
<212> TYPE: DNA
<213> ORGANISM: Homo Sapiens

<400> SEQUENCE: 634

```
tataatcaag ttaccaatta ctggc                                          25
```

<210> SEQ ID NO 635
<211> LENGTH: 22
<212> TYPE: DNA
<213> ORGANISM: Homo Sapiens

<400> SEQUENCE: 635

```
ttttgtaaca ttgaatggca aa                                             22
```

<210> SEQ ID NO 636
<211> LENGTH: 460
<212> TYPE: DNA
<213> ORGANISM: Homo Sapiens

<400> SEQUENCE: 636

| | | | | | |
|---|---|---|---|---|---|
| tattacaaaa | tatggaaaca | aggcaacatc | aaaacacaaa | tagacaaact | tgccagccac | 60 |
| ccttctcctg | ccaattatta | taggaatata | cgtgtcattt | aaaatatact | atttaaaatt | 120 |
| tttacctgta | gaaatttaat | tcttgcagca | agcgtagagg | tattactaca | acgtttgctt | 180 |
| ctagctgcat | ttaggtagca | tttaatggca | tcttgaggtt | gattgcagga | ttcatagaga | 240 |
| gtacctaggt | ccatccaggc | tgcggcatgc | ccatggtcca | attgtacagc | acaaatatat | 300 |
| gcctgtaaag | catccatagg | ctgattttgc | tgctgataca | acacactgga | agaaaaaga | 360 |
| atgctgtcaa | aaactactgg | ttactttcgt | tcgtttattt | ttcygttgtt | ttcagacagt | 420 |
| gtctcacact | gtctcccagg | ctggagtgaa | gtggcatttc | | | 460 |

<210> SEQ ID NO 637
<211> LENGTH: 24
<212> TYPE: DNA
<213> ORGANISM: Homo Sapiens

<400> SEQUENCE: 637
tattacaaaa tatggaaaca aggc 24

<210> SEQ ID NO 638
<211> LENGTH: 20
<212> TYPE: DNA
<213> ORGANISM: Homo Sapiens

<400> SEQUENCE: 638
gaaatgccac ttcactccag 20

<210> SEQ ID NO 639
<211> LENGTH: 386
<212> TYPE: DNA
<213> ORGANISM: Homo Sapiens

<400> SEQUENCE: 639

| | | | | | |
|---|---|---|---|---|---|
| gtaaaactca | gatatataca | tcccatgaaa | tatacacaga | aactataaat | tagcattaat | 60 |
| atcctctaaa | atgatactgt | agtaaagaaa | tattctcaaa | ctgttggtaa | attttagaga | 120 |
| aaataaaaat | attatacata | cttgctgcat | taagacaaac | tgrctttcta | actgttccag | 180 |
| ctgatgcttc | tgtgctggat | ttaaattatc | tctatttgct | cgcagttgtt | ccaagtgcta | 240 |
| gaagaaaaga | gattaatata | atcaaagttt | aatctaaaat | ttaagacaat | ataaggcaac | 300 |
| tcctcactaa | aaagactaca | cagaaccttt | gcaggatgaa | agacagtgat | tcctaatgaa | 360 |
| cgttaagata | gtgattcttt | tttttt | | | | 386 |

<210> SEQ ID NO 640
<211> LENGTH: 27
<212> TYPE: DNA
<213> ORGANISM: Homo Sapiens

<400> SEQUENCE: 640
gtaaaactca gatatataca tcccatg 27

<210> SEQ ID NO 641
<211> LENGTH: 26
<212> TYPE: DNA
<213> ORGANISM: Homo Sapiens -continued

```
<400> SEQUENCE: 641
aaaaaaaaag aatcactatc ttaacg                                          26

<210> SEQ ID NO 642
<211> LENGTH: 557
<212> TYPE: DNA
<213> ORGANISM: Homo Sapiens

<400> SEQUENCE: 642
ctcaaccagt ttttatgaag ctagaaaaaa attcctttat taaagaaatg taayattcaa     60
caggtataca taactagcag tgtcagaatt cagatttaga accatgttta ctaaaagctt    120
accctggaac aattatcttt tgctactctc atataatccc agtcaatatt tgagaaggcc    180 ttaattttc tagacaaaat ctgtttgcat atctggtggt caagaaccctt ttctgtcaaa    240 ggccagataa taaatatttt tggctttatg ggcaacctag tctctttagc aaactctgtc    300
aatgtactgc aaatgcaatc ataaagacag taactaaata aataagcata gttatgttcc    360
aatagaattt tatttcaaa agcaggttgg tgggcagcac ttcgagtaag agcattcatt    420
tgttaagtgc cctgaaatat aaacatgttc ttctgaaata ttaaaccttt gagagtaaag    480
tctatgctcc ctaaggcaat ctggcttgat ttaaagaata catcgatttt ctacaagaca    540
cattagttca gactctc                                                    557

<210> SEQ ID NO 643
<211> LENGTH: 24
<212> TYPE: DNA
<213> ORGANISM: Homo Sapiens

<400> SEQUENCE: 643
ctcaaccagt ttttatgaag ctag                                            24

<210> SEQ ID NO 644
<211> LENGTH: 25
<212> TYPE: DNA
<213> ORGANISM: Homo Sapiens

<400> SEQUENCE: 644
gagagtctga actaatgtgt cttgt                                           25

<210> SEQ ID NO 645
<211> LENGTH: 461
<212> TYPE: DNA
<213> ORGANISM: Homo Sapiens

<400> SEQUENCE: 645
gcttattttt agtctctctt ccatgactct tctaatacca tcgtcaataa atttcaacta     60
ggtaaaaaat taatattgaa catctgtcca agaaaggcc agtatctcca aaatcctctc    120
gtacagatct gtttcgagat cattctaatt actgtatctt catatttag gttaagattc    180 tttaacttgt gaaggagaat gaaaaagttg ggtgacacma actcttcaga aggaaaaata    240
cataaaaatt attttgatga aagccacagc agctttatca aatgcttacg ttgctaaata    300
gtaaaaaaag ccacttaaat tccaatggaa attttatacc cacatgtatt tatgtaaaac    360
ttttaaataa catgtattca taatcacttt tatatcctca accagttttt atgaagctag    420
aaaaaaattc ctttattaaa gaaatgtaac attcaacagg t                         461
```

<210> SEQ ID NO 646
<211> LENGTH: 24
<212> TYPE: DNA
<213> ORGANISM: Homo Sapiens

<400> SEQUENCE: 646
gcttattttt agtctctctt ccat 24

<210> SEQ ID NO 647
<211> LENGTH: 24
<212> TYPE: DNA
<213> ORGANISM: Homo Sapiens

<400> SEQUENCE: 647
acctgttgaa tgttacattt cttt 24

<210> SEQ ID NO 648
<211> LENGTH: 482
<212> TYPE: DNA
<213> ORGANISM: Homo Sapiens

<400> SEQUENCE: 648
ttgtgagttt ttttccatca atctggctat taaaaatctg cagtgcatcc taacctttga 60
tattatgttg ctacatatta cagtattgta tcatttgtct tgtcaggaaa gtgtggaggt 120
aatagctaaa aaaacccctc tcttttaaaa attacatttt aaatttgatt cactttaaaa 180
ctgttaccta tctcttatac cacagtgatt tataaaattc ttttaaatta gttgagttgt 240
tcgaaagtat ttcccaagca tattttttga gttatcttct attgcttctt aaatgagaca 300
acaggtagaa gagacattta aagtttaaaa tcaaactgtt ttataaacta ttaacaaaac 360
ttttagagaa taaaaaccay aacaggcaaa ccttaaattt gtatttattg cctcaaagtt 420
tcaactgaaa cgcttatttt tagtctctct tccatgactc ttctaatacc atcgtcaata 480
aa 482

<210> SEQ ID NO 649
<211> LENGTH: 23
<212> TYPE: DNA
<213> ORGANISM: Homo Sapiens

<400> SEQUENCE: 649
ttgtgagttt ttttccatca atc 23

<210> SEQ ID NO 650
<211> LENGTH: 25
<212> TYPE: DNA
<213> ORGANISM: Homo Sapiens

<400> SEQUENCE: 650
tttattgacg atggtattag aagag 25

<210> SEQ ID NO 651
<211> LENGTH: 482
<212> TYPE: DNA
<213> ORGANISM: Homo Sapiens

<400> SEQUENCE: 651
ttgtgagttt ttttccatca atctggctat taaaaatctg cagtgcatcc taacctttga 60
tattatgttg ctacatatta cagtattgta tcatttgtct tgtcaggaaa gtgtggaggt 120
aatagctaaa aaaacccctc tcttttaaaa attacatttt aaatttgatt cactttaaaa 180

```
ctgttaccta tctcttatac cacagtgatt tataaaattc ttttaaatta gytgagttgt      240
tcgaaagtat ttcccaagca tatttttga gttatcttct attgcttctt aaatgagaca       300
acaggtagaa gagacattta aagtttaaaa tcaaactgtt ttataaacta ttaacaaaac     360
ttttagggaa taaaaccac aacaggcaaa ccttaaattt gtatttattg cctcaaagtt       420
tcaactgaaa cgcttatttt tagtctctct tccatgactc ttctaatacc atcgtcaata     480
aa                                                                     482
```

<210> SEQ ID NO 652
<211> LENGTH: 23
<212> TYPE: DNA
<213> ORGANISM: Homo Sapiens

<400> SEQUENCE: 652

```
ttgtgagttt ttttccatca atc                                              23
```

<210> SEQ ID NO 653
<211> LENGTH: 25
<212> TYPE: DNA
<213> ORGANISM: Homo Sapiens

<400> SEQUENCE: 653

```
tttattgacg atggtattag aagag                                            25
```

<210> SEQ ID NO 654
<211> LENGTH: 482
<212> TYPE: DNA
<213> ORGANISM: Homo Sapiens

<400> SEQUENCE: 654

```
ttgtgagttt ttttccatca atctggctat taaaaatctg cagtgcatcc taacctttga     60
tattatgttg ctacatatta cagtattgta tcatttgtct tgtcaggaaa gtgtggaggt   120
aatagctaaa aaaaccctc tcttttaaaa attacatttt aaatttgatt cacttttaaa     180
ctgttaccta tctcttatac cacagtgatt tataaaattc ttttaaatta gctgagttgt      240
tcgaaagtat tatttttga gttatcttct attgcttctt aaatgagaca                   300
acaggtagaa gagacattta aagtttaaaa tcaaactgtt ttataaacta ttaacaaaac    360
ttttagrgaa taaaaccac aacaggcaaa ccttaaattt gtatttattg cctcaaagtt      420
tcaactgaaa cgcttatttt tagtctctct tccatgactc ttctaatacc atcgtcaata     480
aa                                                                     482
```

<210> SEQ ID NO 655
<211> LENGTH: 23
<212> TYPE: DNA
<213> ORGANISM: Homo Sapiens

<400> SEQUENCE: 655

```
ttgtgagttt ttttccatca atc                                              23
```

<210> SEQ ID NO 656
<211> LENGTH: 25
<212> TYPE: DNA
<213> ORGANISM: Homo Sapiens -continued

```
<400> SEQUENCE: 656
tttattgacg atggtattag aagag                                              25

<210> SEQ ID NO 657
<211> LENGTH: 324
<212> TYPE: DNA
<213> ORGANISM: Homo Sapiens

<400> SEQUENCE: 657
gggaaatgtg aaaggaaaat atcttgggta cctgaaatca ctatcctaaa gggaaaggtc        60
aaactgggta ctgcttaggg caaacctgcc tccattctat tcaaagtcac tcctctgttt      120
actgagctaa atgtatatct gttattatcc gtatatatct gtatatgata tctatattat      180
cacttgcatc agtgctaaag atgcttgctc atgcacaaga ggtataaaat tgagtgagaa      240
agaaagataa cacacattaa ataaagact cagaatgttg ggggaaaaaa tcagtgagtt       300
tctgtcagtg ttataaaagt ttaa                                             324

<210> SEQ ID NO 658
<211> LENGTH: 21
<212> TYPE: DNA
<213> ORGANISM: Homo Sapiens

<400> SEQUENCE: 658
gggaaatgtg aaaggaaaat a                                                  21

<210> SEQ ID NO 659
<211> LENGTH: 27
<212> TYPE: DNA
<213> ORGANISM: Homo Sapiens

<400> SEQUENCE: 659
ttaaactttt ataacactga cagaaac                                            27

<210> SEQ ID NO 660
<211> LENGTH: 208
<212> TYPE: DNA
<213> ORGANISM: Homo Sapiens

<400> SEQUENCE: 660
ttcagcaaga gtaagcaaga ggcactgagc cgctggagtc tgcacattga taaatttact        60
tacagtygta aataaattgc atcatcttca gctagtaaca cagagtctaa ttttatagc       120 ggcatacttg cctccacgac tttcctagac accagaaaga aaggcgagag ccagccttag      180
cctaatcaag aaccatgatc caaaaagg                                         208

<210> SEQ ID NO 661
<211> LENGTH: 22
<212> TYPE: DNA
<213> ORGANISM: Homo Sapiens

<400> SEQUENCE: 661
ttcagcaaga gtaagcaaga gg                                                 22

<210> SEQ ID NO 662
<211> LENGTH: 21
<212> TYPE: DNA
<213> ORGANISM: Homo Sapiens
```

<400> SEQUENCE: 662 ccttttttgga tcatggttct t    21

<210> SEQ ID NO 663
<211> LENGTH: 301
<212> TYPE: DNA
<213> ORGANISM: Homo Sapiens

<400> SEQUENCE: 663
cttcaggcat tatttttttt ggttctccac tacaggagaa atgtaaatgt gatgagtcag    60
aatttaggat ggctgtatgg gtttctttga ctaatacaag aaatcacttt gtaatgaatg   120
aaatcagtgg tttctgcatt actccgtatg ttcgacatga acacaaattg atacacttaa   180
caaagatact tctttcygcc cttccaaata tttcaaaata agctggtcat agtacttgct   240
tttcataaaa agatggtaag cttccaatat ttagatttaa ggaaggtga aggaacacta    300
t    301

<210> SEQ ID NO 664
<211> LENGTH: 22
<212> TYPE: DNA
<213> ORGANISM: Homo Sapiens

<400> SEQUENCE: 664
cttcaggcat tatttttttt gg    22

<210> SEQ ID NO 665
<211> LENGTH: 23
<212> TYPE: DNA
<213> ORGANISM: Homo Sapiens

<400> SEQUENCE: 665
atagtgttcc ttcaccttc ctt    23

<210> SEQ ID NO 666
<211> LENGTH: 528
<212> TYPE: DNA
<213> ORGANISM: Homo Sapiens

<400> SEQUENCE: 666
aaggaaaaaa gctgaggcaa agacttaagc taccgaagca cgggcagcgg aactcggcta    60
cctggatcac atctgggaaa ctacagggaa ggcagaagct cgcagtgctg gagagcacag   120
cagaatttct taaaatcaca aactttgcca gcaccagcac aaagttgtaa ttgtgtcacg   180
ggcgaacccc acgcagccgc cgcgacctcc ccgctcccaa ccacttagtt gtagccaatc   240
taggcgactg attcgtctca cgtgatcttt gttgacttac gtcaggcatt gctccactgt   300
actcctaggc tgctgggacc ccgcccagcc agttcgccaa ggacctagga acatgacaga   360
ggctgactra ttctgaccgc tggttggttg atggtcacgt ctatgagaa agggtagtc    420
tctgggatgg aacaacctgt aggttgtgct agttaaatgc attaagatag aaaatggagt   480
gtctgtgctg ggtgttttg cagttgcgat acgcttgaag gggaagag    528

<210> SEQ ID NO 667
<211> LENGTH: 19
<212> TYPE: DNA
<213> ORGANISM: Homo Sapiens

<400> SEQUENCE: 667
aaggaaaaaa gctgaggca    19

```
<210> SEQ ID NO 668
<211> LENGTH: 20
<212> TYPE: DNA
<213> ORGANISM: Homo Sapiens

<400> SEQUENCE: 668
ctcttcccct tcaagcgtat                                                  20

<210> SEQ ID NO 669
<211> LENGTH: 380
<212> TYPE: DNA
<213> ORGANISM: Homo Sapiens

<400> SEQUENCE: 669
gagtgccaag ctgaggatga ccccgtcatc aacgtgggca agctgcgtcc aggccttccc     60
ggagagtatc gccagccaac caggcgggtg atggaggtgc gtacctgtcc atgccaccaa    120
gcgcctccct ttcctcgact gtcaggctaa cagacysytc ttcactctcg cggctcgctt    180
ttccttccgc cattttcttt gcctcatcac cgaaggcaac agcggcggta gtgagcgaca    240
ctgcgcasga tttcatggaa acaacaaatt tccaagtccc acgacgatac ccaaccttaa    300
tcgagtagtt gaaaagacgc cttcaatcgc tgcttgagac tgtgacgcca attttatcgc    360
ctcctcagcg gctgcaagga                                                380

<210> SEQ ID NO 670
<211> LENGTH: 19
<212> TYPE: DNA
<213> ORGANISM: Homo Sapiens

<400> SEQUENCE: 670
gagtgccaag ctgaggatg                                                  19

<210> SEQ ID NO 671
<211> LENGTH: 20
<212> TYPE: DNA
<213> ORGANISM: Homo Sapiens

<400> SEQUENCE: 671
aaattctgct gtgctctcca                                                 20

<210> SEQ ID NO 672
<211> LENGTH: 380
<212> TYPE: DNA
<213> ORGANISM: Homo Sapiens

<400> SEQUENCE: 672
gagtgccaag ctgaggatga ccccgtcatc aacgtgggca agctgcgtcc aggccttccc     60
ggagagtatc gccagccaac caggcgggtg atggaggtgc gtacctgtcc atgccaccaa    120
gcgcctccct ttcctcgact gtcaggctaa cagacysytc ttcactctcg cggctcgctt    180
ttccttccgc cattttcttt gcctcatcac cgaaggcaac agcggcggta gtgagcgaca    240
ctgcgcasga tttcatggaa acaacaaatt tccaagtccc acgacgatac ccaaccttaa    300
tcgagtagtt gaaaagacgc cttcaatcgc tgcttgagac tgtgacgcca attttatcgc    360
ctcctcagcg gctgcaagga                                                380

<210> SEQ ID NO 673
<211> LENGTH: 19
<212> TYPE: DNA
<213> ORGANISM: Homo Sapiens
```

<400> SEQUENCE: 673
gagtgccaag ctgaggatg                                             19

<210> SEQ ID NO 674
<211> LENGTH: 20
<212> TYPE: DNA
<213> ORGANISM: Homo Sapiens

<400> SEQUENCE: 674
aaattctgct gtgctctcca                                            20

<210> SEQ ID NO 675
<211> LENGTH: 380
<212> TYPE: DNA
<213> ORGANISM: Homo Sapiens

<400> SEQUENCE: 675
gagtgccaag ctgaggatga ccccgtcatc aacgtgggca agctgcgtcc aggccttccc    60
ggagagtatc gccagccaac caggcgggtg atggaggtgc gtacctgtcc atgccaccaa   120
gcgcctccct ttcctcgact gtcaggctaa cagacysytc ttcactctcg cggctcgctt   180
ttccttccgc cattttcttt gcctcatcac cgaaggcaac agcggcggta gtgagcgaca   240
ctgcgcasga tttcatggaa acaacaaatt tccaagtccc acgacgatac ccaaccttaa   300
tcgagtagtt gaaaagacgc cttcaatcgc tgcttgagac tgtgacgcca attttatcgc   360
ctcctcagcg gctgcaagga                                            380

<210> SEQ ID NO 676
<211> LENGTH: 19
<212> TYPE: DNA
<213> ORGANISM: Homo Sapiens

<400> SEQUENCE: 676
gagtgccaag ctgaggatg                                             19

<210> SEQ ID NO 677
<211> LENGTH: 20
<212> TYPE: DNA
<213> ORGANISM: Homo Sapiens

<400> SEQUENCE: 677
aaattctgct gtgctctcca                                            20

<210> SEQ ID NO 678
<211> LENGTH: 554
<212> TYPE: DNA
<213> ORGANISM: Homo Sapiens

<400> SEQUENCE: 678
ggtacacacc tgtagtccca actgcttggg agtctgagat ggaaggatca ctttgggcca    60
ggaattccac gcgttgtact atgattatgc ctgtgaatag ccactgcact caatcctgga   120
aaacagtgag agccagtctc ttaaagtata atttccttma ataaaatata tttcaaaatc   180
tctcattctt atttatgatc aaaaaatgtt attcatcaat gtagactttg agcttggtca   240
atactgagca aataaagccc tcaaatatcc ttttcatttg acaggtaact acatgcctac   300
taaggccacg tattatgcat ataacaataa acaaacataa tccctccacg aaaaagctcc   360
agccagagaa aaatattaaa gtaaataatt atgctcatct aatccattca gcaatggcaa   420
gaatttcaca tgaaagtaca agatgtccag cacagatcta accacctaca aatggatgcc   480

```
tccttgagaa aatgttatta aggtaggacc tgcatggata agtaaaagtt accatgaaag    540
agttctaaaa aatg                                                     554

<210> SEQ ID NO 679
<211> LENGTH: 22
<212> TYPE: DNA
<213> ORGANISM: Homo Sapiens

<400> SEQUENCE: 679
ggtacacacc tgtagtccca ac                                             22

<210> SEQ ID NO 680
<211> LENGTH: 26
<212> TYPE: DNA
<213> ORGANISM: Homo Sapiens

<400> SEQUENCE: 680
cattttttag aactctttca tggtaa                                         26

<210> SEQ ID NO 681
<211> LENGTH: 449
<212> TYPE: DNA
<213> ORGANISM: Homo Sapiens

<400> SEQUENCE: 681
aatgtcacat ttagtcttaa cccatagact tctaaatgaa acaaatgtc taagcagagg     60 gaaaaaatt gaacctcaaa aggcaaatct cttcaaatta atgtaatgta taataaaagt    120
tttcatgtac ctaactgttg caatacagtt gcttttactt gtgcaggaag gttttctgtc   180
tgcaaaagtt gttcatatgc ctcctttgca gaatgatact tcctctaaag agcaaaggaa   240
aaagaatatt tagagaaaaa taatattaa aataaaaata ctcttgattt taacaatata    300
tacatggcca tacttaactt ataagtaaca aataataaat caatacgtaa tgatgaatat   360
taaaaawtat aaatgtgata ataaaaaata aagtaatatt acaatattat taaaatagct   420
agcaatgaag atttacatac taataatgt                                    449

<210> SEQ ID NO 682
<211> LENGTH: 25
<212> TYPE: DNA
<213> ORGANISM: Homo Sapiens

<400> SEQUENCE: 682
aatgtcacat ttagtcttaa cccat                                          25

<210> SEQ ID NO 683
<211> LENGTH: 28
<212> TYPE: DNA
<213> ORGANISM: Homo Sapiens

<400> SEQUENCE: 683
acattattag tatgtaaatc ttcattgc                                       28

<210> SEQ ID NO 684
<211> LENGTH: 331
<212> TYPE: DNA
<213> ORGANISM: Homo Sapiens

<400> SEQUENCE: 684
cctattatcc tggaaaatgt gggctcgttt taattatatt catattaatt tagttaatca    60
tcattcaatt aatacctaaa aaacaacatt tactgtttct actgctttcr aattgggga    120
```

```
aagatcgtca aagaattcat acctgtaatt tctgtggtgt caaacacaac gaataaactt      180
gctgtactgg atgatgtgaa agactctggc caccattcca gttatcagaa ccattctaag      240
gaaaatttag tgtaaaagat taagaatatt tgcttaattt catacactta gagttatgac      300
tagtgagaac caagtgacta ggaatcggaa t                                     331
```

<210> SEQ ID NO 685
<211> LENGTH: 22
<212> TYPE: DNA
<213> ORGANISM: Homo Sapiens

<400> SEQUENCE: 685

```
cctattatcc tggaaaatgt gg                                                22
```

<210> SEQ ID NO 686
<211> LENGTH: 22
<212> TYPE: DNA
<213> ORGANISM: Homo Sapiens

<400> SEQUENCE: 686

```
attccgattc ctagtcactt gg                                                22
```

<210> SEQ ID NO 687
<211> LENGTH: 461
<212> TYPE: DNA
<213> ORGANISM: Homo Sapiens

<400> SEQUENCE: 687

```
gcttatttt agtctctctt ccatgactct tctaatayca tcgtcaataa atttcaacta      60
ggtaaaaaat taatattgaa catctgtcca agaaaggcc agtatctcca aaatcctctc     120
gtacagatct gtttcgagat cattctaatt actgtatctt catattttag gttaagattc    180
tttaacttgt gaaggagaat gaaaaagttg ggtgacacaa actcttcaga aggaaaaata   240
cataaaaatt attttgatga aagccacagc agctttatca aatgcttacg ttgctaaata   300
gtaaaaaaag ccacttaaat tccaatggaa atttatacc cacatgtatt tatgtaaaac    360
ttttaaataa catgtattca taatcacttt tatatcctca accagttttt atgaagctag    420
aaaaaaattc ctttattaaa gaaatgtaac attcaacagg t                         461
```

<210> SEQ ID NO 688
<211> LENGTH: 24
<212> TYPE: DNA
<213> ORGANISM: Homo Sapiens

<400> SEQUENCE: 688

```
gcttattttt agtctctctt ccat                                              24
```

<210> SEQ ID NO 689
<211> LENGTH: 24
<212> TYPE: DNA
<213> ORGANISM: Homo Sapiens

<400> SEQUENCE: 689

```
acctgttgaa tgttacattt cttt                                              24
```

<210> SEQ ID NO 690
<211> LENGTH: 465
<212> TYPE: DNA
<213> ORGANISM: Homo Sapiens

```
<400> SEQUENCE: 690
atcacttgca tcagtgctaa agatgcttgc tcatgcacaa gaggtataaa attgagtgag      60
aaagaaagat aacacacatt aaaataaaga ctcagaatgt tgggggaaaa aatcagtgag     120
tttctgtcag tgttataaaa gtttaaagay agtaaaatat atattcaatc ttggttttaa     180
gcttacctaa tttaagagct ccagcaaggc cacgtattac tgtaacaggg ttttttggat     240
ttgtacaaaa ttgatgtaat ggaggaaaga aagcatcacg tttatttttcc aactgtaaaa     300 gcaaaatatt ttgttaggtc tcagataaat gacaaaatat acctcagatt tgtgccttta     360
ataaaatgat taaatacaat acttcaaatt tgtgagtttt tttccatcaa tctggctatt     420
aaaaatctgc agtgcatcct aacctttgat attatgttgc tacat                    465

<210> SEQ ID NO 691
<211> LENGTH: 23
<212> TYPE: DNA
<213> ORGANISM: Homo Sapiens

<400> SEQUENCE: 691
atcacttgca tcagtgctaa aga                                             23

<210> SEQ ID NO 692
<211> LENGTH: 26
<212> TYPE: DNA
<213> ORGANISM: Homo Sapiens

<400> SEQUENCE: 692
atgtagcaac ataatatcaa aggtta                                          26

<210> SEQ ID NO 693
<211> LENGTH: 533
<212> TYPE: DNA
<213> ORGANISM: Homo Sapiens

<400> SEQUENCE: 693
tctccattag caatgtgtgt tttacatact gtaattttgc ttacattttt aaaagtttac      60
cgggcatggt ggctcacacc tgtaatccca gcactttggg atgctgaggc aagcagacca     120
cctgaggtca ggagttcaag acaagcctgg ccaacatggt gaaaccctgt ctctacaaaa     180
atacaaaaat tagttgggca tgatggcagg tgcctgtaat tccagctatt cgggaggctg     240
aggtgggaga atygcttgaa cccaggaggc ggaggctgca gtgagctgag atcacaccat     300
tgcattccag cctgggtgag agagaatgag actctgtctc aaaaacaata aaaataata     360 aaataaaata aaagtttaat aatctatgag cactttaaaa acatactatt aacagtatgc     420
actagacaat aattatgaaa gtaatatgca ctattaaaaa atagcaacaa ttaaaaaagg     480
aagaaagaaa aacttactct caatgattcc tggaaggagg aagcctggta ttg            533

<210> SEQ ID NO 694
<211> LENGTH: 23
<212> TYPE: DNA
<213> ORGANISM: Homo Sapiens

<400> SEQUENCE: 694
tctccattag caatgtgtgt ttt                                             23

<210> SEQ ID NO 695
<211> LENGTH: 20
<212> TYPE: DNA
<213> ORGANISM: Homo Sapiens
```

```
<400> SEQUENCE: 695
caataccagg cttcctcctt                                                    20

<210> SEQ ID NO 696
<211> LENGTH: 317
<212> TYPE: DNA
<213> ORGANISM: Homo Sapiens

<400> SEQUENCE: 696
tagatatttt tccttaatct gtggtttaaa tttggaatat ttaattttta attaagactt        60
catcacctga ttcttccaat gagaattccg tagcaactcc tcctccagag gaacaagggc       120
aaggtgatgc cccaccacag catgaagatg aagakcctgc atttccacat actgagctgg       180
caaacctgga tgacatgatc aacaggtgca tttgtttgga tttgttttat taatggatgc       240
agtaaactag aaaagcaaaa ctacttccag cattgcaact agtagtaaat gagaaaaaga       300
aaagagtaga ttgtagt                                                     317

<210> SEQ ID NO 697
<211> LENGTH: 25
<212> TYPE: DNA
<213> ORGANISM: Homo Sapiens

<400> SEQUENCE: 697
tagatatttt tccttaatct gtggt                                             25

<210> SEQ ID NO 698
<211> LENGTH: 27
<212> TYPE: DNA
<213> ORGANISM: Homo Sapiens

<400> SEQUENCE: 698
actacaatct actcttttct ttttctc                                           27

<210> SEQ ID NO 699
<211> LENGTH: 366
<212> TYPE: DNA
<213> ORGANISM: Homo Sapiens

<400> SEQUENCE: 699
ttgcatttac tgttctagag agttctcaaa aagaaatasg aaaccacttg aacagtttgg        60
ggaagttgta tagaagatct catttccttc cagctctctg ttctcctaac tccttgtcct       120
tttctatctc catgttgtga gttgggccta taatatttt cctttttgcag gataatgtta       180 aaaacacagg tgaaacaggt gtcgaagagc caatactgga aggccacctt ggggtaacaa       240
aagagttatt ggcctttcaa acttctgaga aaaagtatca ctttggttgt gaaaaggag       300 gtgctaatct cattaaagta agtacttttt tttttctttt tttgagatg gagtcttgct       360 ctgtgg                                                                 366

<210> SEQ ID NO 700
<211> LENGTH: 26
<212> TYPE: DNA
<213> ORGANISM: Homo Sapiens

<400> SEQUENCE: 700
ttgcatttac tgttctagag agttct                                            26
```

<210> SEQ ID NO 701
<211> LENGTH: 25
<212> TYPE: DNA
<213> ORGANISM: Homo Sapiens

<400> SEQUENCE: 701
gtacttactt taatgagatt agcac                                          25

<210> SEQ ID NO 702
<211> LENGTH: 348
<212> TYPE: DNA
<213> ORGANISM: Homo Sapiens

<400> SEQUENCE: 702
gtactaaatg gcacataatt aggaactsaa atgttagcta ctattggata ttacaaagtt     60
ttacatctgc ttctgtttta gaattcataa tgcacttaaa ggaattccag atgacagaga   120
tgggctgttc gatacaatac agcgctcraa gaatcactat caaaaacgag catatcagtg   180
cataaaatgt atggtagctc tatttagcag ttgtcctgtt gcttaccaga tcttacaggt   240
gagggttttt ctcttataaa tttgtagaaa cctctgtcac aagtaaggaa atgatcgtga   300
aatttttgta ttagcatttt aagctgatac tgaaaatcat tctaaatt               348

<210> SEQ ID NO 703
<211> LENGTH: 25
<212> TYPE: DNA
<213> ORGANISM: Homo Sapiens

<400> SEQUENCE: 703
gtactaaatg gcacataatt aggaa                                          25

<210> SEQ ID NO 704
<211> LENGTH: 26
<212> TYPE: DNA
<213> ORGANISM: Homo Sapiens

<400> SEQUENCE: 704
aatttagaat gattttcagt atcagc                                         26

<210> SEQ ID NO 705
<211> LENGTH: 348
<212> TYPE: DNA
<213> ORGANISM: Homo Sapiens

<400> SEQUENCE: 705
gtactaaatg gcacataatt aggaactsaa atgttagcta ctattggata ttacaaagtt     60
ttacatctgc ttctgtttta gaattcataa tgcacttaaa ggaattccag atgacagaga   120
tgggctgttc gatacaatac agcgctcraa gaatcactat caaaaacgag catatcagtg   180
cataaaatgt atggtagctc tatttagcag ttgtcctgtt gcttaccaga tcttacaggt   240
gagggttttt ctcttataaa tttgtagaaa cctctgtcac aagtaaggaa atgatcgtga   300
aatttttgta ttagcatttt aagctgatac tgaaaatcat tctaaatt               348

<210> SEQ ID NO 706
<211> LENGTH: 25
<212> TYPE: DNA
<213> ORGANISM: Homo Sapiens

<400> SEQUENCE: 706
gtactaaatg gcacataatt aggaa                                          25

```
<210> SEQ ID NO 707
<211> LENGTH: 26
<212> TYPE: DNA
<213> ORGANISM: Homo Sapiens

<400> SEQUENCE: 707
aatttagaat gattttcagt atcagc                                            26

<210> SEQ ID NO 708
<211> LENGTH: 424
<212> TYPE: DNA
<213> ORGANISM: Homo Sapiens

<400> SEQUENCE: 708
ctgtggaatt cttgaagacg agtgactata atatagcaca acgtaayaag tatcctgtat       60
cttgtttctg gtggggtccc gtagccacgg agcaaccgtt gcccgggtgc tgagcgtgcc      120
gaaactgggc ttccggtatg gaaagttttg tgacgcagaa ggaccggaaa gggatggtgg      180
ggagggtagg gaaggatggc tgccgcgtgc ttctcttgac cctgtagaaa taatggaaat      240
tggacgcccg cggaaagaca cctggaaggt tagagatcca gcattgcgct acaccccttt      300
gttaattcag tcactggaca gccgcctagc cgagagctgt gcggttttta tatggtattg      360
tatctttact ttaggcgata catgcagaag tcgtccggta gaaaactaac ctcgaatgtt      420
gatt                                                                   424

<210> SEQ ID NO 709
<211> LENGTH: 22
<212> TYPE: DNA
<213> ORGANISM: Homo Sapiens

<400> SEQUENCE: 709
ctgtggaatt cttgaagacg ag                                                22

<210> SEQ ID NO 710
<211> LENGTH: 24
<212> TYPE: DNA
<213> ORGANISM: Homo Sapiens

<400> SEQUENCE: 710
aatcaacatt cgaggttagt tttc                                              24

<210> SEQ ID NO 711
<211> LENGTH: 366
<212> TYPE: DNA
<213> ORGANISM: Homo Sapiens

<400> SEQUENCE: 711
aactcttgat aaaccgtgct gtctagttca ctagaattaa gtagtaaatt cagatgrcaa       60
gatttttaag tacagtagta tcttaattga tgattcatgt aatgtgatag tatcttgaac      120
ttatatatgt aagctttcta cggcatagaa agtttgtgca aaaaggtgac caaggtgctc      180
ttggcattgg tcttaacgtg ttttttgaaa aaatctatt ttaacgtaca tggttttttc      240
ccccaccccc gccaccgctt cagagttgtt ctaggtaagg tattatgctg aaagccctta      300
aagcgaaata accttttttc tagttttaaa atccatcagt ataaggaggc atgaattgag      360
attgga                                                                 366
```

```
<210> SEQ ID NO 712
<211> LENGTH: 21
<212> TYPE: DNA
<213> ORGANISM: Homo Sapiens

<400> SEQUENCE: 712
aactcttgat aaaccgtgct g                                              21

<210> SEQ ID NO 713
<211> LENGTH: 21
<212> TYPE: DNA
<213> ORGANISM: Homo Sapiens

<400> SEQUENCE: 713
tccaatctca attcatgcct c                                              21

<210> SEQ ID NO 714
<211> LENGTH: 366
<212> TYPE: DNA
<213> ORGANISM: Homo Sapiens

<400> SEQUENCE: 714
aactcttgat aaaccgtgct gtctagttca ctagaattaa gtagtaaatt cagatggcaa     60
gatttttaag tacagtagta tcttaattga tgattcatgt aatgtgatag tatcttgaac    120
ttatatatgt aagctttcta cggcatagaa agtttgtgca aaaaggtgac caaggtgcty    180
ttggcattgg tcttaacgtg ttttttgaaa aaaatctatt ttaacgtaca tggttttttc    240
ccccaccccc gccaccgctt cagagttgtt ctaggtaagg tattatgctg aaagccctta    300
aagcgaaata acctttttc tagttttaaa atccatcagt ataaggaggc atgaattgag     360
attgga                                                              366

<210> SEQ ID NO 715
<211> LENGTH: 21
<212> TYPE: DNA
<213> ORGANISM: Homo Sapiens

<400> SEQUENCE: 715
aactcttgat aaaccgtgct g                                              21

<210> SEQ ID NO 716
<211> LENGTH: 21
<212> TYPE: DNA
<213> ORGANISM: Homo Sapiens

<400> SEQUENCE: 716
tccaatctca attcatgcct c                                              21

<210> SEQ ID NO 717
<211> LENGTH: 401
<212> TYPE: DNA
<213> ORGANISM: Homo Sapiens

<400> SEQUENCE: 717
ttttgagctt ttgatgttta ggaatttatc tgcattaaaa atagttgtac cgtcttcagg     60
gcaaagataa attaaggaat cttcaaatga ttttaatgtc catttatttt tagggttaga    120
atatcaagaa aaccactgtc aytgggaaca tttcactatc atgactgtag ctaaattgga    180
tgttgaagtt actgagaaat tgatggtaaa tttttttagt taggaaagtt ttcacttcgg    240
aaaattgtta aggaaaattt gttttgaatt aatgaatttg aactcattac tgtgaaactg    300
```

```
ctggtattca gctgatgcca tttgcatttg tcatggttgg tagacctgga catctttaaa      360
atttggcagg taataccagg ccgacatggc agctaagttt g                         401
```

<210> SEQ ID NO 718
<211> LENGTH: 23
<212> TYPE: DNA
<213> ORGANISM: Homo Sapiens

<400> SEQUENCE: 718

```
ttttgagctt tgatgtttta gga                                              23
```

<210> SEQ ID NO 719
<211> LENGTH: 20
<212> TYPE: DNA
<213> ORGANISM: Homo Sapiens

<400> SEQUENCE: 719

```
caaacttagc tgccatgtcg                                                  20
```

<210> SEQ ID NO 720
<211> LENGTH: 401
<212> TYPE: DNA
<213> ORGANISM: Homo Sapiens

<400> SEQUENCE: 720

```
ttttgagctt tgatgtttta ggaatttatc tgcattaaaa atagttgtac cgtcttcagg      60
gcaaagataa attaaggaat cttcaaatga ttttaatgtc catttatttt tagggttaga     120
atatcaagaa aaccactgtc attgggaaca tttcactatc atgactgtag ctamattgga     180
tgttgaagtt actgagaaat tgatggtaaa tttttttagt taggaaagtt ttcacttcgg     240
aaaattgtta aggaaaattt gttttgaatt aatgaatttg aactcattac tgtgaaactg     300
ctggtattca gctgatgcca tttgcatttg tcatggttgg tagacctgga catctttaaa     360
atttggcagg taataccagg ccgacatggc agctaagttt g                         401
```

<210> SEQ ID NO 721
<211> LENGTH: 23
<212> TYPE: DNA
<213> ORGANISM: Homo Sapiens

<400> SEQUENCE: 721

```
ttttgagctt tgatgtttta gga                                              23
```

<210> SEQ ID NO 722
<211> LENGTH: 20
<212> TYPE: DNA
<213> ORGANISM: Homo Sapiens

<400> SEQUENCE: 722

```
caaacttagc tgccatgtcg                                                  20
```

<210> SEQ ID NO 723
<211> LENGTH: 436
<212> TYPE: DNA
<213> ORGANISM: Homo Sapiens

<400> SEQUENCE: 723

```
gacgaagaac ctaacattca gtgataaaac caagctcatc tgattttaag gtgatgagtt      60
agctatattc ctgtgaaagg aaattagtta taaagacatt cttttgaaat acttggtctt     120
gtttggtttt ggaagattgg gtgaggttag tatttggata ggagagtaag gctggtggtt     180
```

```
attcagtagt atccctggtt tgagtccagg tttcttactg ttgttcaaca aggaaagtag      240
ttggtatgct ttgaaacaaa acaaaacaga acacttttaa gttktataaa tttatttcaa      300
actttgtcgt tatatgaaca ttacagatat ttaaatggta gagacatttt tggatattta      360
gttaaatcca aaagtaggag gtttagttca aatttggatt tttgagttac aaaatcaggt      420
agttaagtac tgtcta                                                     436

<210> SEQ ID NO 724
<211> LENGTH: 23
<212> TYPE: DNA
<213> ORGANISM: Homo Sapiens

<400> SEQUENCE: 724
gacgaagaac ctaacattca gtg                                              23

<210> SEQ ID NO 725
<211> LENGTH: 27
<212> TYPE: DNA
<213> ORGANISM: Homo Sapiens

<400> SEQUENCE: 725
tagacagtac ttaactacct gattttg                                          27

<210> SEQ ID NO 726
<211> LENGTH: 436
<212> TYPE: DNA
<213> ORGANISM: Homo Sapiens

<400> SEQUENCE: 726
gacgaagaac ctaacattca gtgataaaac caagctcatc tgattttaag gtgatgagtt       60
agctatattc ctgtgaaagg aaattagtta taaagacatt cttttgaaat acttggtctt      120
gtttggtttt ggaagattgg gtgaggttag tatttggata ggagagtaag gctggtggtt      180
attcagtagt atccctggtt tgagtccagg tttcttactg ttgttcaaca aggaaagtag      240
ttggtatgct ttgaaacaaa acaaaacaga acacttttaa gttktataaa tttatttcaa      300
actttgtcgt tatatgaaca ttacagatat ttaaatggta gagacatttt tggatattta      360
gttaaatcca aaagtaggag gtttagttca aatttggatt tttgagttac aaaatcaggt      420
agttaagtac tgtcta                                                     436

<210> SEQ ID NO 727
<211> LENGTH: 23
<212> TYPE: DNA
<213> ORGANISM: Homo Sapiens

<400> SEQUENCE: 727
gacgaagaac ctaacattca gtg                                              23

<210> SEQ ID NO 728
<211> LENGTH: 27
<212> TYPE: DNA
<213> ORGANISM: Homo Sapiens

<400> SEQUENCE: 728
tagacagtac ttaactacct gattttg                                          27

<210> SEQ ID NO 729
<211> LENGTH: 522
<212> TYPE: DNA
<213> ORGANISM: Homo Sapiens
```

```
<400> SEQUENCE: 729
atggtagaga catttttgga tatttagtta aatccaaaag taggaggttt agttcaaatt      60 tggattttg agttacaaaa tcaggtagtt aagtactgtc tacttcataa gttcttttac     120
ttcttaatca tagactggcc tgttgattta actgaaaaca cttgatttgt tttccagatc    180
attttcactt tccaactttt catgtgtttt tatggtatca cttyaatcta ccagtacaga    240
attttttttc ttttttgag acggagtctc gctctgtcgc ccaggctgga gtgcagtggc     300
gcgatctcgg ctcaccccaa gctcccctc ccaggttcat gccattctcc tgcctcagcc    360
tcctgagtag ctgggactgc aggtgccggc caccatgccc ggctaatttt ttctattttt   420
ttttagtaga cagggtttt caccttgtta gccaggatgg tctcgatctc ctgacctcgt    480
gatctgcccg ccttggcctc ccaaagtgct gggattacag gc                      522

<210> SEQ ID NO 730
<211> LENGTH: 25
<212> TYPE: DNA
<213> ORGANISM: Homo Sapiens

<400> SEQUENCE: 730
atggtagaga cattttgga tattt                                          25

<210> SEQ ID NO 731
<211> LENGTH: 20
<212> TYPE: DNA
<213> ORGANISM: Homo Sapiens

<400> SEQUENCE: 731
gcctgtaatc ccagcacttt                                               20

<210> SEQ ID NO 732
<211> LENGTH: 522
<212> TYPE: DNA
<213> ORGANISM: Homo Sapiens

<400> SEQUENCE: 732
atggtagaga catttttgga tatttagtta aatccaaaag taggaggttt agttcaaatt     60 tggattttg agttacaaaa tcaggtagtt aagtactgtc tacttcataa gttcttttac    120
ttcttaatca tagactggcc tgttgattta actgaaaaca cttgatttgt tttccagatc   180
attttcactt tccaactttt catgtgtttt tatggtatca ctttaatcta ccagtacaga   240
attttttttc ttttttgag acggagtctc gctctgtcgc ccaggctgga gtgcagtggc    300
gcgatctcgg ctcaccccaa gctcccctc ccaggttcat gccattctcc tgcctcagcc   360
tcctgagtag ctgggactgc aggtgccggc caccatgccc ggctaatttt ttctattttt  420
ttttagtaga cagggtttt caccttgtta gccaggatgg tctcgatctc ctgacctcgt   480
gatctgcccg cctyggcctc ccaaagtgct gggattacag gc                     522

<210> SEQ ID NO 733
<211> LENGTH: 25
<212> TYPE: DNA
<213> ORGANISM: Homo Sapiens

<400> SEQUENCE: 733
atggtagaga cattttgga tattt                                          25
```

```
<210> SEQ ID NO 734
<211> LENGTH: 20
<212> TYPE: DNA
<213> ORGANISM: Homo Sapiens

<400> SEQUENCE: 734
gcctgtaatc ccagcacttt                                                    20

<210> SEQ ID NO 735
<211> LENGTH: 439
<212> TYPE: DNA
<213> ORGANISM: Homo Sapiens

<400> SEQUENCE: 735
tttcaccttg ttagccagga tggtctcgat ctcctgacct cgtgatctgc ccgccttggc        60
ctcccaaagt gctgggatta caggcgtgag ccaccgtgac cagcccagta cagatttttt       120
aaaagcctct tactggttag ttaatttagt atagcacata agagtctttt ttccctagta       180 ggctttata ctggggtaat taccatgttt aatggtcagt gttgattcat gaagcagtta        240
ttggaaatag atccttttaa aagataattg ttagataacc actactagct actgaaatat       300
ttgtggtttg cartgtattt tagagtaagc attttttccg ctcatcttgc aaagtagttt       360
attgtataaa atacaggttt taaaagtttg ttttccagga cctattttt aatagacatt        420 ttctaaaagc agtatcttg                                                   439

<210> SEQ ID NO 736
<211> LENGTH: 21
<212> TYPE: DNA
<213> ORGANISM: Homo Sapiens

<400> SEQUENCE: 736
tttcaccttg ttagccagga t                                                  21

<210> SEQ ID NO 737
<211> LENGTH: 26
<212> TYPE: DNA
<213> ORGANISM: Homo Sapiens

<400> SEQUENCE: 737
caagatactg cttttagaaa atgtct                                             26

<210> SEQ ID NO 738
<211> LENGTH: 420
<212> TYPE: DNA
<213> ORGANISM: Homo Sapiens

<400> SEQUENCE: 738
taacagttgt taagattacc acttttggcc acatccaata agctggtgag attgtctggt        60
ttcagcctaa acaacttcat ttgaaaggtg ttgcatgaaa tgccttaaaa cacttaggat       120
ggtttactat taaatttgta atttagaaaa gtttaattgg ggtgatgttt tgagtgctgc       180
atatacatca aaaaaattct aggagaagga aaggtcagga aaagtattta aaaccaaaag       240
gaaagaaggt aatgataaag gggtgtgag tgggtttgta tttctatgtt tagtctgtrg        300
cctctttagg tctgtttatc agaagaccac ttagctaatg attgtattat tttttcagaa       360
taactggaga attgttattc tgaaaaaata ttgcatctgg ctggaattgc atcaaaggtt       420
```

<210> SEQ ID NO 739
<211> LENGTH: 26
<212> TYPE: DNA
<213> ORGANISM: Homo Sapiens

<400> SEQUENCE: 739
taacagttgt taagattacc actttt                                     26

<210> SEQ ID NO 740
<211> LENGTH: 20
<212> TYPE: DNA
<213> ORGANISM: Homo Sapiens

<400> SEQUENCE: 740
aacctttgat gcaattccag                                            20

<210> SEQ ID NO 741
<211> LENGTH: 418
<212> TYPE: DNA
<213> ORGANISM: Homo Sapiens

<400> SEQUENCE: 741
aaatattgca tctggctgga attgcatcaa aggtttatta actgccttaa ggagagttgg    60
caatatttta gtatttgagg ggatggaaga gaccttaaac atctaacttc ctaaatctgg   120
gaagtacaat cgatttagta caatagatct agatttagga agtacaatta ttcatttgtc   180
taatattgga gatttaaaag caggggaaaa taactttatt aacttgtaac tttaaacatt   240
cattgaaatg tttgaattta ggtaagtgtg tggttgtgra gtgagtttac tcttgtcatt   300 tttttttat cagtttgtag acatggaaag taggcaacaa tgagggtttt tttgttttaa   360
cacaagtata ccttattctt aacgagcata ttaagattac atagttactt ttggactt     418

<210> SEQ ID NO 742
<211> LENGTH: 20
<212> TYPE: DNA
<213> ORGANISM: Homo Sapiens

<400> SEQUENCE: 742
aaatattgca tctggctgga                                            20

<210> SEQ ID NO 743
<211> LENGTH: 26
<212> TYPE: DNA
<213> ORGANISM: Homo Sapiens

<400> SEQUENCE: 743
aagtccaaaa gtaactatgt aatctt                                     26

<210> SEQ ID NO 744
<211> LENGTH: 20
<212> TYPE: DNA
<213> ORGANISM: Homo Sapiens

<400> SEQUENCE: 744
aatgacaaga gtaaactcac                                            20

<210> SEQ ID NO 745
<211> LENGTH: 419
<212> TYPE: DNA
<213> ORGANISM: Homo Sapiens

<400> SEQUENCE: 745

```
aaatattgca tctggctgga attgcatcaa aggtttatta actgccttaa ggagagttgg      60
caatatttta gtatttgagg ggatggaaga gaccttaaac atctaacttc ctaaatctgg     120
gaagtacaat cgatttagta caatagatct agatttagga agtacaatta ttcatttgtc     180
taatattgga gatttaaaag cagggaaaa taactttatt aacttgtaac tttaaacatt     240
cattgaaatg tttgaattta gtaagtgtg tggttgtgaa gtgagtttac tcttgtcatt     300
ttttttttat cagtttgtag acatggaaag taggcaacaa tgagggtttt ttttgttta     360
acacaagtat accttattct taacgagcat attaagatta catagttact tttggactt     419
```

<210> SEQ ID NO 746
<211> LENGTH: 20
<212> TYPE: DNA
<213> ORGANISM: Homo Sapiens

<400> SEQUENCE: 746

```
aaatattgca tctggctgga                                                  20
```

<210> SEQ ID NO 747
<211> LENGTH: 26
<212> TYPE: DNA
<213> ORGANISM: Homo Sapiens

<400> SEQUENCE: 747

```
aagtccaaaa gtaactatgt aatctt                                           26
```

<210> SEQ ID NO 748
<211> LENGTH: 400
<212> TYPE: DNA
<213> ORGANISM: Homo Sapiens

<400> SEQUENCE: 748

```
gcaacaatga gggtttttt gttttaacac aagtataccct tattcttaac gagcatatta      60
agattacata gttactttg gacttttaga attgaggct attttagagg tctggtagag     120
caaagtagac aacatggaaa ttccttgttt tgtattgact acttccattt agctgatctg     180
tttcttttg gtgttactag acaaagctag attttaaaag atgaattaag atgctcagct     240
aactagtcct gtttatagta ttgttgatag atagcaagtt gayttctcca ggttcttcat     300
tgaatgagtc cttgtttact atgatgcttg ctacatacag ttgctacata ctactatgta     360
tgagtagttt ttggtcataa actgcataga ggtggagctg                           400
```

<210> SEQ ID NO 749
<211> LENGTH: 21
<212> TYPE: DNA
<213> ORGANISM: Homo Sapiens

<400> SEQUENCE: 749

```
gcaacaatga gggtttttt g                                                21
```

<210> SEQ ID NO 750
<211> LENGTH: 22
<212> TYPE: DNA
<213> ORGANISM: Homo Sapiens

<400> SEQUENCE: 750

```
cagctccacc tctatgcagt tt                                               22
```

```
<210> SEQ ID NO 751
<211> LENGTH: 418
<212> TYPE: DNA
<213> ORGANISM: Homo Sapiens

<400> SEQUENCE: 751
gcaacaatga gggtttttttt gttttaacac aagtatacct tattcttaac gagcatatta      60
agattacata gttacttttg gacttttaga atttgaggct attttagagg tctggtagag     120
caaagtagac aacatggaaa ttccttgttt tgtattgact acttccattt agctgatctg     180 tttcttttg  gtgttactag acaaagctag attttaaaag atgaattaag atgctcagct     240
aactagtcct gtttatagta ttgttgatag atagcaagtt gacttctcca ggttcttcat     300
tgaatgagtc cttgtttact atgatgcttg ctacatacta ctatgtttac tatgatrstt     360
gctacatact actatgtatg agtagttttt ggtcataaac tgcatagagg tggagctg      418

<210> SEQ ID NO 752
<211> LENGTH: 21
<212> TYPE: DNA
<213> ORGANISM: Homo Sapiens

<400> SEQUENCE: 752
gcaacaatga gggtttttttt g                                                21

<210> SEQ ID NO 753
<211> LENGTH: 22
<212> TYPE: DNA
<213> ORGANISM: Homo Sapiens

<400> SEQUENCE: 753
cagctccacc tctatgcagt tt                                                22

<210> SEQ ID NO 754
<211> LENGTH: 471
<212> TYPE: DNA
<213> ORGANISM: Homo Sapiens

<400> SEQUENCE: 754
ttttttttga gacggagtct tgctgtgttg tccaggctgg agtacagtgg cgcgatctca      60
gctcactgca agctccacct cttgggttca tgccattctc ctgcctyagg ctcctgagta     120
gctgggacta cataggtgcc cgccaccatg cccagctaat ttttttgtat ttttagtaga     180
gacgggtttc accgtgttta gccaggatgg tcttgatctc ctgaccttgt gatctgcctg     240
ccttagccct cccaaagtgc tgggattaca ggtgtgagcc atccctgttt taatccatct     300
gacatatttc ttctgattat gtagctctct tagttcaagc ttttctgtag gtaacccaca     360
gtccctgagg taatctttta cttagctggg ccttcccaaa atgtgtatta tatatagcat     420
atgttaaatg tttaggttta acaccttttg tattattcag gatttgtcaa g             471

<210> SEQ ID NO 755
<211> LENGTH: 22
<212> TYPE: DNA
<213> ORGANISM: Homo Sapiens

<400> SEQUENCE: 755
ttttttttga gacggagtct tg                                                22
```

<210> SEQ ID NO 756
<211> LENGTH: 25
<212> TYPE: DNA
<213> ORGANISM: Homo Sapiens

<400> SEQUENCE: 756
cttgacaaat cctgaataat acaaa                                           25

<210> SEQ ID NO 757
<211> LENGTH: 471
<212> TYPE: DNA
<213> ORGANISM: Homo Sapiens

<400> SEQUENCE: 757 tttttttga gacggagtct tgctgtgttg tccaggctgg agtacagtgg cgcgatctca      60
gctcactgca agctccacct cttgggttca tgccattctc ctgcctcagg ctcctgagta    120
gctgggacta cataggtgcc cgccaccatg cccagctaat tttttgtat ttttagtaga    180
gacggggttt caccgtgtta gccaggatgg tcttgatctc ctgaccttgt gatctgcctg    240
ccttagccct cccaaagtgc tgggattaca ggtgtgagcc atccctgttt taatccatct    300
gacatatttc ttctgattat gtagctctct tagttcaagc ttttctgtag gtaacccaca    360
gtccctgagg taatctttta cttagctggg ccttcccaaa atgtgtatta tatatagcat    420
atgttaaatg tttaggttta acaccttttg tattattcag gatttgtcaa g             471

<210> SEQ ID NO 758
<211> LENGTH: 22
<212> TYPE: DNA
<213> ORGANISM: Homo Sapiens

<400> SEQUENCE: 758 tttttttga gacggagtct tg                                              22

<210> SEQ ID NO 759
<211> LENGTH: 25
<212> TYPE: DNA
<213> ORGANISM: Homo Sapiens

<400> SEQUENCE: 759
cttgacaaat cctgaataat acaaa                                           25

<210> SEQ ID NO 760
<211> LENGTH: 470
<212> TYPE: DNA
<213> ORGANISM: Homo Sapiens

<400> SEQUENCE: 760 tttttttga gacggagtct tgctgtgttg tccaggctgg agtacagtgg cgcgatctca      60
gctcactgca agctccacct cttgggttca tgccattctc ctgcctcagg ctcctgagta    120
gctgggacta cataggtgcc cgccaccatg cccagctaat tttttgtat ttttagtaga    180
gacggggttt caccgtgtta gccaggatgg tcttgatctc ctgaccttgt gatctgcctg    240
ccttagcctc ccaaagtgct gggattacag gtgtgagcca tccctgtttt aatccatctg    300
acatatttct tctgattatg tagctctctt agttcaagct tttctgtagg taacccacag    360
tccctgaggt aayctttac ttagctgggc cttcccaaaa tgtgtattat atatagcata    420
tgttaaatgt ttaggtttaa caccttttgt attattcagg atttgtcaag               470

```
<210> SEQ ID NO 761
<211> LENGTH: 22
<212> TYPE: DNA
<213> ORGANISM: Homo Sapiens

<400> SEQUENCE: 761
ttttttttga gacggagtct tg                                                  22

<210> SEQ ID NO 762
<211> LENGTH: 25
<212> TYPE: DNA
<213> ORGANISM: Homo Sapiens

<400> SEQUENCE: 762
cttgacaaat cctgaataat acaaa                                               25

<210> SEQ ID NO 763
<211> LENGTH: 475
<212> TYPE: DNA
<213> ORGANISM: Homo Sapiens

<400> SEQUENCE: 763
tatatagcat atgttaaatg tttaggttta acaccttttg tattattcag gatttgtcaa         60
ggatgggaca taactaagaa actaacaatg ggcttgcact agctacaagt tcagcttaaa        120
aaytgggaac ttggaatccc tcttagtcat agcttaaaaa aagactcatc ttaaataatt        180
taattggagt aggtttatat tttggatatg taacatttac acttaaaaaa tgaatgaaaa        240
aaattgttac gatagtatag tattaatagc atagctatgt tacatgcaag ctaccttgtt        300
ctcaggtcat gagattactt tgcttcatat aataatctct ggtggaagaa aacattaaag        360
cttttaacaa ttctgcttat gggacttgta gaccattggt cccataaaga taacataaag        420
gaagactaca tgtgaaggac ttcatatttt gaaagatgca aattattcaa aagtc            475

<210> SEQ ID NO 764
<211> LENGTH: 27
<212> TYPE: DNA
<213> ORGANISM: Homo Sapiens

<400> SEQUENCE: 764
tatatagcat atgttaaatg tttaggt                                             27

<210> SEQ ID NO 765
<211> LENGTH: 25
<212> TYPE: DNA
<213> ORGANISM: Homo Sapiens

<400> SEQUENCE: 765
gacttttgaa taatttgcat ctttc                                               25

<210> SEQ ID NO 766
<211> LENGTH: 396
<212> TYPE: DNA
<213> ORGANISM: Homo Sapiens

<400> SEQUENCE: 766
cagaatgttg gtttactcat tgttttgtta gcagtaagag gtctttatta atttattaaa         60
ttagatgaat atggtatttg acacagtgaa atctgtttca acttaaatga tacttaaagc        120
ctgtctgtga cagcttttaaa cacttcattt ktgatgtgtg ttataagttg atcttaaaaa       180
cctaatggct gtatttaatc ctttctgttt ttcacaaata ggagtaaaac tctaaaaata        240
```

```
ttctcttgtc acatgtctac tttcatataa aggagaaatt caagtgttat tcctgctttc      300
ctactagtaa atatatttag atgatactat tttaaatgaa gatgtaaagt acgtaactag      360
ttataagtat ctaaaaacct aattcttagc atgtga                                396

<210> SEQ ID NO 767
<211> LENGTH: 24
<212> TYPE: DNA
<213> ORGANISM: Homo Sapiens

<400> SEQUENCE: 767
cagaatgttg gtttactcat tgtt                                             24

<210> SEQ ID NO 768
<211> LENGTH: 24
<212> TYPE: DNA
<213> ORGANISM: Homo Sapiens

<400> SEQUENCE: 768
tcacatgcta agaattaggt tttt                                             24

<210> SEQ ID NO 769
<211> LENGTH: 343
<212> TYPE: DNA
<213> ORGANISM: Homo Sapiens

<400> SEQUENCE: 769
ccacacccag ctcattttg tactttagt agagacaggg tttcgccatg ttggccaggc        60
tggtctcaaa ttcctgatct caagtgatct tcatgcctta gcctcccaga gtgctgggac     120
tacaggcatc agccaccata cctggcctcc aaaaactttt ttcaatgtag attaaaccca     180
ggcattttct taaaaaatgc catgaatctt ttactgaaat catagcatct gtaaactaaa     240
tcagacagtt tarttggtta cttccattaa tatgttagta taaaacagaa attgcgacag     300
atacagcatt ttatatctgc tatgtttact tctgtattta ctt                       343

<210> SEQ ID NO 770
<211> LENGTH: 19
<212> TYPE: DNA
<213> ORGANISM: Homo Sapiens

<400> SEQUENCE: 770
ccacacccag ctcattttt                                                   19

<210> SEQ ID NO 771
<211> LENGTH: 27
<212> TYPE: DNA
<213> ORGANISM: Homo Sapiens

<400> SEQUENCE: 771
aagtaaatac agaagtaaac atagcag                                          27

<210> SEQ ID NO 772
<211> LENGTH: 284
<212> TYPE: DNA
<213> ORGANISM: Homo Sapiens

<400> SEQUENCE: 772
atttgaggct ctgagcttca ttttaacaat caacatgggt aattcggttg ttaccttgag      60
catttcatct catgattttg tgtgtgtttg tgtgtatg catttgttga gtatatgtca       120
aattgtgaca ctgcaatagt tactacttga gttactatat tagtgcaatt aattacacaa     180
```

```
ctatatatag taattagttt ctcagatcta atratccagt atcaactgag ggttttcgta      240
ataggtactt agtgttggat gaagctgata ggatgctgga tatg                       284
```

<210> SEQ ID NO 773
<211> LENGTH: 20
<212> TYPE: DNA
<213> ORGANISM: Homo Sapiens

<400> SEQUENCE: 773

```
atttgaggct ctgagcttca                                                   20
```

<210> SEQ ID NO 774
<211> LENGTH: 21
<212> TYPE: DNA
<213> ORGANISM: Homo Sapiens

<400> SEQUENCE: 774

```
catatccagc atcctatcag c                                                 21
```

<210> SEQ ID NO 775
<211> LENGTH: 502
<212> TYPE: DNA
<213> ORGANISM: Homo Sapiens

<400> SEQUENCE: 775

```
agctgtttgg acttgagtag ttgtagaata actgaaaata ggaaactgct atatatatat       60
gtatgtataa tatatataac cttttttcag gtactcctat tgcaatacct gcatttcagc      120
actattcaaa agtaaaataa gtcccagagc caggttagtc attatgtcct atttattgct      180
aattttcata tacaaatgag agctgtcaga attcacagct tctgaatatc agaagctcat      240
gttttccctg gtctatacaa aaggaaaata agtgaggcca aaaatgtact ttaacagtgc      300
tccataatac gaatctcata atgagctgg aatagaccct gaggtcttca agcctagttt      360
ctcaagatcg tattttgtaa acttgtgcta gcagttttga atatcacaat gattggcatg      420
ggctgctgac attttagcag gcagggctca gggtgttaga tgtcctgtaa ttcagggaca      480
ttcacagtag aaaatacttt gg                                                502
```

<210> SEQ ID NO 776
<211> LENGTH: 23
<212> TYPE: DNA
<213> ORGANISM: Homo Sapiens

<400> SEQUENCE: 776

```
agctgtttgg acttgagtag ttg                                               23
```

<210> SEQ ID NO 777
<211> LENGTH: 26
<212> TYPE: DNA
<213> ORGANISM: Homo Sapiens

<400> SEQUENCE: 777

```
ccaaagtatt ttctactgtg aatgtc                                            26
```

<210> SEQ ID NO 778
<211> LENGTH: 515
<212> TYPE: DNA
<213> ORGANISM: Homo Sapiens

```
<400> SEQUENCE: 778
ccactcagct ttcctcaggt gcagtcaggt ccatcctgca gagggacctt ctgcggacct      60
gttctttcac ctccctaacc tgaagattgt attcaaacca ccgtggatcg ctcacgtaaa     120
atggtcactg cgcctaacac ctgggatccc gtaaacccta tctatcttgg cttcagagag     180
ttttttgact agttccaact ttgctgaagc ttgtcaaagg taggtgacgg ctagttggaa     240
cggaaaaatt ttacgaaact tcctattctc agaagtaaaa gggaagagag agtgcttaag     300
gaagaaggga agttgagggt gggtaaggag gsagcgggag ttagtggtag attgtcactg     360
tgtttaagat ttccccaagg cgaaaaaggc gaaagatatc ttgctagatc cctagaattc     420
gaaggcatta ggagagggcg gggatagcaa acatcgcgcg aattttgaga ggcgctggga     480
ctacgtaatc ccgcgatctt atgactaaac gaacg                                515

<210> SEQ ID NO 779
<211> LENGTH: 20
<212> TYPE: DNA
<213> ORGANISM: Homo Sapiens

<400> SEQUENCE: 779
ccactcagct ttcctcaggt                                                  20

<210> SEQ ID NO 780
<211> LENGTH: 22
<212> TYPE: DNA
<213> ORGANISM: Homo Sapiens

<400> SEQUENCE: 780
cgttcgttta gtcataagat cg                                               22

<210> SEQ ID NO 781
<211> LENGTH: 552
<212> TYPE: DNA
<213> ORGANISM: Homo Sapiens

<400> SEQUENCE: 781
tccaactcta gatttctttt actggttttta tgttaaagta cttgagaaaa aaaggtatt      60 aacgaatgac ttaatttctc tctaaacatt tttcttgata ggtggctatg gaggyttcta     120
caatagtgat ggatatggag gaaattataa ctcccagggg gttgactggt ggggcaactg     180
aatctgcttt gcagcaaagt caccttaca aagaagctaa tatggaaacc acatgtaact      240
tagccagact atattgtgta gcttcaagaa cttgcagtac attaccagct gtgattctcc     300
tgataattca agggagctca agtcacaag aagaaaaatg aaaggaaaaa acagcagccc      360
tattcagaaa ttggtttgaa gatgtaattg ctctagtttg gattaaactc ttcccctcct     420
gctttagtgc caccccaaac tgcatttata attttgtgac tgaggatcgt ttgtttgtta     480
acgtactgtg actttaactt tagacaactt actactttga tgtcctgttg gctcagtaat     540
gctcacgata cc                                                         552

<210> SEQ ID NO 782
<211> LENGTH: 25
<212> TYPE: DNA
<213> ORGANISM: Homo Sapiens

<400> SEQUENCE: 782
tccaactcta gatttctttt actgg                                            25
```

```
<210> SEQ ID NO 783
<211> LENGTH: 22
<212> TYPE: DNA
<213> ORGANISM: Homo Sapiens

<400> SEQUENCE: 783
ggtatcgtga gcattactga gc                                              22

<210> SEQ ID NO 784
<211> LENGTH: 445
<212> TYPE: DNA
<213> ORGANISM: Homo Sapiens

<400> SEQUENCE: 784
ttagacaact tactactttg atgtcctgtt ggctcagtaa tgctcacgat accaattgtt     60
ttgacaaaat aaatttacta aacttggcct aaaatcaaac cttggcacag aggtatgata    120
caactttaac aggagtcatc aattcatcca taaatataaa aagggaaaaa aacttaaggc    180
agtagtctgc attaggactg tttgagtttt gcagacttgg ggttgggaga acatcttaaa    240
gcattaaagc atagtttttt gtatggccaa ccttactaaa ttaagttctg acttgctmac    300
tctatcctgg ataggcactt gggaacttac actctttaag ccattccagt catgatgagg    360
tggaatgtat cagtatacca attaatattt ttgaaagagc tcttttaggt taatttaagt    420
acagcaattt ctcatgtaat gttta                                         445

<210> SEQ ID NO 785
<211> LENGTH: 27
<212> TYPE: DNA
<213> ORGANISM: Homo Sapiens

<400> SEQUENCE: 785
ttagacaact tactactttg atgtcct                                         27

<210> SEQ ID NO 786
<211> LENGTH: 25
<212> TYPE: DNA
<213> ORGANISM: Homo Sapiens

<400> SEQUENCE: 786
taaacattac atgagaaatt gctgt                                           25

<210> SEQ ID NO 787
<211> LENGTH: 444
<212> TYPE: DNA
<213> ORGANISM: Homo Sapiens

<400> SEQUENCE: 787
tgaggtggaa tgtatcagta taccaattaa tattttgaa agagctcttt taggttaatt     60
taagtacagc aatttctcat gtaatgttta gggagtttat tctaacctag gcaaacggca   120
tgctatcaca agaaaggttt aaagctttga taaaatgggg gagatttaat cagttttttt   180
aatgcctgct ataaaatttt gaaatatyag aatggccgac catggcagtg accaggcctc   240
actacaggcc tggttggatt ctggtctta atgcatgcta gtgttgatgt tttttggtca    300
agaacggttt aaacaggaag gattgtgcag caggctttaa tttaatgtag attcatactg   360
ctctgttaaa gctgcattga aatgttaaaa tggcttacac ttgcagactt tgcaaatctt   420
aagactaaca aatccttgaa atca                                          444
```

```
<210> SEQ ID NO 788
<211> LENGTH: 24
<212> TYPE: DNA
<213> ORGANISM: Homo Sapiens

<400> SEQUENCE: 788
tgaggtggaa tgtatcagta tacc                                          24

<210> SEQ ID NO 789
<211> LENGTH: 24
<212> TYPE: DNA
<213> ORGANISM: Homo Sapiens

<400> SEQUENCE: 789
tgatttcaag gatttgttag tctt                                          24

<210> SEQ ID NO 790
<211> LENGTH: 287
<212> TYPE: DNA
<213> ORGANISM: Homo Sapiens

<400> SEQUENCE: 790
ttatcctgag ccgttgtccc tgtgtttcca tttctctttt cctcatttct catcatctac   60
atttctcctg tacttgttca ttaaataatg attccttgga tataccaagt ctggatagcg  120
gattcgatgg aagcattttt gtaaatakac gttcagtatt ttgtgtggaa gaacacaatc  180
tagctgatgc ctgcaatccc agcccttggg aaagcgaggt gggtggattg cttgaagcta  240
cgagtttgac actagcctgg gcaacagggt acaaccgtgt ctctaca                287

<210> SEQ ID NO 791
<211> LENGTH: 22
<212> TYPE: DNA
<213> ORGANISM: Homo Sapiens

<400> SEQUENCE: 791
ttatcctgag ccgttgtccc tg                                            22

<210> SEQ ID NO 792
<211> LENGTH: 22
<212> TYPE: DNA
<213> ORGANISM: Homo Sapiens

<400> SEQUENCE: 792
tgtagagaca cggttgtacc ct                                            22

<210> SEQ ID NO 793
<211> LENGTH: 426
<212> TYPE: DNA
<213> ORGANISM: Homo Sapiens

<400> SEQUENCE: 793
ctaaagatca gagtatctcc ctttgcaaaa tgtccattaa atctttgctg atgttattat   60
ccctgtacct gactctatcc ttaaatagta aggcttcctt tattcttgta gggtagaact  120
tttaaactga gtgatgccta aaatgttct  caataaagag agtatctcca aaacacgtcg  180
gatttgttta agaggaagt gtggattttt tgatcttaga aggaaacga gataaaatat   240 taaacgactt taatttttgt atgatcatgc ctagcctcat tcctctaaaa trtaatttaa  300
agtggattct gttacatggt atcacaatag aaggggaatg atcagggttt ggttaattct  360
```

```
ggtaaattga aaacaatttt ttttttatc atatgtgcct cagaaggcac acaaaagaag    420
tatagt                                                              426
```

<210> SEQ ID NO 794
<211> LENGTH: 25
<212> TYPE: DNA
<213> ORGANISM: Homo Sapiens

<400> SEQUENCE: 794

```
ctaaagatca gagtatctcc ctttg                                          25
```

<210> SEQ ID NO 795
<211> LENGTH: 24
<212> TYPE: DNA
<213> ORGANISM: Homo Sapiens

<400> SEQUENCE: 795

```
actatacttc ttttgtgtgc cttc                                           24
```

<210> SEQ ID NO 796
<211> LENGTH: 426
<212> TYPE: DNA
<213> ORGANISM: Homo Sapiens

<400> SEQUENCE: 796

```
ctaaagatca gagtatctcc ctttgcaaaa tgtccattaa atctttgctg atgttattat    60
ccctgtacct gactctatcc ttaaatagta aggcttcctt tattcttgta gggtagaact   120
tttaaactga gtgatgccta aaatgttct caataaagag agtatctcca aaacacgtcg   180
gatttgttta agaggaagt gtggatttttt tgatcttaga aaggaaacga gataaaatat   240
taaacgactt taattttgt atgatcatgc ctagcctcat tcctctaaaa tataatttaa    300
agtggattct gttacatggt atcacaatag aaggggaatg atcagggttt ggttaatyct   360
ggtaaattga aaacaatttt ttttttatc atatgtgcct cagaaggcac acaaaagaag    420
tatagt                                                              426
```

<210> SEQ ID NO 797
<211> LENGTH: 25
<212> TYPE: DNA
<213> ORGANISM: Homo Sapiens

<400> SEQUENCE: 797

```
ctaaagatca gagtatctcc ctttg                                          25
```

<210> SEQ ID NO 798
<211> LENGTH: 24
<212> TYPE: DNA
<213> ORGANISM: Homo Sapiens

<400> SEQUENCE: 798

```
actatacttc ttttgtgtgc cttc                                           24
```

<210> SEQ ID NO 799
<211> LENGTH: 426
<212> TYPE: DNA
<213> ORGANISM: Homo Sapiens

<400> SEQUENCE: 799

```
ctaaagatca gagtatctcc ctttgcaaaa tgtccattaa atctttgctg atgttattat    60
ccctgtacct gactctatcc ttaaatagta aggcttcctt tattcttgta gggtagaact   120
```

| | |
|---|---:|
| tttaaactga gtgatgccta aaaatgttct caataaagag agtatctcca aaacacgtcg | 180 |
| gatttgttta aagaggaagt gtggattttt tgatcttaga aaggaaacga gataaaatat | 240 |
| taaacgactt taattttgt atgatcatgc ctagcctcat tcctctaaaa tataatttaa | 300 |
| agtggattct gttacatggt atcacaatag aagggaatg atcagggttt ggttaattct | 360 |
| ggtaaattga aaacaatttt ttttttatc atatgtgcct cagaaggcac acaaaagaag | 420 |
| tatagt | 426 |

<210> SEQ ID NO 800
<211> LENGTH: 25
<212> TYPE: DNA
<213> ORGANISM: Homo Sapiens

<400> SEQUENCE: 800

| | |
|---|---:|
| ctaaagatca gagtatctcc ctttg | 25 |

<210> SEQ ID NO 801
<211> LENGTH: 24
<212> TYPE: DNA
<213> ORGANISM: Homo Sapiens

<400> SEQUENCE: 801

| | |
|---|---:|
| actatacttc ttttgtgtgc cttc | 24 |

<210> SEQ ID NO 802
<211> LENGTH: 461
<212> TYPE: DNA
<213> ORGANISM: Homo Sapiens

<400> SEQUENCE: 802

| | |
|---|---:|
| gcttattttt agtctctctt ccatgactct tctaatacca tcgtcaataa atttcaacta | 60 |
| ggtaaaaaat taatattgaa catctgtcca aagaaaggcc agtatctcca aaatcctctc | 120 |
| gtacagatct gtttcgagat cattctaatt actgtatctt catattttag gttaagattc | 180 |
| tttaacttgt gaaggagaat gaaaaagttg ggtgacacaa actcttcaga aggaaaaata | 240 |
| cataaaaatt attttgatga aagccacagc agctttatca aatgcttacg ttgctmaata | 300 |
| gtaaaaaaag ccacttaaat tccaatggaa atttatacc cacatgtatt tatgtaaaac | 360 |
| ttttaaataa catgtattca taatcacttt tatatcctca accagttttt atgaagctag | 420 |
| aaaaaaattc ctttattaaa gaaatgtaac attcaacagg t | 461 |

<210> SEQ ID NO 803
<211> LENGTH: 24
<212> TYPE: DNA
<213> ORGANISM: Homo Sapiens

<400> SEQUENCE: 803

| | |
|---|---:|
| acctgttgaa tgttacattt cttt | 24 |

<210> SEQ ID NO 804
<211> LENGTH: 496
<212> TYPE: DNA
<213> ORGANISM: Homo Sapiens

<400> SEQUENCE: 804

| | |
|---|---:|
| caggagggga ccatgtttta tagtccacaa aaactctgtt tagattattc cttcctggga | 60 |
| cccagaccaa tttgtcttct ttttacttgc ctgttggcag catggaatct gtttcatttt | 120 |
| ctcttttag ctgtcacgac acacagctct tgaggtactt ggtgacagta cagtgcagtc | 180 |

```
tttcctgggc attactcttt gctctcccga aracccacta acgggttgtg tgtataataa      240
ggttttattt tattttattt tattttttac tgcaaaatta ttggaggata aagtgtattc      300
tgggagaagt ctaattagaa agagttagca aaggcttatg cttttcact  aacattttct     360 cagatggtac tgaacaactt cagtaggtat cttgttctca cctttatttc tagtgatgag     420
attcccagtt ctctaagcca tcagctctaa agatcagagt atctccctt  gcaaaatgtc     480 cattaaatct ttgctg                                                     496
```

<210> SEQ ID NO 805
<211> LENGTH: 19
<212> TYPE: DNA
<213> ORGANISM: Homo Sapiens

<400> SEQUENCE: 805

```
caggaggga ccatgtttt                                                    19
```

<210> SEQ ID NO 806
<211> LENGTH: 23
<212> TYPE: DNA
<213> ORGANISM: Homo Sapiens

<400> SEQUENCE: 806

```
cagcaaagat ttaatggaca ttt                                              23
```

<210> SEQ ID NO 807
<211> LENGTH: 502
<212> TYPE: DNA
<213> ORGANISM: Homo Sapiens

<400> SEQUENCE: 807

```
cacatcagga aagggcatc  ctttggccta tacttgtgaa gagctagagt aaggtgctcc      60
ccacctttga gattgctaaa gttgtcattc ttttggaaat ttatgagcta atcatcattt     120
agtcatttga aaagctgcca aactttgta  aaacccagta aggaaagcag gtatgatctt     180
tgtcctgasg cagctaagtt caggcacgat taattgctcg aaatatagaa tgtgttttcc     240
tttgtagaaa tttagttttg gcatgccta  aaatgcatca gaatctggat aaatcacaga     300
gttctggaag cccaattgtc ttctatagtg gcacagaaca atgtgagact gccccagagg     360
tagtgggtga attcaagaag ttagatgtct ggctttatgg tggccaggta tatgttttat     420
tctatttgca gtgttaacat ttttattcaa attcttcaat cgatccctta atattactgt     480
aatttgtagc ctttctccct cc                                              502
```

<210> SEQ ID NO 808
<211> LENGTH: 20
<212> TYPE: DNA
<213> ORGANISM: Homo Sapiens

<400> SEQUENCE: 808

```
cacatcagga aagggcatc                                                   20
```

<210> SEQ ID NO 809
<211> LENGTH: 21
<212> TYPE: DNA
<213> ORGANISM: Homo Sapiens

<400> SEQUENCE: 809

```
ggagggagaa aggctacaaa t                                                21
```

<210> SEQ ID NO 810
<211> LENGTH: 457
<212> TYPE: DNA
<213> ORGANISM: Homo Sapiens

<400> SEQUENCE: 810

| | | | | | |
|---|---|---|---|---|---|
| gccatgccca | agaataaagg | tactgctgta | agcctctggg | actatayctc | ggcttgctct | 60 |
| gccagtaacc | ccgacgcctg | ttccaggccg | cagtgactgt | tctaacgcg | gtactggcca | 120 |
| ctgcgacccc | agcactgtgt | tcgggaaagg | agctgggaat | gccctatttg | gtcacattgg | 180 |
| ggtgggacag | acgccatttt | tgtgggcct | ccttcggaag | atagcgggct | tttgctgctg | 240 |
| atttcacgcc | agacggaaaa | cgtataggta | gggacggttg | agggaccta | accggacggc | 300 |
| ctggctttcc | agaataggca | catgsaaaca | cttccctgct | actttcctgg | aagcggttct | 360 |
| taactttgaa | gacttaccta | tctggacagt | taaaagtatt | gctaaggata | ctccctttc | 420 |
| cttgttaaac | agtggggaag | ccttgaagca | tgtttag | | | 457 |

<210> SEQ ID NO 811
<211> LENGTH: 19
<212> TYPE: DNA
<213> ORGANISM: Homo Sapiens

<400> SEQUENCE: 811
gccatgccca agaataaag                                                    19

<210> SEQ ID NO 812
<211> LENGTH: 21
<212> TYPE: DNA
<213> ORGANISM: Homo Sapiens

<400> SEQUENCE: 812
ctaaacatgc ttcaaggctt c                                                 21

<210> SEQ ID NO 813
<211> LENGTH: 457
<212> TYPE: DNA
<213> ORGANISM: Homo Sapiens

<400> SEQUENCE: 813

| | | | | | |
|---|---|---|---|---|---|
| gccatgccca | agaataaagg | tactgctgta | agcctctggg | actatayctc | ggcttgctct | 60 |
| gccagtaacc | ccgacgcctg | ttccaggccg | cagtgactgt | tctaacgcg | gtactggcca | 120 |
| ctgcgacccc | agcactgtgt | tcgggaaagg | agctgggaat | gccctatttg | gtcacattgg | 180 |
| ggtgggacag | acgccatttt | tgtgggcct | ccttcggaag | atagcgggct | tttgctgctg | 240 |
| atttcacgcc | agacggaaaa | cgtataggta | gggacggttg | agggaccta | accggacggc | 300 |
| ctggctttcc | agaataggca | catgsaaaca | cttccctgct | actttcctgg | aagcggttct | 360 |
| taactttgaa | gacttaccta | tctggacagt | taaaagtatt | gctaaggata | ctccctttc | 420 |
| cttgttaaac | agtggggaag | ccttgaagca | tgtttag | | | 457 |

<210> SEQ ID NO 814
<211> LENGTH: 19
<212> TYPE: DNA
<213> ORGANISM: Homo Sapiens

<400> SEQUENCE: 814
gccatgccca agaataaag                                                    19

<210> SEQ ID NO 815
<211> LENGTH: 21
<212> TYPE: DNA
<213> ORGANISM: Artificial Sequence
<220> FEATURE:
<223> OTHER INFORMATION: synthetic oligo

<400> SEQUENCE: 815
ctaaacatgc ttcaaggctt c                                              21

<210> SEQ ID NO 816
<211> LENGTH: 287
<212> TYPE: DNA
<213> ORGANISM: Homo Sapiens

<400> SEQUENCE: 816
ttatcctgag ccgttgtccc tgtgtttcca tttctctttt cctcatttct catcatcwac    60
atttctcctg tacttgttca ttaaataatg attccttgga tataccaagt ctggatagcg   120
gattcgatgg aagcattttt gtaaatatac gttcagtatt ttgtgtggaa gaacacaatc   180
tagctgatgc ctgcaatccc agccctttgg aaagcgaggt gggtggattg cttgaagcta   240
cgagtttgac actagcctgg gcaacagggt acaaccgtgt ctctaca                 287

<210> SEQ ID NO 817
<211> LENGTH: 22
<212> TYPE: DNA
<213> ORGANISM: Homo Sapiens

<400> SEQUENCE: 817
ttatcctgag ccgttgtccc tg                                             22

<210> SEQ ID NO 818
<211> LENGTH: 22
<212> TYPE: DNA
<213> ORGANISM: Homo Sapiens

<400> SEQUENCE: 818
tgtagagaca cggttgtacc ct                                             22

<210> SEQ ID NO 819
<211> LENGTH: 287
<212> TYPE: DNA
<213> ORGANISM: Homo Sapiens

<400> SEQUENCE: 819
ttatcctgag ccgttgtccc tgtgtttcca tttctctttt cctcatttct catcatctac    60
atttctcctg tacttgttca ttaaataatg attccttgga tataccaagt ctggatagcg   120
gattcgatgg aagcattttt gtaaatatac kttcagtatt ttgtgtggaa gaacacaatc   180
tagctgatgc ctgcaatccc agccctttgg aaagcgaggt gggtggattg cttgaagcta   240
cgagtttgac actagcctgg gcaacagggt acaaccgtgt ctctaca                 287

<210> SEQ ID NO 820
<211> LENGTH: 22
<212> TYPE: DNA
<213> ORGANISM: Homo Sapiens

<400> SEQUENCE: 820
ttatcctgag ccgttgtccc tg                                             22

<210> SEQ ID NO 821
<211> LENGTH: 22
<212> TYPE: DNA
<213> ORGANISM: Homo Sapiens

<400> SEQUENCE: 821
tgtagagaca cggttgtacc ct                                              22

<210> SEQ ID NO 822
<211> LENGTH: 418
<212> TYPE: DNA
<213> ORGANISM: Homo Sapiens

<400> SEQUENCE: 822
aaatattgca tctggctgga attgcatcaa aggtttatta actgccttaa ggagagttgg     60
caatatttta gtatttgagg ggatggaaga gaccttaaac atctaacttc ctaaatctgg    120
gaagtacaat cgatttagta caatagatct agatttagga agtacaatta ttcatttgtc   180
taatattgga gatttaaaag caggggaaaa taactttatt aacttgtaac tttaaacatt    240
cattgaaatg tttgaattta ggtaagtgtg tggttgtgga gtgagtttac tcttgtcatt    300
ttttttttat cagtttgtag acatggaaag taggcaacaa tgagggtttt tttgttttaa    360
cacaagtata cctkattctt aacgagcata ttaagattac atagttactt ttggactt     418

<210> SEQ ID NO 823
<211> LENGTH: 20
<212> TYPE: DNA
<213> ORGANISM: Homo Sapiens

<400> SEQUENCE: 823
aaatattgca tctggctgga                                                20

<210> SEQ ID NO 824
<211> LENGTH: 26
<212> TYPE: DNA
<213> ORGANISM: Homo Sapiens

<400> SEQUENCE: 824
aagtccaaaa gtaactatgt aatctt                                         26

<210> SEQ ID NO 825
<211> LENGTH: 20
<212> TYPE: DNA
<213> ORGANISM: Homo Sapiens

<400> SEQUENCE: 825
aatgacaaga gtaaactcac                                                20

<210> SEQ ID NO 826
<211> LENGTH: 418
<212> TYPE: DNA
<213> ORGANISM: Homo Sapiens

<400> SEQUENCE: 826
aaatattgca tctggctgga attgcatcaa aggtttatta actgccttaa ggagagttgg     60
caatatttta gtatttgagg ggatggaaga gaycttaaac atctaacttc ctaaatctgg    120
gaagtacaat cgatttagta caatagatct agatttagga agtacaatta ttcatttgtc   180
taatattgga gatttaaaag caggggaaaa taactttatt aacttgtaac tttaaacatt    240
cattgaaatg tttgaattta ggtaagtgtg tggttgtgga gtgagtttac tcttgtcatt    300

-continued

```
tttttttttat cagtttgtag acatggaaag taggcaacaa tgagggtttt tttgttttaa    360
cacaagtata ccttattctt aacgagcata ttaagattac atagttactt ttggactt      418
```

<210> SEQ ID NO 827
<211> LENGTH: 20
<212> TYPE: DNA
<213> ORGANISM: Homo Sapiens

<400> SEQUENCE: 827

```
aaatattgca tctggctgga                                                  20
```

<210> SEQ ID NO 828
<211> LENGTH: 26
<212> TYPE: DNA
<213> ORGANISM: Homo Sapiens

<400> SEQUENCE: 828

```
aagtccaaaa gtaactatgt aatctt                                           26
```

<210> SEQ ID NO 829
<211> LENGTH: 20
<212> TYPE: DNA
<213> ORGANISM: Homo Sapiens

<400> SEQUENCE: 829

```
aatgacaaga gtaaactcac                                                  20
```

<210> SEQ ID NO 830
<211> LENGTH: 386
<212> TYPE: DNA
<213> ORGANISM: Homo Sapiens

<400> SEQUENCE: 830

```
ccagtcagca gtacaaaagt tgacagcttc agcaaaattg tagccttggt taaaaccact    60
gtggtaagca cgaggaaaag tgatgacaaa ctcccctgca cactggtttg tgcggacaac   120
ctaaaaagga gaaaaagca gaaagaggtg tgggtcagaa ctaatgggcc agatgtgaac    180
tcaaagatgt ctctagatgc tgtaacagat gtaggaagag tggaaaggct ctatcttcaa   240
gtacgtgtcc taaagaaaaa tgagattgtg aatttaaaar tggtattcat agaaaagtac   300
tcaaaatatg tgtaattcaa aaaacaaata tagaggggtc cacgaacaag tgaaaagact   360
ctttgcttct ataatcaaag aaatgc                                          386
```

<210> SEQ ID NO 831
<211> LENGTH: 22
<212> TYPE: DNA
<213> ORGANISM: Homo Sapiens

<400> SEQUENCE: 831

```
ccagtcagca gtacaaaagt tg                                               22
```

<210> SEQ ID NO 832
<211> LENGTH: 24
<212> TYPE: DNA
<213> ORGANISM: Homo Sapiens

<400> SEQUENCE: 832

```
gcatttcttt gattatagaa gcaa                                             24
```

```
<210> SEQ ID NO 833
<211> LENGTH: 393
<212> TYPE: DNA
<213> ORGANISM: Homo Sapiens

<400> SEQUENCE: 833
tggtaaactc tacttagttg cctttggaa atgaataaat caaggtagaa aagcaattga      60
gatactaatt catgctctca ggggaaaatc tgaataaagc tatcttttct aacacagagc    120
aagtgactct caaagtcaca gtatctgaac tagcatatca gcatcgcctg aatacctaga    180
aatgcaaatt cctgggcaac accagaatct aacaaagcaa aaaactatgg ggggaacagg    240
gaagtcrgtt taataatact gagtttgtgc aacctcaact ttgctttata ggaaagcaaa    300
atctcaatat gataaagttt tcttcaacaa aactctgaga taactatgtt gagggaaaga    360
agttgatcac atgcaagaaa atctaattcg ctg                                 393

<210> SEQ ID NO 834
<211> LENGTH: 25
<212> TYPE: DNA
<213> ORGANISM: Homo Sapiens

<400> SEQUENCE: 834
tggtaaactc tacttagttg cettt                                           25

<210> SEQ ID NO 835
<211> LENGTH: 21
<212> TYPE: DNA
<213> ORGANISM: Homo Sapiens

<400> SEQUENCE: 835
cagcgaatta gattttcttg c                                               21

<210> SEQ ID NO 836
<211> LENGTH: 393
<212> TYPE: DNA
<213> ORGANISM: Homo Sapiens

<400> SEQUENCE: 836
tggtaaactc tacttagttg cctttggaa atgaataaat caaggtagaa aagcaattga      60
gatactaatt catgctctca ggggaaaatc tgaataaagc tatcttttct aacacagagc    120
aagtgactct caaagtcaca gtatctgaac tagcatatca gcatcgcctg aatacctaga    180
aatgcaaatt cctgggcaac accagaatct aacaaagcaa aaaactatgg ggggaacagg    240
gaagtcggtt taataatact gagtttgtgc aacctcaact ttgctttata ggaaagcaaa    300
atctcaatat gataargttt tcttcaacaa aactctgaga taactatgtt gagggaaaga    360
agttgatcac atgcaagaaa atctaattcg ctg                                 393

<210> SEQ ID NO 837
<211> LENGTH: 25
<212> TYPE: DNA
<213> ORGANISM: Homo Sapiens

<400> SEQUENCE: 837
tggtaaactc tacttagttg cettt                                           25

<210> SEQ ID NO 838
<211> LENGTH: 21
<212> TYPE: DNA
<213> ORGANISM: Homo Sapiens
```

```
<400> SEQUENCE: 838
cagcgaatta gattttcttg c                                              21

<210> SEQ ID NO 839
<211> LENGTH: 429
<212> TYPE: DNA
<213> ORGANISM: Homo Sapiens

<400> SEQUENCE: 839
ggcttacact tgcagacttt gcaaatctta agactaacaa atccttgaaa tcacacagct    60
tgcaaatacg tactaaactg cacaaggtgt gtgttctata tgtgcagttt tagcgtattt   120
tagttgcata ggttttccatg gtatttatag tctcttgtgc taaatttggc caaagatgat  180
tgtccaccac taaaaatgcc tctcccactt ggaattctgt actgattttg tggccagatg   240
caatgatctt taaaaacaaa tcttttcaat ggcataagaa gttgacraaa atttcttaaa   300
gtgcaataga ttttcaagtg tattgtgcct tgttctaaaa cttttaagta ggtgcacttg   360
acagtattga ggtcatttgt taaggtgcta tttcaattag tgtaggttta gactcttgta   420
catttctcc                                                          429

<210> SEQ ID NO 840
<211> LENGTH: 21
<212> TYPE: DNA
<213> ORGANISM: Homo Sapiens

<400> SEQUENCE: 840
ggcttacact tgcagacttt g                                              21

<210> SEQ ID NO 841
<211> LENGTH: 25
<212> TYPE: DNA
<213> ORGANISM: Homo Sapiens

<400> SEQUENCE: 841
ggagaaatgt acaagagtct aaacc                                          25

<210> SEQ ID NO 842
<211> LENGTH: 399
<212> TYPE: DNA
<213> ORGANISM: Homo Sapiens

<400> SEQUENCE: 842
ggcagttttc atttaagcag aggcaacaaa tgtaatacta atgtttgatt attatagaaa    60
aaagtattca tcttagcaaa gttttaacta tgggattatt tttaacaaac aattgtgttt   120 tcttttttctt aaagacaaac acaatgcata cttactgccg aaagcttgac aagattaaaa  180
taagtccctc atgacaccat caaagagaat atgcactgtt gtaaagcctg cgtattttac   240
ttggcagcta ttttcattat ttatcatatt gcatttatg aaaagatttt tatataaaca    300
tgaagatctt gatgaaatta ttggcatttc aggaagtgct gaaatgttat tggaagtgat   360
gaaattattg gcatttcagg aagtgctgaa agtttcgct                          399

<210> SEQ ID NO 843
<211> LENGTH: 21
<212> TYPE: DNA
<213> ORGANISM: Homo Sapiens

<400> SEQUENCE: 843
ggcagttttc atttaagcag a                                              21
```

```
<210> SEQ ID NO 844
<211> LENGTH: 20
<212> TYPE: DNA
<213> ORGANISM: Homo Sapiens

<400> SEQUENCE: 844
agcgaaactt tcagcacttc                                              20

<210> SEQ ID NO 845
<211> LENGTH: 287
<212> TYPE: DNA
<213> ORGANISM: Homo Sapiens

<400> SEQUENCE: 845
ttatcctgag ccgttgtccc tgtgtttcca tttctctttt cctcatttct catcatctac   60
atttctcctg tacttgttca ttaaataatg attccttgga tataccaagt ctggatagcg  120
gattcgatgg aagcattttt gtaaatatac gttcagtatt ttgtgtggaa gaacacaatc  180
tagctgatgc ctgcaatccc agcccttggg aaagcgaggt gggtggattg cttgaagcta  240
cgagtttgac actagcctgg gcaacagggt acaaccgtgt ctctaca              287

<210> SEQ ID NO 846
<211> LENGTH: 22
<212> TYPE: DNA
<213> ORGANISM: Homo Sapiens

<400> SEQUENCE: 846
ttatcctgag ccgttgtccc tg                                           22

<210> SEQ ID NO 847
<211> LENGTH: 22
<212> TYPE: DNA
<213> ORGANISM: Homo Sapiens

<400> SEQUENCE: 847
tgtagagaca cggttgtacc ct                                           22

<210> SEQ ID NO 848
<211> LENGTH: 287
<212> TYPE: DNA
<213> ORGANISM: Homo Sapiens

<400> SEQUENCE: 848
ttatcctgag ccgttgtccc tgtgtttcca tttctctttt cctcatttct catcatctac   60
atttctcctg tacttgttca ttaaataatg attccttgga tataccaagt ctggatagcg  120
gattcgatrg aagcattttt gtaaatatac gttcagtatt ttgtgtggaa gaacacaatc  180
tagctgatgc ctgcaatccc agcccttggg aaagcgaggt gggtggattg cttgaagcta  240
cgagtttgac actagcctgg gcaacagggt acaaccgtgt ctctaca              287

<210> SEQ ID NO 849
<211> LENGTH: 22
<212> TYPE: DNA
<213> ORGANISM: Homo Sapiens

<400> SEQUENCE: 849
ttatcctgag ccgttgtccc tg                                           22
```

```
<210> SEQ ID NO 850
<211> LENGTH: 22
<212> TYPE: DNA
<213> ORGANISM: Homo Sapiens

<400> SEQUENCE: 850
tgtagagaca cggttgtacc ct                                              22

<210> SEQ ID NO 851
<211> LENGTH: 287
<212> TYPE: DNA
<213> ORGANISM: Homo Sapiens

<400> SEQUENCE: 851
ttatcctgag ccgttgtccc tgtgtttcca tttctctttt cctcatttct catcatctac    60
atttctcctg tacttgttca ttaaataatg attccttggw tataccaagt ctggatagcg   120
gattcgatgg aagcattttt gtaaatatac gttcagtatt ttgtgtggaa gaacacaatc   180
tagctgatgc ctgcaatccc agcccttggg aaagcgaggt gggtggattg cttgaagcta   240
cgagtttgac actagcctgg gcaacagggt acaaccgtgt ctctaca                 287

<210> SEQ ID NO 852
<211> LENGTH: 22
<212> TYPE: DNA
<213> ORGANISM: Homo Sapiens

<400> SEQUENCE: 852
ttatcctgag ccgttgtccc tg                                              22

<210> SEQ ID NO 853
<211> LENGTH: 22
<212> TYPE: DNA
<213> ORGANISM: Homo Sapiens

<400> SEQUENCE: 853
tgtagagaca cggttgtacc ct                                              22

<210> SEQ ID NO 854
<211> LENGTH: 386
<212> TYPE: DNA
<213> ORGANISM: Homo Sapiens

<400> SEQUENCE: 854
ccagtcagca gtacaaaagt tgacagcttc agcaaaattg tagccttggt taaaaccact    60
gtggtaagca cgaggaaaag tgatgacaaa ctcccctgca cactggtttg tgcggacaac   120
ctaaaaagga gaaaaaagca gaaagaggtg tgggtcagaa ctaatgggcc agatgtgaac   180
tcaaagatgt ctctagatgc tgtaacagat gtaggaagag tggaaargct ctatcttcaa   240
gtacgtgtcc taaagaaaaa tgagattgtg aatttaaaag tggtattcat agaaaagtac   300
tcaaaatatg tgtaattcaa aaacaaata tagagggtc caggaacaag tgaaaagact     360
ctttgcttct ataatcaaag aaatgc                                        386

<210> SEQ ID NO 855
<211> LENGTH: 22
<212> TYPE: DNA
<213> ORGANISM: Homo Sapiens

<400> SEQUENCE: 855
ccagtcagca gtacaaaagt tg                                              22
```

<210> SEQ ID NO 856
<211> LENGTH: 24
<212> TYPE: DNA
<213> ORGANISM: Homo Sapiens

<400> SEQUENCE: 856
gcatttcttt gattatagaa gcaa                                          24

<210> SEQ ID NO 857
<211> LENGTH: 386
<212> TYPE: DNA
<213> ORGANISM: Homo Sapiens

<400> SEQUENCE: 857
ccagtcagca gtacaaaagt tgacagcttc agcaaaattg tagccttggt taaaaccact    60
gtggtaagca cgaggaaaag tgatgacaaa ctcccctgca cactggtttg tgcggacaac   120
ctaaaaagga gaaaaagca gaaagaggtg tgggtcagaa ctaatgggcc agatgtgaac   180
tcaaagatgt ctctagatgc tgtaacagat gtaggaagag tggaaaggct ctatcttcaa   240
gtacgtgtcc taaaagaaaa tgagattgtg aatttaaaag tggtattcat agaaaagtac   300
tcaaaatatg tgtaattcaa aaacaaata tagaggggtc caygaacaag tgaaaagact   360
ctttgcttct ataatcaaag aaatgc                                       386

<210> SEQ ID NO 858
<211> LENGTH: 22
<212> TYPE: DNA
<213> ORGANISM: Homo Sapiens

<400> SEQUENCE: 858
ccagtcagca gtacaaaagt tg                                            22

<210> SEQ ID NO 859
<211> LENGTH: 24
<212> TYPE: DNA
<213> ORGANISM: Homo Sapiens

<400> SEQUENCE: 859
gcatttcttt gattatagaa gcaa                                          24

<210> SEQ ID NO 860
<211> LENGTH: 480
<212> TYPE: DNA
<213> ORGANISM: Homo Sapiens

<400> SEQUENCE: 860
cggagtctgg ctttgttggc caggttggag tgcagtggca tgatctcggc tcagggcaat    60
gtccgtctcc tggactcaag cagttctcct gcctcagcct ccccagtagc tgggattaga   120
ggtgtgtgac accatgcccg gctaattttt gtattttag tagagatggg gtttcaccat   180
gttggccagg ctggtctcga actcctgacc tcaggtaatg cacccgcctc ggcctcccaa   240
agtggtggga ttataggcgt gagtaaccat gcctggcctt tcactcttat tttctaagaa   300
ctttagaata atcaccgaga tattctaaag taaacaggaa ttttaatgg ttaagctrtt   360 atttgtcttt gtcatttctg agtttaggga tagtgaagat agagttaggc ctcatgtgtg   420
agagactgat gtagcattat agtgtatatt ttgaaatgtg ccaccgtgat gttcaaaagt   480

```
<210> SEQ ID NO 861
<211> LENGTH: 20
<212> TYPE: DNA
<213> ORGANISM: Homo Sapiens

<400> SEQUENCE: 861
cggagtctgg ctttgttggc                                                    20

<210> SEQ ID NO 862
<211> LENGTH: 20
<212> TYPE: DNA
<213> ORGANISM: Homo Sapiens

<400> SEQUENCE: 862
acttttgaac atcacggtgg                                                    20

<210> SEQ ID NO 863
<211> LENGTH: 556
<212> TYPE: DNA
<213> ORGANISM: Homo Sapiens

<400> SEQUENCE: 863
tttaacaaat gtggaccaag atctcaacct tttttttat ctcctctcct cagagtatgc         60
tcaggtaatc aaaatgttgg gaaatggacg attggaagca ttgtgttttg atggtgtaaa       120
gaggttatgc catatcagag ggaaattgag aaaaaaggta ggtgtgtagg ttacttttca       180
ataaaaattt gccgcaaaaa atgtctctgc tttaaataca tggtccaagc aatttatttt       240
tgtgagttcc caaataatt tatacagcaa tgattcatgt gacaatgtga ataaatagaa        300
aaagtctttg ataactttta gatttacttt taaagaataa tttgtttgtt taacttctgt       360
tgtattccta ccrgaaatgt ttactctgat attagtattg aagaaccag acaaatctaa        420 tataacac aaatggtctt gactcagatg ttaatgctgt gaaagaatga aaaatctggg         480
aattacttta gcttaaaaga gattgatcgg tgcatatccc tttgttaggt tttggattgg       540
gggaaatagt tttagg                                                       556

<210> SEQ ID NO 864
<211> LENGTH: 21
<212> TYPE: DNA
<213> ORGANISM: Homo Sapiens

<400> SEQUENCE: 864
tttaacaaat gtggaccaag a                                                  21

<210> SEQ ID NO 865
<211> LENGTH: 20
<212> TYPE: DNA
<213> ORGANISM: Homo Sapiens

<400> SEQUENCE: 865
acttttgaac atcacggtgg                                                    20

<210> SEQ ID NO 866
<211> LENGTH: 507
<212> TYPE: DNA
<213> ORGANISM: Homo Sapiens

<400> SEQUENCE: 866
catggtccaa gcaatttatt tttgtgagtt cccaaaataa tttatacagc aatgattcat        60
gtgacaatgt gaataaatag aaaaagtctt tgataacttt tagatttact tttaaagaat       120
```

```
aatttgtttg tttaacttct gttgtattcc taccagaaat gtttactctg atattagtat    180
tgaagaaacc agacaaatct aatatataac acaaatggtc ttgactcaga tgttaatgct    240
gtgaaagaat gaaaaatctg ggaattactt tagcttaaaa gagattgatc ggtgcatakc    300
cctttgttag gttttggatt gggggaaata gttttaggtg gtactaggaa aattggaata    360
tggaatatgt tagaaactct atttgttagt aataccacat caggtagttt tataaattac    420
actgattaaa agtctctact actcagattt ttaattaaaa taataaaaac ttattttt gg    480 ctgagctctg tggaagtatt agccagc                                        507
```

<210> SEQ ID NO 867
<211> LENGTH: 24
<212> TYPE: DNA
<213> ORGANISM: Homo Sapiens

<400> SEQUENCE: 867

```
catggtccaa gcaatttatt tttg                                            24
```

<210> SEQ ID NO 868
<211> LENGTH: 22
<212> TYPE: DNA
<213> ORGANISM: Homo Sapiens

<400> SEQUENCE: 868

```
gctggctaat acttccacag ag                                              22
```

<210> SEQ ID NO 869
<211> LENGTH: 507
<212> TYPE: DNA
<213> ORGANISM: Homo Sapiens

<400> SEQUENCE: 869

```
catggtccaa gcaatttatt tttgtgagtt cccaaaataa tttatacagc aatgattcat     60
gtgacaatgt gaataaatag aaaaagtctt tgataacttt tagatttact tttaaagaat    120
aatttgtttg tttaacttct gttgtattcc taccagaaat gtttactctg atattagtat    180
tgaagaaacc agacaaatct aatatataac acaaatggtc ttgactcaga tgttaatgct    240
gtgaaagaat gaaaaatctg ggaattactt tagcttaaaa gagattgatc ggtgcatatc    300
ccttygttag gttttggatt gggggaaata gttttaggtg gtactaggaa aattggaata    360
tggaatatgt tagaaactct atttgttagt aataccacat caggtagttt tataaattac    420
actgattaaa agtctctact actcagattt ttaattaaaa taataaaaac ttattttt gg    480 ctgagctctg tggaagtatt agccagc                                        507
```

<210> SEQ ID NO 870
<211> LENGTH: 24
<212> TYPE: DNA
<213> ORGANISM: Homo Sapiens

<400> SEQUENCE: 870

```
catggtccaa gcaatttatt tttg                                            24
```

<210> SEQ ID NO 871
<211> LENGTH: 22
<212> TYPE: DNA
<213> ORGANISM: Homo Sapiens

<400> SEQUENCE: 871

```
gctggctaat acttccacag ag                                              22
```

<210> SEQ ID NO 872
<211> LENGTH: 506
<212> TYPE: DNA
<213> ORGANISM: Homo Sapiens

<400> SEQUENCE: 872

```
catggtccaa gcaatttatt tttgtgagtt cccaaaataa tttatacagc aatgattcat      60
gtgacaatgt gaataaatag aaaaagtctt tgataacttt tagatttact tttaaagaat     120
aatttgtttg tttaacttct gttgtattcc taccagaaat gtttactctg atattagtat     180
tgaagaaacc agacaaatct aatatataac acaaatggtc ttgactcaga tgttaatgct     240
gtgaaagaat gaaaaatctg ggaattactt tagcttaaaa gagattgatc ggtgcatatc     300
cctttgttag gttttggatt gggggaaata gttttaggtg gtactaggaa aattggaata     360
tggaatatgt tagaaactct atttgttagt aataccacat caggtagttt yataaattac     420
actgattaaa agtctctact actcagattt ttaattaaaa taataaaaac ttattttttgg    480
ctgagctctg tggaagtatt agccag                                         506
```

<210> SEQ ID NO 873
<211> LENGTH: 24
<212> TYPE: DNA
<213> ORGANISM: Homo Sapiens

<400> SEQUENCE: 873

```
catggtccaa gcaatttatt tttg                                            24
```

<210> SEQ ID NO 874
<211> LENGTH: 22
<212> TYPE: DNA
<213> ORGANISM: Homo Sapiens

<400> SEQUENCE: 874

```
gctggctaat acttccacag ag                                              22
```

<210> SEQ ID NO 875
<211> LENGTH: 536
<212> TYPE: DNA
<213> ORGANISM: Homo Sapiens

<400> SEQUENCE: 875

```
gattggggga aatagttttta ggtggtacta ggaaaattgg aatatggaat atgttagaaa     60
ctctatttgt tagtaatacc acatcaggta gttttataaa ttacactgat taaaagtctc    120
tactactcag attttaatt aaaataataa aaacttattt ttggytgagc tctgtggaag     180
tattagccag catacacctg tagtcccagc tactgaggag gctgagccca ggagttcaag    240
gttcccatga gctaaaaatt gtgctaatgc tctccagtct gggtgataga gcgaatctct    300
atctcaaaaa gaaaaaaaaa aaaatctttc tggtatgtta acattctttc ttttccaaat    360
tagtggcatt ttagggattc tcttagtcca tttgggctgt cactgactgg gtagattata    420
aaaagcagaa attttatttc tcatagtttt ggagaaagag aaatctattt aatatttggt    480
gaggacccat ttcctgatta ttatgtggtg ccttctggct tagtccacac atagtg        536
```

<210> SEQ ID NO 876
<211> LENGTH: 22
<212> TYPE: DNA
<213> ORGANISM: Homo Sapiens

```
<400> SEQUENCE: 876
gattggggga aatagttttta gg                                             22

<210> SEQ ID NO 877
<211> LENGTH: 22
<212> TYPE: DNA
<213> ORGANISM: Homo Sapiens

<400> SEQUENCE: 877
cactatgtgt ggactaagcc ag                                              22

<210> SEQ ID NO 878
<211> LENGTH: 506
<212> TYPE: DNA
<213> ORGANISM: Homo Sapiens

<400> SEQUENCE: 878
ttggttggtc tacgggacta tcaggtaaaa ataacattta aagttgtggt atgtctgtgt     60
ttaagcagtt gttaatgttt ggaaggtaac tatactagca tctttgaccc attccagccc    120
aggttgcttt ctcaccattc tgcctgccat catcatttat taagggccag ttgtatttca    180
gactatagta ttttcaaat ttgacataat tctcactgat agtaaatggt acatatattt     240
ttgtggaaag acataaagtt tttaattctt tgttttcatt gttaatataa tgtgcagtaa    300
atrttttctt gcaggcttgg gcaagtactg tagaccatct gtcctcatcc atttaaaggc    360
caatggtgtt tcaggcattc agctaggtat ttcagacatt gtagttccca aatgccggtc    420
tgttaaatag tattggtgca ggctgaattt tcagtgctct gaagtcaaat tagaagatac    480
atagttacga tgttttcat ggagca                                          506

<210> SEQ ID NO 879
<211> LENGTH: 19
<212> TYPE: DNA
<213> ORGANISM: Homo Sapiens

<400> SEQUENCE: 879
ttggttggtc tacgggact                                                  19

<210> SEQ ID NO 880
<211> LENGTH: 20
<212> TYPE: DNA
<213> ORGANISM: Homo Sapiens

<400> SEQUENCE: 880
tgctccatga aaaacatcgt                                                 20

<210> SEQ ID NO 881
<211> LENGTH: 445
<212> TYPE: DNA
<213> ORGANISM: Homo Sapiens

<400> SEQUENCE: 881
aaataccatt ttcataattt ccttaatatt tttagacatt atttcttttt aagtcttaga     60
taaactaagt ccaacttctg ggattcctca ggaatagtat ttttttttc cctgtgtttg     120 agccactttt ttaaatcttt ttttttttt taaaccgaac aatttaacta caacatagca    180
gttctggaaa tcagattgct gcctctcggg gctgttgttg atactgcttr tttggtgact    240
tttctgaact aattctttgg ccattgaata gttggttagt ttagtgggca gttcatgttt    300
gaactaagat ttcattaaaa ccaccaagaa tttaatcatt taaagaggaa tcttgtacat    360
```

```
gtagaggaat actttgagca ttcagccaat gttggtaaac tgacacctct tccttagtct    420
tcatttcttg ctgtgcagga tctca                                          445

<210> SEQ ID NO 882
<211> LENGTH: 24
<212> TYPE: DNA
<213> ORGANISM: Homo Sapiens

<400> SEQUENCE: 882
aaataccatt ttcataattt cctt                                           24

<210> SEQ ID NO 883
<211> LENGTH: 20
<212> TYPE: DNA
<213> ORGANISM: Homo Sapiens

<400> SEQUENCE: 883
tgagatcctg cacagcaaga                                                20

<210> SEQ ID NO 884
<211> LENGTH: 483
<212> TYPE: DNA
<213> ORGANISM: Homo Sapiens

<400> SEQUENCE: 884
cggacttggt ctgtgctttt cagtagctgc tattgtgttg gttttattat aactgaggta    60
aggaatggga ataggggaac ttaaaagccc acactgcttt ttcttagtaa ggttcaccta    120
tttttcktga ataaacgctc cttagtgttt attgcattca tttggttaat tttcagattt    180
ctgatatatg gattttgacc atgtttgtca atgttcttat ttcttttctg aaggaacaaa    240
ttttagcaag tccttattct gccattcctg caatcactgc aagaaagcat ttattttgat    300
aagacttaat tacacattga ctttgtttct ttttcatata tcaaataaaa agttgtactg    360
tgcttttaaa atgttatttt tatgtccatt atattattcg aattatcatt ttaacaaaaa    420
ctggtttgca cattacagtt tgaaaagtgt tggtctattt catactgcca ttgtgacaga    480
tca                                                                  483

<210> SEQ ID NO 885
<211> LENGTH: 21
<212> TYPE: DNA
<213> ORGANISM: Homo Sapiens

<400> SEQUENCE: 885
cggacttggt ctgtgctttt c                                              21

<210> SEQ ID NO 886
<211> LENGTH: 20
<212> TYPE: DNA
<213> ORGANISM: Homo Sapiens

<400> SEQUENCE: 886
tgatctgtca caatggcagt                                                20

<210> SEQ ID NO 887
<211> LENGTH: 500
<212> TYPE: DNA
<213> ORGANISM: Homo Sapiens
```

```
<400> SEQUENCE: 887
caggcaggtc tactttcaat cttaaggaag taggtatgta tttttaaaat caagctattt      60
ttcaagttcc atagacaatt ctgttagata atctatacta agaactactg atgcatagaa     120
aagtttatta ttgttgtttt tgttttttg aargagtttc gctctgttgc ccaggctgga     180
gtgcagtggc ttgatctcgg ctcactgcaa gctgcgcctc ctgggttcat gccattctcc     240
tgcctcagcc tcctgagtag ctgggactac agatgcctgc caccacgccc agctaatttt     300
ttgtatttt agtagagatg gggtttcatc atgttagcca gtatggtctc gatctcctga     360
cctcatgatc cgcccgcctt ggcctcccaa agtgctggga ttacaggcgc gagccaccgt     420
gcctggccta gaaaagtgta ttacctttt aacatcatta ttctttactc cattttagt     480
tttgaattgc agtgtttgac                                                  500

<210> SEQ ID NO 888
<211> LENGTH: 22
<212> TYPE: DNA
<213> ORGANISM: Homo Sapiens

<400> SEQUENCE: 888
caggcaggtc tactttcaat ct                                                22

<210> SEQ ID NO 889
<211> LENGTH: 22
<212> TYPE: DNA
<213> ORGANISM: Homo Sapiens

<400> SEQUENCE: 889
gtcaaacact gcaattcaaa ac                                                22

<210> SEQ ID NO 890
<211> LENGTH: 500
<212> TYPE: DNA
<213> ORGANISM: Homo Sapiens

<400> SEQUENCE: 890
caggcaggtc tactttcaat cttaaggaag taggtatgta tttttaaaat caagctattt      60
ttcaagttcc atagacaatt ctgttagata atctatacta agaactactg atgcatagaa     120
aagtttatta ttgttgtttt tgttttttg aaggagtttc gctctgttgc ccaggctgga     180
gtgcagtggc ttgatctcgg ctcactgcaa gctgcgcctc ctgggttcat gccattctcc     240
tgcctcagcc tcctgagtag ctgggactac agatgcctgc caccacgccc agctaatttt     300
ttgtatttt agtagagatg gggtttcatc atgttagccm gtatggtctc gatctcctga     360
cctcatgatc cgcccgcctt ggcctcccaa agtgctggga ttacaggcgc gagccaccgt     420
gcctggccta gaaaagtgta ttacctttt aacatcatta ttctttactc cattttagt     480
tttgaattgc agtgtttgac                                                  500

<210> SEQ ID NO 891
<211> LENGTH: 22
<212> TYPE: DNA
<213> ORGANISM: Homo Sapiens

<400> SEQUENCE: 891
caggcaggtc tactttcaat ct                                                22
```

<210> SEQ ID NO 892
<211> LENGTH: 22
<212> TYPE: DNA
<213> ORGANISM: Homo Sapiens

<400> SEQUENCE: 892
gtcaaacact gcaattcaaa ac                                              22

<210> SEQ ID NO 893
<211> LENGTH: 527
<212> TYPE: DNA
<213> ORGANISM: Homo Sapiens

<400> SEQUENCE: 893
caaagtgctg ggattacagg cgcgagccac cgtgcctggc ctagaaaagt gtattacctt    60
tttaacatca ttattcttta ctccattttt agttttgaat tgcagtgttt gaccttaaaa   120
gttttatatt acaattttt taattagtct tttattttt ccaagagact tctaattaaa     180
agggaatagt aaataaaagc actgtgcttg cctttttgtgc ttttattaar gtgaaatctc   240
tacaatcttt cctaagctgt taatcactgt ttactaatga acataaacca cttcctaatt   300
attcagactc aagaattttt ttctagaggg tattgggta ggcaaagaaa agcaggagag     360
tttgtaacaa acagtatgtg ggattttttt agatgtgttc aatttgaaag taacttgtga   420
aacaactggt gatattttgg tataagacgt tttgaaagtt atttgtttat ttctaaggat   480
aacaaagctg atgtaatttt aaagtacaat gcagatgaag ctagaag                  527

<210> SEQ ID NO 894
<211> LENGTH: 20
<212> TYPE: DNA
<213> ORGANISM: Homo Sapiens

<400> SEQUENCE: 894
caaagtgctg ggattacagg                                                 20

<210> SEQ ID NO 895
<211> LENGTH: 22
<212> TYPE: DNA
<213> ORGANISM: Homo Sapiens

<400> SEQUENCE: 895
cttctagctt catctgcatt gt                                              22

<210> SEQ ID NO 896
<211> LENGTH: 527
<212> TYPE: DNA
<213> ORGANISM: Homo Sapiens

<400> SEQUENCE: 896
caaagtgctg ggattacagg cgcgagccac cgtgcctggc ctagaaaagt gtattacctt    60
tttaacatca ttattcttta ctccattttt agttttgaat tgcagtgttt gaccttaaaa   120
gttttatatt acaattttt taattagtct tttattttt ccaagagact tctaattaaa     180
agggaatagt aaataaaagc actgtgcttg cctttttgtgc ttttattaaa gtgaaatctc   240
tacaatcttt cctaagctgt taatcactgt ttactaatga acataaacca cttcctaatt   300
attcagactc aagaattttt ttctagaggg tattgggta ggcaaagaaa ascaggagag     360
tttgtaacaa acagtatgtg ggattttttt agatgtgttc aatttgaaag taacttgtga   420

```
aacaactggt gatattttgg tataagacgt tttgaaagtt atttgtttat ttctaaggat    480
aacaaagctg atgtaatttt aaagtacaat gcagatgaag ctagaag                 527
```

<210> SEQ ID NO 897
<211> LENGTH: 20
<212> TYPE: DNA
<213> ORGANISM: Homo Sapiens

<400> SEQUENCE: 897

```
caaagtgctg ggattacagg                                                20
```

<210> SEQ ID NO 898
<211> LENGTH: 22
<212> TYPE: DNA
<213> ORGANISM: Homo Sapiens

<400> SEQUENCE: 898

```
cttctagctt catctgcatt gt                                             22
```

<210> SEQ ID NO 899
<211> LENGTH: 527
<212> TYPE: DNA
<213> ORGANISM: Homo Sapiens

<400> SEQUENCE: 899

```
caaagtgctg ggattacagg cgcgagccac cgtgcctggc ctagaaaagt gtattacctt    60
tttaacatca ttattcttta ctccattttt agttttgaat tgcagtgttt gaccttaaaa   120
gttttatatt acaatttttt taattagtct tttattttt ccaagagact tctaattaaa    180
agggaatagt aaataaaagc actgtgcttg cctttgtgc ttttattaaa gtgaaatctc    240
tacaatcttt cctaagctgt taatcactgt ttactaatga acataaacca cttcctaatt   300
attcagactc aagaattttt ttctagaggg tattgggta ggcaaagaaa agcaggagag    360
tttgtaacaa acagtatgtg ggattttttt agatgtgttc aatttgaaag taacttgtga   420
macaactggt gatattttgg tataagacgt tttgaaagtt atttgtttat ttctaaggat   480
aacaaagctg atgtaatttt aaagtacaat gcagatgaag ctagaag                 527
```

<210> SEQ ID NO 900
<211> LENGTH: 20
<212> TYPE: DNA
<213> ORGANISM: Homo Sapiens

<400> SEQUENCE: 900

```
caaagtgctg ggattacagg                                                20
```

<210> SEQ ID NO 901
<211> LENGTH: 22
<212> TYPE: DNA
<213> ORGANISM: Homo Sapiens

<400> SEQUENCE: 901

```
cttctagctt catctgcatt gt                                             22
```

<210> SEQ ID NO 902
<211> LENGTH: 545
<212> TYPE: DNA
<213> ORGANISM: Homo Sapiens

```
<400> SEQUENCE: 902
aacttgtgaa acaactggtg atattttggt ataagacgtt tgaaagtta tttgttttatt      60 tctaaggata acaaagctga tgtaatttta aagtacaatg cagatgaagc tagaagcctg     120
aaggcatatg gcgagcttcc agaacatggt aagatcaaaa tgattttatc tcctcattat    180
ttgatattaa tgtttgttgg tatttaggtg aaggtatttc cgtagaactc ttgttttaca    240 tactgttttta gtgtatactt aaaaatttgt tataagtagt cttgcctata cttcagttta    300
cttatgatac tttggaaaag atattaataa ytggaaatct ctaataaaaa cgttatgaac    360
ttgaaagtag aagtctctaa taaagagatt atgaattatg aaagttcctt tagtgacaac    420
tttataaatt cataagctct ggatttgtat ataagatctg tcaaagaaat acgttttta    480 tagtgttttt ctaaacagtt ctcaagactg gcagttttca tttaagcaga ggcaacaaat    540
gtaat                                                                 545

<210> SEQ ID NO 903
<211> LENGTH: 22
<212> TYPE: DNA
<213> ORGANISM: Homo Sapiens

<400> SEQUENCE: 903
aacttgtgaa acaactggtg at                                              22

<210> SEQ ID NO 904
<211> LENGTH: 22
<212> TYPE: DNA
<213> ORGANISM: Homo Sapiens

<400> SEQUENCE: 904
attacatttg ttgcctctgc tt                                              22

<210> SEQ ID NO 905
<211> LENGTH: 399
<212> TYPE: DNA
<213> ORGANISM: Homo Sapiens

<400> SEQUENCE: 905
ggcagttttc atttaagcag aggcaacaaa tgtaatacta atgtttgatt attatagaaa      60
aaagtattca tcttagcaaa gttttaacta tgggattatt tttaacaaac aattgtgttt    120 tcttttttctt aaagacaaac acaatgcata cttactgccg aaagcttgac aagattaaaa    180
taagtccctc atgacaccat caaagagaat atgcactgtt gtaaagcctg cgtatttac    240 ttggcagcta ttttcattat ttatcatatt gcattttatg aaaagatttt tatataaaca    300
tgaagatctt gatgaaatta ttggcatttc aggaagtgct gaaatgttat tggaagtgat    360
gaaattattg gcatttcagg aagtgctgaa agtttcgct                            399

<210> SEQ ID NO 906
<211> LENGTH: 21
<212> TYPE: DNA
<213> ORGANISM: Homo Sapiens

<400> SEQUENCE: 906
ggcagttttc atttaagcag a                                               21

<210> SEQ ID NO 907
<211> LENGTH: 20
<212> TYPE: DNA
<213> ORGANISM: Homo Sapiens
```

<400> SEQUENCE: 907

| agcgaaactt tcagcacttc | 20 |

<210> SEQ ID NO 908
<211> LENGTH: 500
<212> TYPE: DNA
<213> ORGANISM: Homo Sapiens

<400> SEQUENCE: 908

| ttattggcat ttcaggaagt gctgaaatgt tattggaagt gatgaaatta ttggcatttc | 60 |
| aggaagtgct gaaagtttcg ctttcattac ttggggataa gcatgatcat gatttaacca | 120 |
| agtatttctc actgatttga taagtctgtt taaataattg gttaactagt tgttgtaatt | 180 |
| tcaagagaac tttatgtatt ttgaggataa gttgttaacc tgtgctcaaa tccttttga | 240 |
| aggctacatg gaaatggttg gctattgagt tagcataatc artctgccta ccatacttaa | 300 |
| agtaccttt tgtatgtgc taagtgagaa ttaaaaatac cttttaaaaa caaatgaaaa | 360 |
| atacagcaca atacagcaca ttcgttcttt gtttttgaa acagagtctt gctctgtcac | 420 |
| ccaggcagga gtgcagtggc accatctcag ctccctgcat tctacgcctg ccaagttcaa | 480 |
| gctatttcc tgcctcaccc | 500 |

<210> SEQ ID NO 909
<211> LENGTH: 21
<212> TYPE: DNA
<213> ORGANISM: Homo Sapiens

<400> SEQUENCE: 909

| ttattggcat ttcaggaagt g | 21 |

<210> SEQ ID NO 910
<211> LENGTH: 20
<212> TYPE: DNA
<213> ORGANISM: Homo Sapiens

<400> SEQUENCE: 910

| gggtgaggca ggaaaatagc | 20 |

<210> SEQ ID NO 911
<211> LENGTH: 444
<212> TYPE: DNA
<213> ORGANISM: Homo Sapiens

<400> SEQUENCE: 911

| aaactttaca gtcctttggg atagtattta ctgcaaaaat caattttagc ttcggcagta | 60 |
| ggcacttcay aatcaacgtt aagtaagagt gtctaaagag atagttttga gaacacgtcc | 120 |
| tctattaaga gaaatgctta gtatgttaaa agaagaattt tgtttgaacc agtttgatgc | 180 |
| agcactgaaa ttcaacata cttcaaaggt ttgttaaaat gaagggcctg ttgccaggac | 240 |
| atgtaataga attacatggt tgagcatcag tttgtactgg ccagactctt gttttggagt | 300 |
| tagtttgtgc ttatttgtg gaaatgattg ttttcctag taacaaagca gcgcagttca | 360 |
| caaagcagta aatgcttcag ctctcttttt cagttaacta tattgaaatt aaattcactt | 420 |
| tgatttttct tccctctctt gaga | 444 |

<210> SEQ ID NO 912
<211> LENGTH: 23
<212> TYPE: DNA
<213> ORGANISM: Homo Sapiens

```
<400> SEQUENCE: 912
aaactttaca gtcctttggg ata                                              23

<210> SEQ ID NO 913
<211> LENGTH: 23
<212> TYPE: DNA
<213> ORGANISM: Homo Sapiens

<400> SEQUENCE: 913
tctcaagaga gggaagaaaa atc                                              23

<210> SEQ ID NO 914
<211> LENGTH: 444
<212> TYPE: DNA
<213> ORGANISM: Homo Sapiens

<400> SEQUENCE: 914
aaactttaca gtcctttggg atagtattta ctgcaaaaat caattttagc ttcggcagta      60
ggcacttcat aatcaacgtt aagtaagagt gtctaaagag atagttttga gaacacgtcc    120
tctattaaga gaaatgctta gtatgttaaa agaagaattt tgtttgaacc agtttgatgc    180
agcactgaaa ttacaacatr cttcaaaggt ttgttaaaat gaagggcctg ttgccaggac    240
atgtaataga attacatggt tgagcatcag tttgtactgg ccagactctt gttttggagt    300
tagtttgtgc ttattttgtg gaaatgattg ttttttcctag taacaaagca gcgcagttca    360
caaagcagta aatgcttcag ctctctttt cagttaacta tattgaaatt aaattcactt    420
tgatttttct tccctctctt gaga                                           444

<210> SEQ ID NO 915
<211> LENGTH: 23
<212> TYPE: DNA
<213> ORGANISM: Homo Sapiens

<400> SEQUENCE: 915
aaactttaca gtcctttggg ata                                              23

<210> SEQ ID NO 916
<211> LENGTH: 23
<212> TYPE: DNA
<213> ORGANISM: Homo Sapiens

<400> SEQUENCE: 916
tctcaagaga gggaagaaaa atc                                              23

<210> SEQ ID NO 917
<211> LENGTH: 444
<212> TYPE: DNA
<213> ORGANISM: Homo Sapiens

<400> SEQUENCE: 917
aaactttaca gtcctttggg atagtattta ctgcaaaaat caattttagc ttcggcagta      60
ggcacttcat aatcaacgtt aagtaagagt gtctaaagag atagttttga gaacacgtcc    120
tctattaaga gaaatgctta gtatgttaaa agaagaattt tgtttgaacc agtttgatgc    180
agcactgaaa ttacaacata cttcaaaggt ttgttaaaat gaagggcctg ttgccaggac    240
atgtaataga attacatggt tgagcatcag tttgtactgg ccagactctt gttttggagt    300
tagtttgtgc ttattttgtg gaaatgattg ttttttcctag taacaaagca gygcagttca    360
```

```
caaagcagta aatgcttcag ctctcttttt cagttaacta tattgaaatt aaattcactt    420 tgattttct tccctctctt gaga                                            444
```

<210> SEQ ID NO 918
<211> LENGTH: 23
<212> TYPE: DNA
<213> ORGANISM: Homo Sapiens

<400> SEQUENCE: 918

```
aaactttaca gtcctttggg ata                                             23
```

<210> SEQ ID NO 919
<211> LENGTH: 23
<212> TYPE: DNA
<213> ORGANISM: Homo Sapiens

<400> SEQUENCE: 919

```
tctcaagaga gggaagaaaa atc                                             23
```

<210> SEQ ID NO 920
<211> LENGTH: 460
<212> TYPE: DNA
<213> ORGANISM: Homo Sapiens

<400> SEQUENCE: 920

```
cgagaacagc ctaaccaaca tggtgaaacc ccatctctgc taaaaatata aaaattagcc     60
aggcatggta gtgcacacct gtagtcccag ctactcagga ggctgaggca ggataatcac    120
ttggacccag gagacagagg ttgcagtgaa ccgagattgc accactgcac tccagcctgg    180
gcaatagagc gagactccat ctcaaaaaaa aaaaaaaaat tacaaaggct aaactttgga    240
aagtctaaga cagacatagg tgatggtcac acactccatt gagaaccatt gttctacatc    300
aggkttctct acagcttttg ttttaccaac atgtttatta agattgtttc cagactgttc    360
agaggagtag aaggattttt aaatttattt gtaaacattc aaatactcac caacaatatt    420
gtacaattta cagtttttct ctgcttcatc tatcacaccc                          460
```

<210> SEQ ID NO 921
<211> LENGTH: 20
<212> TYPE: DNA
<213> ORGANISM: Homo Sapiens

<400> SEQUENCE: 921

```
cgagaacagc ctaaccaaca                                                 20
```

<210> SEQ ID NO 922
<211> LENGTH: 22
<212> TYPE: DNA
<213> ORGANISM: Homo Sapiens

<400> SEQUENCE: 922

```
gggtgtgata gatgaagcag ag                                              22
```

<210> SEQ ID NO 923
<211> LENGTH: 456
<212> TYPE: DNA
<213> ORGANISM: Homo Sapiens

<400> SEQUENCE: 923

```
gtttccagac tgttcagagg agtagaagga tttttaaatt tatttgtawa cattcaaata     60
ctcaccaaca atattgtaca atttacagtt tttctctgct tcatctatca cacccatcct    120
```

```
tctattcatc tgatattaca ccttatattt tggcacattt ccaaactatt acttacactt      180
tgagttgaag aaaataaact gagtccttaa ttgtattgta tatatgcatt tataaatttt      240
tacaacataa agtactctat atttacaaaa ttttttagtt ttttttttct ttggaattgt      300
ttctgagtag tacttagtaa cactactcta atgtaatata aattttaaag tatacccaaa      360
aagaaaatga aaagagatga aaaatgcatt gttcttgtga tcccaggaaa tctgagacag      420
gtctcagtta atttacaaag ttgattttgc caaagt                                456
```

<210> SEQ ID NO 924
<211> LENGTH: 22
<212> TYPE: DNA
<213> ORGANISM: Homo Sapiens

<400> SEQUENCE: 924

```
gtttccagac tgttcagagg ag                                                22
```

<210> SEQ ID NO 925
<211> LENGTH: 22
<212> TYPE: DNA
<213> ORGANISM: Homo Sapiens

<400> SEQUENCE: 925

```
actttggcaa aatcaacttt gt                                                22
```

<210> SEQ ID NO 926
<211> LENGTH: 456
<212> TYPE: DNA
<213> ORGANISM: Homo Sapiens

<400> SEQUENCE: 926

```
gtttccagac tgttcagagg agtagaagga ttttttaaatt tatttgtawa cattcaaata      60
ctcaccaaca atattgtaca atttacagtt tttctctgct tcatctatca cacccatcct      120
tctattcatc tgatattaca ccttatattt tggcacattt ccaaactatt acttacactt      180
tgagttgaag aaaataaact gagtccttaa ttgtattgta tatatgcatt tataaatttt      240
tacaacataa agtactctat atttacaaaa ttttttagtt ttttttttct ttggaattgt      300
ttctgagtag tacttagtaa cactactcta atgtaatata aattttaaag tatacccaaa      360
aagaaaatga aaagagatga aaaatgcatt gttcttgtga tcccaggaaa tctgagacag      420
gtctcagtta atttacaaag ttgattttgc caaagt                                456
```

<210> SEQ ID NO 927
<211> LENGTH: 22
<212> TYPE: DNA
<213> ORGANISM: Homo Sapiens

<400> SEQUENCE: 927

```
gtttccagac tgttcagagg ag                                                22
```

<210> SEQ ID NO 928
<211> LENGTH: 22
<212> TYPE: DNA
<213> ORGANISM: Homo Sapiens

<400> SEQUENCE: 928

```
actttggcaa aatcaacttt gt                                                22
```

```
<210> SEQ ID NO 929
<211> LENGTH: 623
<212> TYPE: DNA
<213> ORGANISM: Homo Sapiens

<400> SEQUENCE: 929
gtttccagac tgttcagagg agtagaagga ttttaaatt tatttgtaaa cattcaaata      60
ctcaccaaca atattgtaca atttacagtt tttctctgct tcatctatca cacccatcct     120
tctattcatc tgatattaca ccttatattt tggcacattt ccaaactatt acttacactt     180
tgagttgaag aaaataaact gagtccttaa ttgtattgta tatatgcatt tataaatttt     240
tacaacataa agtactctat atttacaaaa ttttttagtt ttttttttct ttggaattgt     300
ttctgagtag tacttagtaa cactactcta atgtaatata aattttaaag tatacccaaa     360
aagaaaatga aagagatga aaaatgcatt gttcttgtga tcccaggaaa tctgagacmg      420
gtctcagtta atttacaaag ttgattttgc caaagttgag gacgcaccca tgacacagcc     480
tcgggaagcc ctgaggacat gtacccaagg tgtttggggc acagcttggt ttactacatc     540
ttcagggaga catgagacat caatcaatat atgtgaaaag aacgttggtt cagtttggaa     600
agggagggca tcttgttagc ctt                                             623

<210> SEQ ID NO 930
<211> LENGTH: 20
<212> TYPE: DNA
<213> ORGANISM: Homo Sapiens

<400> SEQUENCE: 930
gtttccagac tgttcagagg                                                  20

<210> SEQ ID NO 931
<211> LENGTH: 20
<212> TYPE: DNA
<213> ORGANISM: Homo Sapiens

<400> SEQUENCE: 931
aaggctaaca agatgccctc                                                  20

<210> SEQ ID NO 932
<211> LENGTH: 512
<212> TYPE: DNA
<213> ORGANISM: Homo Sapiens

<400> SEQUENCE: 932
gttcttgtga tcccaggaaa tctgagacag gtctcagtta atttacaaag ttgattttgc      60
caaagttgag gacgcaccca tgacacagcc tcgggaagcc ctgaggacat gtacccaagg     120
tgtttggggc acagcttggt ttactacatc ttcagggaga catgagacat caatcaatat     180
atgtgaaaag aacgttggtt cagtttggaa agggagggca tcttgttagc ctttctaaag     240
gaggcagtca gctatgcatc taactcaatg agcgaaagga taacttttga atagaatggg     300
aggccggttt gtcttaagca gtttccacct tgagttttc atagtaattt tgggggccaa      360
agatattttc gtttcacatt ctaatatttt cttcmtgtac ctccctttgg ggaccctgag     420
ccagaggttt tttgggggat taaacagaat tggcatttac ttcatgttgc aataaccaaa     480
agcataaata ttttgttgta gattaagggc aa                                   512
```

```
<210> SEQ ID NO 933
<211> LENGTH: 21
<212> TYPE: DNA
<213> ORGANISM: Homo Sapiens

<400> SEQUENCE: 933
gttcttgtga tcccaggaaa t                                              21

<210> SEQ ID NO 934
<211> LENGTH: 22
<212> TYPE: DNA
<213> ORGANISM: Homo Sapiens

<400> SEQUENCE: 934
ttgcccttaa tctacaacaa aa                                             22

<210> SEQ ID NO 935
<211> LENGTH: 513
<212> TYPE: DNA
<213> ORGANISM: Homo Sapiens

<400> SEQUENCE: 935
aattggcatt tacttcatgt tgcaataacc aaaagcataa atattttgtt gtagattaag    60
ggcaaatctg aacatttcca cagttggtgg ccttggaggc ctctttggaa aattcagaga   120
acctatccag actacctagt ggaacacaaa gctacaaaca cagatgttag aataaggatc   180
tagacatggc taagattttt tctcagggag tggggggggag tatcttagag ttatgccatt   240
tcctttggaa ctaggcccat taaggtaacg ggaaggaatg taaagacaat ggctattaaa   300
ggaagtttag tttcttttga gtttcttttg cttattacaa gagaacactg tagatttata   360
gatgttctag ttttacttct gtgactacat ggactcagaa tttggttacg accatattta   420
tcccattttt aaaggaatta catctatttt gtctgtgtcc accctcagaa tataagatct   480
gtaaccacta ccacaaaagg aagtaaggac atg                                513

<210> SEQ ID NO 936
<211> LENGTH: 23
<212> TYPE: DNA
<213> ORGANISM: Homo Sapiens

<400> SEQUENCE: 936
aattggcatt tacttcatgt tgc                                            23

<210> SEQ ID NO 937
<211> LENGTH: 22
<212> TYPE: DNA
<213> ORGANISM: Homo Sapiens

<400> SEQUENCE: 937
catgtcctta cttcctttg tg                                              22

<210> SEQ ID NO 938
<211> LENGTH: 523
<212> TYPE: DNA
<213> ORGANISM: Homo Sapiens

<400> SEQUENCE: 938
tggttctaca gttgggattt tggccatcat caaccaagaa gagaaattca tttagtgtgt    60
agtttctgaa agcaaactga tttatttca ttgttttaaa gtatttattt ctttaaaagc    120
tgaggacact gaattacctt aagttaaatg ttaatacttt attgtttga tgtaatggaa    180
```

```
cttaaggata aaagaccata atatttgctg ttaaaataaa taaacgagtg cctttcctac      240
tgtgataacg tcaagtaatt ggatattttg aatacatttc tgcctgataa tcatgctggg      300
ttctaataag ccctacttcc acctaatctg tttacagtct tttggtatgt ttcagttact      360
tagatggtct cataaggttt ctgatacaat ttgaagacag aaatctgcat ttagaatcag      420
aaaacatgga catattttc atatttatct agtcatatgt aattttatgc taacattgat       480
agtttataaa tcctttcat cctttgtgcc tcggttatta agg                         523

<210> SEQ ID NO 939
<211> LENGTH: 22
<212> TYPE: DNA
<213> ORGANISM: Homo Sapiens

<400> SEQUENCE: 939
tggttctaca gttgggattt tg                                                22

<210> SEQ ID NO 940
<211> LENGTH: 20
<212> TYPE: DNA
<213> ORGANISM: Homo Sapiens

<400> SEQUENCE: 940
ccttaataac cgaggcacaa                                                   20

<210> SEQ ID NO 941
<211> LENGTH: 507
<212> TYPE: DNA
<213> ORGANISM: Homo Sapiens

<400> SEQUENCE: 941
catggtccaa gcaatttatt tttgtgagtt cccaaaataa tttatacagc aatgattcat       60
gtgacaatgt gaataaatag aaaaagtctt tgataacttt tagatttact tttaaagaat      120
aatttgtttg tttaacttct gttgtattcc taccagaaat gtttactctg atattagtat      180
tgaagaaacc agacaaatct aatatataac acaaatggtc ttgactcaga tgttaatgct      240
gtgaaagaat gaaaaatctg ggaattactt tagcttaaaa gagattgatc ggtgcatatc      300
ccttcgttag gttttggatt gggggaaata gttttaggtg gtactaggaa aaytggaata      360
tggaatatgt tagaaactct atttgttagt aataccacat caggtagttt tataaattac      420
actgattaaa agtctctact actcagattt ttaattaaaa taataaaaac ttattttttgg     480 ctgagctctg tggaagtatt agccagc                                          507

<210> SEQ ID NO 942
<211> LENGTH: 24
<212> TYPE: DNA
<213> ORGANISM: Homo Sapiens

<400> SEQUENCE: 942
catggtccaa gcaatttatt tttg                                              24

<210> SEQ ID NO 943
<211> LENGTH: 22
<212> TYPE: DNA
<213> ORGANISM: Homo Sapiens

<400> SEQUENCE: 943
gctggctaat acttccacag ag                                                22
```

<210> SEQ ID NO 944
<211> LENGTH: 386
<212> TYPE: DNA
<213> ORGANISM: Homo Sapiens

<400> SEQUENCE: 944

| | | | | | | |
|---|---|---|---|---|---|---|
| gtaaaactca | gatatataca | tcccatgaaa | tatacacaga | aactataaat | tagcattaat | 60 |
| atcctctaaa | atgatactgt | agtaaagaaa | tattctcaaa | ctgttggtaa | attttagaga | 120 |
| aaawaaaaat | attatacata | cttgctgcat | taagacaaac | tgactttcta | actgttccag | 180 |
| ctgatgcttc | tgtgctggat | ttaaattatc | tctatttgct | cgcagttgtt | ccaagtgcta | 240 |
| gaagaaaaga | gattaatata | atcaaagttt | aatctaaaat | ttaagacaat | ataaggcaac | 300 |
| tcctcactaa | aaagactaca | cagaaccttt | gcaggatgaa | agacagtgat | tcctaatgaa | 360 |
| cgttaagata | gtgattcttt | tttttt | | | | 386 |

<210> SEQ ID NO 945
<211> LENGTH: 27
<212> TYPE: DNA
<213> ORGANISM: Homo Sapiens

<400> SEQUENCE: 945
gtaaaactca gatatataca tcccatg        27

<210> SEQ ID NO 946
<211> LENGTH: 26
<212> TYPE: DNA
<213> ORGANISM: Homo Sapiens

<400> SEQUENCE: 946
aaaaaaaaag aatcactatc ttaacg         26

<210> SEQ ID NO 947
<211> LENGTH: 444
<212> TYPE: DNA
<213> ORGANISM: Homo Sapiens

<400> SEQUENCE: 947

| | | | | | | |
|---|---|---|---|---|---|---|
| tgaggtggaa | tgtatcagta | taccaattaa | tattttgaa | agagctcttt | taggttaatk | 60 |
| taagtacagc | aatttctcat | gtaatgttta | gggagtttat | tctaacctag | gcaaacggca | 120 |
| tgctatcaca | agaaaggttt | aaagctttga | taaaatgggg | gagatttaat | cagtttttt | 180 |
| aatgcctgct | ataaaatt | gaaatattag | aatggccgac | catggcagtg | accaggcctc | 240 |
| actacaggcc | tggttggatt | ctggtctta | atgcatgcta | gtgttgatgt | ttttggtca | 300 |
| agaacggttt | aaacaggaag | gattgtgcag | caggctttaa | tttaatgtag | attcatactg | 360 |
| ctctgttaaa | gctgcattga | aatgttaaaa | tggcttacac | ttgcagactt | tgcaaatctt | 420 |
| aagactaaca | aatccttgaa | atca | | | | 444 |

<210> SEQ ID NO 948
<211> LENGTH: 24
<212> TYPE: DNA
<213> ORGANISM: Homo Sapiens

<400> SEQUENCE: 948
tgaggtggaa tgtatcagta tacc        24

```
-continued

<210> SEQ ID NO 949
<211> LENGTH: 24
<212> TYPE: DNA
<213> ORGANISM: Homo Sapiens

<400> SEQUENCE: 949
tgatttcaag gatttgttag tctt                                          24

<210> SEQ ID NO 950
<211> LENGTH: 443
<212> TYPE: DNA
<213> ORGANISM: Homo Sapiens

<400> SEQUENCE: 950
tgaggtggaa tgtatcagta taccaattaa tatttttgaa agagctcttt taggttaatt    60
aagtacagca atttctcatg taatgtttag ggagtttatt ctaacctagg caaacggcat   120
gctatcacaa gaaaggttta aagctttgat aaaatggggg agatttaaty agttttttta   180
atgcctgcta taaaaatttg aaatattaga atggccgacc atggcagtga ccaggcctca   240
ctacaggcct ggttggattc tggtctttaa tgcatgctag tgttgatgtt ttttggtcaa   300
gaacggttta aacaggaagg attgtgcagc aggctttaat ttaatgtaga ttcatactgc   360
tctgttaaag ctgcattgaa atgttaaaat ggcttacact tgcagactt  gcaaatctta   420 agactaacaa atccttgaaa tca                                          443

<210> SEQ ID NO 951
<211> LENGTH: 24
<212> TYPE: DNA
<213> ORGANISM: Homo Sapiens

<400> SEQUENCE: 951
tgaggtggaa tgtatcagta tacc                                          24

<210> SEQ ID NO 952
<211> LENGTH: 24
<212> TYPE: DNA
<213> ORGANISM: Homo Sapiens

<400> SEQUENCE: 952
tgatttcaag gatttgttag tctt                                          24
```

METHOD FOR DETERMINING GENETIC AFFILIATION, SUBSTRUCTURE AND GENE FLOW WITHIN HUMAN POPULATIONS

CROSS-REFERENCE

This application claims the benefit of U.S. Provisional Application No. 06/245,355, filed Nov. 1, 2000, which application is incorporated herein by reference.

STATEMENT REGARDING FEDERALLY SPONSORED RESEARCH

This invention was made with government support under grant nos. GM55273 and GM 28428 awarded by the NIH. The government may have certain rights in this invention.

FIELD OF THE INVENTION

The present invention relates to nucleic acid polymorphisms and their methods of use in, for example, determination of paternity and forensics.

BACKGROUND OF THE INVENTION

The science of genetics has taken a keen interest in the identification of human individuals and genetic relationships between individuals. The genome of an individual is unique to that individual, and can be used for identification purposes, e.g., testing for paternity and/or forensic testing (e.g. to identify an individual in the context of post-mortem identification or in the criminal justice system). Procedures have been developed which are based on identification and characterization of changes in an individual's DNA, referred to as DNA polymorphisms, where such changes are due to nucleotide substitution, insertion, or deletion within the chains of DNAs.

In forensics, for example, there is an interest in polymorphisms for identification purposes. Techniques have been developed to compare homologous segments of DNA to determine if the segments are identical or if they differ in one or more nucleotides. Practical applications of these techniques relate to fields other than forensic medicine, for example, genetic disease diagnosis and human genome mapping.

The most accurate and informative way to compare DNA segments requires a method which provides the complete nucleotide sequence for each DNA segment. Particular techniques have been developed for determining actual sequences in order to study mutation in human genes. See, for example, Proc. Natl. Acad. Sci. U.S.A. 85, 544–548 (1988) and Nature 330, 384–386 (1987). However, because of the extensive amounts of time and high costs to determine, interpret, and compare sequence information, presently it is not practical to use extensive sequencing for compare more than just a few DNA segments.

A frequently used technique for screening for DNA polymorphisms arising from mutations consist of digesting the DNA strand with restriction endonucleases and analyzing the resulting fragments by means of Southern blots. See Am. J. Hum.Genet. p32, 314–331 (1980) or Sci. Am. 258, 40–48 (1988). Since mutations often occur randomly they may affect the recognition sequence of the endonuclease and preclude the enzymatic cleavage at that site. Restriction fragment length polymorphism mappings (RFLPS) are based on changes at the restriction site. They are accurate but not very informative (PIC>0.3). The major problem with RFLPs is the inability of a test to detect changes that do not affect cleavage with a restriction endonuclease. In addition, the methods used to detect RFLPs are very labor intensive and expensive, especially the techniques which includes Southern blot analysis.

Another technique for detecting specific mutations in particular DNA segment involves hybridizing DNA segments which are being analyzed with a complementary, labeled oligonucleotide probe. See Nucl. Acids Res. 9, 879–894 (1981). Since DNA duplexes containing even a single base pair mismatch exhibit high thermal instability, the differential melting temperature can be used to distinguish target DNAs that are perfectly complimentary to the probe from target DNAs that only differ by a single nucleotide. See, e.g., U.S. Pat. No. 4,683,194. Further, subtle genetic differences among related individuals regarding nucleotides which are substituted in the DNA chains are difficult to detect. VNTR's or Jeffrey's probes are very informative but labor intensive, in distinction to microsatellites which are equally informative PCR based tests.

Short tandem repeat (STR) polymorphisms are commonly used in DNA identification, either as adjuncts to other genetic tests, or as stand-alone tests. Typically, when STRs are used for human identification, they are amplified in groups of three to four loci (multiplex amplification). Generally, the resulting amplified fragments are analyzed by polyacrylamide gel electrophoresis. Polymorphisms are thus typed according to size by comparing to similarly labeled known external standards or differently labeled internal standards. U.S. Pat. No. 5,364,759 describes the genus of simple tandem repeats as well as a DNA typing method employing the simple tandem repeats and PCR amplification of the loci. Fragments are analyzed by differential labeling of the products.

A critical parameter in DNA typing is the power of exclusion for the system. Power of exclusion is the ability of a test to exclude a falsely accused individual based on the individual's genetic characteristics. The commonly used STR multiplexes have exclusion probabilities in the range of 85% to 91%. This compares unfavorably with restriction fragment length polymorphic loci (RFLP loci), which often provide an equivalent power with just one locus. STR testing batteries which include greater numbers of lower power systems are more susceptible to this problem than are RFLP testing batteries which include a smaller number of higher power systems. The low exclusion probabilities of commonly used STR loci are the most negative aspect of their use, although the frequencies of both alleles of an individual can be included in calculating match. Although it is simpler and faster to perform DNA typing with STR loci than with RFLP loci and it can be performed with much smaller quantities of DNA, typing using STR loci sacrifice in exclusion power. Another disadvantage of current STR multiplex DNA typing systems is that the amplification is rarely, if ever, clean. In other words there is considerable formation of spurious bands, which is thought to be due to DNA polymerase slippage and mis-priming events (see e.g., Tautz D., Hyper variability of Simple Sequences as a General Source for Polymorphic DNA Markers, Nuc. Acids Res., 17(16) 6463–70 (1989)).

Other polymorphisms take the form of single nucleotide variations between individuals of the same species. Such polymorphisms are far more frequent than RFLPS, STRs and VNTRs. Some single nucleotide polymorphisms occur in protein-coding sequences, in which case, one of the polymorphic forms may give rise to the expression of a defective or other variant protein and, potentially, a genetic disease. Other single nucleotide polymorphisms occur in noncoding regions. Some of these polymorphisms may also result in defective protein expression (e.g., as a result of defective splicing). Other single nucleotide polymorphisms have no phenotypic effects.

Single nucleotide polymorphisms (SNPs) can be used in the same manner as RFLPs, and VNTRs but offer several advantages. Single nucleotide polymorphisms occur with greater frequency and are spaced more uniformly throughout the genome than other forms of polymorphism. The greater frequency and uniformity of single nucleotide polymorphisms means that there is a greater probability that such a polymorphism will be found in close proximity to a genetic locus of interest than would be the case for other polymorphisms. Also, the different forms of characterized single nucleotide polymorphisms are often easier to distinguish than other types of polymorphism, e.g., by use of assays employing allele-specific hybridization probes or primers).

There is a need in the art for a very accurate genetic relationship test procYedure which uses very small amounts of an original DNA sample, yet produces very accurate results. This is particularly true in the forensic medicine area and criminology because often only very small samples of DNA available.

SEQUENCE LISTING

The present specification incorporates herein by reference, each in its entirety, the sequence information on the Compact Disks (CDs) labeled Copy 1 and Copy 2. The CDs are formatted on IBM-PC, with operating system compatibility with MS-Windows. The files on each of the CDS are as follows:

Copy 1—Seqlist.txt 268 KB; and
Copy 2—Seqlist.txt 268 KB.

SUMMARY OF THE INVENTION

The present invention provides novel polymorphisms on the Y chromosome and methods of using Y chromosome polymorphisms as indicators of evolutionary heritage. The polymorphisms of particular interest in the present invention are clustered to specific regions of the Y chromosome, with polymorphisms of particular use found mostly in the Non-recombining Region of the human Y chromosome (NRY). These polymorphisms, including but not limited to SNPs, insertions, and deletions, may be useful for numerous applications, including forensics, paternity testing, diagnosis and the like.

In one embodiment, the present invention provides nucleic acid segments of between 10 and 100 bases containing at least 10, 15 or 20 contiguous nucleotides from any of the polymorphic regions of the Y chromosome shown in TABLE 1, and may include a polymorphic site. Complements of these segments are also included. The segments can be DNA or RNA, and can be double or single-stranded. Some segments are 10–20 or 10–50 bases long and may be less than 20 or 50 bases long. Preferred nucleic acid segments allow for the identification and analysis of nucleic acid sequences on the Y chromosome which include at least one polymorphic site that is at least diallelic.

The invention further provides allele-specific oligonucleotides that hybridize to a polymorphic region marker (M1 to M319 (excluding unassigned markers) of the Y chromosome as shown in TABLE 1, or its complement. These oligonucleotides can be probes or primers. In a particular embodiment, the nucleic acid segments include the forward and/or reverse primer sequences (e.g. primer pairs) as in Table 1. Primer pairs allow for the amplification and identification of specific polymorphic regions of the Y chromosome. Polymorphic regions of interest for amplification and/or identification include but are not limited to the NRY regions of the Y chromosome. The polymorphic regions (polymorphic markers) shown in TABLE 1 are nucleic acids of about between 100 and 700 bases, about 200 to about 600 bases and, in some embodiments, about 250 to about 500 bases in length. Many of the polymorphic nucleic acids (polymorphic regions (markers) shown in TABLE 1 may include more than one polypmorphic site.

The invention further provides a method of analyzing a nucleic acid from an individual. The method determines which base is present at any one of the polymorphic sites of the Y chromosome as shown in TABLE 1 in bold type. Optionally, a set of bases occupying a set of the polymorphic sites shown in TABLE 1 is determined. This type of analysis can be performed on a plurality of individuals who are tested for the presence of a particular polymorphism by identifying specific polymorphic markers. The polymorphism can be correlated with a base or set of bases present at the polymorphic sites in the individuals tested, and the evolutionary heritage of the individual can be indicated by the presence or absence of a particular polymorphism.

In one embodiment, the invention provides a method for determining the ethnic origin of a male, comprising obtaining a nucleic acid sample from the male and identifying at least two polymorphic markers in the nucleic acid sample indicative of the ethnic origin of the male, using at least one primer pair from TABLE 1. The identifying of the polymorphic markers may indicate the ethnic origin of the male as being at least one of the haplotype groups selected from the group consisting of haplotype Group I, Group II, Group III, Group IV, Group V, Group VI, Group VII, Group VIII, Group IX or Group X. In some embodiments, at least one polymorphic marker identified is a polymorphic marker from TABLE 1. The polymorphic markers may identify a haplotype associated with a haplotype group selected from the group consisting of haplotype Group I, Group II, Group III, Group IV, Group V, Group VI, Group VII, Group VIII, Group IX or Group X, or a sub-haplotype group for the ethnic origin of the male.

In another embodiment, the invention provides a method for identifying a plurality of polymorphic sites in a nucleic acid, comprising obtaining a sample of the nucleic acid from at least one individual, and identifying, in the nucleic acid, at least one of the polymorphic sites in at least two polymorphic markers of TABLE 1. The sample of nucleic acids may be obtained from a plurality of individuals, with the presence of the polymorphic markers in each sample of the nucleic acid determined for each of the individuals. The method may further comprise testing each individual for presence of a group of polymorphic markers which identify the haplotype of each individual, wherein the haplotype is indicative of a geographic distribution of a population or an ancestral population.

In still other embodiments, the invention provides a method for determining the ethnic origin of a human male individual, comprising obtaining a nucleic acid sample from the male, testing the nucleic acid sample for presence of a plurality of polymorphic markers selected from TABLE 1, identifying which polymorphic markers are present in the nucleic acid sample, and assigning a haplotype group to the male based on the identified markers, wherein the haplotype group is indicative of the ethnic origin of the male.

In certain embodiments, the invention provides a method for determining the paternity of a human male individual, comprising obtaining a nucleic acid sample from the male, testing the nucleic acid sample for the presence of a plurality of polymorphic markers from TABLE 1, identifying which polymorphic markers are present in the nucleic acid sample, and comparing the identified polymorphic markers to a set of polymorphic markers identified in nucleic acid samples from potential fathers.

The invention additionally provides a kit for determining ethnic origin of an individual, comprising at least two primer pairs capable of identifying at least two polymorphic markers from TABLE 1. The kit may further comprise a control nucleic acid for detecting the presence or absence of the polymorphic markers from TABLE 1.

The invention further comprises a set of primers and enzymes useful in performing an assay to identify particular polymorphisms in human male DNA. A method of identifying polymorphisms is disclosed whereby a sample is provided and subjected to amplification using primers of the invention and thereafter determining sequences (polymorphic regions) which were amplified.

A feature of the invention is that polymorphisms not previously identified are described herein, and are associated with a particular haplotype, indicative of a specific evolutionary heritage.

An advantage of the invention is that the sequences disclosed herein can be used in a range of different assay systems to determine the presence of a polymorphism in a sample.

A feature of the invention is a method for analyzing a set of unique polymorphisms on the Y chromosome to determine and identify an individual's evolutionary heritage and/or ethnicity.

A feature of the invention is to provide a kit for determining an individual's geographical or ethnic origins.

These and other objects, advantages, and features of the invention will become apparent to those persons skilled in the art upon reading the details of the invention as fully described below.

DETAILED DESCRIPTION OF PREFERRED EMBODIMENTS

Figure 1:
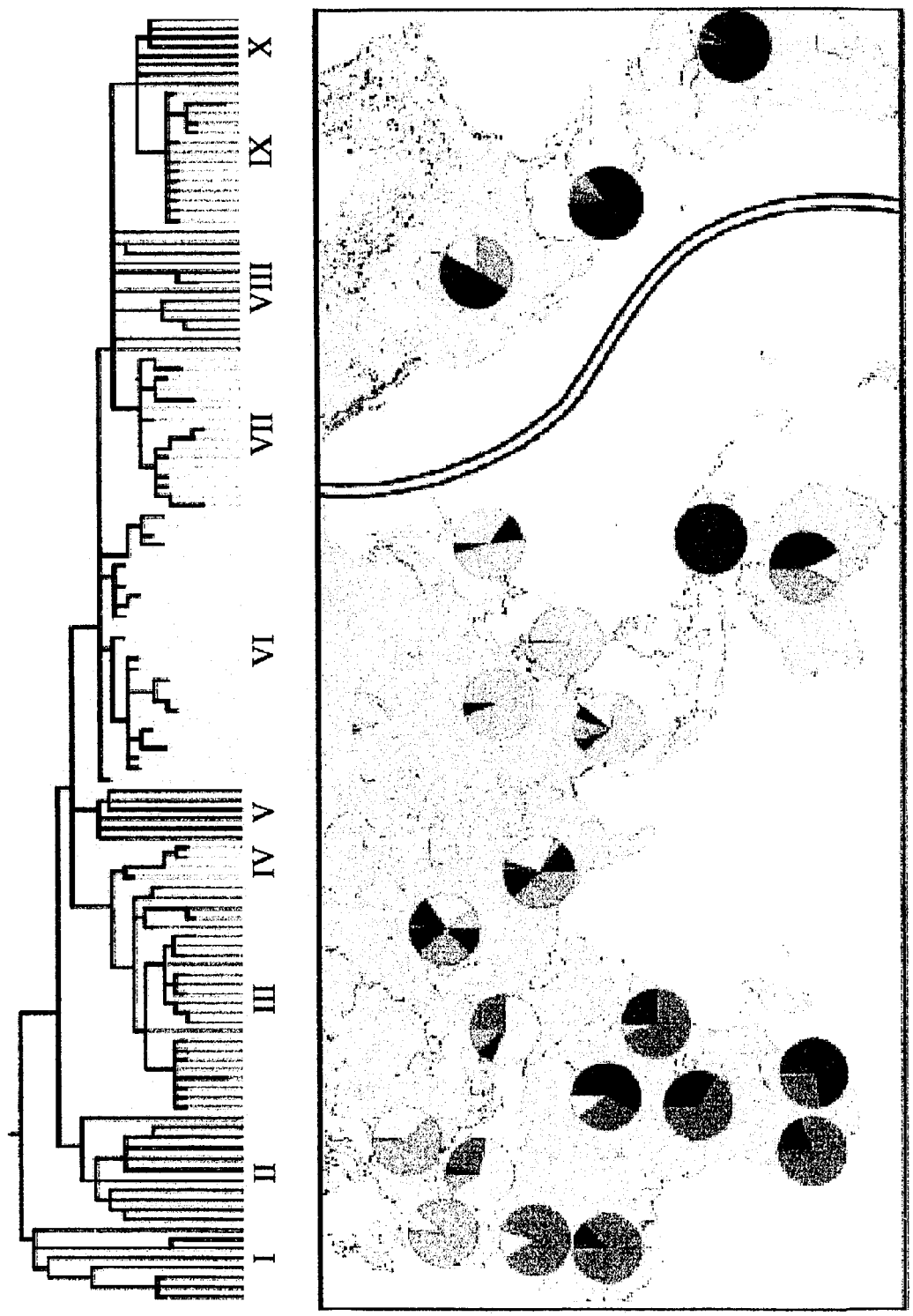
FIG. 1. Contemporary worldwide distribution of Y chromosome groups in 22 regions determined by the methods and compositions of the invention.

Before the present polymorphisms and detection methods are described, it is to be understood that this invention is not limited to particular methods or polymorphisms described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a nucleic acid" includes a plurality of such nucleic acids and reference to "the primer" includes reference to one or more primers and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

THE INVENTION IN GENERAL

The use of certain nucleotide repeat polymorphisms for identifying or comparing DNA segments have been described. (See e.g., Weber & May Am Hum Genet 44:388 (1989), Litt & Luthy Am Hum Genet 44:397(1989)). The present invention is based on the finding that particular polymorphisms on the Y chromosome, including the novel polymorphisms included herein, are indicative of the evolutionary heritage and/or a paternal lineage in an individual having a Y chromosome (e.g., a male or XXY individual). These particular polymorphic genetic segments, and primers used to identify the polymorphisms for identification and comparison purposes, correspond to regions of the Y chromosome having clustered polymorphisms that are homopolymeric in regions which exhibit a very low mutation rate. An advantage of the polymorphisms of the invention is that no recombination occurs in the regions containing these markers, and thus the accumulation of mutations is preserved as an intact haplotype. This creates a genetic profile that remains intact across the generations. If men share the same derived allele, then they are identical by descent, not just by state. While a very small amount of recurrent or revertant back mutation has been observed at some markers, these anomalies are easily recognized as such because of the high resolution of the Y tree. The recognition of new Y-chromosome markers represents a major leap in the investigation of human genetic diversity (in male lineages, complementing the information from female lineages derived from mitochondrial DNA).

The polymorphisms and methods of the present invention provide a simple way of identifying male siblingship as well as a genetic route to identify male children by so called "genebanking" using DNA or blood, or saliva from a child. Also the Y chromosome polymorphisms can reveal patterns (estimates) of recent gene flow from one gene pool to another, i.e. admixture. The methods of the present invention make the large amount of information contained in the phylogeny of haplotypes accessible for analysis.

DEFINITIONS

The term "oligonucleotide" as used herein can be DNA, RNA, or a substituted variation of these nucleic acids. The oligonucleotide may be single- or double-stranded. Oligonucleotides can be naturally occurring or synthetic, but are typically prepared by synthetic means. Preferred oligonucleotides of the invention include segments of DNA, or their complements including any one of the polymorphic sites shown in TABLE 1. The segments are usually between 5 and 100 bases (nucleotides), and often between 5–10, 5–20, 10–20, 10–50, 20–50 or 20–100 bases. The polymorphic site can occur within any position of the segment. The segments can be from any of the allelic forms of DNA shown in TABLE 1.

The term "hybridization probes" as used herein refers to oligonucleotides capable of binding in a base-specific manner to a complementary strand of nucleic acid. Such probes include peptide nucleic acids, as described in Nielsen et al., Science 254, 1497–1500 (1991).

The term "primer" as used herein refers to an oligonucleotide having at least a single-stranded portion that is adapted to act as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. A primer need not reflect the exact sequence of the template but must be sufficiently complementary to hybridize with a template.

The term "primer site" as used herein refers to the area of the target DNA to which a primer hybridizes. The term "primer pair" as used herein refers to a set of primers including at least one 5' upstream primer that hybridizes with the 5' end of the DNA sequence to be amplified (a forward or "for" primer) and at least one 3' downstream primer that hybridizes with the complement of the 3' end of the sequence to be amplified (a reverse or "rev" primer). Primer pairs allow for the amplification and identification of corresponding polymorphic regions.

The term "polymorphic site" is used herein to describe mutations within a nucleic acid sequence which include but are not limited to site specific mutations, insertions and deletions, these mutations being found in the nucleic acid of some individuals and not in others, e.g. the polymorphic site identifies a specific polymorphism of an individual. The present invention provides segments of nucleic acid which contain at least one polymorphic site (i.e. polymorphic region). These "polymorphic regions" of the Y chromosome can be analyzed to identify a specific polymorphic site which in turn identifies a specific polymorphism associated with certain individuals.

The polymorphic regions of the present invention are also defined as "polymorphic markers" due to their usefulness in marking (identifying specific polymorphic sites). The polymorphic markers of the present invention identify specific haplotypes in the male population, these haplotypes being indicative of a specific geographical or ethnic origin. Certain polymorphic markers which identify a polymorphism shared by a large group of individuals allow for the grouping of those haplotypes which share that marker. These more commonly found markers are found at the branch points of a phylogenetic tree and are crucial in separating individuals into unique haplotype groups. The haplotype groups have this ancestral marker which branches off from a point earlier in the phylogenetic tree. The polymorphic markers of the present invention have identified over 171 haplotypes which can be divided into ten haplotype groups.

The term "polymorphism" as used herein refers to the occurrence of two or more genetically determined alternative sequences or alleles in a population. A polymorphic marker or site is the locus at which divergence occurs. Preferred markers have at least two alleles, each occurring at a frequency of greater than 1%, and more preferably greater than 10% or 20% of a selected population, and can be present at a frequency greater than 30% to 50% or more in selected portions of the population. A polymorphic locus may be as small as one base pair. Polymorphic markers include restriction fragment length polymorphisms, VNTR's, hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. Polymorphisms refer to sequence differences between a reference form and a selected allele, and encompasses single or multiple nucleotide differences which can result from nucleotide insertion(s), deletion(s), substitution(s) and/or a combination thereof. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. The term "polymorphism" as used herein refers to any detectable polymorphic site in DNA or RNA that is detectable using the present methods. The term as used herein encompasses, for example, polymorphisms associated with a disease state (i.e. mutations), "silent" polymorphisms (i.e. associated with a wild-type phenotype or in a non-coding region), and polymorphisms associated with a predisposition and/or response to treatment (i.e. a polymorphism in an allele of a gene).

The term "single nucleotide polymorphism" and "SNP" as used interchangeably herein refers to a polymorphic site occupied by a single nucleotide (i.e. single base), which is the site of variation between allelic sequences. In general, SNPs are DNA sequence variations that occur when a single nucleotide (A, T, C or G) in the genomic sequence is altered. For example a SNP might change the DNA sequence AAGGCTAA to ATGGCTAA. SNPs can occur in both coding (gene) and noncoding regions of the genome. The site is usually preceded by and followed by highly conserved sequences of the allele (e.g., sequences that vary in less than $\frac{1}{100}$ or $\frac{1}{1000}$ members of the population).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele. Hybridizations are usually performed under stringent conditions, for example, at a salt concentration of no more than 1M and a temperature of at least 25° C. For example, conditions of 5×SSPE (750 mM NaCl, 50 mM NaPhosphate, 5 mM EDTA, pH 7.4) and a temperature of 25°–30° C. are suitable for allele-specific probe hybridizations.

The term "isolated nucleic acid" as used herein refers to a nucleic acid isolated from an individual that is the predominant species present (i.e., on a molar basis it is more abundant than any other individual species in the composition). Preferably, an isolated nucleic acid comprises at least about 50, 80 or 90 percent (on a molar basis) of all macromolecular species present. Most preferably, the object species is purified to essential homogeneity, i.e. contaminant species cannot be detected in the composition by conventional detection methods. The isolated nucleic acid includes a selected DNA fragment (e.g., isolated by an amplification reaction), and an isolated mRNA.

The term "evolutionary heritage" as used herein refers to the association of a particular polymorphism with a population having a particular geographic distribution. This includes polymorphisms that are indicative of an ancestral population, i.e. a population from which an individual is a descendant.

GENERAL ASPECTS OF THE INVENTION

The present application provides novel polymorphisms, including polymorphisms clustered in and around a non-recombining portion of the human Y chromosome (NRY) The polymorphic sites and the regions flanking these polymorphic sites are shown in TABLE 1.

By knowing sequences which include particular polymorphisms on the Y chromosome, primers based on these sequences can be used in detection assays. The primers can be provided in assay kits which cover from one to any and all of the polymorphisms developed here and the kits may further comprise appropriate enzymes for use with the primers and/or reagents for the isolation and processing of nucleic acids from an individual.

The methods and compositions of the present invention allow for the genetic typing of male individuals into ten major haplotype groups. The markers and primer sets shown in TABLE 1 allow not only for typing males into one of the haplotype groups or a combination of haplotype groups, but also enables an individual to be identified to a specific geographical area associated with haplotype group. FIG. 1 shows a contemporary worldwide frequency distribution of the 10 Y chromosome groups in 22 regions. Each group is represented by a distinguishing color. Colored sectors reflect representative group frequencies. The frequency distribution of the ten groups is based on >1000 globally diverse samples genotyped using a hierarchical top down approach as illustrated in FIG. 1 above the global map. The representative branching and frequency of polymorphic markers in TABLE 1 are also shown in FIG. 1 (individual marker numbers are not shown).

Figure 2:
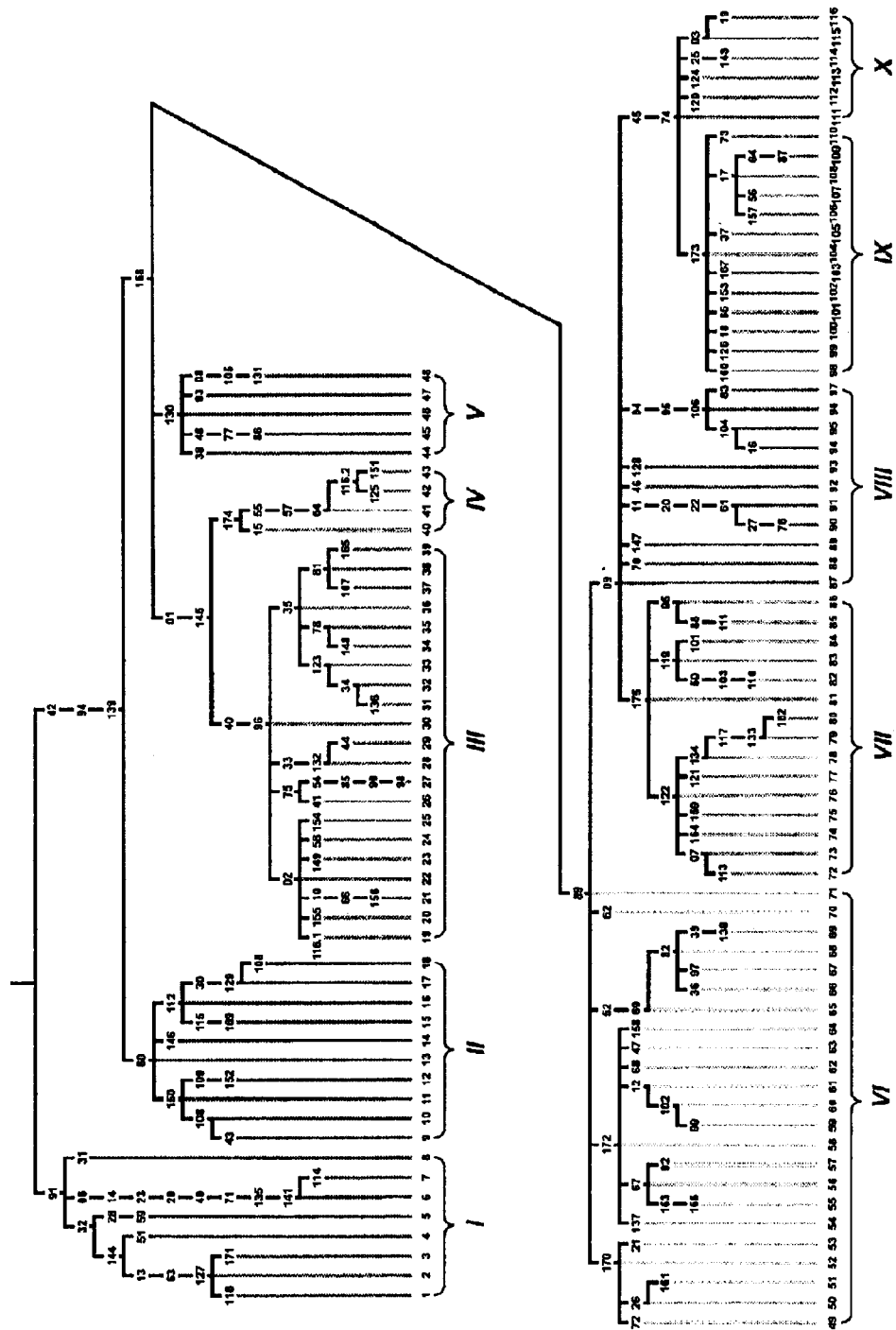
FIG. 2. A phylogenetic tree deduced from 167 NRY polymorphisms on the principle of maximum parsimony.
Figure 4:
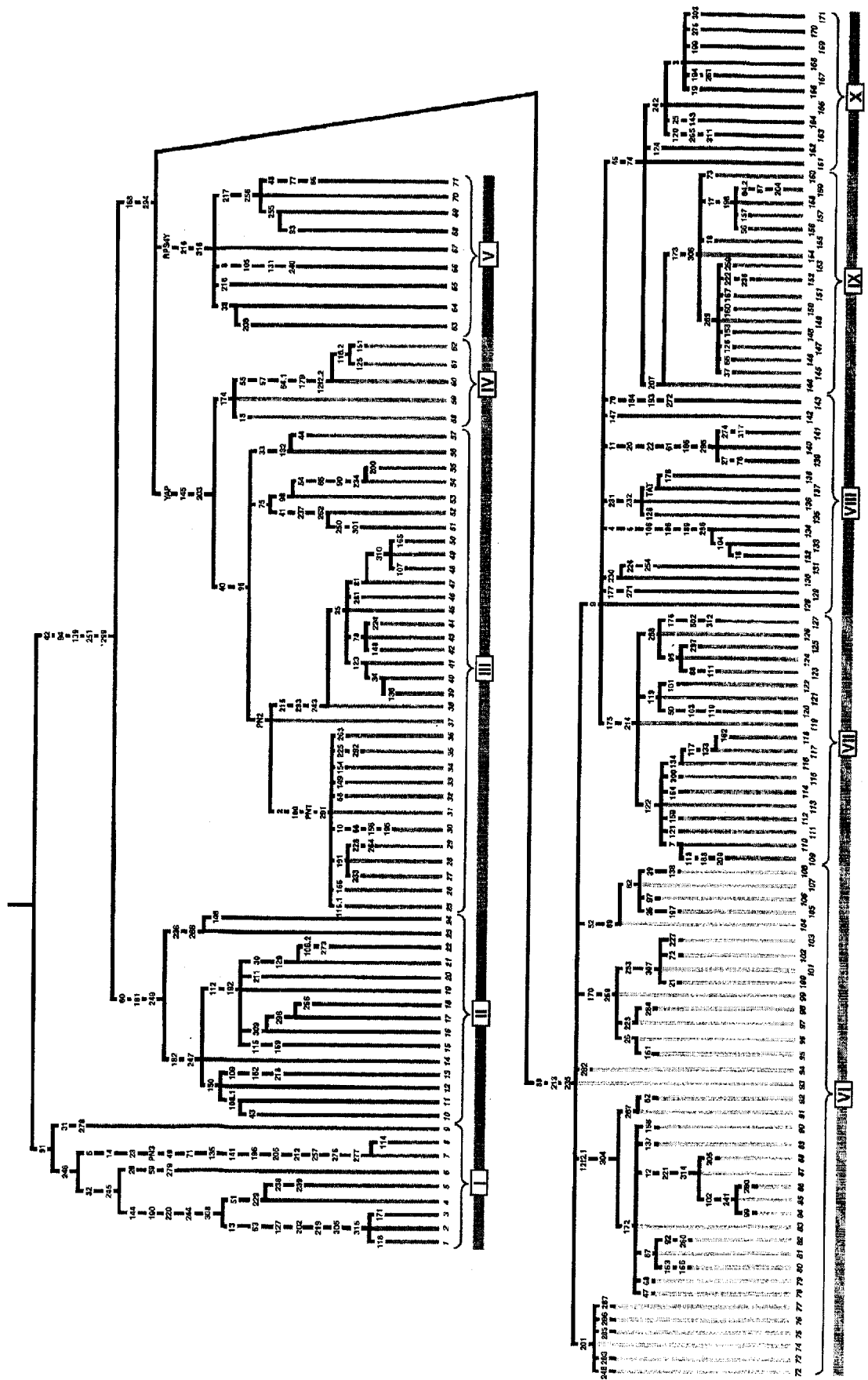
FIG. 4. Maximum parsimony phylogeny of human NRY chromosome biallelic variation.

The identification of an individuals haplotype is base on identifying the presence of at least two distinct polymorphic markers (i.e. at least two distinct polymorphic sites must be identified), for example, polymorphic markers M91 and M278 identify haplotype 9 (shown in FIG. 2 and FIG. 4). More likely, determining the haplotype of an individual involves the identification of 3 or more markers, usually at least about 3 to 7 markers, or 7 to 9 markers or even 9 or more markers.

Haplotype groups comprise haplotypes which have at least one ancestral marker which branches off from a point earlier in the phylogenetic tree. For example, marker 91 (M91) identifies haplotypes in Group I while haplotypes in group V are identified by one marker from each of the following sets of markers; one marker from {M42, M94, M139, M251, M299} plus one from {M168, M294} and one marker from {RPS4Y, M216, M316}. To determine which haplotype group and individual is associated with, the individuals nucleic acid would need to be analyzed with at least eleven polymorphic markers. For exemplary purposes, an individuals nucleic acid could be assayed for the presence and absence of the following markers; M91, M299, M249, M294, M203, M96, M316, M9, M74, M207, M214 to determine which haplotype group they are associated with which is indicative of a certain geographical or ethnic origin.

FIG. 1 illustrates that haplotype Group I is mainly associated with Africa and in particular, southern and eastern Africa (approximately about 90% of males of haplotype Group I are of African origin). Haplotype Groups II (about 80% to about 99% frequency distribution (f.d.)) and III (about 75% to about 95% f.d.) are also strongly related to Africa compared to Groups IV through X. Populations represented in Groups I and II include some Khoisan and Bantu speakers from South Africa, Pygmies from central Africa, and lineages in Sudan, Ethiopia and Mali. Virtually all men with Group I and II haplotypes are of African affiliation from a paternal perspective. Group III lineages are predominantly African, although a sub-set of Group III lineages occur in populations bordering the Mediterranean (Middle East, Turkey, North Africa, Southern Europe).

Approximately about 70% to about 99% of the males in Group IV are of Japanese origin. Group V is slightly associated with Japan (about 10% to about 25% f.d.) and Indonesia (about 10% to about 35% frequency) with the largest frequency being associated with Australia and central Asians (about 45% to about 75% f d.).

Group VI is more widely distributed than other haplotypes, covering the geographical area of Europe, Eastern Europe, Asia, and India The presence of haplotype group VI in North America, Australia and Polynesia is a consequence of recent human movements since C. Columbus catalyzed the age of exploration. The largest Group VI frequency is associated with southern Europe and the middle east, with a distribution frequency of about 60% to about 85%.

Group VII is more widely associated with eastern Asia and Indonesia with distribution frequencies ranging from about 75% to about 99%. Group VIII is almost exclusively found in Papua-New Guniea (distribution frequencies of about 70% to about 95%) with a slight distribution in central Asia (distribution frequency of about 1% to about 30%). Recently, there is evidence which indicates the presence of Group VIII in Indonesia. Other specific Group VIII lineages occur in India and Europe. Individuals of haplotype Group IX are mostly associated Europe (about 75% to about 95% f.d.), India (about 25% to about 50% f.d.). Their occurrence in North America (about 35% to about 55%) Australia (35%), Polynesia is a consequence of European gene flow during the last 500 years.

Group X individuals are geographically associated with Central Asia and the Americas with a frequency distribution in North America of about 25% to about 50%, Central America of about 75% to about 95% and in South America of about 80% to about 99%. The above distribution frequencies of the various haplotypes in the geographic regions mentioned above are only representative ranges of the haplotype frequencies worldwide.

Analysis of Polymorphisms

Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed. For purposes of the present invention, the sample is obtained from a male, and preferably a human male.

Many of the methods described below require amplification of DNA from target samples. This can be accomplished by e.g., PCR. See generally PCR Technology: Principles and Applications for DNA Amplification (ed. H. A. Erlich, Freeman Press, N.Y., N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, Genomics 4, 560 (1989), Landegren et al., Science 241, 1077 (1988), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Detection of Polymorphisms in Target DNA

There are two distinct types of analysis depending whether a polymorphism in question has already been characterized. The first type of analysis is sometimes referred to as de novo characterization. This analysis compares target sequences in different individuals to identify points of variation, e.g., polymorphic sites, SNPs. By analyzing groups of individuals representing the greatest ethnic diversity among humans and greatest breed and species variety in plants and animals, patterns characteristic of the most common alleles/haplotypes of the locus can be identified, and the frequencies of such populations in the population determined. Additional allelic frequencies can be determined for subpopulations characterized by criteria such as geographical distribution and ancestral ethnicity. The de novo identification of the polymorphisms of the invention is described in the Examples section. The second type of analysis is determining which form(s) of a characterized polymorphism are present in individuals under test. There are a variety of suitable procedures, which are discussed in turn.

Allele-Specific Probes

The design and use of allele-specific probes for analyzing polymorphisms is described by e.g., Saiki et al., Nature 324, 163–166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Probes with such specificity allow for the determination of a specific base occupying a polymorphic site in a sequence of a polymorphic region. Some probes are designed to hybridize to a segment of target DNA such that the polymorphic site aligns with a central position (e.g., in a 15 mer at the 7 position; in a 16 mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

Tiling Arrays

The polymorphisms can also be identified by hybridization to nucleic acid arrays, some example of which are described by WO 95/11995. The same array or a different array can be used for analysis of characterized polymorphisms. WO 95/11995 also describes subarrays that are optimized for detection of a variant form of a precharacterized polymorphism. Such a subarray contains probes designed to be complementary to a second reference sequence, which is an allelic variant of the first reference sequence. The second group of probes is designed by the same principles as described in the Examples except that the probes exhibit complementarily to the second reference sequence. The inclusion of a second group (or further groups) can be particular useful for analyzing short subsequences of the primary reference sequence in which multiple mutations are expected to occur within a short distance commensurate with the length of the probes (i.e., two or more mutations within 9 to 21 bases).

Allele-Specific Primers

An allele-specific primer hybridizes to a site on target DNA overlapping a polymorphism and only primes amplification of an allelic form to which the primer exhibits perfect complementarily. See Gibbs, Nucleic Acid Res. 17, 2427–2448 (1989). This primer is used in conjunction with a second primer which hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. The method works best when the mismatch is included in the 3'-most position of the oligonucleotide aligned with the polymorphism because this position is most destabilizing to elongation from the primer. See, e.g., WO 93/22456.

Direct-Sequencing

The direct analysis of the sequence of polymorphisms of the present invention can be accomplished using either the dideoxy chain termination method or the Maxam Gilbert method (see Sambrook et al., Molecular Cloning, A Laboratory Manual ($2^{nd}$ Ed., CSHP, New York 1989); Zyskind et al., Recombinant DNA Laboratory Manual, (Acad. Press, 1988)). In a preferred embodiment, the direct sequencing would be carried using fluorescent sequencing, e.g., using a PE Biosystems 373A sequencer.

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., PCR Technology, Principles and Applications for DNA Amplification, (W.H. Freeman and Co, New York, 1992), Chapter 7.

Single-Strand Conformation Polymorphism Analysis

Alleles of target sequences can he differentiated using single-strand conformation polymorphism analysis, which identifies base differences by alteration in electrophoretic migration of single stranded PCR products, as described in Orita et al., Proc. Nat Acad. Sci. 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

Detection of SNP Polymorphisms

Where the polymorphism is a SNP, any suitable method known in the art can be used in their detection. For example, the present methods can utilize the detection of SNPs by DHPLC (see U.S. Pat. No. 5,795,976) to isolate and analyze specific SNPs on the Y chromosome of a large number of individuals in a fast, efficient and inexpensive manner. This method involves separating heteroduplex and homoduplex nucleic acid molecules (e.g., DNA or RNA) in a mixture using high performance liquid chromatography under partially denaturing conditions. In a preferred embodiment, the SNPs are identified on the Y chromosome using techniques such as those disclosed in co-pending application U.S. application Ser. No. 09/502,558, Feb. 10, 2000.

Mass Spectrometry

Mass spectrometry can also be used in the methods of the present invention to verify a polymorphism and/or to identify additional polymorphisms. The mass spectrum of a nucleic acid containing the polymorphic site can be compared to the mass spectrum of nucleic acids obtained from samples of known residues at the polymorphic site. These known spectra are referred to as "signature" spectra. A simple comparison of the sample spectrum vs. signature spectra will reveal whether an individual's DNA has a specific base occupying the polymorphic site. Although sequencing of fragments of nucleic acids is possible using mass spectrometry, actual sequencing of the nucleic acid is not required for this mutational analysis. Less preparation and analysis is needed to prepare and analyze a complete, intact fragment as compared to treating a sample for actual sequencing.

Certain mass spectrometry techniques can be used to analyze for polymorphisms. Short oligomers, e.g., from one nucleotide up to approximately 50 nucleotides, can be analyzed and the resulting spectra compared with signature spectra of samples known to be wild-type or to contain a known polymorphism. A comparison of the locations (mass) and heights (relative amounts) of peaks in the sample with the known signature spectra indicate what type of polymorphism, if any, is present. Exemplary protocols are described in U.S. Pat Nos. 5,872,003, 5,869,242, 5,851,765, 5,622,824, and 5,605,798, which are incorporated herein by reference for teaching such techniques.

After determining polymorphic form(s) present in an individual at one or more polymorphic site on the Y chromosome, this information can be used in a number of methods.

Methods of Use of the Polymorphisms of the Invention

The methods of the invention have utility in a wide variety of fields where it is desirable to identify known polymorphisms of a particular individual and/or to determine allelic distribution in a group or population. Such methods include, but are not limited to, linkage analysis for the identification of disease loci, evolutionary studies to determine rates of evolution in a population, identification of polymorphisms useful in forensic identification, identification of mutations associated with a disease or predisposition, genetic marker development, and the like.

Forensics

Determination of which polymorphic sites an individual possesses, identifies a haplotype, which refers to a set of polymorphic markers that distinguishes the individual. See generally National Research Council, *The Evaluation of Forensic DNA Evidence* (Eds. Pollard et al., National Academy Press, DC, 1996). Since the polymorphic sites of the invention are generally within a region of about 50,000 bp in the human genome, the probability of recombination between these polymorphic sites is low. The more sites that are analyzed the lower the probability that the set of polymorphic markers for one individual is the same as that in an unrelated individual. If multiple polymorphic sites are analyzed, the sites are usually in different polymorphic regions (on different polymorphic markers). Thus, polymorphisms of the invention may be used in conjunction with polymorphisms in distal genes. Preferred polymorphisms for use in forensics are diallelic because the population frequencies of two polymorphic forms can usually be determined with greater accuracy than those of multiple polymorphic forms at multi-allelic loci.

An exemplary set of polymorphic markers useful for identifying the haplotype group of an individual are the following; Markers 304(Group VI, Mediterranean), 242 (Group X, C. Asia, India, Americas), 269 (Group IX, W. Europe), 207 (Group IX, Europe, W. Asia), 74 (Groups IX–X, global), 214 (Group VII, E. Asia), 9 (Groups VII–X, global), 235 (Groups VI–X, global), 316 (Group V, Asia, America, Polynesia, Melanesia), 174 (Group IV, Asia, Japan), Groups II–X, global), 246 (Group I, Africa), 249 (Group II, Africa) 294 (Groups III–X, global), 96 (Group III, Africa, Mediterranean).

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance. If several polymorphic loci are tested, the cumulative probability of non-identity for random individuals becomes very high (e.g., one billion to one). Such probabilities can be taken into account together with other evidence in determining the innocence or guilt of an individual suspected of a criminal act.

The polymorphisms of the present invention are especially useful in identifying samples having genetic material from multiple individuals, since the polymorphisms are single copy. Thus, the detection of more than one polymorphic Y chromosome allele in a single sample is indicative of the presence of nucleic acids from multiple individuals within the sample. Such information can be useful, for example, when multiple perpetrators are suspected of participating in a crime, or in the case of mixed unidentified remains at a grave site or accident scene.

The polymorphic sites and methods of the present invention are also useful in categorizing victims of violent crimes into ethnic and geographical groups. When a large number of victims need to be identified at a crime site, categorizing recovered victims by ethnicity can decrease the overall time for victim identification by reducing the number of comparison samples (samples from members of the victims family) to those of similar geographical origin.

Paternity Testing

The object of paternity testing is usually to determine whether a male is the father of a child. In most cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms (polymorphic markers) in the putative father and the child. The polymorphic markers of the present invention can be useful in determining paternity of a male child, as they are specific to the Y chromosome. The mother need not be tested in such a case, as the mother has no contribution to the child's genotype as it pertains to the Y chromosome.

If the set of polymorphisms in the child attributable to the father does not match the putative father, it can be concluded, barring experimental error, that the putative father is not the real father. If the set of polymorphisms in the child attributable to the father does match the set of polymorphisms of the putative father, a statistical calculation can be performed to determine the probability of coincidental match. An exemplary method of determining the probability of parentage exclusion, i.e. the probability that a random male will have a polymorphic form at a given polymorphic site that makes him incompatible as the father) is described in WO 95/12607.

If several polymorphic loci are included in the analysis, the cumulative probability of exclusion of a random male is very high. This probability can be taken into account in assessing the liability of a putative father whose polymorphic marker set matches the child's polymorphic marker set attributable to his father. This analysis can be further expanded to identify ancestral males (e.g., grandfather, great grandfather and so on). Such analysis can be useful in genealogical analysis, or in tracing the origin of ancestral man (e.g.) using samples obtained from an archeological site).

Longer-term Family Heritage

In addition to the use in paternity testing, the polymorphisms and methods of the present invention can be used to determine relationships through a paternal lineage for multiple generations. The constancy and low mutational rate of these regions of the Y chromosome allow an individual to trace his specific ancestral lineage using the Y chromosome polymorphisms. For example, a specific residue (base) in a polymorphic site may be indicative of a population that is in or from a certain region in Europe. Assaying an individual for this polymorphism can indicate that the individual's paternal ancestors were in or descended from this particular region.

Correlation of Polymorphisms with Phenotypic Traits

The polymorphisms of the invention may contribute to the phenotype of an organism in different ways. Some polymorphisms occur within a protein coding sequence and contribute to phenotype by affecting protein structure. The effect may be neutral, beneficial or detrimental, or both beneficial and detrimental, depending on the circumstances. Other polymorphisms occur in noncoding regions but may exert phenotypic effects indirectly via influence on replication, transcription, and translation.

A single polymorphism may affect more than one phenotypic trait. Likewise, a single phenotypic trait may be affected by polymorphisms in different genes. Further, some polymorphisms predispose an individual to a distinct mutation that is causally related to a certain phenotype.

Phenotypic traits include diseases that have known but hitherto unmapped genetic components. Phenotypic traits also include symptoms of, or susceptibility to, multifactorial diseases of which a component is or may be genetic, such as autoimmune diseases, inflammation, cancer, diseases of the nervous system, and infection by pathogenic microorganisms. Phenotypic traits also include characteristics such as longevity, appearance (e.g., baldness, obesity), strength, speed, endurance, fertility, and susceptibility or receptivity to particular drugs or therapeutic treatments.

Correlation is performed for a population of individuals who have been tested for the presence or absence of a phenotypic trait of interest and for polymorphic markers sets. To perform such analysis, the presence or absence of a set of polymorphisms (i.e. a polymorphic set) is determined for a set of the individuals, some of whom exhibit a particular trait, and some of which exhibit lack of the trait. The alleles of each polymorphism of the set are then reviewed to determine whether the presence or absence of a particular allele is associated with the trait of interest. Correlation can be performed by standard statistical methods such as a κ-squared test and statistically significant correlations between polymorphic form(s) and phenotypic characteristics are noted.

The polymorphisms and assays of the present invention arc of particular use in determining the appropriate populations for mapping complex genetic traits and/or disorders. Population choice can be crucial for the success of gene mapping for particular traits and/or disorders. Populations having a high degree of inbreeding are also useful for linkage analysis (see, e.g., Sheffield, V C et al., Trends in Genetics 4:391–6 (1998)), and the polymorphisms of the invention can be useful in determining the genetic heterogeneity of a population.

Antibodies to Specific Polymorphisms

Polyclonal and/or monoclonal antibodies that specifically bind to variant gene products but not to corresponding prototypical gene products are also provided. Antibodies can be made by injecting mice or other animals with the variant gene product or synthetic peptide fragments thereof. Monoclonal antibodies are screened as are described, for example, in Harlow & Lane, Antibodies, A Laboratory Manual, Cold Spring Harbor Press, New York (1988); Goding, Monoclonal antibodies, Principles and Practice (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

Use of the Present Method to Produce a Database of Y Chromosome Polymorphisms

The polymorphisms of the invention can be used as the basis for, or combined with other such polymorphisms to provide, a general catalog of genome variation to address the large-scale sampling designs required by association studies, gene mapping, and evolutionary biology. There is widespread interest in documenting the amount and geographic distribution of genetic variation in the human species. This information is desired by the biomedical community, whose work would be greatly facilitated by a densely packed map of polymorphic markers, particularly SNPs in the NRY region, to be used to for example, identify genes associated with disease by linkage disequilibrium between sets of adjacent markers and the occurrence of disease in populations, and to characterize disease-related variation among populations.

Anthropologists and archeologists use genetic variation to reconstruct our species' history, and to understand the role of culture and geography in the global distribution of human variation. The requirements for these two perspectives seem to be converging on a need for an accessible, representative DNA bank and statistical database of human variation.

In addition, these systems have potential in both routine forensic and intelligence database applications, either in place of or in conjunction with more traditional "DNA fingerprinting" databases produced using methods such as restriction fragment length polymorphism mapping.

The invention may be embodied in computer-readable media containing an electronically, magnetically, or optically stored code representative of the markers for polymorphic regions of Table 1, and/or stored code configured to create the electronically stored representation of Table 1 and the corresponding geographic distributions for these polymorphic markers (see TABLE 3). Such databases may be produced using a variety of different data configurations and processing capabilities. Examples include, but are not limited to, logical databases, physical databases, relational databases, central configuration databases, and the like. Database structures for genomic information may be based on, for example, the database structures disclosed in U.S. Pat. No. 6,229,911. In other examples, the data generated for use in the present invention may be used to create a general database such as that described in U.S. Pat. No. 4,970,672 or a relational database such as that described in U.S. Pat. No. 5,884,311. Databases containing data generated for use in the methods of the invention may also be a central configuration database for data that is shared among multiprocessor computer systems. See U.S. Pat. No. 6,014,669. Other database systems and design methodologies can be found in I. Fogg and M. Orlowska, *Computers Math. Applic.* (UK), (1993) 25:97–106; S. Ceri, et al., Proceedings of the IEEE (1987) 75:533–545.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

A phylogenetic tree was deduced from 167 polymorphisms from a Non-recombining Region of the human Y chromosome (NRY) on the principle of maximum parsimony (FIG. 2). Seven of the 167 polymorphisms had been detected by means other than DHPLC and were taken from the literature to demonstrate the applicability of the method of the invention to polymorphisms with less demographic specificity than those in TABLE 1. Seventy-three of the 160 polymorphisms detected by DHPLC had been reported previously. Underhill, P. A. el al *Genome Res.* 7:996–1005 (1997). Shen, P. et al *Proc. Natl. Acad Sci. USA* 97:7354–7359 (2000). Of the remaining 87 unreported polymorphisms, 53 were discovered in a set of 53 individuals of diverse geographic origin during the screening of the unique sequences and repeat elements, other than long interspersed elements, contained in three overlapping cosmid sequences (GenBank accession nos. AC003032, AC003095, AC003097) and a few small fragments scattered throughout the NRY. Finally, 34 were detected during genotyping. In total, the marker panel comprises 91 transitions, 53 transversions, 22 small insertions or deletions, and an Alu insertion. All polymorphisms are biallelic, except a double transversion, M 116, that has three alleles, A, C or T, defining quite different haplotypes. Two non-CpG associated transitions (M64 and M108) showed evidence of recurrence but generated no ambiguities when considered in the context of other markers. The primer sequences used to detect the 167 polymorphisms are given in Table 1).

Methods

DNA samples. The ascertainment set consisted of the following 53 samples with their subsequently determined haplogroup designations: Africa: 3 Central African Republic Biaka II, III (1); 2 Zaire Mbuti II, III; 2 Lissongo II, III; 2 Khoisan I, III; 1 Berta VI; 1 Surma I; 1 Mali Tuareg III; 1 Mali Bozo III; Europe: 1 Sardinian VI; 2 Italian VI IX; 1 German VI; 3 Basque VI, IX (2); Asia: 3 Japanese IV, V, VII; 2 Han Chinese VII, 1 Taiwan Atayal VII, Taiwan Ami, VII, 2 Cambodian VI, VII; Pakistan: 2 Hunza VI, IX; 2 Pathan VI, VII; 1 Brahui VIII; 1 Baloochi VI; 3 Sindhi III, VI, VIII; Central Asia 2 Arab IX; 1 Uzbek IX; 1 Kazak V; MidEast: 1 Druze VI; Pacific: 2 New Guinean V, VIII; 2 Bougainville Islanders VIII; 2 Australian VI, X: America: 1 Brazil Surui, 1 Brazil Karatina, 1 Columbian, 1 Mayan all X. An additional 1,009 chromosomes, representing 21 geographic regions, were genotyped by DHPLC for all markers other than those on the terminal branches of the phylogeny. The latter were genotyped only in individuals from the haplogroup to which those markers belonged. This hierarchic genotyping protocol was necessitated by the minute amounts of genomic DNA available for most samples.

PCR. The RepeatMasker2 program (available at ftp.genome.washington.edu) was used to identify human repeat DNA sequences. Primers were designed to amplify unique sequences and repeat elements other than LINE as confirmed by a negative female control, yielding amplicons 300–500 bp in length. All primers had a uniform annealing temperature, which allowed a single PCR protocol to be used. It comprised an initial denaturation at 95° C. for 10 min to activate AmpliTaq Gold®, 14 cycles of denaturation at 94° C. for 20s, primer annealing at 63–56° C. using 0.5°

C. decrements, and extension at 72° C. for 1 min, followed by 20 cycles at 94° C. for 20 s, 56° C. for 1 min, and 72° C. for 1 min, and a final 5-min extension at 72° C. Each 50-μl PCR reaction contained 1 U of AmpliTaq Gold® polymerase, 10 mM Tris-HCl, pH 8.3, 50 mM KCl, 2.5 mM $MgCl_2$, 0.1 mM each of the four deoxyribonucleotide triphosphates, 0.2 μM each of forward/reverse primers, and 50 ng of genomic DNA. PCR yields were determined semi-quantitatively on ethidium bromide stained agarose gels.

DHPLC Analysis

Unpurified PCR products were mixed at an equimolar ratio with a reference Y chromosome and subjected to a 3-minute 95° C. denaturing step followed by gradual reannealing from 95 to 65° C. over 30 min. Ten microliters of each mixture were loaded onto a DNASep™ column (Transgenomic, San Jose, Calif.), and the amplicons were eluted in 0.1 M triethylammonium acetate, pH 7, with a linear acetonitrile gradient at a flow rate of 0.9 ml/min². Under appropriate temperature conditions, which were optimized by computer simulation (available at insertion.stanford.edu/melt.html), mismatches were recognized by the appearance of two or more peaks in the elution profiles.

DNA Sequencing

Polymorphic and reference PCR samples were purified with QIAGEN (Valencia, Calif.) QIAquick spin columns. Both strands were sequenced to determine the location and chemical nature of any polymorphic sites, using the amplimers as sequencing primers and ABI Dye-terminator cycle sequencing reagents (PE Biosystems, Foster City, Calif.). Each cycle sequencing reaction contained 6 μl of purified PCR product, 4 μl dye terminator reaction mix, and 0.8 μl of primer (5 μM). Cycle sequencing was started at 94° C. for 1 min, followed by 25 cycles of 96° C. for 10s, 50° C. for 2s, and 60° C. for 4 min. The sequencing products were purified with Centrifex™ gel filtration cartridges (Edge Biosystems, Gaithersburg, Md.) and analyzed on a PE Biosystems 373A sequencer.

Statistical Analysis

The program CONTML in PHYLIP, version 3.57c, was used to construct a frequency based maximum likelihood network. The expected Luria-Delbrück/Lea-Coulson distribution of the number of mutants for each gene was fitted by maximum likelihood, treating each nucleotide of the screened sequence as analogous to a parallel, independent bacterial culture Luria, S. E. & Delbrück, *Genetics* 28:491–511 (1943); Lea, D. E. & Coulson, A. C. *Genetics* 49:264–285 (1949). The distributions under the expectation of constant population size were calculated according to Watterson, G. A. *Theor. Popul. Biol.* 7: 256–276 (1975). Mismatch distributions were calculated as described previously (Shen et al., supra). The NRY mutation rate per nucleotide per year ($1.53 \times 10^{-9}$) was calculated on the basis of 597 nucleotide substitution differences between human and chimpanzee observed over 39,931 bp of non-coding sequence (Shen et al., supra). The corresponding mutation rates for mtDNA ($1.65 \times 10^{-8}$) and X chromosome ($7.54 \times 10^{-10}$) were calculated on the basis of 581 and 58 nucleotide substitution differences, respectively, between human and chimpanzee observed over 6,176 bp of coding mtDNA (mictochondrial DNA) sequence comprising the genes ND1, ND2, COX1, COX2, ATP8, ATP6, COX3, and ND3, and 7,853 bp of flanking non-coding sequence of the DIAPH2 gene on Xq22.

Accession Numbers

Most of the NRY sequence surveyed was derived from 5 cosmid sequences retrievable from Genbank using the accession numbers AC003031, AC003032, AC003094, AC003095, and AC003097. Six polymorphisms were affiliated with genomic regions for DFFRY (AC00253 1), one each for DBY (AC004474) and UTY1 (AC006376), 3 for SRY (NM003140), and 15 for random genomic STSs reported by Vollrath D, et al. *Science* 258:52–59 (1992).

The tree of FIG. 2 is rooted with respect to non-human primate sequences. The 116 numbered compound haplotypes were constructed from 167 mutations (markers) of which 160 were discovered by DHPLC (Table 1). Seven haplotypes from the literature with less geographical heritage specificity were also analyzed in this study, including YAP (M1), DYS271 (M2), PN3 (M29), SRY 4064 (M40), TAT (M46), RPS4YC711T (M130), and SRY 2627 (M167), (the sequences for these markers are not shown in TABLE 1). Marker numbers indicated on the segments are discontinuous because of the removal of all but one polymorphism associated with tandem repeats and homopolymer tracts whose ancestral state is uncertain. Haplotypes are assorted into ten haplogroups (I–X) using principles commonly applied to haploid mtDNA phylogenies. Macaulay, V. et al. *Am. J Hum. Genet.* 64: 232–249 (1999). Haplogroup I members, ancestral for M42, M94 and M139, also share the only homopolymer-associated marker M91. All haplogroup I individuals have an 8-T length variant, while 1,009 men in haplogroups II–X have 9 T's and in two cases 10 (not shown). Only one inconsistent haplogroup X individual had 8 T's (not shown). Haplogroups I and II, both of which are almost exclusively represented in Africa only, share the ancestral allele of M168. Haplogroup III is generally the most frequent one in Africa. Its frequency decreases with increasing distance from Africa, from 27% in the Mid-East to a few percent in Northern Europe and South and Central Asia. Haplogroup IV, related to the former through M1 and M145, is found mainly in Japan.

In a recent cladistic analysis of nine diallelic NRY polymorphisms, including M1, in 1,544 individuals, it was hypothesized that haplogroup II comprises descendents of a range expansion that brought Y-chromosomes back to Africa (M. F. Hammer et al. 15:427–441 (1998)). Haplogroups V and VIII are prevalent in New Guinea and Australia, but they are also found at varying though smaller frequencies throughout Asia. Haplogroups VI and IX are found mostly in Europe and the Indus Valley. They are not observed in East Asia, where haplogroup VII dominates, suggesting that this part of the world where agriculture developed independently resisted effectively subsequent gene flow Macaulay, V. et al supra. The distinction between Eurasians and East Asians was also observed with mtDNA Macaulay, V. et al., supra., and autosomal genes (Diamond, J. *Guns, Germs, and Steel* (Norton & Co., New York, p. 99, 1999). Haplogroup X is common in the Americas, although its origin may have been in Central Asia where traces of it persist, as shown in Table 2:

TABLE 2

| Haplogroup | Exemplary Defining Mutation | Avg. no. of Mutations from Root to Individual Haplotypes | Total no. of Individuals | No. of Mutations per Haplogroup Minus Defining Mutation(s) | No. Haplotypes per Haplogroup |
|---|---|---|---|---|---|
| I | M91 | 6.1 ± 0.95 | 52 | 20 | 8 |
| II | M60 | 6.1 ± 0.41 | 52 | 12 | 10 |
| III | M96 | 10.4 ± 0.24 | 218 | 27 | 21 |
| IV | M124 | 10.5 ± 0.56 | 9 | 7 | 4 |
| V | M130 | 6.6 ± 0.6 | 40 | 8 | 5 |
| VI | M89 & absence of M9 | 7.4 ± 0.25 | 163 | 25 | 23 |
| VII | M175 | 9.5 ± 0.35 | 137 | 18 | 15 |
| VIII | M9 & Absence of M175 and M45 | 8.9 ± 0.63 | 67 | 16 | 11 |
| IX | M173 | 10.2 ± 0.20 | 195 | 13 | 13 |
| X | M74 & Absence of M173 | 9.2 ± 0.1 | 129 | 6 | 6 |
| Totals | | 8.59 ± 0.20 | 1052 | 152 | 116 |

Example 2

The root of the phylogeny was placed using sequence information generated from the three great ape species. The sequential succession of mutational events is unequivocal, except for those appearing in the same tree segment (e.g., M42, M94, M139). The phylogeny is composed of 116 haplotypes and their frequencies in 21 general populations are listed in Table 3. Forty-two haplotypes (36.2%) are represented by just one individual. Several haplotypes, however, display higher frequencies and/or geographic associations that reveal patterns of population affinities apparent from a maximum likelihood analysis (FIG. 3) performed on the haplotype frequencies reported in Table 3. To facilitate presentation, the 116 haplotypes were grouped into 10 haplogroups as defined either by the presence or absence of mutations occupying strategic positions in the phylogeny. Haplogroups VI, VIII, and X, although polyphyletic, are distinguished by the criteria in Table 2.

Three mutually reinforcing mutations, M42, M94 and M139 (2 transversions and a 1-bp deletion) unequivocally distinguish haplogroup I which is represented today by a minority of Africans, mainly Sudanese, Ethiopians, and Khoisans (Table 2). All non-African, except a single Sardinian, and the majority of African males sampled, carry only the derived alleles at the three sites. This implies that modern extant human Y-chromosomes trace ancestry to Africa and that the descendents of the derived lineage left Africa and eventually replaced archaic human Y-chromosomes in Eurasia.

An important property of a phylogeny is the randomness of number of mutations per segment of the tree. Forty-one of the total 166 segments carry no mutation, while 98, 16, 8, 2, and 1 segment have 1, 2, 3, 4, and 8 mutations, respectively. The mean number of mutations per segment is 1.024 with a variance of 0.945. Applying the G-test for goodness of fit and Williams' correction to the observed G, the data do not fit a Poisson distribution ($G_{adj}$=34.98, df=3, P~$10^{-7}$). This is due to an excess of segments with one mutation, as expected in an exponentially growing population. Similar results were obtained recently for the separate analysis of 4 Y-chromosome genes. Further support that the human population has undergone a major expansion comes from the consistently negative values of Tajima's D (Lea, D E & Coulson, A C Genetics 49: 264–285 (1949)) for not only the Y-chromosome, but also for mitochondrial DNA, X-chromosomal and autosomal genes. Interestingly, NRY shows evidence of significantly reduced variability to the other genetic systems (Shen et al., supra), confirming a similar comparison of a smaller number of polymorphisms on previously reported NRY sequences with eight X-linked (Hudson, R. et al, *Genetics* 116:153–159 (1987); Nachman, M. W. *Mol. Biol. Evol.* 15: 1744–1750 (1998) and 16 autosomal human genes. Possible explanations include positive selection on NRY Jaruzelska, J et al., D. *Mol. Biol. Evol.* 16:1633–1640 (1999) and a difference between male and female effective population sizes Wyckoff, G. J et al., *Nature* 403:304–309 (2000). Assuming expansion, the age of the most recent common ancestor ($T_{MRCA}$) was previously estimated at 59,000 years with a 95% probability interval of 40,000–140,000 years (Thomson, R. et al. supra).

This value is similar to an estimate of 46,000 to 91,000 years based on 8 Y chromosome microsatellites (Pritchard, J. K et al, *Mol. Biol. Evol.* 16:1791–1798 (1999) and, therefore, is considerably less than estimates of >100,000 years obtained previously (Hammer et al, supra). Of course, this assumes that selection or population structure have not had a major effect on NRY diversity, an assumption that may be wrong in light of our findings of significantly reduced variability on NRY. As the average number of mutations of all segments departing from the root is 8.60 (Table 3), and with a $T_{MRCA}$ value of 59,000 years, the average time for adding a new mutation to the tree is 6,900 year. This puts the age of M168 that marks the expansion of anatomically modern humans out of Africa at approx. 44,000 years, in agreement with a previous estimate of 47,000 years with 95% probability intervals of 35,000 to 89,000 years using the program GENETREE (Thomson, R. et al. *Proc. Natl. Acad Sci.* USA 97:7360–7365 (2000).

TABLE 3

| | Haplotype Group | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|
| | I | | | | | | | | | | | II | | | | | | | | | | | | | | | III | | | | | | | | | | | | | | IV | |
| Haplotype # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
| Sudan | | 17 | 1 | | | | | | | | | 5 | 1 | | | | | | | | | 3 | | | | 2 | | | 1 | | | | | | 7 | | | | | | | |
| Ethiopia | 6 | 5 | | | 1 | | | | | 3 | 3 | 4 | 1 | | | | | | | | | 7 | | | | 15 | | 13 | 16 | | | 2 | | | 20 | 6 | | 2 | | | | |
| Mali | | | | | | | 1 | 1 | 3 | | 1 | 1 | | 1 | | | 1 | | | | | 2 | | | | | | | 2 | | | | | | | | 1 | 12 | 1 | | | |
| Morocco | | | | | | | | | | | | | | | | | 1 | | | | 1 | | | | | | | | | | | | | | | | | | | | | |
| C. Africa | | | | 11 | | 5 | | | | | | | | | 1 | 7 | 1 | 1 | | | | 20 | | | | 3 | | | | | | | | | | 4 | | | | | | |
| Khoisan | | | | 3 | | | | | | | | | | | | 11 | | | | | | 7 | | | | | | | | | | | | | | 1 | | | | | | |
| S. Africa | | | | | | | | | | | | | 7 | | | | | | | | | 28 | 1 | 3 | 2 | 8 | | | 1 | | | | | | | | | | | | | |
| Europe | | | 1 | | | | | | | | | | | | | | | | | | | | | | | | | | | | | | | | | | | | | | | |
| Sardinia | | | | | | | | | | | | | | | | | | | | | | | | | | | | | | | | 1 | | | 4 | | | | | | | |
| Basque | | | | | | | | | | | | | | | | | | | | | | | | | | | | | | | | 1 | | | | | | | 1 | | | |
| Mid-east | | | | | | | | | | | | | | | | | | | | | | 2 | | | | | | 1 | | | | 1 | 1 | | 2 | | | | | | | |
| C. Asia + Siberia | | | | | | | | | | | | | | | | | | | | | | | | | | | | | | | | 2 | | | 1 | | | | | | | |
| Pakistan + Hunza | | | | | | | | | | | 2 | | | | | | | | | | | | | | | | | | | | 2 | | | 1 | | | | | | | | |
| India | | | | | | | | | | | | | | | | | | | | | | | | | | | | | | | | | | | | | | | | | | |
| Japan | | | | | | | | | | | | | | | | | | | | | | | | | | | | | | | | | | | | | | | | | 1 | |
| China | | | | | | | | | | | | | | | | | | | | | | | | | | | | | | | | | | | | | | | | 1 | 1 | 5 |
| Taiwan | | | | | | | | | | | | | | | | | | | | | | | | | | | | | | | | | | | | | | | | | | |
| Cambo + Laos | | | | | | | | | | | | | | | | | | | | | | | | | | | | | | | | | | | | | | | 1 | | | |
| New Guinea | | | | | | | | | | | | | | | | | | | | | | | | | | | | | | | | | | | | | | | | | | |
| Australia | | | | | | | | | | | | | | | | | | | | | | | | | | | | | | | | | | | | | | | | | | |
| America | | | | | | | | | | | | | | | | | | | | | | | | | | | | | | | 2 | | | | 1 | | | | | | | |
| Total | 6 | 23 | 1 | 14 | 1 | 5 | 1 | 1 | 3 | 3 | 3 | 19 | 2 | 1 | 1 | 1 | 1 | 1 | 1 | 1 | 1 | 71 | 1 | 3 | 2 | 17 | 12 | 14 | 19 | 2 | 7 | 1 | 1 | 1 | 36 | 11 | 1 | 16 | 1 | 2 | 1 | 5 |

| | Group | | | | | | | | | | | | | | | | | | VI | | | | | | | | | | | | VII | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| | IV | V | | | | | | | | | | | | | | | | | | | | | | | | | | | | | | | | | | | | | | |
| Haplotype# | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
| Sudan | | | | | | | | | | | | | | | | | | | | | | | | | | | | | 4 | | | | | | | | | | | | | |
| Ethiopia | | | | | | | | | | | | | | | | | | | | | | | | | | | | | 4 | | | | | | | | | | | | | |
| Mali | | | | | | | | | | | | | | | | | | | | | | | | | | | | | | | | | | | | | | | | | | |
| Morocco | | | | | | | 1 | | | | | | | | | 3 | | | | | | | | | | | | | 14 | | | | | | | | | | | | | |
| C. Africa | | | | | | | | | | | | | | | | | | | | | | | | | | | | | | | | | | | | | | | | | | |
| Khoisan | | | | | | | | | | | | | | | | | | | | | | | | | | | | | | | | | | | | | | | | | | |
| S. Africa | | | | | | | | | | | | | | | | | | | | | | | | | | | | | | | | | | | | | | | | | | |
| Europe | | | | | | | 1 | 1 | | 8 | | | | | | | | 2 | 1 | | | | | | | | | | 9 | | | | | | | 6 | 9 | | | | | |
| Sardinia | | | | | | | | 11 | | 1 | | | | 1 | | | | | | | | | | | | | | | 2 | | | | | | | | | | | | | |
| Basque | | | | | | | | 2 | | | | | | | | | | | | | | | | | | | | | 1 | | | | | | | | 1 | 1 | | | | |
| Mid-east | | | | | | | | | | | | | | 2 | 1 | 2 | | 4 | | 1 | | 2 | | | | | | | 8 | | | | | | | | | | | | | |
| C. Asia + Siberia | | 10 | 16 | | | | | | | | | 1 | 2 | 2 | 1 | 12 | 4 | 3 | 2 | 1 | | 1 | 1 | | | 1 | | 1 | 17 | | | | | | 1 | | | | 1 | 2 | 2 | |
| Pakistan + Siberia | | 1 | | | | | | | | | | | 4 | 3 | | | | | | | | 1 | | | 1 | 4 | | | 7 | | | | | | | | 1 | 1 | | | | |

TABLE 3-continued

|  | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | Total |
|---|---|---|---|---|---|---|---|---|---|---|---|---|---|---|---|---|---|---|---|---|---|---|---|---|---|---|---|---|---|---|---|---|---|
| India |  |  |  |  |  |  |  |  |  |  |  |  |  |  |  |  |  |  |  |  |  |  |  |  |  |  |  |  |  | 1 |  |  |  |
| Hunza | 1 |  | 1 | 1 | 1 |  |  |  |  |  |  |  |  |  |  |  |  |  |  |  |  |  |  |  |  |  |  |  |  |  |  |  |  |
| Japan |  |  |  |  | 1 | 1 | 1 |  |  |  |  |  |  |  |  |  |  |  |  |  |  |  | 1 |  |  |  |  | 2 | 1 |  | 6 |  |  |
| China |  |  |  | 1 |  |  |  |  |  |  |  |  |  |  |  |  |  |  |  |  |  |  |  |  |  |  |  | 2 | 2 | 1 | 3 |  |  |
| Taiwan |  |  |  |  |  |  |  |  |  |  |  |  |  |  |  |  |  |  |  |  |  |  | 2 | 1 |  | 1 | 2 | 4 | 1 | 2 |  | 1 |  |
| Cambo+Laos |  |  |  |  |  |  |  |  |  |  |  |  |  |  |  |  |  |  |  | 2 |  |  |  |  |  | 4 | 1 | 18 |  | 1 |  | 5 | 46 |
| New Guinea | 4 |  |  |  |  |  |  |  |  |  |  |  |  |  |  |  |  |  |  |  |  |  |  |  |  |  |  |  |  | 1 |  |  | 1 |
| Australia |  |  |  |  |  |  | 3 |  |  |  |  |  |  |  |  |  |  |  |  |  |  |  |  |  |  |  |  |  |  |  |  |  |  |
| America |  |  |  |  |  | 1 |  |  |  | 1 | 1 |  |  |  |  |  |  |  |  |  |  |  |  | 1 |  |  |  |  |  |  |  |  |  |
| Total | 1 | 4 | 10 | 24 | 1 | 1 | 1 | 15 | 1 | 10 | 1 | 5 | 5 | 23 | 1 | 10 | 2 | 1 | 1 | 3 | 3 | 1 | 1 | 7 | 1 | 68 | 1 | 4 | 1 | 22 | 2 | 12 | 16 | 1 | 10 | 5 | 52 | 1 |

|  | VII |  |  |  | VIII |  |  |  |  |  |  |  |  | IX |  |  |  |  |  |  |  |  |  |  | X |  |  |  |  |  |  |  |  |
|---|---|---|---|---|---|---|---|---|---|---|---|---|---|---|---|---|---|---|---|---|---|---|---|---|---|---|---|---|---|---|---|---|---|
| Group | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | Total |
| Sudan |  |  |  |  |  |  |  |  |  |  |  |  |  |  |  |  |  |  |  | 1 |  |  |  |  |  |  |  |  |  |  |  |  | 40 |
| Ethiopia |  |  |  |  |  |  |  |  |  |  |  |  |  |  |  |  |  |  |  | 1 |  |  |  |  |  |  |  |  |  |  |  |  | 88 |
| Mali |  |  | 1 |  |  |  |  |  |  |  |  |  |  |  |  |  |  |  |  | 5 |  |  |  |  |  |  |  |  |  |  |  |  | 44 |
| Morocco |  |  |  |  |  |  |  |  |  |  |  |  |  |  |  |  |  |  |  |  |  |  |  |  |  |  |  |  |  |  |  |  | 26 |
| C. Africa |  |  |  |  |  |  |  |  |  |  |  |  |  |  |  |  |  |  |  |  |  |  |  |  |  |  |  |  |  |  | 37 |  |  |
| Khoisan |  |  |  |  |  |  |  |  |  |  |  |  |  |  |  |  |  |  |  |  |  |  |  |  |  |  |  |  |  |  | 39 |  |  |
| S. Africa |  |  |  |  |  |  |  |  |  |  |  |  |  |  |  |  |  |  |  |  |  |  |  |  |  |  |  |  |  |  | 53 |  |  |
| Europe |  |  |  |  |  |  |  |  |  |  |  | 3 | 1 |  |  |  |  |  |  | 29 |  |  |  | 3 |  |  |  |  |  |  |  |  | 60 |
| Sardinia |  |  |  |  |  |  |  |  |  |  |  |  |  |  | 2 |  |  |  |  |  |  |  |  |  |  |  |  |  |  |  |  |  | 22 |
| Basque |  |  |  |  |  | 2 |  |  |  |  |  |  |  |  |  |  | 2 | 7 | 5 | 26 |  |  |  |  |  |  |  |  |  |  |  |  | 48 |
| Mid-east |  |  |  |  |  | 2 | 2 |  |  |  |  |  |  |  |  |  |  |  |  | 2 |  |  |  |  |  |  |  |  |  |  |  |  | 24 |
| C. Asia+Siberia | 1 | 5 |  |  | 2 | 2 | 12 | 1 |  |  |  |  |  |  |  |  |  |  |  | 10 |  |  | 1 | 30 | 3 | 6 | 3 |  | 12 | 6 |  |  | 184 |
| Pakistan+India |  |  |  |  | 8 | 2 |  |  |  |  |  |  |  |  |  |  |  |  |  | 6 |  | 1 |  | 28 |  |  | 2 |  | 4 |  |  |  | 88 |
| Hunza |  | 2 |  |  |  | 3 |  |  |  |  |  |  |  |  |  |  |  |  |  | 3 |  |  |  | 11 |  |  | 2 |  | 7 |  |  |  | 38 |
| Japan |  |  |  | 1 |  |  |  |  | 1 |  |  |  |  |  |  |  |  |  |  |  |  |  |  |  |  |  |  |  |  |  |  |  | 23 |
| China | 1 | 1 |  |  |  |  |  |  |  |  |  |  |  |  |  |  |  |  |  |  |  |  |  |  |  |  |  |  |  |  |  |  | 20 |
| Taiwan |  | 6 | 1 |  |  |  |  |  |  |  |  |  |  |  |  |  |  |  |  |  |  |  |  |  |  |  |  | 1 |  |  |  |  | 74 |
| Cambo+Laos | 1 |  |  |  |  |  |  |  |  |  |  |  |  |  |  |  |  |  |  |  |  |  |  | 1 |  |  |  |  |  |  |  |  | 18 |
| New Guinea |  | 7 |  |  |  |  |  |  |  | 2 | 5 | 4 | 1 |  |  |  |  |  |  |  |  |  |  |  |  |  |  |  |  |  |  |  | 23 |
| Australia |  | 1 | 1 |  |  |  |  |  |  |  |  |  |  |  |  |  |  |  |  | 1 | 2 |  |  |  |  |  |  |  |  |  |  |  | 7 |
| America |  |  |  |  |  |  |  |  |  |  |  |  |  |  |  |  |  |  |  | 5 |  |  |  |  |  |  | 5 |  |  |  | 83 | 4 | 106 |
| Total | 2 | 7 | 17 | 3 | 2 | 12 | 7 | 12 | 2 | 2 | 5 | 4 | 1 | 3 | 1 | 2 | 2 | 7 | 9 | 89 | 2 | 1 | 1 | 73 | 3 | 6 | 12 | 1 | 23 | 6 | 83 | 4 | 1062 |

This concurs with recent archeological and mtDNA data, and is also consistent, though at a compressed time scale, with the weak Garden of Eden hypothesis. Under this hypothesis, a small subgroup of behaviorally modern humans left Africa and separated into several fairly isolated groups represented today by the major haplogroups III–X. Those groups remained small throughout the last glaciation before they underwent roughly simultaneous expansions in size as suggested by the star-like genealogy shown in FIG. 1. In conclusion, the new levels of biallelic variation revealed here suggest a recent ancestry of the paternal lineages of our species from Africa and testify to the informativeness of the Y chromosome in deciphering the evolution of humankind.

The gene frequencies of New Guineans and Australian aborigines were grouped together because of the small sample size of the latter. Values at nodes indicate number of 1,000 bootstrap trees presenting cluster distal of node. Sudanese and Ethiopians are distinct from the other Africans and appear to be more associated with samples from the Mediterranean basin. This may reflect either repeated genetic contact between Arabia and East Africa during the last 5,000 to 6,000 years or a Middle Eastern origin with subsequent acquisition of Negroid genes on the way southwest with agricultural expansion. Native Americans are located between Eurasians and East Asian indicating common ancestry with both. This network is consistent with the first two principal components capturing 18% of the variation present in the 116 haplotypes.

Example 3

Figure 3:
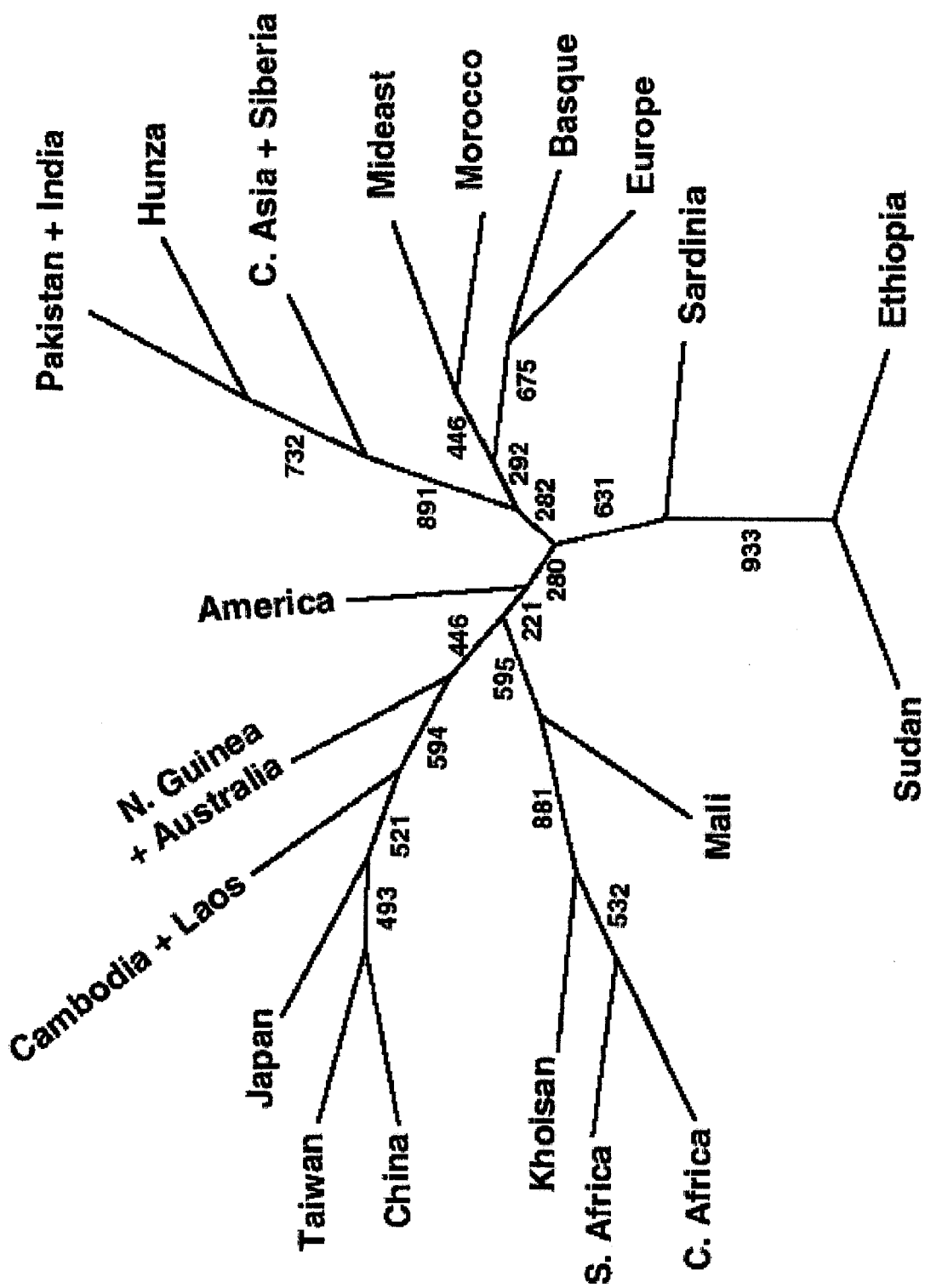
FIG. 3. Maximum likelihood network inferred from the haplotype frequencies.

A phylogenetic tree was deduced from NRY polymorphisms on the principle of maximum parsimony (FIG. 3). FIG. 3 shows the phylogenetic tree deduced from 304 polymorphisms including those presented in Examples 1 and 2 as well as other novel markers.

The contemporary global frequency distribution of the 10 Groups based on >1000 globally diverse samples genotyped using a hierarchical top down approach is illustrated in FIG. 3. 171 haplotypes are identified in FIG. 3 as well as their relationship with 309. However 4 markers are recurrent but define distinctive haplotypes when considered in the context of the other markers. The 4 markers are M64.1 (M64.2), M108.1 (M108.2), M116.1 (M116.2) and 12f2.1 (12f2.2). For example M64.1 occurs on haplotype #80 in Group V and M64.2 on ht#159 in Group IX.

The relationship of the haplotypes to the ten haplogroups is also shown in FIG. 3. Each haplotype can be related to a specific geographical region within the haplotype group, allowing for very specific geographic association and ethnic identity of male individuals. FIG. 3 also shows which specific markers, are important branching points for distinguishing between haplotype groups and also sub-haplotype groups such as haplotypes 10–13 of group II. This composite collection of 315 NRY variants (polymorphic markers) provides improved resolution of extant patri-lineages.

Example 4

The methods of the invention can be utilized in the area of forensics to determine the ethnic affiliation of an individual.

The method involves, obtaining a nucleic acid sample from the individual and processing the sample sufficiently to conduct PCR amplification on the sample. The method exploits the hierarchical property of the Y chromosome gene tree that reveals the unequivocal sequential accumulation of DNA variation during the lineal life spans of these haplotypic molecules. Since Y chromosome haplotypes display a strong correlation with geography, such data provides insights into the affinity and diversification of populations. The sample is analyzed at polymorphic sites defining key internal nodes within the phylogeny. At least 11 primers sets, with each primer set recognizing at least one polymorphic region on the Y chromosome from a different haplotype group (Group I through Group X) are required to begin localizing a sample within the phylogeny. Additional haplotype resolution can be obtained by typing a subset of related markers. Each PCR reaction carried out on the sample, may include one or more primer sets/reaction vessel.

The PCR amplified products are analyzed by DHPLC (or any other suitable PCR product detection technique, such as DNA chips, direct sequencing, Taqman and the like) genotyping technology to define the haplotype which is then compared to a data base detailing the geographic association of the haplotype. The data base utilizes the markers identified in TABLE 1 and various combinations thereof which enables the identification of an individual to a particular haplotype group (Group I through Group X) as well as haplotype which are indicated in FIG. 2 and FIG. 4.

In certain instances, primer sets to the following markers are utilized to identify which haplotype group an individual originates from; Markers-M91, M60, M96, M174, (M216 or M316), M89, M9, M175, M45, M173. These markers identify the following haplotype groups; Group I=M91, Group II=M60, Group III=M96, Group IV=M174, Group V=M316, Group VI=M89 without M9, Group VII=M9 without M175 or M45, Group VIII=M9, Group IX=M173 and Group X is represented by marker M74 without M173. This approach can be expanded to increase criteria for inclusion/exclusion decisions.

TABLE 4 shows a two stage scheme of 30 markers, the haplotype groups they help define as well as geographical region associated with the haplotype group and the polymorphic markers which provides considerable power in facilitating localization any Y chromosome in the phylogeny. In cases where more than one marker is listed in TABLE 4, any one marker in the subset will provide comparable information.

TABLE 4

| Markers analyzed Analysis #1 | Assoc. Geographical region | Markers analyzed Analysis #2 | Assoc. Geographical region |
|---|---|---|---|
| M42, M94, M251, or M299 (Groups II–X) | Global | M215, M243, or M293 (Group III) | Africa, Med |
| M246 (Group I) | Africa | M2, M180 or M291 (Group III) | Sub Saharan Africa |
| M181 or M249 (Group II) | Africa | M191 (Group III) | Sub Saharan Africa |
| M168 or M294 (Groups III–X) | Global | M35 (Group III) | Africa, Med, S. Europe |
| M96 (Group III) | Africa, Med. | M217 (Group V) | E. Asia, India, N. America, |
| M174 (Group IV) | Asia, Japan | M201 (Group VI) | Med., S. Europe |
| M216 or M316 (Group V) | Asia, America, Polynesia, Melansia | M172 (Group VI) | Med., S. Europe |
| M89, M213 or M235 (Groups VI–X) | Global | M267 (Group VI) | Med., S. Europe |

TABLE 4-continued

| Markers analyzed Analysis #1 | Assoc. Geographical region | Markers analyzed Analysis #2 | Assoc. Geographical region |
|---|---|---|---|
| M9 (Groups VII–X) | Global | M170 or M258 (Group VI) | Europe |
| M175 or M214 (Group VII) | E. Asian | M52 or M69 (Group VI) | India |
| M45 or M74 (Groups IX–X) | Global | M122 (Group VII) | E. Asia |
| M173 or M207 (Group IX) | Europe, W. Asia | M119 (Group VII) | E. Asia |
| M269 (Group IX) | W. Europe | M268 (Group VII) | E. Asia |
| M242 (Group X) | C. Asia, India, Americas | M17 or M198 (Group IX) | E. Europe, W. Asia |
| M304 (Group VI) | Med. | M3 (Group X) | N. & S America |

This example demonstrates that by using about 10% of the markers, one can localize any sample to a "neighborhood" or sub-haplotype group in the tree. These markers are useful in identifying a male for which no ethnic origin is known. If it was known that the individual to be typed was for example, from Peking, then the assemblage of a more "Asian" group of markers would be more useful than those in TABLE 4.

The methods of the invention allow for the ability of Y markers to define (on a general geographic or population level) male ethnic affiliation.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

TABLE 1

```
M2 = DYS271 (209 bp) A to G at position 168
aggcactggtcagaatgaagTGAATGGCACACAGGACAAGTCCAGACCCAGGAAGGTCC
AGTAACATGGGAGAAGAACGGAAGGAGTTCTAAAATTCAGGGCTCCCTTGGG
CTCCCCTGTTTAAAAATGTAGGTTTTATTATTATATTTCATTGTTAACAAAAGT
CCRTGAGATCTGTGGAGGATAAAGggggagctgtattttccatt (SEQ ID NO: 1)
For: 5'-3' = aggcactggtcagaatgaag (SEQ ID NO: 2)
Rev 5'-3' = aatggaaaatacagctcccc (SEQ ID NO: 3)

M3 = DYS199 (241 bp) C to T at position 181
taatcagtctcctcccagcaAGTGATATGCAACTGAGATTCCTTATGACACATCTGAACA
CTAGTGGATTTGCTTTGTAGTAGGAACAAGGTACATTCGCGGGATAAATGTG
GCCAAGTTTTATCTGCTGCCAGGGCTTTCAAATAGGTTGACCTGACAATGGGT
CACCTCTGGGACTGAYAATTAGGAAGAGCTGGTACCTAAAATGAAAGATGCc
cttaaatttcagattcacaattt (SEQ ID NO: 4)
For: 5'-3' = taatcagtctcctcccagca (SEQ ID NO: 5)
Rev 5'-3' = aaaattgtgaatctgaaatttaagg (SEQ ID NO: 6)

M4 = DYS234 (273 bp) A to G at position 88
tcctaggttatgattacagagcgAGGATTATTATAATATTGGAATAAAGAATAATTGCTACA
AACTAATGATTAATGATATTCATATRTAATCATATCTAAGATCTATATCTAGT
ATAACTATTCTTATTTTATATATTTTATTGTACTGGAACAGCTTGTGCCCTTGG
TCTCTTGCCTCGGCACCTGGGTGGCTTGCCATCCACAGAAGTGTTTTAACAGC
AAAAATTACTGTGAATTTTCTGCCCAAAAccttgtcatgtttacaagacgt (SEQ ID NO: 7)
For: 5'-3' = tcctaggttatgattacagagcg (SEQ ID NO: 8)
Rev 5'-3' = acgtcttgtaaacatgacaagg (SEQ ID NO: 9)

M5 = DYS214a (322 bp) C to T at position 73
gggtttatactgacctgccaatgttAAAAGGGACCTAAATTCACTTTGGGGAAGTGGCCAGA
AAGGAAGAAGYAGAAGGAGAAGAGTGCAAGAAACCTCCAGTTGTGGGGGTT
GAGCCTCCAGGATAAGAAAGAAAGAAATCTCCAGTAGGGGGGATTGAGCCT
AACACAAACCTTTGGTAATAGACAAGGCAAGACATTTCCAATAGGGGAGATT
GAGTGTCACCTCAAAACTATTAAGATGGGAAATACCCCAGGTAAGATAGAGG
GTAAAAAAGGATAAAGCTAGCAGCAATAACATTCccctgaaagttcccaataa (SEQ ID NO: 10)
For: 5'-3' = gggtttatactgacctgccaatgtt (SEQ ID NO: 11)
Rev 5'-3' = ttattgggaactttcagggg (SEQ ID NO: 12)

DYS214 complete. (656 bp) This fragment was converted into two STSs, a & b,
containing M4 and M16 respectively. The two new STSs (a & b) omit an extra internal
68 bp region within the complete STS.
GggtttatactgacctgccaatgttAAAAGGGACCTAAATTCACTTTGGGGAAGTGGCCAGA
AAGGAAGAAGCAGAAGGAGAAGAGTGCAAGAAACCTCCAGTTGTGGGGGTT
GAGCCTCCAGGATAAGAAAGAAAGAAATCTCCAGTAGGGGGGATTGAGCCT
AACACAAACCTTTGGTAATAGACAAGGCAAGACATTTCCAATAGGGGAGATT
GAGTGTCACCTCAAAACTATTAAGATGGGAAATACCCCAGGTAAGATAGAGG
GTAAAAAAGGATAAAGCTAGCAGCAATAACATTCccctgaaagttcccaataaTTTATG
CTAAAATATTGGAAAGACAACGAAAGGACTAAGCACAAGAGAAAGCAACAG
ATGATAAATATtgttatgtcatttgaacccagGAACCAATCTTCGAACCCTCAGTTTTCTGG
CCAAAGTTGGAGTCAAATGAGGATTGGATTTGTCAGCTTTTAATAGAACATA
```

TABLE 1-continued

```
TGATGACAAAACCTTCATCTCCCAGGAGGAGATAAATTATGCCCTATGTTGGT
GGCAAGGACCTGTCCTCCTTTACCCTCTAAAAACTGGAGGGAGAAAGTCAAA
GACTAACTCCTCTGAAAAAGATAAAGTCCCTATTCCTAgacagcccagcaacacacgg (SEQ ID NO: 13)
For 3'-5' = gggtttatactgacctgccaatgtt (SEQ ID NO: 14)
Rev 5'-3' = ccgtgtgttgctgggctgtc (SEQ ID NO: 15)

M6 = DYS198 (218 bp) T to C at position 37
CactaccacatttctggttggCTTGTAGTTCTTTCTYGGAAAAATATTATTCTAATTTCCTT
ATAGTATTAGCCATCAAAGTAGGGGAAGCAGATCAAATCTACCATAAGACCA
AGTCATAGGAAGAAGATCAAATTAAGATGCTAGGCAAAAGTCTCAGCACATA
TGGATTATGAGAAGCACATTCACACATCCAAActcaaagaatggactcagcg (SEQ ID NO: 16)
For: 5'-3' = cactaccacatttctggttgg (SEQ ID NO: 17)
Rev 5'-3' = cgctgagtccattctttgag (SEQ ID NO: 18)

M7 = DYS253 (300 bp). C to G at position 236
ActgtgagcgagctgaaaatGCCTGATTTTCTCCCTTGGTTTAATGTAAAGGAAGGGATC
CAAAGGCTTAGGGAGATTGGGATGGTGGATTAGTCACTTTAGACCTACTCAT
TCCAATAGGGAGGGTCCAGAAGATGTACCCTTGACCAATGCCTTGCAAAATA
GATTCGTGAGGGCAGCACCTGCATCACCAAAGGGCATGTAATCATTCCTCTCT
GTATGTCAGATCTAACAASAAGAAGAACAGTAACTCAACTACAAAATTTAAA
CACAATGGAAAtaattggttcacaaggctgc (SEQ ID NO: 19)
For: 5'-3' = actgtgagcgagctgaaaat (SEQ ID NO: 20)
Rev 5'-3' = gcagccttgtgaaccaatta (SEQ ID NO: 21)

M8 = DYS263 (267 bp). G to T at position 137
CccacccacttcagtatgaaTTTTGGGATCTGTTACCTATTTTTTGATATAAAATCAACTG
CAAGTTTAGTGCCTCAGTATCACAAACACTGTATTTGCTCATATGTCTGTGAA
TCAATAACTTGGACTGGGTTCAKTTGGGCAGTTCTTCTATTGGTCTTGCCTGG
GGTCTTTAATGCAGCTTCCATTTTCTGGCAGCTTGATGAGACTGGATGGTCTA
AGGTACATTCATGAACACATCTGTTTGgtggacttgtctgtcagcct (SEQ ID NO: 22)
For: 5'-3' = cccacccacttcagtatgaa (SEQ ID NO: 23)
Rev 5'-3' = aggctgacagacaagtccac (SEQ ID NO: 24)

M9 (340 bp) G10.35a C to G substitution at position 68
GcagcatataaaactttcaggACCCTGAAATACAGAACTGCAAAGAAACGGCCTAAGAT
GGTTGAATSCTCTTTATTTTTCTTTAATTTAGACATGTTCAAACGTTCAATGTC
TTACATACTTAGTTATGTAAGTAAGGTAGCGCTTACTTCATTATGCATTTCAA
TACTCAAAAAAAATTCCTTTGTGAAATGTTGAAATATTTTTCTAATCTGTTTC
ACGAGCTTCAAAAATGAGGAAAAAAGATTCAGTTTACATTTCAGCAAAATGC
CTCTTTTTAATCGGATTTATGTTTACTTAACATTTACAGTACATTTACgcttgagcaa
agttaggtttt (SEQ ID NO: 25)
For: 5'-3' = gcagcatataaaactttcagg (SEQ ID NO: 26)
Rev 5'-3' = aaaacctaactttgctcaagc (SEQ ID NO: 27)

M10 = G10.10 (343 bp). T to C at position 156
GcattgctataagttacctgcAATTTATAAAGTTGTGAAATAGTTCAAGACAATGAAGGG
AGAGACTCTCTGGTAACTACAGAGTATGAGCTCATCATTGCTTAGTTTCCACA
AGAGGTATCTCTGAATTTTTTGTTTATTCCCAATGATCTTAYAGCACTTGTA
AAGTTTTTACATTAGTTACAAAATGCAATTTGAAGTGAAAGAAACAGAAATA
CAAAATATTAGTTTCTCTTTTTCTCCTACATTCCTACATGGATTTGTAGAAGAG
CTGACCTTTACTTATAAAATAAATCAGCAAATGAGTGTCTTTTCTAGAATGggg
tgacccaattttttatta (SEQ ID NO: 28)
For 5'-3' = gcattgctataagttacctgc (SEQ ID NO: 29)
Rev 5'-3' = taataaaaattgggtcaccc (SEQ ID NO: 30)

M11 = G10.37 (222 p) A to G at position 44.
TctctctgtctgtctctccctccCTCTCTCCTTGTATTCTAACRGAAAGGTTTAGAACTTGCA
TAATTGGGAAAGAAGCTGTTGCCTGAACTTACTGGGGGATTCAGCATTGTCA
TTTTGGACATGTCACTTATCCTCAGTATTTGCTTCCCCCAGGAGAGAGCTGTA
ATAAAAAAGCATTGCAATTTAATACATAAgctcagtaagttcttgtttatgctc (SEQ ID NO: 31)
For: 5'-3' = tctctctgtctgtctctccctcc (SEQ ID NO: 32)
Rev 5'-3' = gagcataaacaagaacttactgagc (SEQ ID NO: 33)

M12 = DYS260a (309 bp) G to T at position 286
ActaaaacaccattagaaacaaaggACTTAAACTAGGAATTAATTATTTCTCTTTCTCTTTC
CATGGCCAACAAACATTGAAAAAAAATTGCCATCTTTTTTTTATTTGTTTGTT
AGAGATGGGGATCTCACTCTGTTTCTTAGATTGTAGTGCCATGGCACAATAAT
GGCTCACTGCAGCCTCAAACTCCTGGGCTCAAGTGATCACCCCCATACAGAC
TCCCGAGTAGCTGGGAACACAGGCACATGCCACCACCCCTAGCTAATTTTTT
ATTATTTGTAGAKATGggggtcactatgttgctcag (SEQ ID NO: 34)
For: 5'-3' = actaaaacaccattagaaacaaagg (SEQ ID NO: 35)
Rev 5'-3' = ctgagcaacatagtgacccc (SEQ ID NO: 36)

M13 = G10.06 (233 bp) G to C at position 157
TcctaacctggtggtctttcATTGTTTTACAAAGGTGATTTAGTTTTGGGAAGGACTATTC
TCCTTTAAACTATAGACTAAATTTTTCTCAAAGTTAGGTTAGTTTATGCCCAG
GAATGAACAAGGGCAGTAGGTAGGTTAAGGGCAAGACGGTTASATCAGTTCT
CTGTTACTGTTATAATTTTCTCATTGTTATATTTTTTGCAAATGTGgttggataaaatca
tggctca (SEQ ID NO: 37)
```

TABLE 1-continued

For: 5'-3' = tcctaacctggtggtctttc (SEQ ID NO: 38)
Rev 5'-3' = tgagccatgattttatccaac (SEQ ID NO: 39)

M14 = G10.07 (287 bp) T to C at position 180
AgacggttagatcagttctctgTTACTGTTATAATTTTCTCATTGTTATATTTTTTGCAAAT
GTGGTTGGATAAAATCATGGCTCATACAAATATACAAAAAATACATATTAAA
ATTTTATTTAACATAAAACATTAAAATTTATTTAATAAATTATAAATGAAAAA
ATCAGTAACATGYTATAAGCAGTTTAAAAAAGTTAATGAAGCTCAGTTTTAA
CATGAAGTATAGGAATGGTGAAATTATATAAATGAAATTTGTAAATggtgtcaatgt
gcttttatcta (SEQ ID NO: 40)
For: 5'-3' = agacggttagatcagttctctg (SEQ ID NO: 41)
Rev 5'-3' = tagataaaagcacattgacacc (SEQ ID NO: 42)

M15 = G10.16 (295 bp = ancestral state); derived allele = 9 bp insertion (304 bp) after
position 109; Note that there are also two T to G changes immediately before the 9 bp
insertion.
AcaaatcctgaacaatcgcCATCACCTATTTGGTGGACGCATAGGCCTGGTCTCTGATCT
GGTCGCATGTCCAGAGGGTCTGCTAACCCACTGCACCTAGGGAGACA**TTGTA
CAGAGA**CATTGTACCACCTTTTCTCTACTcttcccagactcaacacatttGATTGTATATGC
GCATGAGGTAGAAATATAAGATGAAGCAGGGACAGAGTCAACAAGCCAGAA
CTAGATGCTTCTACCTGGACAGAAGACCTAGAATTCTTTTTTGGATCCTAAAT
TCACCAggaaattttaaccacatgca (SEQ ID NO: 43)
For: 5'-3' = acaaatcctgaacaatcgc (SEQ ID NO: 44)
Rev 5'-3' = tgcatgtggttaaaatttcc (SEQ ID NO: 45)
M15 polymorphic region in more detail
mutant sequence = GACA TT GTACAGAGA CA (SEQ ID NO: 46)
ancestral sequence = GACA GG ********* CA (SEQ ID NO: 47)

M16 = DYS214b (266 bp) C to A
TgttatgtcatttgaacccagGAACCAATCTTCGAACMCTCAGTTTTCTGGCCAAAGTTG
GAGTCAAATGAGGATTGGATTTGTCAGCTTTTAATAGAACATATGATGACAA
AACCTTCATCTCCCAGGAGGAGATAAATTATGCCCTATGTTGGTGGCAAGGA
CCTGTCCTCCTTTACCCTCTAAAAACTGGAGGGAGAAAGTCAAAGACTAACT
CCTCTGAAAAAGATAAAGTCCCTATTCCTAgacagcccagcaacacacgg (SEQ ID NO: 48)
For: 5'-3' = tgttatgtcatttgaacccag (SEQ ID NO: 49)
Rev 5'-3' = ccgtgtgttgctgggctgt (SEQ ID NO: 50)

M17 = G10.47a (333 bp) -1bp deletion (4G's to 3G's) at position 68
CtggtcataacactggaaatcAGATTCTGTCTACTCACCAGAGTTTGTGGTTGCTGGTTGT
TACGGGGTTTTTTTAAGTGAATTTTGGGGTTTGTTAAGTGGCCAAACTATTTT
TGTGAAGACTGTTGTATGTGGGTTTCAGATGTCTCTACATCAGTTTGTGGTCA
GCTAGTGAGTTAAATTTTATGAAAAGCCTGGAGAAACAAGAATAGCAGTAAA
AACTTCCAGTCTTTGTAGATTGGGTGTCTTCAGTGCTTAGCTGGGCAATTTAA
AACTTACCTTAAGTAGTACAGTTGGCCCTTTGTGTCTGTgagtttcacatttgtaggttca (SEQ ID NO: 51)
For: 5'-3' = ctggtcataacactggaaatc (SEQ ID NO: 52)
Rev 5'-3' = tgaacctacaaatgtgaaact (SEQ ID NO: 53)

M18 = G10.47b (333 bp = ancestral size) +2 bp (extra AA) insertion after position 62
CtggtcataacactggaaatcAGATTCTGTCTACTCACCAGAGTTTGTGGTTGCTGGTTGT
TAAACGGGGTTTTTTAAGTGAATTTTGGGGTTTGTTAAGTGGCCAAACTATT
TTTGTGAAGACTGTTGTATGTGGGTTTCAGATGTCTCTACATCAGTTTGTGGT
CAGCTAGTGAGTTAAATTTTATGAAAAGCCTGGAGAAACAAGAATAGCAGTA
AAAACTTCCAGTCTTTGTAGATTGGGTGTCTTCAGTGCTTAGCTGGGCAATTT
AAAACTTACCTTAAGTAGTACAGTTGGCCCTTTGTGTCTGTgagtttcacatttgtaggttc
a (SEQ ID NO: 54)
For: 5'-3' = ctggtcataacactggaaatc (SEQ ID NO: 55)
Rev 5'-3' = tgaacctacaaatgtgaaactc (SEQ ID NO: 56)

M19 = G10.47c (333 bp) T to A at position at 131
ctggtcataacactggaaatcAGATTCTGTCTACTCACCAGAGTTTGTGGTTGCTGGTTGT
TACGGGGTTTTTTAAGTGAATTTTGGGGTTTGTTAAGTGGCCAAACTATTTT
TGTGAAGACTGTTGTAWGTGGGTTTCAGATGTCTCTACATCAGTTTGTGGTC
AGCTAGTGAGTTAAATTTTATGAAAAGCCTGGAGAAACAAGAATAGCAGTAA
AAACTTCCAGTCTTTGTAGATTGGGTGTCTTCAGTGCTTAGCTGGGCAATTTA
AAACTTACCTTAAGTAGTACAGTTGGCCCTTTGTGTCTGTgagtttcacatttgtaggttca (SEQ ID NO: 57)
For: 5'-3' = ctggtcataacactggaaatc (SEQ ID NO: 58)
Rev 5'-3' = tgaacctacaaatgtgaaactc (SEQ ID NO: 59)

M20 = G10.48. (413 bp) A to G at position 118
GattgggtgtcttcagtgctTAGCTGGGCAATTTAAAACTTACCTTAAGTAGTACAGTTGG
CCCTTTGTGTCTGTGAGTTTCACATTTGTAGGTTCAACCAACTGTGGATTGAA
AATRTTTGAAAAATTAAAAATAGATGGTTGCATTTGCACTGAACATGTAGAC
TTTTTTTTCTTGTAATTTCTCTTAAACCATACAGCATAACAACTCTTTACATAG
CATGTACATTGTATTAGGTATTCTGAGTACTCTAAAGTATACGGGAGGATGTG
TGTAGGTTATGTGCAAATACTATAACATTATATGTAAGGGATTTGAAAATTCT
GGGATTTTGGTATTTGCAGGTGGTGTGGGATGGGGGTCTGCCTGGAACCAAG
GAATGCCCCAAAGGAGgatggtgccttgttgtgtg (SEQ ID NO: 60)
For: 5'-3' = gattgggtgtcttcagtgct (SEQ ID NO: 61)
Rev 5'-3' = cacacaacaaggcaccat (SEQ ID NO: 62)

TABLE 1-continued

M21 = G10.43 (415 bp) A to T at position 357
CttttatttctgactacagggCCCTCTTTTGCATTGTTTTTGTAGGTCAGATTTATTAGTAGT
ATGTTCTTTCAGCTTTTGTGTATCTGGGAATATTTCAGTTTCTCCTTTATTTTG
AAGGATAGTCTTTGAGTTTTTCCTACTTAACAGATCCTGGAGCTTCTTGGATG
TGTAAATTAATGATTTTCATCAAATGTGAAGTTGTTTTCGGCTATTCTGCAGA
TATCCTTTACCACCCCTTTGCTGCCTCTTCCTATTGTGGGTAATAGGCATGTCT
CTGTATGTTGGAGAGAATCAAAGGTCTTTTAAGCCCTTGATTTTTATTTATCTT
TTGTTTTTTGTTCCTCAGACTGTATWGTTTCAGTTGACTTAGCTTCCAGTTTGT
TGATTCTTCTGcctgctcaaatctgctgtt (SEQ ID NO: 63)
For: 5'-3' = cttttatttctgactacaggg (SEQ ID NO: 64)
Rev 5'-3' = aacagcagatttgagcagg (SEQ ID NO: 65)

M22 = DYS273 (327 bp) A to G at position 129.
AgaagggtctgaaagcaggtTCGTGATTTCACCCTTTACAGTTTAATACAAGGGATTTTA
CATACAGACATATAAGCTGATAGTCCTGGTTTCCCTATTTGTTTTAAGGTGCC
ATTCCTGGTGGCTCTRCCTCCTTCCCCCAGTGCCCATATGGGCCCTTAGTCTG
CTGTAGGCATGCTCAGGCAAGCCCTTGAGCAAATTCCCTTAATCTGCACGAA
ACATGGGCTGGAGATTCAGTGGGACCCTTTCTTTAGTGTCTGCCTAATGCAAG
CTGGCTAACTCCTTTCAAAAGTTTTGTCTTGCTGATgaagcctccaggtagtaggc (SEQ ID NO: 66)
For: 5'-3' = agaagggtctgaaagcaggt (SEQ ID NO: 67)
Rev 5'-3' = gcctactacctggaggctt (SEQ ID NO: 68)

M23 = G10.57a (327 bp) A to G at position 159
TctctaacttctgtgagccacTCTAGCAAATTAATTGAACCAAAGGAGGAGGTTAAGGAC
AGCATAGTTTACAAAATGAGCCCTGTTTCTGACATCTGAAGTGGGGGCAGTC
TAGTGGGCCTGACCTCTTAACTTGTAGAAACATTCTTTCTTTCTAGRTGACTA
GTGACCAGAATTAAATTGAATCCTAGGCCACCCATTTATTGTCTTCTGCAGAA
TTGGCGAGAATGGAGAGGAATCCTCACCTATCGGTGACCAGAGATGAAATAT
TCTGAATTGAGAGTTTAAAAGAGCACACTTAGAagagatttagagtttagttttttcc (SEQ ID NO: 69)
For: 5'-3' = tctctaacttctgtgagccac (SEQ ID NO: 70)
Rev 5'-3' = ggaaaaactaaactctaaatctct (SEQ ID NO: 71)

M24 (tetranucleotide TAAA motif) = SRY 8299c. Internal primer regions for SRY4064
which contain M40 and M41.
AcagcacattagctggtatgacAGGGGAGATGTGATTAATTGACCTACTGATAAGACTCA
TTTCAGTAAATGCCACACAAGAATgtataataggctgggtgctgTGGGTCACACCTGTAA
TCCCAGCCCTTCGAGAGGTCAAGGCGAGCGGATCACAGGGTGGAAGAGATT
GAGACCATCCTGGCCAACATGGTGAAACTGGGTCTCTACTAAAAATACAAAA
AATTAGCTGGGCGTGGTGACATGTGCCTGTAATCCCAGTTACTCGGGAGGCT
GAGGCAGAagaatcatttgaactcatgAGGCAGAGGTTGCAGTAAGCTGAGATTGCGCCG
CTGCACCCCAGCCTGGCAACAGAGCGAGACTTTGTCTCAAAAAAAAAWAAAT
AAATAAATAAATAAACAATAATAAAAAAAGCGTAATAGCTAGCCTATC
CTACCCTATATTCTAAAATTCAAAAGTAATGGTTTTTGTTATGAAATCTcgtaagt
cttgccataaagaga (SEQ ID NO: 72)
For: 5'-3' = acagcacattagctggtatgac (SEQ ID NO: 73)
Rev 5'-3' = tctctttatggcaagacttacg (SEQ ID NO: 74)

M25 = B9.008b. (340 bp) G to C substitution. Position 121
AaagcgagagattcaatccagGATGACAGAATGCGTTCACCTTTAAAGGGATTAAAAGA
AGTATAATACAGTCTGTATTATTAGATCACCCAGAGACACACAAAACAAGAA
CCGTGAATTSAATTAGTGGTATACTAATAGAGTGGTTTTACCTGAAATATTTA
CACATCAATCCTACTGAATTCTTACAACAAATGATTTAGATTAGCTATTGTAT
TCACCAGTTGAAAGAACAGAAAATATTGAGGGAGATAACTTGTGTCAGTGCA
ACTTAATCAGATTTAGGACACAAAAGCAACTACATAATGAAAAAGAGAgctggt
gacttaacttgctaaaa (SEQ ID NO: 75)
For: 5'-3' = aaagcgagagattcaatccag (SEQ ID NO: 76)
Rev 5'-3' = ttttagcaagttaagtcaccagc (SEQ ID NO: 77)

M26 = B9.005 (321 bp) G to A at position 68
CcagtggtaaagttttattacaatttTTTTAAACCAAGATTCAATTTTTTTCTGAATTAGAATT
ATCRCAGAGAACACTGAATGGCCTATGAAATTCAATTTTTGCTGCAGATTTC
GTCATGTTTCTTAATGAACATATAACTAACTTCTAATCACAAGATAAATTCTT
GCCTATGTGCAAAAACTTAGTGCTGCATCCTTGTGTATGGTTTTAAAAAGTGT
CAAAACTGGCCCCTCATGTCAAATACAGCCCCAATTAGGGGAGGCAACCTAA
GAAAGGTGTACAACTGTCCTGACATTGgattgcctgcttactgtgaa (SEQ ID NO: 78)
For: 5'-3' = ccagtggtaaagttttattacaattt (SEQ ID NO: 79)
Rev 5'-3' = ttcacagtaagcaggcaatcc (SEQ ID NO: 80)

M27 = G10.65. (526 bp). C to G at position 398.
CggaagtcaaagttatagttactggAAATACAAACTGTGGCAGTAGAAAACCCTAGGCACA
AGGGAAGTAAAATATTAACCACTCCAGGCTGGAGTGCAGTGGCGCAATCTGG
GCTCACAGCAAGCTCTGCCTCCTGGGTTCACACCATTCTCCTGCCTCAGGCTC
CCGAGTAGCAGGGAGTACAGGCACCCGCCACCAGGCCTGGCTAGTTTTTTTTT
GTATTTTTTAGTAGAGATGGGGTTTTACTGTGTTAGCCAGTATGGCCTCGATT
TCCTGACCTCGTGATCCGCCCACGTCAGCCTCCTAAAGTGTGGGGATTACAG
GAGTGAGCCACCATGCCCAGCTGAAACAATAGTTCTTCACAATGGCATCTAC
CACTATGTCCACATTTGCACCTSTGTCCTGAACCTCGATTCCTATAGGTTGAT
GTGTTGAGAACCAGACAATACGAAATAGAAGACAAATCATGAGCTTACAGA
ACCTGAAACTTTTTACACTGGGCAGtgtggtagacagaacagcagtg (SEQ ID NO: 81)

TABLE 1-continued

For: 5'-3' = cggaagtcaaagttatagttactgg (SEQ ID NO: 82)
Rev 5'-3' = cactgctgttctgtctaccaca (SEQ ID NO: 83)

M28 = G10.33n (332 bp). T to G at position 277.
GcttacttgggacacaggctAGTTCTCTCCTGAAGCTATTGAGCAGTATGTGTTGAGGTG
CGCTACGCCAGTTGAGGTGAAGCTGTTACACAGTATGAAAGCCGGGCTTTGT
AGCTGCAGCTGCGCATTGCACCCCCAGCTACGCAGTCTCCTTTCCTTCTCAGT
CACAGGACCGGATGGCAAGTGGCCGCAGCCAGTCGGTGAGACCGACTGAGC
TCTGGGGCTTCAGTTCTTGACGCTACCTACATGGCTACATCTCCAGCCAAGGA
TGAGAGGKGATGCCAGAGGACCTCGATCTAAATTGGGCAccattatcgtatgacaacttct
ct (SEQ ID NO: 84)
For: 5'-3' = gcttacttgggacacaggct (SEQ ID NO: 85)
Rev 5'-3' = agagaagttgtcatacgataatgg (SEQ ID NO: 86)

M30 = G10.66 a (486 bp) G to A at position 132.
GaaccagacaatacgaaatagaagACAAATCATGAGCTTACAGAACCTGAAACTTTTTACA
CTGGGCAGTGTGGTAGACAGAACAGCAGTGGCTGCCCAAAGATGATCATGTT
TTAAGTCCTGACATCTGTRAATTATCATATTGGGAAAAGGTGTTATTGTAGAT
GTTGTTTAAAGTTAGGATTTTGAGAGAGGAAAATTATGTAGGGTTATCTGGCT
GTGCCCAGTGAAATCACAAGAATCTTTATAAATGAAAAAAGAAAGCAGAAG
AATCAGAACCAGAGACACGGCATTATGCATAGGACTGGACTTGTCATTACTA
GTTTTAAAGGTAGAGGAAGCAGAGATCTAAGAAATGCAGGCAGCCTCTAACT
AATGTTAACAAATCTCATTTTCTAATATTGTAAGCCTGTGGAAGAGGCTAGGG
CACAGATGCTCCCATAGAGTCTCCAGAAGGAACCTAAggtaatgagataagccgctaaa (SEQ ID NO: 87)
For: 5'-3' = gaaccagacaatacgaaatagaag (SEQ ID NO: 88)
Rev 5'-3' = tttagcggcttatctcattacc (SEQ ID NO: 89)

M31 = G10.66 b (486 bp) G to C at position 71.
GaaccagacaatacgaaatagaagACAAATCATGAGCTTACAGAACCTGAAACTTTTTACA
CTGGGCAGTSTGGTAGACAGAACAGCAGTGGCTGCCCAAAGATGATCATGTT
TTAAGTCCTGACATCTGTGAATTATCATATTGGGAAAAGGTGTTATTGTAGAT
GTTGTTTAAAGTTAGGATTTTGAGAGAGGAAAATTATGTAGGGTTATCTGGCT
GTGCCCAGTGAAATCACAAGAATCTTTATAAATGAAAAAAGAAAGCAGAAG
AATCAGAACCAGAGACACGGCATTATGCATAGGACTGGACTTGTCATTACTA
GTTTTAAAGGTAGAGGAAGCAGAGATCTAAGAAATGCAGGCAGCCTCTAACT
AATGTTAACAAATCTCATTTTCTAATATTGTAAGCCTGTGGAAGAGGCTAGGG
CACAGATGCTCCCATAGAGTCTCCAGAAGGAACCTAAggtaatgagataagccgctaaa (SEQ ID NO: 90)
For: 5'-3' = gaaccagacaatacgaaatagaag (SEQ ID NO: 91)
Rev 5'-3' = tttagcggcttatctcattacc (SEQ ID NO: 92)

M32 = G10.68a (370 bp) T to C at position 166.
TtgaaaaaatacagtggaacAAAGATCCTCTGTATCTCTGCTCCTAAGATAGCAGAGACA
GCatactggcttctgttcaattttcCTTTGATTACACAACTTCATTGGCTACGGTGTTTAATAT
GACCGTCATAGGCTGAGACAAGATCTGTTCAGTTTATCTCAYAAGTTACTAG
TTAAATCTCAGACATATTATACTTTTGTAACTGAGTGACTCCCATTGTAAGGA
TAACTACTTCAATGTGCGTATAAATGAGTCAGTTGTCTCTCTTGGGGGCTTCA
ACAAATAAGCAAAGATAACCTCATTGTGGAGAGCACTTCACATTTGTTTTTAG
GGTTACATAGTCTActctgtatccttaaacacttgC (SEQ ID NO: 93)
For: 5'-3' = ttgaaaaaatacagtggaac (SEQ ID NO: 94)
NewF 5'-3' = atactggcttctgttcaattttc (SEQ ID NO: 95)
Rev 5'-3' = caagtgtttaaggatacaga (SEQ ID NO: 96)

M33 = G10.68b (370 bp) A to C at position 180.
TtgaaaaaatacagtggaacAAAGATCCTCTGTATCTCTGCTCCTAAGATAGCAGAGACA
GCatactggcttctgttcaattttcCTTTGATTACACAACTTCATTGGCTACGGTGTTTAATAT
GACCGTCATAGGCTGAGACAAGATCTGTTCAGTTTATCTCATAAGTTACTAGT
TAMATCTCAGACATATTATACTTTTGTAACTGAGTGACTCCCATTGTAAGGA
TAACTACTTCAATGTGCGTATAAATGAGTCAGTTGTCTCTCTTGGGGGCTTCA
ACAAATAAGCAAAGATAACCTCATTGTGGAGAGCACTTCACATTTGTTTTTAG
GGTTACATAGTCTActctgtatccttaaacacttg (SEQ ID NO: 97)
For: 5'-3' = ttgaaaaaatacagtggaac (SEQ ID NO: 98)
New F 5'-3' = atactggcttctgttcaattttc (SEQ ID NO: 99)
Rev 5'-3' = caagtgtttaaggatacaga (SEQ ID NO: 100)

M34 = G10.69 (372 bp) G to T at position 131
CacttcacatttgtttttaggGTTACATAGTCTACTCTGTATCCTTAAACACTTGAAGATCT
GTTATAACTACATCTGAGATAGTAGTCACAGTGTTTTCTCATGTTAATGCCTG
GCTTCCACCCAGGAGKCACATGTGGTGTGTCTGCAAATAAAGTGTTTATGAT
TATTGGGGTCCCCCAAGCTGGACCTGTATCCATGTTCAAGTGGCCACAGGGTT
ACTTGCTTTAGCATGGCTCCTTGGCTGGCTGTTAAGTGAATAATTAAACTGAG
TCTTTTTTGCAGGAGCTAACTGAGACCAATCAATCAGTCAATTTTCCCTTTCT
GTGTGTAACACAAGCTGGATGTCCctggaatgactaaataatgact (SEQ ID NO: 101)
For 3'-5' = cacttcacatttgttttagg (SEQ ID NO: 102)
Rev 5'-3' = agtcattatttagtcattccag (SEQ ID NO: 103)

M35 = G10.72a (514 bp) G to C at position 168
TaagcctaaagagcagtcagagTAGAATGCTGAATTTTCAGAAGTTTTATATTAACATAA
TCATTCATCTTTTTTGTCCTGATAATTACTCAGGAGGAAACTGAGAGGGCATG
GTCCCTTTCTATGGATAGCAATACTCAGTGTCCCAATTTTCCTTTGGGACACT TABLE 1-continued

```
GSGACACAGGCAGAGACTCCGAAAGTCTGCATGGATTAGTTGTTCATTCACC
ACAGCTCCTTAGTGTGCCAGGAGAACTATATATGGCCTTTGGTTTCATTCAGG
GACAGGGAAACTTGAACCCATGCCTATTCATTCTCATTAAAGTAGCAGAAGT
CATGTTAGAGACAGTATTGCTGCATTCAGTACTCCTGCCTTTAACGCTTCTGA
CGCTTCCTGAAAGCAGCCCCAGCTCTCCATATGGCAAAACAAAGGCAACCTT
ATGCAAAGCCTTCTCAGGGAACCCTCAGAAAGGTTTAAACTTAGGTTCACAG
TTTTTAGAGAATAAtgtcctcattgctccctctg (SEQ ID NO: 104)
For: 5'-3' = taagcctaaagagcagtcagag (SEQ ID NO: 105)
Rev 5'-3' = cagagggagcaatgaggaca (SEQ ID NO: 106)
```

M36 = G10.82a (436 bp) T to G at position 74
```
AgatcatcccaaaacaatcataaCTTGTTTAAATTGTTCATAGCAAAAGTTACATATTATA
AAGAGTTATGAGKGTCTTAGGCAGTGAATAGTAACTGAATATCCTTTTATAG
TTGTCCTTCACTAGCAGGAAGCCTTATTCCCTGCCCTTTTACATATCTTAACTT
AGAATGTTACTGTCTAAATAGTGGTTAGGCAAGAGTAGTTCTTAAACGTGCA
GTAATTATCTTGCACTACATTTAAGGGCTAAATAGCTAGTAGTGGTGCTTGAT
AATTGAAGAAATTTGTACAGCTGGAGGAAGTACCTGCTAAATTTTCAAAAGT
TACCTGAATTTAATAGGTAAATCTGTTTTTAATTAGAGCTATATCATTTTACTC
TGAATGTCTTAACATAGAAGTTTACATAAAATTTAcagattggattgatttcagccett (SEQ ID NO: 107)
For: 5'-3' = agatcatcccaaaacaatcataa (SEQ ID NO: 108)
Rev 5'-3' = aaggctgaaatcaatccaatctg (SEQ ID NO: 109)
```

M37 = G10.STS 84 (422 bp) C to T at position 203. This STS also contains M61 at position 101 which is defined in G10.83.
```
CagattggattgatttcagccttCTTCTGGTACTTTTTAAAATCTTATTAATCATTAGGAAAA
GAAGTTTTATTATTGATGCAAGCCCTAAACACTCTTTCGACTCCAGAGGAGAA
GCTGGCAGCTCTCTGTAAGAAATATGCTGATCTTGTGAGTATTTATTTAATGG
AGCAAGGAACACAGAAAATAAAATCTATGTGTGYTTGATAAGATTTTTAAAT
ATTATTTTGATGTAACTTTAAATGTAAAATGATATTTTATCTCAAAATTGAAA
ACAATCTCCTTTCTTTAGTACTTATGATTGGTGTGTGTGACTTCATCTTATGAA
ATGATGTATAGAACATAATAATACTTTTTTAAATGTGAAATAAATTTCCTAAA
ACTTAATATGCTAGATCAgcagttttttttttttgtatgct (SEQ ID NO: 110)
For: 5'-3' = cagattggattgatttcagcctt (SEQ ID NO: 111)
Rev 5'-3' = agcatacaaaaaaaaaaactgc (SEQ ID NO: 112)
```

M38 = G10.73a (337 bp) T to G at position 146
```
CagtttttagagaataatgtcctCATTGCTCCCTCTGGCACTAGCAGTTTGTACCAGGAGAT
CTGTTGGCTACTGTTACCCTAGGGTATGGCAATGGTATGTAGGCAATGAAAA
ATCTTACAGTACTTATTATGGAAAACCAACTKTTTTATTCAGTAAGCATTCCC
CTGTGTTGTAAGGTTTTTAAAAGATTGTGGAAGTATGAAAAAGTTTATTATGA
CAGATGTGCCAGCTCCAGCTGTTTTGTGGAGAGTGACCCTTGGATTTTCGTAT
GCCCCCATTATATGATGATACCTTGTAATGATTTAATTTTAGcatctgcttttcttttcttttaa (SEQ ID NO: 113)
For: 5'-3' = cagtttttagagaataatgtcct (SEQ ID NO: 114)
Rev 5'-3' = ttaaagaaaagaaaagcagatg (SEQ ID NO: 115)
```

M39 = G10.73a (337 bp) −1 bp (−C) deletion at position 236
```
CagtttttagagaataatgtcctCATTGCTCCCTCTGGCACTAGCAGTTTGTACCAGGAGAT
CTGTTGGCTACTGTTACCCTAGGGTATGGCAATGGTATGTAGGCAATGAAAA
ATCTTACAGTACTTATTATGGAAAACCAACTTTTTTATTCAGTAAGCATTCCC
CTGTGTTGTAAGGTTTTTAAAAGATTGTGGAAGTATGAAAAAGTTTATTATGA
CAGATGTGCCAGCTCCAGCTGTTTTGTGGAGAGTGACCCTTGGATTTTCGTAT
GCCCCCATTATATGATGATACCTTGTAATGATTTAATTTTAGcatctgcttttcttttcttttaa (SEQ ID NO: 116)
For: 5'-3' = cagtttttagagaataatgtcct (SEQ ID NO: 117)
Rev 5'-3' = ttaaagaaaagaaaagcagatg (SEQ ID NO: 118)
```

M41 = SRY 4064b (218 bp) G to T at position 117. Site is located within SRY 8299 509 bp STS.
```
GtataataggctgggtgctgTGGGTCACACCTGTAATCCCAGCCCTTCGAGAGGTCAAGG
CAAGCGGATCACAGGGTGGAAGAGATTGAGACCATCCTGGCCAACATGGTG
AAACTKGGTCTCTACTAAAAATACAAAAAATTAGCTGGGCGTGGTGACATGT
GCCTGTAATCCCAGTTACTCGGGAGGCTGAGGCAGaagaatcatttgaactcatg (SEQ ID NO: 119)
For: 5'-3' = gtataataggctgggtgctg (SEQ ID NO: 120)
Rev 5'-3' = catgagttcaaatgattctt (SEQ ID NO: 121)
```

M42 = B9.008a (340 bp) A to T substitution at position 297
```
AaagcgagagattcaatccagGATGACAGAATGCGTTCACCTTTAAAGGGATTAAAAGA
AGTATAATACAGTCTGTATTATTAGATCACCCAGAGACACACAAAACAAGAA
CCGTGAATTGAATTAGTGGTATACTAATAGAGTGGTTTTACCTGAAATATTTA
CACATCAATCCTACTGAATTCTTACAACAAATGATTTAGATTAGCTATTGTAT
TCACCAGTTGAAAGAACAGAAAATATTGAGGGAGATAACTTGTGTCAGTGCA
ACTTAATCAGATTTAGGACACAAAAGCWACTACATAATGAAAAAGAGAgctgg
tgacttaacttgctaaaa (SEQ ID NO: 122)
For: 5'-3' = aaagcgagagattcaatccag (SEQ ID NO: 123)
Rev 5'-3' = ttttagcaagttaagtcaccagc (SEQ ID NO: 124)
```

M43 = DYS260b (309 bp) A to G at position 77
```
ActaaaacaccattagaaacaaaggACTTAAACTAGGAATTAATTATTTCTCTTTCTCTTTC
CATGGCCAACAAACRTTGAAAAAAAATTGCCATCTTTTTTTTTATTTGTTTGT
TAGAGATGGGGATCTCACTCTGTTTCTTAGATTGTAGTGCCATGGCACAATAA
```

TABLE 1-continued

```
TGGCTCACTGCAGCCTCAAACTCCTGGGCTCAAGTGATCACCCCCATACAGA
CTCCCGAGTAGCTGGGAACACAGGCACATGCCACCACCCCTAGCTAATTTTTT
ATTATTTGTAGAGATGggggtcactatgttgctcag (SEQ ID NO: 125)
For: 5'-3' = actaaaacaccattagaaacaaagg (SEQ ID NO: 126)
Rev 5'-3' = ctgagcaacatagtgacccc (SEQ ID NO: 127)
```

M44 = G10.87 (389 bp) G to C at position 263
```
CtggcaccttctgatattttgagAAGCAGGAATCCCTGAGCATAAATGTAAATAGCTTAGA
ACTGTCCAAAAGCAAAGACAGCAGAAAATAAAATTGTTGCTTGCTATGTTCA
GGAAAGGAATGCTTCCATTGGATATGGAAGCCAGTCTCAATTGTTACATCAG
CCTGAGGAAACTCATGCGAGAAATGCCAGAAAAAGAAGACAGCAACAAAGA
AGATAAAAGAAAGACTGACAAAAGCATTGAATTTCTGGTAGAAAAASCAGT
GTACTAGAAGGTTAGGAGATTTCCTAGCTGTCAGCCATGAAAGGGTTGGGGA
AGAAAGAGCAATTTGGTTGCATACTGTAGCATGGTCATCTAGGGTGgtcctcaaac
acatagaaatcaca (SEQ ID NO: 128)
For: 5'-3' = ctggcaccttctgatattttgag (SEQ ID NO: 129)
Rev 5'-3' = tgtgatttctatgtgtttgaggac (SEQ ID NO: 130)
```

M45 = B9.12(352 bp) G to A substitution at position 109
```
GctggcaagacacttctgagCATCGGGGTGTGGACTTTACGAACCAACCTTTTAACAGTA
ACTCTAGGAGAGAGGATATCAAAAATTGGCAGTGAAAAATTATAGATARGC
AAAAAGCTCCTTCTGAGGTCCAGGCCAGGAGATAGTAGGATTTAAGAAACAA
ACAAACAAAAACAACCACAAATGACCTTTGGTGCCACTGTCACAACTGTTGC
TCATCAGAGTAGGAGAGTTGTAGCAAAGGCATTAAAGAAGGACAAGCAGCT
GAAGAGCCTGAATCCTTGTGTTGTAAGCTATTTTGGTTTCCTTTCAAGAAAGG
GCTGTGGTCTGTggaaggtgtcaggaacatatt (SEQ ID NO: 131)
For: 5'-3' = gctggcaagacacttctgag (SEQ ID NO: 132)
Rev 5'-3' = aatatgttcctgacaccttcc (SEQ ID NO: 133)
```

M47 = G10.82b (436 bp) G to A at position 395
```
AgatcatcccaaaacactcataaCTTGTTTAAATTGTTCATAGCAAAAGTTACATATTATA
AAGAGTTATGAGTGTCTTAGGCAGTGAATAGTAACTGAATATCCTTTTATAGT
TGTCCTTCACTAGCAGGAAGCCTTATTCCCTGCCCTTTTACATATCTTAACTTA
GAATGTTACTGTCTAAATAGTGGTTAGGCAAGAGTAGTTCTTAAACGTGCAG
TAATTATCTTGCACTACATTTAAGGGCTAAATAGCTAGTAGTGGTGCTTGATA
ATTGAAGAAATTTGTACAGCTGGAGGAAGTACCTGCTAAATTTTCAAAAGTT
ACCTGAATTTAATAGGTAAATCTGTTTTTAATTAGAGCTATATCATTTTACTCT
GAATGTCTTAACATARAAGTTTACATAAAATTTAcagattggattgatttcagcctt (SEQ ID NO: 134)
For 5'-3' = agatcatcccaaaacaatcataa (SEQ ID NO: 135)
Rev 5'-3' = aaggctgaaatcaatccaatctg (SEQ ID NO: 136)
```

M48 = G10.79n (240 bp). A to G at position 160
```
AaacaatatgtatgctaattttgctTAAAAGATTATACACTGAAATTTAGAGAGGATATAATG
TTATCTGTAGTGTAGAAAGAGTTAAATAAGACTGATTTTTAGAATTTGTTTTA
TCCCTTCCACTCTTAGCTTGACAATTAGGATTAAGAATATGATRTGTCAAATT
TCATGACTGAAATCTGAAATGCCTTAATAGTTGCCCTCAGTGTTTcatccttatactaa
catttacattga (SEQ ID NO: 137)
For: 5'-3' = aaacaatatgtatgctaattttgct (SEQ ID NO: 138)
Rev 5'-3' = tcaatgtaaatgttagtataaggatg (SEQ ID NO: 139)
```

M49 = B9.15new a (354 bp) T to C at position 229
```
CggcaacagtgaggacagtAGCTCCAGGTCTGGGCGGAAGGTGGTGCGGTGAAAGGTG
CAGGGACAGACTGGGTTAGAGGCCACTCTTGGTCTTATCCTCCATGGCCACA
ACAGAGGTGACAAATACATGGGTCACTCAGTTATGTTTAGCCAACAGCCTAC
CCAAACCACACCTGTCTTACCAGAGCCCTTTCCTGGAGCCATGTTCTCAGGAC
TGGTCACACTGTCYCCATTCTCCAGCAGCCCTTGGACCTATCGGAAAAAAAG
AATGGGTAACAATAATTGAGCTGATGAACCAGGTCCTATCTTTCCTCCCACAA
CTCCAAAACTTGGgagcctctatctcctgaagca (SEQ ID NO: 140)
For 5'-3' = cggcaacagtgaggacagt (SEQ ID NO: 141)
Rev 5'-3' = tgcttcaggagatagaggctc (SEQ ID NO: 142)
```

M50 = B9.15new b (354 bp) T to C at position 175
```
CggcaacagtgaggacagtAGCTCCAGGTCTGGGCGGAAGGTGGTGCGGTGAAAGGTG
CAGGGACAGACTGGGTTAGAGGCCACTCTTGGTCTTATCCTCCATGGCCACA
ACAGAGGTGACAAATACATGGGTCACTCAGTTATGTTTAGCCAACAGCCTAC
CCAAACCACACCYGTCTTACCAGAGCCCTTTCCTGGAGCCATGTTCTCAGGA
CTGGTCACACTGTCTCCATTCTCCAGCAGCCCTTGGACCTATCGGAAAAAAA
GAATGGGTAACAATAATTGAGCTGATGAACCAGGTCCTATCTTTCCTCCCACA
ACTCCAAAACTTGGgagcctctatctcctgaagca (SEQ ID NO: 143)
For: 5'-3' = cggcaacagtgaggacagt (SEQ ID NO: 144)
Rev 5'-3' = tgcttcaggagatagaggctc (SEQ ID NO: 145)
```

M51 = B9.16 (339 bp) G to A at position 33
```
GagcctctatctcctgaagcAGAGTAGACACARGCTTCCAACAGGGATCAGAGTTTAGG
GATCTGGATAGGTATAGAATGGAGCAAAGGGACTAGGCCAAAGGAGATTGA
AAACTGGGGAACAGGGACAAGACTGGAGCTACAAGAAGGACAGGGGCTAGA
AGACAGAAATATGAGGACAATGGCTGGCCTGGAAAGCTCACCTTAGAAATAT
TGTTGCCACTGCCTTCTCTGATAGGGTCACAGGCAGTGGCTGAAGTGTAGACT
GAGGCCTCCTCTGGTCTGGGTTTGGCCTGTAGCTGTTGGCGAAGCTCAGCCAG
```

Ctgtcgcaacagagcagtca (SEQ ID NO: 146)
For: 5'-3' = gagcctctatctcctgaagc (SEQ ID NO: 147)
Rev 5'-3' = tgactgctctgttgcgaca (SEQ ID NO: 148)

M52 = G10.88 (534 bp) A to C at position 477
ActgtagcatggtcatctagggtgGTCCTCAAACACATAGAAATCACACAAGAATTGTCAA
ATTGAAGATTTGGATTTAGTAGATCTGAAAACGCACTTTGTAAAATTGGCCAC
AGTAGAGGTGGAAGTGACTGAAATACTGCATTATTTATTTATTTAATTAATTT
ATTTTAGTCAGAGTCTTGCACTGTCGCTAAGGCTGGTATACCATGGTTCAGTC
ACAGTTCACTACAGTCTTGAACTCCTAGGCTCAAACAATTCTCCTGTATCGGC
CTCCTGAGTACCTGGCACTACAGACATGCACAAGCATGCATGGCTAATTTTA
AAAAAATTTTTGTAGAAATGGAGTCATGAACTCCTGGGCTCAAGTGATCCTC
CCACCTCAACTTCCCAGAGTGTTGAGTGAGATTACAGTTATGAGCCACCATCC
CTGGCCAATAAAGGTGTTTTTAATACCTATAAGAATATTGCCTGCAMGGATG
TTTGATAGGTTTCTTGATATTTCATTCTctctcttgaaatgtttgcttcgtc (SEQ ID NO: 149)
For: 5'-3' = actgtagcatggtcatctagggtg (SEQ ID NO: 150)
Rev 5'-3' = gacgaagcaaacatttcaagagag (SEQ ID NO: 151)

M53 in tree (tetranucleotide TAAA motif) = SRY 8299d. Internal primer regions for
SRY4064 which contain M40 and M41.
AcagcacattagctggtatgacAGGGGAGATGTGATTAATTGACCTACTGATAAGACTCA
TTTCAGTAAATGCCACACAAGAATgtataataggctgggtgctgTGGGTCACACCTGTAA
TCCCAGCCCTTCGAGAGGTCAAGGCGAGCGGATCACAGGGTGGAAGAGATT
GAGACCATCCTGGCCAACATGGTGAAACTGGGTCTCTACTAAAAATACAAAA
AATTAGCTGGGCGTGGTGACATGTGCCTGTAATCCCAGTTACTCGGGAGGCT
GAGGCAGAagaatcatttgaactcatgAGGCAGAGGTTGCAGTAAGCTGAGATTGCGCCG
CTGCACCCCAGCCTGGCAACAGAGCGAGACTTTGTCTCAAAAAAAATAAAW
AAATAAATAAATAAATAAACAATAATAAAAAAAAGCGTAATAGCTAGCCTATC
CTACCCTATATTCTAAAATTCAAAAGTAATGGTTTTTGTTATGAAATCTcgtaagt
cttgccataaagaga (SEQ ID NO: 152)
For: 5'-3' = acagcacattagctggtatgac (SEQ ID NO: 153)
Rev 5'-3' = tctctttatggcaagacttacg (SEQ ID NO: 154)

M54 = B9.17 (360 bp) G to A at position 164
CctcctctggtctgggtttGGCCTGTAGCTGTTGGCGAAGCTCAGCCAGCTGTCGCAACA
GAGCAGTCACATCTTCAGAGGCCAGAGCCTTTCTGGCACGGTCTTGCCAGCC
AATGGCCCTCTCTGTGAGACACTGAAGGGCCTCACCCTCAGGCAGCCGCACR
GGCAGCCTCTGCAGGGCAACCAGCAAGGCTAGGATTGTCTCTAGGCGTGGCC
GTCGTGAGCGCATACACAGTGGACACAGGAATTTTGTGTCCCATTCCCACCA
GGCTAGCAGTGGAGATGAAGTGAGACTGGGCTTTGGAGAGGTGAGGAGATG
GGGCACTGACACACACTGCCCatgaaccagtcctgacaca (SEQ ID NO: 155)
For: 5'-3' = cctcctctggtctgggttt (SEQ ID NO: 156)
Rev 5'-3' = tgtgtcaggactggttccat (SEQ ID NO: 157)

M55 = B9.28 (382 bp) T to C at position 228
CgtaggcgtttgacagcagTTAATAGAGACTACAGATATCAAAGTCAGAGAGTCCAGCT
TCCTGAGAAAACGTTAACAGTATTAATCTGCTACCACTATGGCTACTAATACC
ATGCCACCACGGTACTACCTGGCTAGTACCATTCCACAGAAGAACAGAAATA
AATACAAATAGGTGGGGCAAGAGAAAAGAAACATGTGAAAAGGCCCCTGGA
TGGTTTAAGTTAYATTTTCATCAGTCATCCAGTTAAGAGTTAAAGAATGAGG
AAGAGATGTAAAAACAGCCATTAGGATTCAGAAGTAGTAGCTTTCACAGTGA
GACAAAACATCTATTAAGCCAGAAACTGAAGTACAAATGCAATgggaggattacgaa
gaaaagg (SEQ ID NO: 158)
For: 5'-3' = cgtaggcgtttgacagcag (SEQ ID NO: 159)
Rev 5'-3' = cctttcttcgtaatcctccc (SEQ ID NO: 160)

M56 = B9.29 (399 bp) A to T at position 39
CcagaaactgaagtacaaatgcAATGGGAGGATTACGAWGAAAGGAGGGCTAAGTGAT
GATAAGTATGGTCAGAATAATAAATTTATTCTAGACAAGAAATGAGAGTTCA
TTATGTCAGAAGCAAATAGTACTACAGGATGACAACTTCTGAGATTTACTCT
TTGGTTCCAACTGCCTACAAGACAAAGAAAACTGAAGAGGCCAGGAAGTTAA
ATGCATGAGGAAAACTTGAGGCAGATTAAAATGGAAATGCAGGGCATGTTAT
TTGGGTATCATGGGTTCAATCTGGAAAAGCCTTATTTCTCCTGAACCACAGTA
GGGAAAGGAGTTATCCAGAAAAGTGAAATTTATTCTAAAATTTTAAGTTTCC
ATGTTTTaaagagaggcagcaatgaga (SEQ ID NO: 161)
For: 5'-3' = ccagaaactgaagtacaaatgc (SEQ ID NO: 162)
Rev 5'-3' = tctcattgctgcctctcttt (SEQ ID NO: 163)

M57 = G10.85n (326 bp ancestral); +1 bp insertion (327 bp = Derived). Extra A inserted
at position 133
AttgggaggaagtggtttctgTATTTAAAATTTTCCGAAGGAATTCTGCAGATTCAAGCTC
TAACCATTCTTGATTAAAATTGTGAGTTAGATAAGATTGTTTAGTAAAATTGT
ACTATGGCTCAGGAAATAATTTATTTAATATCTACTGTATGCCAAGCATTGTT
CTTTTTTCCATCTTCCAGGGAAATTCACCTCTTCTATAGAAGAGTTTGTTTTGA
ACTATACGATTTGAAACAAAATTCTTTTTTTGGAGACTATGGAAACATTCTCA
ACAGGGAAACCCTACTAGACTTTGTAAAgcaaataatggaaaagatacagaac (SEQ ID NO: 164)
For: 5'-3' = attgggaggaagtggtttctg (SEQ ID NO: 165)
Rev 5'-3' = gttctgtatcttttccattatttgc (SEQ ID NO: 166)

TABLE 1-continued

M58 = G10.57b (327 bp) G to A at position 224
TctctaacttctgtgagccacTCTAGCAAATTAATTGAACCAAAGGAGGAGGTTAAGGAC
AGCATAGTTTACAAAATGAGCCCTGTTTCTGACATCTGAAGTGGGGCAGTC
TAGTGGGCCTGACCTCTTAACTTGTAGAAACATTCTTTCTTTCTAGATGACTA
GTGACCAGAATTAAATTGAATCCTAGGCCACCCATTTATTGTCTTCTGCAGAA
TTGGCRAGAATGGAGAGGAATCCTCACCTATCGGTGACCAGAGATGAAATA
TTCTGAATTGAGAGTTTAAAAGAGCACACTTAGAagagatttagagtttagttttttcc (SEQ ID NO: 167)
For: 5'-3' = tctctaacttctgtgagccac (SEQ ID NO: 168)
Rev 5'-3' = ggaaaaactaaactctaaatctct (SEQ ID NO: 169)

M59 = B9.15new c (354 bp) A to C at position 279
CggcaacagtgaggacagtAGCTCCAGGTCTGGGCGGAAGGTGGTGCGGTGAAAGGTG
CAGGGACAGACTGGGTTAGAGGCCACTCTTGGTCTTATCCTCCATGGCCACA
ACAGAGGTGACAAATACATGGGTCACTCAGTTATGTTTAGCCAACAGCCTAC
CCAAACCACACCTGTCTTACCAGAGCCCTTTCCTGGAGCCATGTTCTCAGGAC
TGGTCACACTGTCTCCATTCTCCAGCAGCCCTTGGACCTATCGGAAAAAAAG
AATGGGTAACAMTAATTGAGCTGATGAACCAGGTCCTATCTTTCCTCCCACA
ACTCCAAAACTTGGgagcctctatctcctgaagca (SEQ ID NO: 170)
For: 5'-3' = cggcaacagtgaggacagt (SEQ ID NO: 171)
Rev 5'-3' = tgcttcaggagatagaggctc (SEQ ID NO: 172)

M60 = B9.34 (388 bp ancestral); +1 bp insertion (389 bp = DERIVED). Extra T
inserted after position 242
GcactggcgttcatcatctGGGAGCAGCTCAAAAGCCTCTCGCTCAGCCTCCGTGACGCC
CTGGGGGTGTTCAACCCACATATACTGTAAAGACTAGGAGTAGGGTTGTGGA
CACCCCACCTCAGCCAACACTGAGCCCTGATGTGGACTCAACCTTGTAAGGA
AAGCTGTAGAGAAATTGGAAGAAAAAATATAAACACATACAGACTCTGTCTT
TACATTTCAAAATGCATGACTTAAAGTATCAGGCACACAGTGGTTACTCAAT
GTTGGTCTGTGTCTCTGTAACGTAATATATGTGACTAAATCCCTAAGCTCTGC
TCTTGACCACCCACCTTCTCCAAAAGGGCCTTTCGTAGACGTCGCTcctcctgaacca
taatgaacat (SEQ ID NO: 173)
For: 5'-3' = gcactggcgttcatcatct (SEQ ID NO: 174)
Rev 5'-3' = atgttcattatggttcaggagg (SEQ ID NO: 175)

M61 = G10.83new a (190 bp) C to T at position 98.
AttggattgatttcagccttcTTCTGGTACTTTTTAAAATCTTATTAATCATTAGGAAAAGA
AGTTTTATTATTGATGCAAGCCCTAAACACTCTTTYGACTCCAGAGGAGAAG
CTGGCAGCTCTCTGTAAGAAATATGCTGATCTTGTGAGTATTTATTTAATGGA
gcaaggaacacagaaaataaaat (SEQ ID NO: 176)
For: 5'-3' = attggattgatttcagccttc (SEQ ID NO: 177)
Rev 5'-3' = attttattttctgtgttccttgc (SEQ ID NO: 178)

M62 = DYS260c (309 bp) T to C at position 60
ActaaaacaccattagaaacaaaggACTTAAACTAGGAATTAATTATTTCTCTTTCTCTYTC
CATGGCCAACAAACATTGAAAAAAAATTGCCATCTTTTTTTTTATTTGTTTGTT
AGAGATGGGGATCTCACTCTGTTTCTTAGATTGTAGTGCCATGGCACAATAAT
GGCTCACTGCAGCCTCAAACTCCTGGGCTCAAGTGATCACCCCCATACAGAC
TCCCGAGTAGCTGGGAACACAGGCACATGCCACCACCCCTAGCTAATTTTTT
ATTATTTGTAGAGATGgggtcactatgttgctcag (SEQ ID NO: 179)
For: 5'-3' = actaaaacaccattagaaacaaagg (SEQ ID NO: 180)
Rev 5'-3' = ctgagcaacatagtgacccc (SEQ ID NO: 181)

M63 = B9.22 (308 bp) G to A at position 43
CtcttcccttggttcctattcTGACACGCTCAGGTACCTCAARGAATCCTCCAACTTCCCAC
CTTCACTTTCTAGCACAACCCAACCGAGTAAAAACTATAAAGTATATCTATCT
CTCTTCTAACTGCTGGCCTGACGCAGTAAAGCAGAAATACTGATCCTCACTTG
GATCTCATCCACATCAGCAATCCAAGCTTGTGCCTTAGTCAGAGCTTCTTTGA
GAGCCTGGATGTTAGGCAGGTGAACAGGGATGTTTTCTGTCTCACGAATTAT
GGCTTCCAATGTGGCTggtggatgcttctgcctaa (SEQ ID NO: 182)
For: 5'-3' = ctcttcccttggttcctattc (SEQ ID NO: 183)
Rev 5'-3' = ttaggcagaagcatccacc (SEQ ID NO: 184)

M64 = B9.t23 (325 bp) A to G at position 279 RECURRENT
TatagaccctgactactcaagagaaAAGTCCAATCCAAAGAAAAAATACAAAAGAAAACA
AAATCACATCAGGCCACAAACCAGTTTAAGGGCCCTCACCACATGGTTGGCT
CCAGACTGAAACATTTCATAGGGGTAAATAATGCGTTCGTAATGTGATCGTA
GCAGGGAGCCAATGTTTTTTGCCTGGTGGGTAGTGGAGACGCTGGGCAACTCG
AGCCCACCGACGATCCTTGCAGATGGCTTCATAGCCACCTTCCTCAATCACAA
TCTGAAAGTRTAAGAAACAATATGGATGAACTGTGAacagactggaaagggctacc (SEQ ID NO: 185)
For: 5'-3' = tatagaccctgactactcaagagaa (SEQ ID NO: 186)
Rev 5'-3' = ggtagccctttccagtctgt (SEQ ID NO: 187)

M65 = B9.t26 (436 bp) A to T at position 152
TtctgatgccagcttgttcgGGTCAGAAAAGTTAAATGAGAAATTTGGTGCTAAGGGTTT
CTGGTCATGAGTGTAAATAACGCCTCGCCAAGTGGTAAACTGCCCCAACGTT
CAAACCAAAGGCTACCCATTCCCAAATTTTGTTTCAAAGWCTTACCGCGGGT
GGGCGGATTTTGCAGATGCCAGACTTCTCTGCTATGGGCCTTATTTTCGCAAT
GTAGCCAAGCGGGTCTTGGAATTCAGCCCAGCTAGGCTCAAAAACCGGGCAC
TCCGGTGGCGGCAGGAACTCGTCACACCCCGGTTCCATGTCGGGCCTTAATG TABLE 1-continued

```
CTAAGCTGTAAAATAAGAATCACATTGTCTTTAATGACGCGCTGGTTCCTCCT
ACTAAAAGGCCTATGAAAATTTCATTTTCTTGAGAATTTcaaggttactttaatcccgtagc (SEQ ID NO: 188)
For: 5'-3' = ttctgatgccagcttgttcg (SEQ ID NO: 189)
Rev 5'-3' = gctacgggattaaagtaaccttg (SEQ ID NO: 190)

M66 = B9.41 (415 bp) A to C at position 135
CtgtgtaacaccatcaagtgcACCCATATATGCAGAATGGGAATTTCGTAAGAAAAGAGA
AGGAAAAAGGCAGAACAGTTGAAGCAAAAATGGTTAAACAATTTCCAAATTT
GTGGAAAGCCCTGAAAGTCTACMACCAAGAAGCTCAGTGCACTCCAACTAG
ATAAACTCCAGGAGACACAACATAGTCGAACCAACAAAAGGTAAGACACCA
AGATGGAGTTTGAAAGCAGTATGACAGACATGATTCTTCGCATATAATGGAT
GCTTAATAGAATTATCAATAGATTTCTCATTAGAAATAACGGAGGCCAGAAG
CCAGTTGGATGACACGTTAAAAGTCATGCAATGGGAAAAAAAATTAAATAAA
TTGACAGAGAATTAAAAATTGTggaagtatgtctccagaagatgt (SEQ ID NO: 191)
For: 5'-3' = ctgtgtaacaccatcaagtgc (SEQ ID NO: 192)
Rev 5'-3' = acatcttctggagacatacttcc (SEQ ID NO: 193)

M67 old = B9.36new a (409 bp) A to T at position 377
CcatattctttatactttctacctgcAGGCCCACTGCATGCTCACTCACCCAGTCAGCAGTACA
AAAGTTGACAGCTTCAGCAAAATTGTAGCCTTGGTTAAAACCACTGTGGTAA
GCACGAGGAAAAGTGATGACAAACTCCCCTGCACACTGGTTTGTGCGGACAA
CCTAAAAAGGAGAAAAAAGCAGAAAGAGGTGTGGGTCAGAACTAATGGGCC
AGATGTGAACTCAAAGATGTCTCTAGATGCTGTAACAGATGTAGGAAGAGTG
GAAAGGCTCTATCTTCAAGTACGTGTCCTAAAAGAAAAATGAGATTGTGAAT
TTAAAAGTGGTATTCATAGAAAAGTACTCAAAATATGTGTAATTCAAAAAAC
AWATATAGAGGGgtccacgaacaagtgaaaagac (SEQ ID NO: 194)
For: 5'-3' = ccatattctttatactttctacctgc (SEQ ID NO: 195)
Rev 5'-3' = gtcttttcacttgttcgtggac (SEQ ID NO: 196)

M67 revised B9.36new a (386 bp) STS A to T at position 327
ccagtcagcagtacaaaagttgACAGCTTCAGCAAAATTGTAGCCTTGGTTAAAACCACTG
TGGTAAGCACGAGGAAAAGTGATGACAAACTCCCCTGCACACTGGTTTGTGC
GGACAACCTAAAAAGGAGAAAAAAGCAGAAAGAGGTGTGGGTCAGAACTAA
TGGGCCAGATGTGAACTCAAAGATGTCTCTAGATGCTGTAACAGATGTAGGA
AGAGTGGAAAGGCTCTATCTTCAAGTACGTGTCCTAAAAGAAAATGAGATTG
TGAATTTAAAAGTGGTATTCATAGAAAAGTACTCAAAATATGTGTAATTCAA
AAAACAWATATAGAGGGGTCCACGAACAAGTGAAAAGACTCTttgcttctataatcaa
agaaatgc (SEQ ID NO: 197)
newFor 5'-3' = ccagtcagcagtacaaaagttg (SEQ ID NO: 198)
newRev 5'-3' = gcatttctttgattatagaagcaa (SEQ ID NO: 199)

M68 old = B9.36new b (409 bp) A to G at position 268
CcatattctttatactttctacctgcAGGCCCACTGCATGCTCACTCACCCAGTCAGCAGTACA
AAAGTTGACAGCTTCAGCAAAATTGTAGCCTTGGTTAAAACCACTGTGGTAA
GCACGAGGAAAAGTGATGACAAACTCCCCTGCACACTGGTTTGTGCGGACAA
CCTAAAAAGGAGAAAAAAGCAGAAAGAGGTGTGGGTCAGAACTAATGGGCC
AGATGTGAACTCAAAGATGTCTCTAGATGCTGTAACAGATGTAGGAAGRGTG
GAAAGGCTCTATCTTCAAGTACGTGTCCTAAAAGAAAAATGAGATTGTGAAT
TTAAAAGTGGTATTCATAGAAAAGTACTCAAAATATGTGTAATTCAAAAAAC
AAATATAGAGGGgtccacgaacaagtgaaaagac (SEQ ID NO: 200)
For: 5'-3' = ccatattctttatactttctacctgc (SEQ ID NO: 201)
Rev 5'-3' = gtcttttcacttgttcgtggac (SEQ ID NO: 202)

M68 revised B9.36new b (386 bp) STS A to G at position 219
ccagtcagcagtacaaaagttgACAGCTTCAGCAAAATTGTAGCCTTGGTTAAAACCACTG
TGGTAAGCACGAGGAAAAGTGATGACAAACTCCCCTGCACACTGGTTTGTGC
GGACAACCTAAAAAGGAGAAAAAAGCAGAAAGAGGTGTGGGTCAGAACTAA
TGGGCCAGATGTGAACTCAAAGATGTCTCTAGATGCTGTAACAGATGTAGGA
AGRGTGGAAAGGCTCTATCTTCAAGTACGTGTCCTAAAAGAAAATGAGATTG
TGAATTTAAAAGTGGTATTCATAGAAAAGTACTCAAAATATGTGTAATTCAA
AAAACAAATATAGAGGGGTCCACGAACAAGTGAAAAGACTCTttgcttctataatcaaa
gaaatgc (SEQ ID NO: 203)
newFor 5'-3' = ccagtcagcagtacaaaagttg (SEQ ID NO: 204)
newRev 5'-3' = gcatttctttgattatagaagcaa (SEQ ID NO: 205)

M69 = B9.62a (257 bp) T to C at position 222
GgttatcatagcccactatactttgGACTCATGTCTCCATGAGAACTAAGACTACCACAACA
GAATCCCTATAGTCCAGCCCTCAGATCACATACATGTACAGGCATGTTGAAG
TAGTCGGACTTGAAGGAATCAGCCATTTCACCAAAACTCTGCAAACTGTACT
CCTGGGTAGCCTGTTCAAATCCAAAAGCTTCAGGAGGCTGTTTACACTCCTGA
AAYAAAATATATTTCagcaagacaaagggaataaagat (SEQ ID NO: 206)
For: 5'-3' = ggttatcatagcccactatactttg (SEQ ID NO: 207)
Rev 5'-3' = atctttattcccttgtcttgct (SEQ ID NO: 208)

M70 = B9.62b (257 bp) A to C at position 45
GgttatcatagcccactatactttgGACTCATGTCTCCATGAGAMCTAAGACTACCACAACA
GAATCCCTATAGTCCAGCCCTCAGATCACATACATGTACAGGCATGTTGAAG
TAGTCGGACTTGAAGGAATCAGCCATTTCACCAAAACTCTGCAAACTGTACT
CCTGGGTAGCCTGTTCAAATCCAAAAGCTTCAGGAGGCTGTTTACACTCCTGA
```

TABLE 1-continued

AATAAAATATATTTCagcaagacaaagggaataaagat (SEQ ID NO: 209)
For: 5'-3' = ggttatcatagcccactatactttg (SEQ ID NO: 210)
Rev 5'-3' = atctttattccctttgtcttgct (SEQ ID NO: 211)

M71 = B9.63b (328 bp) C to T at position 197
TtgaattatagtcccttgcctcTGGTTCAGTCAAGTCTCTATCATTCTAGAGTTAGTGTGTT
CAATCGTTCTTGTATAGTAGCTCACTGATAGCTTAATCAAAACCTAACACAAA
TATTAACTTATAAAAGGGCAGAAACTACCTTCCCAAAACCCAGAAGGGGAGA
TTACAGAAAATCACCAACCAAAAATAAAGYATCTGTGACAGACAGATCTTAC
CGCCAAGATACATTTTGGGCACCTCCAGATGCCTCTGGGGATTTCAGGAAGG
GGTGGTAACAAGCAGAAGATGTGGTAATTGTCATCAcagccatcacagaaaagaagc (SEQ ID NO: 212)
For: 5'-3' = ttgaattatagtcccttgcctc (SEQ ID NO: 213)
Rev 5'-3' = gcttcttttctgtgatggctg (SEQ ID NO: 214)

M72 = B9.63a (328) A to G at position 157
TtgaattatagtcccttgcctcTGGTTCAGTCAAGTCTCTATCATTCTAGAGTTAGTGTGTT
CAATCGTTCTTGTATAGTAGCTCACTGATAGCTTAATCAAAACCTAACACAAA
TATTAACTTATAAAAGGGCAGAAACTACCTTCCCAAAACCCRGAAGGGGAG
ATTACAGAAAATCACCAACCAAAAATAAAGCATCTGTGACAGACAGATCTTA
CCGCCAAGATACATTTTGGGCACCTCCAGATGCCTCTGGGGATTTCAGGAAG
GGGTGGTAACAAGCAGAAGATGTGGTAATTGTCATCAcagccatcacagaaaagaagc (SEQ ID NO: 215)
For: 5'-3' = ttgaattatagtcccttgcctc (SEQ ID NO: 216)
Rev 5'-3' = gcttcttttctgtgatggctg (SEQ ID NO: 217)

M73 = B9.47a (361 bp ancestral & 359 bp derived) **-2bp deletion,
(-GT)** at position 260
cagaataataggagaattttttggtCAAATAAAAGGCCATATTATATTTCTTTTGATAAAAGT
ATCATGTGTTCAGTATGTTTTATTATTTGAAATAATTAACATGACAGGAATAT
ATTTGAAAAAAATTCCAAAAAAAGCTAAATATACAAACTAAGAAAATTATAT
GATTATACTTATCTGCAGTATTGTAAAACAATAGTTCCAAAAACTTCTGAATT
ACAAGTTTAATACATACAACTTCAATTTTCAACTACATTGTGGTTAGACGTTC
AGAGGAATCACAAAGGACCTCAACATGCTAGATAAGAAAATGTATTTTTTAA
ATGTTTTGGCTCAgctgcttagaaaataaggaaaat (SEQ ID NO: 218)
For: 5'-3' = cagaataataggagaattttttggt (SEQ ID NO: 219)
Rev 5'-3' = attttccttattttctaagcagc (SEQ ID NO: 220)

M74 = B9.50a (385 bp) G to A at position 195.
AtgctataataactaggtgttgaagATAAAATCAGTTTAATTTAAATAAGAGGATAAAAGAA
GTATGAGCAGAAAAAGGTTTTCAATATTAACTAGGAAAGTCTGAAAAATAAT
CAGAAATTCTAAAGATAAAAACATAACATTAAAAATTATAAACTAAGTTGTT
TAATAGATTAGGTATTTTAAAAACTGGTRCATTTTTAAGTTGCTTTAAGTAAG
TTACTTAAAAGACAACAGCAGCAAAAGAATTAAAAAAAAATGAAAGGTGAA
GAAACACATACAAGAGAACCTTAGAACAGTAAGGTTCTAGCTAACAGGAGA
AATAAATTACAGACTGTAAAAGTTGATGACCAAGAATTTTttcagaagtggtaaaagctg
aatt (SEQ ID NO: 221)
For: 5'-3' = atgctataataactaggtgttgaag (SEQ ID NO: 222)
Rev 5'-3' = aattcagcttttaccacttctgaa (SEQ ID NO: 223)

M75 = B9.51 (355 bp) G to A at position 296
GctaacaggagaaataaattacagacTGTAAAAGTTGATGACCAAGAATTTTTCAGAAGTGG
TAAAAGCTGAATTCTCAAGTTTGAGAATTCCTATCTATTCCCAGAAATATTAA
GTAAAAAGTCACATTCCACACATCAAGAAAACTTGCAAGACACTAAAAGAG
ATATTATAGCAGTCAAATAGAAAAAGCAAAATAGACTACTACAAATTAATGT
AAGATTCAGAATTGACTTGTCAAAAGCCAAAACAGATTTCTAATGTACTGTG
AAAAGACAATTATCAAACCACATCCRTATATATACAGAGAAATACCTTTATA
AGAATAAAAATcacaaatgcctctgttcaata (SEQ ID NO: 224)
For: 5'-3' = gctaacaggagaaataaattacagac (SEQ ID NO: 225)
Rev 5'-3' = tattgaacagaggcatttgtga (SEQ ID NO: 226)

M76 = G10.100a (493 bp) T to G at position 339
TagaagtagcagattgggagaggACATGTGTTCAAGTTGTACTACTTGTATGTCTTGTTTA
GATATTACAGTCTTTTTCTTTTATCAGAAAATAATTGAATAATGATAAAATCA
GTTGCAGATTAAGACAGATTATCTGTTGCAGTCTTCTCAAAACTTAATTTAAG
TACATTATTTTCAGCTAGCATTTCTTCCTTCACATAGAACCTCCATGTGTGGA
GGGATTTCCTAATGAGTCTATTGTATGTACAATAGCACTTAATGACATAGCTT
TTAAATAATAACAGGATTTTACCAAATGTTTAATATGTGCCAGGCATCAAGC
ACCTTACACAGTTKAATTATTGCATAGATTTGGACAGCAACTCTGCAAGTTA
GGTATGGTCATGAACCTTTGCAGATAAGGAAACTGTGTTTCACAAGGAGAAG
AAATTGTCCTGGATCATACAATAAGCTAGGATTTGCTCCAgaccattttttttcattttatcagg (SEQ ID NO: 227)
For: 5'-3' = tagaagtagcagattgggagagg (SEQ ID NO: 228)
Rev 5'-3' = cctgataaaatgaaaaaaatggtc (SEQ ID NO: 229)

M77 = G10.105 (371 bp) C to T at position 129
CttttcttcccttagctgttccTTTCCTGTGGTTTAAAAAAGTGACCAGAAACTAGGTCTCT
ATTTTCATTGCTTTGCTGCATATTCTTTTAACCTGCTTTTATCTTTTACAGAGTT
GAGGGGCTTTYTAAATAACCTAGACAATGTCAAGATTCTTAGCTGCGTTTTCT
GTCTAAAAGTGTAGATGTCTAGTTATTCCTCATGTAAAACACAACATTTCAAC
CCTGAGTACTATAAACTTTATTATGCTTCTAGGTTACTTTTTCTCTTTAAGCAA
TTATTCCTACATTCCTAAGTGTTCACCAGTGGAACAGATAAGAGATAGAAGT TABLE 1-continued AGTTAGAAAATTGAGATAATTGggttgacctgtcattgttgc (SEQ ID NO: 230)
For: 5'-3' = cttttcttcccttagctgttcc (SEQ ID NO: 231)
Rev 5'-3' = gcaacaatgacaggtcaacc (SEQ ID NO: 232)

M78 = B9.60a (301 bp) C to T at position 197
CttcaggcattattttttttggtTCTCCACTACAGGAGAAATGTAAATGTGATGAGTCAGAAT
TTAGGATGGCTGTATGGGTTTCTTTGACTAATACAAGAAATCACTTTGTAATG
AATGAAATCAGTGGTTTCTGCATTACTCCGTATGTTCGACATGAACACAAATT
GATACACTTAACAAAGATACTTCTTTCYGCCCTTCCAAATATTTCAAAATAAG
CTGGTCATAGTACTTGCTTTTCATAAAAAGATGGTAAGCTTCCAATATTTAGA
TTTaaggaaaggtgaaggaacactat (SEQ ID NO: 233)
For: 5'-3' = cttcaggcattatttttttggt (SEQ ID NO: 234)
Rev 5'-3' = atagtgttccttcacctttcctt (SEQ ID NO: 235)

M79 = B9.42 Homopolymer in tree (425 bp = majority men). A's. 8 A's to 9 A's (426 bp derived). Extra "A" inserted after position 212.
AgccagttggatgacacgttAAAAGTCATGCAATGGGAAAAAAAATTAAATAAATTGAC
AGAGAATTAAAAATTGTGGAAGTATGTCTCCAGAAGATGTGCCTACAGGGAA
AACAGAAGGACTCCTTCAGGCTGACATGAAAGGATATTACTGAGTAGTTCAG
AGCTACATAAAGAAAGTAATACCCCTGAGAAAGGCAACTATAAAAAAAAATA
TAAAAGTTAGTATTACATATACAGCACGAGAGACAAAAAAAAATATAGTTAGT
TCAGAACTAGAATCAGAAAGCAAGACAAATGGTGTTAATTAGATTGCTTGAT
GAGCTCATTATCATCAATATATTTTTCTTGTGAGACGAGGAATACTAGGAAAA
AAGGTACAAGTTAGAATTCATAAAATGTATAaaatgtcaggaaacgaagagg (SEQ ID NO: 236)
For: 5'-3' = agccagttggatgacacgtt (SEQ ID NO: 237)
Rev 5'-3' = cctcttcgtttcctgacattt (SEQ ID NO: 238)

M80 = G10.107. Homopolymer in tree (290 bp = most men). 9 T's to 10 T's (291 bp derived). Extra "T" inserted after position 55.
ActttctcttcttttagggtgaccAATTAATTCTGATTTGCCTTGATTTTTTTTTTGGCATTTTT
ATGGCACCATAAAAACCATAAATGATTTGTATTCATTTTGGCAACCCTAGTTC
CAGGTTGATTGTGATGGCTGGTTGTGATGGCTATTTTGAAAGTTGGCTTTCCT
CTGTCCCAGATATTTTCTCTAAAACCTTTATAATTTTGTCTTATGGCTAGCTAC
ATAGAATTTTAAAATATTACAAATGGCCAGACAGTCCTACTTCAccataagattttgtgt
gtgtgt (SEQ ID NO: 239)
For: 5'-3' = actttctcttcttttagggtgacc (SEQ ID NO: 240)
Rev 5'-3' = acacacacacaaaatcttatgg (SEQ ID NO: 241)

M81 = B9.58a (422 bp) C to T at position 147.
ActtaatttatagtttcaatccctcaGTAATTTTAACTTACTTCTATTTTAAGAACTATAACCA
AACTATCTGTAAGACTTTTAAGCACTATCATACTCAGCTACACATCTCTTAAC
AAAAGAGGTAAATTTTGTCCTTTTTTGAAYGTCATAGAGTATACTCACACAA
ACCAAGAAGAAACAATCTACTACATACCTACGCTATATGGTATATAACTATT
GCTCCTAGGCTACAAATTAGTGCGACACTATTGTACTGAATATTATAGGCCAT
GTAACACAATGGTTTAAGTATCTGTGCCTCTAAACACAGAAAAGATAGTG
AAAGTACAGTATTGCTCCTTTATTAAAACTCAAAATGTTATGCAGCATATGACC
GACTATAAAATAGCGCTTATCcagatacagacatctccatgaa (SEQ ID NO: 242)
For: 5'-3' = acttaatttatagtttcaatccctca (SEQ ID NO: 243)
Rev 5'-3' = ttcatggagatgtctgtatctgg (SEQ ID NO: 244)

M82 = B9.t18 (328 bp ancestral). Two bp deletion (-AT) at position 179. (326 bp derived). This STS also contains M69 which is normally associated with STS B9.62 at site a. The M82 deletion mutation is always linked to the M69 mutant C allele.
CtgtactcctgggtagcctgtTCAAATCCAAAAGCTTCAGGAGGCTGTTTACACTCCTGAA
ATAAAATATATTTCAGCAAGACAAAGGGAATAAAGATCCAAAAAAACAGGA
GAGCTAAGGGGAGATAAATTTTTCATGTTACATTCAATATCTCATGCAATAAT
TCTGCATTTTCATATATGTTTCCAGGTAGGTTTGTTTCTTCAGTAGGTATTAAAC
ATTATTTTATAATCTTTCCTTACATGCTTCATGCCATTTGAATTATAGTCCCTT
GCCTCTGGTTCAGTCAAGTCTCTATCATTCTAgagttagtgtgttcaatcgttcctt (SEQ ID NO: 245)
For: 5'-3' = ctgtactcctgggtagcctgt (SEQ ID NO: 246)
Rev 5'-3' = aagaacgattgaacacactaactc (SEQ ID NO: 247)

M83 = B9. Alu01 (503 bp) C to T at position 120
GggaaaggagttatccagaaaAGTGAAATTTATTCTAAAATTTTAAGTTTCCATGTTTTA
AAGAGAGGCAGCAATGAGAAAAAAGGTTAAGAACAAGTAGGAAATACTGAA
ATAATGGGYCAGGCACGGTGGCTCATGCTTGTAATCCCAGCACTTTGGGAGG
CCAAGGCAGGCAGATCACAAGGTGAGGAGATTGAAACCATCCTGGCTAACAT
GGTGAAACCCCATCTCTACTAAAAATACAAAAAAATTAGCCAGGTGTGGTGG
CACACACCTGTAGACCCAGCTACTTGGGAGGCTGAGGCAGGATAATGGCCTG
AACCCGGGAGGTGGAGCTTGCAATGAGCTGAGATCGTGCCACTGCACTCCAG
CCAGGGTGACAGAGTGAGACCCCGTCTCAAAAAAAAAAAAAAGAATATTTG
AAATAATGTGTCTCTAAAATATGACAGACATGAGAATGAAGACAAAACATAA
GAAACTAAgctaagtaagcatgggtcatt (SEQ ID NO: 248)
For: 5'-3' = gggaaaggagttatccagaaa (SEQ ID NO: 249)
Rev 5'-3' = aatgacccatgcttacttagc (SEQ ID NO: 250)

M84 = B9.72 Homopolymer in tree (439 bp = most men). 9 T's to 8 T's (438 bp derived). One deleted "T" at position 400.
CccctctccaactgagttcaagATGGAAACAGTTAAGACAGGAAAAATTCTATTCCATTTA TABLE 1-continued

```
AACTCATATCATTAGAATCATAACTGCTTTCAGACCACAATATAATCACAAAC
CTGGGAAAATGGAAACTCATTAAGTATCAAAATACAAATCATATGCCACATA
TATTATATACCATTTTCAGCACTTGTCTCTTCTTAGAGGACACTGTAAAATAT
ATTTTATCATTGTTTAAAATAATTTGTTATATTTTGAAATTAAGCTCTATTACA
TTTTCCGTTTATTTTAAAGCTTTATTCTTACAAATTTTCTATACAGAGGTAAGT
TTTCTTCTATTTACATATATAAACATACATGTATACACAGAGAGACACAGTAA
CATATTTTATGCTTTTTTTTTATTCCCACGGCAATTTCtggaagcagaaacgtatattgc (SEQ ID NO: 251)
For: 5'-3' = ccctctccaactgagttcaag (SEQ ID NO: 252)
Rev 5'-3' = gcaatatacgtttctgcttcca (SEQ ID NO: 253)
```

M85 = B9.67a (568 bp) C to A at position 437
```
AacagaattatcaggaaaaggtttCATAAAATAAAAATCTTTTAAACTTATGAAAGATGCT
CAATATAAAAAACTGTAAACCAGGGAAATGCAAATAAAAATTACAATGAAA
TACTACACACCTCCCAGAATGGCTAAAATGAAAACAAAACTGTCAATTCTAA
GTGTTAGTGAGGACATGTGGTAACCAGAACTGGCATCCAATACTAGCTGATA
AACTCGTCAATCATTTGTAAAAACAGTCTGACAATAATCCACTAGTGAAAAT
ATACATAGTCTCAGTCACAGCAATTCTATCCTGTCTATCTAGGTAACAGAAAT
GTCTACATACGTTACCTAGAAACATATACTTTAATATCCACAGAATTACTTGA
AATAGCCAAAAATTGGTAACTACCAAAAGTTGAATGGTAAAACAGATAGAA
AAAAAGCTATGMCTAACAAAACTACACTTAATAGAACACAAGCGTGAGCAT
TAATAGAACCATATAAATGCATTTTTTGAACCACTAAAAGAAGAAGCCAATA
CAAAAGAGGTGATTAAttgaaagtacacgaacaagtaaaa (SEQ ID NO: 254)
For: 5'-3' = aacagaattatcaggaaaaggttt (SEQ ID NO: 255)
Rev 5'-3' = gcaatatacgtttctgcttcca (SEQ ID NO: 256)
```

M86 = B9.t25a (324 bp) T to G at position 85
```
TcccattatttgctatatttgctACATACATCTAAGGTCATATCAAAGAAAGAAAACACCAG
TCCAAGTGGTTAACACACAAGCKTATATAACTTGCTTCTGTCATAGATCAAG
TACTTCTGAGTAAGCTATTTTTTTGCGGTTAAATGTAATAAAAGCTTGTGTAT
GCCTAAACTATATTTAATAACAGCAGAACGTAGAAATATTTGAATCTTATATT
TTTGTCCCTACAGCAGTCAGATGTTTAGAACCCCGTGGAATGTGGCGATCTGA
TACTAATATTCTGATGCCAGCTTGTTCgggtcagaaaagttaaatgagaaa (SEQ ID NO: 257)
For: 5'-3' = tcccattatttgctatatttgct (SEQ ID NO: 258)
Rev 5'-3' = tttctcatttaactttctgaccc (SEQ ID NO: 259)
```

M87 = B9.t25b (324 bp) T to C at position 277
```
TcccattatttgctatatttgctACATACATCTAAGGTCATATCAAAGAAAGAAAACACCAG
TCCAAGTGGTTAACACACAAGCTTATATAACTTGCTTCTGTCATAGATCAAGT
ACTTCTGAGTAAGCTATTTTTTTGCGGTTAAATGTAATAAAAGCTTGTGTATG
CCTAAACTATATTTAATAACAGCAGAACGTAGAAATATTTGAATCTTATATTT
TTGTCCCTACAGCAGTCAGATGTTTAGAACCCCGTGGAATGTGGCGATCTGAT
ACYAATATTCTGATGCCAGCTTGTTCgggtcagaaaagttaaatgagaaa (SEQ ID NO: 260)
For: 5'-3' = tcccattatttgctatatttgct (SEQ ID NO: 261)
Rev 5'-3' = tttctcatttaactttctgaccc (SEQ ID NO: 262)
```

M88 = B9.80 (314 bp) A to G at position 166
```
AttctagggtcaggcaactaggGAATACTGCTGTAGCCTAGAGCCTGCCAAAATTATTCA
AACTAGCCAATCCCATACTTCTTATCCTGCTCTGTCTTGCCTTTCCCTTGGTAA
ACCCAATATAGGCTATGGCCTAGGTGCTTTTCTTATTCCTGCTTCTTCTGCRT
ATCCAAGATAGGTTTTCCTCTCTAGCACTGTGTAGCATATAGTGACTACCTCT
CTAAGGCCTGTGATAATAATAAACTTTGCTTTCCTGAGTCTCTGTGGTCACAC
CTACTGACCATCACATggaagaccatagaatagaacaaaca (SEQ ID NO: 263)
For: 5'-3' = attctagggtcaggcaactagg (SEQ ID NO: 264)
Rev 5'-3' = tgtttgttctattctatggtcttcc (SEQ ID NO: 265)
```

M89 = B9.94 (527 bp) C to T at position 347
```
AgaagcagattgatgtcccactTAAAGAAGCAGTCTAGCCACATTTTGGTAGAGCAGCTG
TGGTGTGCCAGGGAGTCCCTTTCATCCCCTGGTCAGTTTTGTTTGCGCTCTCCT
AAACCTGCAGGCTGGAACAGCTGAGCCATCCAAACAGCAAGGATGACAACC
TTCCCTTTCTCCTAAGAACTCTGCCCCATTCAAGCTTGGCCCAACACTGTTGC
CAGGGGCTGGCTGGAATTCCAAGCTGGTGAGTCTTATCCTATGAGGTGCCAT
GAAAGTGGGGCCCACAGAAGGATGCTGCTCAGCTTCCTGGATTCAGCTCTCT
TCCTAAGGTTATGTACAAAAATCTYATCTCTCACTTTGCCTGAGTTGCAGCTA
CCTTTGCTGGTGATCCTGGACCCAAAGTGTGCCAGCCTCTCCTGATACTCTGT
GTGTACCTGAGCAGCTATTCTGCCAAGACTTCACACAGCTCTGTGCATGAAAC
CCAAGGCCTTAGTGAAGTGGGATCAtgaggggatctcctaactgga (SEQ ID NO: 266)
For: 5'-3' = agaagcagattgatgtcccact (SEQ ID NO: 267)
Rev 5'-3' = tccagttaggagatcccctca (SEQ ID NO: 268)
```

M90 = B9.96 (331 bp) C to G at position 170
```
TgatgtttcttcagtctttgaggTTGCTGTCTTTTGGATTTTTGAAAAAATCCTATTTAATAA
CTTAGTGGGTTGGTTTGTAGCAACAGTGAATTCAATCAACTGGCTTTATTTCT
AGAATATTTTAAAGATATTTTATCTCAGGATTTCTGGATGGTGTTCTGTAACT
STAGGGACTGGGAATGAGCTTTGGCTTTGTTCCTTTACACCCTGAGGTTAGAA
ATCTGCTGCACTGGAGGGACCAAGATGCTCTCAGAGAAATGGTCACAACACT
CTAATGATTGGTAGTAGCCAATGTGCTTCATATGCGggtggtagcaggattcatctt (SEQ ID NO: 269)
For: 5'-3' = tgatgtttcttcagtctttgagg (SEQ ID NO: 270)
Rev 5'-3' = aagatgaatcctgctaccacc (SEQ ID NO: 271)
```

TABLE 1-continued

M91 = B9.87a Homopolymer. (495 bp, most men = 9 T's). Either one T deleted or
inserted at position 368 (i.e. 8 T's or 10 T's)
GagcttggactttaggacggGGAAAAGAAGTGCTAAATGTTTTTGAATAAAACCTTTACT
GCACATGATAAACATCCCTTAAAAATTACCTAGGAGCACCCTAAATTTTAAA
ATGATCACAAAGACCTGGACAGATTACAGTAAACCTTCAACATCGCTAAACA
CACGTACCATAAATCAAAAGAAACACACTGCTAATGATCCGTTTTTTGATGT
GGAAATATCATGCTGTTTTTAAGGGAAATTATACTTTATTGCGATGTTTTATT
TCAAAACAAGATGTTACACTTTATTTCCTATAATTTTATTTACAATATTTTACA
CCCGTTAAGCAAAAATCCCCCTACATTGCTATTCTGTTTTTTTTTTAATCAG
TTCACTACTGTAGTATCTTTTTGTTCTCCATATATTTTTGAAAAATACGCAAAA
GGTAAGTTTTAAAAATCAAATGGTAGATTTTATTTGGAAGGGCACTgccagaagtg
ccttaaagttt (SEQ ID NO: 272)
For: 5'-3' = gagcttggactttaggacgg (SEQ ID NO: 273)
Rev 5'-3' = aaactttaaggcacttctggc (SEQ ID NO: 274)

M92 = B9.G2 (470 bp) T to C at position 340
TtgaatttcccagaattttgcAATCTGATCCAAATAGTTCAATTTCACTCTAGTTTGGGCCT
GGGAAAGAGAGGGCCTTATAAGATTGGCATACTCCTTAACCTGACTTCATCG
AGTATGCAGTAAATGAACAAGTATTATTCTATGCTATCTACACTTCTCCACCA
ACGTGCCGGAGCCCCAGCTTCACTGTCTTATCTCACCAGCGGGGTCCACAAA
AAGCTCAAATAAGCTGAGTCTTTAATCTATAAAGAGCTAAGAATGTGCCGTC
TTAGGATCAACATCATGTCTAAATTTAAGGAATTATTCTTGGACTTAAAGGTG
GCTTGACCAAAAATAYGTAGGCTCCAACAGTATTTAGACTCAATATCATCAA
GACACTCATTTAGAATGTACTGATATATAATTCAAAGAATTAAAATATTTTTC
TAGTTCATGTAAAAGAGCTggacacaaaaccagtttctgaa (SEQ ID NO: 275)
For: 5'-3' = ttgaatttcccagaattttgc (SEQ ID NO: 276)
Rev 5'-3' = ttcagaaactggttttgtgtcc (SEQ ID NO: 277)

M93 = B9.93 (504 bp) C to T at position 459
AacaaaacaaaacaaaaatactgaaTCTTTAGAATTATGTACGCTAAGTGAAACATGTTTAT
AAACATAAATACACAGTTTTTATAAAATATTTTAAAGTTTTACGGATAATAAA
ACCTAAAAACTGGCCAGTCGTGGTGGCTCATGCCTGTAATCCCAACACTTTGG
AAGGCTGAGTCAGGTAGATCACGAGGTCAAAGGATCGAGACTATCCTGGCCA
ACATGGTGAAACCCCATCTCTACGAAAAATACAAAAATGAGTGGGCATAGTC
ACGCGCCTGTAGCCCCAGCTACTCAGGAGGCTGAGGCAGGAGAATCACTTCA
ATCCAGGAGGTGGAGGCCGCCTGGCCAGAGTGATAAGCTGCCTCAAAAACA
AAACAAACAAACAAACAAAAACAATTAACTTATTATGTAAAATTACCC
TGCTAAATCAGTTTCCACACCCTGAGTTAAAYCCAAGTCACACCAAGCTTTtaa
cctaaactatcttcaagtgaacc (SEQ ID NO: 278)
For: 5'-3' = aacaaaacaaaacaaaaatactgaa (SEQ ID NO: 279)
Rev 5'-3' = ggttcacttgaagatagtttaggtta (SEQ ID NO: 280)

M94 = B9.122 (405 bp) C to A at position 227
CacatggagaacagagaaatgcAGTGCAGGGCAAGGGCCCACCCAGAAGCAACACAGTC
AATGGAGCCTCCTTCACCCAGGAAACTGCAAACTGAATGCATGATCCTAGGA
TCCTCTCCCATGGATCTTTGCAACTTTCAGGTCAGGAGATCCAGTCAGGGACC
CATTCCACTAGGGCCTTCAGTTAGAAACACAGAGCTCATGGAGTCTTATCAG
AGTAGCTGTTMAGGCATGCATAGGGACCCAGGAGCTTTATACACCCTGACCG
TAAAGTCCCCAGCAAATATGACTGAAATTCAAGCAAGGTGGAACACTAACCT
TTGCACATACACTTGGGAAGGGAGTGGAAATCAAGATGCCAAGCAGCATTGG
TCTGTGAACCccactttcacaacatttcacaag (SEQ ID NO: 281)
For: 5'-3' = cacatggagaacagagaaatgc (SEQ ID NO: 282)
Rev 5'-3' = cttgtgaaatgttgtgaaagtgg (SEQ ID NO: 283)

M95 = B9.123 (480 bp) C to T at position 172
GagtggaaatcaagatgccaagCAGCATTGGTCTGTGAACCCCACTTTCACAACATTTCA
CAAGCTAAAAGCCCACTGGCTTGGATTTCCAGTCAGCTGCCAGCAATAGTGT
TGCACCTTCTTGGGATCAAATGGAGTTCCTGAGGATAAGGAAAGACTACCAT
ATTAGTGYTGGATGGCTTAGCCTTTCCAACCTGTAGGCTTAGGAGAGTCCAG
ACTTACTAGGGATGTAAGGGATCCTCTTACACAAAACAGGTGCACTACCAAA
ATGTGGCCAGAGTGCTTTAAACAGGACCTTGACCCATTTCTCATCTCTGGGAA
GGACCTCACAACTGGGGCCTTCAAACACACCCACCCTCATTGTCTGGCTGAC
AAAGTTTTTACTTATTGCTGAAAAATAGTGCCCTGAGGGAAAGGCAGGCTCC
CATCACTGATGCTTTAATGACTCATCTGTTCTAGtctccaggttacagaaagccc (SEQ ID NO: 284)
For: 5'-3' = gagtggaaatcaagatgccaag (SEQ ID NO: 285)
Rev 5'-3' = gggctttctgtaacctggaga (SEQ ID NO: 256)

M96 = G3.05a (440 bp) G to C at position 70. Internal lower case denotes location of
alternative reverse primer region to amplify site a only, as 212 bp STS.
GttgccctctcacagagcacTTTAAAGTGAGCTGTGATGTGTAACTTGGAAAACAGGTCT
CTCATAATASGATAAAACACTCAGGTATAATATTAAAAACCTATGGCAAAAT
ATATGGTCCTTTACAAAGCAACAAAGTGGGTGGGTGAATCTCTTCATTCTTGG
CTGGCCATCAGTTCCTGTTACTGTACAggagtgggaaaacagtagccCTGGGAAATGGGT
TAAAACTGAGTAGGCATCTCCTGTGTCCAATAAGAACTCAATATTTTTGTCTG
CTATATCAAGGGTTACTTGAGGCTCCTCTGTGGAGATGGTAAGTTGTCCAGTG
GGAGATATAGAGAATGTTAGGCCTTATAGGTTCTCTACTTTTTTGGCCATTAT
GAGTCTGAATGTCTCAAACTCCCTTTTTATCCTGGTgcaatccttccagtgaccttt (SEQ ID NO: 287)
For: 5'-3' = gttgccctctcacagagcac (SEQ ID NO: 288)
Rev 5'-3' = aaggtcactggaaggattgc (SEQ ID NO: 289)

TABLE 1-continued

M97 = G3.05b (440 bp) T to G at position 355
gttgccctctcacagagcacTTTAAAGTGAGCTGTGATGTGTAACTTGGAAAACAGGTCT
CTCATAATAGGATAAAACACTCAGGTATAATATTAAAAACCTATGGCAAAT
ATATGGTCCTTTACAAAGCAACAAAGTGGGTGGGTGAATCTCTTCATTCTTGG
CTGGCCATCAGTTCCTGTTACTGTACAGGAGTGGGAAAACAGTAGCCCTGGG
AAATGGGTTAAAACTGAGTAGGCATCTCCTGTGTCCAATAAGAACTCAATAT
TTTTGTCTGCTATATCAAGGGTTACTTGAGGCTCCTCTGTGGAGATGGTAAGT
TGTCCAGTGGGAGATATAGAGAATGTTAGGCCKTATAGGTTCTCTACTTTTTT
GGCCATTATGAGTCTGAATGTCTCAAACTCCCTTTTTATCCTGGTgcaatccttccagt
gacctt (SEQ ID NO: 290)
For: 5'-3' = gttgccctctcacagagcac (SEQ ID NO: 291)
Rev 5'-3' = aaggtcactggaaggattgc (SEQ ID NO: 292)

M98 = G3.04a (395 bp) G to C at position 158; has (GTTTT)6 motif
GaatgggtgttacatggagaCTACAGGGCTGTTATATTCATAACTTTAGGCTATCATTAT
TGAGGGCTGGATGTCCCTCTGAGCCTCAGGATTCAAAGGATACTGTTTTGTT
TTGTTTTGTTTTGTTTTGTTTTTTCCCACGGGTAATTAACACTGSGTTTTAGG
ACAGTCTGGACTGGGGGTACATTAACAGTTGTACTAGAAACTTCCATGTCTCA
AACAGAGGGGTCTACTAGAGAAGCAATATGTCATGGAAGGCAGTTCTTCTCC
ATATCTGTGTAAAGGCAAGTATTTGAAGCTAGGAGAACTGTTCCTTCTGGCCT
GTTGCCCTCTCACAGAGCACTTTAAAGTGAGCTGTGATGTGTAACTTggaaaacag
gtctctcataatagg (SEQ ID NO: 293)
For: 5'-3' = gaatgggtgttacatggaga (SEQ ID NO: 294)
Rev 5'-3' = cctattatgagagacctgttttcc (SEQ ID NO: 295)

M99 = G3.04b (395 bp nominal) 1 bp deletion (3A's to 2A's) at position interval 96–98,
STS alos has polymorphic (GTTTT) motif
GaatgggtgttacatggagaCTACAGGGCTGTTATATTCATAACTTTAGGCTATCATTAT
TGAGGGCTGGATGTCCCTCTGAGCCTCAGGATTCAAAGGATACTGTTTTGTT
TTGTTTTGTTTTGTTTTGTTTTTTCCCACGGGTAATTAACACTGGGTTTTAG
GACAGTCTGGACTGGGGGTACATTAACAGTTGTACTAGAAACTTCCATGTCTC
AAACAGAGGGGTCTACTAGAGAAGCAATATGTCATGGAAGGCAGTTCTTCTC
CATATCTGTGTAAAGGCAAGTATTTGAAGCTAGGAGAACTGTTCCTTCTGGCC
TGTTGCCCTCTCACAGAGCACTTTAAAGTGAGCTGTGATGTGTAACTTggaaaaca
ggtctctcataatagg (SEQ ID NO: 296)
For: 5'-3' = gaatgggtgttacatggaga (SEQ ID NO: 297)
Rev 5'-3' = cctattatgagagacctgttttcc (SEQ ID NO: 298)

M100 = G3.04c (395 bp nominal) in tree (penta microsatellite) (GTTTT)5; (GTTTT)6 =
most men); (GTTTT)7; (GTTTT)8 alleles detected
GaatgggtgttacatggagaCTACAGGGCTGTTATATTCATAACTTTAGGCTATCATTAT
TGAGGGCTGGATGTCCCTCTGAGCCTCAGGATTCAAAGGATACTGTTTTGTT
TTGTTTTGTTTTGTTTTGTTTTTTCCCACGGGTAATTAACACTGGGTTTTAG
GACAGTCTGGACTGGGGGTACATTAACAGTTGTACTAGAAACTTCCATGTCTC
AAACAGAGGGGTCTACTAGAGAAGCAATATGTCATGGAAGGCAGTTCTTCTC
CATATCTGTGTAAAGGCAAGTATTTGAAGCTAGGAGAACTGTTCCTTCTGGCC
TGTTGCCCTCTCACAGAGCACTTTAAAGTGAGCTGTGATGTGTAACTTggaaaaca
ggtctctcataatagg (SEQ ID NO: 299)
For: 5'-3' = gaatgggtgttacatggaga (SEQ ID NO: 300)
Rev 5'-3' = cctattatgagagacctgttttcc (SEQ ID NO: 301)

M101 = A8.05a original (460 bp) C to T at position 154
TcacagcagcttcagaaaCACAGATTTCTGGTGTTGGAGGACAGATTTAACTACAGAA
AATTCTGTTGGGCAATCGGAAGCCTCAATCTATACAGACTTTTAGGAGGAGC
CTGCCTGTTTGGTTCAAATTTAGCCAAAATATTTTTTTTTTAYCACTCGATTCA
GTAAATCTCCTAACTTTGCAGGAACTGGGATCCTAAAAATTATGGAACGAAT
TGTAGAAACTCAAGCAACTTTCTCCAAAGCCTAGGGttcagcaagagtaagcaagaggCA
CTGAGCCGCTGGAGTCTGCACATTGATAAATTTACTTACAGTCGTAAATAAAT
TGCATCATCTTCAgctagtaacacagagtctaatttttatAGCGGCATACTTGCCTCCACGACT
TTCCTAGACACCAGAAAGAAGGCGAGAGCCAGCCTTAGCCTAATCaagaaccat
gatccaaaaagg (SEQ ID NO: 302)
For: 5'-3' = tcacagcagcttcagcaaa (SEQ ID NO: 303)
new R 5'-3' = ataaaaattagactctgtgttactagc (SEQ ID NO:304) (used with F primer, just ampli-
fies (369 bp)
the first 2 sites including homopolymer T region
Rev 5'-3' = ccttttggatcatggttctt (SEQ ID NO: 305)

M102 = B9.101 (480 bp) G to C at position 301
AaactgggacacttgtaatgaatAATTACTTTGTTTGTAAATCACAATAGAGATTCTCCATA
TCAAAGCTGTGAACTGTATTCTATAGTATTTAGGCAAATAAGATAGCTACAA
ATTTAAGTACTGTAATAATAGATGCCTGACAATATGTGCTATAGGTAAATCTT
TGAAATTTATTAAATGAAGTATAGATTGAATACAAGTAATATGTAATAATAC
ATTATAATTTAATAACATTTAGAATAATTACATTTTATACAAAAATAAAATTA
AGAtaaaattcacatagtgcaatggtgASTAAGATGTGAAAAGACAATAAGAATAAACAGC
ATTAAAATTATTGATAGAGTTTGTAAAACCCCTAGAGATTAAGGAAAACAAA
CATAGGAATAAATTAGAAACTAGAGACAATAATAATTTCTGTAAATTATAG
GCTACCAAAACCAGAATaagaataaacaaggactcaaaaac (SEQ ID NO: 306)
For: 5'-3' = aaactgggacacttgtaatgaat (SEQ ID NO: 307)
New R 5'-3' -taaaattcacatagtgcaatggtg (SEQ ID NO: 308)

TABLE 1-continued

Rev 5'-3' = gtttttttgagtccttgtttattctt (SEQ ID NO: 309)

M103 = B9.117new (463 bp) C to T at position 259
CagtaagtgaactcacacataattccACAGGCATCTGAGCCCGTAGCAGCCTCAGCTGCCAT
TTTGATGGCAACCTAGATACTGGGGTTCTACAGACACAACTGCAGCCACTGT
ACTGCTCCAAGGACACAGAACAGGTATACACACACACCCATGGAGGGGTATT
TGCCACATTGCTATGAGCTGCTGTTGAGACTGAGAATTGGCCAGACCATGCTC
TTCACAGCTTCTTGCTCCTGCTCCTTGCCTAGGTTCTCCYCCACCTTCTCTGGT
CTTGAACCCAATATGCCATTTTAGAGAGTTTGATGTTGGATAGTACCCCACCC
TTGGCCTGAGTTCAGGTTGATGCAGTTGCAGTCGCTGCCCATCCAAGAAGAG
ACAAAAACACTAGGCTATCCTCTTCATACTTAGAATAATATCCACTGCTCTGC
AACAAGACgctgtgaaactgaaataaaactgg (SEQ ID NO: 310)
For: 5'-3' = cagtaagtgaactcacacataattcc (SEQ ID NO: 311)
Rev 5'-3' = ccagttttatttcagtttcacagc (SEQ ID NO: 312)

M104 = DYS257a (288 bp) Duplicated locus. Most men have both A and G alleles at
position 162, however some have only A allele. The second site at position 202 is often
just C, although sometimes both C and T alleles occur.
GaacttgtcgggaggcaatGGTGACATTCATTGTGACCTTAGCCAGAGCTCACAATCAA
CCATGGTGCACTGAGACTAGCTCATGCACATTCATCAGGCAGATTCAGGCAC
CTGGCTGTCAGAGCTGTCAGCCTTCCTCAGTAGAGGAAAATGCTACAGTCRG
CACTGGCCTGGTATCAGGAAAATAGATGCCTGCAAAAAYCCACTGTGGGACC
CTAAAAGTCTTGACCTCAGGTCCCCTTTGTGCTGTCTCTGTTGTCAGGATccacta
aaggaggaagtgtatca (SEQ ID NO: 313)
For: 5'-3' = gaacttgtcgggaggcaat (SEQ ID NO: 314)
Rev 5'-3' = tgatacacttcctcctttagtgg (SEQ ID NO: 315)

M105 = B9.6-7a (572 bp) C to T at position 478
GggaggcaacctaagaaagGTGTACAACTGTCCTGACATTGGATTGCCTGCTTACTGTG
AAGTATGTGAACAATTTGTGACTCAGAACTTTAGTGAGATTTTTATAGGCAGA
AGTTCTCATCATGCCTCATCAGAATTTTCCGTTAACAAGTGTCAGAGAATCTG
TAATGGCTTGAGAATCATGACTTTCCTCCTATTTATGGAAGAGGAGAAAAAA
GAAATTTCGAAGACAATTCTCAGATTTAGATAAATTATCTCAGGATTTTCTAT
ATATTTTACCTGGTCCCTATGGTGTGGTAAGGTAAAGTACACTGTACTTGGAC
AGGTGAAGCAATTTCTACTCTACTAGGTCATCACCAAGCATAGCTTTGTTACT
GGGAAAGCTAATTATAGTTCCCTATGACAGTATCAAAGAAAGAAAGAGGTGA
AAAGAGTAGACAATAAGGAAGGTAGGTATGATTATAGGCATGAGAAATGYT
ATGGGTAATAACGTGTTCTACACTGACTCAAGTCAGCAAGGAGTAGGTGGAA
AAGCGAGAGATTCAATCCAGGatgacagaatgcgttcacct (SEQ ID NO: 316)
For: 5'-3' = gggaggcaacctaagaaag (SEQ ID NO: 317)
Rev 5'-3' = aggtgaacgcattctgtcat (SEQ ID NO: 318)

M106 = B9.6-7b (572 bp) A to G at position 411
GggaggcaacctaagaaagGTGTACAACTGTCCTGACATTGGATTGCCTGCTTACTGTG
AAGTATGTGAACAATTTGTGACTCAGAACTTTAGTGAGATTTTTATAGGCAGA
AGTTCTCATCATGCCTCATCAGAATTTTCCGTTAACAAGTGTCAGAGAATCTG
TAATGGCTTGAGAATCATGACTTTCCTCCTATTTATGGAAGAGGAGAAAAAA
GAAATTTCGAAGACAATTCTCAGATTTAGATAAATTATCTCAGGATTTTCTAT
ATATTTTACCTGGTCCCTATGGTGTGGTAAGGTAAAGTACACTGTACTTGGAC
AGGTGAAGCAATTTCTACTCTACTAGGTCATCACCAAGCATAGCTTTGTTACT
GGGAAAGCTAATTATAGTTCCCTATGACAGTATCRAAGAAAGAAAGAGGTG
AAAAGAGTAGACAATAAGGAAGGTAGGTATGATTATAGGCATGAGAAATGC
TATGGGTAATAACGTGTTCTACACTGACTCAAGTCAGCAAGGAGTAGGTGGA
AAAGCGAGAGATTCAATCCAGGatgacagaatgcgttcacct (SEQ ID NO: 319)
For: 5'-3' = gggaggcaacctaagaaag (SEQ ID NO: 320)
Rev 5'-3' = aggtgaacgcattctgtcat (SEQ ID NO: 321)

M107 = B9.112n (376 bp) A to G at position 298
CaaaagcactcggggttcctTGTTTCAATCCCACCTCACATACACATAAGCATCATTAACA
GTACAGCGTGGGCTCTTTATCCCATCTTGTGCACCGCTTGCCTGAGAGAATT
TGCTACTGGTCCTGGGGAGCCCTGTCATATTCCCTTAGCAGGCCTGCAAAGAT
CTGTGTCCATTTCTTTTCCAAAAAGTCATTTTTCTCTCAACATCCCAATCTCAT
TTCCAAAACTGTCAATAAATATCAAGTTTCTTAGATTTTACTCATTTCTTAAGC
CAACGTATTAACCTTCTAATTTCRTGAATGCTAATAGAAAGCATGAGACACC
TATGCATCATATAAAAGTGTTTTTTATTcgttgcataagtgggagtaaag (SEQ ID NO: 322)
For: 5'-3' = caaaagcactcggggttcct (SEQ ID NO: 323)
Rev 5'-3' = ctttactcccacttatgcaacg (SEQ ID NO: 324)

M108 = B9.113n (321 bp) T to C at position 40. Probably recurrent
AgatggagccagcagaaagGAGAGAAGTAGATGAACATCYGAAACTATACCTGAATG
TCAGAGAAAAGTGGATTGACTTCAGAGGAACAGCTTGATGGTGTAACTTTGG
AGAAGAATCCGGCTGGAGACTTTAGTGATCTGGGTAGAAGATAAAATCATCC
ACAATATTTACTGGGGTTTTTTTGCATTTCCTGAATTTGAATCTTGGCCAGAG
TAAAGGGAAATATTCATCCCTCCTCCTTTTTAGCACCCATTCCCACTTAAAGC
CACCTCTATCACATAAAATCCTCCACATTTaccatcattcaattcatcgtgt (SEQ ID NO: 325)
For: 5'-3' = agatggagccagcagaaag (SEQ ID NO: 326)
Rev 5'-3' = acacagatgaattgaatgatggt (SEQ ID NO: 327)

M109 = G3.15 (312 bp) C to T at position 264

TABLE 1-continued

```
GggtatcaaatgtcttcaacctAAAGTACAAGGAATTATTTCTCAGTGTTTGGAATGACTT
GACTTCCTTGAAAATATTGTTGCAGAGTTGGGGACTACTTTTAAAATATCCTC
CATTGAATGTAATTCTACATGAAAGCTTGATTTTTCAAGTGCAAAATGCAAGT
GAGAAATAAGGCATATCATTCATTAAACCCTAATTCCAGCACTTTTAAATGA
GCTACTTTCTTGTATAATATTTTAGCTATTAAGGAACAAATTGTYGCTTAAGA
AATGTATCTATCTTAAAAATgcaagtagcaggaaattccc (SEQ ID NO: 328)
For: 5'-3' = gggtatcaaatgtcttcaacct (SEQ ID NO: 329)
Rev 5'-3' = gggaatttcctgctacttgc (SEQ ID NO: 330)

M110 = B9.86n (389 bp) T to C at position 241
CagggaaggaccgtaaaaggCTGTGGTGCTGATCAACGAAGGATTTCTCGGAGAAAATT
CCTCCTTTGCGGAAATGTCCGTAGAAACGCACCTTTTTTTTTCCTGCCAGGA
CAAACCGCCGGCGATATCCGTTCATGTGAAAGTGTTTACTAACATTCTCTGAA
GACTCACTGGGTTCTCAGCTCGAGAACGTTCCTGTCACAAGACGTTTAGGAG
GCAGGATGCCGGTACAATGTATTYATGTTCTTGTAAACTGTTGCATTAACAGT
GCACTTCAAGTGGGCACATTTGTCGTTGGATTTTTTACCAACTCGAGCTTGGA
CTTTAGGACGGGGAAAAGAAGTGCTAAATGTTTTTGAATAAaacctttactgcacatgat
aaacat (SEQ ID NO: 331)
For: 5'-3' = cagggaaggaccgtaaaagg (SEQ ID NO: 332)
Rev 5'-3' = atgtttatcatgtgcagtaaaggtt (SEQ ID NO: 333)

M111 = G3.19 (393 bp) -2bp (TT) deletion at position 188-189 interval. Polymorphic
STS = 391 bp.
AatcttctgcaaagggttccTTTGGGTTTTGTTGTTGTTGTTGTTTCCAATGCTAGCCAGA
GCAATAATTCTGAAAGGAAACCAAATTCCAAAATACAATGCAGATCTTCGTA
ATATTGTATTGTAACACAGTGTATCTAACATAAACAGTATGCCAAAAACAAC
AGAACAAGTTCTGTTTTTCACATTGTTTTCTCCCCAAAATTTACCTTTCACAC
AAAACAAGTACCACAAAGAAGTGTCACAGCCTAAGAAACTGCCTTAGTATAA
CATTAAGAGCTTACATCCAGATTTACATCTGATAAAATATGACTGCTGGTATT
AACTTTAGGGCATATAAGGTATCTTCATCTCTTCTGAAAGAAGTGGgtccagtatttt
gttttgtagctg (SEQ ID NO: 334)
For: 5'-3' = aatcttctgcaaagggttcc (SEQ ID NO: 335)
Rev 5'-3' = cagctacaaaacaaaatactggac (SEQ ID NO: 336)

M112 = G3.17a (445 bp) G to A at position 286
ActttttccaacagttattttgaACTTCACTGTTACACAGTTGAGGTGACATTCATTATAAA
GAATACACAGAGGCTACTATATTAACCATTATATCTATATCTTTAGTTAACCT
GAACGAAGTTGAGTAGATAAAATAAGATTCACATTAGGTAAAAAAACAAAA
ACAAAAACAAAAACAAAAACAAAAAACACAAACTCTACAGAAGTCTTGAAA
AGCAAAAGAGAACTGCCTCTTATAAAATCATATCCTTAAAAAAGAGGTGAGA
TAAAAACAAAGCAGTRTTTTTATCAGTACTGCATCCTTTTTTTCACAGTTATT
TTCATTTACAGTTTGAAAGAGGTAGATAATTCTGCAACAGACAAGAATTGAA
CTGTGATTATCAGGTGTAATAAAATAGTTCCATTAACTTAGAAATattggtctcatcat
caagaaatata (SEQ ID NO: 337)
For: 5'-3' = acttttccaacagttattttga (SEQ ID NO: 338)
Rev 5'-3' = tatatttcttgatgatgagaccaat (SEQ ID NO: 339)

M113 = G3.17b (445 bp) A to G at position 112
ActttttccaacagttattttgaACTTCACTGTTACACAGTTGAGGTGACATTCATTATAAA
GAATACACAGAGGCTACTATATTAACCATTATATCTATATCTTTAGTTRACCT
GAACGAAGTTGAGTAGATAAAATAAGATTCACATTAGGTAAAAAAACAAAA
ACAAAAACAAAAACAAAAACAAAAAACACAAACTCTACAGAAGTCTTGAAA
AGCAAAAGAGAACTGCCTCTTATAAAATCATATCCTTAAAAAAGAGGTGAGA
TAAAAACAAAGCAGTGTTTTTATCAGTACTGCATCCTTTTTTTCACAGTTATT
TTCATTTACAGTTTGAAAGAGGTAGATAATTCTGCAACAGACAAGAATTGAA
CTGTGATTATCAGGTGTAATAAAATAGTTCCATTAACTTAGAAATattggtctcatcat
caagaaatata (SEQ ID NO: 340)
For: 5'-3' = acttttccaacagttattttga (SEQ ID NO: 341)
Rev 5'-3' = tatatttcttgatgatgagaccaat (SEQ ID NO: 342)

M114 = G3.23 (434 bp) T to C at position 387
TtaccacacagttgagtagttctaaaAAAACAGAGATATGGTAGAAAAAGGAGAGGAAATT
TTCATTACAAAATCAATAGTTACAACTAAAAGAGAAACATGTACACAAAATA
TATCCATCAGTACAATGATCACACTTAATCTTAATCAATGCCTAGAGGAGATC
CTGTGGAGAGGGCTTTTGAGTAGCATTTTACTTCATTCATTCCTTTGGGGTCA
GCCTCCAGATGGACTCCTGGGGCTCTTTTAGAGGAAGTGTTCAGCATATTGGA
AGAATCCAGGTCAGCACAGGAATGCGTCACAGGCACTGCTAAATCTACATCT
GCTACTTTCACAGAGACCTGCCCTTTCAGAATTCCCAGTTTCTCACTGAGTTC
ATTCCTTTCYATTTGAAGAGCCTTGTACAGCTTCTCtaaccgctccaatttatttg (SEQ ID NO: 343)
For: 5'-3' = ttaccacacagttgagtagttctaaa (SEQ ID NO: 344)
Rev 5'-3' = caaataaaattggagcggtta (SEQ ID NO: 345)

M115 = G3.22 (413 bp) C to T at position 201
agtttacagtcacatcaatttggaAAGTCATACAAATATTGTCAAAAAACTGATCTGAATCA
AATATGCCATGCTTGTTTCTTAATCCATTGAAGTTTTACTTATCATTTAAATGA
CTTGACAATATTAGTCAGTTTATATTTTCTTTTATGTAGATATTATGGGCTCCA
GAGTTTAAATTAGTATTTGATTTCACATTAYGAAACCATTATAAAAAGTCTC
AAATTAAGATAATTTAAGGTGATGAACACACAAACGTACACTTTGAAAGGAG
AAGGCAATGAAAACATGCATTCCAATAAAGGGGGAAAATGAGGCTGATGTG
```

TABLE 1-continued

CAACATAGTTGGGGAAATTGGTAAGAAGCTTTCTGTTACCACACAGTTGAGT
AGTTCTAAAAaaacagagatatggtagaaaaagga (SEQ ID NO: 346)
For: 5'-3' = agtttacagtcacatcaatttgga (SEQ ID NO: 347)
Rev 5'-3' = tccttttttaccatatctctgttt (SEQ ID NO: 348)

M116 = G3.25a (429 bp) Three alleles. A to T (M116.2) or A to C (M116.1) at
position 176
aagtatgacttatgaagtacgaagaaaATCAAGGCTATTAATCAAAAATACCAGCAAAACTTT
TCCTATAGAAGCAAAGATAATGTTATAATTGTTAATTTCTTTTTTTATATAAAA
TAACTCACCAAAGGAATGCACATCTATCTGCTTTCTGAAAAAATAATTTCAA
ACTGATAHCTGTCAATTTTAATTATCTTAATTAAAATAAGCCATATTATGTTT
TTCTATCATCTAATAAGCTCTTTAGTGAAGAGCTAAAAATATATATAAAGAAC
ATAAAATCATATCCAACTATTAAGGGAAGATGCTATTTTCATCTACTTGCAGT
TTTTTCTACCCAAATATAAATAATTTGTTTTAGCCATATTATCTCATTACTGAAG
TATCATAGGATGACTGAGTAGACtgctcattgtaaaatctaactgaat (SEQ ID NO: 349)
For: 5'-3' = aagtatgacttatgaagtacgaagaaa (SEQ ID NO: 350)
Rev 5'-3' = attcagttagattttacaatgagca (SEQ ID NO: 351)

M117 = G3.25b (429 bp) -4bp deletion at position interval 142 to 145
AagtatgacttatgaagtacgaagaaaATCAAGGCTATTAATCAAAAATACCAGCAAAACTT
TTCCTATAGAAGCAAAGATAATGTTATAATTGTTAATTTCTTTTTTTATATAAA
ATAACTCACCAAAGGAATGCACATCTATCTGCTTTCTGAAAAAATAATTTCA
AACTGATAACTGTCAATTTTAATTATCTTAATTAAAATAAGCCATATTATGTT
TTTCTATCATCTAATAAGCTCTTTAGTGAAGAGCTAAAAATATATATAAAGAA
CATAAAATCATATCCAACTATTAAGGGAAGATGCTATTTTCATCTACTTGCAG
TTTTTCTACCCAAATATAAATAATTTGTTTTAGCCATATTATCTCATTACTGAA
GTATCATAGGATGACTGAGTAGACtgctcattgtaaaatctaactgaat (SEQ ID NO: 352)
For: 5'-3' = aagtatgacttatgaagtacgaagaaa (SEQ ID NO: 353)
Rev 5'-3' = attcagttagattttacaatgagca (SEQ ID NO: 354)

M118 = G3.29 (478 bp) A to T at position 109
AttctaagtttcacttcctgatccACCACAGAAATCACTTTACAATGTTCTTCCCTTCCTCCA
TCACTGCATTCTTCTCAACCAGCTGACACTTGTGTTTTCTTTATAWGAGTAAG
TGGTATCTTTCTTTTGTTAGTAAAGTTTATCTCAGAAGCTCCTATGGTAAAAG
CAGCAGTAACCAAAGCAGAAGTTTCACATTAAAAGAAAACAAAGTTGTTGTC
CTTAATTTCAAGGGAATCAGCACATGGTAGCTGAATTCTCTCAATTAAGACTG
ATGTGTAGCTCAGCTCAGGTGTGGACAGTAGAGCTGAGACCTCCTGCTCCTG
AAGTATATGAAAAAATGTCCCCGAGTTTTCTGGAGAAATGATAAATTACACT
AATCCATCAGATTATTTTATATACTGTCAGTCCCAAAGTAGCTCAAGAATCTG
AAAGGAAATCAGTGTAAGAGCTAgaggtagcgtaatttagggaacta (SEQ ID NO: 355)
For: 5'-3' = attctaagtttcacttcctgatcc (SEQ ID NO: 356)
Rev 5'-3' = tagttccctaaattacgctacctc (SEQ ID NO: 357)

M119 = G3.32 (330 bp) A to C at position 224
GaatgcttatgaatttcccagaCACAGCTACTGTACTATCTCCAATCAGCACATTTTAAAG
AAATCTTAACTTAAATAGGGAAATGCCAAGGTAAATGACTCACCCTAAGGAA
GTCACGAAGTGCAAGTTAGAGATCTCAGTTTCAGAGTTTATGCTCCAAACCG
CAGTGCTATGTGTTTATTTGGGGAGACAGATAATTCTGCTCTTTAAAATTGCT
ATTTTMGCCTGTATGCTGAATTGGAATAACCCATAACATTTTTCTACATCTA
ATTTTAAAAAAACGGTTTAAATTTTGTATTAATTaagaatacatcttgtatattgtgtgaa (SEQ ID NO: 358)
For: 5'-3' = gaatgcttatgaatttcccaga (SEQ ID NO: 359)
Rev 5'-3': ttcacacaatatacaagatgtattctt (SEQ ID NO: 360)

M120 = B9.87b (495 bp) T to C at position 224
GagcttggactttaggacggGGAAAAGAAGTGCTAAATGTTTTTGAATAAAACCTTTACT
GCACATGATAAACATCCCTTAAAAATTACCTAGGAGCACCCTAAATTTTAAA
ATGATCACAAAGACCTGGACAGATTACAGTAAACCTTCAACATCGCTAAACA
CACGTACCATAAATCAAAAGAAACACACTGCTAATGATCCGTTTTTTGATGT
GGAAATAYCATGCTGTTTTTAAGGGAAATTATACTTTATTGCGATGTTTTATT
TCAAAACAAGATGTTACACTTTATTTCCTATAATTTTATTTACAATATTTTACA
CCCGTTAAGCAAAAATCCCCCTACATTGCTATTCTGTTTTTTTTTTAATCAGTT
CACTACTGTAGTATCTTTTTGTTCTCCATATATTTTTGAAAAATACGCAAAAG
GTAAGTTTTAAAAATCAAATGGTAGATTTTATTTGGAAGGGCACTgccagaagtgcc
ttaaagttt (SEQ ID NO: 361)
For: 5'-3' = gagcttggactttaggacgg (SEQ ID NO: 362)
Rev 5'-3': aaactttaaggcacttctggc (SEQ ID NO: 363)

M121 = B9.87c (495 bp) 5 bp deletion at position interval 183-187
GagcttggactttaggacggGGAAAAGAAGTGCTAAATGTTTTTGAATAAAACCTTTACT
GCACATGATAAACATCCCTTAAAAATTACCTAGGAGCACCCTAAATTTTAAA
ATGATCACAAAGACCTGGACAGATTACAGTAAACCTTCAACATCGCTAAACA
CACGTACCATAAATCAAAAGAAACACACTGCTAATGATCCGTTTTTTGATGT
GGAAATATCATGCTGTTTTTAAGGGAAATTATACTTTATTGCGATGTTTTATT
TCAAAACAAGATGTTACACTTTATTTCCTATAATTTTATTTACAATATTTTACA
CCCGTTAAGCAAAAATCCCCCTACATTGCTATTCTGTTTTTTTTTTAATCAGTT
CACTACTGTAGTATCTTTTTGTTCTCCATATATTTTTGAAAAATACGCAAAAG
GTAAGTTTTAAAAATCAAATGGTAGATTTTATTTGGAAGGGCACTgccagaagtgcc
ttaaagttt (SEQ ID NO: 364)
For: 5'-3' = gagcttggactttaggacgg (SEQ ID NO: 365)

TABLE 1-continued

Rev 5'-3' = aaactttaaggcacttctggc (SEQ ID NO: 366)

M122 = G3.27a (393 bp) T to C substitution at position 73
TggtaaactctacttagttgcctttTGGAAATGAATAAATCAAGGTAGAAAAGCAATTGAGA
TACTAATTCAYGCTCTCAGGGGAAAATCTGAATAAAGCTATCTTTTCTAACA
CAGAGCAAGTGACTCTCAAAGTCACAGTATCTGAACTAGCATATCAGCATCG
CCTGAATACCTAGAAATGCAAATTCCTGGGCAACACCAGAATCTAACAAAGC
AAAAAACTATGGGGGGAACAGGGAAGTCGGTTTAATAATACTGAGTTTGTGC
AACCTCAACTTTGCTTTATAGGAAAGCAAAATCTCAATATGATAAAGTTTTCT
TCAACAAAACTCTGAGATAACTATGTTGAGGGAAAGAAGTTGATCACATgcaag
aaaatctaattcgctg (SEQ ID NO: 367)
For: 5'-3' = tggtaaactctacttagttgcctttt (SEQ ID NO: 368)
Rev 5'-3' = cagcgaattagatttcttgc (SEQ ID NO: 369)

M123 = G3.27b (393 bp) G to A at position 161
Tggtaaactctacttagttgcctttt TGGAAATGAATAAATCAAGGTAGAAAAGCAATTGAGA
TACTAATTCATGCTCTCAGGGGAAAATCTGAATAAAGCTATCTTTTCTAACAC
AGAGCAAGTGACTCTCAAAGTCACAGTATCTGAACTAGCATATCARCATCGC
CTGAATACCTAGAAATGCAAATTCCTGGGCAACACCAGAATCTAACAAAGCA
AAAAACTATGGGGGGAACAGGGAAGTCGGTTTAATAATACTGAGTTTGTGCA
ACCTCAACTTTGCTTTATAGGAAAGCAAAATCTCAATATGATAAAGTTTTCTT
CAACAAAACTCTGAGATAACTATGTTGAGGGAAAGAAGTTGATCACATgcaaga
aaatctaattcgctg (SEQ ID NO: 370)
For: 5'-3' = tggtaaactctacttagttgcctttt (SEQ ID NO: 371)
Rev 5'-3' = cagcgaattagatttcttgc (SEQ ID NO: 372)

M124 = G3.27c (393 bp) C to T at position 246
Tggtaaactctacttagttgcctttt TGGAAATGAATAAATCAAGGTAGAAAAGCAATTGAGA
TACTAATTCATGCTCTCAGGGGAAAATCTGAATAAAGCTATCTTTTCTAACAC
AGAGCAAGTGACTCTCAAAGTCACAGTATCTGAACTAGCATATCAGCATCGC
CTGAATACCTAGAAATGCAAATTCCTGGGCAACACCAGAATCTAACAAAGCA
AAAAACTATGGGGGGAACAGGGAAGTYGGTTTAATAATACTGAGTTTGTGC
AACCTCAACTTTGCTTTATAGGAAAGCAAAATCTCAATATGATAAAGTTTTCT
TCAACAAAACTCTGAGATAACTATGTTGAGGGAAAGAAGTTGATCACATgcaag
aaaatctaattcgctg (SEQ ID NO: 373)
For: 5'-3' = tggtaaactctacttagttgccttt (SEQ ID NO: 374)
Rev 5'-3' = cagcgaattagatttcttgc (SEQ ID NO: 375)

M125 = B9.108a (367 bp) T to C at position 301
GccaccctcttatgcctctGGCCTTTACAAAGACAGCTGGTAAGAGGCTGCCCAGCTCAT
CTGAAGTACAGGATAAGATTGTCTGACTTGGAGATACCATTTTCCACTTAGCA
GCCATGTAATCTTTCATATTCATTTTTTCTAAGTGGCACTTTTCTCAGATGTAA
AATGGGGATAATGAGTTTATTCATCTTTGAGTTGCTCCCAAGCAGAAGTCAAC
TTGAGACTATAAACTTGTGCTCACTGCAGTGCTTGAAACCGAGTTTGTACTTA
ATAAATAGCTGCATACATCTTTTTCTAYACATGTCAGATGCTTAATTGTGTTT
CCCGAAGATGTTGCCAAGCCgggtcctcacataactcctga (SEQ ID NO: 376)
For: 5'-3' = gccaccctcttatgcctct (SEQ ID NO: 377)
Rev 5'-3' = tcaggagttatgtgaggaccc (SEQ ID NO: 378)

M126 = B9.108b (367 bp nominal) 4 bp deletion (AATA) at interval 277–280.
GccaccctcttatgcctctGGCCTTTACAAAGACAGCTGGTAAGAGGCTGCCCAGCTCAT
CTGAAGTACAGGATAAGATTGTCTGACTTGGAGATACCATTTTCCACTTAGCA
GCCATGTAATCTTTCATATTCATTTTTTCTAAGTGGCACTTTTCTCAGATGTAA
AATGGGGATAATGAGTTTATTCATCTTTGAGTTGCTCCCAAGCAGAAGTCAAC
TTGAGACTATAAACTTGTGCTCACTGCAGTGCTTGAAACCGAGTTTGTACTTA
ATAAATAGCTGCATACATCTTTTTCTATACATGTCAGATGCTTAATTGTGTTT
CCCGAAGATGTTGCCAAGCCgggtcctcacataactcctga (SEQ ID NO: 379)
For: 5'-3' = gccaccctcttatgcctct (SEQ ID NO: 380)
Rev 5'-3' = tcaggagttatgtgaggaccc (SEQ ID NO: 381)

M127 = G3.30 (412 bp) C to A at position 372 bp
TgaaaggaaatcagtgtaagagcTAGAGGTAGCGTAATTTAGGGAACTAATCAGGAAAGA
GGTATTAACATTTCTGAATCCTTAGTTTCACTTATCCTTTCAATTCACAAGATT
GCTTTATTTCACATTTTGATAAAGACCAAAATGGTCCAAAAATAAGGGGAGG
AAGAACCTATACTACAAGAACCGAATTCCCAGACACTCAGGATAAACTTTAG
GTATATCCTTCAATCAGCTTTGTTCCAAATACAGGTAACGAGCCAGGCAATGT
TACGGAAAATAAGGGTAAGATAAAGCAAATATCCTGTGCTTTGGTTAACAAA
CAAAACTGTATCACAAGTCAAACTCGTACAAAAGGCAGGAGAAGAGGTMTG
GAAGATCTGTTAGGtgctgaactacagtcacctttaca (SEQ ID NO: 382)
For: 5'-3' = tgaaaggaaatcagtgtaagagc (SEQ ID NO: 383)
Rev 5'-3' = tgtaaaggtgactgtagttcagca (SEQ ID NO: 384)

M128 = G3.17c (445 bp vs 443 bp) -2 bp deletion (CA) at position interval 316–317
ActttttccaacagttatttttgaACTTCACTGTTACACAGTTGAGGTGACATTCATTATAAA
GAATACACAGAGGCTACTATATTAACCATTATATCTATATCTTTAGTTAACCT
GAACGAAGTTGAGTAGATAAAATAAGATTCACATTAGGTAAAAAACAAAA
ACAAAAACAAAAACAAAAACAAAAACACAAACTCTACAGAAGTCTTGAAA
AGCAAAAGAGAACTGCCTCTTATAAAATCATATCCTTAAAAAAGAGGTGAGA
TAAAAACAAAGCAGTGTTTTTATCAGTACTGCATCCTTTTTTTCACAGTTATT TABLE 1-continued

```
TTCATTTACAGTTTGAAAGAGGTAGATAATTCTGCAACAGACAAGAATTGAA
CTGTGATTATCAGGTGTAATAAAATAGTTCCATTAACTTAGAAATattggtctcatcat
caagaaatata (SEQ ID NO: 385)
For: 5'-3' = acttttttccaacagttattttttga (SEQ ID NO: 386)
Rev 5'-3' = tatatttcttgatgatgagaccaat (SEQ ID NO: 387)
```

M129 = A8.04 (255 bp) G to A at position 221.
There is a polymorphic (CA)n motif immediately adjacent to the 3' end of STS
```
AatggcttactacaaagaacatttcTGTAGTATATTTTTATGTATGTATGTATTATGTATTTAT
TTATTTATTTATTTTTGAGACAGAGTCACAATGCTGCCCAGGCCCTAGTGCAG
TGGTGTGATCTTAGCTTACTGCAACATCTGCTTCTGTGTTCAAGAGATTCTCCT
GCCCTTAGCCTGTGGAGTAGCTGGAATTACAGGTGCACACCACCAAGCCCRGC
TAATTTTTAtcttcttggtagagaccgtgta (SEQ ID NO: 388)
For: 5'-3' = aatggcttactacaaagaacatttc (SEQ ID NO: 389)
Rev 5'-3' = tacacggtctctaccaaagaaga (SEQ ID NO: 390)
```

M131 = A8.14n (306 bp) 9 bp deletion at interval 93 to 101
```
CacacccagaatacaataattttAAAAACATAATAAAGGTCAATTTAGAGCAGAGAAATTA
TTCTTTTAAATTACAAATGTTTGCTGTTCAGGCAAATTACACAGAAAGTTA
AGAATAACCCTTTAAATGATAGGAAAAGGCATTAGTAAGATAAAATGTGATT
ACTATTGAGATAAATATTTGCTATAAAAATAATTCAATTTGGTTAAACACAAA
TTGACTTCTTAAATAATCTTAAACATTAAGTAGAAGTAATTTTAGCTTATCAG
TAAATTTGAgaaaatgtacacttgtagaataaaaag (SEQ ID NO: 391)
For: 5'-3' = cacacccagaatacaataatttt (SEQ ID NO: 392)
Rev 5'-3' = cttttttattctacaagtgtacattttc (SEQ ID NO: 393)
```

M132 = B9.67b (568 bp) G to T at position 482
```
AacagaattatcaggaaaaggtttCATAAAATAAAAATCTTTTAAACTTATGAAAGATGCT
CAATATAAAAAACTGTAAACCAGGGAAATGCAAATAAAAATTACAATGAAA
TACTACACACCTCCCAGAATGGCTAAAATGAAAACAAAACTGTCAATTCTAA
GTGTTAGTGAGGACATGTGGTAACCAGAACTGGCATCCAATACTAGCTGATA
AACTCGTCAATCATTTGTAAAAACAGTCTGACAATAATCCACTAGTGAAAAT
ATACATAGTCTCAGTCACAGCAATTCTATCCTGTCTATCTAGGTAACAGAAAT
GTCTACATACGTTACCTAGAAACATATACTTTAATATCCACAGAATTACTTGA
AATAGCCAAAAATTGGTAACTACCAAAAGTTGAATGGTAAAACAGATAGAA
AAAAAGCTATGCCTAACAAAACTACACTTAATAGAACACAAGCGTGAGCATT
AATAKAACCATATAAATGCATTTTTTGAACCACTAAAAGAAGAAGCCAATAC
AAAAGAGGTGATTAAttgaaagtacacgaacaagtaaaa (SEQ ID NO: 394)
For: 5'-3' = aacagaattatcaggaaaaggttt (SEQ ID NO: 395)
Rev 5'-3' = ttttacttgttcgtgtactttcaa (SEQ ID NO: 396)
```

M133 = A8.08F-newR (211 bp nominal vs 210) 1bp (T) deletion at position 116. Site a.
STS contains homopolymer A which normally has 10 A's, but sometimes 11 A's (sited).
```
TgaaatggaaatcaataaaactcagtTTCCTCAAAGTTCAAAATACATGAGACTGCCTACCCT
CCTTGGAAGGCAAGGTGGGGCTTTCTGAAGCAAATACCAGCTTTAAAAAAAAA
ATGTATATATATATGAAGATATATACAAAAAAAAAATTTCCCCACAACCAGA
CAATCAGAATCATCAAACCCAgaagggttaaagaaaaagaaaagg (SEQ ID NO: 397)
For: 5'-3' = tgaaatggaaatcaataaaactcagt (SEQ ID NO: 398)
Rev 5'-3' = ccttttcttttctttaaccttc (SEQ ID NO: 399)
```

M134 = A8.08newF-R (232 bp nominal vs 231) 1bp deletion (G) at position 54 (site b).
```
AgaatcatcaaacccagaaggGTTAAAGAAAAAGAAAAGGCCCAGGAAAGTATGATTG
GTGGGGATCAAAAGTATCTCTCCACAGTGGTAAATGAGAATTCTCAAAAAGA
GTAAAATTATAATTCTCATGCACATATAAAATAAATATGTATTACAGATTTTA
CTTAAACCATATAGCTCAAAATTAGCTAACAAGGAAGACATTATAACctgttcaaa
gagaagccaaaga (SEQ ID NO: 400)
For: 5'-3' = agaatcatcaaacccagaagg (SEQ ID NO: 401)
Rev 5'-3' = tctttggcttctcttgaacag (SEQ ID NO: 402)
```

M135 = A8.08F-newR (211 bp nominal vs 212) 1 bp insertion (+C) at position 150 =
site c, within homopolymer A track.
```
tgaaatggaaatcaataaaactcagtTTCCTCAAAGTTCAAAATACATGAGACTGCCTACCCTC
CTTGGAAGGCAAGGTGGGGCTTTCTGAAGCAAATACCAGCTTTAAAAAAAAA
TGTATATATATATGAAGATATATACAAAAAAAAACATTTCCCCACAACCAGA
CAATCAGAATCATCAAACCCAgaagggttaaagaaaaagaaaagg (SEQ ID NO: 403)
Site a (A)₁₀-TTT most males
Site c (A)₉CATTT = M135
Site d (A)₁₁TTT
For: 5'-3' = tgaaatggaaatcaataaaactcagt (SEQ ID NO: 404)
Rev 5'-3' = ccttttcttttctttaaccttc (SEQ ID NO: 405)
```

M136 = B9.61 (339 bp) C to T at position 196
```
AtgtgaagacaacactgtgtggGAGAACCTAGGAAAGTAATTTTACATGCTAAAATGAGT
TTCCCTAGTTAATGTTAACATGAACTACCAACCGTATTACCTTCTCCTCAGGA
GATAAGTTTTGTTTGCTATTGCTGACAGGAAAGCCACTGCCAAATTCTTTGGA
ATGAATATCAGCTCCATATTCAACTGTCAYGTCTTCCTCAATGCTGCTCACCA
GCCTCCAGAATTCCTTCTCTACAAGTTCTGTAGGCACCATCTGTGAAAACACA
TGTAAAAGGTTATCATAGCCCACTATACTTTGGACTCATGTCTccatgagaactaagac
taccacaa (SEQ ID NO: 406)
```

TABLE 1-continued

For: 5'-3' = atgtgaagacaacactgtgtgg (SEQ ID NO: 407)
Rev 5'-3' = ttgtggtagtcttagttctcatgg (SEQ ID NO: 408)

M137 = G3.27d (393 bp) T to C at position 289
TggtaaactctacttagttgcctttTGGAAATGAATAAATCAAGGTAGAAAAGCAATTGAGA
TACTAATTCATGCTCTCAGGGGAAAATCTGAATAAAGCTATCTTTTCTAACAC
AGAGCAAGTGACTCTCAAAGTCACAGTATCTGAACTAGCATATCAGCATCGC
CTGAATACCTAGAAATGCAAATTCCTGGGCAACACCAGAATCTAACAAAGCA
AAAAACTATGGGGGGAACAGGGAAGTCGGTTTAATAATACTGAGTTTGTGCA
ACCTCAACTTTGCTTTAYAGGAAAGCAAAATCTCAATATGATAAAGTTTTCTT
CAACAAAACTCTGAGATAACTATGTTGAGGGAAAGAAGTTGATCACATgcaaga
aaatctaattcgctg (SEQ ID NO: 409)
For: 5'-3' = tggtaaactctacttagttgccttt (SEQ ID NO: 410)
Rev 5'-3' = cagcgaattagattttcttgc (SEQ ID NO: 411)

M138 = A8.17(442 bp) C to T at position 291
AacttccaaaactgtgaaaagattGTTTTTAAAAGGCTATAACAGTGACTTTCAGGTGAAGA
CTTGGACAAATAGATAATTTCTGTACCCATTAAAATCAGGGGCTGTTACTATG
TTTGAAGACATTGTCGCCACAGCTTGAAGTCTGTAAGGAAAACCTGTAAAAT
TAGTGGGTGCCCACTCTAGTTTTAATCATTTGAGTTTCCACTCCTCATTGTGGT
TGAACTATTTTATAACTCTGCAAAATCTAGAAAGTTGAAAAGAAACCAAAGA
TACTTTCCCTTTTCTTCYCACTTCTCCTACCCTTGGCCCACCTCCTTCTCCACC
TACTACTCCACATGGAACCTGGAGATTTGAGTCGGGGAGTGATGTAATACCT
GCGGCGCGTTGGCCCTTTACACACCTGTCAGCCATTTCAAGGCctgaagggctgcttt
aatc (SEQ ID NO: 412)
For: 5'-3' = aacttccaaaactgtgaaaagatt (SEQ ID NO: 413)
Rev: 5'-3' = gattaaagcagccccttcag (SEQ ID NO: 414)

M139 = A8.28a (459 bp nominal vs 460) 1 bp deletion at position 401. **5 G's to 4
G's.**
TtactgataatgccatattgttttgGCTTAATATCAGGCTAAGTAACCACAGTATTCTGATTTA
AAAAAAAACATACTAGAGAGCAAGTTTATTGACAAATCTTTAGGAACTTCAG
GTACAGCATATGATTTCTGAACTATGTGTGTAAATAAGGTTTTGTTTATTCA
ATTTAACACAGGGTAGTCTGTGTATGCCTTCCGATTTGATAGCTCTAATAAAA
CACTTTAATAGTACCATATCAAATAAATTTTATCATCATCGATTTTCTTCTTAA
TATGAAATAACACATATTTGTGATTTTTCTAAGAGTCAAAATCTCAAAAATCA
TTTTAGGTATAAAATATACCCCGAAAGTTTTATTTTATTCCATTTTATAATTAA
TCTGACTTGGAAAGGGGAAAAAAGCTCAAAGGGTATGTGAACATTTCATT
AAGATAggaccattggtgtctgagaa (SEQ ID NO: 415)
For: 5'-3' = ttactgataatgccatattgttttg (SEQ ID NO: 416)
Rev 5'-3' = ttctcagacaccaatggtcct (SEQ ID NO: 417)

M140 = A8.28b (459 bp nominal vs 460) 1 bp insertion within 9 A's
homopolymer (most men) to 11 A's at position 73. Recurrent because 11 A's found in
different haplogroups.
TtactgataatgccatattgttttgGCTTAATATCAGGCTAAGTAACCACAGTATTCTGATTTA
AAAAAAAAACATACTAGAGAGCAAGTTTATTGACAAATCTTTAGGAACTTCA
GGTACAGCATATGATTTCTGAACTATGTGTGTAAATAAGGTTTTGTTTATTCA
AATTTAACACAGGGTAGTCTGTGTATGCCTTCCGATTTGATAGCTCTAATAAA
ACACTTTAATAGTACCATATCAAATAAATTTTATCATCATCGATTTTCTTCTTA
ATATGAAATAACACATATTTGTGATTTTTCTAAGAGTCAAAATCTCAAAAATC
ATTTTAGGTATAAAATATACCCCGAAAGTTTTATTTTATTCCATTTTATAATTA
ATCTGACTTGGAAAGGGGAAAAAAGCTCAAAGGGTATGTGAACATTTCATT
AAGATAggaccattggtgtctgagaa (SEQ ID NO: 418)
For: 5'-3' = ttactgataatgccatattgttttg (SEQ ID NO: 419)
Rev 5'-3' = ttctcagacaccaatggtcct (SEQ ID NO: 420)

M141 = A8.30a (424 bp nominal) T to A at position 51. Locus also has **two
homopolymer** T tracks which are both polymorphic. See next below.
CatcttaaaatacatttcatagctttTCAAACTCAAATATGAAAACAATTWGTTTTTTAGATT
TTTTTTTTCTTTTTACTTCAAGTTCTTTATATTCTAGACTAACACTTTAGGGCA
GATATTGGAGGGTGTGTCTCTCTTGGTGCAACTATTGCCTTTGCTTCAAATGG
TGGCATATGGAGGAGGACACAACCTGTAGGAAGTGTTCAAGGAGTCTGGTAG
TGACACCTGCTCAATATTGCTAGTGATAAAACTGTAGCCACTGTATAGCAATA
TCTGCCTGTAGAATGTCATTTCCTTTGAGGGGTACATTTTTTTTAGAGTTTCC
TATAACCTCTAGAGCTGAACTTCATAAAAATAGGTAAAGGTTGGCCTTAAAA
AGCCTACATTACACACTTTCaggatgctagacctaatagtaagc (SEQ ID NO: 421)
For: 5'-3' = catcttaaaatacatttcatagcttt (SEQ ID NO: 422)
Rev 5'-3' = gcttactattaggtctagcatcct (SEQ ID NO: 423)

M142 = A8.30b,c (424 bp nominal vs 423) T to A, also has Homopolymers 10 T's to 9
T's at position interval 61 to 72 & 8 T's to 9 T's at position interval 311–319 in tree
CatcttaaaatacatttcatagctttTCAAACTCAAATATGAAAACAATTTGTTTTTTAGATTT
TTTTTTTCTTTTTACTTCAAGTTCTTTATATTCTAGACTAACACTTTAGGGCAG
ATATTGGAGGGTGTGTCTCTCTTGGTGCAACTATTGCCTTTGCTTCAAATGGT
GGCATATGGAGGAGGACACAACCTGTAGGAAGTGTTCAAGGAGTCTGGTAGT
GACACCTGCTCAATATTGCTAGTGATAAAACTGTAGCCACTGTATAGCAATAT
CTGCCTGTAGAATGTCATTTCCTTTGAGGGGTACATTTTTTTTAGAGTTTCCT
ATAACCTCTAGAGCTGAACTTCATAAAAATAGGTAAAGGTTGGCCTTAAAAA TABLE 1-continued GCCTACATTACACACTTTCaggatgctagacctaatagtaagc (SEQ ID NO: 424)
For: 5'-3' = catcttaaaatacatttcatagcttt (SEQ ID NO: 425)
Rev 5'-3' = gcttactattaggtctagcatcct (SEQ ID NO: 426)

M143 = B9.50b (385 bp) G to T at position 246
AtgctataataactaggtgttgaagATAAAATCAGTTTAATTTAAATAAGAGGATAAAAGAA
GTATGAGCAGAAAAAGGTTTTCAATATTAACTAGGAAAGTCTGAAAAATAAT
CAGAAATTCTAAAGATAAAAACATAACATTAAAAATTATAAACTAAGTTGTT
TAATAGATTAGGTATTTTAAAAACTGGTGCATTTTTAAGTTGCTTTAAGTAAG
TTACTTAAAAGACAACAGCAGCAAAAKAATTAAAAAAAAATGAAAGGTGAA
GAAACACATACAAGAGAACCTTAGAACAGTAAGGTTCTAGCTAACAGGAGA
AATAAATTACAGACTGTAAAAGTTGATGACCAAGAATTTTttcagaagtggtaaaagctg
aatt (SEQ ID NO: 427)
For: 5'-3' = atgctataataactaggtgttgaag (SEQ ID NO: 428)
Rev 5'-3' = aattcagcttttaccacttctgaa (SEQ ID NO: 429)

M144 = B9.99 (452 bp) T to C at position 342
AgcacaagggtcacattgagAGGTTTTAACTATAATTAAATTTTCATCTAATAAATATGA
TAATTATAAAGAAAACCAGCTGGTTTTTGGAAGACATCAAAGTGTTCTGTATC
AAGCAATAATCTCCATTAACCTATTCTGAATGGCAGGAGCAGTATGGACTGC
ATATTCTGAACTTTGGGAGGTAAATCTGTGTTGGAGCTGCTCACTGTCCATGG
AGGAGTGGAGCACAAAGTATCTGGGGGTGAAGGTCATGGCACCATTTTTCAG
CAGGGGGAGGAATAATTTTTGGTTTGAAATATTCAAAAAAAAATTTGAAAAA
ATTAAACTGGGTATGTGTYATTTGACCATAGTAAAAAAATTTTAACAGACC
TTTTTTTGATTATCATTACATAATACAAATAAAATTTACTGATAATTCAAAAA
TTTGaacaacaaaaagccttgtcct (SEQ ID NO: 430)
For: 5'-3' = agcacaagggtcacattgag (SEQ ID NO: 431)
Rev 5'-3' = aggacaaggcttttgttgtt (SEQ ID NO: 432)

M145 = A8.05b (208 bp) G to A at position 166
TtcagcaagagtaagcaagaggCACTGAGCCGCTGGAGTCTGCACATTGATAAATTTACT
TACAGTCGTAAATAAATTGCATCATCTTCAGCTAGTAACACAGAGTCTAATTT
TTATAGCGGCATACTTGCCTCCACGACTTTCTAGACACCAGAAAGAAAGGC
RAGAGCCAGCCTTAGCCTAATCaagaaccatgatccaaaaagg (SEQ ID NO: 433)
For: 5'-3' = ttcagcaagagtaagcaagagg (SEQ ID NO: 434)
Rev 5'-3' = cctttttggatcatggttctt (SEQ ID NO: 435)

M146 = G3.04d (395 bp) A to C at position 141; has(GTTTT)6 motif
GaatggggtgttacatggagacTACAGGGCTGTTATATTCATAACTTTAGGCTATCATTAT
TGAGGGCTGGATGTCCCTCTGAGCCTCAGGATTCAAAGGATACTGTTTTGTT
TTGTTTTGTTTTGTTTTGTTTTTTCCCMCGGGTAATTAACACTGGGTTTTAG
GACAGTCTGGACTGGGGGTACATTAACAGTTGTACTAGAAACTTCCATGTCTC
AAACAGAGGGGTCTACTAGAGAAGCAATATGTCATGGAAGGCAGTTCTTCTC
CATATCTGTGTAAAGGCAAGTATTTGAAGCTAGGAGAACTGTTCCTTCTGGCC
TGTTGCCCTCTCACAGAGCACTTTAAAGTGAGCTGTGATGTGTAACTTggaaaaca
ggtctctcataatagg (SEQ ID NO: 436)
For: 5'-3' = gaatggggtgttacatggaga (SEQ ID NO: 437)
Rev 5'-3' = cctattatgagagacctgttttcc (SEQ ID NO: 438)

M147 = G3.35 (439 bp nominal) 1 bp insertion (extra T). Associated with GTTT
repeat. 3 T's to 4 T's at position 116. Locus also has T homopolymer which cause stutter
bands during PCR.
GtattctggggcaattttaggGCAAAATACCTGAATAAGCTGGTGAAAGAAAAAAAAAGA
TACTATCAGATTAATATAAACTCATATAAGTGCAATTATGTTTTTTTGTTTGT
TTTGTTTTTTTCTTTCAGAGACAGGGTCTCCCTCTGTCACCTTGGCTGAAGTA
CAGTGACATGATCATGGATCACTGTAGCCTCGACCTCCTGGCCTTAAACAATC
CTTCTACCTTGGCCTCCAGAGTGGCTGGAACTACAACTGCACACCACCCCGTA
TGGCCACTTTTTTTTTTTTCCCACTTTTGTAGCAATATGGTACCCGTGT
CTTGAACTCCTCTTGTCAAGCAATCTTCCTATCTTGGCCTCCCAAAATGCTTG
GATTACAGGTGTGAGCCACCACGCCTGGCCACAGTTAtgcttaaaataacctcttgtatcaa (SEQ ID NO: 439)
For: 5'-3' = gtattctggggcaattttagg (SEQ ID NO: 440)
Rev 5'-3' = ttgatacaagaggttatttaagca (SEQ ID NO: 441)

M147new = G3.35 (276 bp nominal) 1 bp insertion (extra T). Associated with GTTT
repeat. 3 T's to 4 T's at position 97.
GggcaaaatacctgaataagcTGGTGAAAGAAAAAAAAAGATACTATCAGATTAATATA
AACTCATATAAGTGCAATTATGTTTTTTTGTTTGTTTTGTTTTTTTCTTTCAG
AGACAGGGTCTCCCTCTGTCACCTTGGCTGAAGTACAGTGACATGATCATGG
ATCACTGTAGCCTCGACCTCCTGGCCTTAAACAATCCTTCTACCTTGGCCTCC
AGAGTGGCTGGAACTACAACTGCACACCACCCCGTATggccactTtttttttttttccca (SEQ ID NO: 442)

M148 = B9.67c (568 bp) A to G at position 314
AacagaattatcaggaaaaggtttCATAAAATAAAAATCTTTTAAACTTATGAAAGATGCT
CAATATAAAAAACTGTAAACCAGGGAAATGCAAATAAAAATTACAATGAAA
TACTACACACCTCCCAGAATGGCTAAAATGAAAACAAAACTGTCAATTCTAA
GTGTTAGTGAGGACATGTGGTAACCAGAACTGGCATCCAATACTAGCTGATA
AACTCGTCAATCATTTGTAAAAACAGTCTGACAATAATCCACTAGTGAAAAT
ATACATAGTCTCAGTCACAGCAATTCTATCCTGTCTATCTAGGTARCAGAAAT
GTCTACATACGTTACCTAGAAACATATACTTTAATATCCACAGAATTACTTGA TABLE 1-continued

```
AATAGCCAAAAATTGGTAACTACCAAAAGTTGAATGGTAAAACAGATAGAA
AAAAAGCTATGCCTAACAAAACTACACTTAATAGAACACAAGCGTGAGCATT
AATAGAACCATATAAATGCATTTTTTGAACCACTAAAAGAAGAAGCCAATAC
AAAAGAGGTGATTAAttgaaagtacacgaacaagtaaaa (SEQ ID NO: 443)
For: 5'-3' = aacagaattatcaggaaaaggttt (SEQ ID NO: 444)
Rev 5'-3' = ttttacttgttcgtgtactttcaa (SEQ ID NO: 445)

M149 = B9.67d (568 bp) G to A at position 469
AacagaattatcaggaaaaggtttCATAAAATAAAAATCTTTTAAACTTATGAAAGATGCT
CAATATAAAAAACTGTAAACCAGGGAAATGCAAATAAAAATTACAATGAAA
TACTACACACCTCCCAGAATGGCTAAAATGAAAACAAAACTGTCAATTCTAA
GTGTTAGTGAGGACATGTGGTAACCAGAACTGGCATCCAATACTAGCTGATA
AACTCGTCAATCATTTGTAAAAACAGTCTGACAATAATCCACTAGTGAAAAT
ATACATAGTCTCAGTCACAGCAATTCTATCCTGTCTATCTAGGTAACAGAAAT
GTCTACATACGTTACCTAGAAACATATACTTTAATATCCACAGAATTACTTGA
AATAGCCAAAAATTGGTAACTACCAAAAGTTGAATGGTAAAACAGATAGAA
AAAAAGCTATGCCTAACAAAACTACACTTAATAGAACACAAGCRTGAGCAT
TAATAGAACCATATAAATGCATTTTTTGAACCACTAAAAGAAGAAGCCAATA
CAAAAGAGGTGATTAAttgaaagtacacgaacaagtaaaa (SEQ ID NO: 446)
For: 5'-3' = aacagaattatcaggaaaaggttt (SEQ ID NO: 447)
Rev 5'-3' = ttttacttgttcgtgtactttcaa (SEQ ID NO: 448)

M150 = B9.18 (289 bp) C to T at position 146
GcagtggagatgaagtgagacTGGGCTTTGGAGAGGTGAGGAGATGGGGCACTGACACA
CACTGCCCATGGAACCAGTCCTGACACAGGTCACACTGCAGAACTCCCACCC
CAGCTGGCACCTGCCCACACACACAGATAGAAGTYGGAGAAGAGGCCATGA
GGGATGGTGCCAGTGGACTGGGCTTGGCTGAGTTGGTGCGACGCAGCTGCAG
GATACCCTCCTTCTCCTTCTGTTCCCCTTCCTTGAAGGCCACAATCTGCCATAT
Ccagaagaggggaaagtagg (SEQ ID NO: 449)
For: 5'-3' = gcagtggagatgaagtgagac (SEQ ID NO: 450)
Rev 5'-3' = cctactttccccctcttctg (SEQ ID NO: 451)

M151 = B9.58b (422 bp) G to A at position 209.
ActtaatttatagtttcaatccctcaGTAATTTTAACTTACTTCTATTTTAAGAACTATAACCA
AACTATCTGTAAGACTTTTAAGCACTATCATACTCAGCTACACATCTCTTAAC
AAAAGAGGTAAATTTTGTCCTTTTTTGAACGTCATAGAGTATACTCACACAAA
CCAAGAAGAAACAATCTACTACATACCTACGCTATATGRTATATAACTATTG
CTCCTAGGCTACAAATTAGTGCGACACTATTGTACTGAATATTATAGGCCATG
TAACACAATGGTTTAAGTATCTGTGCCTCTAAACACAGAAAAGATATAGTGA
AAGTACAGTATTGCTCCTTTATTAAACTCAAAATGTTATGCAGCATATGACCG
ACTATAAAATAGCGCTTATccagatacagacatctccatgaa (SEQ ID NO: 452)
For: 5'-3' = acttaatttatagtttcaatccctca (SEQ ID NO: 453)
Rev 5'-3' = ttcatggagatgtctgtatctgg (SEQ ID NO: 454)

M152 = B9.13 (287 bp) C to T at position 101
AagctattttggtttccttcaAGAAAGGGCTGTGGTCTGTGGAAGGTGTCAGGAACATATT
TTCCACGGTCTGCTTTCTCCTGATAATGTTCTTCTTCTYGGCCCACCTGAGAC
ATAATCCCTGAGCTCCGAGCCCTTTTTGACTGAAGCTCCTGTTGAACAAGATT
CTCAACGTTTCTACCCTGATCCACCTTCTGCCGCCGCCGTCGCCTCTCCAGAG
CCCGGCTCCTTGTCCGACTCCCTTGATGTTCAAATTTTTCCAGCTGcaatcatacccac
acaaggc (SEQ ID NO: 455)
For: 5'-3' = aagctattttggtttcctttca (SEQ ID NO: 456)
Rev 5'-3' = gccttgtgtgggtatgattg (SEQ ID NO: 457)

M153 = A8.28c (459 bp nominal) T to A at position 427 bp
TtactgataatgccatattgttttgGCTTAATATCAGGCTAAGTAACCACAGTATTCTGATTTA
AAAAAAAACATACTAGAGAGCAAGTTTATTGACAAATCTTTAGGAACTTCAG
GTACAGCATATGATTTCTGAACTATGTGTGTAAATAAGGTTTTGTTTATTCAA
ATTTAACACAGGGTAGTCTGTGTATGCCTTCCGATTTGATAGCTCTAATAAAA
CACTTTAATAGTACCATATCAAATAAATTTTATCATCATCGATTTTCTTCTTAA
TATGAAATAACACATATTTGTGATTTTTCTAAGAGTCAAAATCTCAAAAATCA
TTTTAGGTATAAAATATACCCCGAAAGTTTTATTTTATTCCATTTTATAATTAA
TCTGACTTGGAAAGGGGAAAAAAGCTCAAAGGGTATGTGAACAWTTCATTA
AGATaggaccattggtgtctgagaa (SEQ ID NO: 458)
For: 5'-3' = ttactgataatgccatattgttttg (SEQ ID NO: 459)
Rev 5'-3' = ttctcagacaccaatggtcct (SEQ ID NO: 460)

M154 = B9.58c (422 bp) T to C at position 252.
ActtaatttatagtttcaatccctcaGTAATTTTAACTTACTTCTATTTTAAGAACTATAACCA
AACTATCTGTAAGACTTTTAAGCACTATCATACTCAGCTACACATCTCTTAAC
AAAAGAGGTAAATTTTGTCCTTTTTTGAACGTCATAGAGTATACTCACACAAA
CCAAGAAGAAACAATCTACTACATACCTACGCTATATGGTATATAACTATTG
CTCCTAGGCTACAAATTAGTGCGACACTAYTGTACTGAATATTATAGGCCAT
GTAACACAATGGTTTAAGTATCTGTGCCTCTAAACACAGAAAAGATATAGTG
AAAGTACAGTATTGCTCCTTTATTAAACTCAAAATGTTATGCAGCATATGACC
GACTATAAAATAGCGCTTATccagatacagacatctccatgaa (SEQ ID NO: 461)
For: 5'-3' = acttaatttatagtttcaatccctca (SEQ ID NO: 462)
Rev 5'-3' = ttcatggagatgtctgtatctgg (SEQ ID NO: 463)
```

TABLE 1-continued

M155 = G10.57c (327 bp) G to A at position 251
Tctctaacttctgtgagccac**TCTAGCAAATTAATTGAACCAAAGGAGGAGGTTAAGGAC
AGCATAGTTTACAAAATGAGCCCTGTTTCTGACATCTGAAGTGGGGGCAGTC
TAGTGGGCCTGACCTCTTAACTTGTAGAAACATTCTTTCTTTCTAGATGACTA
GTGACCAGAATTAAATTGAATCCTAGGCCACCCATTTATTGTCTTCTGCAGAA
TTGGCGAGAATGGAGAGGAATCCTCACCTATCRGTGACCAGAGATGAAATA
TTCTGAATTGAGAGTTTAAAAGAGCACACTTAGA**agagatttagagtttagtttttcc (SEQ ID NO: 464)
For: 5'-3' = tctctaacttctgtgagccac (SEQ ID NO: 465)
Rev 5'-3' = ggaaaaactaaactctaaatctct (SEQ ID NO: 466)

M156 = A8.05c (208 bp) A to G at position 147. Linked to M145 derived allele.
Ttcagcaagagtaagcaagagg**CACTGAGCCGCTGGAGTCTGCACATTGATAAATTTACT
TACAGTCGTAAATAAATTGCATCATCTTCAGCTAGTAACACAGAGTCTAATTT
TTATAGCGGCATACTTGCCTCCACGACTTTCCTRGACACCAGAAAGAAAGGC
GAGAGCCAGCCTTAGCCTAATC**aagaaccatgatccaaaaagg (SEQ ID NO: 467)
For: 5'-3' = ttcagcaagagtaagcaagagg (SEQ ID NO: 468)
Rev 5'-3' = ccttttttggatcatggttctt (SEQ ID NO: 469)

M157 = B9.12b (352 bp) A to C at position 176
Gctggcaagacacttctga**GCATCGGGGTGTGGACTTTACGAACCAACCTTTTAACAGT
AACTCTAGGAGAGAGGATATCAAAAATTGGCAGTGAAAAATTATAGATAGG
CAAAAAGCTCCTTCTGAGGTCCAGGCCAGGAGATAGTAGGATTTAAGAAACA
AACAAACAAAAACMACCACAAATGACCTTTGGTGCCACTGTCACAACTGTT
GCTCATCAGAGTAGGAGAGTTGTAGCAAAGGCATTAAAGAAGGACAAGCAG
CTGAAGAGCCTGAATCCTTGTGTTGTAAGCTATTTTGGTTTCCTTTCAAGAAA
GGGCTGTGGTCTGT**ggaaggtgtcaggaacatatt (SEQ ID NO: 470)
For: 5'-3' = gctggcaagacacttctga (SEQ ID NO: 471)
Rev 5'-3' = aatatgttcctgacaccttcc (SEQ ID NO: 472)

M158 = A8.08F-newR (211 bp nominal) G to A at position 77, site e
tgaaatggaaatcaataaactcagt**TTCCTCAAAGTTCAAAATACATGAGACTGCCTACCCTC
CTTGGAAGGCAAGRTGGGGCTTTCTGAAGCAAATACCAGCTTTAAAAAAAA
ATGTATATATATATGAAGATATATACAAAAAAAAAAATTTCCCCACAACCAGA
CAATCAGAATCATCAAACCCA**gaagggttaaagaaaaagaaaagg (SEQ ID NO: 473)
For: 5'-3' = tgaaatggaaatcaataaactcagt (SEQ ID NO: 474)
Rev: 5'-3' = ccttttcttttctttaacccttc (SEQ ID NO: 475)

M159 = G10.83new b (190 bp) A to C at position 89
Attggattgatttcagccttc**TTCTGGTACTTTTTAAAATCTTATTAATCATTAGGAAAAGA
AGTTTTATTATTGATGCAAGCCCTAAMCACTCTTTCGACTCCAGAGGAGAAG
CTGGCAGCTCTCTGTAAGAAATATGCTGATCTTGTGAGTATTTATTTAATGGA**
gcaaggaacacagaaaataaaat (SEQ ID NO: 476)
For: 5'-3' = attggattgatttcagccttc (SEQ ID NO: 477)
Rev 5'-3' = attttattttctgtgttccttgc (SEQ ID NO: 478)

M160 = B9.47b (361 bp) A to C at position 251
Cagaataataggagaattttttggt**CAAATAAAAGGCCATATTATATTTCTTTTGATAAAAGT
ATCATGTGTTCAGTATGTTTTATTATTTGAAATAATTAACATGACAGGAATAT
ATTTGAAAAAAATTCCAAAAAAAGCTAAATATACAAACTAAGAAAATTATAT
GATTATACTTATCTGCAGTATTGTAAAACAATAGTTCCAAAAACTTCTGAATT
ACAAGTTTAATACATACAACTTCAATTTTCMACTACATTGTGGTTAGACGTT
CAGAGGAATCACAAAGGACCTCAACATGCTAGATAAGAAAATGTATTTTTTA
AATGTTTTGGCTCAg**ctgcttagaaaataaggaaaat (SEQ ID NO: 479)
For: 5'-3' = cagaataataggagaattttttggt (SEQ ID NO: 480)
Rev 5'-3' = attttccttattttctaagcagc (SEQ ID NO: 481)

M161 = A8.05d original (460 bp) C to A at position 111
Tcacagcagcttcagcaaa**CACAGATTTCTGGTGTTGGAGGACAGATTTAACTACAGAA
AATTCTGTTGGGCAATCGGAAGCCTCAATCTATACAGACTTTTAGGAGGAGM
CTGCCTGTTTGGTTCAAATTTAGCCAAAATATTTTTTTTTTACCACTGATTCA
GTAAATCTCCTAACTTTGCAGGAACTGGGATCCTAAAAATTATGGAACGAAT
TGTAGAAACTCAAGCAACTTTCTCCAAAGCCTAGGGttcagcaagagtaagcaagaggCA
CTGAGCCGCTGGAGTCTGCACATTGATAAATTTACTTACAGTCGTAAATAAAT
TGCATCATCTTCAg**ctagtaacacagagtctaattttttatAGCGGCATACTTGCCTCCACGACT
TTCCTAGACACCAGAAAGAAAGGCGAGAGCCAGCCTTAGCCTAATCaagaaccat
gatccaaaaagg (SEQ ID NO: 482)
For: 5'-3' = tcacagcagcttcagcaaa (SEQ ID NO: 483)
Rev: 5'-3' = ccttttttggatcatggttctt (SEQ ID NO: 484)
new R 5'ataaaaattagactctgtgttactagc (SEQ ID NO: 485) (used with F primer, just amplifies the first 2 sites
including homopolymer T region.

M162 = DYS257b (288 bp) =
C/T at position 202, most men are just C at position 202
Duplicated locus. Most men have both A and G alleles at position 162, however some
have only the A allele. The second site at position 202 is often just C, although
sometimes both C and T alleles occur on a chromosome background that is both A and G
at position 162.
Gaacttgtcgggaggcaat**GGTGACATTCATTGTGACCCTTAGCCAGAGCTCACAATCAA TABLE 1-continued

```
CCATGGTGCACTGAGACTAGCTCATGCACATTCATCAGGCAGATTCAGGCAC
CTGGCTGTCAGAGCTGTCAGCCTTCCTCAGTAGAGGAAAATGCTACAGTCRG
CACTGGCCTGGTATCAGGAAAATAGATGCCTGCAAAAAYCCACTGTGGGACC
CTAAAAGTCTTGACCTCAGGTCCCCTTTGTGCTGTCTCTGTTGTCAGGATccacta
aaggaggaagtgtatca (SEQ ID NO: 486)
For: 5'-3' = gaacttgtcgggaggcaat (SEQ ID NO: 487)
Rev 5'-3' = tgatacacttcctcctttagtgg (SEQ ID NO: 488)

M163 (340 bp) G10.35b A to C substitution at position 168
Gcagcatataaaactttcagg ACCCTGAAATACAGAACTGCAAAGAAACGGCCTAAGAT
GGTTGAATCCTCTTTATTTTTCTTTAATTTAGACATGTTCAAACGTTCAATGTC
TTACATACTTAGTTATGTAAGTAAGGTAGCGCTTACTTCATTATGCATTTCAA
TMCTCAAAAAAAATTCCTTTGTGAAATGTTGAAATATTTTTCTAATCTGTTTC
ACGAGCTTCAAAAATGAGGAAAAAAGATTCAGTTTACATTTCAGCAAAATGC
CTCTTTTTAATCGGATTTATGTTTACTTAACATTTACAGTACATTTACgcttgagcaa
agttaggtttt (SEQ ID NO: 489)
For: 5'-3' = gcagcatataaaactttcagg (SEQ ID NO: 490)
Rev 5'-3' = aaaacctaactttgctcaagc (SEQ ID NO: 491)

M164 = G10.100b (493 bp) T to C at position 329
Tagaagtagcagattgggagagg ACATGTGTTCAAGTTGTACTACTTGTATGTCTTGTTTA
GATATTACAGTCTTTTTCTTTTATCAGAAAATAATTGAATAATGATAAAATCA
GTTGCAGATTAAGACAGATTATCTGTTGCAGTCTTCTCAAAACTTAATTTAAG
TACATTATTTTCAGCTAGCATTTCTTCCTTCACATAGAACCTCCATGTGTGGA
GGGATTTCCTAATGAGTCTATTGTATGTACAATAGCACTTAATGACATAGCTT
TTAAATAATAACAGGATTTTACCAAATGTTTAATATGTGCCAGGCATCAAGC
ACCYTACACAGTTTAATTATTGCATAGATTTGGACAGCAACTCTGCAAGTTA
GGTATGGTCATGAACCTTTGCAGATAAGGAAACTGTGTTTCACAAGGAGAAG
AAATTGTCCTGGATCATACAATAAGCTAGGATTTGCTCCAgaccattttttttcattttatcagg (SEQ ID NO: 492)
For: 5'-3' = tagaagtagcagattgggagagg (SEQ ID NO: 493)
Rev 5'-3' = cctgataaaatgaaaaaaatggtc (SEQ ID NO: 494)

M165 = B9.008c. (340 bp) A to G at position 132.
Aaagcgagagattcaatccag GATGACAGAATGCGTTCACCTTTAAAGGGATTAAAAGA
AGTATAATACAGTCTGTATTATTAGATCACCCAGAGACACACAAAACAAGAA
CCGTSAATTGAATTAGTGGTATACTAATAGAGTGGTTTTACCTGAAATATTTA
CACATCAATCCTACTGAATTCTTACAACAAATGATTTAGATTAGCTATTGTAT
TCACCAGTTGAAAGAACAGAAAATATTGAGGGAGATAACTTGTGTCAGTGCA
ACTTAATCAGATTTAGGACACAAAAGCAACTACATAATGAAAAAGAGAgctggt
gacttaacttgctaaaa (SEQ ID NO: 495)
For: 5'-3' = aaagcgagagattcaatccag (SEQ ID NO: 496)
Rev 5'-3' = ttttagcaagttaagtcaccagc (SEQ ID NO: 497)

M166 = G3.27e (393 bp) G to A at position 53
tggtaaactctacttagttgccttt TGGAAATGAATAAATCAAGGTAGAAAARCAATTGAGA
TACTAATTCATGCTCTCAGGGGAAAATCTGAATAAAGCTATCTTTTCTAACAC
AGAGCAAGTGACTCTCAAAGTCACAGTATCTGAACTAGCATATCAGCATCGC
CTGAATACCTAGAAATGCAAATTCCTGGGCAACACCAGAATCTAACAAAGCA
AAAAACTATGGGGGGAACAGGGAAGTCGGTTTAATAATACTGAGTTTGTGCA
ACCTCAACTTTGCTTTATAGGAAAGCAAAATCTCAATATGATAAAGTTTTCTT
CAACAAAACTCTGAGATAACTATGTTGAGGGAAAGAAGTTGATCACATgcaaga
aaatctaattcgctg (SEQ ID NO: 498)
For: 5'-3' = tggtaaactctacttagttgccttt (SEQ ID NO: 499)
Rev 5'-3' = cagcgaattagatttcttgc (SEQ ID NO: 500)

M168 = DFFRY Ex01B site a(473 bp) C to T at position 371 noncoding
Agtttgaggtagaatactgtttgct GGTCTTAAAAACTGTGGTATTTTGGTGATTCCATAAAT
TAGGTCAGATACTTCCACTGGAGGGAAACAGTTTAAAGGATATATGTGATAC
TATTAATAGAATGAGGAAGACACACCAGATATTTAGGAGGGAATTAGCGAGC
TTGAAACTAAGAGCTGGTTTGAATGAGACTGGGTCATAAGTGATTTCAAGTA
CCAGATTAAGGCACTGAGATTTTATTTTTAAGCACTGAAGTCAGATTTTTTCC
TTTTAAAAGAAAGGATTCATGATGAAATCTGCTTTTTGTTTTGCAGAGAGCTT
GGGAGATAATTCTGGTGGCTGTGTGGAGTATGTGTTGGAGGTGAGTYGCTAGC
TGAAGAATTAAAACAATAGTTTTAGCAGTTTGGGTAAGAGATGTTTACAGAA
ATGTTTTGTGGAATAAAACtgaacagtcagagacctatgagatt (SEQ ID NO: 501)
For: 5'-3' = agtttgaggtagaatactgtttgct (SEQ ID NO: 502)
Rev: 5'-3' = aatctcataggtctctgactgttc (SEQ ID NO: 503)

M169 = DFFRY Ex01B siteb (473 bp) T to C at position 97 noncoding
Agtttgaggtagaatactgtttgct GGTCTTAAAAACTGTGGTATTTTGGTGATTCCATAAAT
TAGGTCAGATACTTCCACTGGAGGGAAACAGTTYAAAGGATATATGTGATAC
TATTAATAGAATGAGGAAGACACACCAGATATTTAGGAGGGAATTAGCGAGC
TTGAAACTAAGAGCTGGTTTGAATGAGACTGGGTCATAAGTGATTTCAAGTA
CCAGATTAAGGCACTGAGATTTTATTTTTAAGCACTGAAGTCAGATTTTTTCC
TTTTAAAAGAAAGGATTCATGATGAAATCTGCTTTTTGTTTTGCAGAGAGCTT
GGGAGATAATTCTGGTGGCTGTGTGGAGTATGTGTTGGAGGTGAGTCGCTAGC
TGAAGAATTAAAACAATAGTTTTAGCAGTTTGGGTAAGAGATGTTTACAGAA
ATGTTTTGTGGAATAAAACtgaacagtcagagacctatgagatt (SEQ ID NO: 504)
For: 5'-3' = agtttgaggtagaatactgtttgct (SEQ ID NO: 505)
```

TABLE 1-continued

M170 = DFFRY Exon08 (405 bp) A to C at position 327
TgcttcacacaaatgcgtttCAAATAGTAACTTTTTTTCTGAAAGGGGGGAATTAATTTTT
ATTATTAACTGTATTACAGGGTTGGCTAGTGGATCTCATCAATAAATTTGGCA
CATTAAATGGGTTCCAGATTTTGCATGATCGTTTTTTTAATGGATCAGCATTA
AATATTCAAATAATTGCAGCTCTTATTAAGTAAGTTATGTTTTCATGTTTGTTA
AATAATTTCATGTTTGTTCAAATAATTGCAGCTCTTATTAAGTTATGTTTTCAT
ATTCTGTGCATTATACAAATTACTATTTTATTTACTTAAAAATCATTGTTCMT
TTTTTTCAGTGTGGGTTGTGTCTCACTGTAAAATGAGGACCTGTTTTTGTGTggt
cttaaatgttgaaagtaattgg (SEQ ID NO: 507)
For: 5'-3' = tgcttcacacaaatgcgttt (SEQ ID NO: 508)
Rev 5'-3' = ccaattactttcaacatttaagacc-3' (SEQ ID NO: 509)

M171 = DFFRY Ex01B sitec (473 bp) G to C at position 440 noncoding?
AgttttgaggtagaatactgtttgctGGTCTTAAAAACTGTGGTATTTTGGTGATTCCATAAAT
TAGGTCAGATACTTCCACTGGAGGGAAACAGTTTAAAGGATATATGTGATAC
TATTAATAGAATGAGGAAGACACACCAGATATTTAGGAGGGAATTAGCGAGC
TTGAAACTAAGAGCTGGTTGAATGAGACTGGGTCATAAGTGATTTCAAGTA
CCAGATTAAGGCACTGAGATTTTATTTTTAAGCACTGAAGTCAGATTTTTTCC
TTTTAAAAGAAAGGATTCATGATGAAATCTGCTTTTTTGTTTTGCAGAGAGCTT
GGGAGATAATTCTGGTGGCTGTGTGGAGTATGTGTTGGAGGTGAGTCGCTAGC
TGAAGAATTAAAACAATAGTTTTAGCAGTTTGGGTAAGAGATGTTTACAGAA
ATGTTTTGTGSAATAAAACtgaacagtcagagacctatgagatt (SEQ ID NO: 510)
For: 5'-3' = agtttgaggtagaatactgtttgct (SEQ ID NO: 511)
Rev: 5'-3' = ccagggccccgagggactctt (SEQ ID NO: 512)

M172 = DFFRY Ex45 (345 bp) T to G at position 197
TtgaagttacttttataatctaatgcttAATCTCTTTAAATATTTAAAATTAGGAGCCAGATGAC
CAGGATGCCCCAGATGAGCATGAGCCCTCTCCATCAGAAGATGCCCCATTAT
ATCCTCATTCACCTGCCTCTCAGTATCAACAGGTAAAAAGGATTTTTCATTTT
TATCCCCCAAACCCATTTTGATGCTTKACTTAAAAGGTCTTCAATTATTATTT
TCTTAAATATTTTGAAAGTCCAAACTTTCTCTGTACCTGGCTGATATTTAAAA
CTGGATAAACTGTTCCAAACCAACATGGAGTGAAGATGGATccactgtgactgtaaagt
aataaattat (SEQ ID NO: 513)
For: 5'-3' = ttgaagttacttttataatctaatgctt (SEQ ID NO: 514)
Rev: 5'-3' = ataatttattactttacagtcacagtgg (SEQ ID NO: 515)

M173 = DBY Ex08 (417 bp) A to C at position 191. Non-coding (cDNA bp# 745-52)
AagaaatgttgaactgaaagttgatGCCACTTTTCAGAAAAATGGTTGTGTTTTGTACAAAT
TGAAATACATTGTTTAAAAATAAAGCACAGTACTCACTTTAGGTTTGCCATAT
AAATTTACTGTAACTTCCTAGAAAATTGGAAATAAAGTAAGAAAAATTTTCTT
ACAATTCAAGGGCATTTAGAACMCTTTGTCATCTGTTAATATTCAGAAATGA
TAAGCCAGTGTTTTGTTTTCAGGATCTGGGAAAACTGCAGCATTTCTTTTACC
CATACTGAGTCAGATATATACAGATGGTCCAGGAGAAGCTTTGAAGGCTGTG
AAGGTAAAGGTTTTGTTATAAAATCAGACATTTTTGTTTTAAAAAGCTTTGCA
AAGCCCTGTTGACTTTTCtaacggatgccagatacacct (SEQ ID NO: 516)
For: 5'-3' = aagaaatgttgaactgaaagttgat (SEQ ID NO: 517)
Rev: 5'-3' = aggtgtatctggcatccgtta (SEQ ID NO: 518)

M174 = DffryEx38 (348 bp) T to C at position 219
AcatctcagatcgttgtttggtTCATAAAAATCTGTTTCTTCCATGTACCAAGCAAAATAAA
CACATCACTAAAATTTGACGTTCATAGATGTTTCTGTTTTAGGTATGATGCAC
TGTGCGTTCTTCTCCGTCACAGCAAAAATGTACGTTTTTGGTTTACTCATAAT
GTCCTTTTTAATGTATCAAATCGCTTCTCTGAATACCTTCTGGAGTGCCCYAG
TGCAGAAGTGAGGGGTGCATTTGCAAAACTTATAGTGTTTATTGCACACTTTT
CCTTGCAAGATGGGTCTTGTCCTTCTCCTTTTGCATCTCCAGGACCTTCTAGTc
aggtaattgcatggcttttt (SEQ ID NO: 519)
For: 5'-3' = acatctcagatcgttgtttggt (SEQ ID NO: 520)
Rev: 5'-3' = aaaaagccatgcaattacctg (SEQ ID NO: 521)

M175 = UTY1 exon 07 (444 bp) 5 bp deletion at interval 84-88 non coding
TtgagcaagaaaaatagtacccaAATCAACTCAACTCCAGTGATTTAAACTCTCTGAATCA
GGCACATGCCTTCTCACTTCTTTCTCAAGAATGAACAGAAACAAAGGTAT
CAGTAGAAAAAAggtatcattaatattctttactcAAAAGTATTTCATTTAAAAATACTTAC
TTTCAGCATTGGACAAAGTACATGGATTACAGTCAATCAAGGCTAACTGAAA
ATGCTGCAAGAGAAAAGTAAAAATATTAATGCACTAAATTAAGAGTGCATAA
AAGTACATTTTCTATTTTAGCCTTTCAATGTCTATCATAAAATAACAAAGCTA
TGCTATACACCAATGCACTACACTCGACCAAATAAAATTACTGTAATTCCAA
ATTTATTTTGAAAATGTAAGTGCTAATCAAGTTATTtccctgagatagttaagaatggag (SEQ ID NO: 522)
For: 5'-3' = ttgagcaagaaaaatagtaccca (SEQ ID NO: 523)
Rev: 5'-3' = ctccattcttaactatctcaggga (SEQ ID NO: 524)

M178 = G10.72b (514 bp) C to T at position 220
TaagcctaaagagcagtcagagTAGAATGCTGAATTTTCAGAAGTTTTATATTAACATAA
TCATTCATCTTTTTTGTCCTGATAATTACTCAGGAGGAAACTGAGAGGGCATG
GTCCCTTTCTATGGATAGCAATACTCAGTGTCCCAATTTTCCTTTGGGACACT
GGGACACAGGCAGAGACTCCGAAAGTCTGCATGGATTAGTTGTTCATTCACC
AYAGCTCCTTAGTGTGCCAGGAGAACTATATATGGCCTTTGGTTTCATTCAGG TABLE 1-continued

```
GACAGGGAAACTTGAACCCATGCCTATTCATTCTCATTAAAGTAGCAGAAGT
CATGTTAGAGACAGTATTGCTGCATTCAGTACTCCTGCCTTTAACGCTTCTGA
CGCTTCCTGAAAGCAGCCCCAGCTCTCCATATGGCAAAACAAAGGCAACCTT
ATGCAAAGCCTTCTCAGGGAACCCTCAGAAAGGTTTAAACTTAGGTTCACAG
TTTTTAGAGAATAAtgtcctcattgctccctctag (SEQ ID NO: 525)
For: 5'-3' = taagcctaaagagcagtcagag (SEQ ID NO: 526)
Rev 5'-3' = cagagggagcaatgaggaca (SEQ ID NO: 527)

M179 = Dffry exon 07 (426 bp) C to T at position 316
AttatgcagaattaagatgaccagTGCAGAAAAATGGAAAGAGATTATTAATAAAAATTAA
ATGTGTTTGAAATTGCAATGTGTTCTTATTATAAACTGTATCATATCCTATCCA
TGTAACAGAGATGTATTATTAACAATACTCATCGCCTAGTGGAGCTTTGTGTG
GCCAAGTTGTCCCAAGATTGGTTTCCACTTCTAGAACTTCTCGCCATGGCCTT
AAATCCTCACTGCAAGTTTCATATCTACAATGGTACACGTCCGTGTGAATTAA
TTTCCTCAAATGCTCAGTTGCCTGAAGATGAATTATTTGCTYGTTCTTCAGAT
CCTCGATCACCAAAAGTGCGTTGGTTTGTTATTTTCAAGATTAAATATTAATT
TTTTTATTTGCATTTGCCACAGAccattagtgatgtgaacctgtct (SEQ ID NO: 528)
For: 5'-3' = acactactgtgctgtaatttgtgaa (SEQ ID NO: 529)
Rev 5'-3' = agacaggttcacatcactaatgg (SEQ ID NO: 530)

M180 = Dffry exon 11(447 bp) T to C at position 402
AcactactgtgctgtaatttgtgaaTGTATACATAATTTGGACTTTTGAATTCCTACTTAATA
TTATTTAGAAGTTGGAGACATGTTTTTATTTCGCTTTTTAAAAAAATTTCTTTT
TAGTTTCAGCATTGAATTTTTGTATTACATTTAGGAATGGATACAGCAAAATA
ATATCTTATCCATAGTCTTGCAAGACAGTCTTCATCAACCACAATATGTAGAA
AAGCTAGAGAAAATTCTTCGTTTTGTGATTAAAGAAAAGGCTCTTACATTAcag
gaccttgataatatctgGGCAGCACAGGTAAGAAAGTGAGATGATAGCTATTTTCTAAG
AAAGATACCAAAAAGGAGAAAATTTTTGGTAACCCTTATATAATGGCCAGCA
ATTTAGTATTGCCYGACTTTTACTAATGCATGTGctgttcatgtagagaaatcttacca (SEQ ID NO: 531)
For: 5'-3' = acactactgtgctgtaatttgtgaa (SEQ ID NO: 532)
Rev 5'-3' = tggtaagatttctctacatgaacag (SEQ ID NO: 533)

M180 = Dffry exon 11(232 bp) T to C at position 128
CaggaccttgataatatctgGGCAGCACAGGTAAGAAAGTGAGATGATAGCTATTTTCTA
AGAAAGATACCAAAAAGGAGAAAATTTTTGGTAACCCTTATATAATGGCCAG
CAATTTAGTATTGCCYGACTTTTACTAATGCATGTGctgttcatgtagagaaatcttaccaAG
AATTTTTAAACAAAAAATAACATTTTTCTGTCTTTgtatatatattcatggtagcaa (SEQ ID NO: 534)
NEW F 5'-3' = caggaccttgataatatctg (SEQ ID NO: 535)
NEW Rev 5'-3' = ttgctaccatgaatatatatac (SEQ ID NO: 536)

M181 = Dffry exon 12 (294 bp) T to C at position 130
GcttttatttattctacttttgttttTCAACAGGCAGGAAAACATGAAGCCATTGTGAAGAATG
TACATGATCTGCTAGCAAAGTTGGCTTGGGATTTTTCTCCTGGACAACTTGAT
CATCTTTTTGAYTGCTTTAAGGTAGTAGCTTGAATAGTAAAGTATTGCCAAAT
AGTAAATATTGCCAGTTAATTCTAAGTAAAGTTTAATTCGTTAGATTTCTTTT
GCTTATAGCTAGTGTGCTTAACTAACATTTTCATGGAAGAATCTCTGatgaaaaaga
attggtcattgtt (SEQ ID NO: 537)
For: 5'-3' = gcttttatttattctacttttgttttt (SEQ ID NO: 538)
Rev 5'-3' = aacaatgaccaattcttttttcat (SEQ ID NO: 539)

M182 = Dffry exon 13 (364 bp) C to T at position 38
TattcaaagacttaaagcagtggttaATGTAAACAAAYGTAATAAATTATGTGGTATTTATA
TCATTTAAATACTTTCTTTAGGCAAGTTGGACAAATGCAAGTAAAAAGCAAC
GTGAAAAGCTCCTTGAGTTGATACGCCGTCTTGCAGAAGATGATAAAGATGG
TGTGATGGCACACAAAGTGTTGAACCTTCTTTGGAACCTGGCTCAGAGTGAT
GATGTGCCTGTAGACATCATGGACCTTGCTCTTAGTGCCCACATAAAAATACT
AGATTATAGTTGTTCCCAGGTATGGGAGTGTTTCTTTGTTCAGTTTTCTGACTT
TCCTTCACAAGTaggataaacttagttacaagatgattcc (SEQ ID NO: 540)
For: 5'-3' = tattcaaagacttaaagcagtggtta (SEQ ID NO: 541)
Rev 5'-3' = ggaatcatcttgtaactaagttatcct (SEQ ID NO: 542)

M183 = Dffry exon 19 (427 bp) A to C at position 324
ActgggtaaatatgactatgattgagTTACCTTTAAATTGACATTTTACTGCTTTTTATTAGAT
TGATGTCACATTTCATTTGTAAACAACCTGGATTATCTGTATTTGTCCATTATT
TATAGGTGGTTATCCATGAAGACTTCATTCAGTCTTGCTTTGATCGTTTAAAA
GCATCATATGATACACTGTGTGTTTTGATGGTGACAAAAACAGCATTAATTG
TGCAAGACAAGAAGCCATTCGAATGGTTAGAGTATTAACTGTTATAAAAGAG
TACATTAATGAATGTGACAGTGATTATCACAAGGAAAGAATGATTCTMCCTA
TGTCGAGGTTTGTGTGAAGTTGATCTCTAGTGTTAATTTACAATTACTTAATA
TTTTCTTAGAAAATTTACTTAggaaagtaataataggttaaaaggaa (SEQ ID NO: 543)
For: 5'-3' = actgggtaaatatgactatgattgag (SEQ ID NO: 544)
Rev 5'-3' = ttcctttaacctattattactttcc (SEQ ID NO: 545)

M184 = Dffry exon 23 (305 bp) G to A at position 62
CactttattttagtctgtgtcttttcCTTTGCAGATAGAACAGCTGTAGAAAAATTACGARCTG
TTTGTTTGGACCATGCAAAACTTGGAGAAGGCAAACTTAGTCCACCCCTTGAC
TCTCTTTTCTTTGGTCCTTCTGCCTCCCAAGTTCTATACCTAACAGAGGTTGGT
TTTTGCCTTTGCAAAAATGTAATTTTTATATTATACGGTAATGTGAAGAACAC
TGATAAGACTGTAAAGAAAGTTTTTTAAATAGTCGAATTTCTTAGCAATGATC
```

TABLE 1-continued agaggagaaatagatgttactaagttt (SEQ ID NO: 546)
For: 5'-3' = cactttattttagtctgtgtcttttc (SEQ ID NO: 547)
Rev 5'-3' = aaacttagtaacatctatttctcctct (SEQ ID NO: 548)

M185 = Dffry exon 27 (430 bp) C to T at position 89
GgagtacctatcactgaatgtgcTTCTTAAATCCCCCTTGGAGTATATCCCAAAGAGCCTCT
CTAGCCGCAAGTGAAGAGTCTGAGGCYGCATGGTCTTTACCAAGTAGGCAAT
TGTAAATGTTAACCAGAGGGTTTGTGAATTTCTTCTTGAATATGTCTCTAGGT
AACTTGCTCCTGATTCTAATTTTGCAGACCACCAATGGAAGCAATAAGCTGG
AGGTGGAAGATGAACAAGTTTGCTGTGAAGCACTGGAAGTGATGACCTTATG
TTTTGCTTTACTTCCAACAGCGTTGGATGCACTTAGTAAAGAAAAAGCCTGGC
AGACCTTCATCATTGACTTATTATTGCACTGTCCAAGCAAGTATGTGATTTTT
ATGTGTAATTTGAAGGAAGGCTTACCTTACCgttccaagcagaaatgaatgac (SEQ ID NO: 549)
For: 5'-3' = ggagtacctatcactgaatgtgc (SEQ ID NO: 550)
Rev 5'-3' = gtcattcatttctgcttggaac (SEQ ID NO: 551)

M186 = Dffry exon 30 site a (365 bp nominal) -1 bp deletion (4G's to 3 G's) at position 62 (364 bp = mutant) 325 bp w/out homopolymer
TtgcatttactgttctagagagttctCAAAAAGAAATAGGAAACCACTTGAACAGTTTGGGG
AAGTTTGTATAGAAGATCTCATTTCCTTCCAGCTCTCTGTTCTCCTAACTCCTTG
TCCTTTTCTATCTCCATGTTGTGAGTTGGGCCTATAATATTTTTCCTTTTGCAG
GATAATGTTAAAAACACAGGTGAAACAGGTGTCGAAGAGCCAATACTGGAA
GGCCACCTTGGGGTAACAAAAGAGTTATTGGCCTTTCAAACTTCTGAGAAAA
AGTATCACTTTGGTTGTGAAAAAGGAGgtgctaatctcattaaagtaagtacTTTTTTTTTTCT
TTTTTTGAgatggagtcttgctctgtgg (SEQ ID NO: 552)
For: 5'-3' = ttgcatttactgttctagagagttct (SEQ ID NO: 553)
Rev 5'-3' = ccacagagcaagactccatc (SEQ ID NO: 554)
newRev 5'-3' = gtacttactttaatgagattagcac (SEQ ID NO: 555) Homopolymer clipped off

M187 = Dffry exon 30 site b (366) IGNORE Homopolymer in tree T(10 to 11 T's) 325 bp w/out homopolymer
TtgcatttactgttctagagagttctCAAAAAGAAATAGGAAACCACTTGAACAGTTTGGGGA
AGTTGTATAGAAGATCTCATTTCCTTCCAGCTCTCTGTTCTCTAACTCCTTGT
CCTTTTCTATCTCCATGTTGTGAGTTGGGCCTATAATATTTTTCCTTTTGCAGG
ATAATGTTAAAAACACAGGTGAAACAGGTGTCGAAGAGCCAATACTGGAAG
GCCACCTTGGGGTAACAAAAGAGTTATTGGCCTTTCAAACTTCTGAGAAAAA
GTATCACTTTGGTTGTGAAAAAGGAGgtgctaatctcattaaagtaagtacTTTTTTTTTTCT
TTTTTTGAgatggagtcttgctctgtgg (SEQ ID NO: 556)
For: 5'-3' = ttgcatttactgttctagagagttct (SEQ ID NO: 557)
Rev 5'-3' = ccacagagcaagactccatc (SEQ ID NO: 558)
newRev 5'-3' = gtacttactttaatgagattagcac (SEQ ID NO: 559) Homopolymer clipped off

M188 = Dffry exon 31(401 bp) C to T at position 185
GtattcccttttgaagaaacatattgTTCCTAACCTATATTTTCTACTAATAACATGTAATGTCT
TTTTCTAACTTACTAGGAATTAATTGATGATTTCATCTTTCCCGCATCCAAAGT
TTACCTGCAGTATTTAAGAAGTGGAGAACTACCAGCTGAGCAGGCTATTCCA
GTCTGTAGTTCACCYGTTACCATCAATGCCGGTTTTGAGCTACTTGTAGCATT
AGCTATTGGCTGTGTGAGGAATCTCAAACAGATAGTAGACTGTTTGACTGAA
ATGTATTACATGGGCACAGCAATTACTAGTGAGTATTTTAAATTATAAAGCTG
TTTTGTTCATTAATAATACTTCACTGTAAAATTTTATTTGGTGTTTTAgaaaaaatta
acttgtgatggactt (SEQ ID NO: 560)
For: 5'-3' = gtattcccttttgaagaaacatattg (SEQ ID NO: 561)
Rev 5'-3' = aagtccatcacaagttaattttttc (SEQ ID NO: 562)

M189 = Dffry exon 34 (378 bp) G to T at position 191
ActctcagcttatgtttgtcattgTTATTTTTGTTGTTATAAAATATGGATATTCTAGGCATGT
ATTACATAACTCATTTTGTTTCCTTTCCTTCTTAGGCTTTGGGGTGAACCTGTT
AATCTCCGTGAACAACATGATGCCTTAGAGTTTTTTAATTCTTTGGTGGATAG
TTTAGATGAAGCTTTAAAAKCTTTAGGACACCCGGCTATACTAAGTAAAGTC
CTAGGAGGCTCCTTTGCTGATCAGAAGATCTGCCAAGGCTGCCCACATAGGT
AAGTGCTAATTATGTTTTTAATGTATACTTCGTGTTGTTTTTTTTTAATAATA
GTGTAAATCTTTCATTAGTACTTATATaaaagcagagtgtaccaaaagc (SEQ ID NO: 563)
For: 5'-3' = actctcagcttatgtttgtcattg (SEQ ID NO: 564)
Rev 5'-3' = gcttttggtacactctgctttt (SEQ ID NO: 565)

M190 = Dffry exon 44 (346 bp) A to G at position 73
CtctgtcacaagtaaggaaatgatCGTGAAATTTTTGTATTAGCATTTTAAGCTGATACTGA
AAATCATTCTRAATTCTAAATAGTTTTATTTTTTTCTAAAGGGTAACGGAGAT
CTTAAAAGAAAATGGACCTGGGCAGTGGAATGGCTAGGAGATGAACTTGAA
AGAAGACCATATACTGGCAATCCTCAGTATAGTTACAACAATTGGTCTCCTCC
AGTACAAAGCAATGAAACAGCAAATGGTTATTTCTTAGAAAGATCACATAGT
GCTAGGATGACACTTGCAAAAGCTTGTGAACTCTGTCCAGAAGAGGTAAAAA
AAaaaaaggctaccaatggacag (SEQ ID NO: 566)
For: 5'-3' = ctctgtcacaagtaaggaaatgat (SEQ ID NO: 567)
Rev 5'-3' = ctgtccattggtagcctttt (SEQ ID NO: 568)

M191 = DBY exon 2 (429 bp) T to G at position 342. Non-coding (cDNA bp# 175+120)
TtgcatttgtcatggttggtTGACCTGGACATCTTTAAAATTTGGCAGGTAATACCAGGCC
GACATGGCAGCTAAGTTTGTGGTACAGGATAAGATTGGAATCTAGGTCTCAT TABLE 1-continued

```
TTGTCTTTTGTGATGTTATCTGTTCTTGTGTATCAGCATGTGAGCTATTGATAT
CTCTTCTAGCTTGCTAATCTGGACCTGAACTCTGAAAAACAGAGTGGAGGAG
CAAGTACAGCGAGCAGTAAGTAAAACTTTTTTTAAAAATGGAGTGTTTATCA
GAGCTTAATGTTAATGTCTTACTGGACTTGTTAATTTTAAATTTACATTTTTTT
CTTTACAACTTGACTAKATGAAAATATGAGATATTTTGGTGTGTCTGGGTAAT
AAAATACACTGTTTACCTATGTCTGCTgaaaatacaaaaaattatcctggc (SEQ ID NO: 569)
For: 5'-3' = ttgcatttgtcatggttggt (SEQ ID NO: 570)
Rev: 5'-3' = gccaggataattttttgtattttc (SEQ ID NO: 571)

M192 = DBY STS 02 (457 bp) C to T at position 202.
CatgggctgctgacattttGCAGGCAGGGCTCAGGGTGTTAGATGTCCTGTAATTCAGGG
ACATTCACAGTAGAAAATACTTTGGTTAGGATTTAAACCTACAAAATTGCTTT
AAACATAAACTCAAAAGTATTCTTAGGCTGGTTGCAGTGGCCTTGTGTCTGCAA
TCCCAGCACTTTGGGAGGCCAAAGCAGGCAGATCCYTTGAGCTCAGGAGTTT
GAGCCCAGCTTGGGCAAAATGACAAAACCCCTTCTCAGTTAAAAAAAAAAAA
TTAGCCTGGCATGGTGGTGGTGTGCAACTGCGGTCCCAGCTACCGGGAGGC
TAAGGTGAATTACCTGAACCTGGGAGGTGGATGCTGCAGTGAGCCAAGATCC
CACCACTGCACTCCAGCCTGGATGAGGAAGTGAGATCTTGTCACAAAAACAA
AAACAAACaaacaaacaaaccaaaaggattt (SEQ ID NO: 572)
For: 5'-3' = catgggctgctgacatttt (SEQ ID NO: 573)
Rev: 5'-3' = aaatccttttggtttgtttgttt (SEQ ID NO: 574)

M193 = DBY STS 03a (426 bp nominal) +4 bp insertion (CAAA) at position 56.
GcctggatgaggaagtgagTCCTGTCACAAAAACAAAAACAAACAAACAAACAAACA
AACCAAAAGGATTTTTGAATACTTTAAACATACAGGGAGTGTTTTTTTTCCCC
CCGAGAAGGCAACGACTGTATAAATTTATATTGTTTTTACCATTTTAGAAATA
CTACCGTTTGCAACCCTGTTCATAATACAGTGAGTTGTGAATACATTCTGTTT
GTATTTGCAGCTAAATTAGGCAACCACTTGTGTATTTGTCAGTGTAGCAGTGG
CGGTCATTTACATGCCAAAATACATATTTTATTATAAATATTCTTTTAATTATA
TAATAATTAGGTTTGTTAGGGGCCAGAGGGGTGTCATTGTGCATCATTTGAGT
TTATTTCTTTGGGAGGCAAAGAGAGAGGAAAGGAaggtcaaaaatggagaaggc (SEQ ID NO: 575)
For: 5'-3' = gcctggatgaggaagtgag (SEQ ID NO: 576)
Rev: 5'-3' = gccttctccattttttgacct (SEQ ID NO: 577)

M194 = DBY STS 03b (426 bp nominal) T to C at position 101.
GcctggatgaggaagtgagTCCTGTCACAAAAACAAAAACAAACAAACAAACAAACCA
AAAGGATTTTTGAATACTTTAAACATACAGGGAGTGTTTTYTTCCCCCCGAG
AAGGCAACGACTGTATAAATTTATATTGTTTTTACCATTTTAGAAATACTACC
GTTTGCAACCCTGTTCATAATACAGTGAGTTGTGAATACATTCTGTTTGTATTT
GCAGCTAAATTAGGCAACCACTTGTGTATTTGTCAGTGTAGCAGTGGCGGTC
ATTTACATGCCAAAATACATATTTTATTATAAATATTCTTTTAATTATATAATA
ATTAGGTTTGTTAGGGGCCAGAGGGGTGTCATTGTGCATCATTTGAGTTTATT
TCTTTGGGAGGCAAAGAGAGAGGAAAGGAaggtcaaaaatggagaaggc (SEQ ID NO: 578)
For: 5'-3' = gcctggatgaggaagtgag (SEQ ID NO: 579)
Rev: 5'-3' = gccttctccattttttgacct (SEQ ID NO: 580)

M195 = DBY STS 06 (515 bp nominal) A to G at position 430
ccactcagctttcctcaggtGCAGTCAGGTCCATCCTGCAGAGGGACCTTCTGCGGACCT
GTTCTTTCACCTCCCTAACCTGAAGATTGTATTCAAACCACCGTGGATCGCTC
ACGTAAAATGGTCACTGCGCCTAACACCTGGGATCCCGTAACCCTTATCTATC
TTGGCTTCAGAGAGTTTTTTGACTAGTTCCAACTTTGCTGAAGCTTGTCAAAG
GTAGGTGACGGCTAGTTGGAACGGAAAAATTTTACGAAACTTCCTATTCTCA
GAAGTAAAAGGGAAGAGAGAGTGCTTAAGGAAGAAGGGAAGTTGAGGGTGG
GTAAGGAGGGAGCGGGAGTTAGTGGTAGATTGTCACTGTGTTTAAGATTTCC
CCAAGGCGAAAAAGGCGAAAGATATCTTGCTAGATCCCTAGAATTCGAAGGC
ATTRGGAGAGGGCGGGGATAGCAAACATCGCGCGAATTTTTGAGAGGCGCTG
GGACTACGTAATCCCGcgatcttatgactaaacgaacg (SEQ ID NO: 581)
For: 5'-3' = ccactcagctttcctcaggt (SEQ ID NO: 582)
Rev: 5'-3' = cgttcgtttagtcataagatcg (SEQ ID NO: 583)

M196 = DBY STS 07 (445 bp) C to G at position 330.
TtagacaacttactactttgatgtcctGTTGGCTCAGTAATGCTCACGATACCAATTGTTTTGA
CAAAATAAATTTACTAAACTTGGCCTAAAATCAAACCTTGGCACAGAGGTAT
GATACAACTTTAACAGGAGTCATCAATTCATCCATAAATATAAAAAGGGAAA
AAAACTTAAGGCAGTAGTCTGCATTAGGACTGTTTGAGTTTTGCAGACTTGGG
GTTGGGAGAACATCTTAAAGCATTAAAGCATAGTTTTTTGTATGGCCAACCTT
ACTAAATTAAGTTCTGACTTGCTCACTCTATCCTGGATAGGCACTTGGGAACT
TASACTCTTTAAGCCATTCCAGTCATGATGAGGTGGAATGTATCAGTATACCA
ATTAATATTTTTGAAAGAGCTCTTTTAGGTTAATTTAAGTacagcaatttctcatgtaatgttt
a (SEQ ID NO: 584)
For: 5'-3' = ttagacaacttactactttgatgtcct (SEQ ID NO: 585)
Rev: 5'-3' = taaacattacatgagaaattgctgt (SEQ ID NO: 586)

M197 = DBY exon 07 (408 bp) T to C at position 105. Non-coding (cDNA bp# 609-32)
TcagacagtttagttggttacttccATTAATATGTTAGTATAAAACAGAAATTGCGACAGAT
ACAGCATTTTATATCTGCTATGTTTACTTCTGTATTTACTTGYATTTGATTAAC
CTGGTTAAATTTCTTGGCAGTTTAGCGATATTGACATGGGAGAAATTATCATG
GGGAACATTGAACTTACTCGCTATACTCGTCCTACTCCAGTGCAAAAACATGC
CATTCCTATTATTAAGGGAAAAAGAGACTTAATGGCTTGTGCCCAAACAGGT
```

TABLE 1-continued

AAGCTTACTCAATACAAAGTGAAAGTTAAGAATACCTGATCAGACTTACTTT
AAAAGTAGTATGTTCTGAAGGGGATGTCTGAATCCTGTGTTTAGCATTTGAGG
TAGGTaaagattagctgaggatgtgtctt (SEQ ID NO: 587)
For: 5'-3' = tcagacagtttagttggttacttcc (SEQ ID NO: 588)
Rev: 5'-3' = aagacacatcctcagctaatcttt (SEQ ID NO: 589)

M198 = DBY STS 08a (444 bp) C to T at position 45
TgaggtggaatgtatcagtataccAATTAATATTTTTGAAAGAGYTCTTTTAGGTTAATTTA
AGTACAGCAATTTCTCATGTAATGTTTAGGGAGTTTATTCTAACCTAGGCAAA
CGGCATGCTATCACAAGAAAGGTTTAAAGCTTTGATAAAATGGGGGAGATTT
AATCAGTTTTTTTAATGCCTGCTATAAAAATTTGAAATATTAGAATGGCCGAC
CATGGCAGTGACCAGGCCTCACTACAGGCCTGGTTGGATTCTGGTCTTTAATG
CATGCTAGTGTTGATGTTTTTTGGTCAAGAACGGTTTAAACAGGAAGGATTGT
GCAGCAGGCTTTAATTTAATGTAGATTCATACTGCTCTGTTAAAGCTGCATTG
AATGTTAAAATGGCTTACACTTGCAGACTTTGCAAATCTTaagactaacaaatccttgaa
atca (SEQ ID NO: 590)
For: 5'-3' = tgaggtggaatgtatcagtatacc (SEQ ID NO: 591)
Rev: 5'-3' = tgatttcaaggatttgttagtctt (SEQ ID NO: 592)

M199 = DBY STS 08b (444 bp nominal) +1 bp insertion (extra G) at position 404 (445 bp with mutation).
TgaggtggaatgtatcagtataccAATTAATATTTTTGAAAGAGCTCTTTTAGGTTAATTTA
AGTACAGCAATTTCTCATGTAATGTTTAGGGAGTTTATTCTAACCTAGGCAAA
CGGCATGCTATCACAAGAAAGGTTTAAAGCTTTGATAAAATGGGGGAGATTT
AATCAGTTTTTTTAATGCCTGCTATAAAAATTTGAAATATTAGAATGGCCGAC
CATGGCAGTGACCAGGCCTCACTACAGGCCTGGTTGGATTCTGGTCTTTAATG
CATGCTAGTGTTGATGTTTTTTGGTCAAGAACGGTTTAAACAGGAAGGATTGT
GCAGCAGGCTTTAATTTAATGTAGATTCATACTGCTCTGTTAAAGCTGCATTG
AATGTTAAAATGGCTTACACTTGGCAGACTTTGCAAATCTTaagactaacaaatcctt
gaaatca (SEQ ID NO: 593)
For: 5'-3' = tgaggtggaatgtatcagtatacc (SEQ ID NO: 594)
Rev: 5'-3' = tgatttcaaggatttgttagtctt (SEQ ID NO: 595)

M200 = DBY STS 09a (429 bp) G to A at position 318
GgcttacacttgcagactttgCAAATCTTAAGACTAACAAATCCTTGAAATCACACAGCTT
GCAAATACGTACTAAACTGCACAAGGTGTGTGTTCTATATGTGCAGTTTTAGC
GTATTTTAGTTGCATAGGTTTCCATGGTATTTATAGTCTCTTGTGCTAAATTTG
GCCAAAGATGATTGTCCACCACTAAAAATGCCTCTCCCACTTGGAATTCTGTA
CTGATTTTGTGGCCAGATGCAATGATCTTTAAAAACAAATCTTTTCAATGGCA
TAAGAAGTTGACAAAAATTTCTTAAAGTGCAATAGATTTTCAARTGTATTGT
GCCTTGTTCTAAAACTTTTAAGTAGGTGCACTTGACAGTATTGAGGTCATTTG
TTAAGGTGCTATTTCAATTAGTGTAggtttagactcttgtacatttctcc (SEQ ID NO: 596)
For: 5'-3' = ggcttacacttgcagactttg (SEQ ID NO: 597)
Rev: 5'-3' = ggagaaatgtacaagagtctaaacc (SEQ ID NO: 598)

M201 (326 bp) DBY exon 11&12 G to T at position 136
TatgcatttgttgagtatatgtcAAATTGTGACACTGCAATAGTTACTACTTGAGTTACTATA
TTAGTGCAATTAATTACACAACTATATATAGTAAttagtttctcagatctaataatccagTATC
AACTGAGGKTTTTCGTAATAGGTACTTAGTGTTGGATGAAGCTGATAGGATG
CTGGATATGGGATTTGAACCTCAGATACGTCGTATAGTTGAACAAGATACTA
TGCCACCAAAGGGCGTTCGTCACACCATGATGTTTAGTGCTACTTTTCCTAAG
GAAATACAGGTACTGTTTGAcgtttgaactttcattcagaac (SEQ ID NO: 599)
For: 5'-3' = ttagtttctcagatctaataatccagt (SEQ ID NO: 600)
Rev: 5'-3' = gttctgaatgaaagttcaaacg (SEQ ID NO: 601)

M202 = DBY exon 16 (392 bp) T to G at position 259. Non-coding (cDNA bp# 1974+38)
GgaattgcagggtttaagcAGTAATTTTCAGTTTAATTGAACTTTGTACTTAACACTGCC
ATGCCATATTTTTGCTTACAGTAATAGATTCAGTGGAGGATTTGGTGCCAGAG
ACTATCGACAAAGTAGTGGTTCCAGCAGTTCTGGCTTTGGTGCTAGTCGCGGA
AGCAGCAGCCGCAGTGGTGGAGGTGGTTACGGCAACAGCAGAGGATTTGGT
GGAGGTAATGTTAATTTTTCTTTTAGGAAGGGCTTTTTGTTKTTCTTTTTTTTT
TTTTTTTGAGATGGAGTCCCACTCTGTCACTCAAGCTGGAGTGCAGTGGCCTG
ATCTCGGCTCACTGGAAGTGACTCTCCTGCCTCAGCCTCCTAAGTAGGTGgatt
acaggtgggtggc (SEQ ID NO: 602)
For: 5'-3' = ggaattgcagggtttaagc (SEQ ID NO: 603)
Rev: 5'-3' = gccacccacctgtaatcc (SEQ ID NO: 604)

M203 = UTY1 exon01 (1014) (503 bp) G to C at position 248; synonymous substitution, SER
GagtgccaagctgaggatgaCCCCGTCATCAACGTGGGCAAGCTGCGTCCAGGCCTTCC
CGGAGAGTATCGCCAGCCAACCAGGCGGGTGATGGAGGTGCGTACCTGTCCA
TGCCACCAAGCGCCTCCCTTTCCTCGACTGTCAGGCTAACAGACTCCTCTTCA
CTCTCGCGGCTCGCTTTTCCTTCCGCCATTTTCTTTGCCTCATCACCGAAGGCA
ACAGCGGCGGTAGTGAGCGACACTGCCGCASGATTTCATGGAAACAACAAATT
TCCAAGTCCCACGACGATACCCAACCTTAATCGAGTAGTTGAAAAGACGCCT
TCAATCGCTGCTTGAGACTGTGACGCCAATTTTATCGCCTCCTCAGCGGCTGC
AAGGAAAAAAGCTGAGGCAAAGACTTAAGCTACCGAAGCACGGGCAGCGGA
ACTCGGCTACCTGGATCACATCTGGGAAACTACAGGGAAGGCAGAAGCTCGC TABLE 1-continued AGTGCtggagagcacagcagaattt (SEQ ID NO: 605)
For: 5'-3' = gagtgccaagctgaggatga (SEQ ID NO: 606)
Rev 5'-3': aaattctgctgtgctctcca (SEQ ID NO: 607)
New Rev 5'-3': ttccttggcagccgctgaggag (SEQ ID NO: 608)

M204 = UTY1 ex 02 = Intron 1 (1158-4) (286 bp) T to G at position 234; non coding
AagggcgaagtattccagAGTACGGGGACAGCAAAGGCAAGAAACACTTTTCCGACC
CCTTGGCCATGGAGCAGAGCCAAAATAAATACTGGCTGGGCGGTAAGGAAC
GCGGGGCCTTGGTAGAGCAAAGTGCGGACCAAAGACTTTGCGTCTGGTTGCT
TTTACCTTGCCTAGTAGGGTCTTCGTTCTGGCGCCATCTTCATGAAGCCTCAC
GAACCCGAAGAGACGGCTGKAGAGAGAGAGACACAGAGCTTGTTAATGGTC
TGAGAAAGCCAGTGACTTGCTCCTTCCCGAGTCCAAGAGCGACAGCGACAGA
TTGGTGAGTGCCAAGCTGAGGATGACCCCGTCATCAACGTGGGCAAGCTGCG
TCCAGGCCTTCCCGGAGAGTATCGCCAGCCAACCAGGCGGGTGATGGAGGTG
CGTACCTGTCCATGCCACCAAGCGCCTCCCTTTCCTCGACTGTcaggctaacagactcct
cttca (SEQ ID NO: 609)
For: 5'-3' = aaggggcgaagtattccag (SEQ ID NO: 607)
Rev 5'-3': tgaagaggagtctgttagcctg (SEQ ID NO: 608)

M205 = UTY Intron 2a (1221+3624) (541 bp) T to A at position 78.
GtataatactgtggttggaaagcaCTAAAATTTAATTTTGGCTTACAGCATTATGCCTATAA
ATAAATTTTGCCACCWGAGTCACAGACAAAACAGGCAAAACAATCTTATTTG
GCAATTTAAATAATATCAAATGTTCCCTAGTTATTTCAATTTGACTCTTTTAAA
AGCTAGCTAGTTAGTAATAAAAGTAGGCTGGATGCAGTGGCTCACTCCTGTA
ATCCCAGCACTTTGGGAGGCTGAGGAGAGCAGATCACCTGAGGTCAGGAGTT
CCAGACCAGCCTGGCCAACATGATGAAACCCTGTCTCTACTACAAATACAAA
AAATTAGCCAAGCATGGTGGTGGATACCTGTAATCCCAGCTACTTGGGAGGC
TGAGGCAGGAGAATCACTTGAACCCAGAACACAGAGGTTGCAGTGAGGTGA
GACCGCACTATTCCACTCCAGCCAGGGCAACAAGAGTGAAACTCCATCTCGG
GGGAAAAAAAAGTAAAGTAAACCAATACCAGAAAAGTGcccatttattatcacatagtttgg (SEQ ID NO: 609)
For: 5'-3' = gtataatactgtggttggaaagca (SEQ ID NO: 610)
Rev 5'-3': ccaaactatgtgataataaatggg (SEQ ID NO: 611)

M206 = UTY Intron 2b (1221+3671) (541 bp) T to G at position 31.
GtataatactgtggttggaaagcaTAAAAKTTAATTTTGGCTTACAGCATTATGCCTATAA
ATAAATTTTGCCACCTGAGTCACAGACAAAACAGGCAAAACAATCTTATTTG
GCAATTTAAATAATATCAAATGTTCCCTAGTTATTTCAATTTGACTCTTTTAAA
AGCTAGCTAGTTAGTAATAAAAGTAGGCTGGATGCAGTGGCTCACTCCTGTA
ATCCCAGCACTTTGGGAGGCTGAGGAGAGCAGATCACCTGAGGTCAGGAGTT
CCAGACCAGCCTGGCCAACATGATGAAACCCTGTCTCTACTACAAATACAAA
AAATTAGCCAAGCATGGTGGTGGATACCTGTAATCCCAGCTACTTGGGAGGC
TGAGGCAGGAGAATCACTTGAACCCAGAACACAGAGGTTGCAGTGAGGTGA
GACCGCACTATTCCACTCCAGCCAGGGCAACAAGAGTGAAACTCCATCTCGG
GGGAAAAAAAAGTAAAGTAAACCAATACCAGAAAAGTGcccatttattatcacatagtttgg (SEQ ID NO: 612)
For: 5'-3' = gtataatactgtggttggaaagca (SEQ ID NO: 613)
Rev 5'-3': ccaaactatgtgataataaatggg (SEQ ID NO: 614)

M207 = UTY1 ex03 = Intron 3a (1330+18) (423 bp) A to G at position 79 ; non coding
AggaaaaatcagaagtatccctgAAGAAGGAAAAAACGTTACAACTATGGGCAAATGTA
AGTCAAGCAAGAAATTTARAAAGAGAATAACAATACCTTTTGAATAATCTTC
CAACAAGAGGTTGAAGTGACCTAATTGGCAAAAGAAGTCAGACTCCACTTTT
CCTTCAGCTTTTAAGATTAAAGATTCGTAGCAGCGAACAGCCTAGAAATAAA
AATTATAAACATTAAGAAAAAGGCATGTCCTTCCTGGAAGAATACATACATC
TGCACGAGATTCTTAAAGAAATCAAAGCAACCATAAATGTATGTCATTTCTTC
CATAGGCATAGGATTAAATTCGGCATTTCAGAGAGGAAATAACTTCTCTTTA
AGAATTTACTAATGAAGAAATTAGATCCcaaggattcttggtgaattttg (SEQ ID NO: 615)
For: 5'-3' = aggaaaaatcagaagtatccctg (SEQ ID NO: 616)
Rev 5'-3': caaaattcaccaagaatccttg (SEQ ID NO: 617)

M208 = UTY1 = Intron 3b (1330+5798) (507 bp) C to T at position 352.
AtaaatacaaaatcacctgatggatATGCAAAAATTTATCAGCTTTACAAAGACATATAATA
CCATTCTATGAGCACAAGTTTATTGCAATATTTTGTCCTTTACTGTCAACAAA
AGAACACAGCCACATGATATAGGAAAAATCTATATTCTTTACAAATTTTCCAT
GAATCTCTAGCTAAAAGATCATATGACATATATGCAACGATTTATCAGCTTTC
AGAGCTTTAATTGATATTCATTACTTGTGGGTTCTGTTATTTGACTCACGAAA
ATTTATATATACACAAAATCAATACTTAATGATGGTTTCAAAGATATTCACAG
ACCTGCTCAGGGCAGCAATAAATTYGACCCACTGGATACACACTCCCAGCTA
ATGTTAGAAGCGGTGGGCCTTTCTCTGACTTCATGTGTCAAGTATTCTAAACA
AACAGGCTTTTCCTGCTGTATGCAGTGTCACATTTTTCTGATTTTTGCTcttttgtta
gtaatttcgctgtttaa (SEQ ID NO: 618)
For: 5'-3' = ataaatacaaaatcacctgatggat (SEQ ID NO: 619)
Rev 5'-3': ttaaacagcgaaattactaacaaaa (SEQ ID NO: 620)

M209 = UTY1 = Intron 3c (1330+6211) (550 bp) A to G at position 471.
CactgtcttccacaatggttgAACTAGTTTACAGTTCCACCAACAGTGTATAAGTTTTCCT
ATTTCTCCATATCCTCTCCAGCACCTGTTGACATTACTAAAATAACATTCTCAT
CAAGGTCATCAGGGTCTCAGAACTGGCTACATACAACCTCCAAGAAAGTTTC
GTTCTTTCTGTTTTTGCAATGTGTTCTGCCACAAATTCATCAGTTCTCAAAGCT
AACAGAACTTTTACTAGTTGCCCAATGCATCAATTCCATAGTTCTGAGAGCAT TABLE 1-continued

```
GGGCATGAATGTCTGAAAACCTGAGGTATGATCACTAATATGCTATTCTCTGA
ACTTCTCAATTGCATTTTCCTCCTTGAATAAATCAGACTAAATTAGTGACACC
ACAAATTGTGATCATTGAGAAATCTCTAAAGGTTTTTCAGAAGCCGAGTAGG
AAGCTATCTATGACTTTTTAAAACTCTGACTGAATTCTRAATATATTTAATTG
GACATTACATGAAGACGTTGTGTATTTAACTTCTGAATGCAgggaagataaatacaaaat
cacct (SEQ ID NO: 621)
For: 5'-3' = cactgtcttccacaatggttg (SEQ ID NO: 622)
Rev 5'-3': aggtgattttgtatttatcttccc (SEQ ID NO: 623)
```

M210 = UTY1 = Intron 3d (1330+6221) (550 bp) A to T at position 461.
```
CactgtcttccacaatggttgAACTAGTTTACAGTTCCACCAACAGTGTATAAGTTTTCCT
ATTTCTCCATATCCTCTCCAGCACCTGTTGACATTACTAAAATAACATTCTCAT
CAAGGTCATCAGGGTCTCAGAACTGGCTACATACAACCTCCAAGAAAGTTTC
GTTCTTTCTGTTTTTGCAATGTGTTCTGCCACAAATTCATCAGTTCTCAAAGCT
AACAGAACTTTTACTAGTTGCCCAATGCATCAATTCCATAGTTCTGAGAGCAT
GGGCATGAATGTCTGAAAACCTGAGGTATGATCACTAATATGCTATTCTCTGA
ACTTCTCAATTGCATTTTCCTCCTTGAATAAATCAGACTAAATTAGTGACACC
ACAAATTGTGATCATTGAGAAATCTCTAAAGGTTTTTCAGAAGCCGAGTAGG
AAGCTATCTATGACTTTTTAAAACTCTGWCTGAATTCTAAATATATTTAATTG
GACATTACATGAAGACGTTGTGTATTTAACTTCTGAATGCAgggaagataaatacaaaat
cacct (SEQ ID NO: 624)
For: 5'-3' = cactgtcttccacaatggttg (SEQ ID NO: 625)
Rev 5'-3': aggtgattttgtatttatcttccc (SEQ ID NO: 626)
```

M211 = UTY1 = Intron 4a (1381+16283) C to T at position 381.
```
CaattcactatttgaggaatccaAGTATTCCCCCTGGGGCACAGTTTAGGTATAAACACACT
TCCACTACTAACTATCTCCAGCAGTTGCCTACCTATAAGCTCCACCTACAGGC
CTGAAGTCCAGGTCACACAGCCAGCTGCAATCACTGACAACACAAGTGCACA
AACACAGGAAGCAGAACATACTACCGATGCTAGTATCACTGCACACACTACA
CTGACCACCTAGGGGCTCAGAAACTCATTTACCCACCCAATCCACTGCTACC
ACACTGGCATCTAAGAAGTCCACCCAGAGGCCCACCACGTGGTCCACCTGGA
ATTGCCAATACAGATGCTGGCAAACAATGTCGTAGGCAAAAGGATGTTAACA
ACAAGYACACCACTGAGACCAGTGAAACCTGACTACAGGCCTAACTGGCAC
TGCAGTTTCCAGCAAATTTCTCCACAGCCTCCATTAGTAACCACATCCTAGTA
TACCAAGGAAACCACAGGTACCATTAAGGGTATATActgccaaataaatcagagacttc (SEQ ID NO: 627)
For: 5'-3' = caattcactatttgaggaatcca (SEQ ID NO: 628)
Rev 5'-3': gaagtctctgatttatttggcag (SEQ ID NO: 629)
```

M212 = UTY1 ex05a (409 bp) Intron 4b (1381-22) C to A at position 234; non coding
```
TataatcaagttaccaattactggcCAAGATGAAAGAATGATGGGCTGAACTTGATTAGAAA
CTGCAGTAAAATAAGTGATACTACTGGAAATGTATGGTTACAGACATTAAAA
TCACCATTTACTGGAAACAAATGGTATAAGTCAACTTACCAATGAAATGCAT
TGTAGTAGAAGTAGACCAAACCAAGGCCATATAAAAACGCAGCATTCTGTTA
ATATAAAACACAAAAMAACCTTTATAACAGATTTTATATCTATTACTATTAC
ATATATTAATAAGAAGTCATGTAACGAGATGTTTAAGTTCTGAATATTTTAC
CATATATTACAATATTCTTCTCTACTTTTTCTCAAGTTCTCTCCATTTTGAAAA
TTGGAATCAAtttgccattcaatgttacaaaa (SEQ ID NO: 630)
For: 5'-3' = tataatcaagttaccaattactggc (SEQ ID NO: 631)
Rev 5'-3': ttttgtaacattgaatggcaaa (SEQ ID NO: 632)
```

M213 = UTY1 ex05b = Intron 4c (1381-78) T to C at position 290. Mimics M89 (409 bp); non coding
```
TataatcaagttaccaattactggcCAAGATGAAAGAATGATGGGCTGAACTTGATTAGAAA
CTGCAGTAAAATAAGTGATACTACTGGAAATGTATGGTTACAGACATTAAAA
TCACCATTTACTGGAAACAAATGGTATAAGTCAACTTACCAATGAAATGCAT
TGTAGTAGAAGTAGACCAAACCAAGGCCATATAAAAACGCAGCATTCTGTTA
ATATAAAACACAAAACAACCTTTATAACAGATTTTATATCTATTACTATTACA
TATATTAATAAGAAGTCAYGTAACGAGATGTTTTAAGTTCTGAATATTTTACC
ATATATTACAATATTCTTCTCTACTTTTTCTCAAGTTCTCTCCATTTTGAAAAT
TGGAATCAAtttgccattcaatgttacaaaa (SEQ ID NO: 633)
For: 5'-3' = tataatcaagttaccaattactggc (SEQ ID NO: 634)
Rev 5'-3': ttttgtaacattgaatggcaaa (SEQ ID NO: 635)
```

M214 = UTY1 ex12 = Intron 11 (1971-60) (460 bp) T to C at position 404; non coding
```
TattacaaaatatggaaacaaggcAACATCAAAACACAAATAGACAAACTTGCCAGCCACC
CTTCTCCTGCCAATTATTATAGGAATATACGTGTCATTTAAAATATACTATTT
AAAATTTTTACCTGTAGAAATTTAATTCTTGCAGCAAGCGTAGAGGTATTACT
ACAACGTTTGCTTCTAGCTGCATTTAGGTAGCATTTAATGGCATCTTGAGGTT
GATTGCAGGATTCATAGAGAGTACCTAGGTCCATCCAGGCTGCGGCATGCCC
ATGGTCCAATTGTACAGCACAAATATATGCCTGTAAAGCATCCATAGGCTGA
TTTTGCTGCTGATACAACACACTGGAAAGAAAAAGAATGCTGTCAAAAACTA
CTGGTTACTTTCGTTCGTTTATTTTTCYGTTGTTTTCAGACAGTGTCTCACACT
GTCTCCCAGGctggagtgaagtggcatttc (SEQ ID NO: 636)
For: 5'-3' = tattacaaaatatggaaacaaggc (SEQ ID NO: 637)
Rev 5'-3': gaaatgccacttcactccag (SEQ ID NO: 638)
```

M215 = UTY1 exon 14 (2358) (386 bp) A to G at position 163; silent substitution, SER
```
GtaaaactcagatatatacatcccatgAAATATACACAGAAACTATAAATTAGCATTAATATC
CTCTAAAATGATACTGTAGTAAAGAAATATTCTCAAACTGTTGGTAAATTTTA
```

TABLE 1-continued

```
GAGAAAATAAAAATATTATACATACTTGCTGCATTAAGACAAACTGRCTTTC
TAACTGTTCCAGCTGATGCTTCTGTGCTGGATTTAAATTATCTCTATTTGCTCG
CAGTTGTTCCAAGTGCTAGAAGAAAAGAGATTAATATAATCAAAGTTTAATC
TAAAATTTAAGACAATATAAGGCAACTCCTCACTAAAAAGACTACACAGAAC
CTTTGCAGGATGAAAGACAGTGATTCCTAATGAAcgttaagatagtgattcttttttttt (SEQ ID NO: 639)
For: 5'-3' = gtaaaactcagatatatacatcccatg (SEQ ID NO: 640)
Rev 5'-3': aaaaaaaaagaatcactatcttaacg (SEQ ID NO: 641)

M216 = UTY1 intron 18 3678+537 (557 bp) C to T at position 54.
CtcaaccagttttttatgaagctagAAAAAAATTCCTTTATTAAAGAAATGTAAYATTCAACA
GGTATACATAACTAGCAGTGTCAGAATTCAGATTTAGAACCATGTTTACTAA
AAGCTTACCCTGGAACAATTATCTTTTGCTACTCTCATATAATCCCAGTCAAT
ATTTGAGAAGGCCTTAATTTTTCTAGACAAAATCTGTTTGCATATCTGGTGGT
CAAGAACCTTTTCTGTCAAAGGCCAGATAATAAATATTTTTGGCTTTATGGGC
AACCTAGTCTCTTTAGCAAACTCTGTCAATGTACTGCAAATGCAATCATAAAG
ACAGTAACTAAATAAATAAGCATAGTTATGTTCCAATAGAATTTTATTTTCAA
AAGCAGGTTGGTGGGCAGCACTTCGAGTAAGAGCATTCATTTGTTAAGTGCC
CTGAAATATAAACATGTTCTTCTGAAATATTAAACCTTTGAGAGTAAAGTCTA
TGCTCCCTAAGGCAATCTGGCTTGATTTAAAGAATACATCGATTTTCTacaagaca
cattagttcagactctc (SEQ ID NO: 642)
For: 5'-3' = ctcaaccagttttttatgaagctag (SEQ ID NO: 643)
Rev 5'-3': gagagtctgaactaatgtgtcttgt (SEQ ID NO: 644)

M217 = UTY1 intron 17 3678+768 (461 bp) A to C at position 219.
GcttattttttagtctctcttccatGACTCTTCTAATACCATCGTCAATAAATTTCAACTAGGTA
AAAAATTAATATTGAACATCTGTCCAAAGAAAGGCCAGTATCTCCAAAATCC
TCTCGTACAGATCTGTTTCGAGATCATTCTAATTACTGTATCTTCATATTTTAG
GTTAAGATTCTTTAACTTGTGAAGGAGAATGAAAAAGTTGGGTGACACMAA
CTCTTCAGAAGGAAAAATACATAAAAATTATTTTGATGAAAGCCACAGCAGC
TTTATCAAATGCTTACGTTGCTAAATAGTAAAAAAAGCCACTTAAATTCCAAT
GGAAATTTTATACCCACATGTATTTATGTAAAACTTTTAAATAACATGTATTC
ATAATCACTTTTATATCCTCAACCAGTTTTTATGAAGCTAGAAAAAAATTCCT
TTATTAaagaaatgtaacattcaacaggt (SEQ ID NO: 645)
For: 5'-3' = gcttattttttagtctctcttccat (SEQ ID NO: 646)
Rev: 5'-3': acctgttgaatgttacatttcttt (SEQ ID NO: 647)

M218 = UTY1 intron 16 3679-281+768 (482 bp) C to T at position 380.
TtgtgagttttttttccatcaatcTGGCTATTAAAAATCTGCAGTGCATCCTAACCTTTGATAT
TATGTTGCTACATATTACAGTATTGTATCATTTGTCTTGTCAGGAAAGTGTGG
AGGTAATAGCTAAAAAAAACCCTCTCTTTTAAAAATTACATTTTAAATTTGAT
TCACTTTAAAACTGTTACCTATCTCTTATACCACAGTGATTTATAAAATTCTTT
TAAATTAGTTGAGTTGTTCGAAAGTATTTCCCAAGCATATTTTTGAGTTATC
TTCTATTGCTTCTTAAATGAGACAACAGGTAGAAGAGACATTTAAAGTTTAA
AATCAAACTGTTTTATAAACTATTAACAAAACTTTTAGAGAATAAAAACCAY
AACAGGCAAACCTTAAATTTGTATTTATTGCCTCAAAGTTTCAACTGAAACGC
TTATTTTTAGTCTCTCTTCCATGActcttctaataccatcgtcaataaa (SEQ ID NO: 648)
For: 5'-3' = ttgtgagttttttttccatcaatc (SEQ ID NO: 649)
Rev 5'-3': tttattgacgatggtattagaagag (SEQ ID NO: 650)

M219 = UTY1 intron 16 3676-294 (482 bp) T to C at position 232.
TtgtgagttttttttccatcaatcTGGCTATTAAAAATCTGCAGTGCATCCTAACCTTTGATAT
TATGTTGCTACATATTACAGTATTGTATCATTTGTCTTGTCAGGAAAGTGTGG
AGGTAATAGCTAAAAAAAACCCTCTCTTTTAAAAATTACATTTTAAATTTGAT
TCACTTTAAAACTGTTACCTATCTCTTATACCACAGTGATTTATAAAATTCTTT
TAAATTAGYTGAGTTGTTCGAAAGTATTTCCCAAGCATATTTTTGAGTTATC
TTCTATTGCTTCTTAAATGAGACAACAGGTAGAAGAGACATTTAAAGTTTAA
AATCAAACTGTTTTATAAACTATTAACAAAACTTTTAGGGAATAAAAACCAC
AACAGGCAAACCTTAAATTTGTATTTATTGCCTCAAAGTTTCAACTGAAACGC
TTATTTTTAGTCTCTCTTCCATGActcttctaataccatcgtcaataaa (SEQ ID NO: 651)
For: 5'-3' = ttgtgagttttttttccatcaatc (SEQ ID NO: 652)
Rev 5'-3': tttattgacgatggtattagaagag (SEQ ID NO: 653)

M220 = UTY1 intron 16 3676-329 (482 bp) A to G at position 367.
TtgtgagttttttttccatcaatcTGGCTATTAAAAATCTGCAGTGCATCCTAACCTTTGATAT
TATGTTGCTACATATTACAGTATTGTATCATTTGTCTTGTCAGGAAAGTGTGG
AGGTAATAGCTAAAAAAAACCCTCTCTTTTAAAAATTACATTTTAAATTTGAT
TCACTTTAAAACTGTTACCTATCTCTTATACCACAGTGATTTATAAAATTCTTT
TAAATTAGCTGAGTTGTTCGAAAGTATTTCCCAAGCATATTTTTGAGTTATC
TTCTATTGCTTCTTAAATGAGACAACAGGTAGAAGAGACATTTAAAGTTTAA
AATCAAACTGTTTTATAAACTATTAACAAAACTTTTAGRGAATAAAAACCAC
AACAGGCAAACCTTAAATTTGTATTTATTGCCTCAAAGTTTCAACTGAAACGC
TTATTTTTAGTCTCTCTTCCATGActcttctaataccatcgtcaataaa (SEQ ID NO: 654)
For: 5'-3' = ttgtgagttttttttccatcaatc (SEQ ID NO: 655)
Rev 5'-3': tttattgacgatggtattagaagag (SEQ ID NO: 656)

M221 = UTY1 intron 18 (3784+165) (324 bp) G to A at position 200.
GggaaatgtgaaaggaaaataTCTTGGGTACCTGAAATCACTATCCTAAAGGGAAAGGT
CAAACTGGGTACTGCTTAGGGCAAACCTGCCTCCATTCTATTCAAAGTCACTC
CTCTGTTTACTGAGCTAAATGTATATCTGTTATTATCCGTATATATCTGTATAT
```

TABLE 1-continued

```
GATATCTATATTATCACTTGCATCAGTGCTAAAGATGCTTGCTCATGCACAAG
AGGTATAAAATTGAGTGAGAAAGAAAGATAACACACATTAAAATAAAGACT
CAGAATGTTGGGGGAAAAAATCAGTGAgtttctgtcagtgttataaaagtttaa (SEQ ID NO: 657)
For: 5'-3' = gggaaatgtgaaaggaaaata (SEQ ID NO: 658)
Rev 5'-3': ttaaacttttataacactgacagaaac (SEQ ID NO: 659)

M223 = A8.05e (208 bp) C to T at position 67.
ttcagcaagagtaagcaagaggCACTGAGCCGCTGGAGTCTGCACATTGATAAATTTACTT
ACAGTYGTAAATAAATTGCATCATCTTCAGCTAGTAACACAGAGTCTAATTT
TTATAGCGGCATACTTGCCTCCACGACTTTCCTAGACACCAGAAAGAAAGGC
GAGAGCCAGCCTTAGCCTAATCaagaaccatgatccaaaaagg (SEQ ID NO: 660)
For: 5'-3' = ttcagcaagagtaagcaagagg (SEQ ID NO: 661)
Rev 5'-3' = cctttttggatcatggttctt (SEQ ID NO: 662)

M224 = B9.60b (301 bp) T to C at position 193
CttcaggcattattttttttggtTCTCCACTACAGGAGAAATGTAAATGTGATGAGTCAGAAT
TTAGGATGGCTGTATGGGTTTCTTTGACTAATACAAGAAATCACTTTGTAATG
AATGAAATCAGTGGTTTCTGCATTACTCCGTATGTTCGACATGAACACAAATT
GATACACTTAACAAAGATACTTCTTTCYGCCCTTCCAAATATTTCAAAATAAG
CTGGTCATAGTACTTGCTTTTCATAAAAAGATGGTAAGCTTCCAATATTTAGA
TTTaaggaaaggtgaaggaacactat (SEQ ID NO: 663)
For: 5'-3' = cttcaggcattattttttttgg (SEQ ID NO: 664)
Rev 5'-3' = atagtgttccttcacctttcctt (SEQ ID NO: 665)

M225 = UTY1 Exon1b, (528 bp) G to A at position 369. (518 C to T in cDNA utr region
AaggaaaaaagctgaggcaAAGACTTAAGCTACCGAAGCACGGGCAGCGGAACTCGGC
TACCTGGATCACATCTGGGAAACTACAGGGAAGGCAGAAGCTCGCAGTGCTG
GAGAGCACAGCAGAATTTCTTAAAATCACAAACTTTGCCAGCACCAGCACAA
AGTTGTAATTGTGTCACGGGCGAACCCCACGCAGCCGCCGCGACCTCCCCGC
TCCCAACCACTTAGTTGTAGCCAATCTAGGCGACTGATTCGTCTCACGTGATC
TTTGTTGACTTACGTCAGGCATTGCTCCACTGTACTCCTAGGCTGCTGGGACC
CCGCCCAGCCAGTTCGCCAAGGACCTAGGAACATGACAGAGGCTGACTRATT
CTGACCGCTGGTTGGTTGATGGTCACGTCTATGGAGAAAAGGGTAGTCTCTG
GGATGGAACAACCTGTAGGTTGTGCTAGTTAAATGCATTAAGATAGAAAATG
GAGTGTCTGTGCTGGGTGTTTTTGCAGTTGCGatacgcttgaaggggaagag (SEQ ID NO: 666)
For 5'-3' = aaggaaaaaagctgaggca (SEQ ID NO: 667)
Rev 5'-3' = ctcttcccttcaagcgtat (SEQ ID NO: 668)

M226 UTY Ex1c 1104 silent/glu (380 bp) C to T at position 158
gagtgccaagctgaggatgaCCCCGTCATCAACGTGGGCAAGCTGCGTCCAGGCCTTCCC
GGAGAGTATCGCCAGCCAACCAGGCGGGTGATGGAGGTGCGTACCTGTCCAT
GCCACCAAGCGCCTCCCTTTCCTCGACTGTCAGGCTAACAGACYSYTCTTCAC
TCTCGCGGCTCGCTTTTCCTTCCGCCATTTTCTTTGCCTCATCACCGAAGGCAA
CAGCGGCGGTAGTGAGCGACACTGCGCASGATTTCATGGAAACAACAAATTT
CCAAGTCCCACGACGATACCCAACCTTAATCGAGTAGTTGAAAAGACGCCTT
CAATCGCTGCTTGAGACTGTGACGCCAATTTTATCGCctcctcagcggctgcaagga (SEQ ID NO: 669)
For 5'-3' = gagtgccaagctgaggatg (SEQ ID NO: 670)
Rev 5'-3' = aaattctgctgtgctctcca (SEQ ID NO: 671)

M227 UTY Ex1c 1105 Glu/Gln C to G in at position 157
GagtgccaagctgaggatgaCCCCGTCATCAACGTGGGCAAGCTGCGTCCAGGCCTTCC
CGGAGAGTATCGCCAGCCAACCAGGCGGGTGATGGAGGTGCGTACCTGTCCA
TGCCACCAAGCGCCTCCCTTTCCTCGACTGTCAGGCTAACAGACYSYTCTTCA
CTCTCGCGGCTCGCTTTTCCTTCCGCCATTTTCTTTGCCTCATCACCGAAGGCA
ACAGCGGCGGTAGTGAGCGACACTGCGCASGATTTCATGGAAACAACAAATT
TCCAAGTCCCACGACGATACCCAACCTTAATCGAGTAGTTGAAAAGACGCCT
TCAATCGCTGCTTGAGACTGTGACGCCAATTTTATCGCctcctcagcggctgcaagga (SEQ ID NO: 672)
For 5'-3' = gagtgccaagctgaggatg (SEQ ID NO: 673)
Rev 5'-3' = aaattctgctgtgctctcca (SEQ ID NO: 674)

M228 UTY Ex1c (380 bp) 1106 Glu/Gly T to C at position 156
GagtgccaagctgaggatgaCCCCGTCATCAACGTGGGCAAGCTGCGTCCAGGCCTTCC
CGGAGAGTATCGCCAGCCAACCAGGCGGGTGATGGAGGTGCGTACCTGTCCA
TGCCACCAAGCGCCTCCCTTTCCTCGACTGTCAGGCTAACAGACYSYTCTTCA
CTCTCGCGGCTCGCTTTTCCTTCCGCCATTTTCTTTGCCTCATCACCGAAGGCA
ACAGCGGCGGTAGTGAGCGACACTGCGCASGATTTCATGGAAACAACAAATT
TCCAAGTCCCACGACGATACCCAACCTTAATCGAGTAGTTGAAAAGACGCCT
TCAATCGCTGCTTGAGACTGTGACGCCAATTTTATCGCctcctcagcggctgcaagga (SEQ ID NO: 675)
For 5'-3' = gagtgccaagctgaggatg (SEQ ID NO: 676)
Rev 5'-3' = aaattctgctgtgctctcca (SEQ ID NO: 677)

M229 = UTY1 Int12, A to C at position 159. (1560+7060 T to G in intron6)
Group I
GgtacacacctgtagcccaacTGCTTGGGAGTCTGAGATGGAAGGATCACTTTGGGCCAG
GAATTCCACGCGTTGTACTATGATTATGCCTGTGAATAGCCACTGCACTCAAT
CCTGGAAAACAGTGAGAGCCAGTCTCTTAAAGTATAATTTCCTTMAATAAAT
ATATTTCAAAATCTCTCATTCTTATTTATGATCAAAAAATGTTATTCATCAATG
TAGACTTTGAGCTTGGTCAATACTGAGCAAATAAAGCCCTCAAATATCCTTTT
CATTTGACAGGTAACTACATGCCTACTAAGGCCACGTATTATGCATATAACAA
```

TABLE 1-continued

```
TAAACAAACATAATCCCTCCACGAAAAAGCTCCAGCCAGAGAGAAATATTAA
AGTAAATAATTATGCTCATCTAATCCATTCAGCAATGGCAAGAATTTCACATG
AAAGTACAAGATGTCCAGCACAGATCTAACCACCTACAAATGGATGCCTCCTT
GAGAAAATGTTATTAAGGTAGGACCTGCATGGATAAGTAAAAGttaccatgaaagagtt
ctaaaaaatg (SEQ ID NO: 678)
For 5'-3' = ggtacacacctgtagtcccaac (SEQ ID NO: 679)
Rev 5'-3' = cattttttagaactctttcatggtaa (SEQ ID NO: 680)

M230 (449 bp) UTY Ex9 intron 8 1651-143 T to A at position 367
Group VIII
AatgtcacatttagtcttaacccatAGACTTCTAAATGAAAACAAATGTCTAAGCAGAGGGA
AAAAAATTGAACCTCAAAAGGCAAATCTCTTCAAATTAATGTAATGTATAAT
AAAAGTTTTCATGTACCTAACTGTTGCAATACAGTTGCTTTTACTTGTGCAGG
AAGGTTTTCTGTCTGCAAAAGTTGTTCATATGCCTCCTTTGCAGAATGATACT
TCCTCTAAAGAGCAAAGGAAAAAGAATATTTAGAGAAAAATAAATATTAAA
ATAAAAATACTCTTGATTTTAACAATATATACATGGCCATACTTAACTTATAA
GTAACAAATAATAAATCAATACGTAATGATGAATATTAAAAAWTATAAATG
TGATAATAAAAAATAAAGTAATATTACAATATTATTAAAATAGCTAgcaatgaaga
tttacatactaataatgt (SEQ ID NO: 681)
For 5'-3' = aatgtcacatttagtcttaacccat (SEQ ID NO: 682)
Rev 5'-3' = acattattagtatgtaaatcttcattgc (SEQ ID NO: 683)

M231 UTY Ex13 Intron 13 2283+33 G to A at position 110 in
Group VIII
CctattatcctggaaaatgtgGGCTCGTTTTAATTATATTCATATTAATTTAGTTAATCATC
ATTCAATTAATACCTAAAAAACAACATTTACTGTTTCTACTGCTTTCRAATTG
GGGGAAAGATCGTCAAAGAATTCATACCTGTAATTTCTGTGGTGTCAAACAC
AACGAATAAACTTGCTGTACTGGATGATGTGAAAGACTCTGGCCACCATTCC
AGTTATCAGAACCATTCTAAGGAAAATTTAGTGTAAAAGATTAAGAATATTT
GCTTAATTTCATACACTTAGAGTTATGACTAGTGAGAAccaagtgactaggaatcggaat
(SEQ ID NO: 684)
For 5'-3' = cctattatcctggaaaatgtgg (SEQ ID NO: 685)
Rev 5'-3' = attccgattcctagtcacttgg (SEQ ID NO: 686)

M232 =UTY1 intron 17 3679-566 (461 bp) C to T at position 38
Group VIII
gcttatttttagtctctcttccatGACTCTTCTAATAYCATCGTCAATAAATTTCAACTAGGTA
AAAAATTAATATTGAACATCTGTCCAAAGAAAGGCCAGTATCTCCAAAATCC
TCTCGTACAGATCTGTTTCGAGATCATTCTAATTACTGTATCTTCATATTTTAG
GTTAAGATTCTTTAACTTGTGAAGGAGAATGAAAAAGTTGGGTGACACAAAC
TCTTCAGAAGGAAAAATACATAAAAATTATTTTGATGAAAGCCACAGCAGCT
TTATCAAATGCTTACGTTGCTAAATAGTAAAAAAAGCCACTTAAATTCCAATG
GAAATTTTATACCCACATGTATTTATGTAAAACTTTTAAATAACATGTATTCA
TAATCACTTTTATATCCTCAACCAGTTTTTATGAAGCTAGAAAAAAAATTCCTT
TATTaaagaaatgtaacattcaacaggt (SEQ ID NO: 687)
For 5'-3' = gcttatttitagtctctcttccat (SEQ ID NO: 688)
Rev 5'-3' = acctgttgaatgttacatttcttt (SEQ ID NO: 689)

M233 = UTY1 Exon18n, T to C at position 50, (3784+37 A to G at intron18)
Group III
AtcacttgcatcagtgctaaagaTGCTTGCTCATGCACAAGAGGTATAAAATTGAGTGAGA
AAGAAAGATAACACACATTAAAATAAAGACTCAGAATGTTGGGGGAAAAAT
CAGTGAGTTTCTGTCAGTGTTATAAAAGTTTAAAGAYAGTAAAATATATATTC
AATCTTGGTTTTAAGCTTACCTAATTTAAGAGCTCCAGCAAGGCCACGTATTA
CTGTAACAGGGTTTTTTGGATttgtacaaaattgatgtaatggagGAAAGAAAGCATCACGTT
TATTTTCCAACTGTAAAAGCAAAATATTTTGTTAGGTCTCAGATAAATGACAA
AATATACCTCAGATTTGTGCCTTTAATAAAATGATTAAATACAATACTTCAAA
TTTGTGAGTTTTTTTCCATCAATCTGGCTATTAAAAATCTGCAGTGCATCCtaacct
ttgatattatgttgctacat (SEQ ID NO: 690)
For 5'-3' = atcacttgcatcagtgctaaaga (SEQ ID NO: 691)
Rev 5'-3' = atgtagcaacataatatcaaaggtta (SEQ ID NO: 692)

M234 = UTY1 Exon20n, C to T at position 253, (4049 G to A in cDNA, codon 1015,
Arg/Gln)
Group III
tctccattagcaatgtgtgttttACATACTGTAATTTTGCTTACATTTTTAAAAGTTTACCGGG
CATGGTGGCTCACACCTGTAATCCCAGCACTTTGGGATGCTGAGGCAAGCAGA
CCACCTGAGGTCAGGAGTTCAAGACAAGCCTGGCCAACATGGTGAAACCCTG
TCTCTACAAAAATACAAAAATTAGTTGGGCATGATGGCAGGTGCCTGTAATTC
CAGCTATTCGGGAGGCTGAGGTGGGAGAATYGCTTGAACCCAGGAGGCGGAG
GCTGCAGTGAGCTGAGATCACACCATTGCATTCCAGCCTGGGTGAGAGAGAA
TGAGACTCTGTCTCAAAAACAATAAAAAATAATAAAATAAAATAAAAGTTTA
ATAATCTATGAGCACTTTAAAAACATACTATTAACAGTATGCACTAGACAATA
ATTATGAAAGTAATATGCACTATTAAAAAATAGCAACAATTAAAAAAGGAAG
AAAGAAAAACTTACTCTCAATGATTCCTGGaaggaggaagcctggtattg (SEQ ID NO: 693)
For 5'-3' = tctccattagcaatgtgtgtttt (SEQ ID NO: 694)
Rev 5'-3' = caataccaggcttcctcctt (SEQ ID NO: 695)
```

TABLE 1-continued

M235 = (317 bp) DFFRY Exon4, T to G at position 155. (1859 in cDNA, codon 65, Asp to Glu
tagatattttccttaatctgtggtTTAAATTTGGAATATTTAATTTTTAATTAAGACTTCATCA
CCTGATTCTTCCAATGAGAATTCCGTAGCAACTCCTCCTCCAGAGGAACAAG
GGCAAGGTGATGCCCCACCACAGCATGAAGATGAAGAKCCTGCATTTCCACA
TACTGAGCTGGCAAACCTGGATGACATGATCAACAGGTGCATTTGTTTGGATT
TGTTTTATTAATGGATGCAGTAAACTAGAAAAGCAAAACTACTTCCAGCATT
GCAACTAGTAGTAAATgagaaaaagaaaagagtagattgtagt (SEQ ID NO: 696)
For 5'-3' = tagatattttccttaatctgtggt (SEQ ID NO: 697)
Rev 5'-3' = actacaatctactcttttctttttctc (SEQ ID NO: 698)

M237 = DFFRY Exon30, (366 bp) G to C at position 39. (5903-132 in intron29)
Group III, 325 bp w/out homopolymer region in STS.
TtgcatttactgttctagagagttctCAAAAAGAAATASGAAACCACTTGAACAGTTTGGGGA
AGTTGTATAGAAGATCTCATTTCCTTCCAGCTCTCTGTTCTCCTAACTCCTTGT
CCTTTTCTATCTCCATGTTGTGAGTTGGGCCTATAATATTTTTCCTTTTGCAGGA
TAATGTTAAAAACACAGGTGAAACAGGTGTCGAAGAGCCAATACTGGAAGGC
CACCTTGGGGTAACAAAAGAGTTATTGGCCTTTCAAACTTCTGAGAAAAAGTA
TCACTTTGGTTGTGAAAAAGGAGgtgctaatctcattaaagtaagtacTTTTTTTTTTTCTTTTT
TTGAgatggagtcttgctctgtgg (SEQ ID NO: 699)
For 5'-3' = ttgcatttactgttctagagagttct (SEQ ID NO: 700)
newRev 5'-3' = gtacttactttaatgagattagcac (SEQ ID NO: 701) Homopolymer clipped off M238 = DFFRY Exon43, C to G at position 28 (8729-54 in intron42)
Group I
GtactaaatggcacataattaggaaCTSAAATGTTAGCTACTATTGGATATTACAAAGTTTT
ACATCTGCTTCTGTTTTAGAATTCATAATGCACTTAAAGGAATTCCAGATGAC
AGAGATGGGCTGTTCGATACAATACAGCGCTCRAAGAATCACTATCAAAAAC
GAGCATATCAGTGCATAAAATGTATGGTAGCTCTATTTAGCAGTTGTCCTGTT
GCTTACCAGATCTTACAGGTGAGGGTTTTTCTCTTATAAATTTGTAGAAACCT
CTGTCACAAGTAAGGAAATGATCGTGAAATTTTTGTATTAGCATTTTAAgctgata
ctgaaaatcattctaaatt (SEQ ID NO: 702)
For 5'-3' = gtactaaatggcacataattaggaa (SEQ ID NO: 703)
Rev 5'-3' = aatttagaatgattttcagtatcagc (SEQ ID NO: 704)

M239 = DFFRY Exon43, G to A at position 148 (8795 in cDNA, codon 2377, silent/Ser
Group I
GtactaaatggcacataattaggaaCTSAAATGTTAGCTACTATTGGATATTACAAAGTTTTA
CATCTGCTTCTGTTTTAGAATTCATAATGCACTTAAAGGAATTCCAGATGACA
GAGATGGGCTGTTCGATACAATACAGCGCTCRAAGAATCACTATCAAAAACG
AGCATATCAGTGCATAAAATGTATGGTAGCTCTATTTAGCAGTTGTCCTGTTG
CTTACCAGATCTTACAGGTGAGGGTTTTTCTCTTATAAATTTGTAGAAACCTC
TGTCACAAGTAAGGAAATGATCGTGAAATTTTTGTATTAGCATTTTAAgctgatac
tgaaaatcattctaaatt (SEQ ID NO: 705)
For 5'-3' = gtactaaatggcacataattaggaa (SEQ ID NO: 706)
Rev 5'-3' = aatttagaatgattttcagtatcagc (SEQ ID NO: 707)

M240 = DBY int2n, C to T at position 47, (116+613 in intron1.
CtgtggaattcttgaagacgagTGACTATAATATAGCACAACGTAAYAAGTATCCTGTATC
TTGTTTCTGGTGGGGTCCCGTAGCCACGGAGCAACCGTTGCCCGGGTGCTGAG
CGTGCCGAAACTGGGCTTCCGGTATGGAAAGTTTTGTGACGCAGAAGGACCG
GAAAGGGATGGTGGGGAGGGTAGGGAAGGATGGCTGCCGCGTGCTTCTCTTG
ACCCTGTAGAAATAATGGAAATTGGACGCCCGCGGAAAGACACCTGGAAGGT
TAGAGATCCAGCATTGCGCTACACCCCTTTGTTAATTCAGTCACTGGACAGCC
GCCTAGCCGAGAGCTGTGCGGTTTTTATATGGTATTGTATCTTTACTTTAGGCG
ATACATGCAGAAGTCGTCCGGTAgaaaactaacctcgaatgttgatt (SEQ ID NO: 708)
For 5'-3' = ctgtggaattcttgaagacgag (SEQ ID NO: 709)
Rev 5'-3' = aatcaacattcgaggttagttttc (SEQ ID NO: 710)

M241 DBY Intron 4 (intron 1) G to A at position 57 cDNA# 117-989
AactcttgataaaccgtgctgTCTAGTTCACTAGAATTAAGTAGTAAATTCAGATGRCAA
GATTTTTAAGTACAGTAGTATCTTAATTGATGATTCATGTAATGTGATAGTAT
CTTGAACTTATATATGTAAGCTTTCTACGGCATAGAAAGTTTGTGCAAAAAGG
TGACCAAGGTGCTCTTGGCATTGGTCTTAACGTGTTTTTTGAAAAAAATCTAT
TTTAACGTACATGGTTTTTTCCCCCACCCCCGCCACCGCTTCAGAGTTGTTCTA
GGTAAGGTATTATGCTGAAAGCCCTTAAAGCGAAATAACCTTTTTTCTAGTTT
TAAAAATCCATCAGTATAAGgaggcatgaattgagattgga (SEQ ID NO: 711)
5'-3' For aactcttgataaaccgtgctg (SEQ ID NO: 712)
5'-3' Rev tccaatctcaattcatgcctc (SEQ ID NO: 713)

M242 DBY Intron 4 (intron 1) C to T at position 337 cDNA# 117-866
Group X
AactcttgataaaccgtgctgTCTAGTTCACTAGAATTAAGTAGTAAATTCAGATGG CAA
GATTTTTAAGTACAGTAGTATCTTAATTGATGATTCATGTAATGTGATAGTAT
CTTGAACTTATATATGTAAGCTTTCTACGGCATAGAAAGTTTGTGCAAAAAGG
TGACCAAGGTGCTYTTGGCATTGGTCTTAACGTGTTTTTTGAAAAAAATCTAT
TTTAACGTACATGGTTTTTTCCCCCACCCCCGCCACCGCTTCAGAGTTGTTCTA
GGTAAGGTATTATGCTGAAAGCCCTTAAAGCGAAATAACCTTTTTTCTAGTTT
TAAAAATCCATCAGTATAAGgaggcatgaattgagattgga (SEQ ID NO: 714)

TABLE 1-continued

5'-3' For aactcttgataaaccgtgctg (SEQ ID NO: 715)
5'-3' Rev tccaatctcaattcatgcctc (SEQ ID NO: 716)

M243 = DBY int6, (401 bp) T to C at position 142, (117-356 in intron1)
Group III
ttttgagcttttgatgtttaggaATTTATCTGCATTAAAAATAGTTGTACCGTCTTCAGGGCAA
AGATAAATTAAGGAATCTTCAAATGATTTTAATGTCCATTTATTTTTAGGGTTA
GAATATCAAGAAAACCACTGTCAYTGGGAACATTTCACTATCATGACTGTAGC
TAAATTGGATGTTGAAGTTACTGAGAAATTGATGGTAAATTTTTTTAGTTAGG
AAAGTTTTCACTTCGGAAAATTGTTAAGGAAAATTTGTTTTGAATTAATGAAT
TTGAACTCATTACTGTGAAACTGCTGGTATTCAGCTGATGCCATTTGCATTTGT
CATGGTTGGTAGACCTGGACATCTTTAAAATTTGGCAGGTAATACCAGGCcgaca
tggcagctaagtttg (SEQ ID NO: 717)
For 5'-3' = ttttgagcttttgatgtttagga (SEQ ID NO: 718)
Rev 5'-3' = caaacttagctgccatgtcg (SEQ ID NO: 719)

M244 = DBY int6, (401 bp) A to C at position 174, (117-323 in intron1)
Group I
ttttgagcttttgatgtttaggaATTTATCTGCATTAAAAATAGTTGTACCGTCTTCAGGGCAA
AGATAAATTAAGGAATCTTCAAATGATTTTAATGTCCATTTATTTTTAGGGTTA
GAATATCAAGAAAACCACTGTCATTGGGAACATTTCACTATCATGACTGTAGC
TAMATTGGATGTTGAAGTTACTGAGAAATTGATGGTAAATTTTTTTAGTTAGG
AAAGTTTTCACTTCGGAAAATTGTTAAGGAAAATTTGTTTTGAATTAATGAAT
TTGAACTCATTACTGTGAAACTGCTGGTATTCAGCTGATGCCATTTGCATTTGT
CATGGTTGGTAGACCTGGACATCTTTAAAATTTGGCAGGTAATACCAGGCcgaca
tggcagctaagtttg (SEQ ID NO: 720)
For 5'-3' = ttttgagcttttgatgtttagga (SEQ ID NO: 721)
Rev 5'-3' = caaacttagctgccatgtcg (SEQ ID NO: 722)

M245 = DBY int8, del AAACA at position 264, (174+779 in intron2)
Group I
gacgaagaacctaacattcagtgATAAAACCAAGCTCATCTGATTTTAAGGTGATGAGTTA
GCTATATTCCTGTGAAAGGAAATTAGTTATAAAGACATTCTTTTGAAATACTT
GGTCTTGTTTGGTTTTGGAAGATTGGGTGAGGTTAGTATTTGGATAGGAGAGT
AAGGCTGGTGGTTATTCAGTAGTATCCCTGGTTTGAGTCCAGGTTTCTTACTGT
TGTTCAACAAGGAAAGTAGTTGGTATGCTTTGAAACAAAACAAACAGAAC
ACTTTTAAGTTKTATAAATTTATTTCAAACTTTGTCGTTATATGAACATTACAG
ATATTTAAATGGTAGAGACATTTTTGGATATTTAGTTAAATCCAAAAGTAGGA
GGTTTAGTTCAAATTTGGATTTTTGAGTTAcaaaatcaggtagttaagtactgtcta (SEQ ID NO: 723)
For 5'-3' = gacgaagaacctaacattcagtg (SEQ ID NO: 724)
Rev 5'-3' = tagacagtacttaactacctgattttg (SEQ ID NO: 725)

M246 = DBY int8, T to G at position 284, (174+799 in intron2)
Group I
gacgaagaacctaacattcagtgATAAAACCAAGCTCATCTGATTTTAAGGTGATGAGTTA
GCTATATTCCTGTGAAAGGAAATTAGTTATAAAGACATTCTTTTGAAATACTT
GGTCTTGTTTGGTTTTGGAAGATTGGGTGAGGTTAGTATTTGGATAGGAGAGT
AAGGCTGGTGGTTATTCAGTAGTATCCCTGGTTTGAGTCCAGGTTTCTTACTGT
TGTTCAACAAGGAAAGTAGTTGGTATGCTTTGAAACAAAACAAACAGAACA
CTTTTAAGTTKTATAAATTTATTTCAAACTTTGTCGTTATATGAACATTACAGA
TATTTAAATGGTAGAGACATTTTTGGATATTTAGTTAAATCCAAAAGTAGGAG
GTTTAGTTCAAATTTGGATTTTTGAGTTAcaaaatcaggtagttaagtactgtcta (SEQ ID NO: 726)
For 5'-3' = gacgaagaacctaacattcagtg (SEQ ID NO: 727)
Rev 5'-3' = tagacagtacttaactacctgattttg (SEQ ID NO: 728)

M247 = DBY int9n, T to C at position 224, (175-693 in intron2)
Group II
AtggtagagacattttttggatatttAGTTAAATCCAAAAGTAGGAGGTTTAGTTCAAATTTGG
ATTTTTGAGTTACAAAATCAGGTAGTTAAGTACTGTCTACTTCATAAGTTCTT
TTACTTCTTAATCATAGACTGGCCTGTTGATTTAACTGAAAACACTTGATTTG
TTTTTCCAGATCATTTTCACTTTCCAACTTTTCATGTGTTTTTATGGTATCACTT
YAATCTACCAGTACAGAATTTTTTTCTTTTTTTGAGACGGAGTCTCGCTCTG
TCGCCCAGGCTGGAGTGCAGTGGCGCGATCTCGGCTCACCCCAAGCTCCCCC
TCCCAGGTTCATGCCATTCTCCTGCCTCAGCCTCCTGAGTAGCTGGGACTGCA
GGTGCCGGCCACCATGCCCGGCTAATTTTTTCTATTTTTTTTTAGTAGAGACA
GGGTTTCACCTTGTTAGCCAGGATGGTCTCGATCTCCTGACCTCGTGATCTGC
CCGCCTTGGCCTCCCaaagtgctgggattacaggc (SEQ ID NO: 729)
For 5'-3' = atggtagagacattttttggatattt (SEQ ID NO: 730)
Rev 5'-3' = gcctgtaatcccagcacttt (SEQ ID NO: 731)

M248 = DBY int9n, T to C at position 494, (175-444 in intron2)
Group VI
AtggtagagacattttttggatatttAGTTAAATCCAAAAGTAGGAGGTTTAGTTCAAATTTGG
ATTTTTGAGTTACAAAATCAGGTAGTTAAGTACTGTCTACTTCATAAGTTCTT
TTACTTCTTAATCATAGACTGGCCTGTTGATTTAACTGAAAACACTTGATTTG
TTTTTCCAGATCATTTTCACTTTCCAACTTTTCATGTGTTTTTATGGTATCACTTT
AATCTACCAGTACAGAATTTTTTTCTTTTTTTGAGACGGAGTCTCGCTCTGTC
GCCCAGGCTGGAGTGCAGTGGCGCGATCTCGGCTCACCCCAAGCTCCCCCTC
CCAGGTTCATGCCATTCTCCTGCCTCAGCCTCCTGAGTAGCTGGGACTGCAGG TABLE 1-continued

```
TGCCGGCCACCATGCCCGGCTAATTTTTTCTATTTTTTTTAGTAGAGACAGG
GTTTCACCTTGTTAGCCAGGATGGTCTCGATCTCCTGACCTCGTGATCTGCCC
GCCTYGGCCTCCCaaagtgctgggattacaggc (SEQ ID NO: 732)
For 5'-3' = atggtagagacattttttggatattt (SEQ ID NO: 733)
Rev 5'-3' = gcctgtaatcccagcacttt (SEQ ID NO: 734)
```

M249 = DBY int10, A to G at position 313, (175-167 in intron2)
Group II
```
Tttcaccttgttagccaggat GGTCTCGATCTCCTGACCTCGTGATCTGCCCGCCTTGGCCT
CCCAAAGTGCTGGGATTACAGGCGTGAGCCACCGTGACCAGCCCAGTACAGA
TTTTTTAAAAGCCTCTTACTGGTTAGTTAATTTAGTATAGCACATAAGAGTCT
TTTTTCCCTAGTAGGCTTTTATACTGGGGTAATTACCATGTTTAATGGTCAGTG
TTGATTCATGAAGCAGTTATTGGAAATAGATCCTTTTAAAAGATAATTGTTAG
ATAACCACTACTAGCTACTGAAATATTTGTGGTTTGCARTGTATTTTAGAGTA
AGCATTTTTTCCGCTCATCTTGCAAAGTAGTTTATTGTATAAAATACAGGTTTT
AAAAGTTTGTTTTCCAGGACCTATTTTTTAATagacattttctaaaagcagtatcttg (SEQ ID NO: 735)
For 5'-3' = tttcaccttgttagccaggat (SEQ ID NO: 736)
Rev 5'-3' = caagatactgcttttagaaaatgtct (SEQ ID NO: 737)
```

M250 = DBY int11n, A to G at position 299, (223+687 in intron3)
Group III
```
Taacagttgttaagattaccactttt GGCCACATCCAATAAGCTGGTGAGATTGTCTGGTTTCA
GCCTAAACAACTTCATTTGAAAGGTGTTGCATGAAATGCCTTAAAACACTTA
GGATGGTTTACTATTAAATTTGTAATTTAGAAAAGTTTAATTGGGGTGATGTT
TTGAGTGCTGCATATACATCAAAAAAATTCTAGGAGAAGGAAAGGTCAGGAA
AAGTATTTAAAACCAAAAGGAAAGAAGGTAATGATAAAGGGGTGTGGAGTG
GGTTTGTATTTCTATGTTTAGTCTGTRGCCTCTTTAGGTCTGTTTATCAGAAGA
CCACTTAGCTAATGATTGTATTATTTTTTCAGAATAACTGGAGAATT GTTATT
CTGAAAAAATATTGCATCTGGctggaattgcatcaaaggtt (SEQ ID NO: 738)
For 5'-3' = taacagttgttaagattaccactttt (SEQ ID NO: 739)
Rev 5'-3' = aacctttgatgcaattccag (SEQ ID NO: 740)
```

M251 = DBY int12n,(site a) (nominal, 418 bp) G to A at position 279, (223+1051 in intron3. Site within STS with a 7 T homopolymer length polymorphism allele.
```
aaatattgcatctggctgga ATTCATCAAAGGTTTATTAACTGCCTTAAGGAGAGTTGGC
AATATTTTAGTATTTGAGGGGATGGAAGAGACCTTAAACATCTAACTTCCTAA
ATCTGGGAAGTACAATCGATTTAGTACAATAGATCTAGATTTAGGAAGTACA
ATTATTCATTTGTCTAATATTGGAGATTTAAAAGCAGGGGAAAATAACTTTAT
TAACTTGTAACTTTAAACATTCATTGAAATGTTTGAATTTAGGTAAGTGTGTG
GTTGTGRAgtgagtttactcttgtcattTTTTTTTTATCAGTTTGTAGACATGGAAAGTAG
GCAACAATGAGGGTTTTTTTGTTTTAACACAAGTATACCTTATTCTTAACGAG
CATATTaagattacatagttacttttggactt (SEQ ID NO: 741)
For 5'-3' = aaatattgcatctggctgga (SEQ ID NO: 742)
Rev 5'-3' = aagtccaaaagtaactatgtaatctt (SEQ ID NO: 743)
New Rev 5'-3' =aatgacaagagtaaactcac (SEQ ID NO: 744) to exclude poly T region
```

M252 = DBY int12n, (419 bp)ins T at position 354, (223+1127 in intron3. (site b)
Homopolymer 7T's to 8T's
Group VI.
```
AaatattgcatctggctggaATTCATCAAAGGTTTATTAACTGCCTTAAGGAGAGTTGG
CAATATTTTAGTATTTGAGGGGATGGAAGAGACCTTAAACATCTAACTTCCTA
AATCTGGGAAGTACAATCGATTTAGTACAATAGATCTAGATTTAGGAAGTAC
AATTATTCATTTGTCTAATATTGGAGATTTAAAAGCAGGGGAAAATAACTTTA
TTAACTTGTAACTTTAAACATTCATTGAAATGTTTGAATTTAGGTAAGTGTGT
GGTTGTGAAGTGAGTTTACTCTTGTCATTTTTTTTTTATCAGTTTGTAGACATG
GAAAGTAGGCAACAATGAGGGTTTTTTTGTTTTAACACAAGTATACCTTATT
CTTAACGAGCATATTaagattacatagttactttggactt (SEQ ID NO: 745)
For 5'-3' = aaatattgcatctggctgga (SEQ ID NO: 746)
Rev 5'-3' = aagtccaaaagtaactatgtaatctt (SEQ ID NO: 747)
```

M253 = DBY int13, (400 bp nominal) C to T at position 283
Group VI
```
gcaacaatgagggttttttttg TTTTAACACAAGTATACCTTATTCTTAACGAGCATATTAAG
ATTACATAGTTACTTTTGGACTTTTAGAATTTGAGGCTATTTTAGAGGTCTGGT
AGAGCAAAGTAGACAACATGGAAATTCCTTGTTTTGTATTGACTACTTCCATT
TAGCTGATCTGTTTCTTTTTGGTGTTACTAGACAAAGCTAGATTTTAAAAGATG
AATTAAGATGCTCAGCTAACTAGTCCTGTTTATAGTATTGTTGATAGATAGCA
AGTTGAYTTCTCCAGGTTCTTCATTGAATGAGTCCTTGTTTACTATGATGCTTG
CTACATACAGTTGCTACATACTACTATGTATGAGTAGTTTTTGGTCATaaactgcata
gaggtggagctg (SEQ ID NO: 748)
For 5'-3' = gcaacaatgagggttttttttg (SEQ ID NO: 749)
Rev 5'-3' = cagctccacctctatgcagttt (SEQ ID NO: 750)
```

M254 = DBY int13, (400 bp nominal, 418 bp derived)18bp INSERTION + 2 bp substitution, A to G and G to C at positions 339, 340
Group VIII
```
gcaacaatgagggttttttttgTTTTAACACAAGTATACCTTATTCTTAACGAGCATATTAAG
ATTACATAGTTACTTTTGGACTTTTAGAATTTGAGGCTATTTTAGAGGTCTGG
TAGAGCAAAGTAGACAACATGGAAATTCCTTGTTTTGTATTGACTACTTCCAT
```

TABLE 1-continued

```
TTAGCTGATCTGTTTCTTTTTGGTGTTACTAGACAAAGCTAGATTTTAAAAGA
TGAATTAAGATGCTCAGCTAACTAGTCCTGTTTATAGTATTGTTGATAGATAG
CAAGTTGACTTCTCCAGGTTCTTCATTGAATGAGTCCTTGTTTACTATGATGCT
TGCTACATACTACTATGTTTACTATGATRSTTGCTACATACTACTATGTATG
AGTAGTTTTTGGTCATaaactgcatagaggtggagctg (SEQ ID NO: 751)
For 5'-3' = gcaacaatgagggttttttg (SEQ ID NO: 752)
Rev 5'-3' = cagctccacctctatgcagttt (SEQ ID NO: 753)
```

M255 = DBY int14, (within derived 471 bp) C to T at position 107, (224-813, in intron3)
Group V
```
ttttttttgagacggagtcttgCTGTGTTGTCCAGGCTGGAGTACAGTGGCGCGATCTCAGC
TCACTGCAAGCTCCACCTCTTGGGTTCATGCCATTCTCCTGCCTYAGGCTCCT
GAGTAGCTGGGACTACATAGGTGCCCGCCACCATGCCCAGCTAATTTTTTTGT
ATTTTTAGTAGAGACGGGGTTTCACCGTGTTAGCCAGGATGGTCTTGATCTCC
TGACCTTGTGATCTGCCTGCCTTAGCCCTCCCAAAGTGCTGGGATTACAGGT
GTGAGCCATCCCTGTTTTAATCCATCTGACATATTTCTTCTGATTATGTAGCTC
TCTTAGTTCAAGCTTTTCTGTAGGTAACCCACAGTCCCTGAGGTAATCTTTTA
CTTAGCTGGGCCTTCCCAAAATGTGTATTATATATAGCATATGTTAAATGTTT
AGGTTTAACACCTttttgtattattcaggatttgtcaag (SEQ ID NO: 754)
For 5'-3' = ttttttttgagacggagtcttg (SEQ ID NO: 755)
Rev 5'-3' = cttgacaaatcctgaataatacaaa (SEQ ID NO: 756)
```

M256 = DBY int14, (derived 471 bp) ins C at position 249, (224-672 in intron3)
Group V
```
ttttttttgagacggagtcttgCTGTGTTGTCCAGGCTGGAGTACAGTGGCGCGATCTCAGC
TCACTGCAAGCTCCACCTCTTGGGTTCATGCCATTCTCCTGCCTCAGGCTCCT
GAGTAGCTGGGACTACATAGGTGCCCGCCACCATGCCCAGCTAATTTTTTTGT
ATTTTTAGTAGAGACGGGGTTTCACCGTGTTAGCCAGGATGGTCTTGATCTCC
TGACCTTGTGATCTGCCTGCCTTAGCCCTCCCAAAGTGCTGGGATTACAGGT
GTGAGCCATCCCTGTTTTAATCCATCTGACATATTTCTTCTGATTATGTAGCTC
TCTTAGTTCAAGCTTTTCTGTAGGTAACCCACAGTCCCTGAGGTAATCTTTTA
CTTAGCTGGGCCTTCCCAAAATGTGTATTATATATAGCATATGTTAAATGTTT
AGGTTTAACACCTttttgtattattcaggatttgtcaag (SEQ ID NO: 757)
For 5'-3' = ttttttttgagacggagtcttg (SEQ ID NO: 758)
Rev 5'-3' = cttgacaaatcctgaataatacaaa (SEQ ID NO: 759)
```

M257 = DBY int14, (nominal 470 bp) T to C at position 373, (224-547 in intron3)
Group I
```
ttttttttgagacggagtcttgCTGTGTTGTCCAGGCTGGAGTACAGTGGCGCGATCTCAGC
TCACTGCAAGCTCCACCTCTTGGGTTCATGCCATTCTCCTGCCTCAGGCTCCT
GAGTAGCTGGGACTACATAGGTGCCCGCCACCATGCCCAGCTAATTTTTTTGT
ATTTTTAGTAGAGACGGGGTTTCACCGTGTTAGCCAGGATGGTCTTGATCTCC
TGACCTTGTGATCTGCCTGCCTTAGCCTCCCAAAGTGCTGGGATTACAGGTGT
GAGCCATCCCTGTTTTAATCCATCTGACATATTTCTTCTGATTATGTAGCTCTC
TTAGTTCAAGCTTTTCTGTAGGTAACCCACAGTCCCTGAGGTAAYCTTTTACT
TAGCTGGGCCTTCCCAAAATGTGTATTATATATAGCATATGTTAAATGTTTAG
GTTTAACACCTttttgtattattcaggatttgtcaag (SEQ ID NO: 760)
For 5'-3' = ttttttttgagacggagtcttg (SEQ ID NO: 761)
Rev 5'-3' = cttgacaaatcctgaataatacaaa (SEQ ID NO: 762)
```

M258 = DBY int15, (475 bp) T to C, at position 123, (224-388, in intron3)
Group VI
```
TatatagcatatgttaaatgtttaggtTTAACACCTTTTGTATTATTCAGGATTTGTCAAGGATG
GGACATAACTAAGAAACTAACAATGGGCTTGCACTAGCTACAAGTTCAGCTT
AAAAAYTGGGAACTTGGAATCCCTCTTAGTCATAGCTTAAAAAAAGACTCAT
CTTAAATAATTTAATTGGAGTAGGTTTATATTTTGGATATGTAACATTTACAC
TTAAAAAATGAATGAAAAAAATTGTTACGATAGTATAGTATTAATAGCATAG
CTATGTTACATGCAAGCTACCTTGTTCTCAGGTCATGAGATTACTTTGCTTCAT
ATAATAATCTCTGGTGGAAGAAAACATTAAAGCTTTTAACAATTCTGCTTATG
GGACTTGTAGACCATTGGTCCCATAAAGATAACATAAAGGAAGACTACATGT
GAAGGACTTCATATTTTgaaagatgcaaattattcaaaagtc (SEQ ID NO: 763)
For 5'-3' = tatatagcatatgttaaatgtttaggt (SEQ ID NO: 764)
Rev 5'-3' = gacttttgaataatttgcatctttc (SEQ ID NO: 765)
```

M259 = DBY int16, (396 bp)T to G at position 151, (352+271, in intron4)
Group IX
```
CagaatgttggtttactcattgttTTGTTAGCAGTAAGAGGTCTTTATTAATTTATTAAATTA
GATGAATATGGTATTTGACACAGTGAAATCTGTTTCAACTTAAATGATACTTA
AAGCCTGTCTGTGACAGCTTTAAACACTTCATTTKTGATGTGTGTTATAAGTT
GATCTTAAAAACCTAATGGCTGTATTTAATCCTTTCTGTTTTTCACAAATAGG
AGTAAAACTCTAAAAATATTCTCTTGTCACATGTCTACTTTCATATAAAGGAG
AAATTCAAGTGTTATTCCTGCTTTCCTACTAGTAAATATATTTAGATGATACT
ATTTTAAATGAAGATGTAAAGTACGTAACTAGTTATAAGTATCTaaaaacctaattctt
agcatgtga (SEQ ID NO: 766)
For 5'-3' = cagaatgttggtttactcattgtt (SEQ ID NO: 767)
Rev 5'-3' = tcacatgctaagaattaggtttt (SEQ ID NO: 768)
```

M260 = DBY int19, (343 bp) G to A at position 253, (608-124 in intron6)
Group VI TABLE 1-continued

```
Ccacacccagctcattttt GTACTTTTAGTAGAGACAGGGTTTCGCCATGTTGGCCAGGC
TGGTCTCAAATTCCTGATCTCAAGTGATCTTCATGCCTTAGCCTCCCAGAGTG
CTGGGACTACAGGCATCAGCCACCATACCTGGCCTCCAAAAACTTTTTTCAAT
GTAGATTAAACCCAGGCATTTTCTTAAAAAATGCCATGAATCTTTTACTGAAA
TCATAGCATCTGTAAACTAAATCAGACAGTTTARTTGGTTACTTCCATTAATA
TGTTAGTATAAAACAGAAATTGCGACAGATACAGCATTTTATATctgctatgtttacttc
tgtatttactt (SEQ ID NO: 769)
For 5'-3' = ccacacccagctcattttt (SEQ ID NO: 770)
Rev 5'-3' = aagtaaatacagaagtaaacatagcag (SEQ ID NO: 771)

M261 = DBY int22, (284 bp) A to G at position 213, (1090-32 in intron10)
Group X
AtttgaggctctgagcttcaTTTTAACAATCAACATGGGTAATTCGGTTGTTACCTTGAGC
ATTTCATCTCATGATTTTGTGTGTGTTTGTGTGTATGCATTTGTTGAGTATA
TGTCAAATTGTGACACTGCAATAGTTACTACTTGAGTTACTATATTAGTGCAA
TTAATTACACAACTATATATAGTAATTAGTTTCTCAGATCTAATRATCCAGTA
TCAACTGAGGGTTTTCGTAATAGGTACTTAGTGTTGGATGAAgctgataggatgctggat
atg (SEQ ID NO: 772)
For 5'-3' = atttgaggctctgagcttca (SEQ ID NO: 773)
Rev 5'-3' = catatccagcatcctatcagc (SEQ ID NO: 774)

M262 = DBY STS01, (502 bp) del A at position 226, (1-2908 out side of 5' region) Group
III
agctgtttggacttgagtagttgTAGAATAACTGAAAATAGGAAACTGCTATATATATATGT
ATGTATAATATATATAACCTTTTTTCAGGTACTCCTATTGCAATACCTGCATTT
CAGCACTATTCAAAAGTAAAATAAGTCCCAGAGCCAGGTTAGTCATTATGTC
CTATTTATTGCTAATTTTCATATACAAATGAGAGCTGTCAGAATTCACAGCTT
CTGAATATCAGAAGCTCATGTTTTCCCTGGTCTATACAAAAAGGAAATAAGT
GAGGCCAAAAATGTACTTTAACAGTGCTCCATAATACGAATCTCATAAATGA
GCTGGAATAGACCCTGAGGTCTTCAAGCCTAGTTTCTCAAGATCGTATTTTGT
AAACTTGTGCTAGCAGTTTTGAATATCACAATGATTGGCATGGGCTGCTGACA
TTTTAGCAGGCAGGGCTCAGGGTGTTAGATGTCCTGTAATTCAGGgacattcacagta
gaaaatactttgg (SEQ ID NO: 775)
For 5'-3' = agctgtttggacttgagtagttg (SEQ ID NO: 776)
Rev 5'-3' = ccaaagtatttctactgtgaatgtc (SEQ ID NO: 777)

M263 = DBY STS06, (515 bp) G to C at position 332, (1-341 out side of 5' region)
Group III
ccactcagctttcctcaggtGCAGTCAGGTCCATCCTGCAGAGGGACCTTCTGCGGACCT
GTTCTTTCACCTCCCTAACCTGAAGATTGTATTCAAACCACCGTGGATCGCTC
ACGTAAAATGGTCACTGCGCCTAACACCTGGGATCCCGTAACCCTTATCTATC
TTGGCTTCAGAGAGTTTTTTGACTAGTTCCAACTTTGCTGAAGCTTGTCAAAG
GTAGGTGACGGCTAGTTGGAACGGAAAAATTTTACGAAACTTCCTATTCTCA
GAAGTAAAAGGGAAGAGAGAGTGCTTAAGGAAGAAGGGAAGTTGAGGGTGG
GTAAGGAGGSAGCGGGAGTTAGTGGTAGATTGTCACTGTGTTTAAGATTTCC
CCAAGGCGAAAAAGGCGAAAGATATCTTGCTAGATCCCTAGAATTCGAAGGC
ATTAGGAGAGGGCGGGGATAGCAAACATCGCGCGAATTTTGAGAGGCGCTG
GGACTACGTAATCCCGcgatcttatgactaaacgaacg (SEQ ID NO: 778)
For 5'-3' = ccactcagctttcctcaggt (SEQ ID NO: 779)
Rev 5'-3' = cgttcgtttagtcataagatcg (SEQ ID NO: 780)

M264 = DBY Exon17, (552 bp) C to T at position 115, (1988 at cDNA, codon639,
silent/Gly)
Group III.
tccaactctagatttcttttactggTTTTATGTTAAAGTACTTGAGAAAAAAAAGGTATTAAC
GAATGACTTAATTTCTCTCTAAACATTTTTCTTGATAGGTGGCTATGGAGGYT
TCTACAATAGTGATGGATATGGAGGAAATTATAACTCCCAGGGGGTTGACTG
GTGGGGCAATGAACTCTGCTTTGCAGCAAAGTCACCCTTACAAAGAAGCTAA
TATGGAAACCACATGTAACTTAGCCAGACTATATTGTGTAGCTTCAAGAACTT
GCAGTACATTACCAGCTGTGATTCTCCTGATAATTCAAGGGAGCTCAAAGTC
ACAAGAAGAAAATGAAAGGAAAAAACAGCAGCCCTATTCAGAAATTGGTT
TGAAGATGTAATTGCTCTAGTTTGGATTAAACTCTTCCCCTCCTGCTTTAGTGC
CACCCCAAACTGCATTTATAATTTTGTGACTGAGGATCGTTTGTTTGTTAACG
TACTGTGACTTTAACTTTAGACAACTTACTACTTTGATGTCCTGTTGgctcagtaatg
ctcacgatacc (SEQ ID NO: 781)
For 5'-3' = tccaactctagatttcttttactgg (SEQ ID NO: 782)
Rev 5'-3' = ggtatcgtgagcattactgagc (SEQ ID NO: 783)

M265 = DBY STS07, C to A at position 298, (2312+358 outside 3' region)
ttagacaacttactactttgatgtcctGTTGGCTCAGTAATGCTCACGATACCAATTGTTTTGAC
AAAATAAATTTACTAAACTTGGCCTAAAATCAAACCTTGGCACAGAGGTATG
ATACAACTTTAACAGGAGTCATCAATTCATCCATAAATATAAAAAGGGAAAA
AAACTTAAGGCAGTAGTCTGCATTAGGACTGTTTGAGTTTTGCAGACTTGGGG
TTGGGAGAACATCTTAAAGCATTAAAGCATAGTTTTTTGTATGGCCAACCTTA
CTAAATTAAGTTCTGACTTGCTMACTCTATCCTGGATAGGCACTTGGGAACTT
ACACTCTTTAAGCCATTCCAGTCATGATGAGGTGGAATGTATCAGTATACCA
ATTAATATTTTTGAAAGAGCTCTTTTAGGTTAATTTAAGTacagcaatttctcatgtaatgttt
a (SEQ ID NO: 784)
For 5'-3' = ttagacaacttactactttgatgtcct (SEQ ID NO: 785)
```

TABLE 1-continued

Rev 5'-3' = taaacattacatgagaaattgctgt (SEQ ID NO: 786)

M266 = DBY STS08, (444 bp) T to C at position 208, (2312+623 outside 3' region)
Group II
tgaggtggaatgtatcagtataccAATTAATATTTTTGAAAGAGCTCTTTTAGGTTAATTTAA
GTACAGCAATTTCTCATGTAATGTTTAGGGAGTTTATTCTAACCTAGGCAAAC
GGCATGCTATCACAAGAAAGGTTTAAAGCTTTGATAAAATGGGGGAGATTTA
ATCAGTTTTTTTAATGCCTGCTATAAAAATTTGAAATATYAGAATGGCCGACC
ATGGCAGTGACCAGGCCTCACTACAGGCCTGGTTGGATTCTGGTCTTTAATGC
ATGCTAGTGTTGATGTTTTTTGGTCAAGAACGGTTTAAACAGGAAGGATTGTG
CAGCAGGCTTTAATTTAATGTAGATTCATACTGCTCTGTTAAAGCTGCATTGA
AATGTTAAAATGGCTTACACTTGCAGACTTTGCAAATCTTaagactaacaaatccttgaaat
ca (SEQ ID NO: 787)
For 5'-3' = tgaggtggaatgtatcagtatacc (SEQ ID NO: 788)
Rev 5'-3' = tgatttcaaggatttgttagtctt (SEQ ID NO: 789)

M267 EIF1A Y STS12 (site a) (287 bp) T to G at position 148. STS also contains two
Group I associated mutations
ttatcctgagccgttgtccctgTGTTTCCATTTCTCTTTTCCTCATTTCTCATCATCTACATTT
CTCCTGTACTTGTTCATTAAATAATGATTCCTTGGATATACCAAGTCTGGATA
GCGGATTCGATGGAAGCATTTTTGTAAATAKACGTTCAGTATTTTGTGTGGA
AGAACACAATCTAGCTGATGCCTGCAATCCCAGCCCTTTGGAAAGCGAGGTG
GGTGGATTGCTTGAAGCTACGAGTTTGACACTAGCCTGGGCAACagggtacaaccgt
gtctctaca (SEQ ID NO: 790)
newFor 5'-3 = ttatcctgagccgttgtccctg (SEQ ID NO: 791)
Rev 5'-3' = tgtagagacacggttgtaccct (SEQ ID NO: 792)

M268 = EIF1A_Y STS5a, (427 bp) A to G at position 292,
GROUP VII
ctaaagatcagagtatctcccttgCAAAATGTCCATTAAATCTTTGCTGATGTTATTATCCCT
GTACCTGACTCTATCCTTAAATAGTAAGGCTTCCTTTATTCTTGTAGGGTAGA
ACTTTTAAACTGAGTGATGCCTAAAAATGTTCTCAATAAAGAGAGTATCTCCA
AAACACGTCGGATTTGTTTAAAGAGGAAGTGTGGATTTTTTGATCTTAGAAA
GGAAACGAGATAAAATATTAAACGACTTTAATTTTTGTATGATCATGCCTAGC
CTCATTCCTCTAAAATRTAATTTAAAGTGGATTCTGTTACATGGTATCACAAT
AGAAGGGGAATGATCAGGGTTTGGTTAATTCTGGTAAATTGAAAACAATTTT
TTTTTT(T)ATCATATGTGCCTCAgaaggcacacaaaagaagtatagt (SEQ ID NO: 793)
For: 5'-3' = ctaaagatcagagtatctcccttg (SEQ ID NO: 794)
Rev: 5'-3' = actatacttcttttgtgtgccttc (SEQ ID NO: 795)

M269 = EIF1A_Y STS5b, (427 bp) T to C at position 358,
Group IX
CtaaagatcagagtatctcccttgCAAAATGTCCATTAAATCTTTGCTGATGTTATTATCCC
TGTACCTGACTCTATCCTTAAATAGTAAGGCTTCCTTTATTCTTGTAGGGTAG
AACTTTTAAACTGAGTGATGCCTAAAAATGTTCTCAATAAAGAGAGTATCTCC
AAAACACGTCGGATTTGTTTAAAGAGGAAGTGTGGATTTTTTGATCTTAGAA
AGGAAACGAGATAAAATATTAAACGACTTTAATTTTTGTATGATCATGCCTA
GCCTCATTCCTCTAAAATATAATTTAAAGTGGATTCTGTTACATGGTATCACA
ATAGAAGGGGAATGATCAGGGTTTGGTTAATYCTGGTAAATTGAAAACAATT
TTTTTTTT(T)ATCATATGTGCCTCAgaaggcacacaaaagaagtatagt (SEQ ID NO: 796)
For: 5'-3' = ctaaagatcagagtatctcccttg (SEQ ID NO: 797)
Rev: 5'-3' = actatacttcttttgtgtgccttc (SEQ ID NO: 798)

M270 = EIF1A_Y STS5, (428 bp) ins T at position 387.. Has ancestral T at M281.
HOMOPOLYMER
CtaaagatcagagtatctcccttgCAAAATGTCCATTAAATCTTTGCTGATGTTATTATCCC
TGTACCTGACTCTATCCTTAAATAGTAAGGCTTCCTTTATTCTTGTAGGGTAG
AACTTTTAAACTGAGTGATGCCTAAAAATGTTCTCAATAAAGAGAGTATCTCC
AAAACACGTCGGATTTGTTTAAAGAGGAAGTGTGGATTTTTTGATCTTAGAA
AGGAAACGAGATAAAATATTAAACGACTTTAATTTTTGTATGATCATGCCTA
GCCTCATTCCTCTAAAATATAATTTAAAGTGGATTCTGTTACATGGTATCACA
ATAGAAGGGGAATGATCAGGGTTTGGTTAATTCTGGTAAATTGAAAACAATT
TTTTTTTTTTATCATATGTGCCTCAgaaggcacacaaaagaagtatagt (SEQ ID NO: 799)
For: 5'-3' = ctaaagatcagagtatctcccttg (SEQ ID NO: 800)
Rev: 5'-3' = actatacttcttttgtgtgccttc (SEQ ID NO: 801)

M271 = UTY1 intron 17 3679-566 (461 bp) A to C at position 296
Group VIII. Discovered while typing M232. This STS also contains M217 site.
gcttattttagtctctcttccatGACTCTTCTAATACCATCGTCAATAAATTTCAACTAGGTA
AAAAATTAATATTGAACATCTGTCCAAAGAAAGGCCAGTATCTCCAAAATCC
TCTCGTACAGATCTGTTTCGAGATCATTCTAATTACTGTATCTTCATATTTTAG
GTTAAGATTCTTTAACTTGTGAAGGAGAATGAAAAGTTGGGTGACACAAAC
TCTTCAGAAGGAAAAATACATAAAAATTATTTTGATGAAAGCCACAGCAGCT
TTATCAAATGCTTACGTTGCTMAATAGTAAAAAAAGCCACTTAAATTCCAAT
GGAAATTTTATACCCACATGTATTTATGTAAAACTTTTAAATAACATGTATTC
ATAATCACTTTTATATCCTCAACCAGTTTTTATGAAGCTAGAAAAAAATTCCT
TTATTAaagaaatgtaacattcaacaggt (SEQ ID NO: 802)
Rev: 5'-3': acctgttgaatgttacatttctttt (SEQ ID NO: 803)

TABLE 1-continued

M272 = EIF1A_Y STS4, (496 bp) A to G at position 212,
GROUP VIII
CaggaggggaccatgttttATAGTCCACAAAAACTCTGTTTAGATTATTCCTTCCTGGGA
CCCAGACCAATTTGTCTTCTTTTTACTTGCCTGTTGGCAGCATGGAATCTGTTT
CATTTTCTCTTTTTAGCTGTCACGACACACAGCTCTTGAGGTACTTGGTGACA
GTACAGTGCAGTCTTTCCTGGGCATTACTCTTTGCTCTCCCGAARACCCACTA
ACGGGTTGTGTGTATAATAAGGTTTTATTTTATTTTATTTTATTTTTTACTGCA
AAATTATTGGAGGATAAAGTGTATTCTGGGAGAAGTCTAATTAGAAAGAGTT
AGCAAAGGCTTATGCTTTTTCACTAACATTTTCTCAGATGGTACTGAACAACT
TCAGTAGGTATCTTGTTCTCACCTTTATTTCTAGTGATGAGATTCCCAGTTCTC
TAAGCCATCAGCTCTAAAGATCAGAGTATCTCCCTTTGCAaaatgtccattaaatctttgctg (SEQ ID NO: 804)
For 5'-3' = caggaggggaccatgtttt (SEQ ID NO: 805)
Rev 5'-3' = cagcaaagatttaatggacattt (SEQ ID NO: 806)

M273 = EIF1A STS8, (502 bp) C to G at position 189
GROUP II
CacatcaggaaaagggcatcCTTTGGCCTATACTTGTGAAGAGCTAGAGTAAGGTGCTC
CCCACCTTTGAGATTGCTAAAGTTGTCATTCTTTTGGAAATTTATGAGCTAAT
CATCATTTAGTCATTTGAAAAGCTGCCAAACTTTTGTAAAACCCAGTAAGGA
AAGCAGGTATGATCTTTGTCCTGASGCAGCTAAGTTCAGGCACGATTAATTGC
TCGAAATATAGAATGTGTTTTCCTTTGTAGAAATTTAGTTTTGGCATGCCCTA
AAATGCATCAGAATCTGGATAAATCACAGAGTTCTGGAAGCCCAATTGTCTT
CTATAGTGGCACAGAACAATGTGAGACTGCCCCAGAGGTAGTGGGTGAATTC
AAGAAGTTAGATGTCTGGCTTTATGGTGGCCAGGTATATGTTTTATTCTATTT
GCAGTGTTAACATTTTTATTCAAATTCTTCAATCGATCCCTTAATATTACTGTA
atttgtagcctttctccctcc (SEQ ID NO: 807)
For 5'-3' = cacatcaggaaaagggcatc (SEQ ID NO: 808)
Rev 5'-3' = ggagggagaaaggctacaaat (SEQ ID NO: 809)

M274 = EIF1A_Y STS2a, (457 bp) C to T at position 47,
GROUP VIII w/M11
gccatgcccaagaataaagGTACTGCTGTAAGCCTCTGGGACTATAYCTCGGCTTGCTCT
GCCAGTAACCCGACGCCTGTTCCAGGCCGCAGTGACTGTTCTAACGGCGGT
ACTGGCCACTGCGACCCCAGCACTGTGTTCGGGAAAGGAGCTGGGAATGCCC
TATTTGGTCACATTGGGGTGGGACAGACGCCATTTTTGTGGGGCCTCCTTCGG
AAGATAGCGGGCTTTTGCTGCTGATTTCACGCCAGACGGAAAACGTATAGGT
AGGGACGGTTGAGGGACCTTAACCGGACGGCCTGGCTTTCCAGAATAGGCAC
ATGSAAACACTTCCCTGCTACTTTCCTGGAAGCGGTTCTTAACTTTGAAGACT
TACCTATCTGGACAGTTAAAAGTATTGCTAAGGATACTCCCTTTTCCTTGTTA
AACAGTGGGgaagccttgaagcatgtttag (SEQ ID NO: 810)
For 5'-3' = gccatgcccaagaataaag (SEQ ID NO: 811)
Rev 5'-3' = ctaaacatgcttcaaggcttc (SEQ ID NO: 812)

M275 = EIF1A_Y STS2b, (457 bp) C to G at position 325
GROUP X
gccatgcccaagaataaagGTACTGCTGTAAGCCTCTGGGACTATAYCTCGGCTTGCTCT
GCCAGTAACCCGACGCCTGTTCCAGGCCGCAGTGACTGTTCTAACGGCGGT
ACTGGCCACTGCGACCCCAGCACTGTGTTCGGGAAAGGAGCTGGGAATGCCC
TATTTGGTCACATTGGGGTGGGACAGACGCCATTTTTGTGGGGCCTCCTTCGG
AAGATAGCGGGCTTTTGCTGCTGATTTCACGCCAGACGGAAAACGTATAGGT
AGGGACGGTTGAGGGACCTTAACCGGACGGCCTGGCTTTCCAGAATAGGCAC
ATGSAAACACTTCCCTGCTACTTTCCTGGAAGCGGTTCTTAACTTTGAAGACT
TACCTATCTGGACAGTTAAAAGTATTGCTAAGGATACTCCCTTTTCCTTGTTA
AACAGTGGGgaagccttgaagcatgtttag (SEQ ID NO: 813)
For 5'-3' = gccatgcccaagaataaag (SEQ ID NO: 814)
Rev 5'-3' = ctaaacatgcttcaaggcttc (SEQ ID NO: 815)

M276 EIF1A_Y STS12 (site b) (287 bp) T to A at position 58.
Group I associated mutation. Has another Group I site (M277) and a Group VI site
(M267).
ttatcctgagccgttgtccctgTGTTTCCATTTCTCTTTTCCTCATTTCTCATCATCWACATT
TCTCCTGTACTTGTTCATTAAATAATGATTCCTTGGATATACCAAGTCTGGAT
AGCGGATTCGATGGAAGCATTTTTGTAAATATACGTTCAGTATTTTGTGTGGA
AGAACACAATCTAGCTGATGCCTGCAATCCCAGCCCTTTGGAAAGCGAGGTG
GGTGGATTGCTTGAAGCTACGAGTTTGACACTAGCCTGGGCAACagggtacaaccgt
gtctctaca (SEQ ID NO: 816)
newFor 5'-3' = ttatcctgagccgttgtccctg (SEQ ID NO: 817)
Rev 5'-3' = tgtagagacacggttgtaccct (SEQ ID NO: 818)

M277 EIF1A_Y STS12 (site c) (287 bp) G to T at position.
Group I associated mutation. G to T at position 151. Has another Group I site (M277)
and a Group VI site (M267).
ttatcctgagccgttgtccctgTGTTTCCATTTCTCTTTTCCTCATTTCTCATCATCTACATTT
CTCCTGTACTTGTTCATTAAATAATGATTCCTTGGATATACCAAGTCTGGATA
GCGGATTCGATGGAAGCATTTTTGTAAATATACTTTCAGTATTTTGTGTGGA
AGAACACAATCTAGCTGATGCCTGCAATCCCAGCCCTTTGGAAAGCGAGGTG
GGTGGATTGCTTGAAGCTACGAGTTTGACACTAGCCTGGGCAACagggtacaaccgt
gtctctaca (SEQ ID NO: 819)
newFor 5'-3 = ttatcctgagccgttgtccctg (SEQ ID NO: 820)

TABLE 1-continued

Rev 5'-3' = tgtagagacacggttgtaccct (SEQ ID NO: 821)

M278 = DBY int12n, site c ((nominal, 418 bp)) T to G at position 374, Site within STS with 7 T homopolymer.
Group I.
aaatattgcatctggctggaATTGCATCAAAGGTTTATTAACTGCCTTAAGGAGAGTTGGC
AATATTTTAGTATTTGAGGGGATGGAAGAGACCTTAAACATCTAACTTCCTA
AATCTGGGAAGTACAATCGATTTAGTACAATAGATCTAGATTTAGGAAGTAC
AATTATTCATTTGTCTAATATTGGAGATTTAAAAGCAGGGGAAAATAACTTTA
TTAACTTGTAACTTTAAACATTCATTGAAATGTTTGAATTTAGGTAAGTGTGT
GGTTGTGGAgtgagtttactcttgtcattTTTTTTTTTATCAGTTTGTAGACATGGAAAGTA
GGCAACAATGAGGGTTTTTTTGTTTTAACACAAGTATACCTKATTCTTAACG
AGCATATTaagattacatagttacttttggactt (SEQ ID NO: 822)
For 5'-3' = aaatattgcatctggctgga (SEQ ID NO: 823)
Rev 5'-3' = aagtccaaaagtaactatgtaatctt (SEQ ID NO: 824)
New Rev 5'-3' = aatgacaagagtaaactcac (SEQ ID NO: 825) to exclude poly T region M279 = DBY int12n, site d ((nominal, 418 bp)) C to T at position 93, Site within STS with 7 T homopolymer.
Group I
aaatattgcatctggctggaATTGCATCAAAGGTTTATTAACTGCCTTAAGGAGAGTTGGC
AATATTTTAGTATTTGAGGGGATGGAAGAGAYCTTAAACATCTAACTTCCTA
AATCTGGGAAGTACAATCGATTTAGTACAATAGATCTAGATTTAGGAAGTAC
AATTATTCATTTGTCTAATATTGGAGATTTAAAAGCAGGGGAAAATAACTTTA
TTAACTTGTAACTTTAAACATTCATTGAAATGTTTGAATTTAGGTAAGTGTGT
GGTTGTGGAgtgagtttactcttgtcattTTTTTTTTTATCAGTTTGTAGACATGGAAAGTA
GGCAACAATGAGGGTTTTTTTGTTTTAACACAAGTATACCTTATTCTTAACG
AGCATATTaagattacatagttacttttggactt (SEQ ID NO: 826)
For 5'-3' = aaatattgcatctggctgga (SEQ ID NO: 827)
Rev 5'-3' = aagtccaaaagtaactatgtaatctt (SEQ ID NO: 828)
New Rev 5'-3' = aatgacaagagtaaactcac (SEQ ID NO: 829) to exclude poly T region

M280 revised B9.36 c (386 bp) STS G to A at position 280
Group VI
ccagtcagcagtacaaaagttgACAGCTTCAGCAAAATTGTAGCCTTGGTTAAAACCACTG
TGGTAAGCACGAGGAAAAGTGATGACAAACTCCCCTGCACACTGGTTTGTGC
GGACAACCTAAAAAGGAGAAAAAAGCAGAAAGAGGTGTGGGTCAGAACTAA
TGGGCCAGATGTGAACTCAAAGATGTCTCTAGATGCTGTAACAGATGTAGGA
AGAGTGGAAAGGCTCTATCTTCAAGTACGTGTCCTAAAAGAAAATGAGATTG
TGAATTTAAAARTGGTATTCATAGAAAAGTACTCAAAATATGTGTAATTCAA
AAAACAAATATAGAGGGGTCCACGAACAAGTGAAAAGACTCTttgcttctataatcaaa
gaaatgc (SEQ ID NO: 830)
newFor 5'-3' = ccagtcagcagtacaaaagttg (SEQ ID NO: 831)
newRev 5'-3' = gcatttctttgattatagaagcaa (SEQ ID NO: 832)

M281 = G3.27f (393 bp) G to A at position 247.
Discovered while typing M123
tggtaaactctacttagttgcctttTGGAAATGAATAAATCAAGGTAGAAAAGCAATTGAGAT
ACTAATTCATGCTCTCAGGGGAAAATCTGAATAAAGCTATCTTTTCTAACACA
GAGCAAGTGACTCTCAAAGTCACAGTATCTGAACTAGCATATCAGCATCGCC
TGAATACCTAGAAATGCAAATTCCTGGGCAACACCAGAATCTAACAAAGCAA
AAAACTATGGGGGGAACAGGGAAGTCRGTTTAATAATACTGAGTTTGTGCA
ACCTCAACTTTGCTTTATAGGAAAGCAAAATCTCAATATGATAAAGTTTTCTT
CAACAAAACTCTGAGATAACTATGTTGAGGGAAAGAAGTTGATCACATGcaaga
aaatctaattcgctg (SEQ ID NO: 833)
For = tggtaaactctacttagttgccttt (SEQ ID NO: 834)
Rev 5'-3' = cagcgaattagatttcttgc (SEQ ID NO: 835)

M282 = G3.27g (393 bp) A to G at position 316.
Group VI
tggtaaactctacttagttgcctttTGGAAATGAATAAATCAAGGTAGAAAAGCAATTGAGAT
ACTAATTCATGCTCTCAGGGGAAAATCTGAATAAAGCTATCTTTTCTAACACA
GAGCAAGTGACTCTCAAAGTCACAGTATCTGAACTAGCATATCAGCATCGCC
TGAATACCTAGAAATGCAAATTCCTGGGCAACACCAGAATCTAACAAAGCAA
AAAACTATGGGGGGAACAGGGAAGTCGGTTTAATAATACTGAGTTTGTGCA
CCTCAACTTTGCTTTATAGGAAAGCAAAATCTCAATATGATAARGTTTTCTTC
AACAAAACTCTGAGATAACTATGTTGAGGGAAAGAAGTTGATCACATGcaagaa
aatctaattcgctg (SEQ ID NO: 836)
For = tggtaaactctacttagttgccttt (SEQ ID NO: 837)
Rev 5'-3' = cagcgaattagatttcttgc (SEQ ID NO: 838)

M283 = DBY STS 09b (429 bp) A to G at position
STS also contains M200.
ggcttacacttgcagactttgCAAATCTTAAGACTAACAAATCCTTGAAATCACACAGCTT
GCAAATACGTACTAAACTGCACAAGGTGTGTGTTCTATATGTGCAGTTTTAGC
GTATTTTAGTTGCATAGGTTTCCATGGTATTTATAGTCTCTTGTGCTAAATTTG
GCCAAAGATGATTGTCCACCACTAAAAATGCCTCTCCCACTTGGAATTCTGTA
CTGATTTTGTGGCCAGATGCAATGATCTTTAAAAACAAATCTTTTCAATGGCA
TAAGAAGTTGACRAAAATTTCTTAAAGTGCAATAGATTTTCAAGTGTATTGTG TABLE 1-continued

```
CCTTGTTCTAAAACTTTTAAGTAGGTGCACTTGACAGTATTGAGGTCATTTGT
TAAGGTGCTATTTCAATTAGTGTAggtttagactcttgtacatttctcc (SEQ ID NO: 839)
For = ggcttacacttgcagactttg (SEQ ID NO: 840)
Rev: 5'-3' = ggagaaatgtacaagagtctaaacc (SEQ ID NO: 841)
```

M284 = EIF1AY STS34a, (399 bp nominal) del ACAA at position 105, STS has another marker, M306,
GroupIX.
```
GgcagttttcatttaagcagaGGCAACAAATGTAATACTAATGTTTGATTATTATAGAAAA
AAGTATTCATCTTAGCAAAGTTTTAACTATGGGATTATTTTTAACAAACAAT
TGTGTTTTCTTTTTCTTAAAGACAAACACAATGCATACTTACTGCCGAAAGCT
TGACAAGATTAAAATAAGTCCCTCATGACACCATCAAAGAGAATATGCACTG
TTGTAAAGCCTGCGTATTTTACTTGGCAGCTATTTTCATTATTTATCATATTGC
ATTTTTATGAAAAGATTTTTATATAAACATGAAGATCTTGATGAAATTATTGGC
ATTTCAGGAAGTGCTGAAATGTTATTGGAAGTGATGAAATTATTGGCATTTCA
Ggaagtgctgaaagtttcgct (SEQ ID NO: 842)
F 5'-3' = ggcagttttcatttaagcaga (SEQ ID NO: 843)
R 5'-3' = agcgaaactttcagcacttc (SEQ ID NO: 844)
```

M285 EIF1A_Y STS12 (site d) (287 bp) G to C at position 70
(Group VI)
```
ttatcctgagccgttgtccctgTGTTTCCATTTCTCTTTTCCTCATTTCTCATCATCTACATTT
CTCCTGTACTTGTTCATTAAATAATGATTCCTTGGATATACCAAGTCTGGATA
GCGGATTCGATGGAAGCATTTTTGTAAATATACGTTCAGTATTTTGTGTGGAA
GAACACAATCTAGCTGATGCCTGCAATCCCAGCCCTTTGGAAAGCGAGGTGG
GTGGATTGCTTGAAGCTACGAGTTTGACACTAGCCTGGGCAACagggtacaaccgtgt
ctctaca (SEQ ID NO: 845)
newFor 5'-3' = ttatcctgagccgttgtccctg (SEQ ID NO: 846)
Rev 5'-3' = tgtagagacacggttgtaccct (SEQ ID NO: 847)
```

M286 EIF1A_Y STS12 (site e) (287 bp) G to A at position 129.
(Group VI)
```
ttatcctgagccgttgtccctgTGTTTCCATTTCTCTTTTCCTCATTTCTCATCATCTACATTT
CTCCTGTACTTGTTCATTAAATAATGATTCCTTGGATATACCAAGTCTGGATA
GCGGATTCGATRGAAGCATTTTTGTAAATATACGTTCAGTATTTTGTGTGGA
AGAACACAATCTAGCTGATGCCTGCAATCCCAGCCCTTTGGAAAGCGAGGTG
GGTGGATTGCTTGAAGCTACGAGTTTGACACTAGCCTGGGCAACagggtacaaccgt
gtctctaca (SEQ ID NO: 848)
newFor 5'-3' = ttatcctgagccgttgtccctg (SEQ ID NO: 849)
Rev 5'-3' = tgtagagacacggttgtaccct (SEQ ID NO: 850)
```

M287 EIF1A_Y STS12 (site f) (287 bp) A to T at position 100. This is one of 3 M201 related mutations.
(Group VI)
```
ttatcctgagccgttgtccctgTGTTTCCATTTCTCTTTTCCTCATTTCTCATCATCTACATTT
CTCCTGTACTTGTTCATTAAATAATGATTCCTTGGWTATACCAAGTCTGGAT
AGCGGATTCGATGGAAGCATTTTTGTAAATATACGTTCAGTATTTTGTGTGGA
AGAACACAATCTAGCTGATGCCTGCAATCCCAGCCCTTTGGAAAGCGAGGTG
GGTGGATTGCTTGAAGCTACGAGTTTGACACTAGCCTGGGCAACagggtacaaccgt
gtctctaca (SEQ ID NO: 851)
newFor 5'-3' = ttatcctgagccgttgtccctg (SEQ ID NO: 852)
Rev 5'-3' = tgtagagacacggttgtaccct (SEQ ID NO: 853)
```

M289 = B9.36new d (386 bp) G to A at position 227 Group VI.
```
ccagtcagcagtacaaaagttgACAGCTTCAGCAAAATTGTAGCCTTGGTTAAAACCACTG
TGGTAAGCACGAGGAAAAGTGATGACAAACTCCCCTGCACACTGGTTTGTGC
GGACAACCTAAAAAGGAGAAAAAAGCAGAAAGAGGTGTGGGTCAGAACTAA
TGGGCCAGATGTGAACTCAAAGATGTCTCTAGATGCTGTAACAGATGTAGGA
AGAGTGGAAARGCTCTATCTTCAAGTACGTGTCCTAAAAGAAAATGAGATTG
TGAATTTAAAAGTGGTATTCATAGAAAAGTACTCAAAATATGTGTAATTCAA
AAAACAAATATAGAGGGGTCCAGGAACAAGTGAAAAGACTCTttgcttctataatcaaa
gaaatgc (SEQ ID NO: 854)
For 5'-3' = ccagtcagcagtacaaaagttg (SEQ ID NO: 855)
Rev 5'-3' = gcatttctttgattatagaagcaa (SEQ ID NO: 856)
```

M290 = B9.36new e (386 bp) G to A at position 343. Group III
```
ccagtcagcagtacaaaagttgACAGCTTCAGCAAAATTGTAGCCTTGGTTAAAACCACTG
TGGTAAGCACGAGGAAAAGTGATGACAAACTCCCCTGCACACTGGTTTGTGC
GGACAACCTAAAAAGGAGAAAAAAGCAGAAAGAGGTGTGGGTCAGAACTAA
TGGGCCAGATGTGAACTCAAAGATGTCTCTAGATGCTGTAACAGATGTAGGA
AGAGTGGAAAGGCTCTATCTTCAAGTACGTGTCCTAAAAGAAAATGAGATTG
TGAATTTAAAAGTGGTATTCATAGAAAAGTACTCAAAATATGTGTAATTCAA
AAAACAAATATAGAGGGGTCCAYGAACAAGTGAAAAGACTCTttgcttctataatcaaa
gaaatgc (SEQ ID NO: 857)
newFor 5'-3' = ccagtcagcagtacaaaagttg (SEQ ID NO: 858)
newRev 5'-3' = gcatttctttgattatagaagcaa (SEQ ID NO: 859)
```

M291 = EIF1AY STS16, (480 bp) A to G, at position 358,
(Group III)

TABLE 1-continued

```
cggagtctggctttgttggcCAGGTTGGAGTGCAGTGGCATGATCTCGGCTCAGGGCAAT
GTCCGTCTCCTGGACTCAAGCAGTTCTCCTGCCTCAGCCTCCCCAGTAGCTGG
GATTAGAGGTGTGTGACACCATGCCCGGCTAATTTTTGTATTTTTAGTAGAGA
TGGGGTTTCACCATGTTGGCCAGGCTGGTCTCGAACTCCTGACCTCAGGTAAT
GCACCCGCCTCGGCCTCCCAAAGTGGTGGGATTATAGGCGTGAGTAACCATG
CCTGGCCTTTCACTCTTATTTTCTAAGAACTTTAGAATAATCACCGAGATATT
CTAAAGTAAACAGGAATTTTTAATGGTTAAGCTRTTATTTGTCTTTGTCATTTC
TGAGTTTAGGGATAGTGAAGATAGAGTTAGGCCTCATGTGTGAGAGACTGAT
GTAGCATTATAGTGTATATTTTGAAATGTGccaccgtgatgttcaaaagt (SEQ ID NO: 860)
For = cggagtctggctttgttggc (SEQ ID NO: 861)
Rev 5'-3' = acttttgaacatcacggtgg (SEQ ID NO: 862)
```

M292 = EIF1AY STS19, (556 bp) A to G, at position 373.
Group III
```
TttaacaaatgtggaccaagaTCTCAACCTTTTTTTTTATctcctctcctcagagtatgcTCAGGTAAT
CAAAATGTTGGGAAATGGACGATTGGAAGCATTGTGTTTTGATGGTGTAAAG
AGGTTATGCCATATCAGAGGGAAATTGAGAAAAAAGGTAGGTGTGTAGGTTA
CTTTTCAATAAAAATTTGCCGCAAAAAATGTCTCTGCTTTAAATACATGGTCC
AAGCAATTTATTTTTGTGAGTTCCCAAAATAATTTATACAGCAATGATTCATG
TGACAATGTGAATAAATAGAAAAAGTCTTTGATAACTTTTAGATTTACTTTTA
AAGAATAATTTGTTTGTTTAACTTCTGTTGTATTCCTACCRGAAATGTTTACTC
TGATATTAGTATTGAAGAAACCAGACAAATCTAATATATAACACAAATGGTC
TTGACTCAGATGTTAATGCTGTGAAAGAATGAAAAATCTGGGAATTACTTTA
GCTTAAAAGAGATTGATCGGTGCATATCCCTTTGTTAGGTTTTGgattgggggaaata
gttttagg (SEQ ID NO: 863)
Original F 5'-3' = tttaacaaatgtggaccaaga (SEQ ID NO: 864)
Rev 5'-3' = acttttgaacatcacggtgg (SEQ ID NO: 865)
```

M293 = EIF1AY STS20a, (507bp) T to G, at position 299.
Group III. STS also contains M294
```
CatggtccaagcaatttattttgTGAGTTCCCAAAATAATTTATACAGCAATGATTCATGTG
ACAATGTGAATAAATAGAAAAAGTCTTTGATAACTTTTAGATTTACTTTTAAA
GAATAATTTGTTTGTTTAACTTCTGTTGTATTCCTACCAGAAATGTTTACTCTG
ATATTAGTATTGAAGAAACCAGACAAATCTAATATATAACACAAATGGTCTT
GACTCAGATGTTAATGCTGTGAAAGAATGAAAAATCTGGGAATTACTTTAGC
TTAAAAGAGATTGATCGGTGCATAKCCCTTTGTTAGGTTTTGGATTGGGGGA
AATAGTTTTAGGTGGTACTAGGAAAATTGGAATATGGAATATGTTAGAAACT
CTATTTGTTAGTAATACCACATCAGGTAGTTTTATAAATTACACTGATTAAAA
GTCTCTACTACTCAGATTTTTAATTAAAATAATAAAAACTTATTTTTGGCTGA
Gctctgtggaagtattagccagc (SEQ ID NO: 866)
F 5'-3' = catggtccaagcaatttattttg (SEQ ID NO: 867)
R 5'-3' = gctggctaatacttccacagag (SEQ ID NO: 868)
```

M294 = EIF1AY STS20b, (507bp) C to T, at position 305
```
CatggtccaagcaatttattttgTGAGTTCCCAAAATAATTTATACAGCAATGATTCATGTG
ACAATGTGAATAAATAGAAAAAGTCTTTGATAACTTTTAGATTTACTTTTAAA
GAATAATTTGTTTGTTTAACTTCTGTTGTATTCCTACCAGAAATGTTTACTCTG
ATATTAGTATTGAAGAAACCAGACAAATCTAATATATAACACAAATGGTCTT
GACTCAGATGTTAATGCTGTGAAAGAATGAAAAATCTGGGAATTACTTTAGC
TTAAAAGAGATTGATCGGTGCATATCCCTTYGTTAGGTTTTGGATTGGGGGA
AATAGTTTTAGGTGGTACTAGGAAAATTGGAATATGGAATATGTTAGAAACT
CTATTTGTTAGTAATACCACATCAGGTAGTTTTATAAATTACACTGATTAAAA
GTCTCTACTACTCAGATTTTTAATTAAAATAATAAAAACTTATTTTTGGCTGA
Gctctgtggaagtattagccagc (SEQ ID NO: 869)
F 5'-3' = catggtccaagcaatttattttg (SEQ ID NO: 870)
R 5'-3' = gctggctaatacttccacagag (SEQ ID NO: 871)
```

M295 = EIF1AY STS20c, (507bp) T to C, at position 411,
(Group VIII). STS also contains M294 mutation
```
catggtccaagcaatttattttgTGAGTTCCCAAAATAATTTATACAGCAATGATTCATGTG
ACAATGTGAATAAATAGAAAAAGTCTTTGATAACTTTTAGATTTACTTTTAAA
GAATAATTTGTTTGTTTAACTTCTGTTGTATTCCTACCAGAAATGTTTACTCTG
ATATTAGTATTGAAGAAACCAGACAAATCTAATATATAACACAAATGGTCTT
GACTCAGATGTTAATGCTGTGAAAGAATGAAAAATCTGGGAATTACTTTAGC
TTAAAAGAGATTGATCGGTGCATATCCCTTTGTTAGGTTTTGGATTGGGGGAA
ATAGTTTTAGGTGGTACTAGGAAAATTGGAATATGGAATATGTTAGAAACTC
TATTTGTTAGTAATACCACATCAGGTAGTTTYATAAATTACACTGATTAAAAG
TCTCTACTACTCAGATTTTTAATTAAAATAATAAAAACTTATTTTTGGCTGAGc
tctgtggaagtattagccag (SEQ ID NO: 872)
F 5'-3' = catggtccaagcaatttattttg (SEQ ID NO: 873)
R 5'-3' = gctggctaatacttccacagag (SEQ ID NO: 874)
```

M296 = EIF1AY STS21 = STS20d, (536 bp) C to T, at position 165,
(Group VIII)
```
gattgggggaaatagttttaggTGGTACTAGGAAAATTGGAATATGGAATATGTTAGAAAC
TCTATTTGTTAGTAATACCACATCAGGTAGTTTTATAAATTACACTGATTAAAA
AGTCTCTACTACTCAGATTTTTAATTAAAATAATAAAAACTTATTTTTGGYTG
AGCTCTGTGGAAGTATTAGCCAGCATACACCTGTAGTCCCAGCTACTGAGGA
GGCTGAGCCCAGGAGTTCAAGGTTCCCATGAGCTAAAAATTGTGCTAATGCT
```

TABLE 1-continued

```
CTCCAGTCTGGGTGATAGAGCGAATCTCTATCTCAAAAAGAAAAAAAAAAAA
ATCTTTCTGGTATGTTAACATTCTTTCTTTTCCAAATTAGTGGCATTTTAGGGA
TTCTCTTAGTCCATTTGGGCTGTCACTGACTGGGTAGATTATAAAAAGCAGAA
ATTTTATTTCTCATAGTTTTGGAGAAAGAGAAATCTATTTAATATTTGGTGAG
GACCCATTTCCTGATTATTATGTGGTGCCTTctggcttagtccacacatagtg (SEQ ID NO: 875)
F 5'-3' = gattggggaaatagttttagg (SEQ ID NO: 876)
R 5'-3' = cactatgtgtggactaagccag (SEQ ID NO: 877)

M297 = EIF1AY STS24, (506 bp) A to G, at position 303,
(Group VII)
TtggttggtctacgggactATCAGGTAAAAATAACATTTAAAGTTGTGGTATGTCTGTGT
TTAAGCAGTTGTTAATGTTTGGAAGGTAACTATACTAGCATCTTTGACCCATT
CCAGCCCAGGTTGCTTTCTCACCATTCTGCCTGCCATCATCATTTATTAAGGG
CCAGTTGTATTTCAGACTATAGTATTTTTCAAATTTGACATAATTCTCACTGAT
AGTAAATGGTACATATATTTTTGTGGAAAGACATAAAGTTTTTAATTCTTTGT
TTTCATTGTTAATATAATGTGCAGTAAATRTTTTCTTGCAGGCTTGGGCAAGT
ACTGTAGACCATCTGTCCTCATCCATTTAAAGGCCAATGGTGTTTCAGGCATT
CAGCTAGGTATTTCAGACATTGTAGTTCCCAAATGCCGGTCTGTTAAATAGTA
TTGGTGCAGGCTGAATTTTCAGTGCTCTGAAGTCAAATTAGAAGATACATAGT
Tacgatgttttcatggagca (SEQ ID NO: 878)
F 5'-3' = ttggttggtctacgggact (SEQ ID NO: 879)
R 5'-3' = tgctccatgaaaaacatcgt (SEQ ID NO: 880)

M298 = EIF1A STS 27 (445 bp) G to A at position 230,
Group II
AaataccatttcataatttccttAATATTTTTAGACATTATTTCTTTTTAAGTCTTAGATAAA
CTAAGTCCAACTTCTGGGATTCCTCAGGAATAGTATTTTTTTTTCCCTGTGTT
TGAGCCACTTTTTTAAATCTTTTTTTTTTTTTAAACCGAACAATTTAACTACA
ACATAGCAGTTCTGGAAATCAGATTGCTGCCTCTCGGGGCTGTTGTTGATACT
GCTTRTTTGGTGACTTTTCTGAACTAATTCTTTGGCCATTGAATAGTTGGTTA
GTTTAGTGGGCAGTTCATGTTTGAACTAAGATTTCATTAAAACCACCAAGAAT
TTAATCATTTAAAGAGGAATCTTGTACATGTAGAGGAATACTTTGAGCATTCA
GCCAATGTTGGTAAACTGACACCTCTTCCTTAGTCTTCATTtcttgctgtgtgcaggatctca (SEQ ID NO: 881)
Original F 5'-3' = aaataccattttcataatttcctt (SEQ ID NO: 882)
Original R 5'-3' = tgagatcctgcacagcaaga (SEQ ID NO: 883)

M299 = EIF1AY STS29, (483 bp) T to G, at position 127,
Group I
CggacttggtctgtgcttttcAGTAGCTGCTATTGTGTTGGTTTTTATTAAACTGAGGTAAG
GAATGGGAATAGGGGAACTTAAAAGCCCACACTGCTTTTTCTTAGTAAGGTT
CACCTATTTTTCKTGAATAAACGCTCCTTAGTGTTTATTGCATTCATTTGGTTA
ATTTTCAGATTTCTGATATATGGATTTTGACCATGTTTGTCAATGTTCTTATTT
CTTTTCTGAAGGAACAAATTTTAGCAAGTCCTTATTCTGCCATTCCTGCAATC
ACTGCAAGAAAGCATTTATTTTGATAAGACTTAATTACACATTGACTTTGTTT
CTTTTTCATATATCAAATAAAAAGTTGTACTGTGCTTTTAAAATGTTATTTTA
TGTCCATTATATTATTCGAATTATCATTTTAACAAAAACTGGTTTGCACATTA
CAGTTTGAAAAGTGTTGGTCTATTTCATactgccattgtgacagatca (SEQ ID NO: 884)
F 5'-3' = cggacttggtctgtgctttc (SEQ ID NO: 885)
R 5'-3' = tgatctgtcacaatggcagt (SEQ ID NO: 886)

M300 = EIF1AY STS31, (500 bp) G to A at position 153,
STS also contains M301, Group III
CaggcaggtctactttcaatctTAAGGAAGTAGGTATGTATTTTTAAAATCAAGCTATTTTT
CAAGTTCCATAGACAATTCTGTTAGATAATCTATACTAAGAACTACTGATGCA
TAGAAAAGTTTATTATTGTTGTTTTTGTTTTTTTGAARGAGTTTCGCTCTGTTG
CCCAGGCTGGAGTGCAGTGGCTTGATCTCGGCTCACTGCAAGCTGCGCCTCCT
GGGTTCATGCCATTCTCCTGCCTCAGCCTCCTGAGTAGCTGGGACTACAGATG
CCTGCCACCACGCCCAGCTAATTTTTTGTATTTTTAGTAGAGATGGGGTTTCA
TCATGTTAGCCAGTATGGTCTCGATCTCCTGACCTCATGATCCGCCCGCCTTG
GCCTCCCAAAGTGCTGGGATTACAGGCGCGAGCCACCGTGCCTGGCCTAGAA
AAGTGTATTACCTTTTTAACATCATTATTCTTTACTCCATTTTTAgttttgaattgcagtgt
ttgac (SEQ ID NO: 887)
F 5'-3' = caggcaggtctactttcaatct (SEQ ID NO: 888)
R 5'-3' = gtcaaacactgcaattcaaaac (SEQ ID NO: 889)

M301 = EIF1A STS 31(500 bp) A to C at position 340bp.
(Group III) STS also contains M300, a Group VII marker
CaggcaggtctactttcaatctTAAGGAAGTAGGTATGTATTTTTAAAATCAAGCTATTTTT
CAAGTTCCATAGACAATTCTGTTAGATAATCTATACTAAGAACTACTGATGCA
TAGAAAAGTTTATTATTGTTGTTTTTGTTTTTTTGAAGGAGTTTCGCTCTGTTG
CCCAGGCTGGAGTGCAGTGGCTTGATCTCGGCTCACTGCAAGCTGCGCCTCCT
GGGTTCATGCCATTCTCCTGCCTCAGCCTCCTGAGTAGCTGGGACTACAGATG
CCTGCCACCACGCCCAGCTAATTTTTTGTATTTTTAGTAGAGATGGGGTTTCA
TCATGTTAGCCMGTATGGTCTCGATCTCCTGACCTCATGATCCGCCCGCCTTG
GCCTCCCAAAGTGCTGGGATTACAGGCGCGAGCCACCGTGCCTGGCCTAGAA
AAGTGTATTACCTTTTTAACATCATTATTCTTTACTCCATTTTTAgttttgaattgcagtgt
ttgac (SEQ ID NO: 890)
F 5'-3' = caggcaggtctactttcaatct (SEQ ID NO: 891)
R 5'-3' = gtcaaacactgcaattcaaaac (SEQ ID NO: 892)
```

TABLE 1-continued

M302 = EIFIA STS 32a (527bp) A to G at position 230
(Group VII)
CaaagtgctgggattacaggCGCGAGCCACCGTGCCTGGCCTAGAAAAGTGTATTACCT
TTTTAACATCATTATTCTTTACTCCATTTTTAGTTTTGAATTGCAGTGTTTGAC
CTTAAAAGTTTTATATTACAATTTTTTTAATTAGTCTTTTATTTTTTCCAAGAG
ACTTCTAATTAAAAGGGAATAGTAAATAAAAGCACTGTGCTTGCCTTTTGTGC
TTTTTATTAARGTGAAATCTCTACAATCTTTCCTAAGCTGTTAATCACTGTTTA
CTAATGAACATAAACCACTTCCTAATTATTCAGACTCAAGAATTTTTTTCTAG
AGGGTATTGGGGTAGGCAAAGAAAAGCAGGAGAGTTTGTAACAAACAGTAT
GTGGGATTTTTTTAGATGTGTTCAATTTGAAAGTAACTTGTGAACAACTGGT
GATATTTTGGTATAAGACGTTTTGAAAGTTATTTGTTTATTTCTAAGGATAAC
AAAGCTGATGTAATTTTAAAGTacaatgcagatgaagctagaag (SEQ ID NO: 893)
F 5'-3' = caaagtgctgggattacagg (SEQ ID NO: 894)
R 5'-3' = cttctagcttcatctgcattgt (SEQ ID NO: 895)

M303 = EIFIA STS 32b (527bp) G to C at position 352,
(Group X)
CaaagtgctgggattacaggCGCGAGCCACCGTGCCTGGCCTAGAAAAGTGTATTACCT
TTTTAACATCATTATTCTTTACTCCATTTTTAGTTTTGAATTGCAGTGTTTGAC
CTTAAAAGTTTTATATTACAATTTTTTTAATTAGTCTTTTATTTTTTCCAAGAG
ACTTCTAATTAAAAGGGAATAGTAAATAAAAGCACTGTGCTTGCCTTTTGTGC
TTTTTATTAAAGTGAAATCTCTACAATCTTTCCTAAGCTGTTAATCACTGTTTAC
TAATGAACATAAACCACTTCCTAATTATTCAGACTCAAGAATTTTTTTCTAGA
GGGTATTGGGGTAGGCAAAGAAAASCAGGAGAGTTTGTAACAAACAGTATG
TGGGATTTTTTTAGATGTGTTCAATTTGAAAGTAACTTGTGAACAACTGGTG
ATATTTTGGTATAAGACGTTTTGAAAGTTATTTGTTTATTTCTAAGGATAACA
AAGCTGATGTAATTTTAAAGTacaatgcagatgaagctagaag (SEQ ID NO: 896)
F 5'-3' = caaagtgctgggattacagg (SEQ ID NO: 897)
R 5'-3' = cttctagcttcatctgcattgt (SEQ ID NO: 898)

M304 = EIFIA STS 32c (527bp) A to C at position 421
CaaagtgctgggattacaggCGCGAGCCACCGTGCCTGGCCTAGAAAAGTGTATTACCT
TTTTAACATCATTATTCTTTACTCCATTTTTAGTTTTGAATTGCAGTGTTTGAC
CTTAAAAGTTTTATATTACAATTTTTTTAATTAGTCTTTTATTTTTTCCAAGAG
ACTTCTAATTAAAAGGGAATAGTAAATAAAAGCACTGTGCTTGCCTTTTGTGC
TTTTTATTAAAGTGAAATCTCTACAATCTTTCCTAAGCTGTTAATCACTGTTTAC
TAATGAACATAAACCACTTCCTAATTATTCAGACTCAAGAATTTTTTTCTAGA
GGGTATTGGGGTAGGCAAAGAAAAGCAGGAGAGTTTGTAACAAACAGTATG
TGGGATTTTTTTAGATGTGTTCAATTTGAAAGTAACTTGTGAMACAACTGGT
GATATTTTGGTATAAGACGTTTTGAAAGTTATTTGTTTATTTCTAAGGATAAC
AAAGCTGATGTAATTTTAAAGTacaatgcagatgaagctagaag (SEQ ID NO: 899)
F 5'-3' = caaagtgctgggattacagg (SEQ ID NO: 900)
R 5'-3' = cttctagcttcatctgcattgt (SEQ ID NO: 901)

M305 = EIFIA STS 33 (545 bp) C to T at position 331
(Group I)
AacttgtgaaacaactggtgatATTTTGGTATAAGACGTTTTGAAAGTTATTTGTTTATTTC
TAAGGATAACAAAGCTGATGTAATTTTAAAGTACAATGCAGATGAAGCTAGA
AGCCTGAAGGCATATGGCGAGCTTCCAGAACATGGTAAGATCAAAATGATTT
TATCTCCTCATTATTTGATATTAATGTTTGTTGGTATTTAGGTGAAGGTATTTC
CGTAGAACTCTTGTTTTACATACTGTTTTAGTGTATACTTAAAAATTTGTTATA
AGTAGTCTTGCCTATACTTCAGTTTACTTATGATACTTTGGAAAAGATATTAA
TAAYTGGAAATCTCTAATAAAAACGTTATGAACTTGAAAGTAGAAGTCTCTA
ATAAAGAGATTATGAATTATGAAAGTTCCTTTAGTGACAACTTTATAAATTCA
TAAGCTCTGGATTTGTATATAAGATCTGTCAAAGAAATACGTTTTTTATAGTG
TTTTTCTAAACAGTTCTCAAGACTGGCAGTTTTCATTTaagcagaggcaacaaatgtaat (SEQ ID NO: 902)
F 5'-3' = aacttgtgaaacaactggtgat (SEQ ID NO: 903)
R 5'-3' = attacatttgttgcctctgctt (SEQ ID NO: 904)

M306 = EIFIA STS 34b (399 bp) C to A at position 231.
Group IX. STS also contains M284, a Group VI marker.
GgcagttttcatttaagcagaGGCAACAAATGTAATACTAATGTTTGATTATTATAGAAAA
AAGTATTCATCTTAGCAAAGTTTTAACTATGGGATTATTTTTAACAAAACAATT
GTGTTTTCTTTTTCTTAAAGACAAACACAATGCATACTTACTGCCGAAAGCTT
GACAAGATTAAAATAAGTCCCTCATGACACCATCAAAGAGAATATGCACTGT
TGTAAAGCCTGCGTATTTTACTTGGCAGCTATTTTCATTATTTATCATATTGC
ATTTTATGAAAAGATTTTTATATAAACATGAAGATCTTGATGAAATTATTGGC
ATTTCAGGAAGTGCTGAAATGTTATTGGAAGTGATGAAATTATTGGCATTTCA
Ggaaagtgctgaaagtttcgct (SEQ ID NO: 905)
F 5'-3' = ggcagttttcatttaagcaga (SEQ ID NO: 906)
R 5'-3' = agcgaaactttcagcacttc (SEQ ID NO: 907)

M307 = EIFIA STS 35 (500 bp) G to A at position 282
(Group VI)
TtattggcatttcaggaagtgCTGAAATGTTATTGGAAGTGATGAAATTATTGGCATTTCA
GGAAGTGCTGAAAGTTTCGCTTTCATTACTTGGGGATAAGCATGATCATGATT
TAACCAAGTATTTCTCACTGATTTGATAAGTCTGTTTAAATAATTGGTTAACT
AGTTGTTGTAATTTCAAGAGAACTTTATGTATTTTGAGGATAAGTTGTTAACC
TGTGCTCAAATCCTTTTTGAAGGCTACATGGAAATGGTTGGCTATTGAGTTAG TABLE 1-continued

```
CATAATCARTCTGCCTACCATACTTAAAGTACCTTTTGTATATGTGCTAAGTG
AGAATTAAAAATACCTTTTAAAAACAAATGAAAAATACAGCACAATACAGCA
CATTCGTTCTTTGTTTTTTGAAACAGAGTCTTGCTCTGTCACCCAGGCAGGAG
TGCAGTGGCACCATCTCAGCTCCCTGCATTCTACGCCTGCCAAGTTCAAgctatttt
cctgcctcaccc (SEQ ID NO: 908)
F 5'-3' = ttattggcatttcaggaagtg (SEQ ID NO: 909)
R 5'-3' = gggtgaggcaggaaaatagc (SEQ ID NO: 910)

M308 = EIFIA STS 37a (444 bp) T to C at position 70
(Group I)
AaactttacagtcctttgggataGTATTTACTGCAAAAATCAATTTTAGCTTCGGCAGTAGG
CACTTCAYAATCAACGTTAAGTAAGAGTGTCTAAAGAGATAGTTTTGAGAAC
ACGTCCTCTATTAAGAGAAATGCTTAGTATGTTAAAAGAAGAATTTTGTTTGA
ACCAGTTTGATGCAGCACTGAAATTACAACATACTTCAAAGGTTTGTTAAAAT
GAAGGGCCTGTTGCCAGGACATGTAATAGAATTACATGGTTGAGCATCAGTT
TGTACTGGCCAGACTCTTGTTTTGGAGTTAGTTTGTGCTTATTTTGTGGAAATG
ATTGTTTTTCCTAGTAACAAAGCAGCGCAGTTCACAAAGCAGTAAATGCTTC
AGCTCTCTTTTTCAGTTAACTATATTGAAATTAAATTCACTTTgattttttcttccctctcttg
aga (SEQ ID NO: 911)
F 5'-3' = aaactttacagtcctttgggata (SEQ ID NO: 912)
R 5'-3' = tctcaagagagggaagaaaaatc (SEQ ID NO: 913)

M309 = EIFIA STS 37b (444 bp) A to G at position 200
(Group II)
AaactttacagtcctttgggataGTATTTACTGCAAAAATCAATTTTAGCTTCGGCAGTAGG
CACTTCATAATCAACGTTAAGTAAGAGTGTCTAAAGAGATAGTTTTGAGAAC
ACGTCCTCTATTAAGAGAAATGCTTAGTATGTTAAAAGAAGAATTTTGTTTGA
ACCAGTTTGATGCAGCACTGAAATTACAACATRCTTCAAAGGTTTGTTAAAA
TGAAGGGCCTGTTGCCAGGACATGTAATAGAATTACATGGTTGAGCATCAGT
TTGTACTGGCCAGACTCTTGTTTTGGAGTTAGTTTGTGCTTATTTTGTGGAAAT
GATTGTTTTTCCTAGTAACAAAGCAGCGCAGTTCACAAAGCAGTAAATGCTT
CAGCTCTCTTTTTCAGTTAACTATATTGAAATTAAATTCACTTTgattttttcttccctctctt
gaga (SEQ ID NO: 914)
F 5'-3' = aaactttacagtcctttgggata (SEQ ID NO: 915)
R 5'-3' = tctcaagagagggaagaaaaatc (SEQ ID NO: 916)

M310 = EIFIA STS 37c (444 bp) C to T at position 352
(Group III)
AaactttacagtcctttgggataGTATTTACTGCAAAAATCAATTTTAGCTTCGGCAGTAGG
CACTTCATAATCAACGTTAAGTAAGAGTGTCTAAAGAGATAGTTTTGAGAAC
ACGTCCTCTATTAAGAGAAATGCTTAGTATGTTAAAAGAAGAATTTTGTTTGA
ACCAGTTTGATGCAGCACTGAAATTACAACATACTTCAAAGGTTTGTTAAAAT
GAAGGGCCTGTTGCCAGGACATGTAATAGAATTACATGGTTGAGCATCAGTT
TGTACTGGCCAGACTCTTGTTTTGGAGTTAGTTTGTGCTTATTTTGTGGAAATG
ATTGTTTTTCCTAGTAACAAAGCAGYGCAGTTCACAAAGCAGTAAATGCTTC
AGCTCTCTTTTTCAGTTAACTATATTGAAATTAAATTCACTTTgattttttcttccctctcttg
aga (SEQ ID NO: 917)
F 5'-3' = aaactttacagtcctttgggata (SEQ ID NO: 918)
R 5'-3' = tctcaagagagggaagaaaaatc (SEQ ID NO: 919)

M311 = EIFIA STS 39 (460 bp) G to T at position 304
(Group X)
CgagaacagcctaaccaacaTGGTGAAACCCCATCTCTGCTAAAAATATAAAAATTAGC
CAGGCATGGTAGTGCACACCTGTAGTCCCAGCTACTCAGGAGGCTGAGGCAG
GATAATCACTTGGACCCAGGAGACAGAGGTTGCAGTGAACCGAGATTGCACC
ACTGCACTCCAGCCTGGGCAATAGAGCGAGACTCCATCTCAAAAAAAAAAA
AAAAATTACAAAGGCTAAACTTTGGAAAGTCTAAGACAGACATAGGTGATGG
TCACACACTCCATTGAGAACCATTGTTCTACATCAGGKTTCTCTACAGCTTTT
GTTTTACCAACATGTTTATTAAGATTGTTTCCAGACTGTTCAGAGGAGTAGAA
GGATTTTTAAATTTATTTGTAAACATTCAAATACTCACCAACAATATTGTACA
ATTTACAGTTTTTctctgcttcatctatcacaccc (SEQ ID NO: 920)
F 5'-3' = cgagaacagcctaaccaaca (SEQ ID NO: 921)
R 5'-3' = gggtgtgatagatgaagcagag (SEQ ID NO: 922)

M312 = EIF1AY STS40a, A to T at position 49,
(Group VII)
gtttccagactgttcagaggagTAGAAGGATTTTTAAATTTATTTGTAWACATTCAAATAC
TCACCAACAATATTGTACAATTTACAGTTTTTCTCTGCTTCATCTATCACACCC
ATCCTTCTATTCATCTGATATTACACCTTATATTTTGGCACATTTCCAAACTAT
TACTTACACTTTGAGTTGAAGAAAATAAACTGAGTCCTTAATTGTATTGTATA
TATGCATTTATAAATTTTTACAACATAAAGTACTCTATATTTACAAAATTTTTT
AGTTTTTTTTTTCTTTGGAATTGTTTCTGAGTAGTACTTAGTAACACTACTCTA
ATGTAATATAAATTTTAAAGTATACCCAAAAAGAAAATGAAAAGAGATGAA
AAATGCATTGTTCTTGTGATCCCAGGAAATCTGAGACAGGTCTCAGTTAATTT
acaaagttgattttgccaaagt (SEQ ID NO: 923)
F 5'-3' = gtttccagactgttcagaggag (SEQ ID NO: 924)
R 5'-3' = actttggcaaaatcaactttgt (SEQ ID NO: 925)

M313 = EIFIA STS 40b Homopolymer 9T's to 10T's at position 288
```

TABLE 1-continued

```
gtttccagactgttcagaggagTAGAAGGATTTTTAAATTTATTTGTAWACATTCAAATAC
TCACCAACAATATTGTACAATTTACAGTTTTTCTCTGCTTCATCTATCACACCC
ATCCTTCTATTCATCTGATATTACACCTTATATTTTGGCACATTTCCAAACTAT
TACTTACACTTTGAGTTGAAGAAAATAAACTGAGTCCTTAATTGTATTGTATA
TATGCATTTATAAATTTTTACAACATAAAGTACTCTATATTTACAAAATTTTTT
AGTTTTTTTTTTCTTTGGAATTGTTTCTGAGTAGTACTTAGTAACACTACTCTA
ATGTAATATAAATTTTAAAGTATACCCAAAAAGAAAATGAAAAGAGATGAA
AAATGCATTGTTCTTGTGATCCCAGGAAATCTGAGACAGGTCTCAGTTAATTT
acaaagttgattttgccaaagt (SEQ ID NO: 926)
For 5'-3' = gtttccagactgttcagaggag (SEQ ID NO: 927)
Rev 5'-3' = actttggcaaaatcaactttgt (SEQ ID NO: 928)
```

M314 = EIFIA STS 40c (623 bp) A to C at position 419.
(Group VI)
```
GtttccagactgttcagaggAGTAGAAGGATTTTTAAATTTATTTGTAAACATTCAAATA
CTCACCAACAATATTGTACAATTTACAGTTTTTCTCTGCTTCATCTATCACACC
CATCCTTCTATTCATCTGATATTACACCTTATATTTTGGCACATTTCCAAACTA
TTACTTACACTTTGAGTTGAAGAAAATAAACTGAGTCCTTAATTGTATTGTAT
ATATGCATTTATAAATTTTTACAACATAAAGTACTCTATATTTACAAAATTTTT
TAGTTTTTTTTTTCTTTGGAATTGTTTCTGAGTAGTACTTAGTAACACTACTCT
AATGTAATATAAATTTTAAAGTATACCCAAAAAGAAAATGAAAAGAGATGA
AAAATGCATTGTTCTTGTGATCCCAGGAAATCTGAGACMGGTCTCAGTTAAT
TTACAAAGTTGATTTTGCCAAAGTTGAGGACGCACCCATGACACAGCCTCGG
GAAGCCCTGAGGACATGTACCCAAGGTGTTTGGGGCACAGCTTGGTTTACTA
CATCTTCAGGGAGACATGAGACATCAATCAATATATGTGAAAAGAACGTTGG
TTCAGTTTGGAAAGGgagggcatcttgttagcctt (SEQ ID NO: 929)
F 5'-3' = gtttccagactgttcagagg (SEQ ID NO: 930)
R 5'-3' = aaggctaacaagatgccctc (SEQ ID NO: 931)
```

M315 = EIFIA STS 41(512 bp) A to C at position 395 STS also contains M314
```
GttcttgtgatcccaggaaatCTGAGACAGGTCTCAGTTAATTTACAAAGTTGATTTTGCC
AAAGTTGAGGACGCACCCATGACACAGCCTCGGGAAGCCCTGAGGACATGT
ACCCAAGGTGTTTGGGGCACAGCTTGGTTTACTACATCTTCAGGGAGACATG
AGACATCAATCAATATATGTGAAAAGAACGTTGGTTCAGTTTGGAAAGGGAG
GGCATCTTGTTAGCCTTTCTAAAGGAGGCAGTCAGCTATGCATCTAACTCAAT
GAGCGAAAGGATAACTTTTGAATAGAATGGGAGGCCGGTTTGTCTTAAGCAG
TTTCCACCTTGAGTTTTTCATAGTAATTTTGGGGGCCAAAGATATTTTCGTTTC
ACATTCTAATATTTTCTTCMTGTACCTCCCTTTGGGGACCCTGAGCCAGAGGT
TTTTTGGGGGATTAAACAGAATTGGCATTTACTTCATGTTGCAATAACCAAAA
GCATAAATAttttgttgtagattaagggcaa (SEQ ID NO: 932)
F 5'-3' = gttcttgtgatcccaggaaat (SEQ ID NO: 933)
R 5'-3' = ttgcccttaatctacaacaaaa (SEQ ID NO: 934)
```

M316 = EIFIA STS 42 (512 bp nominal) 5T's to 6T's at position 201
Group V
```
AattggcatttacttcatgttgcAATAACCAAAAGCATAAATATTTTGTTGTAGATTAAGGgc
aaatctgaacatttccacAGTTGGTGGCCTTGGAGGCCTCTTTGGAAAATTCAGAGAACC
TATCCAGACTACCTAGTGGAACACAAAGCTACAAACACAGATGTTAGAATAA
GGATCTAGACATGGCTAAGATTTTTTCTCAGGGAGTGGGGGGGAGTATCTTA
GAGTTATGCCATTTCCTTTGGAACTAGGCCCATTAAGGTAACGGGAAGGAAT
GTAAAGACAATGGCTATTAAAGGAAGTTTAGTTTCTTTTGAGTTTCTTTTGCT
TATTACAAGAGAACACTGTAGATTTATAGATGTTCTAGTTTTACTTCTGTGAC
TACATGGACTCAGAATTTGGTTACGACCATATTTATCCCATTTTTAAAGGAAT
TACATCTATTTTGTCTGTGTCCACCCTCAGAATATAAGATCTGTAACCACTACc
acaaaaggaagtaaggacatg (SEQ ID NO: 935)
F 5'-3' = aattggcatttacttcatgttgc (SEQ ID NO: 936)
R 5'-3' = catgtccttacttcctttttgtg (SEQ ID NO: 937)
```

M317 = EIFIA STS 44 (523 bp nominal) -2bp Deletion of GA at position 400
(Group VIII)
```
TggttctacagttgggattttgGCCATCATCAACCAAGAAGAGAAATTCATTTAGTGTGTA
GTTTCTGAAAGCAAACTGATTTATTTTCATTGTTTTAAAGTATTTATTTCTTTA
AAAGCTGAGGACACTGAATTACCTTAAGTTAAATGTTAATACTTTATTGTTTT
GATGTAATGGAACTTAAGGATAAAAGACCATAATATTTGCTGTTAAAATAAA
TAAACGAGTGCCTTTCCTACTGTGATAACGTCAAGTAATTGGATATTTTGAAT
ACATTTCTGCCTGATAATCATGCTGGGTTCTAATAAGCCCTATTTCCACCTAA
TCTGTTTACAGTCTTTTGGTATGTTTCAGTTACTTAGATGGTCTCATAAGGTTT
CTGATACAATTTGAAGACAGAAATCTGCATTTAGAATCAGAAAACATGGAC
ATATTTTTCATATTTATCTAGTCATATGTAATTTTATGCTAACATTGATAGTTT
ATAAATCCTTTTCATCCTttgtgcctcggttattaagg (SEQ ID NO: 938)
F 5'-3' = tggttctacagttgggattttg (SEQ ID NO: 939)
R 5'-3' = ccttaataaccgaggcacaa (SEQ ID NO: 940)
```

M318 = EIF1AY STS20d, T to C, at position 353 Group VI
```
CatggtccaagcaatttattttTGTGAGTTCCCAAAATAATTTATACAGCAATGATTCATGT
GACAATGTGAATAAATAGAAAAAGTCTTTGATAACTTTTAGATTTACTTTTAA
AGAATAAATTTGTTTGTTTAACTTCTGTTGTATTCCTACCAGAAATGTTTACTCT
GATATTAGTATTGAAGAAACCAGACAAATCTAATATATAACACAAATGGTCT
TGACTCGAGATGTTAATGCTGTGAAAGAATGAAAAATCTGGGAATTACTTTAG
```

TABLE 1-continued

```
CTTAAAAGAGATTGATCGGTGCATATCCCTTCGTTAGGTTTTGGATTGGGGGA
AATAGTTTTAGGTGGTACTAGGAAAAYTGGAATATGGAATATGTTAGAAACT
CTATTTGTTAGTAATACCACATCAGGTAGTTTTATAAATTACACTGATTAAAA
GTCTCTACTACTCAGATTTTTAATTAAAATAATAAAAACTTATTTTTGGCTGA
Gctctgtgaagtattagccagc (SEQ ID NO: 941)
F 5'-3' = catggtccaagcaatttattttg (SEQ ID NO: 942)
Rev 5'-3' = gctggctaatacttccacagag (SEQ ID NO: 943)

M319 = UTY1 exon 14b, T to A at position 124. Group VI
GtaaaactcagatatatacatcccatgAAATATACACAGAAACTATAAATTAGCATTAATATC
CTCTAAAATGATACTGTAGTAAAGAAATATTCTCAAACTGTTGGTAAATTTTA
GAGAAAAWAAAAATATTATACATACTTGCTGCATTAAGACAAACTGACTTTC
TAACTGTTCCAGCTGATGCTTCTGTGCTGGATTTAAATTATCTCTATTTGCTCG
CAGTTGTTCCAAGTGCTAGAAGAAAAGAGATTAATATAATCAAAGTTTAATC
TAAAATTTAAGACAATATAAGGCAACTCCTCACTAAAAAGACTACACAGAAC
CTTTGCAGGATGAAAGACAGTGATTCCTAATGAAcgttaagatagtgattctttttttttt (SEQ ID NO: 944)
F 5'-3' = gtaaaactcagatatatacatcccatg (SEQ ID NO: 945)
Rev 5'-3': aaaaaaaaagaatcactatcttaacg (SEQ ID NO: 946)

M320 = DBY STS08, (444 bp) T to G at position 60
Group VI
tgaggtggaatgtatcagtataccAATTAATATTTTTGAAAGAGCTCTTTTAGGTTAATKTA
AGTACAGCAATTTCTCATGTAATGTTTAGGGAGTTTATTCTAACCTAGGCAAA
CGGCATGCTATCACAAGAAAGGTTTAAAGCTTTGATAAAATGGGGGAGATTT
AATCAGTTTTTTTAATGCCTGCTATAAAAATTTGAAATATTAGAATGGCCGAC
CATGGCAGTGACCAGGCCTCACTACAGGCCTGGTTGGATTCTGGTCTTTAATG
CATGCTAGTGTTGATGTTTTTTGGTCAAGAACGGTTTAAACAGGAAGGATTGT
GCAGCAGGCTTTAATTTAATGTAGATTCATACTGCTCTGTTAAAGCTGCATTG
AAATGTTAAAATGGCTTACACTTGCAGACTTTGCAAATCTTaagactaacaaatccttgaa
atca (SEQ ID NO: 947)
For 5'-3' = tgaggtggaatgtatcagtatacc (SEQ ID NO: 948)
Rev 5'-3' = tgatttcaaggatttgttagtctt (SEQ ID NO: 949)

M321 = DBY STS08, (444 bp) C to T at position 171
group VI
tgaggtggaatgtatcagtataccAATTAATATTTTTGAAAGAGCTCTTTTAGGTTAATTAA
GTACAGCAATTTCTCATGTAATGTTTAGGGAGTTTATTCTAACCTAGGCAAAC
GGCATGCTATCACAAGAAAGGTTTAAAGCTTTGATAAAATGGGGGAGATTTA
ATYAGTTTTTTTAATGCCTGCTATAAAAATTTGAAATATTAGAATGGCCGACC
ATGGCAGTGACCAGGCCTCACTACAGGCCTGGTTGGATTCTGGTCTTTAATGC
ATGCTAGTGTTGATGTTTTTTGGTCAAGAACGGTTTAAACAGGAAGGATTGTG
CAGCAGGCTTTAATTTAATGTAGATTCATACTGCTCTGTTAAAGCTGCATTGA
AATGTTAAAATGGCTTACACTTGCAGACTTTGCAAATCTTaagactaacaaatccttgaaat
ca (SEQ ID NO: 950)
For 5'-3' = tgaggtggaatgtatcagtatacc (SEQ ID NO: 951)
Rev 5'-3' = tgatttcaaggatttgttagtctt (SEQ ID NO: 952)
```

Footnote:
STS sequences (one strand only) for polymorphic Y sequences.
Primer regions = lower case; Reverse compliment made to generate 5'-3' Reverse PCR primer sequence for complimentary strand.
IUB code defines polymorphic site
R = A or G (puRine)
Y = C or T (pYrimidine)
K = G or T (Keto)
M = A or C (aMino)
S = G or C (Strong-3H bonds)
W = A or T (Weak-2H bonds)
H = A, C or T
Markers M1, M29, M40, M46, M130, M167, M176, M177, M222, M236, M288 are unassigned in TABLE 1.

That which is claimed is:

1. A method for determining the ethnic origin of a male, comprising:
   analyzing a nucleic acid sample from a male for the presence or absence of an allelic form of a plurality of Y chromosome polymorphisms, wherein the plurality of polymorphisms includes at least one of M150 (SEQ ID NO: 449), M247 (SEQ ID NO: 729), and M249 (SEQ ID NO: 735),
   wherein detection of an allelic form of a marker is indicative of the haplogroup of the male, which haplogroup is indicative of the ethnic origin of the male.

2. The method of claim 1, wherein the plurality of polymorphic markers identify a sub-haplogroup for the ethnic origin of the male.

3. The method of claim 1, wherein detecting a guanine at position 313 in M249, a cytosine at position 224 in M247, or a thymine at position 146 in M150 indicates the male is a member of haplotype Group II.

4. The method of claim 1, wherein the method further includes analyzing a plurality of polymorphisms of allelic forms of at least one of haplotype Group I, haplotype Group III, haplotype Group IV, haplotype Group V, haplotype Group VI, haplotype Group VII, haplotype Group VIII, haplotype Group IX or haplotype Group X.

5. A method for determining the ethnic origin of a male, comprising:
   analyzing a nucleic acid sample from a male for the presence or absence of an allelic form of a plurality of Y chromosome polymorphisms, wherein the plurality of polymorphisms includes M246 (SEQ ID NO: 726),
   wherein detection of an allelic form of a marker is indicative of the haplogroup of the male, which haplogroup is indicative of the ethnic origin of the male.

6. The method of claim 5, wherein the plurality of polymorphic markers identify a sub-haplogroup for the ethnic origin of the male.

7. The method of claim 5, wherein detecting a guanine at position 284 in M246 indicates the male is a member of haplotype Group I.

8. The method of claim 5, wherein the method further includes analyzing a plurality of polymorphisms of allelic forms of at least one of haplotype Group II, haplotype Group III, haplotype Group IV, haplotype Group V, haplotype Group VI, haplotype Group VII, haplotype Group VIII, haplotype Group IX or haplotype Group X.

9. A method for determining the ethnic origin of a male, comprising:
analyzing a nucleic acid sample from a male for the presence or absence of an allelic form of a plurality of Y chromosome polymorphisms, wherein the plurality of polymorphisms includes M191 (SEQ ID NO: 569), wherein detection of an allelic form of a marker is indicative of the haplogroup of the male, which haplogroup is indicative of the ethnic origin of the male.

10. The method of claim 9, wherein the plurality of polymorphic markers identify a sub-haplogroup for the ethnic origin of the male.

11. The method of claim 9, wherein detecting a guanine at position 342 in M191 indicates the male is a member of haplotype Group III.

12. The method of claim 9, wherein the method further includes analyzing a plurality of polymorphisms of allelic forms of at least one of haplotype Group I, haplotype Group II, haplotype Group IV, haplotype Group V, haplotype Group VI, haplotype Group VII, haplotype Group VIII, haplotype Group IX or haplotype Group X.

13. A method for determining the ethnic origin of a male, comprising:
analyzing a nucleic acid sample from a male for the presence of absence of an allelic form of a plurality of Y chromosome polymorphisms, wherein the plurality of polymorphisms includes M174 (SEQ ID NO: 519), wherein detection of an allelic form of a marker is indicative of the haplogroup of the male, which haplogroup is indicative of the ethnic origin of the male.

14. The method of claim 13, wherein the plurality of polymorphic markers identify a sub-haplogroup for the ethnic origin of the male.

15. The method of claim 13, wherein detecting a cytosine at position 219 in M174 indicates the male is a member of haplotype Group IV.

16. The method of claim 13, wherein the method further includes analyzing a plurality of polymorphisms of allelic forms of at least one of haplotype Group I, haplotype Group II, haplotype Group III, haplotype Group V, haplotype Group VI, haplotype Group VII, haplotype Group VIII, haplotype Group IX or haplotype Group X.

17. A method for determining the ethnic origin of a male, comprising:
analyzing a nucleic acid sample from a male for the presence of absence of an allelic form of a plurality of Y chromosome polymorphisms, wherein the plurality of polymorphisms includes M216 (SEQ ID NO: 642), wherein detection of an allelic form of a marker is indicative of the haplogroup of the male, which haplogroup is indicative of the ethnic origin of the male.

18. The method of claim 17, wherein the plurality of polymorphic markers identify a sub-haplogroup for the ethnic origin of the male.

19. The method of claim 17, wherein detecting a thymine at position 54 in M216 indicates the male is a member of haplotype Group V.

20. The method of claim 17, wherein the method further includes analyzing a plurality of polymorphisms of allelic forms of at least one of haplotype Group I, haplotype Group II, haplotype Group III, haplotype Group IV, haplotype Group VI, haplotype Group VII, haplotype Group VIII, haplotype Group IX or haplotype Group X.

21. A method for determining the ethnic origin of a male, comprising:
analyzing a nucleic acid sample from a male for the presence of absence of an allelic form of a plurality of Y chromosome polymorphisms, wherein the plurality of polymorphisms includes M304 (SEQ ID NO: 899), wherein detection of an allelic form of a marker is indicative of the haplogroup of the male, which haplogroup is indicative of the ethnic origin of the male.

22. The method of claim 21, wherein the plurality of polymorphic markers identify a sub-haplogroup for the ethnic origin of the male.

23. The method of claim 21, wherein detecting a cytosine at position 421 in M304 indicates the male is a member of haplotype Group VI.

24. The method of claim 21, wherein the method further includes analyzing a plurality of polymorphisms of allelic forms of at least one of haplotype Group I, haplotype Group II, haplotype Group III, haplotype Group IV, haplotype Group V, haplotype Group VII, haplotype Group VIII, haplotype Group IX or haplotype Group X.

25. A method for determining the ethnic origin of a male, comprising:
analyzing a nucleic acid sample from a male for the presence of absence of an allelic form of a plurality of Y chromosome polymorphisms, wherein the plurality of polymorphisms includes M214 (SEQ ID NO: 636), wherein detection of an allelic form of a marker is indicative of the haplogroup of the male, which haplogroup is indicative of the ethnic origin of the male.

26. The method of claim 25, wherein the plurality of polymorphic markers identify a sub-haplogroup for the ethnic origin of the male.

27. The method of claim 25, wherein detecting a cytosine at position 404 in M214 indicates the male is a member of haplotype Group VII.

28. The method of claim 25, wherein the method further includes analyzing a plurality of polymorphisms of allelic forms of at least one of haplotype Group I, haplotype Group II, haplotype Group III, haplotype Group IV, haplotype Group V, haplotype Group VI, haplotype Group VIII, haplotype Group IX or haplotype Group X.

29. A method for determining the ethnic origin of a male, comprising:
analyzing a nucleic acid sample from a male for the presence of absence of an allelic form of a plurality of Y chromosome polymorphisms, wherein the plurality of polymorphisms includes M61 (SEQ ID NO: 176), wherein detection of an allelic form of a marker is indicative of the haplogroup of the male, which haplogroup is indicative of the ethnic origin of the male.

30. The method of claim 29, wherein the plurality of polymorphic markers identify a sub-haplogroup for the ethnic origin of the male.

31. The method of claim 29, wherein detecting a thymine at position 98 in M61 indicates the male is a member of haplotype Group VIII.

32. The method of claim 29, wherein the method further includes analyzing a plurality of polymorphisms of allelic forms of at least one of haplotype Group I, haplotype Group II, haplotype Group III, haplotype Group IV, haplotype Group V, haplotype Group VI, haplotype Group VII, haplotype Group IX or haplotype Group X.

33. A method for determining the ethnic origin of a male, comprising:
analyzing a nucleic acid sample from a male for the presence of absence of an allelic form of a plurality of Y chromosome polymorphisms, wherein the plurality of polymorphisms includes M207 (SEQ ID NO: 615), wherein detection of an allelic form of a marker is indicative of the haplogroup of the male, which haplogroup is indicative of the ethnic origin of the male.

34. The method of claim 33, wherein the plurality of polymorphic markers identify a sub-haplogroup for the ethnic origin of the male.

35. The method of claim 33, wherein detecting a guanine at position 79 in M207 indicates the male is a member of haplotype Group IX.

36. The method of claim 33, wherein the method further includes analyzing a plurality of polymorphisms of allelic forms of at least one of haplotype Group I, haplotype Group II, haplotype Group III, haplotype Group IV, haplotype Group V, haplotype Group VI, haplotype Group VII, haplotype Group VIII or haplotype Group X.

37. A method for determining the ethnic origin of a male, comprising:

analyzing a nucleic acid sample from a male for the presence of absence of an allelic form of a plurality of Y chromosome polymorphisms, wherein the plurality of polymorphisms includes M242 (SEQ ID NO: 714), wherein detection of an allelic form of a marker is indicative of the haplogroup of the male, which haplogroup is indicative of the ethnic origin of the male.

38. The method of claim 37, wherein the plurality of polymorphic markers identify a sub-haplogroup for the ethnic origin of the male.

39. The method of claim 37, wherein detecting a thymine at position 337 in M242 indicates the male is a member of haplotype Group X.

40. The method of claim 37, wherein the method further includes analyzing a plurality of polymorphisms of allelic forms of at least one haplotype Group I, haplotype Group II, haplotype Group III, haplotype Group IV, haplotype Group V, haplotype Group VI, haplotype Group VII, haplotype Group up VIII or haplotype Group IX.

* * * * *